United States Patent
Liu et al.

(10) Patent No.: US 11,945,827 B2
(45) Date of Patent: *Apr. 2, 2024

(54) RAPAFUCIN DERIVATIVE COMPOUNDS AND METHODS OF USE THEREOF

(71) Applicants: The Johns Hopkins University, Baltimore, MD (US); Rapafusyn Pharmaceuticals, Inc., Baltimore, MD (US)

(72) Inventors: Jun Liu, Clarksville, MD (US); Sam Hong, Baltimore, MD (US); Brett R. Ullman, Baltimore, MD (US); Joseph E. Semple, Baltimore, MD (US); Kana Yamamoto, Baltimore, MD (US); Puneet Kumar, Baltimore, MD (US); Magesh Sadagopan, Baltimore, MD (US); Jennifer C. Schmitt, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 96 days.

This patent is subject to a terminal disclaimer.

(21) Appl. No.: 17/332,331

(22) Filed: May 27, 2021

(65) Prior Publication Data

US 2022/0363692 A1 Nov. 17, 2022

Related U.S. Application Data

(60) Division of application No. 16/590,087, filed on Oct. 1, 2019, now Pat. No. 11,066,416, which is a continuation-in-part of application No. 16/074,017, filed as application No. PCT/US2017/016481 on Feb. 3, 2017, now Pat. No. 10,662,220.

(60) Provisional application No. 62/291,437, filed on Feb. 4, 2016.

(51) Int. Cl.
*C07D 498/14* (2006.01)
*C07D 498/04* (2006.01)
*C07F 9/32* (2006.01)

(52) U.S. Cl.
CPC ......... *C07D 498/14* (2013.01); *C07D 498/04* (2013.01); *C07F 9/3258* (2013.01)

(58) Field of Classification Search
CPC .................................................. C07D 498/14
USPC ...................................................... 514/233.2
See application file for complete search history.

(56) References Cited

U.S. PATENT DOCUMENTS

| | | | |
|---|---|---|---|
| 5,212,155 A | 5/1993 | Caine | |
| 5,527,907 A | 6/1996 | Or et al. | |
| 5,798,355 A | 8/1998 | Steiner et al. | |
| 6,984,635 B1 | 1/2006 | Schreiber et al. | |
| 7,056,935 B2 | 6/2006 | Steiner et al. | |
| 7,803,808 B2 | 9/2010 | Gregory et al. | |
| 7,989,395 B2 | 8/2011 | Morgan et al. | |
| 8,642,215 B2 | 2/2014 | Kim et al. | |
| 9,250,237 B2 | 2/2016 | Liu et al. | |
| 9,840,518 B2 | 12/2017 | Hird et al. | |
| 9,989,535 B2 | 6/2018 | Verdine et al. | |
| 10,466,249 B2 | 11/2019 | Verdine et al. | |
| 10,533,016 B2 | 1/2020 | Verdine et al. | |
| 10,774,110 B2 | 9/2020 | Liu et al. | |
| 2002/0052410 A1 | 5/2002 | Steiner et al. | |
| 2008/0306098 A1 | 12/2008 | Mutz et al. | |
| 2009/0253732 A1 | 10/2009 | Gregory et al. | |
| 2014/0073581 A1 | 3/2014 | Liu et al. | |
| 2015/0018340 A1 | 1/2015 | Gopalakrishnan et al. | |
| 2015/0203512 A1 | 7/2015 | Reger et al. | |
| 2017/0305926 A1 | 10/2017 | Hird et al. | |
| 2019/0224274 A1 | 7/2019 | Dawson et al. | |
| 2021/0214390 A1 | 7/2021 | Liu et al. | |

FOREIGN PATENT DOCUMENTS

| | | |
|---|---|---|
| JP | 08-333256 A | 12/1996 |
| JP | 2011-524413 A | 9/2011 |
| WO | 96/40140 A1 | 12/1996 |
| WO | WO 2004/093798 A2 | 11/2004 |
| WO | 2010/004304 A1 | 1/2010 |
| WO | 2012/075048 A2 | 6/2012 |
| WO | WO 2012075048 A2 | 6/2012 |
| WO | 2014/201405 A1 | 12/2014 |
| WO | 2017/136708 A1 | 8/2017 |
| WO | 2017/136717 A1 | 8/2017 |
| WO | 2017/136731 A1 | 8/2017 |
| WO | 2018/045250 A1 | 3/2018 |
| WO | 2019/064182 A1 | 4/2019 |

OTHER PUBLICATIONS

King, Med. Chem., Principle and Practice (1994), pp. 206-208.*
MX Office Action in Mexican Application No. MX/a/2018/009405, dated Jan. 18, 2022, 8 pages (with English translation).
Amigo J.; Rama-Garda R.; Bello X.; Sobrino B.; de Blas J.; Martin-Ortega M.; Jessop T. C.; Carracedo.; Loza M. I. G.; Dominguez E. tagFinder: A Novel Tag Analysis Methodology That Enables Detection of Molecules from DNA-Encoded Chemical Libraries. SLAS Discovery 2018,23(5), 397-404. 10.1177/2472555217753840.
Arico-Muendel, From haystack to needle: finding value with DNA encoded library technology at GSK MedChemComm, (2016) 7(10): 1898-1909.

(Continued)

*Primary Examiner* — Taofiq A Solola

(74) *Attorney, Agent, or Firm* — DLA Piper LLP (US)

(57) ABSTRACT

The present disclosure provides macrocyclic compounds inspired by the immunophilin ligand family of natural products FK506 and rapamycin. The generation of a Rapafucin library of macrocyles that contain FK506 and rapamycin binding domains should have great potential as new leads for developing drugs to be used for treating diseases.

4 Claims, No Drawings

(56) References Cited

OTHER PUBLICATIONS

Bao, Svetlana M. Krylova, Leonid T. Cherney, Robert L. Hale, Svetlana L. Belyanskaya, Cynthia H. Chiu, Alex Shaginian, Christopher C. Arico-Muendel, and Sergey N. Krylov Predicting Electrophoretic Mobility of Protein-Ligand Complexes for Ligands from DNA-Encoded Libraries of Small Molecules Anal. Chem., (2016) 88 (10):5498-5506.
Blakskjaer P, Heitner T, Hansen NJ. Fidelity by design: Yoctoreactor and binder trap enrichment for small-molecule DNA-encoded libraries and drug discovery. Curr Opin Chem Biol. 2015;26:62-71. doi:10.1016/j.cbpa.2015.02.003.
Brown MS, Radhakrishnan A, Goldstein JL. Retrospective on Cholesterol Homeostasis: The Central Role of Scap. Annu Rev Biochem. 2018;87:783-807. doi:10.1146/annurev-biochem-062917-011852.
Buller F, Mannocci L, Zhang Y, Dumelin CE, Scheuermann J, Neri D. Design and synthesis of a novel DNA-encoded chemical library using Diels-Alder cycloadditions. Bioorg Med Chem Lett. 2008; 18(22):5926-5931. doi:10.1016/j.bmcl.2008.07.038.
Buller F, Steiner M, Scheuermann J, Mannocci L, Nissen I, Kohler M, Beisel C, Neri D. High-throughput sequencing for the identification of binding molecules from DNA-encoded chemical libraries Bioorg Med Chem Lett. (2010) 15;20(14):4188-92.
Castanon J, Roman JP, Jessop TC, de Blas J, Haro R. Design and Development of a Technology Platform for DNA-Encoded Library Production and Affinity Selection [published correction appears in SLAS Discov. Jun. 2018;23(5):489]. SLAS Discov. 2018;23(5):387-396. doi:10.1177/2472555217752091.
Chakraborty et al., "Design and Synthesis of a Rapamycin-Based High Affinity Binding FKBP12 Ligand", Chemistry & Biology, vol. 2, Mar. 1, 1995, pp. 157-161.
Chan AI, McGregor LM, Liu DR. Novel selection methods for DNA-encoded chemical libraries. Curr Opin Chem Biol. 2015;26:55-61. doi:10.1016/j.cbpa.2015.02.010.
Clark MA, Acharya RA, Arico-Muendel CC, et al. Design, synthesis and selection of DNA-encoded small-molecule libraries [published correction appears in Nat Chem Biol. Oct. 2009;5(10):772]. Nat Chem Biol. 2009;5(9):647-654. doi:10.1038/nchembio.211.
Clark, Selecting chemicals: the emerging utility of DNA-encoded libraries Curr Opin Chem Biol. (2010) 14(3):396-403.
Connors WH, Hale SP, Terrett NK. DNA-encoded chemical libraries of macrocycles. Curr Opin Chem Biol. 2015;26:42-47. doi:10.1016/j.cbpa.2015.02.004.
Cuozzo, Paolo A. Centrella, Diana Gikunju, Sevan Habeshian, Christopher D. Hupp, Anthony D. Keefe, Eric A. Sigel, Holly H. Soutter, Heather A. Thomson, Ying Zhang, Matthew A. Clark Discovery of a Potent BTK Inhibitor with a Novel Binding Mode by Using Parallel Selections with a DNA-Encoded Chemical Library BioChem (2017), 18(9):864-71.
Decurtins W, Wichert M, Franzini RM, et al. Automated screening for small organic ligands using DNA-encoded chemical libraries. Nat Protoc. 2016;11(4):764-780. doi:10.1038/nprot.2016.039.
Deng, Peng Zhao, and Xiaoyu Li Discovery, SAR, and X-ray Binding Mode Study of BCATm Inhibitors from a Novel DNA-Encoded Library Bioconjug Chem. (2017) 20;28(9):2293-2301.
Denton KE, Krusemark CJ. Crosslinking of DNA-linked ligands to target proteins for enrichment from DNA-encoded libraries. Medchemcomm. 2016;7(10):2020-2027. doi:10.1039/C6MD00288A.
Ding Y, O'Keefe H, DeLorey JL, et al. Discovery of Potent and Selective Inhibitors for ADAMTS-4 through DNA-Encoded Library Technology (ELT). ACS Med Chem Lett. 2015;6(8):888-893. Published Jul. 7, 2015. doi:10.1021/acsmedchemlett.5b00138.
Ding, Design and Synthesis of Biaryl DNA-Encoded Libraries ACS Comb Sci. (2016) 10;18(10):625-629.
Eidam & Satz, Analysis of the productivity of DNA encoded libraries MedChemComm, (2016) 7(7): 1323-1331.
Estevez, A carbohydrate-derived trifunctional scaffold for DNA-encoded Libraries Tetrahedron: Asymmetry. (2017) 28:837-842.

European Search Report and Search Opinion Received for EP Application No. 17748264.3, dated Aug. 16, 2019, 18 pages.
Fabian Buller, Luca Mannocci, Jorg Scheuermann, and Dario Neri Drug Discovery with DNA-Encoded Chemical Libraries Bioconjugate Chem. (2010) 21, 1571-80.
Franzini RM, Ekblad T, Zhong N Identification of structure-activity relationships from screening a structurally compact DNA-encoded chemical library. Angew Chem Int Ed Engl. 2015;54(13):3927-3931. doi:10.1002/anie.201410736.
Franzini, Angela Nauer, Jorg Scheuermanna, Dario Neri Interrogating target-specificity by parallel screening of a DNA-encoded chemical library against closely related proteins Chem Commun. (2015) 11;51(38):8014-16.
Franzini, Florent Samain, Maaly Abd Elrahman, Gediminas Mikutis, Angela Nauer, Mauro Zimmermann, Jorg Scheuermann, Jonathan Hall, and Dario Neri Systematic Evaluation and Optimization of Modification Reactions of Oligonucleotides with Amines and Carboxylic Acids for the Synthesis of DNA-Encoded Chemical Libraries Bioconjug Chem. (2014) 20;25(8):1453-61.
Franzini, Neri & Scheuermann, DNA-Encoded Chemical Libraries: Advancing beyond Conventional Small-Molecule Libraries Acc Chem Res. (2014) 15;47(4):1247-55.
Gartner ZJ, Tse BN, Grubina R, Doyon JB, Snyder TM, Liu DR. DNA-templated organic synthesis and selection of a library of macrocycles. Science. 2004;305(5690):1601-1605. doi:10.1126/science.1102629.
Guo Z, Hong SY, Wang J, et al. Rapamycin-inspired macrocycles with new target specificity. Nat Chem. 2019;11(3):254-263. doi:10.1038/s41557-018-0187-4.
Halford, Breakthroughs with Bar Codes C&EN, (2017) 95(25): 28-33.
Harris PA, King BW, Bandyopadhyay D, et al. DNA-Encoded Library Screening Identifies Benzo[b][1,4]oxazepin-4-ones as Highly Potent and Monoselective Receptor Interacting Protein 1 Kinase Inhibitors. J Med Chem. 2016;59(5):2163-2178. doi:10.1021/acs.jmedchem.5b01898.
Hong, "Rapamycin-based macrocyclic library development and Equilibrative Nucleoside Transporter 1 (ENT1) inhibition", A dissertation submitted to John Hopkins University in conformity with the requirements for the degree of Doctor of Philosophy, Jun. 2016, 134 pages.
International Preliminary Report on Patentability received for PCT Patent Application No. PCT/US17/16481, dated Aug. 16, 2018, 7 pages.
International Search Report and Written Opinion received for PCT Patent Application No. PCT/US17/16481, dated Apr. 21, 2017, 7 pages.
Japanese Office Action dated Oct. 27, 2020, regarding JP 2018-540102.
Keefe AD, Clark MA, Hupp CD, Litovchick A, Zhang Y. Chemical ligation methods for the tagging of DNA-encoded chemical libraries. Curr Opin Chem Biol. 2015;26:80-88. doi:10.1016/j.cbpa.2015.02.015.
Kleiner, Christoph E. Dumelin, David R. Liu Small-molecule discovery from DNA-encoded chemical libraries Chem Soc Rev. (2011) 40(12): 5707-17.
Krall N, Scheuermann J, Neri D. Small targeted cytotoxics: current state and promises from DNA-encoded chemical libraries. Angew Chem Int Ed Engl. 2013;52(5):1384-1402. doi:10.1002/anie.201204631.
Kuai L, O'Keeffe T, Arico-Muendel C. Randomness in DNA encoded library selection data can be modeled for more reliable enrichment calculation. SLAS Discov. 2018;23(5):405-416.
Li Y, Zimmermann G, Scheuermann J, Neri D. Quantitative PCR is a Valuable Tool to Monitor the Performance of DNA-Encoded Chemical Library Selections. Chembiochem. 2017;18(9):848-852. doi:10.1002/cbic.201600626.
Lim, Making ring compounds for DNA encoded libraries C&EN, (2017) 95 (29):10.
Luca Mannocci, Markus Leimbacher, Moreno Wichert, Jorg Scheuermann, Dario Neri 20 years of DNA-encoded chemical libraries Chem. Commun. (2011) 47:12747-53.

(56) References Cited

OTHER PUBLICATIONS

Machutta, C., Kollmann, C., Lind, K. et al. Prioritizing multiple therapeutic targets in parallel using automated DNA-encoded library screening. Nat Commun 8,16081(2017). https://doi.org/10.1038/ncomms16081.
Mannocci L, Zhang Y, Scheuermann J, et al. High-throughput sequencing allows the identification of binding molecules isolated from DNA-encoded chemical libraries. Proc Natl Acad Sci U S A. 2008; 105(46):17670-17675. doi:10.1073/pnas.0805130105.
Mannocci, Samu Melkko, Fabian Buller, Ilona Molnar, Jean-Paul Gapian Bianke, Christoph E. Dumelin, Jorg Scheuermann, and Dario Neri Isolation of Potent and Specific Trypsin Inhibitors from a DNA-Encoded Chemical Library Bioconjugate Chem. (2010) 21, 1836-41.
Melkko S, Scheuermann J, Dumelin CE, Neri D. Encoded self-assembling chemical libraries. Nat Biotechnol. 2004;22(5):568-574. doi:10.1038/nbt961.
Neri D, Lerner RA. DNA-Encoded Chemical Libraries: A Selection System Based on Endowing Organic Compounds with Amplifiable Information. Annu Rev Biochem. 2018;87:479-502. doi:10.1146/annurev-biochem-062917-012550.
Neri, Twenty-five Years of DNA-Encoded Chemical Libraries Chembiochem. (2017) 4;18(9):827-828.
PCT International Search Report and Written Opinion in International Application No. PCT/US2020/53549, dated Feb. 4, 2021, 9 pages.
Salamon, Chemical Biology Probes from Advanced DNA-encoded Libraries ACS Chem Biol. (2016) 19;11(2):296-307.
Panchencko et al., "Prediction of functional sites by analysis of sequence and structure conservation", Protein Science, 2004, 13:884-892.
Satz, DNA Compatible Multistep Synthesis and Applications to DNA Encoded Libraries Bioconjug Chem. (2015) 19;26(8):1623-32.
Satz, DNA Encoded Library Selections and Insights Provided by Computational Simulations ACS Chem Biol. (2016) 16;10(10):2237-45.
Satz, Remo Hochstrasser, and Ann C. Petersen Analysis of Current DNA Encoded Library Screening Data Indicates Higher False Negative Rates for Numerically Larger Libraries ACS Comb Sci. (2017) 10;19(4):234-238.
Satz, Simulated Screens of DNA Encoded Libraries: The Potential Influence of Chemical Synthesis Fidelity on Interpretation of Structure-Activity Relationships CS Comb. Sci. (2016) 18 (7):415-424.
Scheuermann & Neri, Dual-pharmacophore DNA-encoded chemical libraries Curr Opin Chem Biol. (2015) 26:99-103.
Scheuermann, J., Dumelin, C. E., Melkko, S., Zhang, Y., Mannocci, L., Jaggi, M., Sobek, J., and Neri, D. DNA-Encoded Chemical Libraries for the Discovery of MMP-3 Inhibitors Bioconjugate Chem. 2008, 19, 778-785.
Shi B, Zhou Y, Huang Y, Zhang J, Li X. Recent advances on the encoding and selection methods of DNA-encoded chemical library. Bioorg Med Chem Lett. 2017;27(3):361-369. doi:10.1016/j.bmcl.2016.12.025.
Skopic, Acid- and Au(I)-mediated synthesis of hexathymidine-DNA-heterocycle chimeras, an efficient entry to DNA-encoded libraries inspired by drug structures Chem Sci. (2017) 1;8(5):3356-3361.
Skopic, Design and synthesis of DNA-encoded libraries based on a benzodiazepine and a pyrazolopyrimidine scaffold MedChemComm, (2016) 7(10): 1957-1965.
Upadhayaya et al., "Inhibition of Ras Signaling by Blocking Ras-Effector Interactions with Cyclic Peptides", Angew. Chem. Int Ed., vol. 54, No. 26, Jun. 22, 2015, pp. 7602-7606.
Wrenn & Harbury, Chemical Evolution as a Tool for Molecular Discovery Annu. Rev. Biochem. (2007) 76:331-49.
Wu et al., "Creating Diverse Target-Binding Surfaces on FKBP12: Synthesis and Evaluation of a Rapamycin Analogue Library", ACS Comb Sci, vol. 13, No. 5, Sep. 12, 2011, pp. 486-495.
Wu, Xianghong et al.: "Inhibition of Ras-effector interactions by cyclic peptides". Med. Chem. Commun., Jan. 1, 2013, vol. 4 No. 2, pp. 378-382, XP55610945.
Xia Tian, Gregory S. Basarab, Nidhal Selmi, Thierry Kogej, Ying Zhang, Matthew Clark, Robert A. Goodnow Jr.. Development and design of the tertiary amino effect reaction for DNA-encoded library synthesis. MedChemComm 2016;7(7), 1316-1322.
Yuen & Franzini, Achievements, Challenges, and Opportunities in DNA Encoded Library Research: An Academic Point of View Chembiochem. (2017) 4;18(9):829-836.
Zhang, "Protein Tyrosine Phosphatases: Structure and Function, Substrate Specificity, and Inhibitor Development", Annu. Rev. Pharmacol. Toxicol., 42:209-234, 2002.
Zimmermann & Neri, DNA-encoded chemical libraries: foundations and applications in lead discovery Drug Discov. Today. (2016) 21(11):1828-1834.
Zimmermann G, Li Y, Rieder U, Mattarella M, Neri D, Scheuermann J. Hit-Validation Methodologies for Ligands Isolated from DNA-Encoded Chemical Libraries. Chembiochem. 2017;18(9):853-857. doi:10.1002/cbic.201600637.

\* cited by examiner

RAPAFUCIN DERIVATIVE COMPOUNDS AND METHODS OF USE THEREOF

CROSS-REFERENCE TO RELATED APPLICATIONS

This application is a divisional application of U.S. application Ser. No. 16/590,087 filed Oct. 1, 2019, which is a continuation-in-part application of U.S. application Ser. No. 16/074,017 filed Jul. 30, 2018, now issued as U.S. Pat. No. 10,662,220; which is a 35 USC § 371 National Stage Application of International Application No. PCT/US2017/016481 filed Feb. 3, 2017; which claims the benefit under 35 USC § 119(e) to U.S. Application Ser. No. 62/291,437 filed Feb. 4, 2016. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant No. CA174428 awarded by the National Institutes of Health. The government has certain rights in the invention.

BACKGROUND INFORMATION

The macrocyclic natural products FK506 and rapamycin are approved immunosuppressive drugs with important biological activities. Both have been shown to inhibit T cell activation, albeit with distinct mechanisms. In addition, rapamycin has been shown to have strong anti-proliferative activity. FK506 and rapamycin share an extraordinary mode of action; they act by recruiting an abundant and ubiquitously expressed cellular protein, the prolyl cis-trans isomerase FKBP, and the binary complexes subsequently bind to and allosterically inhibit their target proteins calcineurin and mTOR, respectively. Structurally, FK506 and rapamycin share a similar FKBP-binding domain but differ in their effector domains. In FK506 and rapamycin, nature has taught us that switching the effector domain of FK506 to that in rapamycin, it is possible to change the targets from calcineurin to mTOR. The generation of a Rapafucin library of macrocyles that contain FK506 and rapamycin binding domains should have great potential as new leads for developing drugs to be used for treating diseases.

With the completion of the sequencing and annotation of the human genome, a complete catalog of all human proteins encoded in the genome is now available. The functions of a majority of these proteins, however, remain unknown. One way to elucidate the functions of these proteins is to find small molecule ligands that specifically bind to the proteins of interest and perturb their biochemical and cellular functions. Thus, a major challenge for chemical biologists today is to discover new small molecule probes for new proteins to facilitate the elucidation of their functions. The recent advance in the development of protein chips has offered an exciting new opportunity to simultaneously screen chemical libraries against nearly the entire human proteome. A single chip, in the form of a glass slide, is sufficient to display an entire proteome in duplicate arrays. Recently, a protein chip with 17,000 human proteins displayed on a single slide has been produced. A major advantage of using human protein chips for screening is that the entire displayed proteome can be interrogated at once in a small volume of assay buffer (<3 mL). Screening of human protein chips, however, is not yet feasible with most, if not all, existing chemical libraries due to the lack of a universal readout for detecting the binding of a ligand to a protein on these chips. While it is possible to add artificial tags to individual compounds in a synthetic library, often the added tags themselves interfere with the activity of ligands. Thus, there remains a need for new compounds and methods for screening chemical libraries against the human proteome.

SUMMARY OF THE INVENTION

The present disclosure is directed to a library of Rapafucin compounds, methods of making these compounds, and methods of using the same. The present disclosure is further directed to DNA-encoded libraries of hybrid cyclic molecules, and more specifically to DNA-encoded libraries of hybrid cyclic compounds based on the immunophilin ligand family of natural products FK506 and rapamycyin.

In some embodiments, the Rapafucin compounds in the present disclosure can have a structure according to Formula (V) or an optically pure stereoisomer or pharmaceutically acceptable salt thereof.

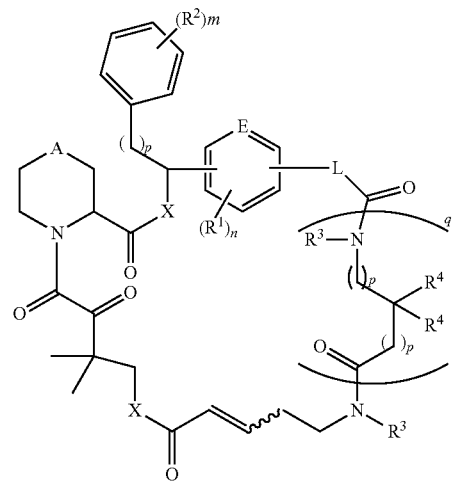

Formula (V)

Wherein L is selected from the groups in Table 1; A is $CH_2$, NH, NMe, O, $S(O)_2$ or S; each D is independently O, NMe, or NH; E is CH or N.

Each of $R^1$, $R^2$, $R^3$, and $R^4$ can be independently selected from the group consisting of H, halogen, hydroxyl, $N_3$, $NH_2$, $NO_2$, $CF_3$, $OCF_3$, $OCHF_2$, $CO_2C_{1-20}$alkyl, $C_{3-8}$cycloalkyl, $C_{2-8}$alkenyl, $C_{2-8}$alkynyl, $C_{1-10}$alkoxy, $C_{6-15}$aryl, $C_{6-15}$ayloxy, $C_{6-15}$arylthio, $C_{2-10}$carboxyl, $C_{1-10}$alkylamino, thiol, $C_{1-10}$alkyldisulfide, $C_{6-15}$arylthio, $C_{1-10}$heteroarylthio, ($C_{3-8}$cycloalkyl)thio, $C_{2-10}$heterocyclylthio, sulfonyl, $C_{1-10}$alkylsulfonyl, amido, $C_{1-10}$alkylamido, selenol, $C_{1-10}$alkylselenol, $C_{6-15}$arylselenol, $C_{1-10}$heteroarylselenol, ($C_{3-8}$cycloalkyl)selenol, $C_{2-10}$heterocyclylselenol, guanidino, $C_{1-10}$alkylguanidino, urea, $C_{1-10}$alkylurea, ammonium, $C_{1-10}$alkylammonium, cyano, $C_{1-10}$alkylcyano, $C_{1-10}$alkylnitro, adamantine, phosphonate, $C_{1-10}$alkylphosphonate, and $C_{6-15}$arylphosphonate, each of the above can be optionally substituted with H, halogen, hydroxyl, $N_3$, $NH_2$, $NO_2$, $CF_3$, $C_{1-20}$alkyl, substituted $C_{1-20}$alkyl, $C_{1-10}$alkoxy, substituted $C_{1-10}$alkoxy, acyl, acylamino, acyloxy, acyl $C_{1-10}$alkyloxy, amino, substituted amino, aminoacyl, aminocarbonyl $C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester)amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, halo, hydroxyl, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, substituted $C_{1-10}$alkylthio, and thiocarbonyl.

n is an integer selected from 0 to 4; m is an integer selected from 0 to 5; each p is independently an integer selected from 0 to 2; q is an integer selected from 1 to 10.

Or any $R^4$ forms a cyclic structure formed with any $R^3$, the cyclic structure so formed is selected from the group consisting of $C_{2-10}$heterocyclyl and $C_{1-10}$heteroaryloptionally substituted with H, halogen, hydroxyl, $N_3$, $NH_2$, $NO_2$, $CF_3$, $C_{1-10}$alkyl, substituted $C_{1-10}$alkyl, $C_{1-10}$alkoxy, substituted $C_{1-10}$alkoxy, acyl, acylamino, acyloxy, acyl $C_{1-10}$alkyloxy, amino, substituted amino, aminoacyl, aminocarbonyl $C_{1-10}$alkyl aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester)amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, halo, hydroxyl, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, substituted $C_{1-10}$alkylthio, and thiocarbonyl.

In some embodiments, q can be 1. In some embodiments, q can be 2. In some embodiments, q can be 3. In some embodiments, q can be 4. In some embodiments, q can be 5. In some embodiments, q can be 6. In some embodiments, q can be 7. In some embodiments, q can be 8. In some embodiments, q can be 9. In some embodiments, q can be 10. In specific embodiments, q is 3 or 4.

Further provided herein is a macrocyclic compound of Formula (XII) or a pharmaceutically acceptable salt, solvate, or stereoisomer thereof:

Formula (XII)

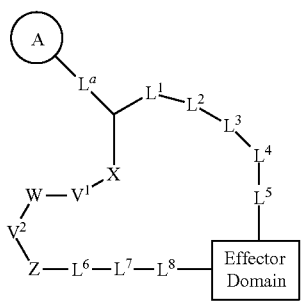

In some embodiments, Ring A is a 5-10 membered aryl, cycloalkyl, heteroaryl or heterocycloalkyl, optionally substituted with 1-17 substituents, each of which is independently selected from the group consisting of hydrogen, hydroxy, halo, alkyl, alkoxy, cyano, haloalkyl, haloalkoxy, alkylthio, oxo, amino, alkylamino, dialkylamino,

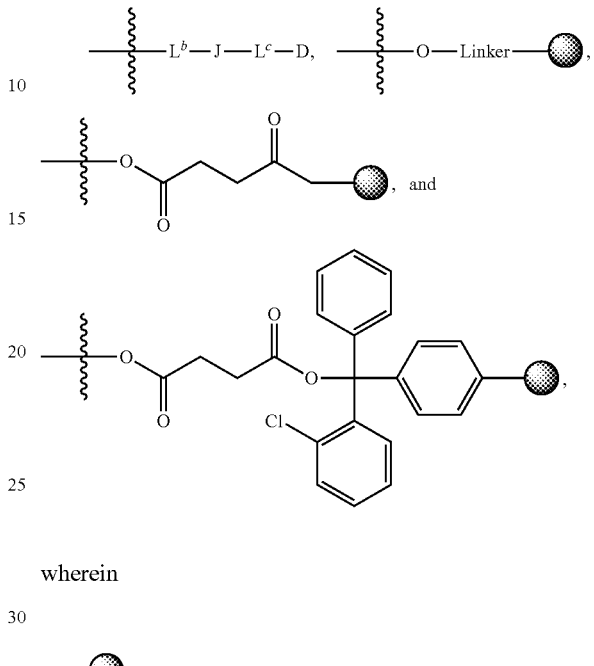

wherein

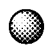

is a resin; J is independently at each occurrence selected from the group consisting of —C(O)NR$^6$—.

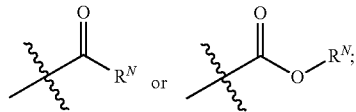

wherein $R^6$ is each hydrogen, alkyl, arylalkyl,

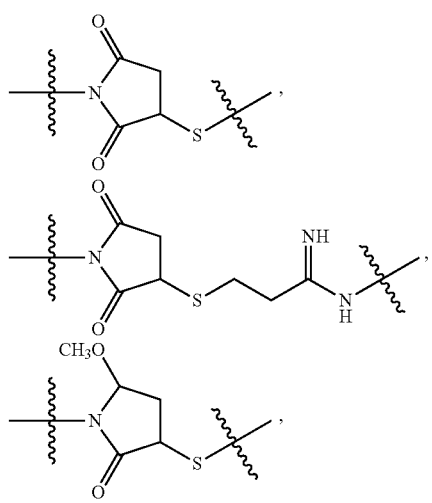

-continued

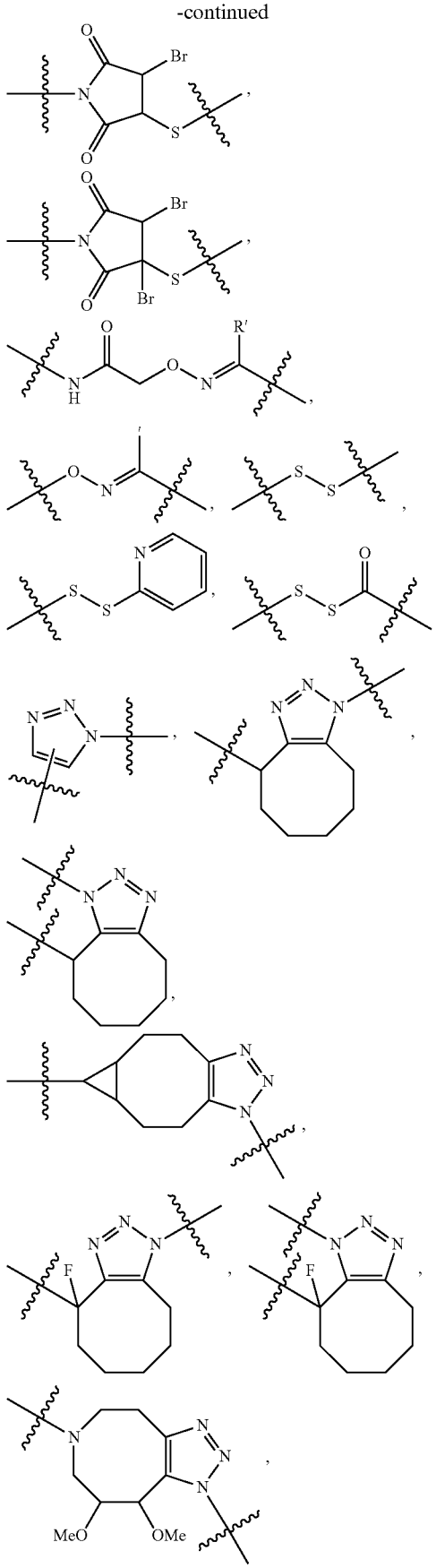

-continued

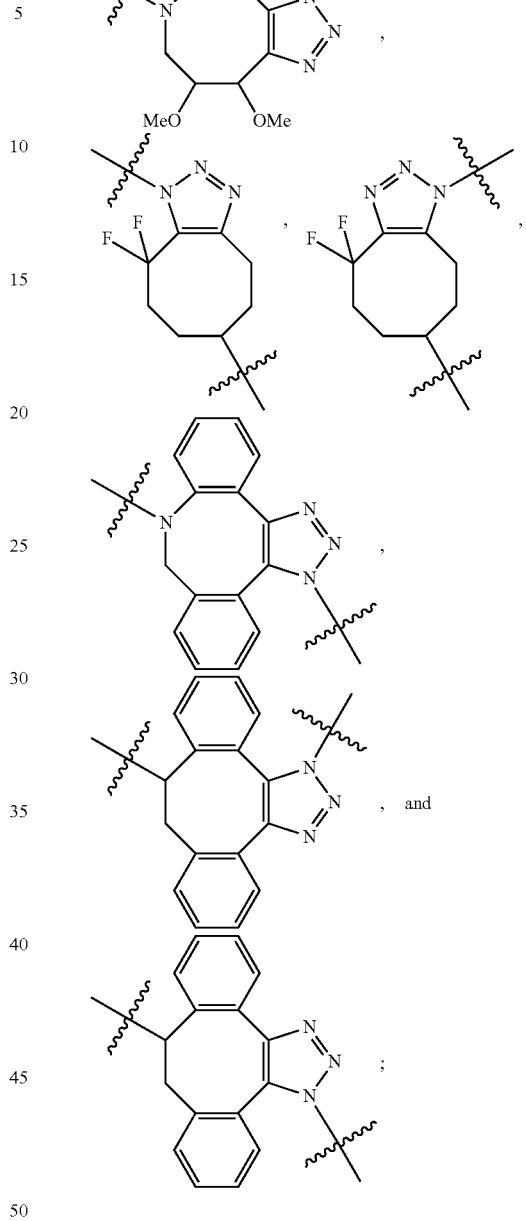

wherein $R^N$ is aryl, alkyl, or arylalkyl; R' is hydrogen, alkyl, arylalkyl, or haloalkyl; D is independently at each occurrence an oligonucleotide; $L^b$ and $L^c$ are independently at each occurrence selected from the group consisting of bond, —O—, —S—, —OC(O)—, —C(O)O—, —(CH$_2$)$_n$C(O)—, —(CH$_2$)$_n$C(O)C(O)—, —(CH$_2$)$_n$NR$^5$C(O)C(O)—, —NR$^5$(CH$_2$)$_n$C(O)C(O)—, optionally substituted (CH$_2$)$_n$C$_{1-6}$ alkylene (CH$_2$)$_n$—, optionally substituted (CH$_2$)$_n$C(O)C$_{1-6}$ alkylene (CH$_2$)$_n$—, optionally substituted (CH$_2$)$_n$NR$^5$C$_{1-6}$ alkylene (CH$_2$)$_n$—, optionally substituted (CH$_2$)$_n$C(O)NR$^5$C$_{1-6}$ alkylene (CH$_2$)$_n$—, optionally substituted (CH$_2$)$_n$NR$^5$C(O)C$_{1-6}$ alkylene (CH$_2$)$_n$—, optionally substituted (CH$_2$)$_n$C(O)OC$_{1-6}$ alkylene (CH$_2$)$_n$—, optionally substituted (CH$_2$)$_n$OC(O)C$_{1-6}$ alkylene (CH$_2$)$_n$—, optionally substituted (CH$_2$)$_n$OC$_{1-6}$ alkylene (CH$_2$)$_n$—, optionally substituted (CH$_2$)$_n$NR$^5$C$_{1-6}$alkylene (CH$_2$)$_n$—, optionally substituted (CH$_2$)$_n$—S—C$_{1-6}$alkylene (CH$_2$)$_n$—, and optionally substituted (CH$_2$CH$_2$O)$_n$; wherein each alkylene is optionally substituted with 1 or 2 groups independently selected from the group consisting of of halo, hydroxy, haloalkyl, haloalkoxy, alkyl, alkoxy, amino, carboxyl, cyano, nitro, NHFmoc; wherein each R$^5$ is independently hydrogen, alkyl, arylalkyl,

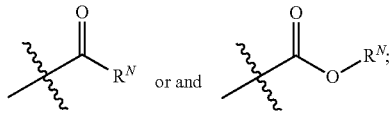
or and wherein R$^N$ is aryl, alkyl, or arylalkyl; X is O, S or NR$^8$, wherein R$^8$ is hydrogen, hydroxy, OR$^9$, NR$^{10}$, R$^{11}$, alkyl, arylalkyl,

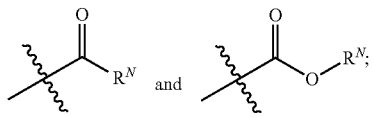
and wherein R$^N$ is aryl, alkyl, or arylalkyl; wherein R$^9$, R$^{10}$ and R$^{11}$ are each independently hydrogen or alkyl; V$^1$ and V$^2$ are each independently

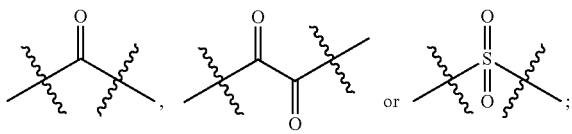

W is

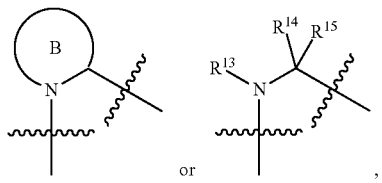
or wherein Ring B is a 4-10 membered heterocycloalkyl, optionally substituted with 1-10 substituents, each of which is selected from the group consisting of hydrogen, hydroxy, halo, alkyl, alkoxy, cyano, haloalkyl, haloalkoxy, alkylthio, oxo, amino, alkylamino, dialkylamino, arylalkyl,

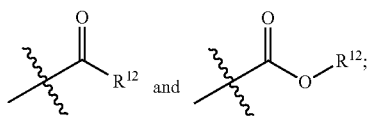
and wherein R$^{12}$ is aryl, alkyl, or arylalkyl; wherein R$^{13}$ is hydrogen, hydroxy, OR$^{16}$, NR$^{17}$R$^{18}$, alkyl, arylalkyl,

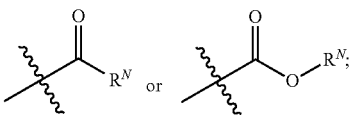
or wherein R$^N$ is aryl, alkyl, or arylalkyl; R$^{14}$ and R$^{15}$ is each independently hydrogen, hydroxy, halo, alkyl, alkoxy, haloalkyl, haloalkoxy, aryl, arylalkyl, or heteroaryl; Z is bond,

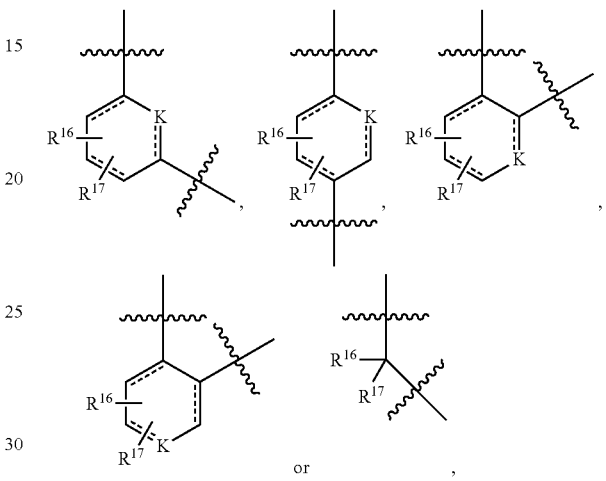
or , wherein R$^{16}$ and R$^{17}$ are each independently selected from the group consisting of of hydrogen, hydroxy, halo, alkyl, alkoxy, cycloalkyl, cyano, alkylthio, amino, alkylamino, and dialkylamino; K is O, CHR$^{18}$, CR$^{18}$, N, or and NR$^{18}$, wherein R$^{18}$ is hydrogen or alkyl;

L$^a$, L$^1$, L$^2$, L$^3$, L$^4$, L$^5$, L$^6$, L$^7$ and L$^8$ are each independently a bond, —O—, —NR$^{19}$—, —SO—, —SO$_2$—, (CH$_2$)$_n$—,

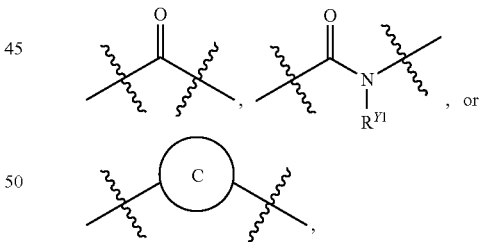
, or or a linking group selected from Table 1; wherein Ring C is a 5-6 membered heteroaryl, optionally substituted with 1-4 substituents, each of which is independently selected from the group consisting of hydrogen, hydroxyl, halo, alkyl, alkoxy, haloalkyl, haloalkoxy, cyano, alkylthio, amino, alkylamino, dialkylamino and

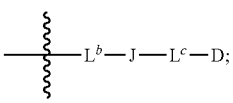

wherein each $R^{19}$, $R^{20}$, and $R^{21}$ is independently is selected from the group consisting of hydrogen, hydroxy, $OR^{22}$, $NR^{23}R^{24}$, alkyl, arylalkyl,

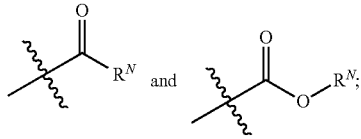

wherein $R^N$ is aryl, alkyl, or arylalkyl; wherein $R^{22}$, $R^{23}$, and $R^{24}$ are each independently hydrogen or alkyl;

n is 0, 1, 2, 3, 4, 5 or 6; wherein the Effector Domain has Formula (XIIa):

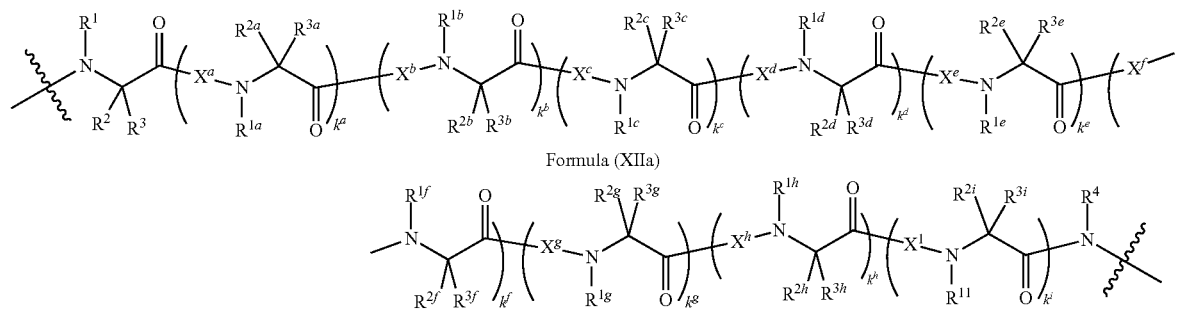

Formula (XIIa)

In some embodiments, each $k^a$, $k^b$, $k^c$, $k^d$, $k^e$, $k^f$, $k^g$, $k^h$, and $k^i$ is independently 0 or 1; each $X^a$, $X^b$, $X^c$, $X^d$, $X^e$, $X^f$, $X^g$, $X^h$, and $X^i$ is independently a bond, —S—, —S—S—, —S(O)—, —S(O)$_2$—, substituted or unsubstituted —(C$_1$-C$_3$) alkylene-, —(C$_2$-C$_4$) alkenylene-, —(C$_2$-C$_4$) alkynylene-, or

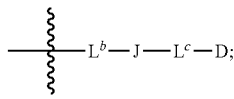

wherein Ring E is phenyl or a 5-6 heteroaryl or heterocycloalkyl; wherein each w is independently 0, 1, or 2; each $R^1$, $R^{1a}$, $R^{1b}$, $R^{1c}$, $R^{1d}$, $R^{1e}$, $R^{1f}$, $R^{1g}$, $R^{1h}$, $R^{1i}$, and $R^4$ is independently hydrogen, alkyl, arylalkyl or $NR^{25}$, wherein $R^{25}$ is hydrogen, hydroxy, $OR^{26}$, $NR^{27}R^{28}$, alkyl, arylalkyl,

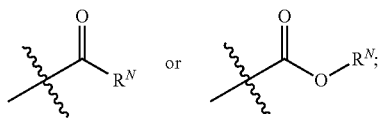

wherein $R^N$ is aryl, alkyl, or arylalkyl; wherein $R^{26}$, $R^{27}$, and $R^{28}$ are each independently hydrogen or alkyl; each $R^2$, $R^3$, $R^{2a}$, $R^{3a}$, $R^{2b}$, $R^{3b}$, $R^{2c}$, $R^{3c}$, $R^{2d}$, $R^{3d}$, $R^{2e}$, $R^{3e}$, $R^{2f}$, $R^{3f}$, $R^{2g}$, $R^{3g}$, $R^{2h}$, $R^{3h}$, $R^{2i}$, and $R^{3i}$ is independently selected from the group consisting of hydrogen, halo, amino, cyano, nitro, haloalkyl, optionally substituted alkyl, optionally substituted alkoxy, optionally substituted alkenyl, optionally substituted alkynyl, optionally substituted cycloalkyl, optionally substituted heterocycloalkyl, optionally substituted alkylamino, optionally substituted dialkylamino, optionally substituted aryl, optionally substituted heteroaryl, optionally substituted arylalkyl, optionally substituted heteroarylalkyl and

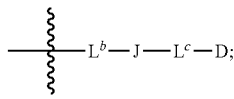

or wherein the Effector Domain has Formula (XIIb):

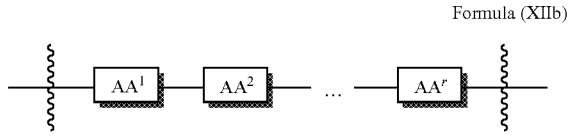

Formula (XIIb)

wherein each of $AA^1$, $AA^2$, ..., and $AA^r$ is an natural or unnatural amino acid residue; and r is 3, 4, 5, 6, 7, 8, 9, or 10;

or wherein the Effector Domain has Formula (XIIc):

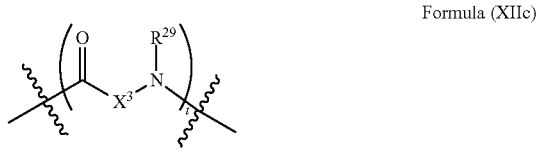

Formula (XIIc)

wherein each t is independently an integer selected from 0, 1, 2, 3, 4, 5, 6, 7, 8, 9, and 10; $R^{29}$ is a hydrogen, hydroxy, $OR^{30}$, $NR^{31}R^{32}$, alkyl, arylalkyl,

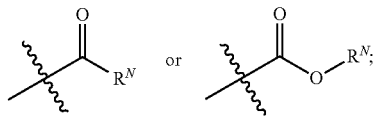

wherein $R^N$ is aryl, alkyl, or arylalkyl; wherein $R^{30}$, $R^{31}$, and $R^{32}$ are each independently hydrogen or alkyl; $X^3$ is substituted or unsubstituted —(C$_1$-C$_6$) alkylene-, —(C$_2$-C$_6$) alkenylene-, —(C$_2$-C$_6$) alkynylene-, or

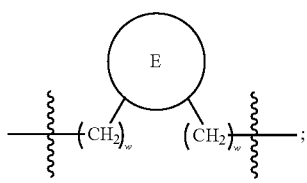

wherein Ring E is phenyl or a 5-6 heteroaryl or heterocycloalkyl; wherein each w is independently 0, 1, or 2;

or wherein the Effector Domain has Formula (XIId):

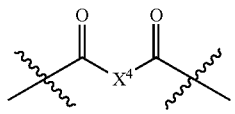

Formula (XIId)

wherein $X^4$ is substituted or unsubstituted —($C_1$-$C_6$) alkylene-, —($C_2$-$C_6$) alkenylene-, —($C_2$-$C_6$) alkynylene-, or

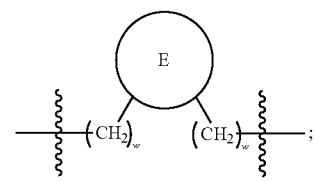

wherein Ring E is phenyl or a 5-6 heteroaryl or heterocycloalkyl; wherein each w is independently 0, 1, or 2;

or wherein the Effector Domain has Formula (XIIe):

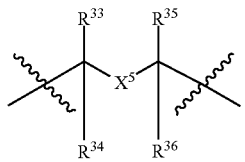

Formula (XIIe)

wherein $R^{33}$, $R^{34}$, $R^{35}$ and $R^{36}$ are each hydrogen or alkyl; $X^5$ is substituted or unsubstituted —($C_1$-$C_6$) alkylene-, —($C_2$-$C_6$) alkenylene-, —($C_2$-$C_6$) alkynylene-, or

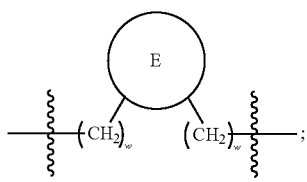

wherein Ring E is phenyl or a 5-6 heteroaryl or heterocycloalkyl; wherein each w is independently 0, 1, or 2;

or wherein the Effector Domain has Formula (XIIf):

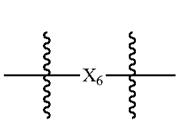

Formula (XIIf)

$X^6$ is substituted or unsubstituted —($C_1$-$C_6$) alkylene-, —($C_2$-$C_6$) alkenylene-, —($C_2$-$C_6$) alkynylene-, or

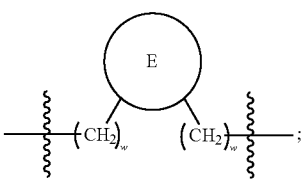

wherein Ring E is phenyl or a 5-6 heteroaryl or heterocycloalkyl; wherein each w is independently 0, 1, or 2; provided that when R is

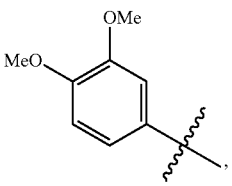

L is ethylene, X is O, W is

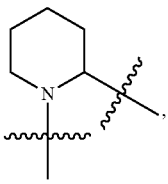 [SMILES: *C1CCCCN1*]

V is

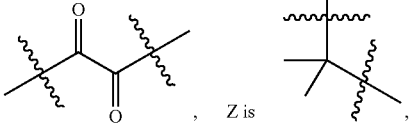

, Z is

-$L^6$-$L^7$-$L^8$- is

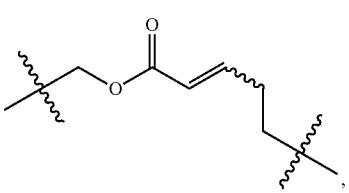 [SMILES: *CCC=CC(=O)OC*]

then -$L^1$-$L^2$-$L^3$-$L^4$-$L^5$- is not

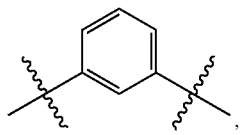 [SMILES: *c1cccc(*)c1]

and; wherein Ring A is substituted with at least one

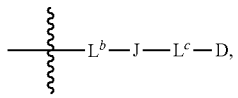

or at least one of $R^2$, $R^3$, $R^{2a}$, $R^{3a}$, $R^{2b}$, $R^{3b}$, $R^{2c}$, $R^{3c}$, $R^{2d}$, $R^{3d}$, $R^{2e}$, $R^{3e}$, $R^{2f}$, $R^{3f}$, $R^{2g}$, $R^{3g}$, $R^{2h}$, $R^{3h}$, $R^{2i}$, and $R^{3i}$ is

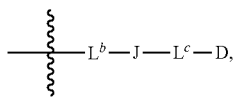

or at least one of $L^a$, $L^1$, $L^2$, $L^3$, $L^4$, $L^5$, $L^6$, $L^7$ and $L^8$ is Ring C substituted with at least one

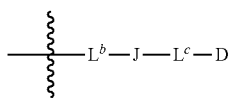

or wherein at least one of the linking groups selected from Table 1 is substituted with at least one

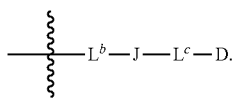

In another aspect, provided herein is a tagged macrocyclic compound of a compound of Formula (XII):

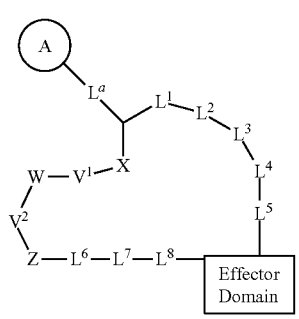

Formula (XII)

with a compound of Formula (XIV):

Q'-$L^c$-D       Formula (XIV)

Ring A is a 5-10 membered aryl, cycloalkyl, heteroaryl or heterocycloalkyl, optionally substituted with 1-17 substituents, each of which is independently selected from the group consisting of hydrogen, hydroxy, halo, alkyl, alkoxy, cyano, haloalkyl, haloalkoxy, alkylthio, oxo, amino, alkylamino, dialkylamino,

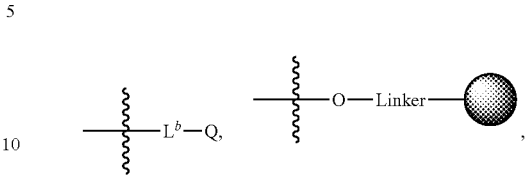

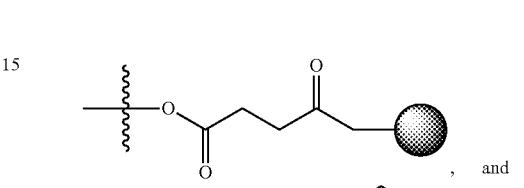

, and

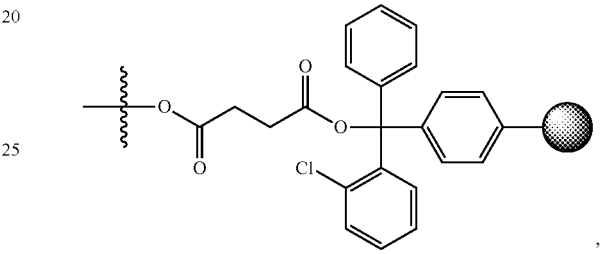

, wherein

is a resin;

$L^b$ and $L^c$ are independently selected from the group consisting of a bond, —O—, —S—, —OC(O)—, —C(O)O—, —$(CH_2)_n$C(O)—, —$(CH_2)_n$C(O)C(O)—, —$(CH_2)_n$NR$^5$C(O)C(O)—, —NR$^5$$(CH_2)_n$C(O)C(O)—, optionally substituted $(CH_2)_n$C$_{1-6}$ alkylene-$(CH_2)_n$—, optionally substituted $(CH_2)_n$C(O)C$_{1-6}$ alkylene-$(CH_2)_n$—, optionally substituted $(CH_2)_n$NR$^5$C$_{1-6}$ alkylene-$(CH_2)_n$—, optionally substituted $(CH_2)_n$C(O)NR$^5$C$_{1-6}$ alkylene-$(CH_2)_n$—, optionally substituted $(CH_2)_n$NR$^5$C(O)C$_{1-6}$ alkylene-$(CH_2)_n$—, optionally substituted $(CH_2)_n$C(O)OC$_{1-6}$ alkylene-$(CH_2)_n$—, optionally substituted $(CH_2)_n$OC(O)C$_{1-6}$ alkylene-$(CH_2)_n$—, optionally substituted $(CH_2)_n$OC$_{1-6}$ alkylene-$(CH_2)_n$—, optionally substituted $(CH_2)_n$NR$^5$C$_{1-6}$ alkylene-$(CH_2)_n$—, optionally substituted $(CH_2)_n$—S—C$_{1-6}$alkylene-$(CH_2)_n$—, and optionally substituted $(CH_2CH_2O)_n$; wherein each alkylene is optionally substituted with 1 or 2 groups independently selected from the group consisting of of halo, hydroxy, haloalkyl, haloalkoxy, alkyl, alkoxy, amino, carboxyl, cyano, nitro, NHFmoc; wherein each $R^5$ is independently hydrogen, alkyl, arylalkyl,

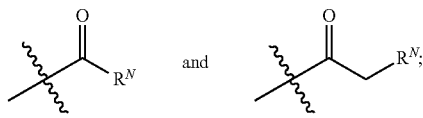

wherein $R^N$ is aryl, alkyl, or arylalkyl;

Q and Q' are independently selected from the group consisting of —$N_3$, —C≡CH, $NR^6R^7$, —COOH, —$ONH_2$, —SH, —$NH_2$,

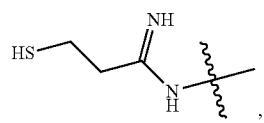

—(C=O)R',

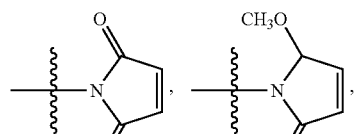

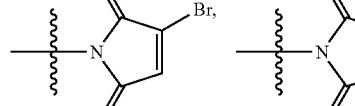

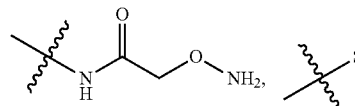

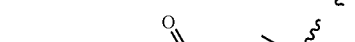

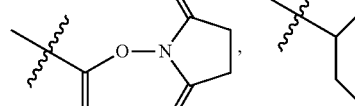

wherein $R^6$ and $R^7$ is each independently hydrogen, alkyl, arylalkyl,

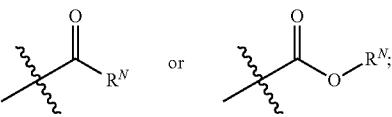

wherein $R^N$ is aryl, alkyl, or arylalkyl; and R' is hydrogen, alkyl, arylalkyl, or haloalkyl; X is O, S or $NR^8$, wherein $R^8$ is hydrogen, hydroxy, $OR^9$, $NR^{10}R^{11}$, alkyl, arylalkyl,

wherein $R^N$ is aryl, alkyl, or arylalkyl; wherein $R^9$, $R^{10}$ and $R^{11}$ are each independently hydrogen or alkyl; $V^1$ and $V^2$ are each independently

W is

wherein Ring B is a 4-10 membered heterocycloalkyl, optionally substituted with 1-10 substituents, each of which is selected from the group consisting of hydrogen, hydroxy, halo, alkyl, alkoxy, cyano, haloalkyl, haloalkoxy, alkylthio, oxo, amino, alkylamino, dialkylamino, arylalkyl,

wherein $R^{12}$ is aryl, alkyl, or arylalkyl; wherein $R^{13}$ is hydrogen, hydroxy, $OR^{16}$, $NR^{17}R^{18}$, alkyl, arylalkyl,

wherein $R^N$ is aryl, alkyl, or arylalkyl; $R^{14}$ and $R^{15}$ is each independently hydrogen, hydroxy, halo, alkyl, alkoxy, haloalkyl, haloalkoxy, aryl, arylalkyl, or heteroaryl;

Z is bond,

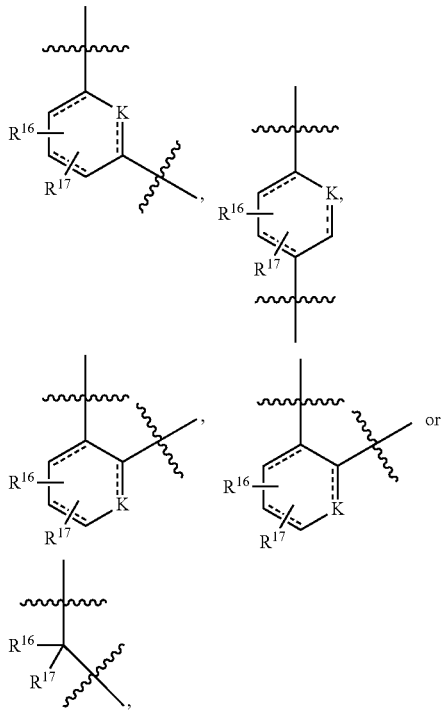

wherein $R^{16}$ and $R^{17}$ are each independently selected from the group consisting of of hydrogen, hydroxy, halo, alkyl, alkoxy, cycloalkyl, cyano, alkylthio, amino, alkylamino, and dialkylamino; K is O, $CHR^{18}$, $CR^{18}$, N, and $NR^{18}$, wherein $R^{18}$ is hydrogen or alkyl;

$L^a$, $L^1$, $L^2$, $L^3$, $L^4$, $L^5$, $L^6$, $L^7$ and $L^8$ are each independently a bond, —O—, —$NR^{19}$—, —SO—, —$SO_2$—, —$(CH_2)_n$—,

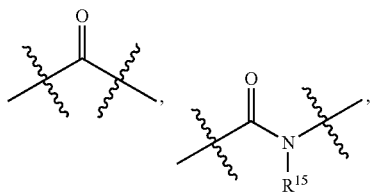

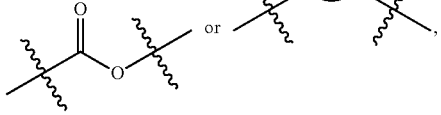

or a linking group selected from Table 1; wherein Ring C is a 5-6 membered heteroaryl, optionally substituted with 1-4 substituents, each of which is independently selected from the group consisting of hydrogen, hydroxy, halo, alkyl, alkoxy, haloalkyl, haloalkoxy, cyano, alkylthio, amino, alkylamino, dialkylamino and

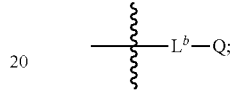

wherein $R^{19}$ is selected from the group consisting of hydrogen, hydroxy, $OR^{22}$, $NR^{23}R^{24}$, alkyl, arylalkyl,

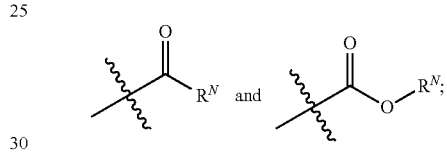

wherein $R^N$ is aryl, alkyl, or arylalkyl; wherein $R^{22}$, $R^{23}$, and $R^{24}$ are each independently hydrogen or alkyl;

n is 0, 1, 2, 3, 4, 5 or 6; wherein the Effector Domain has Formula (XIIa):

Formula (XIIa)

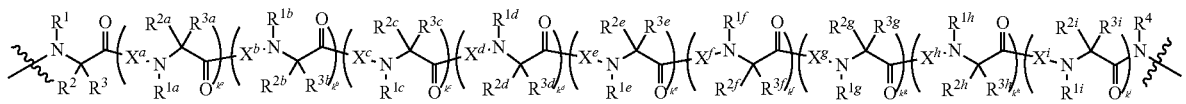

each $k^a$, $k^b$, $k^c$, $k^d$, $k^e$, $k^f$, $k^g$, $k^h$, and $k^i$ is independently 0 or 1; each $X^a$, $X^b$, $X^c$, $X^d$, $X^e$, $X^f$, $X^g$, $X^h$, and $X^i$ is independently a bond, —S—, —S—S—, —S(O)—, —$S(O)_2$—, substituted or unsubstituted —$(C_1-C_3)$ alkylene-, —$(C_2-C_4)$ alkenylene-, —$(C_2-C_4)$ alkynylene-, or

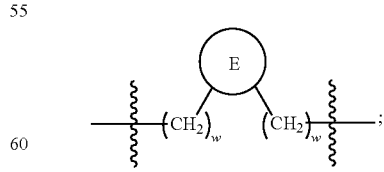

wherein Ring E is phenyl or a 5-6 heteroaryl or heterocycloalkyl; wherein each w is independently 0, 1, or 2; each $R^1$, $R^{1a}$, $R^{1b}$, $R^{1c}$, $R^{1d}$, $R^{1e}$, $R^{1f}$, $R^{1g}$, $R^{1f}$, $R^{1i}$, and $R^4$ is independently hydrogen, alkyl, arylalkyl or $NR^{25}$, wherein $R^{25}$ is hydrogen, hydroxy, $OR^{26}$, $NR^{27}R^{28}$, alkyl, arylalkyl,

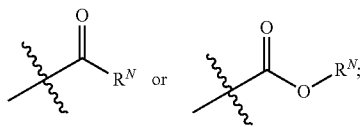

wherein $R^N$ is aryl, alkyl, or arylalkyl; wherein $R^{26}$, $R^{27}$, and $R^{28}$ are each independently hydrogen or alkyl; each $R^2$, $R^3$, $R^{2a}$, $R^{3a}$, $R^{2b}$, $R^{3b}$, $R^{2c}$, $R^{3c}$, $R^{2d}$, $R^{3d}$, $R^{2e}$, $R^{3e}$, $R^{2f}$, $R^{3f}$, $R^{2g}$, $R^{3g}$, $R^{2h}$, $R^{3h}$, $R^{2i}$, and $R^{3i}$ is independently selected from the group consisting of hydrogen, halo, amino, cyano, nitro, haloalkyl, optionally substituted alkyl, optionally substituted alkoxy, optionally substituted alkenyl, optionally substituted alkynyl, optionally substituted cycloalkyl, optionally substituted heterocycloalkyl, optionally substituted alkylamino, optionally substituted dialkylamino, optionally substituted aryl, optionally substituted heteroaryl, optionally substituted arylalkyl, optionally substituted heteroarylalkyl, and

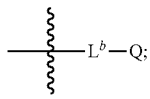

or wherein the Effector Domain has Formula (XIIb):

Formula (XIIb)

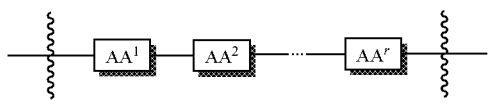

wherein each of $AA^1$, $AA^2$, ..., and $AA^r$ is an natural or unnatural amino acid residue; and r is 3, 4, 5, 6, 7, 8, 9, or 10;

or wherein the Effector Domain has Formula (XIIc):

Formula (XIIc)

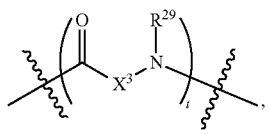

each t is independently an integer selected from 0, 1, 2, 3, 4, 5, 6, 7, 8, 9, and 10; $R^{29}$ is hydrogen, hydroxy, $OR^{30}$, $NR^{31}R^{32}$, alkyl, arylalkyl,

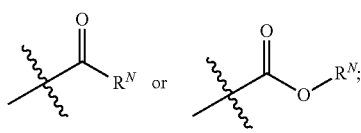

wherein $R^N$ is aryl, alkyl, or arylalkyl; wherein $R^{30}$, $R^{31}$, and $R^{32}$ are each independently hydrogen or alkyl; $X^3$ is substituted or unsubstituted —$(C_1$-$C_6)$ alkylene-, —$(C_2$-$C_6)$ alkenylene-, —$(C_2$-$C_6)$ alkynylene-, or

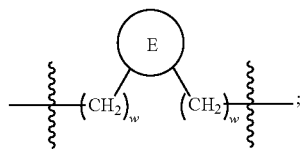

wherein Ring E is phenyl or a 5-6 heteroaryl or heterocycloalkyl; wherein each w is independently 0, 1, or 2;

or wherein the Effector Domain has Formula (XIId):

Formula (XIId)

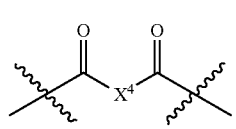

$X^4$ is substituted or unsubstituted —$(C_1$-$C_6)$ alkylene-, —$(C_2$-$C_6)$ alkenylene-, —$(C_2$-$C_6)$ alkynylene-, or

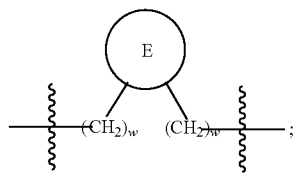

wherein Ring E is phenyl or a 5-6 heteroaryl or heterocycloalkyl; wherein each w is independently 0, 1, or 2;

or wherein the Effector Domain has Formula (XIIe):

Formula (XIIe)

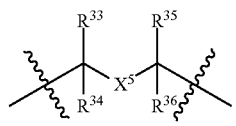

$R^{33}$, $R^{34}$, $R^{35}$ and $R^{36}$ are each hydrogen or alkyl; $X^5$ is substituted or unsubstituted —$(C_1$-$C_6)$ alkylene-, —$(C_2$-$C_6)$ alkenylene-, —$(C_2$-$C_6)$ alkynylene-, or

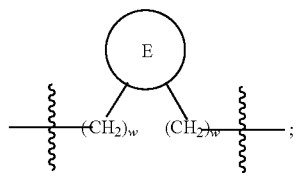

wherein Ring E is phenyl or a 5-6 heteroaryl or heterocycloalkyl; wherein each w is independently 0, 1, or 2;

or wherein the Effector Domain has Formula (XIIf):

Formula (XIIf)

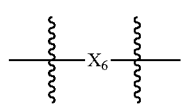

$X^6$ is substituted or unsubstituted —($C_1$-$C_6$) alkylene-, —($C_2$-$C_6$) alkenylene-, —($C_2$-$C_6$) alkynylene-, or

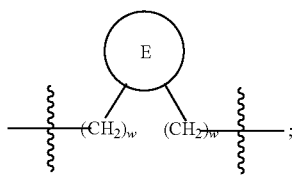

wherein Ring E is phenyl or a 5-6 heteroaryl or heterocycloalkyl; wherein each w is independently 0, 1, or 2; and provided that when Ring A is

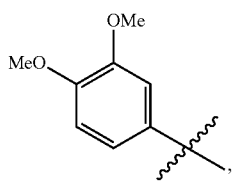 [SMILES: *c1ccc(OC)c(OC)c1]

$L^a$ is ethylene, X is O, W is

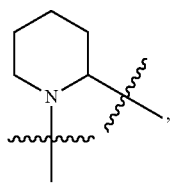 [SMILES: *C1CCCCN1*]

$V^1$ is

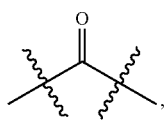 [SMILES: *C(*)=O]

$V^2$ is

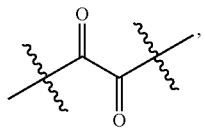 [SMILES: *C(=O)C(*)=O]

Z is

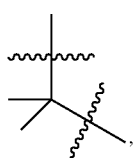

-$L^6$-$L^7$-$L^8$- is

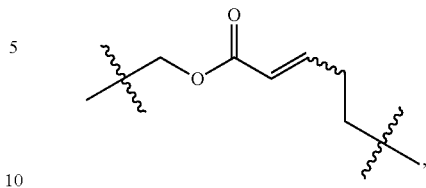

and -$L^1$-$L^2$-$L^3$-$L^4$-$L^5$- is not

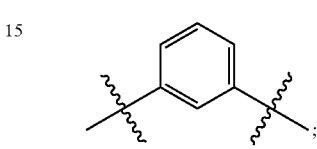

D is an oligonucleotide; wherein Ring A is substituted with at least one

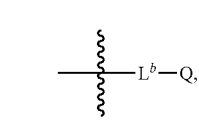

or at least one of $R^2$, $R^3$, $R^{2a}$, $R^{3a}$, $R^{2b}$, $R^{3b}$, $R^{2c}$, $R^{3c}$, $R^{2d}$, $R^{3d}$, $R^{2e}$, $R^{3e}$, $R^{2f}$, $R^{3f}$, $R^{2g}$, $R^{3g}$, $R^{2h}$, $R^{3h}$, $R^{2i}$, and $R^{3i}$ is

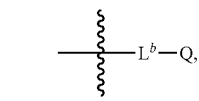

or at least one of $L^a$, $L^1$, $L^2$, $L^3$, $L^4$, $L^5$, $L^6$, $L^7$ and $L^8$ is Ring C substituted with at least one

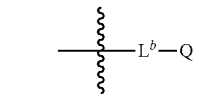

or wherein at least one of the linking groups selected from Table 1 is substituted with at least one

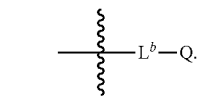

DETAILED DESCRIPTION OF THE INVENTION

Nature is a bountiful source of bioactive small molecules that display a dizzying array of cellular activities thanks to the evolution process over billions of years. Rapamycin and FK506 comprise a unique structural family of macrocyclic natural products with an extraordinary mode of action. On entering cells, both compounds form binary complexes with FKBP12 as well as other members of the FKBP family. The FKBP12-rapamycin complex can then bind to mTOR and block its kinase activity towards downstream substrates such as p70S6K and 4E-BP, while the FKBP12-FK506 complex interacts with calcineurin, a protein phosphatase whose inhibition prevents calcium-dependent signaling and T cell activation. The ability of rapamycin and FK506 to bind FKBPs confers a number of advantages for their use as small molecule probes in biology as well as drugs in medicine. First, the binding of both rapamycin and FK506 to FKBP dramatically increases their effective sizes, allowing for allosteric blockade of substrates to the active sites of mTOR or calcineurin through indirect disruption of protein-protein interactions. Second, the abundance and ubiquitous expression of intracellular FKBPs serves to enrich rapamycin and FK506 in the intracellular compartment and maintain their stability. Third, as macrocycles, FK506 and rapamycin are capable of more extensive interactions with proteins than smaller molecules independent of their ability to bind FKBP. Last, but not least, the high-level expression of FKBPs in blood cells renders them reservoirs and carriers of the drugs for efficient delivery in vivo. It is thus not surprising that both rapamycin and FK506 became widely used drugs in their natural forms without further chemical modifications.

Both rapamycin and FK506 can be divided into two structural and functional domains: an FKBP-binding domain (FKBD) and an effector domain that mediates interaction with mTOR or calcineurin, respectively. The structures of the FKBDs of rapamycin and FK506 are quite similar, but their effector domains are different, accounting for their exclusive target specificity. The presence of the separable and modular structural domains of FK506 and rapamycin have been extensively exploited to generate new analogues of both FK506 and rapamycin, including chemical inducers of dimerization and a large number of rapamycin analogues, known as rapalogs, to alter the specificity of rapamycin for the mutated FKBP-rapamycin binding domain of mTOR and to improve the toxicity and solubility profiles of rapamycin. The existence of two distinct FKBD containing macrocycles with distinct target specificity also raised the intriguing question of whether replacing the effector domains of rapamycin or FK506 could further expand the target repertoire of the resultant macrocycles. In their pioneering work, Chakraborty and colleagues synthesized several rapamycin-peptide hybrid molecules, which retained high affinity for FKBP but showed no biological activity. More recently, we and others independently attempted to explore this possibility by making larger libraries of the FKBD-containing macrocycles. In one study, a much larger library of FKBD-containing macrocycles was made with a synthetic mimic of FKBD, but the resultant macrocycles suffered from a significant loss in binding affinity for FKBP12, probably accounting for the lack of bioactive compounds from that library. Using a natural FKBD extracted from rapamycin, we also observed a significant loss in FKBP binding affinity on formation of macrocycles (vide infra).

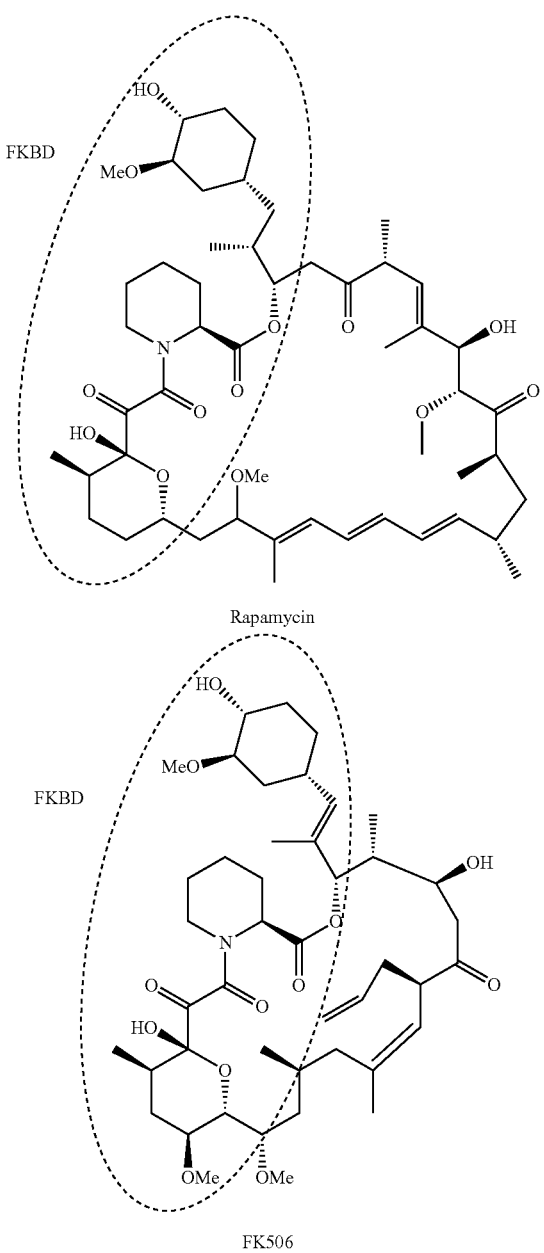

Scheme 1. The structures of rapamycin and FK506 with the FKBD portions highlighted.

A Rapafucin library was synthesized as described in WO2017/136708. Rapadocin compound and analogs thereof are disclosed in WO2017/136717, which are used for inhibiting human equilibrative nucleoside transporter 1 (ENT1). Rapaglutins and analogs thereof are disclosed in WO2017/136731, which are used as inhibitors of cell proliferation and useful for the treatment of cancer. Approximately 45,000 compounds were generated and ongoing screening of the library as described in WO2018/045250 identified several compounds as being inhibitors of MIF nuclease activity. All of these references are incorporated herein by reference.

In a continuing effort to explore the possibility to using FKBD containing macrocycles to target new proteins, we attempted to optimize and succeeded in identifying FKBDs that allowed for significant retention of binding affinity for FKBP12 upon incorporation into macrocycles. We also established a facile synthetic route for parallel synthesis of a large number of FKBD-containing macrocycles.

Below are some acronyms used in the present disclosure. 2-MeTHF refers to 2-methyltetrahydrofuran; DMF refers to dimethylformamide; DMSO refers to dimethyl sulfoxide; DCM refers to dichloromethane; HATU refers to 1-[bis(dimethylamino)methylene]-1H-1,2,3-triazolo[4,5-b]pyridinium 3-oxide hexafluorophosphate; DIEA refers to N,N-Diisopropylethylamine; TFA refers to trifluoroacetic acid; Fmoc refers to fluorenylmethyloxycarbonyl; MeOH refers to methanol; EtOAc refers to ethyl acetate; $MgSO_4$ refers to magnesium sulfate; COMU-$PF_6$ refers to (1-cyano-2-ethoxy-2-oxoethylidenaminooxy)dimethylamino-morpholino-carbenium hexafluorophosphate; CAN refers to acetonitrile; Oxyma refers to ethyl cyanohydroxyiminoacetate; LC-MS refers to liquid chromatography-mass spectrometry; T3P refers to n-propanephosphonic acid anhydride; SPPS refers to solid-phase peptide synthesis.

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements. The term "about" will be understood by persons of ordinary skill in the art. Whether the term "about" is used explicitly or not, every quantity given herein refers to the actual given value, and it is also meant to refer to the approximation to such given value that would be reasonably inferred based on the ordinary skill in the art.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless indicated otherwise, the nomenclature of substituents that are not explicitly defined herein are arrived at by naming the terminal portion of the functionality followed by the adjacent functionality toward the point of attachment. A person of ordinary skill in the art would recognize that the above definitions are not intended to include impermissible substitution patterns (e.g., methyl substituted with 5 different groups, pentavalent carbon, and the like). Such impermissible substitution patterns are easily recognized by a person of ordinary skill in the art. All publications, patent applications, patents, and other references mentioned herein are incorporated by reference in their entirety. All sequences provided in the disclosed Genbank Accession numbers are incorporated herein by reference. In case of conflict, the present specification, including explanations of terms, will control. In addition, the materials, methods, and examples are illustrative only and not intended to be limiting.

Alkyl groups refer to univalent groups derived from alkanes by removal of a hydrogen atom from any carbon atom, which include straight chain and branched chain with from 1 to 12 carbon atoms, and typically from 1 to about 10 carbons or in some embodiments, from 1 to about 6 carbon atoms, or in other embodiments having 1, 2, 3 or 4 carbon atoms. Examples of straight chain alkyl groups include, but are not limited to, methyl, ethyl, n-propyl, n-butyl, n-pentyl, and n-hexyl groups. Examples of branched chain alkyl groups include, but are not limited to isopropyl, isobutyl, sec-butyl and tert-butyl groups. Alkyl groups may be substituted or unsubstituted. Representative substituted alkyl groups may be mono-substituted or substituted more than once, such as, but not limited to, mono-, di-, or tri-substituted. As used herein, the term alkyl, unless otherwise stated, refers to both cyclic and noncyclic groups.

The terms "cyclic alkyl" or "cycloalkyl" refer to univalent groups derived from cycloalkanes by removal of a hydrogen atom from a ring carbon atom. Cycloalkyl groups are saturated or partially saturated non-aromatic structures with a single ring or multiple rings including isolated, fused, bridged, and spiro ring systems, having 3 to 14 carbon atoms, or in some embodiments, from 3 to 12, or 3 to 10, or 3 to 8, or 3, 4, 5, 6 or 7 carbon atoms. Cycloalkyl groups may be substituted or unsubstituted. Representative substituted cycloalkyl groups may be mono-substituted or substituted more than once, such as, but not limited to, mono-, di-, or tri-substituted. Examples of monocyclic cycloalkyl groups include, but are not limited to cyclopropyl, cyclobutyl, cyclopentyl, and cyclohexyl groups. Examples of multicyclic ring systems include, but are not limited to, bicycle [4.4.0]decane, bicycle[2.2.1]heptane, spiro[2.2]pentane, and the like. (Cycloalkyl)oxy refers to —O-cycloalkyl. (Cycloalkyl)thio refers to —S-cycloalkyl. This term also encompasses oxidized forms of sulfur, such as —S(O)-cycloalkyl, or —$S(O)_2$-cycloalkyl.

Alkenyl groups refer to straight and branched chain and cycloalkenyl groups as defined above, with one or more double bonds between two carbon atoms. Alkenyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkenyl groups may be substituted or unsubstituted. Representative substituted alkenyl groups may be mono-substituted or substituted more than once, such as, but not limited to, mono-, di-, or tri-substituted. Examples of alkenyl groups include, but are not limited to, vinyl, allyl, —CH═CH($CH_3$), —CH═C($CH_3$)$_2$, —C($CH_3$)═$CH_2$, cyclopentenyl, cyclohexenyl, butadienyl, pentadienyl, and hexadienyl, among others.

Alkynyl groups refer to straight and branched chain and cycloalknyl groups as defined above, with one or more triple bonds between two carbon atoms. Alkynyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkynyl groups may be substituted or unsubstituted. Representative substituted alkynyl groups may be mono-substituted or substituted more than once, such as, but not limited to, mono-, di-, or tri-substituted. Exemplary alkynyl groups include, but are not limited to, ethynyl, propargyl, and —C≡C($CH_3$), among others.

Aryl groups are cyclic aromatic hydrocarbons that include single and multiple ring compounds, including multiple ring compounds that contain separate and/or fused aryl groups. Aryl groups may contain from 6 to about 18 ring carbons, or in some embodiments from 6 to 14 ring carbons or even 6 to 10 ring carbons in other embodiments. Aryl group also includes heteroaryl groups, which are aromatic ring compounds containing 5 or more ring members, one or more ring carbon atoms of which are replaced with heteroatom such as, but not limited to, N, O, and S. Aryl groups may be substituted or unsubstituted. Representative substituted aryl groups may be mono-substituted or substituted more than once, such as, but not limited to, mono-, di-, or tri-substituted. Aryl groups include, but are not limited to, phenyl, biphenylenyl, triphenylenyl, naphthyl, anthryl, and pyrenyl groups. Aryloxy refers to —O-aryl. Arylthio refers to —S-aryl, wherein aryl is as defined herein. This term also encompasses oxidized forms of sulfur, such as —S(O)-aryl, or —S(O)$_2$-aryl. Heteroaryloxy refers to —O-heteroaryl. Heteroarylthio refers to —S-heteroaryl. This term also encompasses oxidized forms of sulfur, such as —S(O)-heteoaryl, or —S(O)$_2$-heteoaryl.

Suitable heterocyclyl groups include cyclic groups with atoms of at least two different elements as members of its rings, of which one or more is a heteroatom such as, but not limited to, N, O, or S. Heterocyclyl groups may include 3 to about 20 ring members, or 3 to 18 in some embodiments, or about 3 to 15, 3 to 12, 3 to 10, or 3 to 6 ring members. The ring systems in heterocyclyl groups may be unsaturated, partially saturated, and/or saturated. Heterocyclyl groups may be substituted or unsubstituted. Representative substituted heterocyclyl groups may be mono-substituted or substituted more than once, such as, but not limited to, mono-, di-, or tri-substituted. Exemplary heterocyclyl groups include, but are not limited to, pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, aziridinyl, imidazolidinyl, pyrazolidinyl, thiazolidinyl, tetrahydrothiophenyl, tetrahydrofuranyl, dioxolyl, furanyl, thiophenyl, pyrrolyl, imidazolyl, pyrazolyl, pyrazolinyl, triazolyl, tetrazolyl, oxazolyl, isoxazolyl, thiazolyl, thiazolinyl, oxetanyl, thietanyl, homopiperidyl, oxepanyl, thiepanyl, oxazepinyl, diazepinyl, thiazepinyl, 1,2,3,6-tetrahydropyridyl, indolinyl, 2H-pyranyl, 4H-pyranyl, dioxolanyl, dioxanyl, purinyl, quinolizinyl, cinnolinyl, phthalazinyl, pteridinyl, and benzothiazolyl groups. Heterocyclyloxy refers to —O-heterocycyl. Heterocyclylthio refers to —S-heterocycyl. This term also encompasses oxidized forms of sulfur, such as —S(O)-heterocyclyl, or —S(O)$_2$-heterocyclyl.

Polycyclic or polycyclyl groups refer to two or more rings in which two or more carbons are common to the two adjoining rings, wherein the rings are "fused rings"; if the rings are joined by one common carbon atom, these are "spiro" ring systems. Rings that are joined through non-adjacent atoms are "bridged" rings. Polycyclic groups may be substituted or unsubstituted. Representative polycyclic groups may be substituted one or more times.

Halogen groups include F, Cl, Br, and I; nitro group refers to —NO$_2$; cyano group refers to —CN; isocyano group refers to —N≡C; epoxy groups encompass structures in which an oxygen atom is directly attached to two adjacent or non-adjacent carbon atoms of a carbon chain or ring system, which is essentially a cyclic ether structure. An epoxide is a cyclic ether with a three-atom ring.

An alkoxy group is a substituted or unsubstituted alkyl group, as defined above, singular bonded to oxygen. Alkoxy groups may be substituted or unsubstituted. Representative substituted alkoxy groups may be substituted one or more times. Exemplary alkoxy groups include, but are not limited to, methoxy, ethoxy, propoxy, butoxy, pentoxy, hexoxy, isopropoxy, sec-butoxy, tert-butoxy, cyclopropyloxy, cyclobutyloxy, cyclopentyloxy, and cyclohexyloxy groups.

Thiol refers to —SH. Thiocarbonyl refers to (═S). Sulfonyl refers to —SO$_2$-alkyl, —SO$_2$-substituted alkyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclyl, and —SO$_2$-substituted heterocyclyl. Sulfonylamino refers to —NR$^a$SO$_2$alkyl, —NR$^a$SO$_2$-substituted alkyl, —NR$^a$SO$_2$cycloalkyl, —NR$^a$SO$_2$substituted cycloalkyl, —NR$^a$SO$_2$aryl, —NR$^a$SO$_2$substituted aryl, —NR$^a$SO$_2$heteroaryl, —NR$^a$SO$_2$ substituted heteroaryl, —NR$^a$SO$_2$heterocyclyl, —NR$^a$SO$_2$ substituted heterocyclyl, wherein each R$^a$ independently is as defined herein.

Carboxyl refers to —COOH or salts thereof. Carboxyester refers to —C(O)O-alkyl, —C(O)O-substituted alkyl, —C(O)O-aryl, —C(O)O-substituted aryl, —C(O)β-cycloalkyl, —C(O)O-substituted cycloalkyl, —C(O)O-heteroaryl, —C(O)O-substituted heteroaryl, —C(O)O-heterocyclyl, and —C(O)O-substituted heterocyclyl. (Carboxyester) amino refers to —NR$^a$C(O)O-alkyl, —NR$^a$C(O)O-substituted alkyl, —NR$^a$—C(O)O-aryl, —NR$^a$C(O)O-substituted aryl, —NR$^a$C(O)β-cycloalkyl, —NR$^a$C(O)O-substituted cycloalkyl, —NR$^a$C(O)O-heteroaryl, —NR$^a$C(O)O-substituted heteroaryl, —NR$^a$C(O)O-heterocyclyl, and —NR$^a$C(O)O-substituted heterocyclyl, wherein R$^a$ is as recited herein. (Carboxyester)oxy refers to —O—C(O)O-alkyl, —O—C(O)O-substituted alkyl, —O—C(O)O-aryl, —O—C(O)O-substituted aryl, —O—C(O)β-cycloalkyl, —O—C(O)O-substituted cycloalkyl, —O—C(O)O-heteroaryl, —O—C(O)O-substituted heteroaryl, —O—C(O)O-heterocyclyl, and —O—C(O)O-substituted heterocyclyl. Oxo refers to (═O).

The terms "amine" and "amino" refer to derivatives of ammonia, wherein one of more hydrogen atoms have been replaced by a substituent which include, but are not limited to alkyl, alkenyl, aryl, and heterocyclyl groups. Carbamate groups refers to —O(C═O)NR$^1$R$^2$, where R$^1$ and R$^2$ are independently hydrogen, aliphatic groups, aryl groups, or heterocyclyl groups.

Aminocarbonyl refers to —C(O)N(R$^b$)$_2$, wherein each R$^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each R$^b$ may optionally be joined together with the nitrogen bound thereto to form a heterocyclyl or substituted heterocyclyl group, provided that both R$^b$ are not both hydrogen. Aminocarbonylalkyl refers to -alkylC(O)N(R$^b$)$_2$, wherein each R$^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each R$^b$ may optionally be joined together with the nitrogen bound thereto to form a heterocyclyl or substituted heterocyclyl group, provided that both R$^b$ are not both hydrogen. Aminocarbonylamino refers to —NR$^a$C(O)N(R$^b$)$_2$, wherein R$^a$ and each R$^b$ are as defined herein. Aminodicarbonylamino refers to —NR$^a$C(O)C(O)N(R$^b$)$_2$, wherein R$^a$ and each R$^b$ are as defined herein. Aminocarbonyloxy refers to —O—C(O)N(R$^b$)$_2$, wherein each R$^b$ independently is as defined herein. Aminosulfonyl refers to —SO$_2$N(R$^b$)$_2$, wherein each R$^b$ independently is as defined herein.

Imino refers to —N=R$^c$ wherein R$^c$ may be selected from hydrogen, aminocarbonylalkyloxy, substituted aminocarbonylalkyloxy, aminocarbonylalkylamino, and substituted aminocarbonylalkylamino.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those needing preventive measures).

The term "subject" as used herein refers to any individual or patient to which the subject methods are performed. Generally, the subject is human, although as will be appreciated by those in the art, the subject may be an animal.

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. Such amount should be sufficient to inhibit MIF activity.

Also disclosed herein are pharmaceutical compositions including compounds with the structures of Formula (I). The term "pharmaceutically acceptable carrier" refers to a nontoxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable carriers that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

In pharmaceutical composition comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells;

hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of ivermectin, or any other compound described herein, and another therapeutic or prophylactic agent. Additional therapeutic agents that are normally administered to treat a particular disease or condition may be referred to as "agents appropriate for the disease, or condition, being treated."

The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this disclosure are formulated for pharmaceutical administration to a subject or patient, e.g., a mammal, preferably a human being. Such pharmaceutical compositions are used to ameliorate, treat or prevent any of the diseases described herein in a subject.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present disclosure provides pharmaceutically acceptable compositions comprising a therapeutically effective amount of one or more of a described compound, formulated together with one or more pharmaceutically acceptable carriers (additives) and/or diluents for use in treating the diseases described herein, including, but not limited to stroke, ischemia, Alzheimer's, ankylosing spondylitis, arthritis, osteoarthritis, rheumatoid arthritis, psoriatic arthritis, asthma atherosclerosis, Crohn's disease, colitis, dermatitis diverticulitis, fibromyalgia, hepatitis, irritable bowel syndrome, systemic lupus erythematous, nephritis, ulcerative colitis and Parkinson's disease. While it is possible for a described compound to be administered alone, it is preferable to administer a described compound as a pharmaceutical formulation (composition) as described herein. Described compounds may be formulated for administration in any convenient way for use in human or veterinary medicine, by analogy with other pharmaceuticals.

As described in detail, pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient, which can be combined with a carrier material, to produce a single dosage form will vary depending upon the host being treated, and the particular mode of administration. The amount of active ingredient that can be combined with a carrier material to produce a single dosage form will generally be that amount of the compound, which produces a therapeutic effect. Generally, this amount will range from about 1% to about 99% of active ingredient. In some embodiments, this amount will range from about 5% to about 70%, from about 10% to about 50%, or from about 20% to about 40%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a described compound of the present disclosure.

Methods of preparing formulations or compositions comprising described compounds include a step of bringing into association a compound of the present disclosure with the carrier and, optionally, one or more accessory ingredients. In general, formulations may be prepared by uniformly and intimately bringing into association a compound of the present disclosure with liquid carriers, or finely divided solid carriers, or both, and then, if necessary, shaping the product.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80, Cremophor RH40, and Cremophor E1) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The pharmaceutical compositions of this disclosure may be orally administered in any orally acceptable dosage form including, but not limited to, capsules, tablets, and aqueous suspensions and solutions. In the case of tablets for oral use, carriers, which are commonly used include lactose and corn starch. Lubricating agents, such as magnesium stearate, are also typically added. For oral administration in a capsule form, useful diluents include lactose and dried cornstarch. When aqueous suspensions and solutions and propylene glycol are administered orally, the active ingredient is combined with emulsifying and suspending agents. If desired, certain sweetening and/or flavoring and/or coloring agents may be added.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent. If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions of this disclosure may also be administered in the form of suppositories for rectal administration. These compositions can be prepared by mixing a compound of this disclosure with a suitable non-irritating excipient, which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this disclosure is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this disclosure may also be topically applied to the lower intestinal tract by rectal suppository formulation or in a suitable enema formulation. Topically-administered transdermal patches are also included in this disclosure.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the disclosure, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/orantifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In certain embodiments, a described compound or pharmaceutical preparation is administered orally. In other embodiments, a described compound or pharmaceutical preparation is administered intravenously. Alternative routes of administration include sublingual, intramuscular, and transdermal administrations.

When compounds described herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, compounds described herein which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of the disclosure may be varied so as to obtain an amount of the active ingredient that is effective to achieve the desired therapeutic response for a particular patient, composition, and mode of administration, without being toxic to the patient.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrastemal, oral, sublingual buccal, rectal, vaginal, nasal ocular administrations, as well infusion, inhalation, and nebulization.

The crystal structures of the FKBP-FK506-calcineurin and FKBP-rapamycin-TOR complexes revealed that both FK506 and rapamycin can be divided into two functional domains, the "FKBP-binding domain" (FKBD) and the "effector" domain, which mediate their interactions with calcineurin and TOR, respectively. While there are extensive protein-protein interactions between FKBP and calcineurin in their ternary complex, there are far fewer interactions between FKBP and TOR, suggesting that the key role of FKBP in the inhibition of TOR by rapamycin is to bind to FKBD of the drug and present its effector domain to TOR.

A comparison of the structures of FK506 and rapamycin reveal that they share a nearly identical FKBD but each possesses a distinct effector domain. By swapping the effector domain of FK506 with that of rapamycin, it is possible to change the target from calcineurin to TOR, which bears no sequence, functional or structural similarities to each other. In addition, other proteins may be targeted by grafting new structures onto the FKBD of FK506 and rapamycin. Thus, the generation of new compounds with new target specificity may be achieved by grafting a sufficiently large combinatorial library onto FKBD in conjunction with proteome-wide screens through which each compound in the library is tested against every protein in the human proteome.

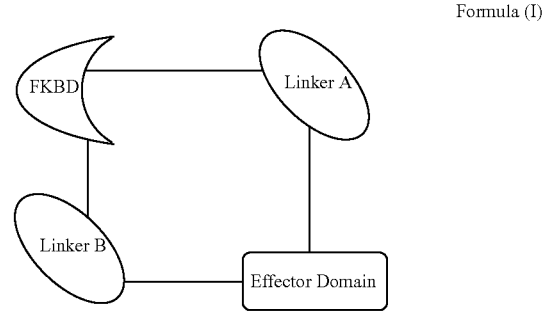

Formula (I)

In some embodiments, provided herein is a macrocyclic compound according to Formula (I), which includes an FKBD, an effector domain, a first linker, and a second linker, wherein the FKBD, the effector domain, the first linker, and the second linker together form a macrocycle.

In some embodiments, provided herein is a macrocyclic compound according to Formula (II) or an optically pure stereoisomer or pharmaceutically acceptable salt thereof.

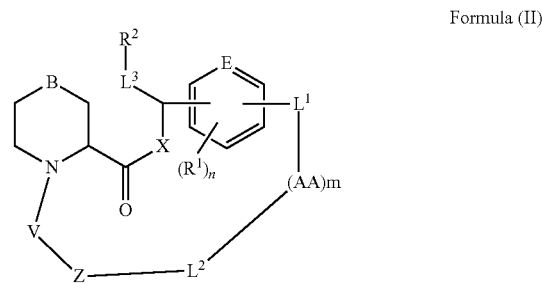

Formula (II)

B can be $CH_2$, NH, NMe, O, S, or $S(O)_2$; X can be O, NH or NMe; E can be CH or N; n is an integer selected from 0 to 4; m is an integer selected from 1 to 10. AA in this formula represents natural and unnatural amino acids, each of which can be selected from Table 4 below.

In some embodiments, m can be 1. In some embodiments, m can be 2. In some embodiments, m can be 3. In some embodiments, m can be 4. In some embodiments, m can be 5. In some embodiments, m can be 6. In some embodiments, m can be 7. In some embodiments, m can be 8. In some embodiments, m can be 9. In some embodiments, m can be 10. In specific embodiment, m is 3 or 4.

Each $R^1$ is selected from the group consisting of H, halogen, hydroxyl, $C_{1-20}$ alkyl, $N_3$, $NH_2$, $NO_2$, $CF_3$, $OCF_3$, $OCHF_2$, $COC_{1-20}$alkyl, and $CO_2C_{1-20}$alkyl. $R^2$ is selected from the group consisting of $C_{6-15}$aryl and $C_{1-10}$heteroaryl optionally substituted with H, halogen, hydroxyl, $N_3$, $NH_2$, $NO_2$, $CF_3$, $C_{1-10}$alkyl, substituted $C_{1-10}$alkyl, $C_{1-10}$alkoxy, substituted $C_{1-10}$alkoxy, acyl, acylamino, acyloxy, acyl $C_{1-10}$alkyloxy, amino, substituted amino, aminoacyl, aminocarbonyl $C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester)amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, substituted $C_{1-10}$alkylthio, and thiocarbonyl.

V is

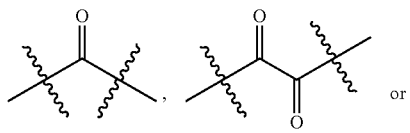

or

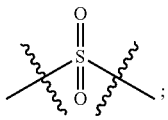

Z is a bond,

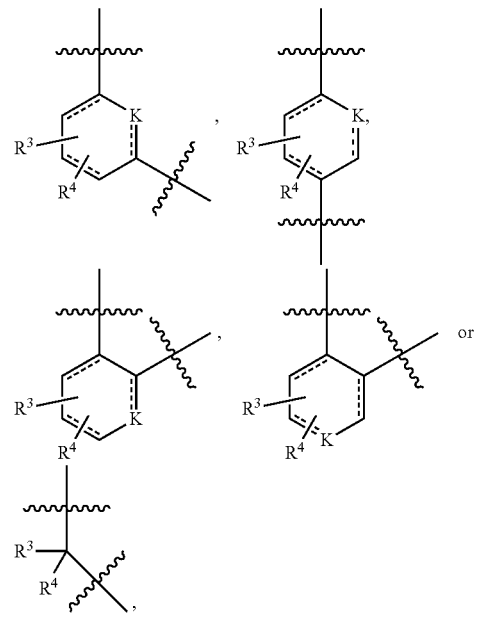

wherein $R^3$ and $R^4$ are each independently selected from the group consisting of of hydrogen, hydroxy, halo, alkyl, alkoxy, cycloalkyl, cyano, alkylthio, amino, alkylamino, and dialkylamino; K is O, $CHR^5$, $CR^5$, N, and $NR^5$, wherein $R^5$ is hydrogen or alkyl.

Each of $L^1$, $L^2$, or $L^3$ can be selected from the group consisting of the structures shown in Table 1 below.

TABLE 1

The linker structures.

| | | | |
|---|---|---|---|
| optionally substituted —$(CH_2)_nC_{1-6}$ alkylene | optionally substituted —$(CH_2)_nC_{2-6}$ alkenylene | optionally substituted —$(CH_2)_nC_{3-6}$ cycloalkylene | optionally substituted —$(CH_2)_nC_{3-6}$ cycloalkenylene |
| optionally substituted —$(CH_2)_nOC_{1-6}$ alkylene | optionally substituted —$(CH_2)_nOC_{2-6}$ alkenylene | optionally substituted —$(CH_2)_nOC_{3-6}$ cycloalkylene | optionally substituted —$(CH_2)_nOC_{3-6}$ cycloalkenylene |
| optionally substituted —$(CH_2)_nC(O)C_{1-6}$ alkylene | optionally substituted —$(CH_2)_nC(O)C_{2-6}$ alkenylene | optionally substituted —$(CH_2)_nC(O)C_{3-6}$ cycloalkylene | optionally substituted —$(CH_2)_nC(O)C_{3-6}$ cycloalkenylene |
| optionally substituted —$(CH_2)_nC(O)OC_{1-6}$ alkylene | optionally substituted —$(CH_2)_nC(O)OC_{2-6}$ alkenylene | optionally substituted —$(CH_2)_nC(O)O$— $C_{3-6}$ cycloalkylene | optionally substituted —$(CH_2)_nC(O)OC_{3-6}$ cycloalkenylene |
| optionally substituted —$(CH_2)_nOC(O)C_{1-6}$ alkylene | optionally substituted —$(CH_2)_nOC(O)C_{2-6}$ alkenylene | optionally substituted —$(CH_2)_nOC(O)$—$C_{3-6}$ cycloalkylene | optionally substituted —$(CH_2)_nOC(O)C_{3-6}$ cycloalkenylene |
| optionally substituted —$(CH_2)_nNR^{20}C_{1-6}$ alkylene | optionally substituted —$(CH_2)_nNR^{20}C_{2-6}$ alkenylene | optionally substituted —$(CH_2)_nNR^{20}C_{3-6}$ cycloalkylene | optionally substituted —$(CH_2)_nNR^{20}C_{3-6}$ cycloalkenylene |
| optionally substituted —$(CH_2)_nNR^{20}C(O)C_{1-6}$ alkylene | optionally substituted —$(CH_2)_nNR^{20}C(O)C_{2-6}$ alkenylene | optionally substituted —$(CH_2)_nNR^{20}C(O)$—$C_{3-6}$ cycloalkylene | optionally substituted —$(CH_2)_nNR^{20}C(O)$—$C_{3-6}$ cycloalkenylene |
| optionally substituted —$(CH_2)_nC(O)NR^{20}C_{1-6}$ alkylene | optionally substituted —$(CH_2)_nC(O)NR^{20}C_{2-6}$ alkenylene | optionally substituted —$(CH_2)_nC(O)NR^{20}$—$C_{3-6}$ cycloalkylene | optionally substituted —$(CH_2)_nC(O)NR^{20}$—$C_{3-6}$ cycloalkenylene |

TABLE 1-continued

The linker structures.

| | | | |
|---|---|---|---|
| optionally substituted —$(CH_2)_n$—S—$C_{1-6}$ alkylene | optionally substituted —$(CH_2)_n$—S—$C_{2-6}$ alkenylene | optionally substituted —$(CH_2)_n$—S—$C_{3-6}$ cycloalkylene | optionally substituted —$(CH_2)_n$—S—$C_{3-6}$ cycloalkenylene |
| optionally substituted —$(CH_2)_nC(O)(CH_2)_n$—S—$C_{1-6}$ alkylene | optionally substituted —$(CH_2)_nC(O)(CH_2)_n$—S—$C_{2-6}$ alkenylene | optionally substituted —$(CH_2)_nC(O)(CH_2)_n$—S—$C_{3-6}$ cycloalkylene | optionally substituted —$(CH_2)_nC(O)(CH_2)_n$—S—$C_{3-6}$ cycloalkenylene |
| optionally substituted —$(CH_2)_n$—$SO_2$—$C_{1-6}$ alkylene | optionally substituted —$(CH_2)_n$—$SO_2$—$C_{2-6}$ alkenylene | optionally substituted —$(CH_2)_n$—$SO_2$—$C_{3-6}$ cycloalkylene | optionally substituted —$(CH_2)_n$—$SO_2$—$C_{3-6}$ cycloalkenylene |
| optionally substituted —$(CH_2)_nC(O)(CH_2)_n$—$SO_2$—$C_{1-6}$ alkylene | optionally substituted —$(CH_2)_nC(O)(CH_2)_n$—$SO_2$—$C_{2-6}$ alkenylene | optionally substituted $(CH_2)_nC(O)(CH_2)_n$—$SO_2$—$C_{3-6}$ cycloalkylene | optionally substituted —$(CH_2)_nC(O)(CH_2)_n$—$SO_2$—$C_{3-6}$ cycloalkenylene |
| optionally substituted —$(CH_2)_n$—SO—$C_{1-6}$ alkylene | optionally substituted —$(CH_2)_n$—SO—$C_{2-6}$ alkenylene | optionally substituted —$(CH_2)_n$—SO—$C_{3-6}$ cycloalkylene | optionally substituted —$(CH_2)_n$—SO—$C_{3-6}$ cycloalkenylene |
| optionally substituted —$(CH_2)_nC(O)(CH_2)_n$—SO—$C_{1-6}$ alkylene | optionally substituted —$(CH_2)_nC(O)(CH_2)_n$—SO—$C_{2-6}$ alkenylene | optionally substituted —$(CH_2)_nC(O)(CH_2)_n$—SO—$C_{3-6}$ cycloalkenylene | optionally substituted —$(CH_2)_nC(O)(CH_2)_n$—SO—$C_{3-6}$ cycloalkenylene |
| optionally substituted —$(CH_2)_n$—S—S—$C_{1-6}$ alkylene | optionally substituted —$(CH_2)_n$—S—S—$C_{2-6}$ alkenylene | optionally substituted —$(CH_2)_n$—S—S—$C_{3-6}$ cycloalkylene | optionally substituted —$(CH_2)_n$—S—S—$C_{3-6}$ cycloalkenylene |
| optionally substituted —$(CH_2)_nC(O)(CH_2)_n$—S—S—$C_{1-6}$ alkylene | optionally substituted —$(CH_2)_nC(O)(CH_2)_n$—S—S—$C_{2-6}$ alkenylene | optionally substituted —$(CH_2)_nC(O)(CH_2)_n$—S—S—$C_{3-6}$ cycloalkylene | optionally substituted —$(CH_2)_nC(O)(CH_2)_n$—S—S—$C_{3-6}$ cycloalkenylene |
| optionally substituted —$(CH_2)_nC_{1-6}$ alkylene-$NR^{21}$- | optionally substituted —$(CH_2)_nC_{2-6}$ alkenylene-$NR^{21}$- | optionally substituted —$(CH_2)_nC_{3-6}$ cycloalkylene-$NR^{21}$- | optionally substituted —$(CH_2)_nC_{3-6}$ cycloalkenylene-$NR^{21}$- |
| optionally substituted —$(CH_2)_nOC_{1-6}$ alkylene-$NR^{21}$- | optionally substituted —$(CH_2)_nOC_{2-6}$ alkenylene-$NR^{21}$- | optionally substituted —$(CH_2)_nOC_{3-6}$ cycloalkylene-$NR^{21}$- | optionally substituted —$(CH_2)_nOC_{3-6}$ cycloalkenylene-$NR^{21}$- |
| optionally substituted —$(CH_2)_nC(O)C_{1-6}$ alkylene-$NR^{21}$- | optionally substituted —$(CH_2)_nC(O)C_{2-6}$ alkenylene-$NR^{21}$- | optionally substituted —$(CH_2)_nC(O)C_{3-6}$ cycloalkylene-$NR^{21}$- | optionally substituted —$(CH_2)_nC(O)C_{3-6}$ cycloalkenylene-$NR^{21}$- |
| optionally substituted —$(CH_2)_nC(O)OC_{1-6}$ alkylene-$NR^{21}$- | optionally substituted —$(CH_2)_nC(O)OC_{2-6}$ alkenylene-$NR^{21}$- | optionally substituted —$(CH_2)_nC(O)O$—$C_{3-6}$ cycloalkylene-$NR^{21}$- | optionally substituted —$(CH_2)_nC(O)OC_{3-6}$ cycloalkenylene-$NR^{21}$- |
| optionally substituted —$(CH_2)_nOC(O)C_{1-6}$ alkylene-$NR^{21}$- | optionally substituted —$(CH_2)_nOC(O)C_{2-6}$ alkenylene-$NR^{21}$- | optionally substituted —$(CH_2)_nOC(O)$—$C_{3-6}$ cycloalkylene-$NR^{21}$- | optionally substituted —$(CH_2)_nOC(O)C_{3-6}$ cycloalkenylene-$NR^{21}$- |
| optionally substituted —$(CH_2)_nNR^{20}C_{1-6}$ alkylene-$NR^{21}$- | optionally substituted —$(CH_2)_nNR^{20}C_{2-6}$ alkenylene-$NR^{21}$- | optionally substituted —$(CH_2)_nNR^{20}C_{3-6}$ cycloalkylene-$NR^{21}$- | optionally substituted —$(CH_2)_nNR^{20}C_{3-6}$ cycloalkenylene-$NR^{21}$- |
| optionally substituted —$(CH_2)_nNR^{20}C(O)C_{1-6}$ alkylene-$NR^{21}$- | optionally substituted —$(CH_2)_nNR^{20}C(O)C_{2-6}$ alkenylene-$NR^{21}$- | optionally substituted —$(CH_2)_nNR^{20}C(O)$—$C_{3-6}$ cycloalkylene-$NR^{21}$- | optionally substituted —$(CH_2)_nNR^{20}C(O)$—$C_{3-6}$ cycloalkenylene-$NR^{21}$- |
| optionally substituted —$(CH_2)_nC(O)NR^{20}C_{1-6}$ alkylene-$NR^{21}$- | optionally substituted —$(CH_2)_nC(O)NR^{20}C_{2-6}$ alkenylene-$NR^{21}$- | optionally substituted —$(CH_2)_nC(O)NR^{20}$—$C_{3-6}$ cycloalkylene-$NR^{21}$- | optionally substituted —$(CH_2)_nC(O)NR^{20}$—$C_{3-6}$ cycloalkenylene-$NR^{21}$- |
| optionally substituted —$(CH_2)_n$—S—$C_{1-6}$ alkylene-$NR^{21}$- | optionally substituted —$(CH_2)_n$—S—$C_{2-6}$ alkenylene | optionally substituted —$(CH_2)_n$—S—$C_{3-6}$ cycloalkylene-$NR^{21}$- | optionally substituted —$(CH_2)_n$—S—$C_{3-6}$ cycloalkenylene-$NR^{21}$- |
| optionally substituted —$(CH_2)_nC(O)(CH_2)_n$—S—$C_{1-6}$ alkylene-$NR^{21}$- | optionally substituted —$(CH_2)_nC(O)(CH_2)_n$—S—$C_{2-6}$ alkenylene-$NR^{21}$- | optionally substituted —$(CH_2)_nC(O)(CH_2)_n$—S—$C_{3-6}$ cycloalkylene-$NR^{21}$- | optionally substituted —$(CH_2)_nC(O)(CH_2)_n$—S—$C_{3-6}$ cycloalkenylene-$NR^{21}$- |
| optionally substituted —$(CH_2)_n$—$SO_2$—$C_{1-6}$ alkylene-$NR^{21}$- | optionally substituted —$(CH_2)_n$—$SO_2$—$C_{1-6}$ alkenylene-$NR^{21}$- | optionally substituted —$(CH_2)_n$—$SO_2$—$C_{3-6}$ cycloalkylene-$NR^{21}$- | optionally substituted —$(CH_2)_n$—$SO_2$—$C_{3-6}$ cycloalkenylene-$NR^{21}$- |
| optionally substituted —$(CH_2)_nC(O)(CH_2)_n$—$SO_2$—$C_{1-6}$ alkylene-$NR^{21}$- | optionally substituted —$(CH_2)_nC(O)(CH_2)_n$—$SO_2$—$C_{2-6}$ alkenylene-$NR^{21}$- | optionally substituted —$(CH_2)_nC(O)(CH_2)_n$—$SO_2$—$C_{3-6}$ cycloalkylene-$NR^{21}$- | optionally substituted —$(CH_2)_nC(O)(CH_2)_n$—$SO_2$—$C_{3-6}$ cycloalkenylene-$NR^{21}$- |
| optionally substituted —$(CH_2)_n$—SO—$C_{1-6}$ alkylene-$NR^{21}$- | optionally substituted —$(CH_2)_n$—SO—$C_{2-6}$ alkenylene-$NR^{21}$- | optionally substituted —$(CH_2)_n$—SO—$C_{3-6}$ cycloalkylene-$NR^{21}$- | optionally substituted —$(CH_2)_n$—SO—$C_{3-6}$ cycloalkenylene-$NR^{21}$- |
| optionally substituted —$(CH_2)_nC(O)(CH_2)_n$—SO—$C_{1-6}$ alkylene-$NR^{21}$- | optionally substituted —$(CH_2)_nC(O)(CH_2)_n$—SO—$C_{2-6}$ alkenylene-$NR^{21}$- | optionally substituted —$(CH_2)_nC(O)(CH_2)_n$—SO—$C_{3-6}$ cycloalkylene-$NR^{21}$- | optionally substituted —$(CH_2)_nC(O)(CH_2)_n$—SO—$C_{3-6}$ cycloalkenylene-$NR^{21}$- |
| optionally substituted —$(CH_2)_n$—S—S—$C_{1-6}$ alkylene-$NR^{21}$- | optionally substituted —$(CH_2)_n$—S—S—$C_{2-6}$ alkenylene-$NR^{21}$- | optionally substituted —$(CH_2)_n$—S—S—$C_{3-6}$ cycloalkylene-$NR^{21}$- | optionally substituted —$(CH_2)_n$—S—S—$C_{3-6}$ cycloalkenylene-$NR^{21}$- |
| optionally substituted —$(CH_2)_nC(O)(CH_2)_n$—S—S—$C_{1-6}$ alkylene-$NR^{21}$- | optionally substituted —$(CH_2)_nC(O)(CH_2)_n$—S—S—$C_{2-6}$ alkenylene-$NR^{21}$- | optionally substituted —$(CH_2)_nC(O)(CH_2)_n$—S—S—$C_{3-6}$ cycloalkylene-$NR^{21}$- | optionally substituted —$(CH_2)_nC(O)(CH_2)_n$—S—S—$C_{3-6}$ cycloalkenylene-$NR^{21}$- |
| optionally substituted —$(CH_2)_nC_{1-6}$ alkylene-C(O)— | optionally substituted —$(CH_2)_nC_{2-6}$ alkenylene-C(O)— | optionally substituted —$(CH_2)_nC_{3-6}$ cycloalkylene-C(O)— | optionally substituted —$(CH_2)_nC_{3-6}$ cycloalkenylene-C(O)— |

TABLE 1-continued

The linker structures.

| | | | |
|---|---|---|---|
| optionally substituted —$(CH_2)_nOC_{1-6}$ alkylene-C(O)— | optionally substituted —$(CH_2)_nOC_{2-6}$ alkenylene-C(O)— | optionally substituted —$(CH_2)_nOC_{3-6}$ cycloalkylene-C(O)— | optionally substituted —$(CH_2)_nOC_{3-6}$ cycloalkenylene-C(O)— |
| optionally substituted —$(CH_2)_nC(O)C_{1-6}$ alkylene-C(O)— | optionally substituted —$(CH_2)_nC(O)C_{2-6}$ alkenylene-C(O)— | optionally substituted —$(CH_2)_nC(O)C_{3-6}$ cycloalkylene-C(O)— | optionally substituted —$(CH_2)_nC(O)C_{3-6}$ cycloalkenylene-C(O)— |
| optionally substituted —$(CH_2)_nC(O)OC_{1-6}$ alkylene-(O)— | optionally substituted —$(CH_2)_nC(O)OC_{2-6}$ alkenylene-C(O)— | optionally substituted —$(CH_2)_nC(O)O—C_{3-6}$ cycloalkylene-C(O)— | optionally substituted —$(CH_2)_nC(O)OC_{3-6}$ cycloalkenylene-C(O)— |
| optionally substituted —$(CH_2)_nOC(O)C_{1-6}$ alkylene-C(O)— | optionally substituted —$(CH_2)_nOC(O)C_{2-6}$ alkenylene-C(O)— | optionally substituted —$(CH_2)_nOC(O)—C_{3-6}$ cycloalkylene-C(O)— | optionally substituted —$(CH_2)_nOC(O)C_{3-6}$ cycloalkenylene-C(O)— |
| optionally substituted —$(CH_2)_nNR^{20}C_{1-6}$ alkylene-C(O)— | optionally substituted —$(CH_2)_nNR^{20}C_{2-6}$ alkenylene-C(O)— | optionally substituted —$(CH_2)_nNR^{20}C_{3-6}$ cycloalkylene-C(O)— | optionally substituted —$(CH_2)_nNR^{20}C_{3-6}$ cycloalkenylene-C(O)— |
| optionally substituted —$(CH_2)_nNR^{20}C(O)C_{1-6}$ alkylene-C(O)— | optionally substituted —$(CH_2)_nNR^{20}C(O)C_{2-6}$ alkenylene-C(O)— | optionally substituted —$(CH_2)_nNR^{20}C(O)—C_{3-6}$ cycloalkylene-C(O)— | optionally substituted —$(CH_2)_nNR^{20}C(O)—C_{3-6}$ cycloalkenylene-C(O)— |
| optionally substituted —$(CH_2)_nNR^{20}C_{1-6}$ alkylene-C(O)— | optionally substituted —$(CH_2)_nNR^{20}C_{2-6}$ alkenylene-C(O)— | optionally substituted —$(CH_2)_nNR^{20}C_{3-6}$ cycloalkylene-C(O)— | optionally substituted —$(CH_2)_nNR^{20}C_{3-6}$ cycloalkenylene-C(O)— |
| optionally substituted —$(CH_2)_nC(O)NR^{20}C_{1-6}$ alkylene-C(O)— | optionally substituted —$(CH_2)_nC(O)NR^{20}C_{2-6}$ alkenylene-C(O)— | optionally substituted —$(CH_2)_nC(O)NR^{20}—C_{3-6}$ cycloalkylene-C(O)— | optionally substituted —$(CH_2)_nC(O)NR^{20}—C_{3-6}$ cycloalkenylene-C(O)— |
| optionally substituted —$(CH_2)_n—S—C_{1-6}$ alkylene-C(O)— | optionally substituted —$(CH_2)_n—S—C_{2-6}$ alkenylene-C(O)— | optionally substituted —$(CH_2)_n—S—C_{3-6}$ cycloalkylene-C(O)— | optionally substituted —$(CH_2)_n—S—C_{3-6}$ cycloalkenylene-C(O)— |
| optionally substituted —$(CH_2)_nC(O)(CH_2)_n—S—C_{1-6}$ alkylene-C(O) | optionally substituted —$(CH_2)_nC(O)(CH_2)_n—S—C_{2-6}$ alkenylene-C(O) | optionally substituted —$(CH_2)_nC(O)(CH_2)_n—S—C_{3-6}$ cycloalkylene-C(O) | optionally substituted —$(CH_2)_nC(O)(CH_2)_n—S—C_{3-6}$ cycloalkenylene-C(O) |
| optionally substituted —$(CH_2)_n—SO_2—C_{1-6}$ alkylene-C(O)— | optionally substituted —$(CH_2)_n—SO_2—C_{2-6}$ alkenylene-C(O)— | optionally substituted —$(CH_2)_n—SO_2—C_{3-6}$ cycloalkylene-C(O)— | optionally substituted —$(CH_2)_n—SO_2—C_{3-6}$ cycloalkenylene-C(O)— |
| optionally substituted —$(CH_2)_nC(O)(CH_2)_n—SO_2—C_{1-6}$ alkylene-C(O) | optionally substituted —$(CH_2)_nC(O)(CH_2)_n—SO_2—C_{2-6}$ alkenylene-C(O) | optionally substituted —$(CH_2)_nC(O)(CH_2)_n—SO_2—C_{3-6}$ cycloalkylene-C(O) | optionally substituted —$(CH_2)_nC(O)(CH_2)_n—SO_2—C_{3-6}$ cycloalkenylene-C(O) |
| optionally substituted —$(CH_2)_n—SO—C_{1-6}$ alkylene-C(O)— | optionally substituted —$(CH_2)_n—SO—C_{2-6}$ alkenylene-C(O)— | optionally substituted —$(CH_2)_n—SO—C_{3-6}$ cycloalkylene-C(O)— | optionally substituted —$(CH_2)_n—SO—C_{3-6}$ cycloalkenylene-C(O)— |
| optionally substituted —$(CH_2)_nC(O)(CH_2)_n—SO—C_{1-6}$ alkylene-C(O) | optionally substituted —$(CH_2)_nC(O)(CH_2)_n—SO—C_{2-6}$ alkenylene-C(O) | optionally substituted —$(CH_2)_n—C(O)(CH_2)_n—SO—C_{3-6}$ cycloalkylene-C(O) | optionally substituted —$(CH_2)_n—C(O)(CH_2)_n—SO—C_{3-6}$ cycloalkenylene-C(O) |
| optionally substituted —$(CH_2)_n—S—S—C_{1-6}$ alkylene-C(O)— | optionally substituted —$(CH_2)_n—S—S—C_{2-6}$ alkenylene-C(O)— | optionally substituted —$(CH_2)_n—S—S—C_{3-6}$ cycloalkylene-C(O)— | optionally substituted —$(CH_2)_n—S—S—C_{3-6}$ cycloalkenylene-C(O)— |
| optionally substituted —$(CH_2)_nC(O)(CH_2)_n—S—S—C_{1-6}$ alkylene-C(O) | optionally substituted —$(CH_2)_nC(O)(CH_2)_n—S—S—C_{2-6}$ alkenylene-C(O) | optionally substituted —$(CH_2)_nC(O)(CH_2)_n—S—S—C_{3-6}$ cycloalkylene-C(O) | optionally substituted —$(CH_2)_nC(O)(CH_2)_n—S—S—C_{3-6}$ cycloalkenylene-C(O)— |
| optionally substituted —$NR^{20}C(O)(CH_2)_nOC_{1-6}$ alkylene-(CO) | optionally substituted —$NR^{20}C(O)(CH_2)_nO—C_{2-6}$ alkenylene-(CO) | optionally substituted —$NR^{20}C(O)(CH_2)_nO—C_{3-6}$ cycloalkylene-(CO) | optionally substituted —$NR^{20}C(O)(CH_2)_nO—C_{3-6}$ cycloalkenylene-(CO) |
| optionally substituted —$NR^{20}C(O)(CH_2)_n—S—C_{1-6}$ alkylene-(CO) | optionally substituted $NR^{20}C(O)(CH_2)_n—S—C_{2-6}$ alkenylene-(CO) | optionally substituted —$NR^{20}C(O)(CH_2)_n—S—C_{3-6}$ cycloalkylene-(CO) | optionally substituted —$NR^{20}C(O)(CH_2)_n—S—C_{3-6}$ cycloalkenylene-(CO) |
| optionally substituted —$NR^{20}C(O)(CH_2)_nNR^{21}C_{1-6}$ alkylene-(CO) | optionally substituted —$NR^{20}C(O)(CH_2)_nNR^{21}-C_{2-6}$ alkenylene-(CO) | optionally substituted —$NR^{20}C(O)(CH_2)_nNR^{21}-C_{3-6}$ cycloalkylene-(CO) | optionally substituted —$NR^{20}C(O)(CH_2)_nNR^{21}-C_{3-6}$ cycloalkenylene-(CO) |
| optionally substituted $C(O)NR^{20}(CH_2)_nOC_{1-6}$ alkylene-(CO) | optionally substituted —$C(O)NR^{20}(CH_2)_nO—C_{2-6}$ alkenylene-(CO) | optionally substituted —$C(O)NR^{20}(CH_2)_nO—C_{3-6}$ cycloalkylene-(CO) | optionally substituted —$C(O)NR^{20}(CH_2)_nO—C_{3-6}$ cycloalkenylene-(CO) |
| optionally substituted —$C(O)NR^{20}(CH_2)_n—S—C_{1-6}$ alkylene-(CO) | optionally substituted —$C(O)NR^{20}(CH_2)_n—S—C_{2-6}$ alkenylene-(CO) | optionally substituted —$C(O)NR^{20}(CH_2)_n—S—C_{3-6}$ cycloalkylene-(CO) | optionally substituted —$C(O)NR^{20}(CH_2)_n—S—C_{3-6}$ cycloalkenylene-(CO) |
| optionally substituted —$C(O)NR^{20}(CH_2)_n—NR^{21}C_{1-6}$ alkylene-(CO) | optionally substituted —$C(O)NR^{20}(CH_2)_n—NR^{21}C_{2-6}$ alkenylene-(CO) | optionally substituted $vC(O)NR^{20}(CH_2)_n—NR^{21}C_{3-6}$ cycloalkylene-(CO) | optionally substituted —$C(O)NR^{20}(CH_2)_n—NR^{21}C_{3-6}$ cycloalkenylene-(CO) |
| optionally substituted —$C(O)(CH_2)_nC_{1-6}$ alkylene —$(CH_2)_n$— | optionally substituted —$C(O)(CH_2)_nC_{1-6}$ alkenylene —$(CH_2)_n$— | optionally substituted —$C(O)(CH_2)_nC_{3-6}$ cycloalkylene —$(CH_2)_n$— | optionally substituted —$C(O)(CH_2)_nC_{3-6}$ cycloalkenylene-$(CH_2)_n$— |
| optionally substituted —$C(O)O(CH_2)_nC_{1-6}$ alkylene-$(CH_2)_n$— | optionally substituted —$C(O)O(CH_2)_nC_{1-6}$ alkenylene-$(CH_2)_n$— | optionally substituted —$C(O)O(CH_2)_nC_{3-6}$ cycloalkylene $(CH_2)_n$— | optionally substituted —$C(O)O(CH_2)_nC_{3-6}$ cycloalkenylene $(CH_2)_n$— |
| optionally substituted —$C(O)O(CH_2)_nC_{1-6}$ alkylene-$(CH_2)_n$—O— | optionally substituted —$C(O)O(CH_2)_nC_{1-6}$ alkenylene-$(CH_2)_n$—O— | optionally substituted —$C(O)O(CH_2)_nC_{3-6}$ cycloalkylene $(CH_2)_n$—O— | optionally substituted —$C(O)O(CH_2)_nC_{3-6}$ cycloalkenylene $(CH_2)_n$—O— |
| optionally substituted —$C(O)O(CH_2)_nC_{1-6}$ alkylene-$(CH_2)_n$—O— | optionally substituted —$C(O)O(CH_2)_nC_{1-6}$ alkenylene-$(CH_2)_n$—O— | optionally substituted —$C(O)O(CH_2)_nC_{3-6}$ cycloalkylene $(CH_2)_n$—O— | optionally substituted —$C(O)O(CH_2)_nC_{3-6}$ cycloalkenylene $(CH_2)_n$—O— |

TABLE 1-continued

The linker structures.

| | | | |
|---|---|---|---|
| optionally substituted —C(O)(CH$_2$)$_n$C$_{1-6}$ alkylene-(CH$_2$)$_n$—C(O)— | optionally substituted —C(O)(CH$_2$)$_n$C$_{1-6}$ alkenylene-(CH$_2$)$_n$—C(O)— | optionally substituted —C(O)(CH$_2$)$_n$C$_{3-6}$ cycloalkylene (CH$_2$)$_n$—C(O)— | optionally substituted —C(O)(CH$_2$)$_n$C$_{3-6}$ cycloalkenylene (CH$_2$)$_n$—C(O)— |
| optionally substituted —C(O)O(CH$_2$)$_n$C$_{1-6}$ alkylene-(CH$_2$)$_n$—C(O)— | optionally substituted —C(O)O(CH$_2$)$_n$C$_{1-6}$ alkenylene-(CH$_2$)$_n$—C(O)— | optionally substituted —C(O)O(CH$_2$)$_n$C$_{3-6}$ cycloalkylene (CH$_2$)$_n$—C(O)— | optionally substituted —C(O)O(CH$_2$)$_n$C$_{3-6}$ cycloalkenylene (CH$_2$)$_n$—C(O)— |
| optionally substituted —OC(O)(CH$_2$)$_n$C$_{1-6}$ alkylene-(CH$_2$)$_n$— | optionally substituted —OC(O)(CH$_2$)$_n$C$_{1-6}$ alkenylene-(CH$_2$)$_n$— | optionally substituted —OC(O)(CH$_2$)$_n$C$_{3-6}$ cycloalkylene-(CH$_2$)$_n$— | optionally substituted —OC(O)(CH$_2$)$_n$C$_{3-6}$ cycloalkenylene-(CH$_2$)$_n$— |
| optionally substituted —O(CH$_2$)$_n$C$_{1-6}$ alkylene-(CH$_2$)$_n$— | optionally substituted —O(CH$_2$)$_n$C$_{1-6}$ alkenylene-(CH$_2$)$_n$— | optionally substituted —O(CH$_2$)$_n$C$_{3-6}$ cycloalkylene-(CH$_2$)$_n$— | optionally substituted —O(CH$_2$)$_n$C$_{3-6}$ cycloalkenylene-(CH$_2$)$_n$— |
| optionally substituted —OC(O)(CH$_2$)$_n$C$_{1-6}$ alkylene-(CH$_2$)$_n$—O— | optionally substituted —OC(O)(CH$_2$)$_n$C$_{1-6}$ alkenylene-(CH$_2$)$_n$—O— | optionally substituted —OC(O)(CH$_2$)$_n$C$_{3-6}$ cycloalkylene-(CH$_2$)$_n$—O— | optionally substituted —OC(O)(CH$_2$)$_n$C$_{3-6}$ cycloalkenylene-(CH$_2$)$_n$—O— |
| optionally substituted —O(CH$_2$)$_n$C$_{1-6}$ alkylene-(CH$_2$)$_n$—O— | optionally substituted —O(CH$_2$)$_n$C$_{1-6}$ alkenylene-(CH$_2$)$_n$—O— | optionally substituted —O(CH$_2$)$_n$C$_{3-6}$ cycloalkylene-(CH$_2$)$_n$—O— | optionally substituted —O(CH$_2$)$_n$C$_{3-6}$ cycloalkenylene-(CH$_2$)$_n$—O— |
| optionally substituted —OC(O)(CH$_2$)$_n$C$_{1-6}$ alkylene-(CH$_2$)$_n$—C(O)— | optionally substituted —OC(O)(CH$_2$)$_n$C$_{1-6}$ alkenylene-(CH$_2$)$_n$—C(O)— | optionally substituted —OC(O)(CH$_2$)$_n$C$_{3\ 6}$ cycloalkylene-(CH$_2$)$_n$—C(O)— | optionally substituted —OC(O)(CH$_2$)$_n$C$_{3-6}$ cycloalkenylene-(CH$_2$)$_n$—C(O)— |
| optionally substituted —O(CH$_2$)$_n$C$_{1-6}$ alkylene-(CH$_2$)$_n$—C(O)— | optionally substituted —O(CH$_2$)$_n$C$_{1-6}$ alkenylene-(CH$_2$)$_n$—C(O)— | optionally substituted —O(CH$_2$)$_n$C$_{3-6}$ cycloalkylene-(CH$_2$)$_n$—C(O)— | optionally substituted —O(CH$_2$)$_n$C$_{3-6}$ cycloalkenylene-(CH$_2$)$_n$—C(O)— |
| optionally substituted —C(O)NR$^{20}$(CH$_2$)$_n$— C$_{1-6}$ alkylene-(CH$_2$)$_n$— | optionally substituted —C(O)NR$^{20}$(CH$_2$)$_n$— C$_{1-6}$ alkenylene-(CH$_2$)$_n$— | optionally substituted —C(O)NR$^{20}$(CH$_2$)$_n$— C$_{3-6}$ cycloalkylene-(CH$_2$)$_n$— | optionally substituted —C(O)NR$^{20}$(CH$_2$)$_n$C$_{3-6}$ cycloalkenylene-(CH$_2$)$_n$— |
| optionally substituted NR$^{20}$C(O)(CH$_2$)$_n$— C$_{1-6}$ alkylene-(CH$_2$)$_n$— | optionally substituted —NR$^{20}$C(O)(CH$_2$)$_n$— C$_{1-6}$ alkenylene-(CH$_2$)$_n$— | optionally substituted —NR$^{20}$C(O)(CH$_2$)$_n$— C$_{3-6}$ cycloalkylene-(CH$_2$)$_n$— | optionally substituted —NR$^{20}$C(O)(CH$_2$)$_n$C$_{3-6}$ cycloalkenylene-(CH$_2$)$_n$— |
| optionally substituted —C(O)NR$^{20}$(CH$_2$)$_n$ C$_{1-6}$ alkylene-(CH$_2$)$_n$—O— | optionally substituted —C(O)NR$^{20}$(CH$_2$)$_n$ C$_{1-6}$ alkenylene-(CH$_2$)$_n$—O— | optionally substituted —C(O)NR$^{20}$(CH$_2$)$_n$— C$_{3-6}$ cycloalkylene-(CH$_2$)$_n$—O— | optionally substituted —C(O)NR$^{20}$(CH$_2$)$_n$C$_{3-6}$ cycloalkenylene-(CH$_2$)$_n$—O— |
| optionally substituted —NR$^{20}$C(O)(CH$_2$)$_n$C$_{1-6}$ alkylene-(CH$_2$)$_n$—O— | optionally substituted —NR$^{20}$C(O)(CH$_2$)$_n$C$_{1-6}$ alkenylene-(CH$_2$)$_n$—O— | optionally substituted —NR$^{20}$C(O)(CH$_2$)$_n$— C$_{3-6}$ cycloalkylene-(CH$_2$)$_n$—O— | optionally substituted —NR$^{20}$C(O)(CH$_2$)$_n$C$_{3-6}$ cycloalkenylene-(CH$_2$)$_n$—O— |
| optionally substituted —C(O)NR$^{20}$(CH$_2$)$_n$C$_{1-6}$ alkylene-(CH$_2$)$_n$—C(O)— | optionally substituted —C(O)NR$^{20}$(CH$_2$)$_n$C$_{1-6}$ alkenylene-(CH$_2$)$_n$—C(O)— | optionally substituted —C(O)NR$^{20}$(CH$_2$)$_n$— C$_{3-6}$ cycloalkylene-(CH$_2$)$_n$—C(O)— | optionally substituted —C(O)NR$^{20}$(CH$_2$)$_n$—C$_{3-6}$ cycloalkenylene-(CH$_2$)$_n$—C(O)— |
| optionally substituted —NR$^{20}$C(O)(CH$_2$)$_n$C$_{1-6}$ alkylene-(CH$_2$)$_n$—C(O)— | optionally substituted —NR$^{20}$C(O)(CH$_2$)$_n$C$_{1-6}$ alkenylene-(CH$_2$)$_n$—C(O)— | optionally substituted —NR$^{20}$C(O)(CH$_2$)$_n$— C$_{3-6}$ cycloalkylene-(CH$_2$)$_n$—C(O)— | optionally substituted —NR$^{20}$C(O)(CH$_2$)$_n$C$_{3-6}$ cycloalkenylene-(CH$_2$)$_n$—C(O)— |
| optionally substituted —(CH$_2$)$_n$C$_{3-6}$ heterocycloalkylene | optionally substituted —(CH$_2$)$_n$C$_{3-6}$ heterocycloalkenylene | optionally substituted —(CH$_2$)$_n$C$_{3-6}$ alkynylene | |
| optionally substituted —(CH$_2$)$_n$OC$_{3-6}$ heterocycloalkylene | optionally substituted —(CH$_2$)$_n$OC$_{3-6}$ heterocycloalkenylene | optionally substituted —(CH$_2$)$_n$OC$_{2-6}$ alkynylene | |
| optionally substituted —(CH$_2$)$_n$C(O)C$_{3-6}$ heterocycloalkylene | optionally substituted —(CH$_2$)$_n$C(O)C$_{3-6}$ heterocycloalkenylene | optionally substituted —(CH$_2$)$_n$C(O)C$_{2-6}$ alkynylene | |
| optionally substituted —(CH$_2$)$_n$C(O)OC$_{3-6}$ heterocycloalkylene | optionally substituted —(CH$_2$)$_n$C(O)O—C$_{3-6}$ heterocycloalkenylene | optionally substituted —(CH$_2$)$_n$C(O)OC$_{2-6}$ alkynylene | |
| optionally substituted —(CH$_2$)$_n$OC(O)C$_{3-6}$ heterocycloalkylene | optionally substituted —(CH$_2$)$_n$OC(O)—C$_{3-6}$ heterocycloalkenylene | optionally substituted —(CH$_2$)$_n$OC(O)C$_{2-6}$ alkynylene | |
| optionally substituted —(CH$_2$)$_n$NR$^{20}$C$_{3-6}$ heterocycloalkylene | optionally substituted —(CH$_2$)$_n$NR$^{20}$—C$_{3-6}$ heterocycloalkenylene | optionally substituted —(CH$_2$)$_n$NR$^{20}$C$_{2-6}$ alkynylene | |
| optionally substituted —(CH$_2$)$_n$NR$^{20}$C(O)—C$_{3-6}$ heterocycloalkylene | optionally substituted —(CH$_2$)$_n$NR$^{20}$C(O)—C$_{3-6}$ heterocycloalkenylene | optionally substituted —(CH$_2$)$_n$NR$^{20}$C(O)C$_{2-6}$ alkynylene | |
| optionally substituted —(CH$_2$)$_n$C(O)NR$^{20}$- C$_{3-6}$ heterocycloalkylene | optionally substituted —(CH$_2$)$_n$C(O)NR$^{20}$- C$_{3-6}$ heterocycloalkenylene | optionally substituted —(CH$_2$)$_n$C(O)NR$^{20}$- C$_{2-6}$ alkynylene | |
| optionally substituted —(CH$_2$)$_n$—S— C$_{3-6}$ heterocycloalkylene | optionally substituted —(CH$_2$)$_n$—S— C$_{3-6}$ heterocycloalkenylene | optionally substituted —(CH$_2$)$_n$—S—C$_{2-6}$ alkynylene | |
| optionally substituted —(CH$_2$)$_n$C(O)(CH$_2$)$_n$—S— C$_{3-6}$ heterocycloalkylene | optionally substituted —(CH$_2$)$_n$C(O)(CH$_2$)$_n$—S— C$_{3-6}$ heterocycloalkenylene | optionally substituted —(CH$_2$)$_n$C(O)(CH$_2$)$_n$—S— C$_{2-6}$ alkynylene | |
| optionally substituted —(CH$_2$)$_n$—SO$_2$—C$_{3-6}$ heterocycloalkylene | optionally substituted —(CH$_2$)$_n$—SO$_2$— C$_{3-6}$ heterocycloalkenylene | optionally substituted —(CH$_2$)$_n$—SO$_2$—C$_{2-6}$ alkynylene | |

TABLE 1-continued

The linker structures.

| | | |
|---|---|---|
| optionally substituted —$(CH_2)_nC(O)(CH_2)_n$—$SO_2$—$C_{3-6}$ heterocycloalkylene | optionally substituted —$(CH_2)_nC(O)(CH_2)_n$—$SO_2$—$C_{3-6}$ heterocycloalkenylene | optionally substituted —$(CH_2)_nC(O)(CH_2)_n$—$SO_2$—$C_{2-6}$ alkynylene |
| optionally substituted —$(CH_2)_n$—$SO$—$C_{3-6}$ heterocycloalkylene | optionally substituted —$(CH_2)_n$—$SO$—$C_{3-6}$ heterocycloalkenylene | optionally substituted —$(CH_2)_n$—$SO$—$C_{2-6}$ alkynylene |
| optionally substituted —$(CH_2)_nC(O)(CH_2)_n$—$SO$—$C_{3-6}$ heterocycloalkylene | optionally substituted —$(CH_2)_nC(O)(CH_2)_n$—$SO$—$C_{3-6}$ heterocycloalkenylene | optionally substituted —$(CH_2)_nC(O)(CH_2)_n$—$SO$—$C_{2-6}$ alkynylene |
| optionally substituted —$(CH_2)_n$—$S$—$S$—$C_{3-6}$ heterocycloalkylene | optionally substituted —$(CH_2)_n$—$S$—$S$—$C_{3-6}$ heterocycloalkenylene | optionally substituted —$(CH_2)_n$—$S$—$S$—$C_{2-6}$ alkynylene |
| optionally substituted —$(CH_2)_nC(O)(CH_2)_n$—$S$—$S$—$C_{3-6}$ heterocycloalkylene | optionally substituted —$(CH_2)_nC(O)(CH_2)_n$—$S$—$S$—$C_{3-6}$ heterocycloalkenylene | optionally substituted —$(CH_2)_nC(O)(CH_2)_n$—$S$—$S$—$C_{2-6}$ alkynylene |
| optionally substituted —$(CH_2)_nC_{3-6}$ heterocycloalkylene-$NR^{21}$- | optionally substituted —$(CH_2)_nC_{3-6}$ heterocycloalkenylene-$NR^{21}$- | optionally substituted —$(CH_2)_nC_{2-6}$ alkynylene-$NR^{21}$- |
| optionally substituted —$(CH_2)_nOC_{3-6}$ heterocycloalkylene-$NR^{21}$- | optionally substituted —$(CH_2)_nOC_{3-6}$ heterocycloalkenylene-$NR^{21}$- | optionally substituted —$(CH_2)_nOC_{2-6}$ alkynylene-$NR^{21}$- |
| optionally substituted —$(CH_2)_nC(O)_{3-6}$ heterocycloalkylene-$NR^{21}$- | optionally substituted —$(CH_2)_nC(O)$—$C_{3-6}$ heterocycloalkenylene-$NR^{21}$- | optionally substituted —$(CH_2)_nC(O)C_{2-6}$ alkynylene-$NR^{21}$- |
| optionally substituted —$(CH_2)_nC(O)O$—$C_{3-6}$ heterocycloalkylene-$NR^{21}$- | optionally substituted —$(CH_2)_nC(O)O$—$C_{3-6}$ heterocycloalkenylene-$NR^{21}$- | optionally substituted —$(CH_2)_nC(O)OC_{2-6}$ alkynylene-$NR^{21}$- |
| optionally substituted —$(CH_2)_nOC(O)$—$C_{3-6}$ heterocycloalkylene-$NR^{21}$- | optionally substituted —$(CH_2)_nOC(O)$—$C_{3-6}$ heterocycloalkenylene-$NR^{21}$- | optionally substituted —$(CH_2)_nOC(O)C_{2-6}$ alkynylene-$NR^2$— |
| optionally substituted —$(CH_2)_nNR^{20}C_{3-6}$ heterocycloalkylene-$NR^{21}$- | optionally substituted —$(CH_2)_nNR^{20}C_{3-6}$ heterocycloalkenylene-$NR^{21}$- | optionally substituted —$(CH_2)_nNR^{20}C_{2-6}$ alkynylene-$NR^{21}$- |
| optionally substituted —$(CH_2)_nNR^{20}C(O)$—$C_{3-6}$ heterocycloalkylene-$NR^{21}$- | optionally substituted —$(CH_2)_nNR^{20}C(O)$—$C_{3-6}$ heterocycloalkenylene-$NR^{21}$- | optionally substituted —$(CH_2)_nNR^{20}C(O)C_{2-6}$ alkynylene-$NR^{21}$- |
| optionally substituted —$(CH_2)_nC(O)NR^{20}$—$C_{3-6}$ heterocycloalkylene-$NR^{21}$- | optionally substituted —$(CH_2)_nC(O)NR^{20}$—$C_{3-6}$ heterocycloalkenylene-$NR^{21}$- | optionally substituted —$(CH_2)_nC(O)NR^{20}C_{2-6}$ alkynylene-$NR^{21}$- |
| optionally substituted —$(CH_2)_n$—$S$—$C_{3-6}$ heterocycloalkylene-$NR^{21}$- | optionally substituted —$(CH_2)_n$—$S$—$C_{3-6}$ heterocycloalkenylene-$NR^{21}$- | optionally substituted —$(CH_2)_n$—$S$—$C_{2-6}$ alkynylene |
| optionally substituted —$(CH_2)_nC(O)(CH_2)_n$—$S$—$C_{3-6}$ heterocycloalkylene-$NR^{21}$- | optionally substituted —$(CH_2)_nC(O)(CH_2)_n$—$S$—$C_{3-6}$ heterocycloalkenylene-$NR^{21}$- | optionally substituted —$(CH_2)_nC(O)(CH_2)_n$—$S$—$C_{2-6}$ alkynylene-$NR^{21}$- |
| optionally substituted —$(CH_2)_n$—$SO_2$—$C_{3-6}$ heterocycloalkylene-$NR^{21}$- | optionally substituted —$(CH_2)_n$—$SO_2$—$C_{3-6}$ heterocycloalkenylene-$NR^{21}$- | optionally substituted —$(CH_2)_n$—$SO_2$—$C_{1-6}$ alkynylene-$NR^{21}$- |
| optionally substituted —$(CH_2)_n$—$C(O)(CH_2)_n$—$SO_2$—$C_{3-6}$ heterocycloalkylene-$NR^{21}$- | optionally substituted —$(CH_2)_nC(O)(CH_2)_n$—$SO_2$—$C_{3-6}$ heterocycloalkenylene-$NR^{21}$- | optionally substituted —$(CH_2)_nC(O)(CH_2)_n$—$SO_2$—$C_{2-6}$ alkynylene-$NR^{21}$- |
| optionally substituted —$(CH_2)_n$—$SO$—$C_{3-6}$ heterocycloalkylene-$NR^{21}$- | optionally substituted —$(CH_2)_n$—$SO$—$C_{3-6}$ heterocycloalkenylene-$NR^{21}$- | optionally substituted —$(CH_2)_n$—$SO$—$C_{2-6}$ alkynylene-$NR^{21}$- |
| optionally substituted —$(CH_2)_nC(O)(CH_2)_n$—$SO$—$C_{3-6}$ heterocycloalkylene-$NR^{21}$- | optionally substituted —$(CH_2)_nC(O)(CH_2)_n$—$SO$—$C_{3-6}$ heterocycloalkenylene-$NR^{21}$- | optionally substituted —$(CH_2)_nC(O)(CH_2)_n$—$SO$—$C_{2-6}$ alkynylene-$NR^{21}$- |
| optionally substituted —$(CH_2)_n$—$S$—$S$—$C_{3-6}$ heterocycloalkylene-$NR^{21}$- | optionally substituted —$(CH_2)_n$—$S$—$S$—$C_{3-6}$ heterocycloalkenylene-$NR^{21}$- | optionally substituted —$(CH_2)_n$—$S$—$S$—$C_{2-6}$ alkynylene-$NR^{21}$- |
| optionally substituted —$(CH_2)_nC(O)(CH_2)_n$—$S$—$S$—$C_{3-6}$ heterocycloalkylene-$NR^{21}$- | optionally substituted —$(CH_2)_nC(O)(CH_2)_n$—$S$—$S$—$C_{3-6}$ heterocycloalkenylene-$NR^{21}$- | optionally substituted —$(CH_2)_nC(O)(CH_2)_n$—$S$—$S$—$C_{2-6}$ alkynylene-$NR^{21}$- |
| optionally substituted —$(CH_2)_nC_{3-6}$ heterocycloalkylene-C(O)— | optionally substituted —$(CH_2)_nC_{3-6}$ heterocycloalkenylene-C(O)— | optionally substituted —$(CH_2)_nC_{2-6}$ alkynylene-C(O)— |
| optionally substituted —$(CH_2)_nOC_{3-6}$ heterocycloalkylene-C(O)— | optionally substituted —$(CH_2)_nOC_{3-6}$ heterocycloalkenylene-C(O)— | optionally substituted —$(CH_2)_nOC_{2-6}$ alkynylene-C(O)— |
| optionally substituted —$(CH_2)_nC(O)C_{3-6}$ heterocycloalkylene-C(O)— | optionally substituted —$(CH_2)_nC(O)C_{3-6}$ heterocycloalkenylene-C(O)— | optionally substituted —$(CH_2)_nC(O)C_{3-6}$ alkynylene-C(O)— |
| optionally substituted —$(CH_2)_nC(O)OC_{3-6}$ heterocycloalkylene-C(O)— | optionally substituted —$(CH_2)_nC(O)O$—$C_{3-6}$ heterocycloalkenylene-C(O)— | optionally substituted —$(CH_2)_nC(O)OC_{2-6}$ alkynylene-C(O)— |

TABLE 1-continued

The linker structures.

| | | |
|---|---|---|
| optionally substituted —$(CH_2)_n OC(O)C_{3-6}$ heterocycloalkylene-C(O)— | optionally substituted —$(CH_2)_n OC(O)$—$C_{3-6}$ heterocycloalkenylene-C(O)— | optionally substituted —$(CH_2)_n OC(O)C_{2-6}$ alkynylene-C(O)— |
| optionally substituted —$(CH_2)_n NR^{20}C_{3-6}$ heteroalkylene-C(O)— | optionally substituted —$(CH_2)_n NR^{20}$—$C_{3-6}$ heterocycloalkenylene-C(O)— | optionally substituted —$(CH_2)_n NR^{20}C_{2-6}$ alkynylene-C(O)— |
| optionally substituted —$(CH_2)_n NR^{20}C(O)C_{3-6}$ heterocycloalkylene-C(O)— | optionally substituted —$(CH_2)_n NR^{20}C(O)$—$C_{3-6}$ heterocycloalkenylene-C(O)— | optionally substituted —$(CH_2)_n NR^{20}C(O)C_{2-6}$ alkynylene-C(O)— |
| optionally substituted —$(CH_2)_n NR^{20}C_{3-6}$ heterocycloalkylene-C(O)— | optionally substituted —$(CH_2)_n NR^{20}$—$C_{3-6}$ heterocycloalkenylene-C(O)— | optionally substituted —$(CH_2)_n NR^{20}C_{2-6}$ alkynylene-C(O)— |
| optionally substituted —$(CH_2)_n C(O)NR^{20}C_{3-6}$ heterocycloalkylene-C(O)— | optionally substituted —$(CH_2)_n C(O)NR^{20}$—$C_{3-6}$ heterocycloalkenylene-C(O)— | optionally substituted —$(CH_2)_n C(O)NR^{20}C_{2-6}$ alkynylene-C(O)— |
| optionally substituted —$(CH_2)_n$—S—$C_{3-6}$ heterocycloalkylene-C(O)— | optionally substituted —$(CH_2)_n$—S—$C_{3-6}$ heterocycloalkenylene-C(O)— | optionally substituted —$(CH_2)_n$—S—$C_{2-6}$ alkynylene-C(O)— |
| optionally substituted —$(CH_2)_n C(O)(CH_2)_n$—S—$C_{3-6}$ heterocycloalkylene-C(O) | optionally substituted —$(CH_2)_n C(O)(CH_2)_n$—S—$C_{3-6}$ heterocycloalkenylene-C(O) | optionally substituted —$(CH_2)_n C(O)(CH_2)_n$—S—$C_{2-6}$ alkynylene-C(O) |
| optionally substituted —$(CH_2)_n SO_2$—$C_{3-6}$ heterocycloalkylene-C(O)— | optionally substituted —$(CH_2)_n SO_2$—$C_{3-6}$ heterocycloalkenylene-C(O)— | optionally substituted —$(CH_2)_n SO_2$—$C_{2-6}$ alkynylene-C(O)— |
| optionally substituted —$(CH_2)_n C(O)(CH_2)_n$—$SO_2$—$C_{3-6}$ heterocycloalkylene-C(O) | optionally substituted —$(CH_2)_n C(O)(CH_2)_n$—$SO_2$—$C_{3-6}$ heterocycloalkenylene-C(O) | optionally substituted —$(CH_2)_n C(O)(CH_2)_n$—$SO_2$—$C_{2-6}$ alkynylene-C(O) |
| optionally substituted —$(CH_2)_n$—SO—$C_{3-6}$ heterocycloalkylene-C(O)— | optionally substituted —$(CH_2)_n$—SO—$C_{3-6}$ heterocycloalkenylene-C(O)— | optionally substituted —$(CH_2)_n$—SO—$C_{2-6}$ alkynylene-C(O)— |
| optionally substituted —$(CH_2)_n C(O)(CH_2)_n$—SO—$C_{3-6}$ heterocycloalkylene-C(O) | optionally substituted —$(CH_2)_n C(O)(CH_2)_n$—SO—$C_{3-6}$ heterocycloalkenylene-C(O) | optionally substituted —$(CH_2)_n C(O)(CH_2)_n$—SO—$C_{2-6}$ alkynylene-C(O) |
| optionally substituted —$(CH_2)_n$—S—S—$C_{3-6}$ heterocycloalkylene-C(O)— | optionally substituted —$(CH_2)_n$—S—S—$C_{3-6}$ heterocycloalkenylene-C(O)— | optionally substituted —$(CH_2)_n$—S—S—$C_{2-6}$ alkynylene-C(O)— |
| optionally substituted —$(CH_2)_n C(O)(CH_2)_n$—S—S—$C_{3-6}$ heterocycloalkylene-C(O) | optionally substituted —$(CH_2)_n C(O)(CH_2)_n$—S—S—$C_{3-6}$ heterocycloalkenylene-C(O) | optionally substituted —$(CH_2)_n C(O)(CH_2)_n$—S—S—$C_{2-6}$ alkynylene-C(O) |
| optionally substituted —$NR^{20}C(O)(CH_2)_n$—O—$C_{3-6}$ heterocycloalkylene-C(O)— | optionally substituted —$NR^{20}C(O)(CH_2)_n$—O—$C_{3-6}$ heterocycloalkenylene-C(O)— | optionally substituted —$NR^{20}C(O)(CH_2)_n$—O—$C_{2-6}$ alkynylene-C(O) |
| optionally substituted $NR^{20}C(O)(CH_2)_n$—S—$C_{3-6}$ heterocycloalkylene-C(O)— | optionally substituted —$NR^{20}C(O)(CH_2)_n$—S—$C_{3-6}$ heterocycloalkenylene-C(O)— | optionally substituted —$NR^{20}C(O)(CH_2)_n$—S—$C_{2-6}$ alkynylene-C(O) |
| optionally substituted —$NR^{20}C(O)(CH_2)_n NR^{21}$—$C_{3-6}$ heterocycloalkylene-C(O)— | optionally substituted —$NR^{20}C(O)(CH_2)_n NR^{21}$—$C_{3-6}$ heterocycloalkenylene-C(O)— | optionally substituted —$NR^{20}C(O)(CH_2)_n NR^{21}$—$C_{2-6}$ alkynylene-C(O) |
| optionally substituted —$C(O)NR^{20}(CH_2)_n$—O—$C_{3-6}$ heterocycloalkylene-(CO) | optionally substituted —$C(O)NR^{20}(CH_2)_n$—O—$C_{3-6}$ heterocycloalkenylene-(CO) | optionally substituted —$C(O)NR^{20}(CH_2)_n$—O—$C_{2-6}$ alkynylene-(CO) |
| optionally substituted —$C(O)NR^{20}(CH_2)_n$—S—$C_{3-6}$ heterocycloalkylene-(CO) | optionally substituted —$C(O)NR^{20}(CH_2)_n$—S—$C_{3-6}$ heterocycloalkenylene-(CO) | optionally substituted —$C(O)NR^{20}(CH_2)_n$—S—$C_{2-6}$ alkynylene-(CO) |
| optionally substituted —$C(O)NR^{20}(CH_2)_n$—$NR^{21}$—$C_{3-6}$ heterocycloalkylene-(CO) | optionally substituted —$C(O)NR^{20}(CH_2)_n$—$NR^{21}$—$C_{3-6}$ heterocycloalkenylene-(CO) | optionally substituted —$C(O)NR^{20}(CH_2)_n$—$NR^{21}C_{2-6}$ alkynylene-(CO) |
| optionally substituted —$C(O)(CH_2)_n C_{3-6}$ heterocycloalkylene-$(CH_2)_n$— | optionally substituted —$C(O)(CH_2)_n C_{3-6}$ heterocycloalkenylene-$(CH_2)_n$— | optionally substituted —$C(O)(CH_2)_n C_{1-6}$ alkynylene-$(CH_2)_n$— |
| optionally substituted —$C(O)O(CH_2)_n$—$C_{3-6}$ heterocycloalkylene-$(CH_2)_n$— | optionally substituted —$C(O)O(CH_2)_n$—$C_{3-6}$ heterocycloalkenylene-$(CH_2)_n$— | optionally substituted —$C(O)O(CH_2)_n C_{1-6}$ alkynylene-$(CH_2)_n$— |
| optionally substituted —$C(O)(CH_2)_n$—$C_{3-6}$ heterocycloalkylene-$(CH_2)_n$—O— | optionally substituted —$C(O)(CH_2)_n$—$C_{3-6}$ heterocycloalkenylene-$(CH_2)_n$—O— | optionally substituted —$C(O)(CH_2)_n C_{1-6}$ alkynylene-$(CH_2)_n$—O— |
| optionally substituted —$C(O)O(CH_2)_n$—$C_{3-6}$ heterocycloalkylene-$(CH_2)_n$—O— | optionally substituted —$C(O)O(CH_2)_n$—$C_{3-6}$ heterocycloalkenylene-$(CH_2)_n$—O— | optionally substituted —$C(O)O(CH_2)_n C_{1-6}$ alkynylene-$(CH_2)_n$—O— |
| optionally substituted —$C(O)(CH_2)_n C_{3-6}$ heterocycloalkylene-$(CH_2)_n$—C(O)— | optionally substituted —$C(O)(CH_2)_n C_{3-6}$ heterocycloalkenylene-$(CH_2)_n$—C(O)— | optionally substituted —$C(O)(CH_2)_n C_{1-6}$ alkynylene-$(CH_2)_n$—C(O)— |
| optionally substituted —$C(O)(CH_2)_n C_{3-6}$ heterocycloalkylene- | optionally substituted —$C(O)(CH_2)_n C_{3-6}$ heterocycloalkenylene- | optionally substituted —$C(O)(CH_2)_n C_{1-6}$ alkynylene-$(CH_2)_n$—C(O)— |

TABLE 1-continued

The linker structures.

| | | |
|---|---|---|
| $(CH_2)_n$—C(O)— | $(CH_2)_n$—C(O)— | |
| optionally substituted —OC(O)$(CH_2)_n$C$_{3-6}$ heterocycloalkylene-$(CH_2)_n$ | optionally substituted —OC(O)$(CH_2)_n$—C$_{3-6}$ heterocycloalkenylene-$(CH_2)_n$ | optionally substituted —OC(O)$(CH_2)_n$C$_{1-6}$ alkynylene-$(CH_2)_n$ |
| optionally substituted —O$(CH_2)_n$—C$_{3-6}$ heterocycloalkylene-$(CH_2)_n$ | optionally substituted —O$(CH_2)_n$—C$_{3-6}$ heterocycloalkenylene-$(CH_2)_n$ | optionally substituted —O$(CH_2)_n$—C$_{1-6}$ alkynylene-$(CH_2)_n$ |
| optionally substituted —OC(O)$(CH_2)_n$C$_{3-6}$ heterocycloalkylene-$(CH_2)_n$—O— | optionally substituted —OC(O)$(CH_2)_n$—C$_{3-6}$ heterocycloalkenylene-$(CH_2)_n$—O— | optionally substituted —OC(O)$(CH_2)_n$C$_{1-6}$ alkynylene-$(CH_2)_n$—O— |
| optionally substituted —O$(CH_2)_n$C$_{3-6}$ heterocycloalkylene-$(CH_2)_n$—O— | optionally substituted —O$(CH_2)_n$C$_{3-6}$ heterocycloalkenylene-$(CH_2)_n$—O— | optionally substituted —O$(CH_2)_n$C$_{1-6}$ alkynylene-$(CH_2)_n$—O— |
| optionally substituted —OC(O)$(CH_2)_n$C$_{3-6}$ heterocycloalkylene-$(CH_2)_n$—C(O)— | optionally substituted —OC(O)$(CH_2)_n$C$_{3-6}$ heterocycloalkenylene-$(CH_2)_n$—C(O)— | optionally substituted —OC(O)$(CH_2)_n$C$_{1-6}$ alkynylene-$(CH_2)_n$—C(O)— |
| optionally substituted —O$(CH_2)_n$—C$_{3-6}$ heterocycloalkylene-$(CH_2)_n$—C(O)— | optionally substituted —O$(CH_2)_n$—C$_{3-6}$ heterocycloalkenylene-$(CH_2)_n$—C(O)— | optionally substituted —O$(CH_2)_n$—C$_{1-6}$ alkynylene-$(CH_2)_n$—C(O)— |
| optionally substituted —C(O)NR$^{20}$$(CH_2)_n$—C$_{3-6}$ heterocycloalkylene-$(CH_2)_n$— | optionally substituted —C(O)NR$^{20}$$(CH_2)_n$—C$_{3-6}$ heterocycloalkenylene-$(CH_2)_n$— | optionally substituted —C(O)NR$^{20}$$(CH_2)_n$—C$_{1-6}$ alkynylene-$(CH_2)_n$— |
| optionally substituted —NR$^{20}$C(O)$(CH_2)_n$—C$_{3-6}$ heterocycloalkylene-$(CH_2)_n$— | optionally substituted —NR$^{20}$C(O)$(CH_2)_n$—C$_{3-6}$ heterocycloalkenylene-$(CH_2)_n$— | optionally substituted NR$^{20}$C(O)$(CH_2)_n$—C$_{1-6}$ alkynylene-$(CH_2)_n$— |
| optionally substituted —C(O)NR$^{20}$$(CH_2)_n$—C$_{3-6}$ heterocycloalkylene-$(CH_2)_n$—O— | optionally substituted —C(O)NR$^{20}$$(CH_2)_n$—C$_{3-6}$ heterocycloalkenylene-$(CH_2)_n$—O— | optionally substituted —C(O)NR$^{20}$$(CH_2)_n$—C$_{1-6}$ alkynylene-$(CH_2)_n$—O— |
| optionally substituted —NR$^{20}$C(O)$(CH_2)_n$—C$_{3-6}$ heterocycloalkylene-$(CH_2)_n$—O— | optionally substituted —NR$^{20}$C(O)$(CH_2)_n$—C$_{3-6}$ heterocycloalkenylene-$(CH_2)_n$—O— | optionally substituted —NR$^{20}$C(O)$(CH_2)_n$—C$_{1-6}$ alkynylene-$(CH_2)_n$—O— |
| optionally substituted —C(O)NR$^{20}$$(CH_2)_n$—C$_{3-6}$ heterocycloalkylene-$(CH_2)_n$—C(O)— | optionally substituted —C(O)NR$^{20}$$(CH_2)_n$—C$_{3-6}$ heterocycloalkenylene-$(CH_2)_n$—C(O)— | optionally substituted —C(O)NR$^{20}$$(CH_2)_n$—C$_{1-6}$ alkynylene-$(CH_2)_n$—C(O)— |
| optionally substituted —NR$^{20}$C(O)$(CH_2)_n$—C$_{3-6}$ heterocycloalkylene-$(CH_2)_n$—C(O)— | optionally substituted —NR$^{20}$C(O)$(CH_2)_n$—C$_{3-6}$ heterocycloalkenylene-$(CH_2)_n$—C(O)— | optionally substituted —NR$^{20}$C(O)$(CH_2)_n$—C$_{1-6}$ alkynylene-$(CH_2)_n$—C(O)— |

\* Each R$^{20}$ and R$^{21}$ is independently selected from the group consisting of hydrogen, hydroxy, OR$^{22}$, NR$^{23}$R$^{24}$, alkyl, arylalkyl,

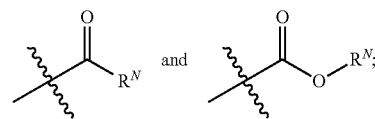

wherein R$^N$ is aryl, alkyl, or arylalkyl; wherein R$^{22}$, R$^{23}$, and R$^{24}$ are each independently hydrogen or alkyl.

In some embodiments, the FKBD-containing moiety before incorporated into the macrocycle can have a structure according to Formula (III) or an optically pure stereoisomer or pharmaceutically acceptable salt thereof.

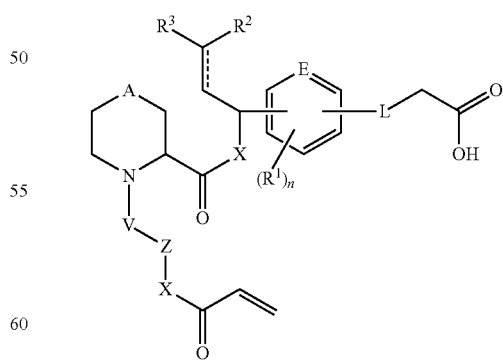

Formula (III)

Wherein L is selected from the structure in Table 1; A is CH$_2$, NH, O, or S; each X is independently O, NH, or NMe; E is CH or N; ═══ represents a single or a double bond. n is an integer selected from 0 to 4.

Each $R^1$ is selected from the group consisting of H, halogen, hydroxyl, $C_{1-20}$ alkyl, $N_3$, $NH_2$, $NO_2$, $CF_3$, $OCF_3$, $OCHF_2$, $COC_{1-20}$alkyl, and $CO_2C_{1-20}$alkyl. $R^2$ is selected from the group consisting of H, halogen, hydroxyl, $C_{1-20}$ alkyl, $N_3$, $NH_2$, $NO_2$, $CF_3$, $OCF_3$, $OCHF_2$, $COC_{1-20}$alkyl, and $CO_2C_{1-20}$alkyl. $R^3$ is selected from the group consisting of $C_{6-15}$aryl and $C_{1-10}$heteroaryl optionally substituted with H, halogen, hydroxyl, $N_3$, $NH_2$, $NO_2$, $CF_3$, $C_{1-10}$alkyl, substituted $C_{1-10}$alkyl, $C_{1-10}$alkoxy, substituted $C_{1-10}$alkoxy, acyl, acylamino, acyloxy, acyl $C_{1-10}$alkyloxy, amino, substituted amino, aminoacyl, aminocarbonyl $C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester)amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, substituted $C_{1-10}$alkylthio, and thiocarbonyl.

V is

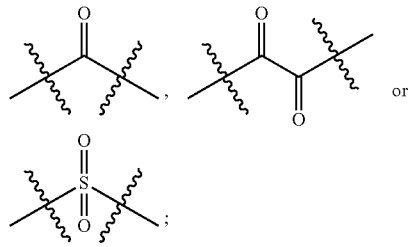

Z is a bond,

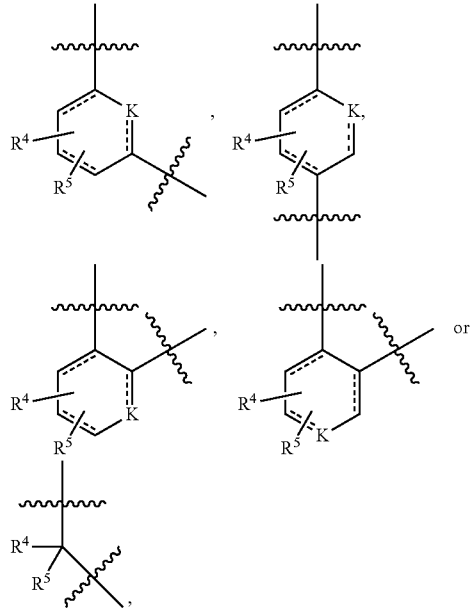

wherein $R^4$ and $R^5$ are each independently selected from the group consisting of of hydrogen, hydroxy, halo, alkyl, alkoxy, cycloalkyl, cyano, alkylthio, amino, alkylamino, and dialkylamino; K is O, $CHR^6$, $CR^6$, N, and $NR^6$, wherein $R^6$ is hydrogen or alkyl.

In some embodiments, the FKBD-containing moiety before incorporated into the macrocycle can have a structure according to Formula (IV) or an optically pure stereoisomer or pharmaceutically acceptable salt thereof.

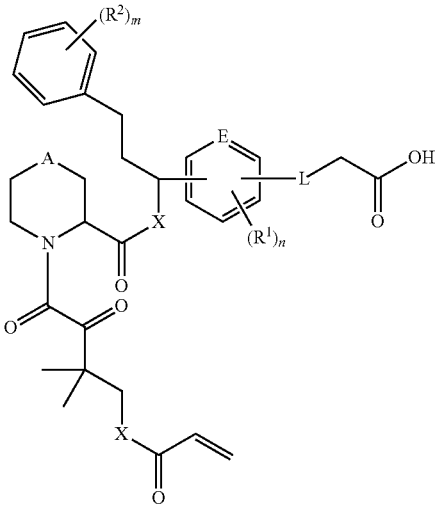

Formula (IV)

Wherein L is selected from the structures in Table 1; A is $CH_2$, NH, O, or S; each X is independently O or NH; E is CH or N; each $R^1$ is selected from the group consisting of H, halogen, hydroxyl, $C_{1-20}$ alkyl, $N_3$, $NH_2$, $NO_2$, $CF_3$, $OCF_3$, $OCHF_2$, $COC_{1-20}$alkyl, and $CO_2C_{1-20}$alkyl; each $R^2$ is selected from the group consisting of H, halogen, hydroxyl, $N_3$, $NH_2$, $NO_2$, $CF_3$, $C_{1-10}$alkyl, substituted $C_{1-10}$alkyl, $C_{1-10}$alkoxy, substituted $C_{1-10}$alkoxy, acyl, acylamino, acyloxy, acyl $C_{1-10}$alkyloxy, amino, substituted amino, aminoacyl, aminocarbonyl $C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester)amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, substituted $C_{1-10}$alkylthio, and thiocarbonyl; n is an integer selected from 0 to 4; and m is an integer selected from 0 to 5.

In some embodiments, the Rapafucin compounds in the present disclosure can have a structure according to Formula (V) or an optically pure stereoisomer or pharmaceutically acceptable salt thereof.

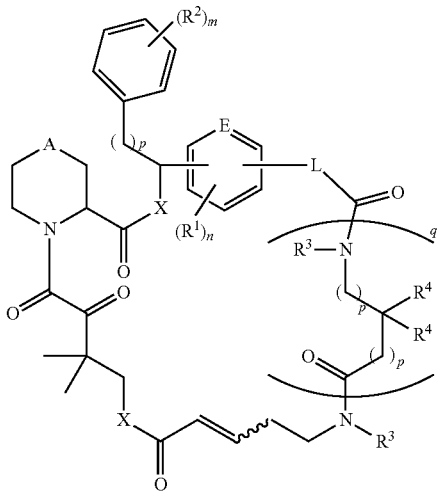

Formula (V)

Wherein L is selected from the groups in Table 1; A is CH$_2$, NH, NMe, O, S(O)$_2$ or S; each X is independently O, NMe, or NH; E is CH or N.

Each of R$^1$, R$^2$, R$^3$, and R$^4$ can be independently selected from the group consisting of H, halogen, hydroxyl, N$_3$, NH$_2$, NO$_2$, CF$_3$, OCF$_3$, OCHF$_2$, COC$_{1-20}$alkyl, CO$_2$C$_{1-20}$alkyl, C$_{3-8}$cycloalkyl, C$_{2-8}$alkenyl, C$_{2-8}$alkynyl, C$_{1-10}$alkoxy, C$_{6-15}$aryl, C$_{6-15}$aryloxy, C$_{6-15}$arylthio, C$_{2-10}$carboxyl, C$_{1-10}$alkylamino, thiol, C$_{1-10}$alkyldisulfide, C$_{6-15}$arylthio, C$_{1-10}$heteroarylthio, (C$_{3-8}$cycloalkyl)thio, C$_{2-10}$heterocyclylthio, sulfonyl, C$_{1-10}$alkylsulfonyl, amido, C$_{1-10}$alkylamido, selenol, C$_{1-10}$alkylselenol, C$_{6-15}$arylselenol, C$_{1-10}$heteroarylselenol, (C$_{3-8}$cycloalkyl)selenol, C$_{2-10}$heterocyclylselenol, guanidino, C$_{1-10}$alkylguanidino, urea, C$_{1-10}$alkylurea, ammonium, C$_{1-10}$alkylammonium, cyano, C$_{1-10}$alkylcyano, C$_{1-10}$alkylnitro, adamantine, phosphonate, C$_{1-10}$alkylphosphonate, and C$_{6-15}$arylphosphonate, each of the above can be optionally substituted with H, halogen, hydroxyl, N$_3$, NH$_2$, NO$_2$, CF$_3$, C$_{1-20}$alkyl, substituted C$_{1-20}$alkyl, C$_{1-10}$alkoxy, substituted C$_{1-10}$alkoxy, acyl, acylamino, acyloxy, acyl C$_{1-10}$alkyloxy, amino, substituted amino, aminoacyl, aminocarbonyl aminocarbonylamino, aminodicarbonylamino, aminocarbonyloxy, aminosulfonyl, C$_{6-15}$aryl, substituted C$_{6-15}$aryl, C$_{6-15}$aryloxy, substituted C$_{6-15}$aryloxy, C$_{6-15}$arylthio, substituted C$_{6-15}$arylthio, carboxyl, carboxyester, (carboxyester)amino, (carboxyester)oxy, cyano, C$_{3-8}$cycloalkyl, substituted C$_{3-8}$cycloalkyl, (C$_{3-8}$cycloalkyl)oxy, substituted (C$_{3-8}$cycloalkyl)oxy, (C$_{3-8}$cycloalkyl)thio, substituted (C$_{3-8}$cycloalkyl)thio, halo, hydroxyl, C$_{1-10}$heteroaryl, substituted C$_{1-10}$heteroaryl, C$_{1-10}$heteroaryloxy, substituted C$_{1-10}$heteroaryloxy, C$_{1-10}$heteroarylthio, substituted C$_{1-10}$heteroarylthio, C$_{2-10}$heterocyclyl, C$_{2-10}$substituted heterocyclyl, C$_{2-10}$heterocyclyloxy, substituted C$_{2-10}$heterocyclyloxy, C$_{2-10}$heterocyclylthio, substituted C$_{2-10}$heterocyclylthio, imino, oxo, sulfonyl, sulfonylamino, thiol, C$_{1-10}$alkylthio, substituted C$_{1-10}$alkylthio, and thiocarbonyl.

Or any R$^4$ forms a cyclic structure formed with any R$^3$, the cyclic structure is selected from the group consisting of C$_{2-10}$heterocyclyl and C$_{1-10}$heteroaryloptionally substituted with H, halogen, hydroxyl, N$_3$, NH$_2$, NO$_2$, CF$_3$, C$_{1-10}$alkyl, substituted C$_{1-10}$alkyl substituted C$_{1-10}$alkoxy, acyl, acylamino, acyloxy, acyl C$_{1-10}$alkyloxy, amino, substituted amino, aminoacyl, aminocarbonyl C$_{1-10}$alkyl, aminocarbonylamino, aminodicarbonylamino, aminocarbonyloxy, aminosulfonyl, C$_{6-15}$aryl, substituted C$_{6-15}$aryl, C$_{6-15}$aryloxy, substituted C$_{6-15}$aryloxy, C$_{6-15}$arylthio, substituted C$_{6-15}$arylthio, carboxyl, carboxyester, (carboxyester)amino, (carboxyester)oxy, cyano, C$_{3-8}$cycloalkyl, substituted C$_{3-8}$cycloalkyl, (C$_{3-8}$cycloalkyl)oxy, substituted (C$_{3-8}$cycloalkyl)oxy, (C$_{3-8}$cycloalkyl)thio, substituted (C$_{3-8}$cycloalkyl)thio, halo, hydroxyl, C$_{1-10}$heteroaryl, substituted C$_{1-10}$heteroaryl, C$_{1-10}$heteroaryloxy, substituted C$_{1-10}$heteroaryloxy, C$_{1-10}$heteroarylthio, substituted C$_{1-10}$heteroarylthio, C$_{2-10}$heterocyclyl, C$_{2-10}$substituted heterocyclyl, C$_{2-10}$heterocyclyloxy, substituted C$_{2-10}$heterocyclyloxy, C$_{2-10}$heterocyclylthio, substituted C$_{2-10}$heterocyclylthio, imino, oxo, sulfonyl, sulfonylamino, thiol, C$_{1-10}$alkylthio, substituted C$_{1-10}$alkylthio, and thiocarbonyl.

n is an integer selected from 0 to 4; m is an integer selected from 0 to 5; each p is an integer independently selected from 0 to 2; q is an integer selected from 1 to 10.

In some embodiments, q can be 1. In some embodiments, q can be 2. In some embodiments, q can be 3. In some embodiments, q can be 4. In some embodiments, q can be 5. In some embodiments, q can be 6. In some embodiments, q can be 7. In some embodiments, q can be 8. In some embodiments, q can be 9. In some embodiments, q can be 10. In specific embodiments, q is 3 or 4.

In some embodiments, the Rapafucin compounds in the present disclosure can have a structure according to Formula (VI) or an optically pure stereoisomer or pharmaceutically acceptable salt thereof.

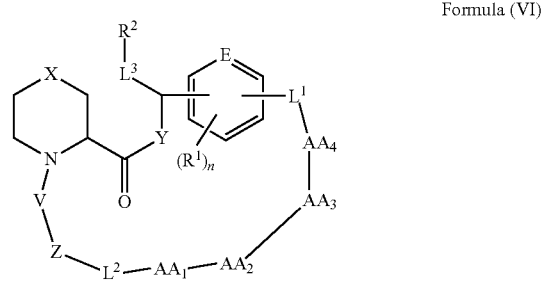

Formula (VI)

Each L$^1$, L$^2$, or L$^3$ can be independently selected from the linker structures in Table 1. Each AA$_1$, AA$_2$, AA$_3$, or AA$_4$ can be independently selected from the amino acid monomers shown in Table 3 below. X can be CH$_2$, NH, O, or S; Y can be O, NH, or N-alkyl; E can be CH or N; n is an integer selected from 0 to 4. Amino acids can be either N—C linked or C—N linked.

Each R$^1$ is selected from the group consisting of H, halogen, hydroxyl, C$_{1-20}$ alkyl, N$_3$, NH$_2$, NO$_2$, CF$_3$, OCF$_3$, OCHF$_2$, COC$_{1-20}$alkyl, and CO$_2$C$_{1-20}$alkyl. R$^2$ is selected from the group consisting of C$_{6-15}$aryl and C$_{1-10}$heteroaryl optionally substituted with H, halogen, hydroxyl, N$_3$, NH$_2$, NO$_2$, CF$_3$, C$_{1-10}$alkyl, substituted C$_{1-10}$alkyl, C$_{1-10}$alkoxy, substituted C$_{1-10}$alkoxy, acyl, acylamino, acyloxy, acyl C$_{1-10}$alkyloxy, amino, substituted amino, aminoacyl, aminocarbonyl C$_{1-10}$alkyl, aminocarbonylamino, aminodicarbonylamino, aminocarbonyloxy, aminosulfonyl, C$_{6-15}$aryl, substituted C$_{6-15}$aryl, C$_{6-15}$aryloxy, substituted C$_{6-15}$aryloxy, C$_{6-15}$arylthio, substituted C$_{6-15}$arylthio, carboxyl, carboxyester, (carboxyester)amino, (carboxyester)oxy, cyano, C$_{3-8}$cycloalkyl, substituted C$_{3-8}$cycloalkyl, (C$_{3-8}$cycloalkyl)oxy, substituted (C$_{3-8}$cycloalkyl)oxy, (C$_{3-8}$cycloalkyl)thio, substituted (C$_{3-8}$cycloalkyl)thio, C$_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, substituted $C_{1-10}$alkylthio, and thiocarbonyl.

V is

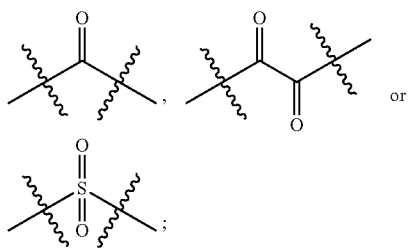

Z is a bond,

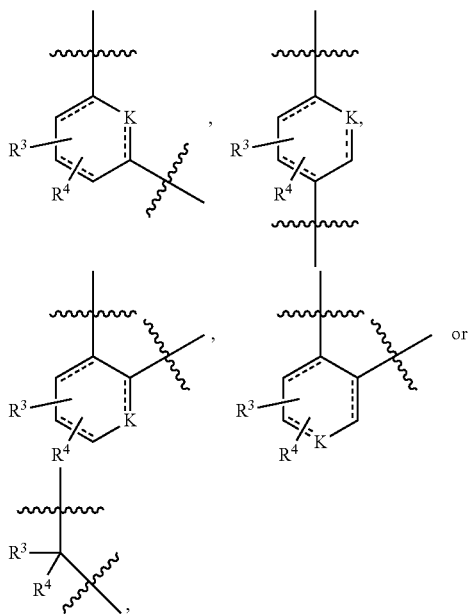

wherein $R^3$ and $R^4$ are each independently selected from the group consisting of of hydrogen, hydroxy, halo, alkyl, alkoxy, cycloalkyl, cyano, alkylthio, amino, alkylamino, and dialkylamino; K is O, $CHR^5$, $CR^5$, N, and $NR^5$, wherein $R^5$ is hydrogen or alkyl.

Synthetic route to Rapafucins. There are several methods for the synthesis of rapafucins including both solid and solution phase synthesis. These methods can result in modifications to the linker(s) and/or the effector domain which include alkylations, amide bond formations, double bond metathesis, oxadiazole formation, triazole formations, dithiol formations, sulfone formations, Diels-Alder cycloadditions, and others.

We applied solid-phase peptide synthesis to assemble the polypeptide effector domains. The pre-assembled FKBD capped with a carboxylic acid at one end and an olefin at the other was subsequently coupled to the polypeptide that remained tethered on beads. To facilitate purification of the newly formed macrocycles, we adopted a coupled macrocyclization and cyclative release strategy whereby the macrocyclization is accompanied by the concurrent release of the macrocyclic products from the solid beads. One skilled in the art can contemplate different macrocyclization methods for the synthesis of Rapafucin molecules in the present disclosure. In some embodiments, a ring-closing metathesis/cyclative release (RCM) is used. In some embodiments, macrolactamization can be used for efficient parallel synthesis of different Rapafucins. A cis-$C_6$ linker can be used for construction of Rapafucin libraries. A combination of medium temperature and catalyst loading (140° C., 30 mol % Hoveyda-Grubbs II catalyst) for the ensuing large-scale synthesis of Rapafucin libraries.

Other ring-closing methods can be used to synthesize the Rapafucin molecules disclosed herein. Exemplary methods can include, but not limited to aminolysis, chemoenzymatic method, click chemistry, macrocyclization through ring contraction using auxiliary groups, macrocylization mediated through sulfur containing groups, macrocylization via cycloaddition, macrocylization via Wittiga or Wittig like reactions, macrocylization from multicomponent reactions, metal-assisted macrocylization, macrocylization through C—N bond formation, macrocylization through C—O bond formation, alkylation with or without metal assistance, intramolecular cyclopropanation, oxidative coupling of arenes, side chain cyclization, and oxidative coupling of arenes. Each of these macrocyclization method can be conducted in solid phase or solution phase. The macrocyclization reactions through ring contraction using auxiliary groups can include, but not limited to using hydroxyl benzaldehyde, using hydroxyl nitro phenol, and using nitro vinyl phenol. The macrocylization reactions mediated through sulfur containing groups can include, but not limited to thiazolidine formation O to N acyl transfer, transesterification S to N acyl transfer, ring chain tautomerization S to N acyl transfer, Staudinger ligation ring contraction, bis-thiol-ene macrocyclization, thiol-ene macrocyclization, thiolalkylation, and disulfide formation. The macrocyclization reactions via cycloaddtion can include, but not limited to phosphorene-azide ligation and oxadiazole graft. Metal assisted macrocyclization can include, but not limited to C—C bond formation, Suzuki coupling, Sonogashira coupling, Tasuji-Trost reaction, Glaser-Hay coupling, and Nickel catalyzed macrocylication. Macrocyclization reactions via C—N bond formation can include, but not limited to Ullmann coupling and Buchwald-Hartwig animation. Macrocyclization reactions via C—O bond formation can include, but not limited to Chan-Lam-Evans coupling, C—H activation, and Ullmann coupling. Macrocyclization reactions via alkylation can include enolate chemistry, Williamson etherification, Mitsunobu reaction, aromatic nucleophilic substitution (SNAr), and Friedel-Crafts type alkylation.

In some embodiments, Rapafucin molecules can be cyclized using the methods described in Marsault, E., & Peterson, M. L. (Eds.). (2017). Practical Medicinal Chemistry with Macrocycles: Design, Synthesis, and Case Studies, which is hereby incorporate d by reference in its entirety. Some non-limiting examples of the macrocyclization methods are shown in Table 2 below, each n can be independently an integer selected from 0 to 10.

TABLE 2

Additional macrocyclization methods that can be used for Rapafucin synthesis.

| Macrocyclization reactions | Reaction scheme |
|---|---|
| Cyclization by intramolecular aminolysis | 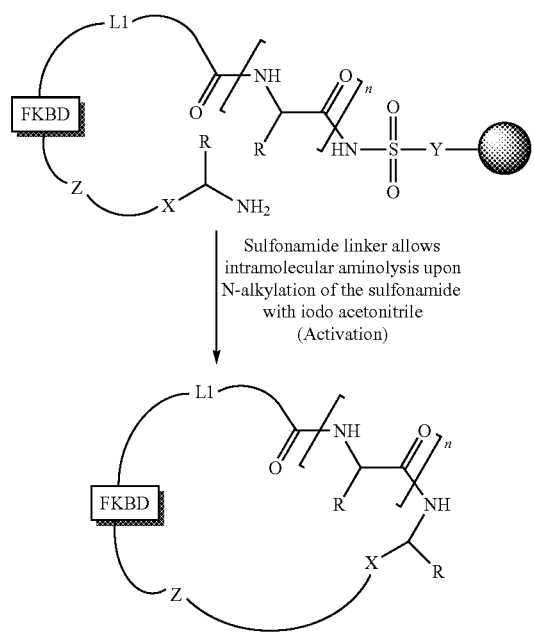<br>Sulfonamide linker allows intramolecular aminolysis upon N-alkylation of the sulfonamide with iodo acetonitrile (Activation) |
| Macrocyclization via Chemoenzymatic methods | 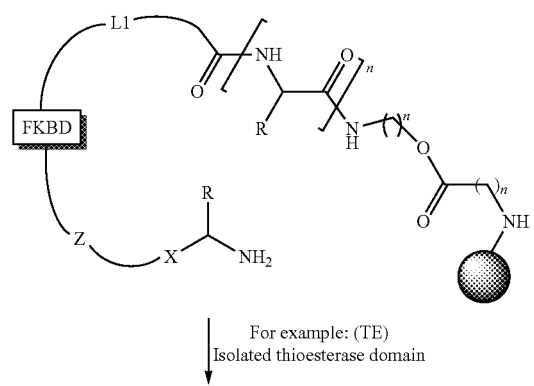<br>For example: (TE) Isolated thioesterase domain<br>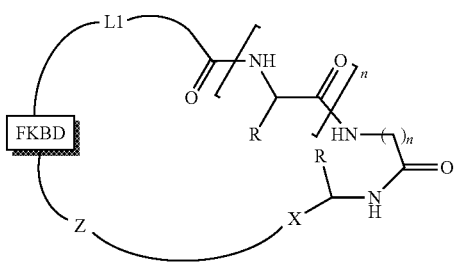 |

TABLE 2-continued

Additional macrocyclization methods that can be used for Rapafucin synthesis.

| Macrocyclization reactions | Reaction scheme |
|---|---|
| Cyclization by intramolecular aminolysis-II | 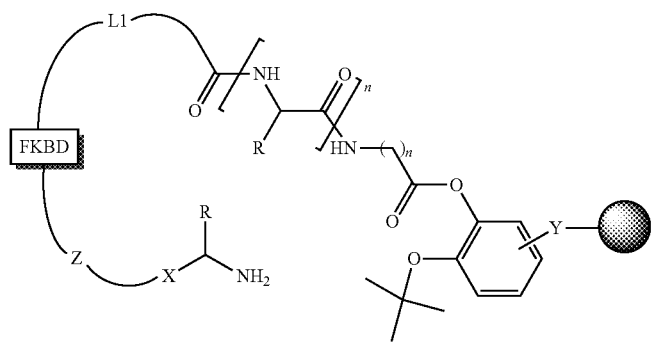<br>mono-O-tert-butyl-protected catechol linker undergo cyclative cleavage after activation with TFA to remove the t-butyl ether<br>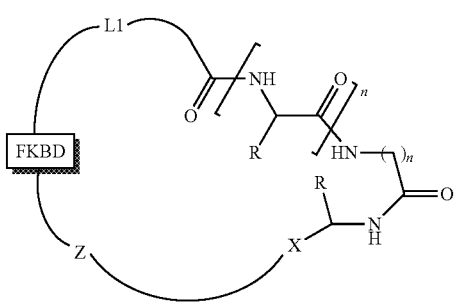 |
| Macrocyclization through ring contraction using auxiliary groups-using hydroxyl benzaldehyde | 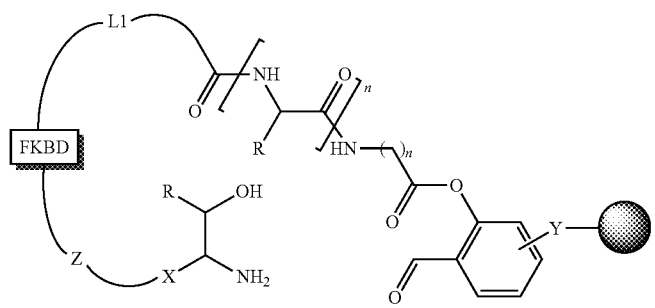<br>Imine formation<br>O to N Acyl transfer<br>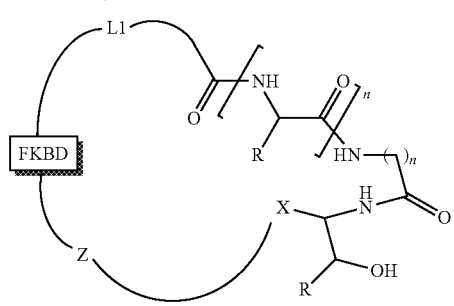 |

TABLE 2-continued
Additional macrocyclization methods that can be used for Rapafucin synthesis.
| Macrocyclization reactions | Reaction scheme |
|---|---|
| Macrocyclization through ring contraction using auxiliary groups- using hydroxyl nitro phenol | 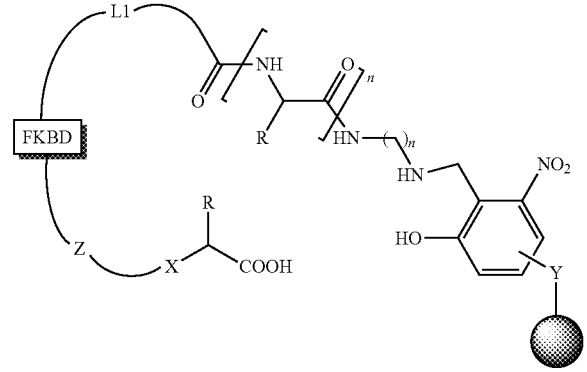 |
| Macrocyclization through ring contraction using auxiliary groups- using nitro vinyl phenol | 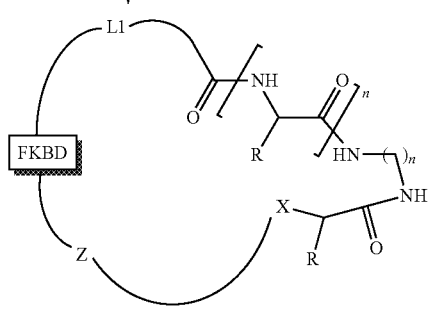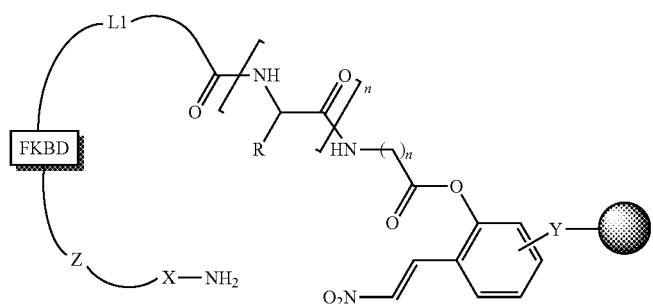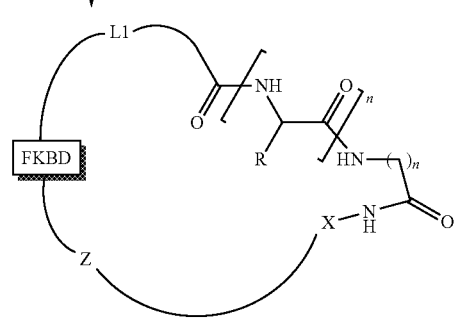 |

TABLE 2-continued

Additional macrocyclization methods that can be used for Rapafucin synthesis.

| Macrocyclization reactions | Reaction scheme |
|---|---|
| Macrocyclization mediated through sulfur containing groups- via thiazolidine formation O to N acyl transfer | 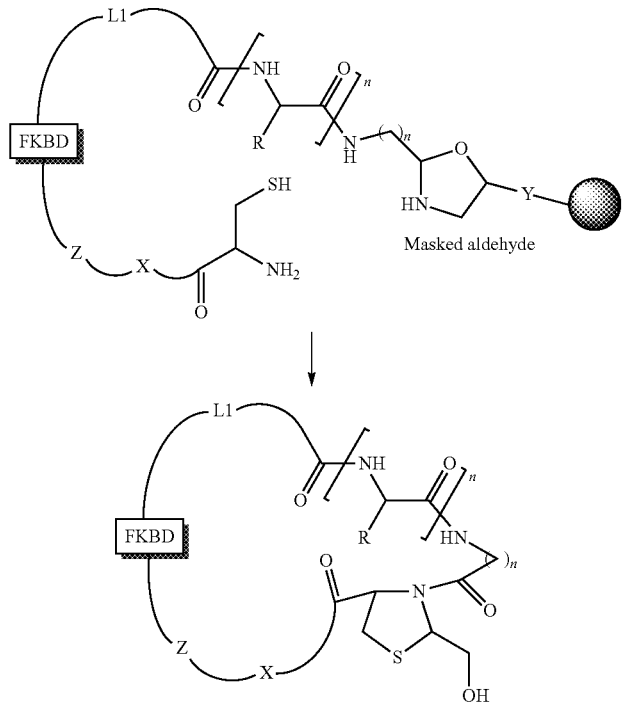 |
| Macrocyclization mediated through sulfur containing groups-via transesterification S to N acyl transfer | 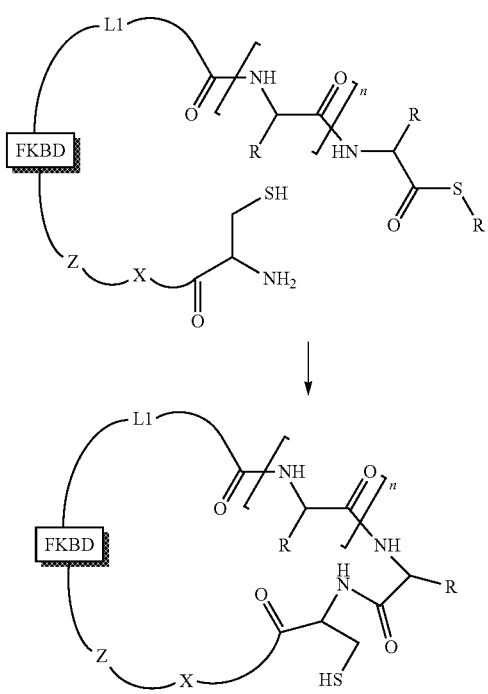 |

TABLE 2-continued

Additional macrocyclization methods that can be used for Rapafucin synthesis.

| Macrocyclization reactions | Reaction scheme |
|---|---|
| Macrocyclization mediated through sulfur containing groups- via ring chain tautomerization S to N acyl transfer | 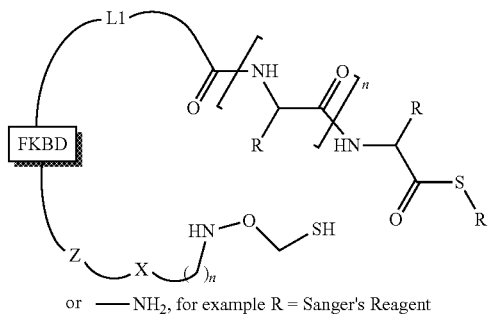<br>or ——NH₂, for example R = Sanger's Reagent<br>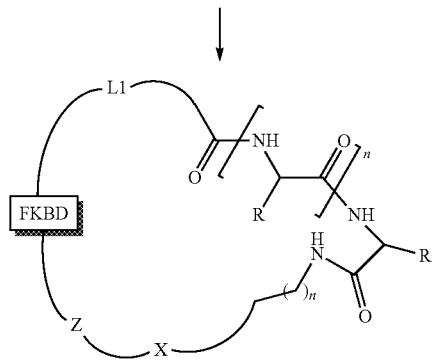 |
| Macrocyclization mediated through sulfur containing groups- Staudinger ligation ring contraction | 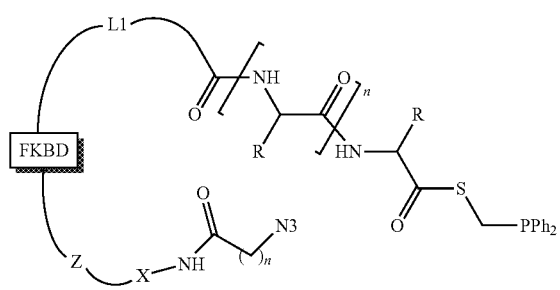<br>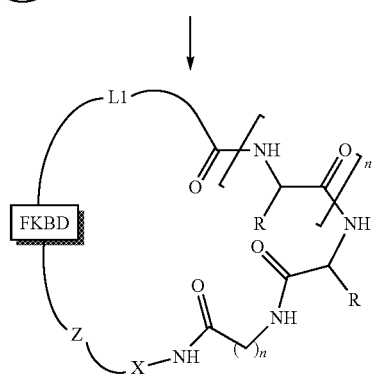 |

TABLE 2-continued
Additional macrocyclization methods that can be used for Rapafucin synthesis.
| Macro-cyclization reactions | Reaction scheme |
|---|---|
| Macrocyclization mediated through sulfur containing groups-bisthiolene macrocyclization | 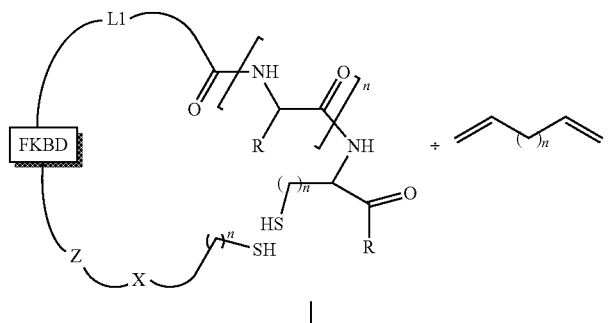 |
| Macrocyclization mediated through sulfur containing groups-thiol-ene macrocyclization | 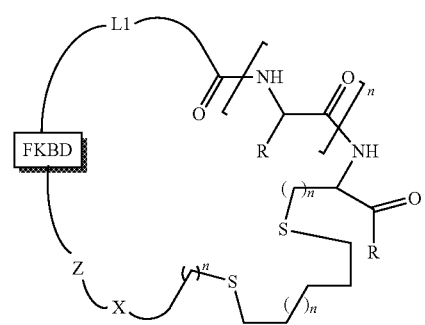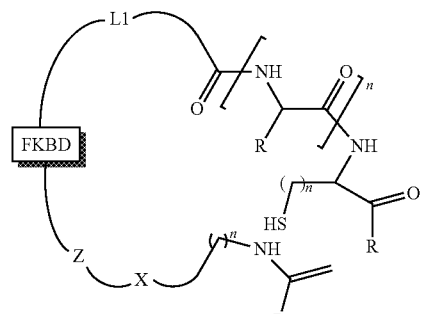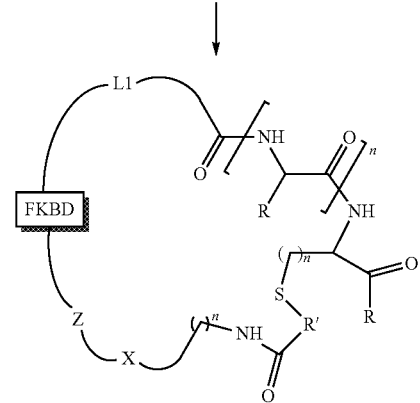 |

TABLE 2-continued
Additional macrocyclization methods that can be used for Rapafucin synthesis.
| Macrocyclization reactions | Reaction scheme |
|---|---|
| Macrocyclization mediated through sulfur containing groups-thioalkylation | 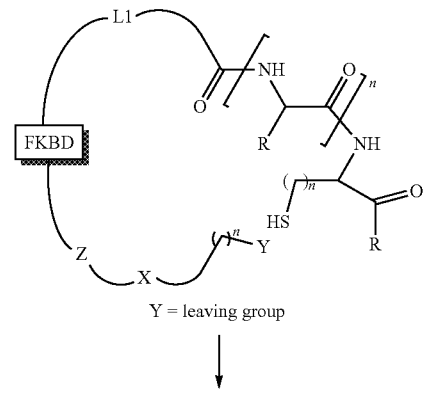<br>Y = leaving group |
| Macrocyclization mediated through sulfur containing groups-disulfide formation | 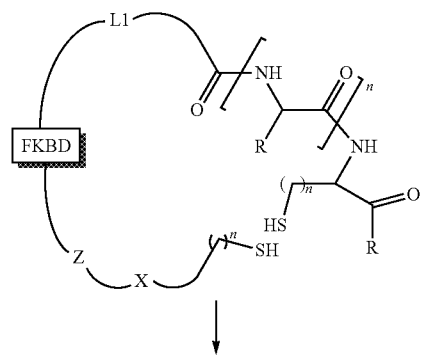<br>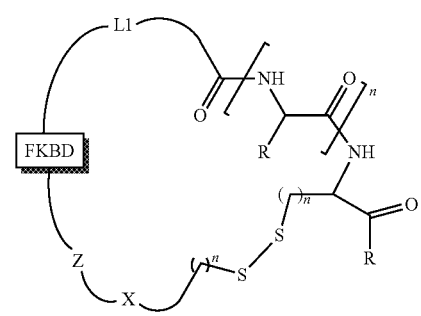 |

TABLE 2-continued

Additional macrocyclization methods that can be used for Rapafucin synthesis.

| Macrocyclization reactions | Reaction scheme |
|---|---|
| Macrocyclization via cycloaddition-phosphorene-azide ligation | |
| Macrocyclization via azide-alkyne cycloaddition-1,3-dipolar Huisgen cycloaddition | |
| Macrocyclization via cycloaddition-oxadiazole graft using (N-isocyanimino) triphenylphosphorane | |

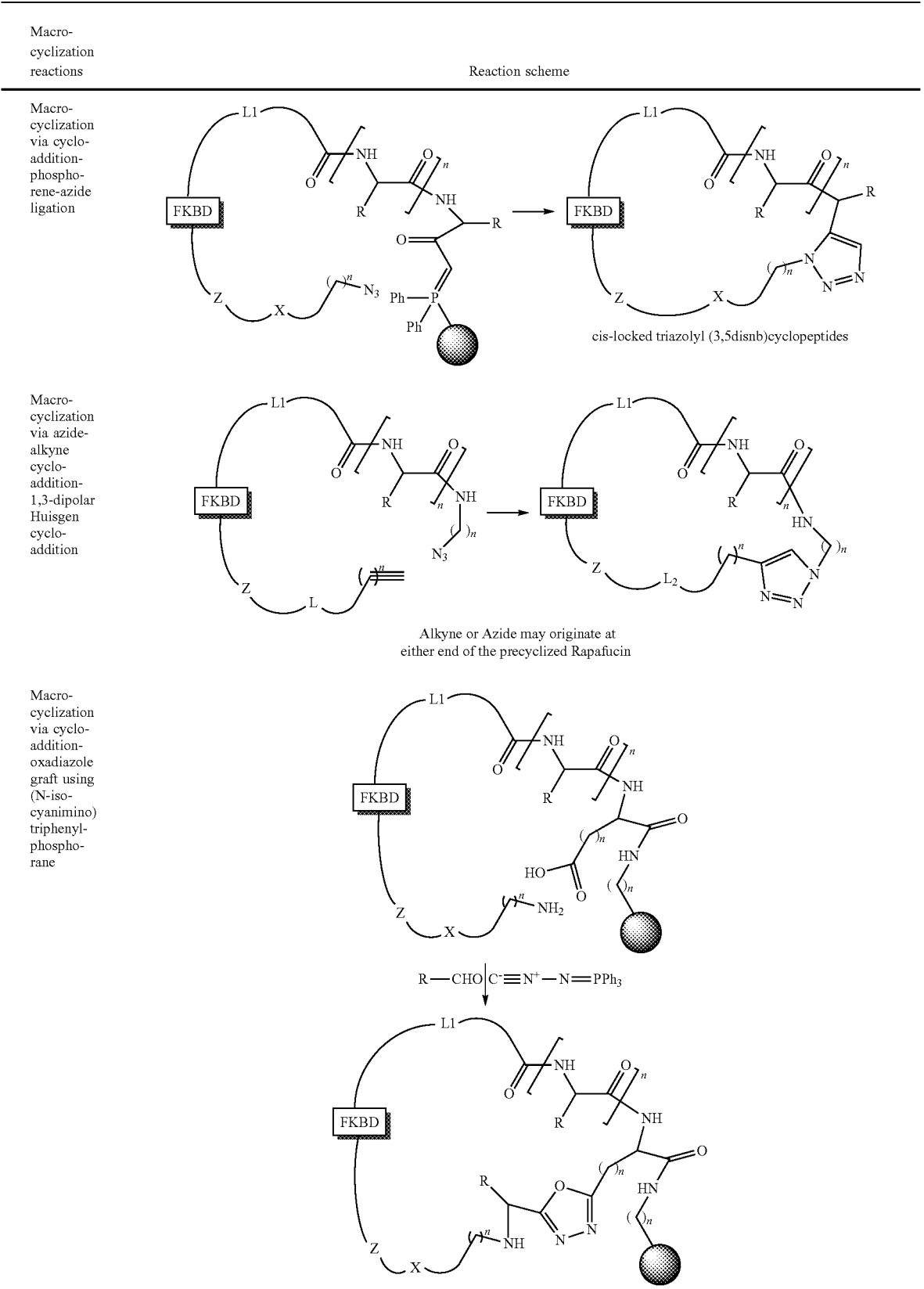

TABLE 2-continued

Additional macrocyclization methods that can be used for Rapafucin synthesis.

| Macro-cyclization reactions | Reaction scheme |
|---|---|
| Macro-cyclization via Wittig or Horner-Wadsworth-Emmons or Masamune-Roush reactions or Still-Gennari olefination | 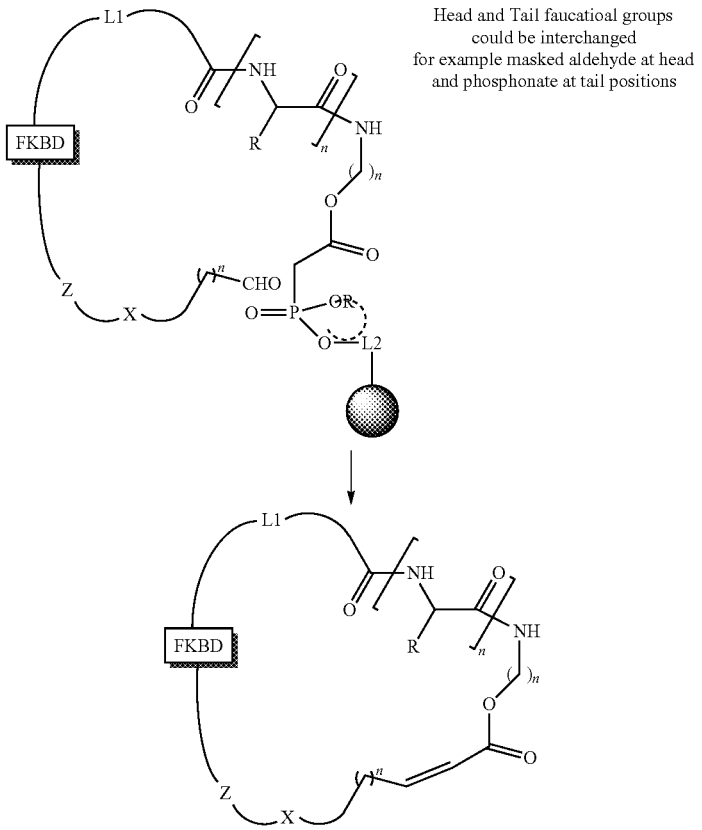 Head and Tail faucatioal groups could be interchanged for example masked aldehyde at head and phosphonate at tail positions |
| Macro-cyclization from multi-component reactions | 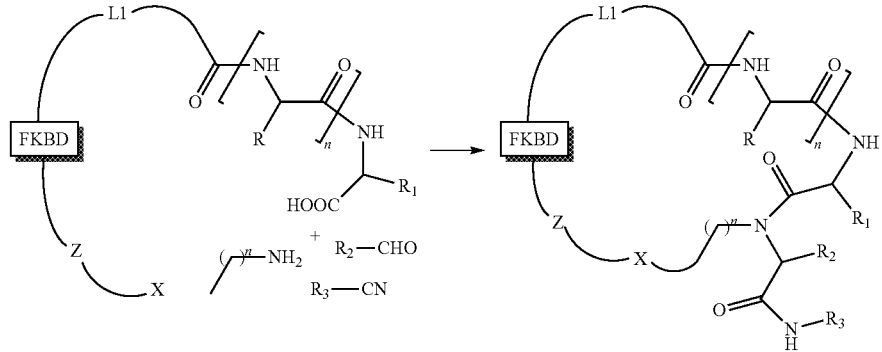 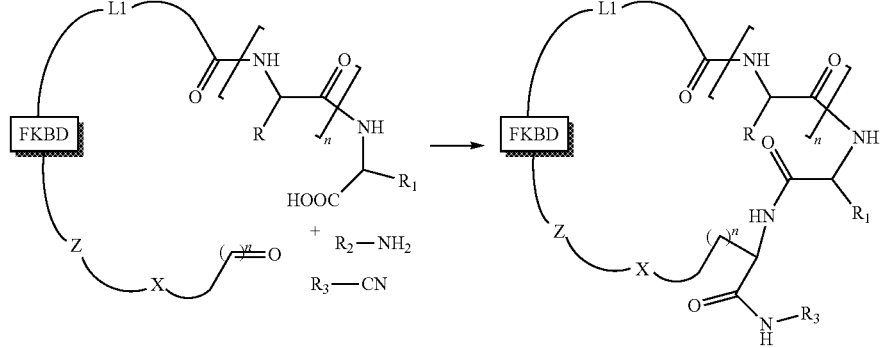 |

TABLE 2-continued
Additional macrocyclization methods that can be used for Rapafucin synthesis.
Macro-
cyclization
reactions      Reaction scheme
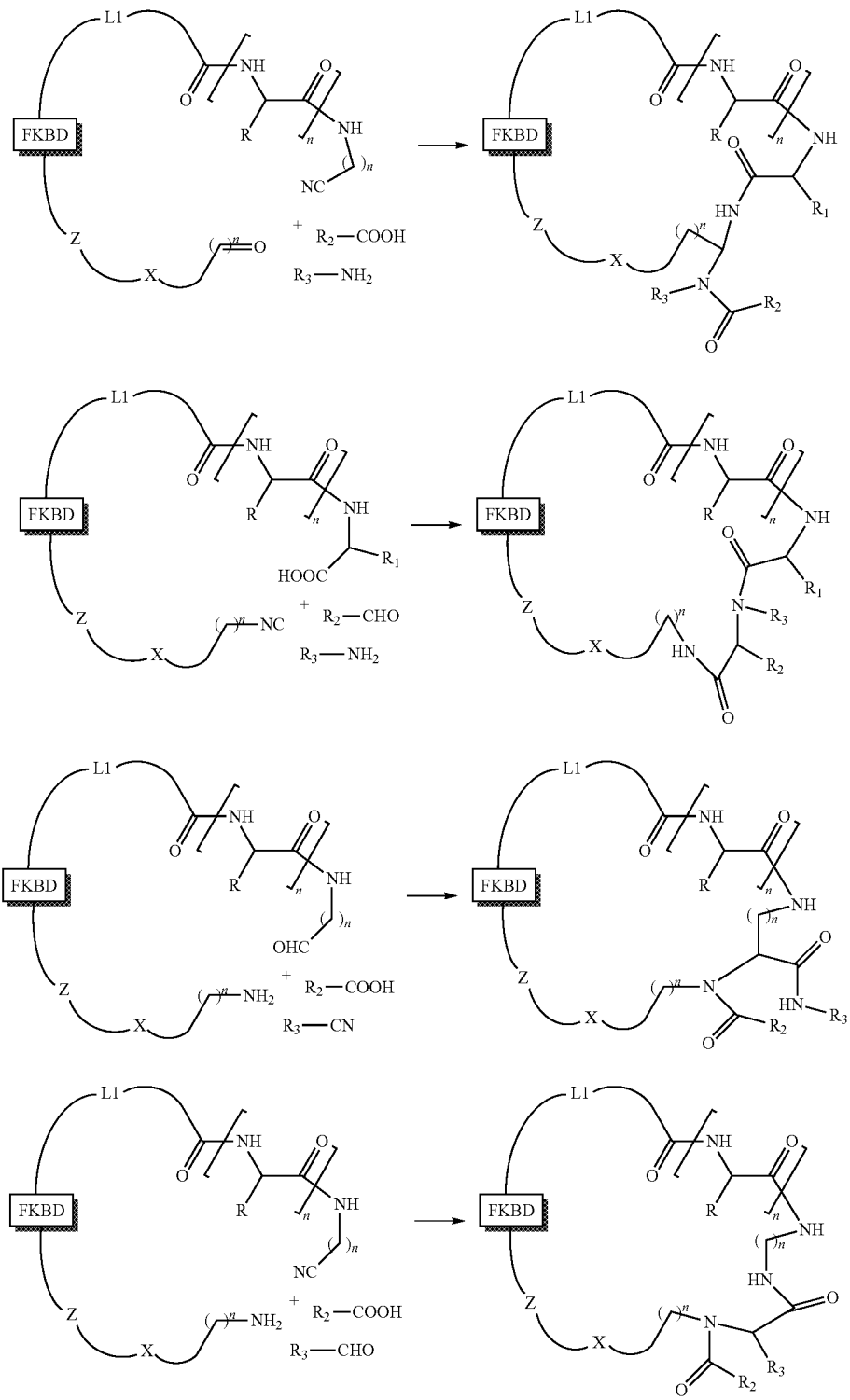

TABLE 2-continued

Additional macrocyclization methods that can be used for Rapafucin synthesis.

| Macrocyclization reactions | Reaction scheme |
|---|---|
| Metal assisted macrocyclization- C—C bond formation (Metals include Pd, Ni, Cu, Ru, or Au) | 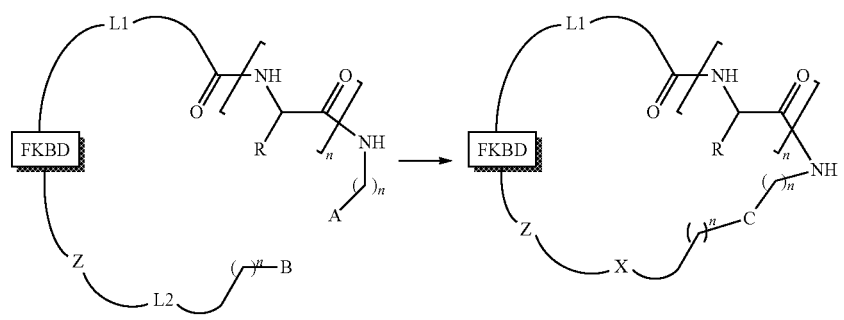 A = Allyl, Alkenyl, Aryl<br>B = halides (Cl, Br, I), pseudohalides (OTf, OPO(OR)$_2$ or SnR$_3$)<br>C = a functional group after reaction between A and B |
| Metal assisted macrocylization C=C bond formation (Metals include Pd, Ni, Cu, Ru, or Au) | 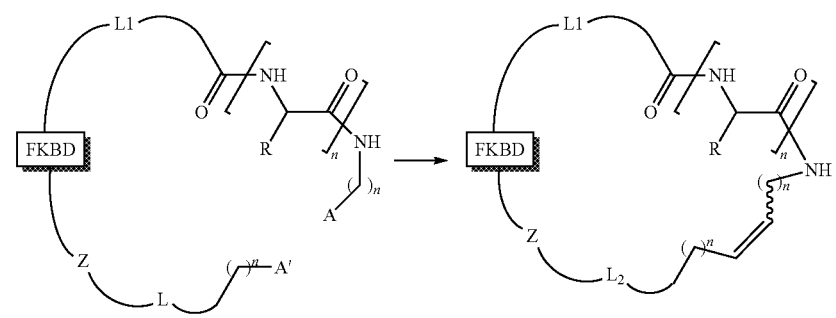 A = Substituted or unsubstituted alkene |
| Metal assisted macrocyclization- Suzuki coupling | 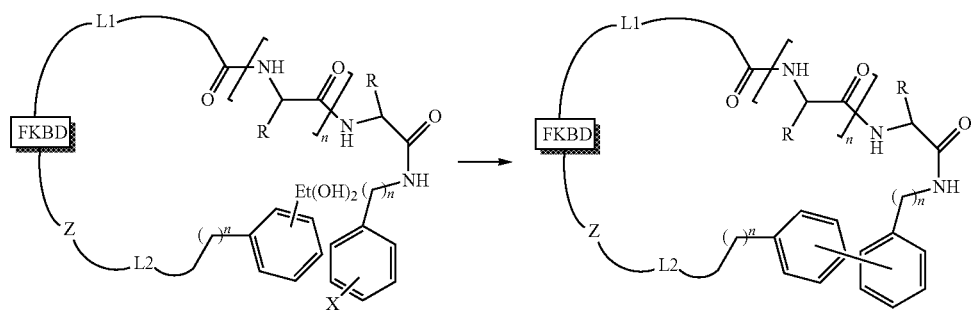 |
| Metal assisted macrocyclization- Sonogashira coupling | 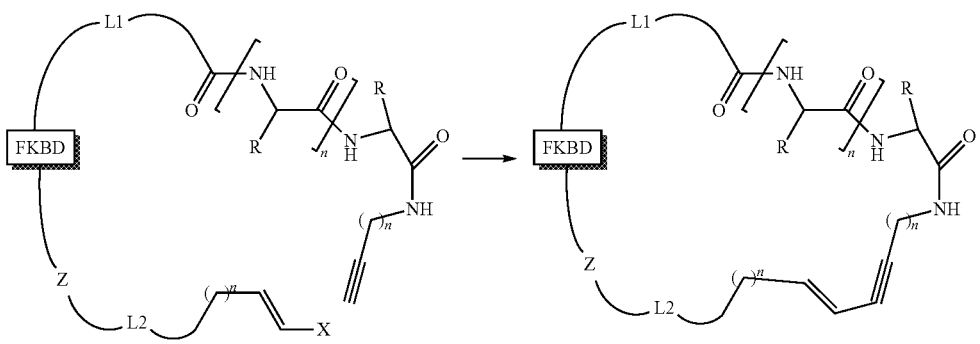 |

TABLE 2-continued

Additional macrocyclization methods that can be used for Rapafucin synthesis.

| Macrocyclization reactions | Reaction scheme |
|---|---|
| Metal assisted macrocyclization-Tsuji-Trost reaction | allylations of nucleophiles |
| Metal assisted macrocyclization-Glaser-Hay coupling | cyclization of dialkynes |
| Metal assisted macrocyclization-Nickel catalyzed macrocyclization | |
| Macrocyclization via C—N bond formation-Ullmann coupling | |

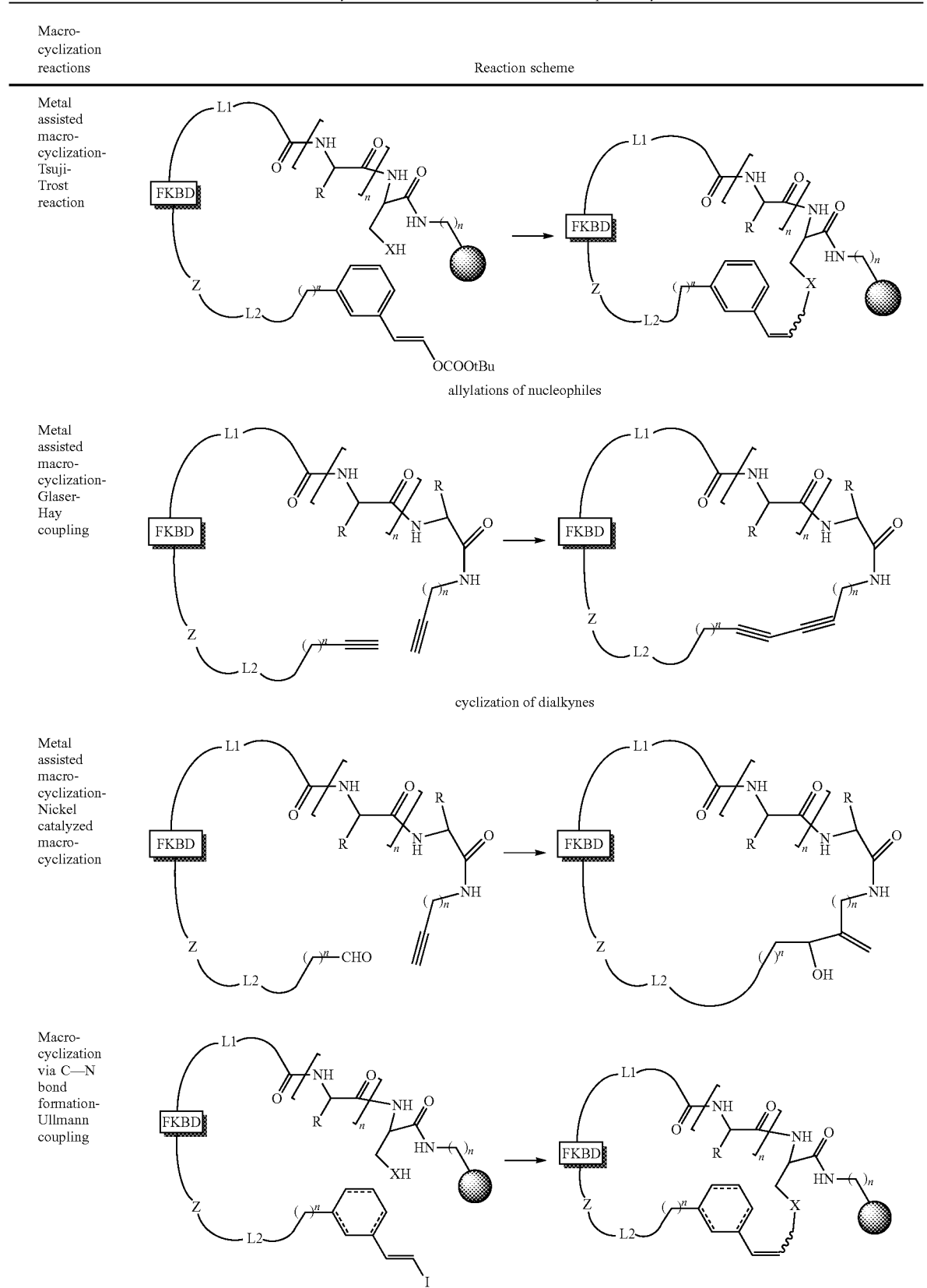

TABLE 2-continued

Additional macrocyclization methods that can be used for Rapafucin synthesis.

| Macro-cyclization reactions | Reaction scheme |
|---|---|
| Macrocyclization via C—N bond formation-Buchwald-Hartwig amination | 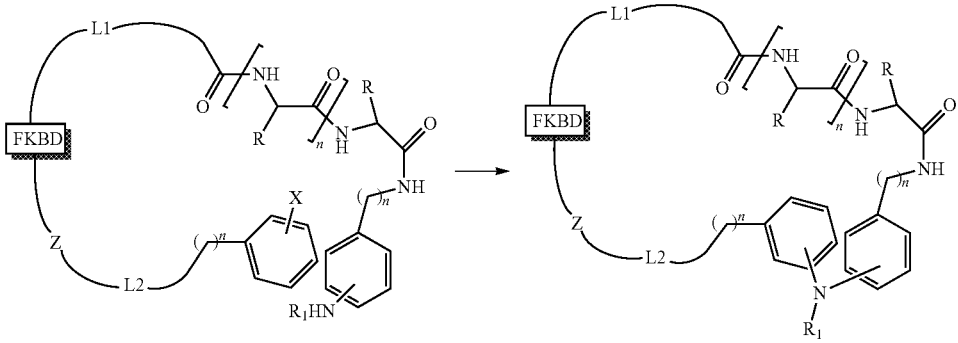 |
| Macrocyclization via C—N bond formation-Chan-Lam-Evans coupling | 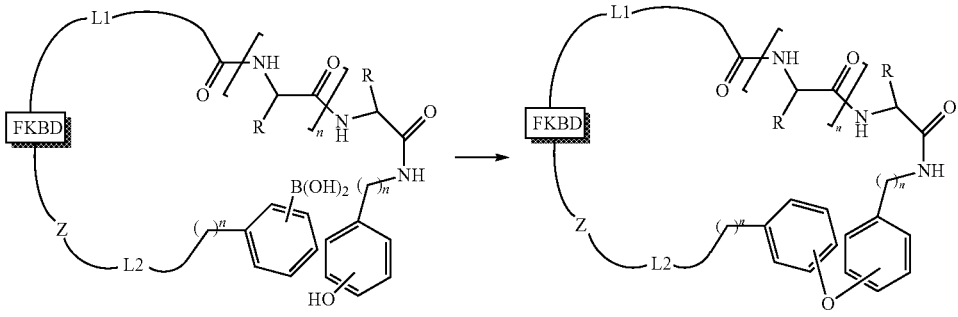 |
| Macrocyclization via C—N bond formation-C—H activation | 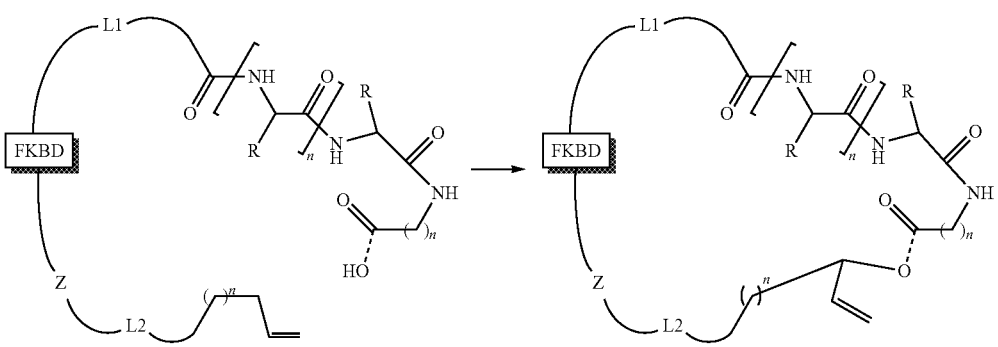 |
| Macrocyclization via C—N bond formation-Ullmann coupling | 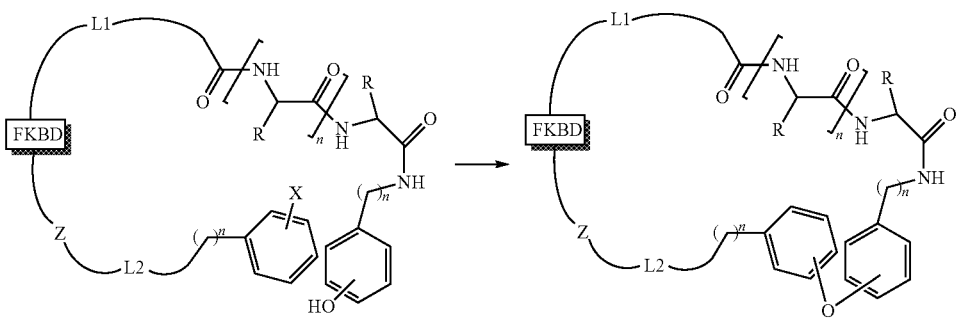 |

TABLE 2-continued

Additional macrocyclization methods that can be used for Rapafucin synthesis.

| Macrocyclization reactions | Reaction scheme |
|---|---|
| Macrocyclization via alkylation-enolate chemistry | 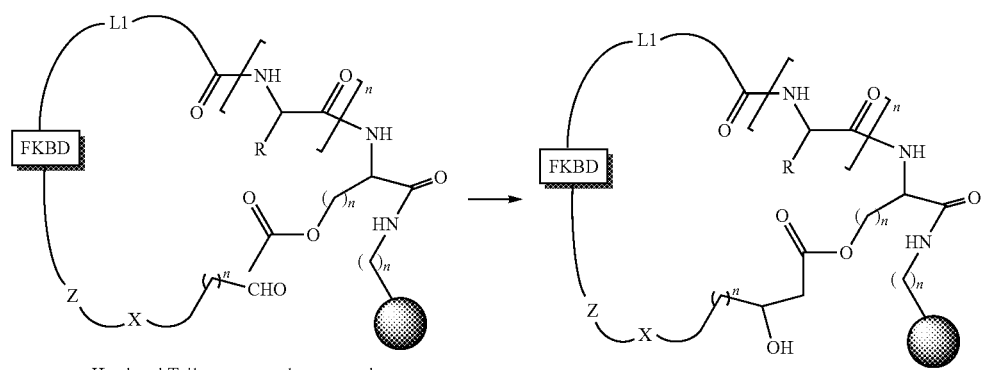<br>Head and Tail groups can be reversed<br>aldol and Dieckmann like reactions<br>Head and Tail groups can be reversed |
| Macrocyclization via alkylation-Williamson etherification | 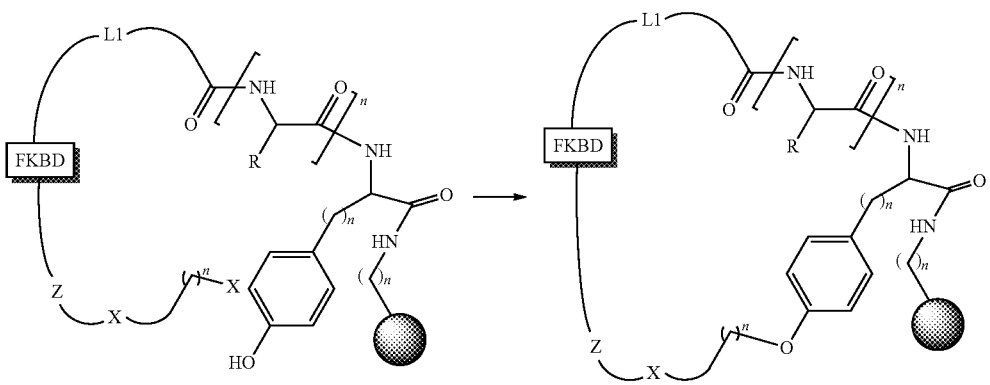 |
| Macrocyclization via alkylation-Mitsunobu reaction | 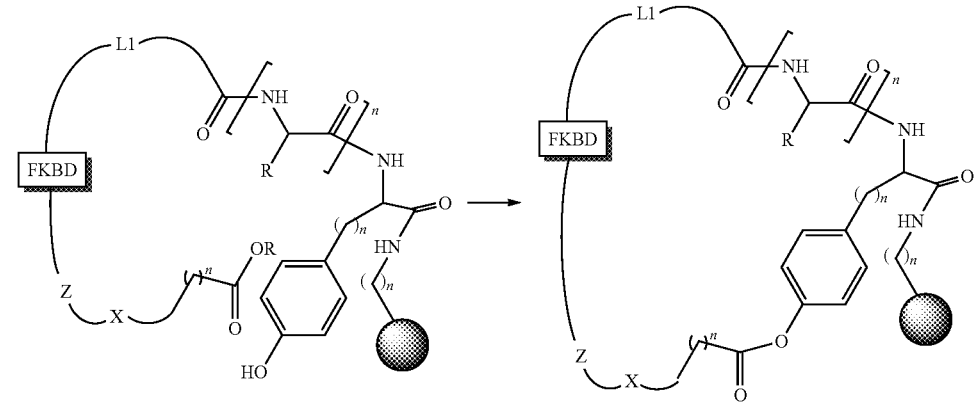 |

TABLE 2-continued

Additional macrocyclization methods that can be used for Rapafucin synthesis.

| Macrocyclization reactions | Reaction scheme |
|---|---|
| Macrocyclization via alkylation-aromatic nucleophilic substitution (SNAr) | 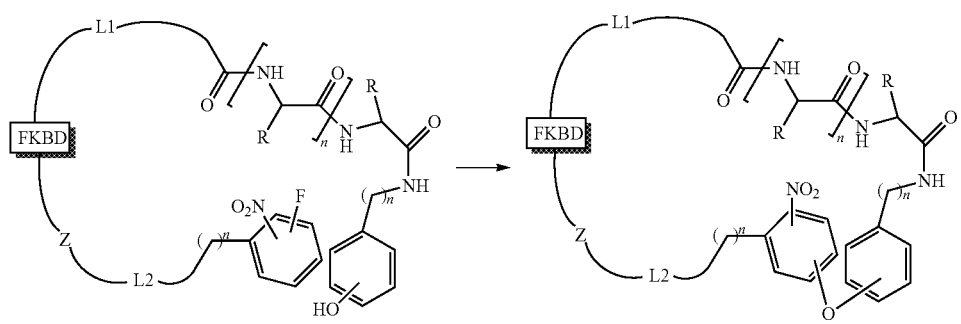 |
| Macrocyclization via alkylation-Friedel-Crafts type alkylations | 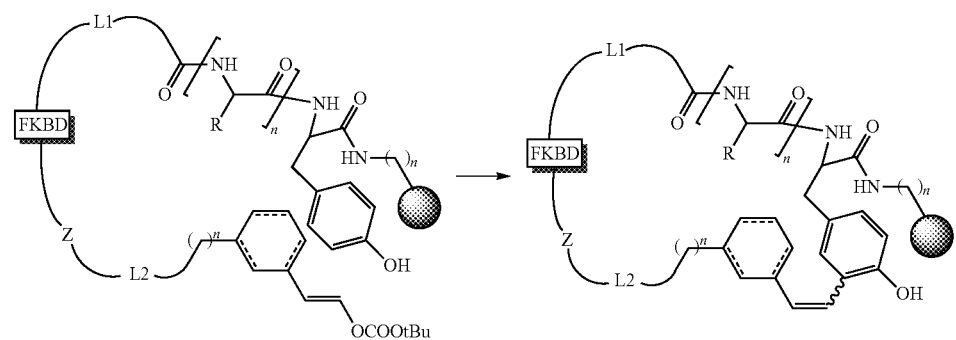 |
| Macrocyclization through intramolecular cyclopropanation | 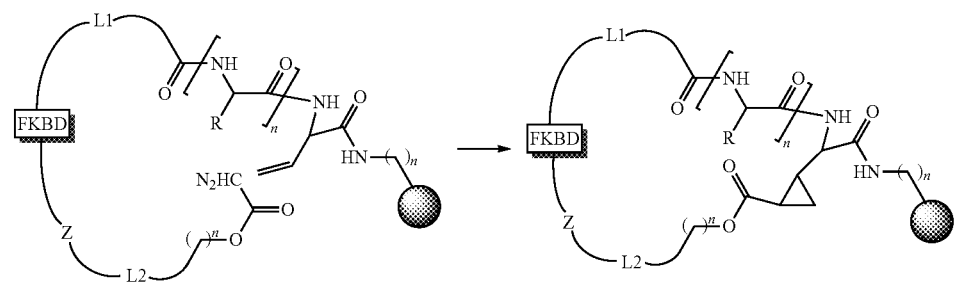<br>(cycloporpanation to aromatic heterocyclic rigs)<br>Head and Tail groups can be reversed |
| Macrocyclization through oxidative coupling of Arenes | 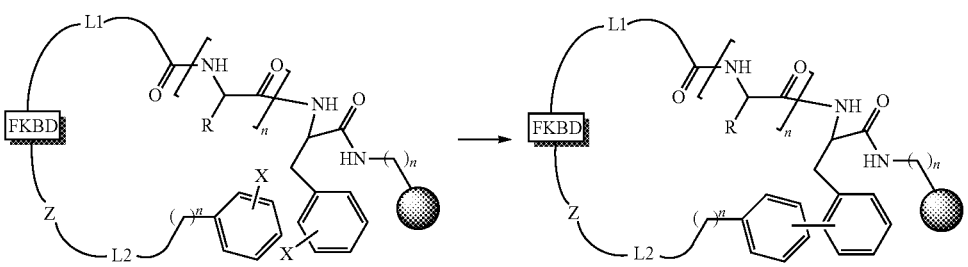 |

TABLE 2-continued

Additional macrocyclization methods that can be used for Rapafucin synthesis.

| Macro-cyclization reactions | Reaction scheme |
|---|---|
| Macro-cyclization-side chain cyclization | 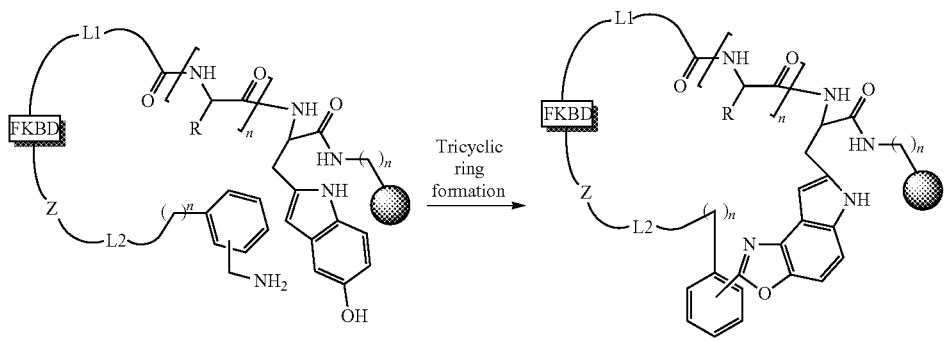  Macrocyliczation using non proteinogenic amino acids  include three- and 4-membered, 5-membered heterocycles including indoles, furans, thiophenes, and oxazoles, six-membered heterocycles including quinolines, isoquinolines, and pyrrolidines, and other heterocycles |
| Macro-cyclization-oxidative coupling of arenes | Imine Macrocyclization Employing Intermolecular Imine Traps  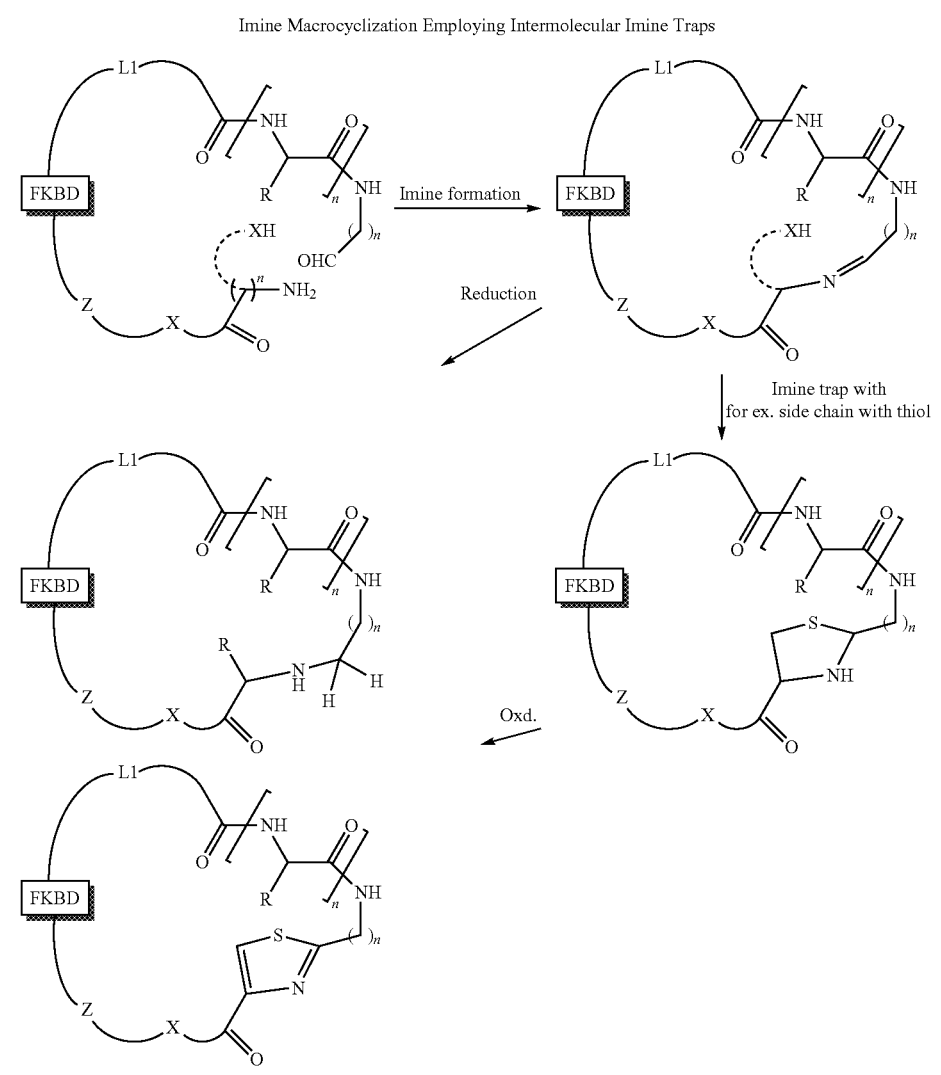 |

In some embodiments, the Rapafucin compounds in the present disclosure can have a structure according to Formula (VII) or an optically pure stereoisomer or pharmaceutically acceptable salt thereof.

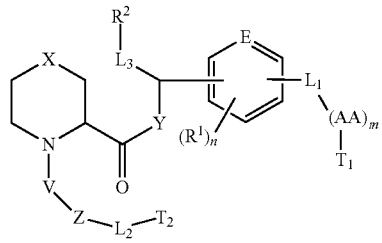

Formula (VII)

Each $T_1$ or $T_2$ can be independently selected from the terminal structures as outlined in Table 2 above before macrocyclization. Each $L_1$, $L_2$, or $L_3$ can be independently selected from the linker structures in Table 1. Each AA can be independently selected from the amino acid monomers shown in Table 3 below. X can be $CH_2$, NH, O, or S; Y can be O, NH, or N-alkyl; E can be CH or N; n is an integer selected from 0 to 4. Amino acids can be either N—C linked or C—N linked.

In some embodiments, m can be 1. In some embodiments, m can be 2. In some embodiments, m can be 3. In some embodiments, m can be 4. In some embodiments, m can be 5. In some embodiments, m can be 6. In some embodiments, m can be 7. In some embodiments, m can be 8. In some embodiments, m can be 9. In some embodiments, m can be 10. In a specific embodiment, m is 3 or 4.

V is

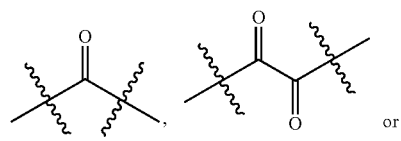

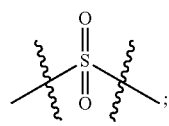

Z is a bond,

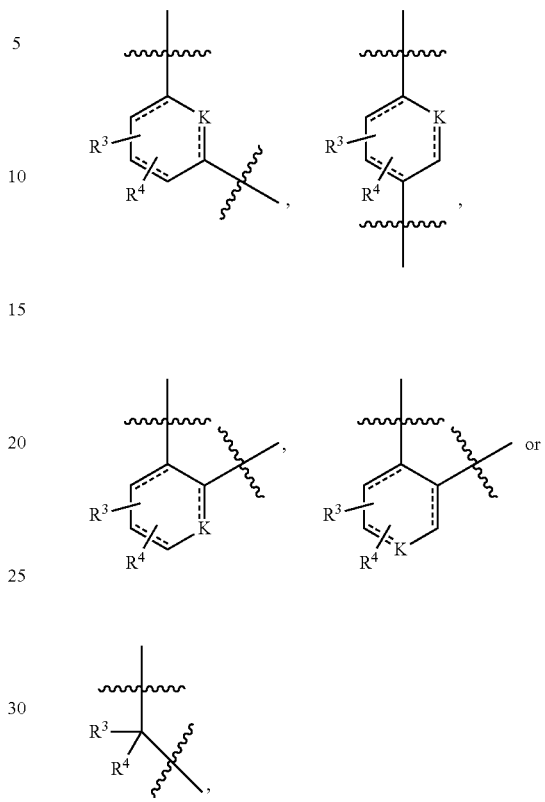

wherein $R^3$ and $R^4$ are each independently selected from the group consisting of of hydrogen, hydroxy, halo, alkyl, alkoxy, cycloalkyl, cyano, alkylthio, amino, alkylamino, and dialkylamino; K is O, $CHR^5$, $CR^5$, N, and $NR^5$, wherein $R^5$ is hydrogen or alkyl.

Each $R^1$ is selected from the group consisting of H, halogen, hydroxyl, $C_{1-20}$ alkyl, $N_3$, $NH_2$, $NO_2$, $CF_3$, $OCF_3$, $OCHF_2$, $COC_{1-20}$alkyl, and $CO_2C_{1-20}$alkyl. $R^2$ is selected from the group consisting of $C_{6-15}$aryl and $C_{1-10}$heteroaryl optionally substituted with H, halogen, hydroxyl, $N_3$, $NH_2$, $NO_2$, $CF_3$, $C_{1-10}$alkyl, substituted $C_{1-10}$alkyl, $C_{1-10}$alkoxy, substituted $C_{1-10}$alkoxy, acyl, acylamino, acyloxy, acyl $C_{1-10}$alkyloxy, amino, substituted amino, aminoacyl, aminocarbonyl $C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester)amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, substituted $C_{1-10}$alkylthio, and thiocarbonyl.

Table 3 below shows the FKBD moieties with linkers before incorporated into the Rapafucin macrocylic structure.

TABLE 3
The FKBD/linker moieties used in the present disclosure.
| FKBD identifier | Chemical Structure |
|---|---|
| aFKBD | 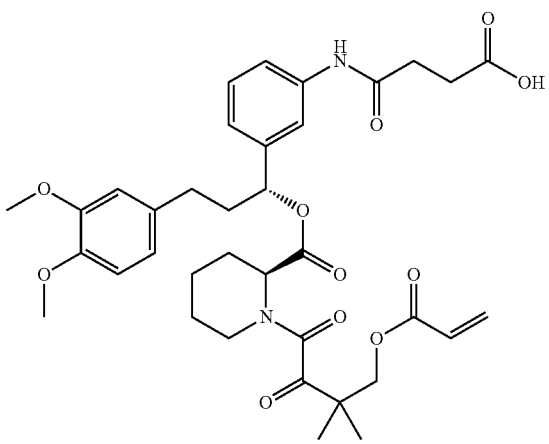 [SMILES: C=CC(=O)OCC(C)(C)C(=O)C(=O)N1CCCC[C@H]1C(=O)O[C@H](CCc1ccc(OC)c(OC)c1)c1cccc(NC(=O)CCC(=O)O)c1] |
| eFKBD | 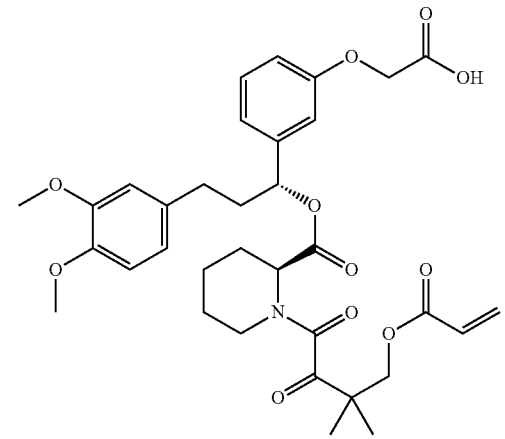 [SMILES: C=CC(=O)OCC(C)(C)C(=O)C(=O)N1CCCC[C@H]1C(=O)O[C@H](CCc1ccc(OC)c(OC)c1)c1cccc(OCC(=O)O)c1] |
| Raa1 | 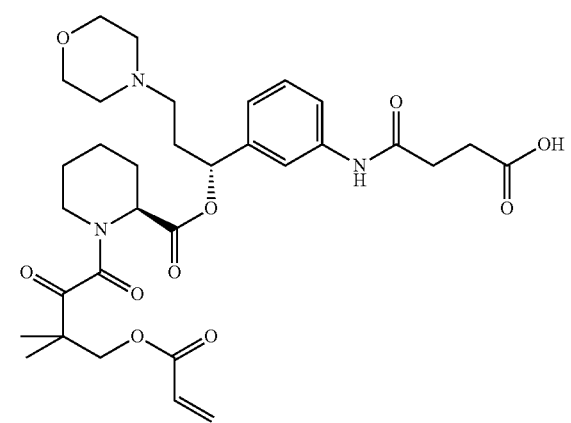 [SMILES: C=CC(=O)OCC(C)(C)C(=O)C(=O)N1CCCC[C@H]1C(=O)O[C@H](CCN1CCOCC1)c1cccc(NC(=O)CCC(=O)O)c1] |

TABLE 3-continued
The FKBD/linker moieties used in the present disclosure.
| FKBD identifier | Chemical Structure |
|---|---|
| Raa2 | 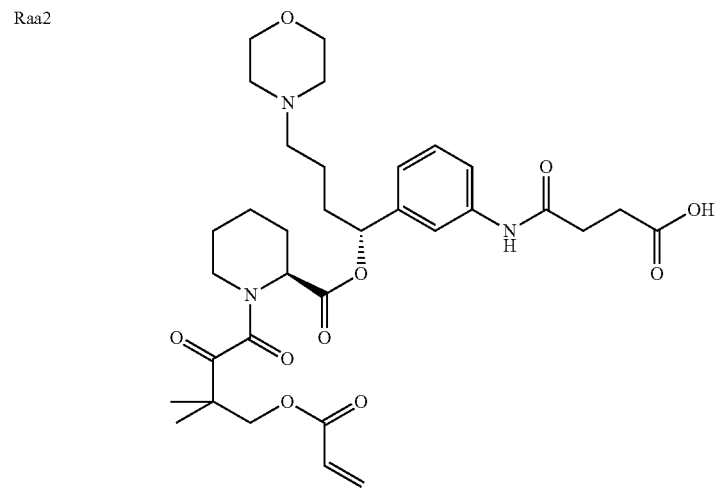 |
| Raa3 | 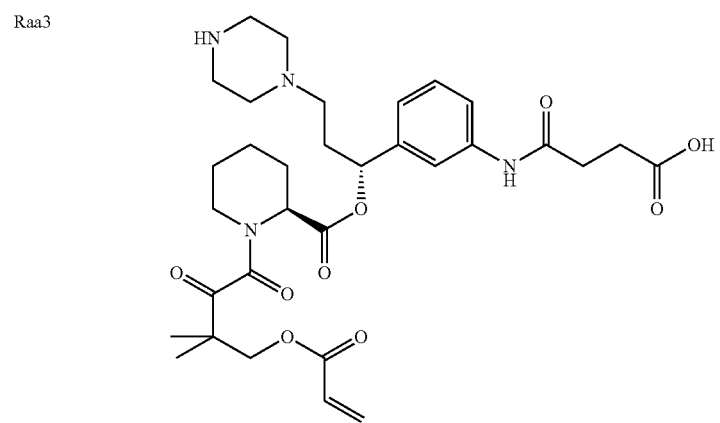 |
| Raa4 | 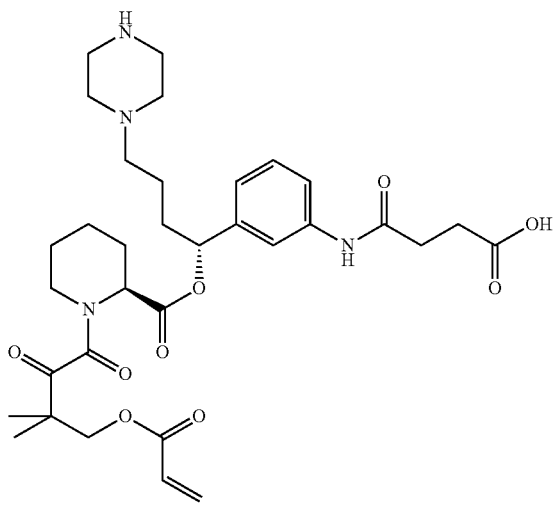 [SMILES: C=CC(=O)OCC(C)(C)C(=O)C(=O)N1CCCC[C@H]1C(=O)O[C@H](CCCN1CCNCC1)c1cccc(NC(=O)CCC(=O)O)c1] |

TABLE 3-continued

The FKBD/linker moieties used in the present disclosure.

| FKBD identifier | Chemical Structure |
|---|---|
| Raa5 | (structure) |
| Raa6 | (structure) |
| Raa7 | (structure) |

TABLE 3-continued
The FKBD/linker moieties used in the present disclosure.
| FKBD identifier | Chemical Structure |
|---|---|
| Raa8 | 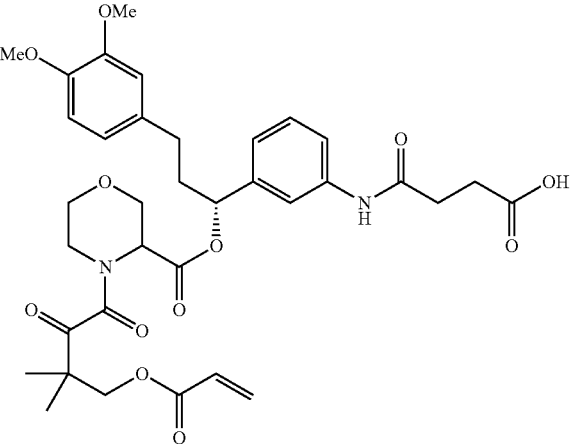 [SMILES: C=CC(=O)OCC(C)(C)C(=O)C(=O)N1CCOCC1C(=O)O[C@H](CCc1ccc(OC)c(OC)c1)c1cccc(NC(=O)CCC(=O)O)c1] |
| Raa9 | 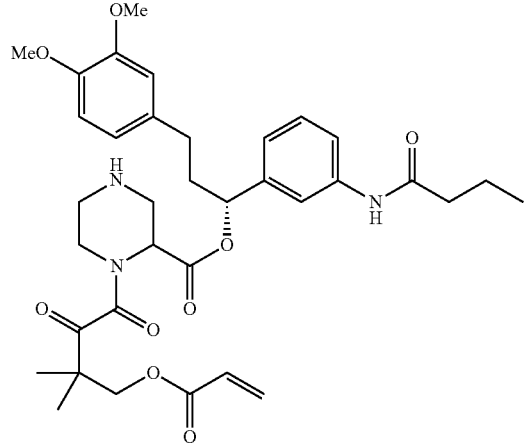 [SMILES: C=CC(=O)OCC(C)(C)C(=O)C(=O)N1CCNCC1C(=O)O[C@H](CCc1ccc(OC)c(OC)c1)c1cccc(NC(=O)CCC)c1] |
| Raa10 | 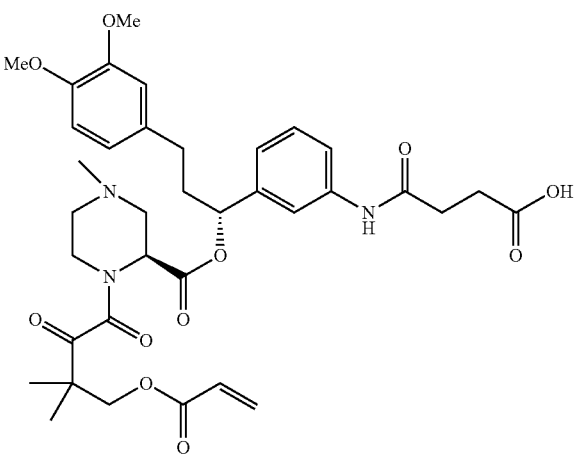 [SMILES: C=CC(=O)OCC(C)(C)C(=O)C(=O)N1CCN(C)C[C@H]1C(=O)O[C@H](CCc1ccc(OC)c(OC)c1)c1cccc(NC(=O)CCC(=O)O)c1] |

TABLE 3-continued
The FKBD/linker moieties used in the present disclosure.
| FKBD identifier | Chemical Structure |
|---|---|
| Raa11 | 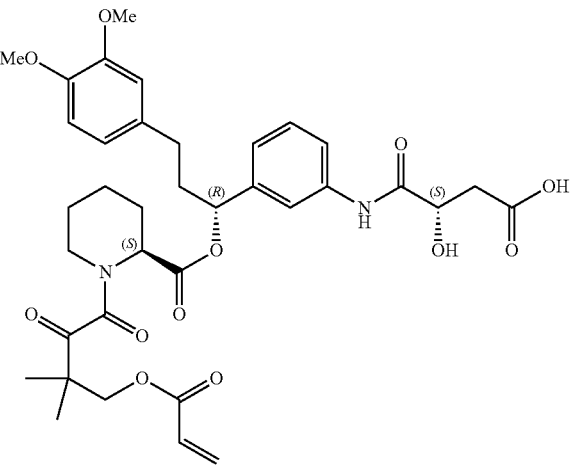 |
| Raa12 | 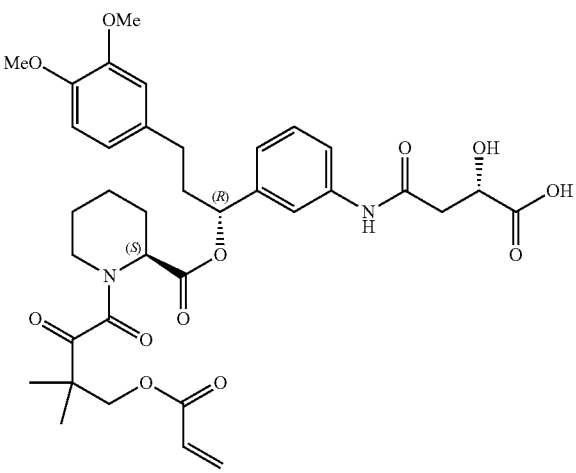 |
| Raa13 | 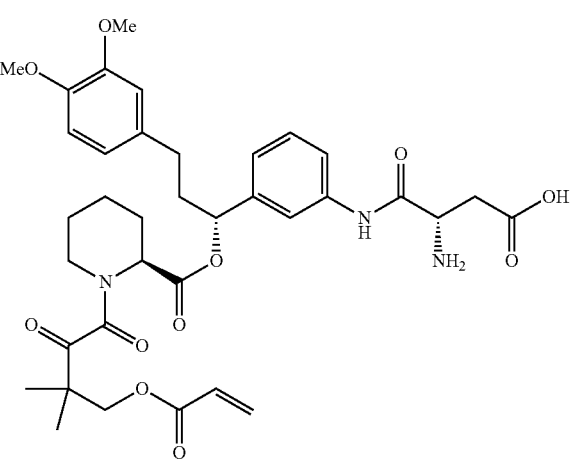 [SMILES: C=CC(=O)OCC(C)(C)C(=O)C(=O)N1CCCC[C@H]1C(=O)O[C@H](CCc1ccc(OC)c(OC)c1)c1cccc(NC(=O)[C@@H](N)CC(=O)O)c1] |

TABLE 3-continued

The FKBD/linker moieties used in the present disclosure.

| FKBD identifier | Chemical Structure |
|---|---|
| Raa14 | 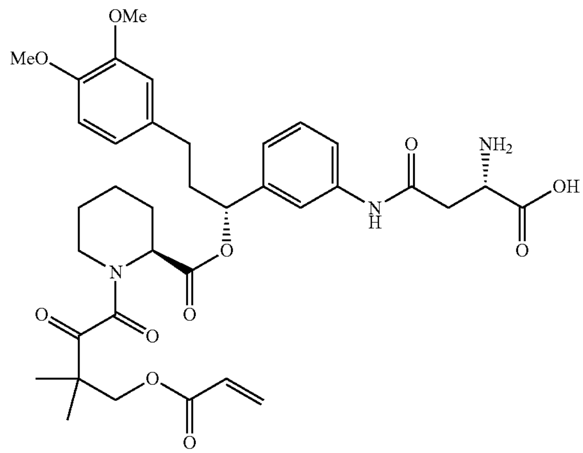 [SMILES: C=CC(=O)OCC(C)(C)C(=O)C(=O)N1CCCC[C@H]1C(=O)O[C@H](CCc1ccc(OC)c(OC)c1)c1cccc(NC(=O)C[C@H](N)C(=O)O)c1] |
| Raa15 | 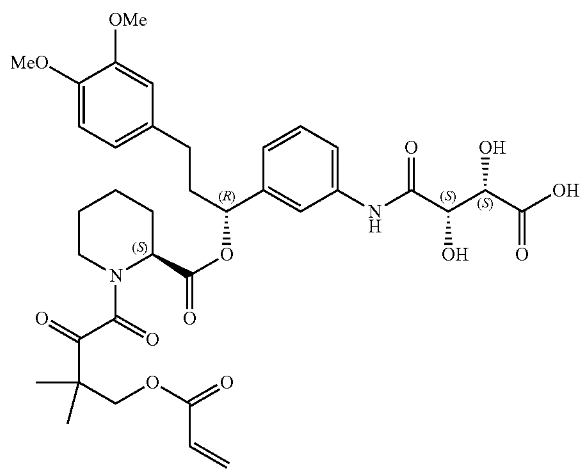 |
| Raa16 | 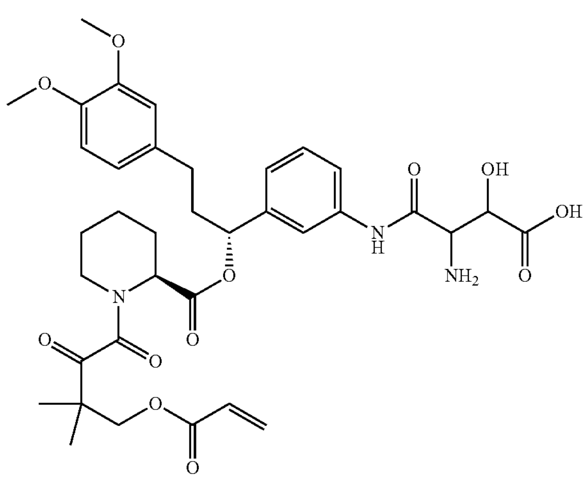 [SMILES: C=CC(=O)OCC(C)(C)C(=O)C(=O)N1CCCC[C@H]1C(=O)O[C@H](CCc1ccc(OC)c(OC)c1)c1cccc(NC(=O)C(N)C(O)C(=O)O)c1] |

TABLE 3-continued
The FKBD/linker moieties used in the present disclosure.
| FKBD identifier | Chemical Structure |
|---|---|
| Raa17 | 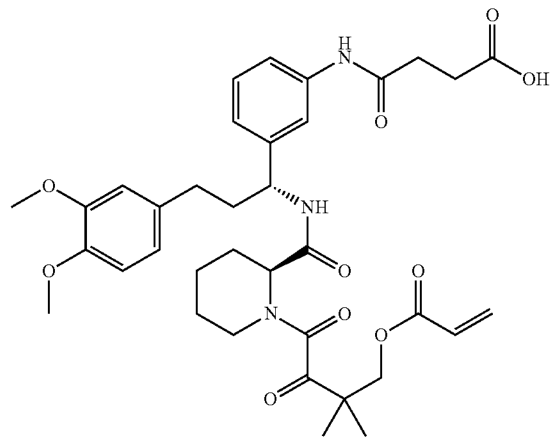 [SMILES: C=CC(=O)OCC(C)(C)C(=O)C(=O)N1CCCC[C@H]1C(=O)N[C@H](CCc1ccc(OC)c(OC)c1)c1cccc(NC(=O)CCC(=O)O)c1] |
| Raa18 | 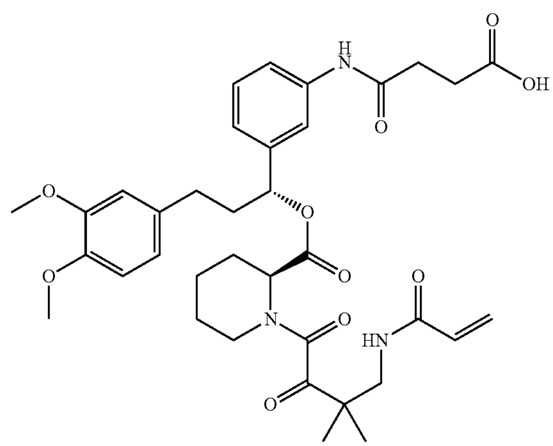 [SMILES: C=CC(=O)NCC(C)(C)C(=O)C(=O)N1CCCC[C@H]1C(=O)O[C@H](CCc1ccc(OC)c(OC)c1)c1cccc(NC(=O)CCC(=O)O)c1] |
| Raa19 | 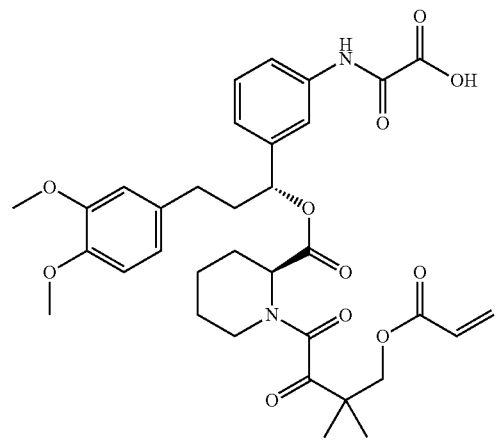 [SMILES: C=CC(=O)OCC(C)(C)C(=O)C(=O)N1CCCC[C@H]1C(=O)O[C@H](CCc1ccc(OC)c(OC)c1)c1cccc(NC(=O)C(=O)O)c1] |

TABLE 3-continued
The FKBD/linker moieties used in the present disclosure.
| FKBD identifier | Chemical Structure |
|---|---|
| Raa20 | 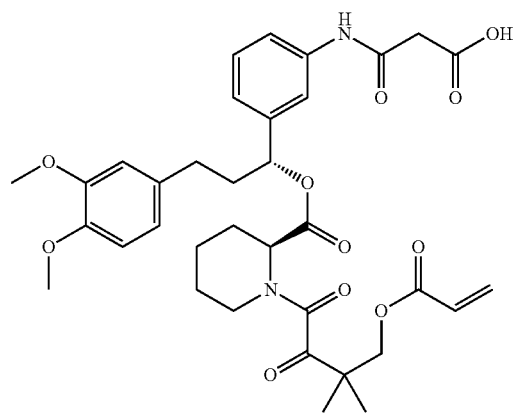 [SMILES: C=CC(=O)OCC(C)(C)C(=O)C(=O)N1CCCC[C@H]1C(=O)O[C@H](CCc1ccc(OC)c(OC)c1)c1cccc(NC(=O)CC(=O)O)c1] |
| Raa21 | 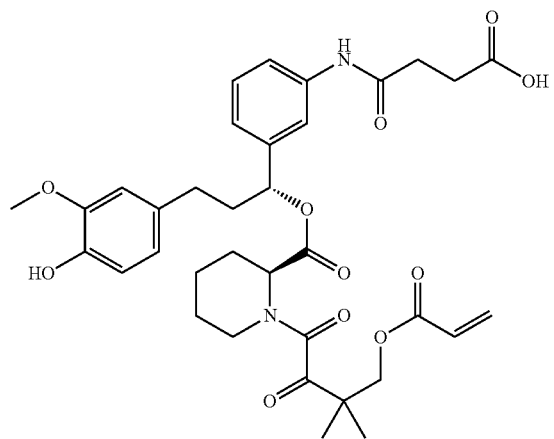 [SMILES: C=CC(=O)OCC(C)(C)C(=O)C(=O)N1CCCC[C@H]1C(=O)O[C@H](CCc1ccc(O)c(OC)c1)c1cccc(NC(=O)CCC(=O)O)c1] |
| Raa22 | 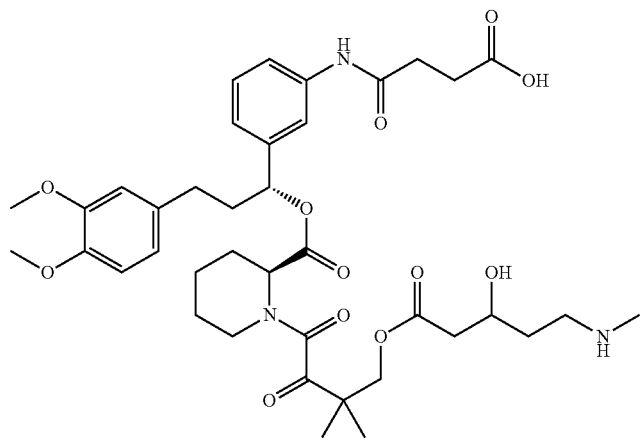 |

TABLE 3-continued
The FKBD/linker moieties used in the present disclosure.
| FKBD identifier | Chemical Structure |
|---|---|
| Raa25 | 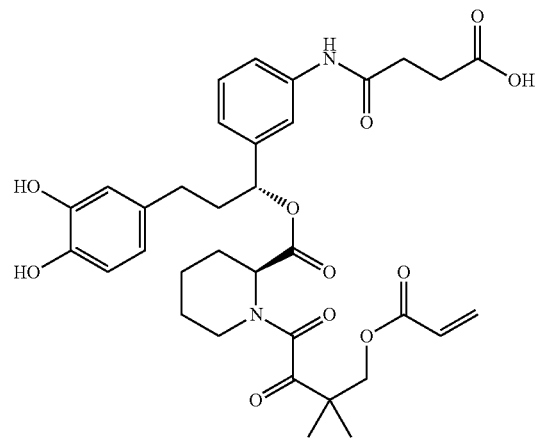 [SMILES: C=CC(=O)OCC(C)(C)C(=O)C(=O)N1CCCC[C@H]1C(=O)O[C@H](CCc1ccc(O)c(O)c1)c1cccc(NC(=O)CCC(=O)O)c1] |
| Raa26 | 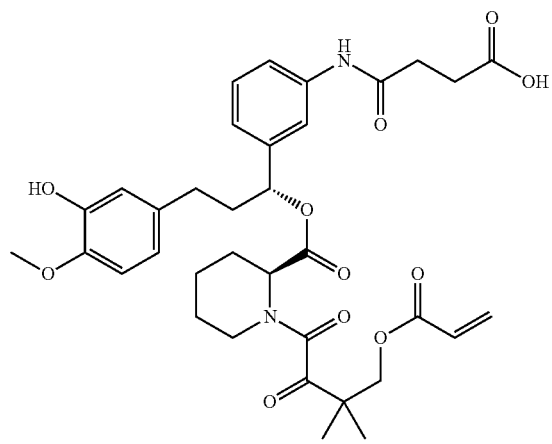 [SMILES: C=CC(=O)OCC(C)(C)C(=O)C(=O)N1CCCC[C@H]1C(=O)O[C@H](CCc1ccc(OC)c(O)c1)c1cccc(NC(=O)CCC(=O)O)c1] |
| Raa27 | 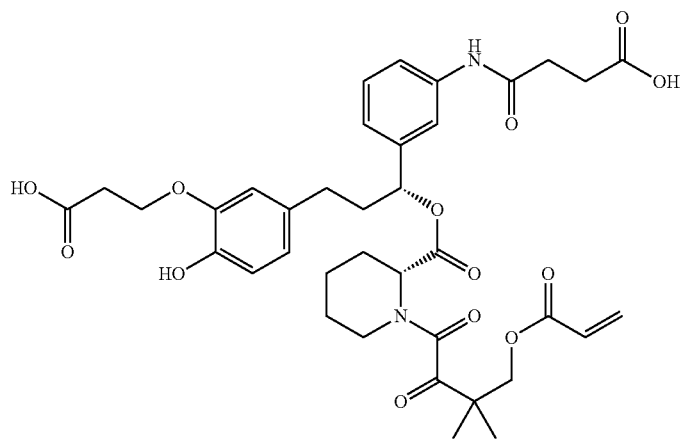 [SMILES: C=CC(=O)OCC(C)(C)C(=O)C(=O)N1CCCC[C@@H]1C(=O)O[C@H](CCc1ccc(O)c(OCCC(=O)O)c1)c1cccc(NC(=O)CCC(=O)O)c1] |

TABLE 3-continued

The FKBD/linker moieties used in the present disclosure.

| FKBD identifier | Chemical Structure |
|---|---|
| Raa28 | 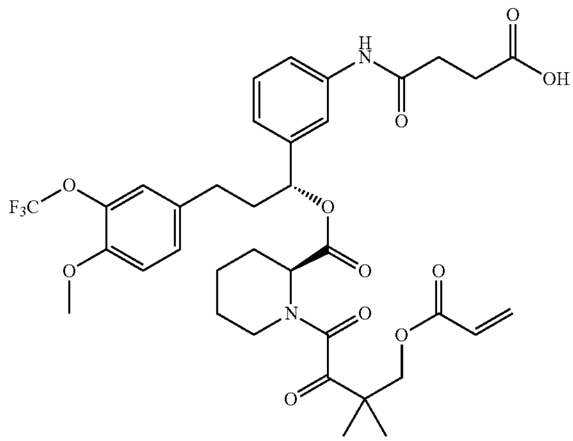 [SMILES: C=CC(=O)OCC(C)(C)C(=O)C(=O)N1CCCC[C@H]1C(=O)O[C@H](CCc1ccc(OC)c(OC(F)(F)F)c1)c1cccc(NC(=O)CCC(=O)O)c1] |
| Raa29 | 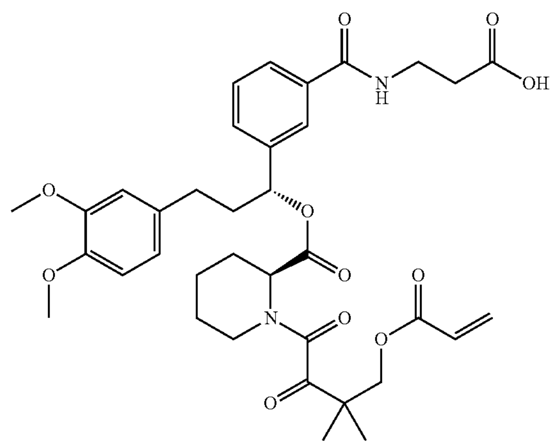 [SMILES: C=CC(=O)OCC(C)(C)C(=O)C(=O)N1CCCC[C@H]1C(=O)O[C@H](CCc1ccc(OC)c(OC)c1)c1cccc(C(=O)NCCC(=O)O)c1] |
| Raa30 | 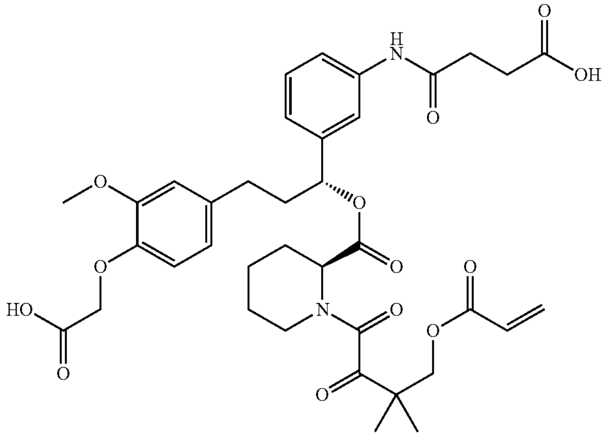 [SMILES: C=CC(=O)OCC(C)(C)C(=O)C(=O)N1CCCC[C@H]1C(=O)O[C@H](CCc1ccc(OCC(=O)O)c(OC)c1)c1cccc(NC(=O)CCC(=O)O)c1] |

TABLE 3-continued
The FKBD/linker moieties used in the present disclosure.
| FKBD identifier | Chemical Structure |
|---|---|
| Rae1 | 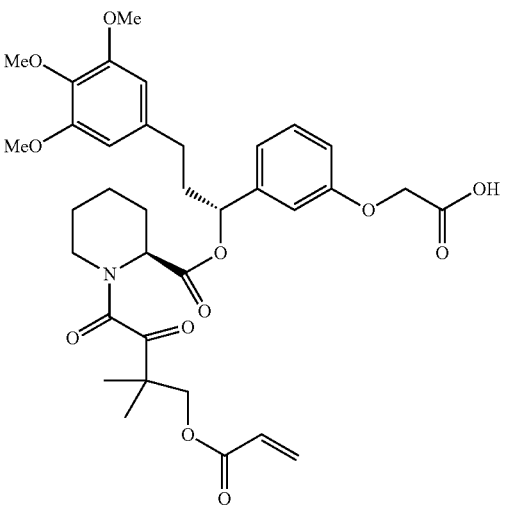 [SMILES: C=CC(=O)OCC(C)(C)C(=O)C(=O)N1CCCC[C@H]1C(=O)O[C@H](CCc1cc(OC)c(OC)c(OC)c1)c1cccc(OCC(=O)O)c1] |
| Rae2 | 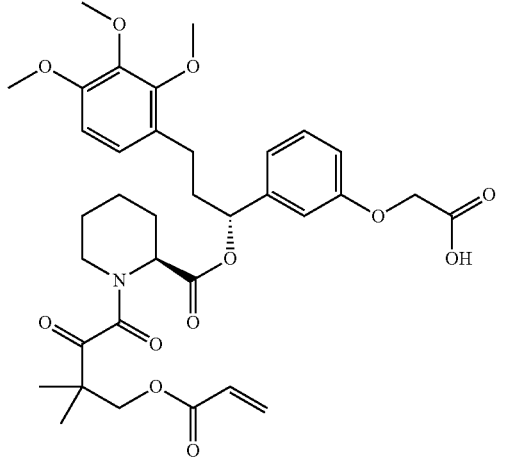 [SMILES: C=CC(=O)OCC(C)(C)C(=O)C(=O)N1CCCC[C@H]1C(=O)O[C@H](CCc1ccc(OC)c(OC)c1OC)c1cccc(OCC(=O)O)c1] |
| Rae3 | 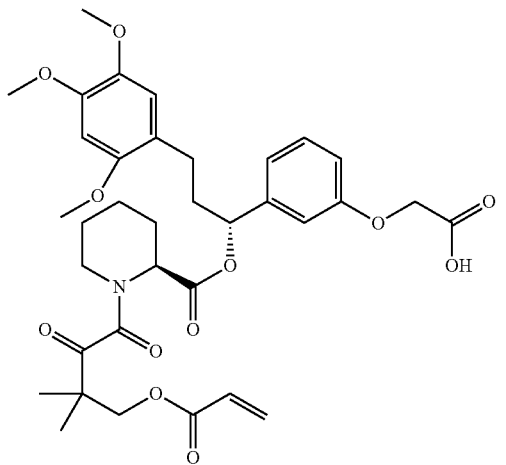 [SMILES: C=CC(=O)OCC(C)(C)C(=O)C(=O)N1CCCC[C@H]1C(=O)O[C@H](CCc1cc(OC)c(OC)cc1OC)c1cccc(OCC(=O)O)c1] |

TABLE 3-continued
The FKBD/linker moieties used in the present disclosure.
| FKBD identifier | Chemical Structure |
|---|---|
| Rae4 | 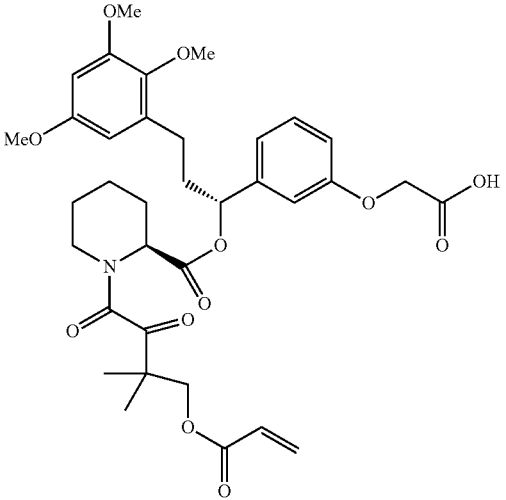 [SMILES: C=CC(=O)OCC(C)(C)C(=O)C(=O)N1CCCC[C@H]1C(=O)O[C@H](CCc1cc(OC)cc(OC)c1OC)c1cccc(OCC(=O)O)c1] |
| Rae5 | 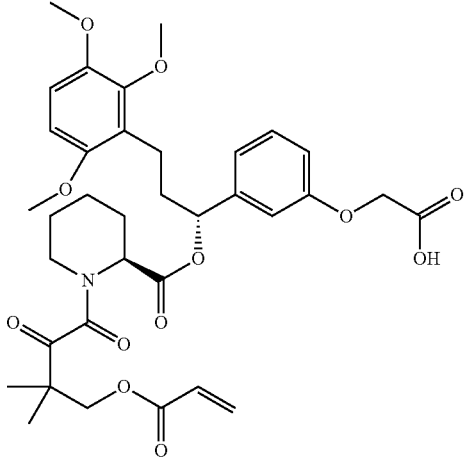 [SMILES: C=CC(=O)OCC(C)(C)C(=O)C(=O)N1CCCC[C@H]1C(=O)O[C@H](CCc1c(OC)ccc(OC)c1OC)c1cccc(OCC(=O)O)c1] |
| Rae9 | 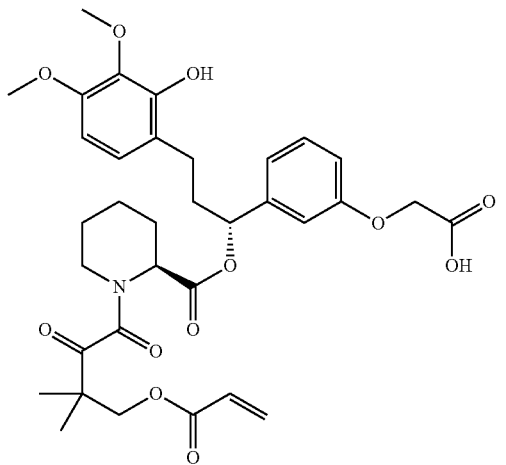 [SMILES: C=CC(=O)OCC(C)(C)C(=O)C(=O)N1CCCC[C@H]1C(=O)O[C@H](CCc1ccc(OC)c(OC)c1O)c1cccc(OCC(=O)O)c1] |

TABLE 3-continued

The FKBD/linker moieties used in the present disclosure.

| FKBD identifier | Chemical Structure |
|---|---|
| Rae10 | 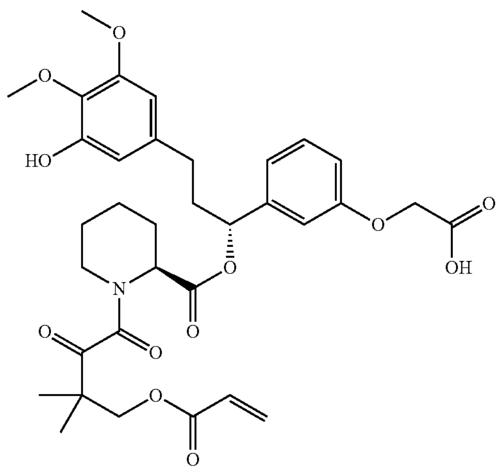 [SMILES: C=CC(=O)OCC(C)(C)C(=O)C(=O)N1CCCC[C@H]1C(=O)O[C@H](CCc1cc(O)c(OC)c(OC)c1)c1cccc(OCC(=O)O)c1] |
| Rae11 | 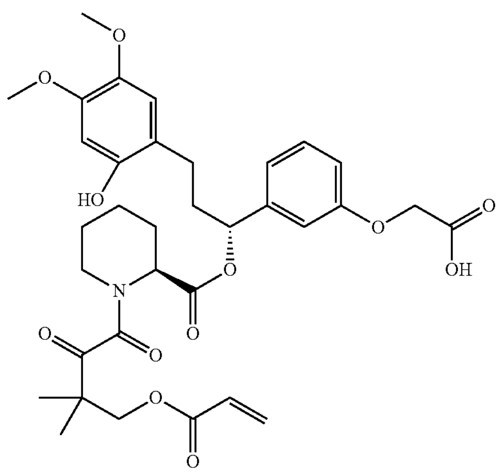 [SMILES: C=CC(=O)OCC(C)(C)C(=O)C(=O)N1CCCC[C@H]1C(=O)O[C@H](CCc1cc(OC)c(OC)cc1O)c1cccc(OCC(=O)O)c1] |
| Rae12 | 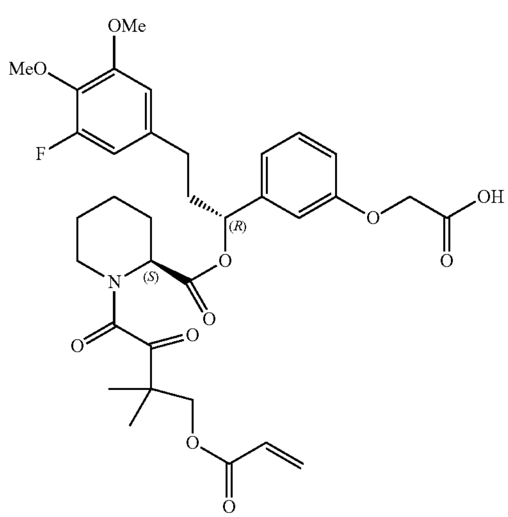 |

TABLE 3-continued

The FKBD/linker moieties used in the present disclosure.

| FKBD identifier | Chemical Structure |
|---|---|
| Rae13 | 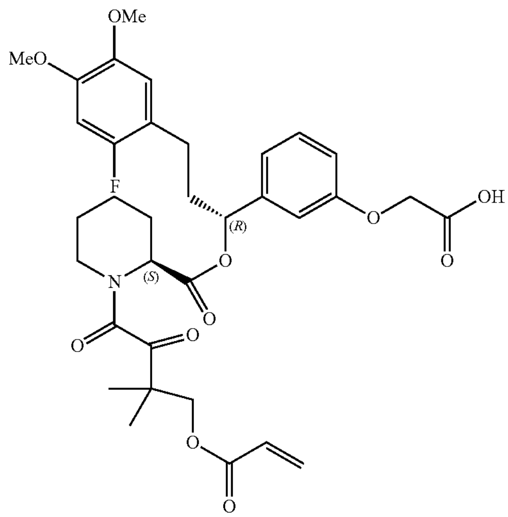 |
| Rae14 | 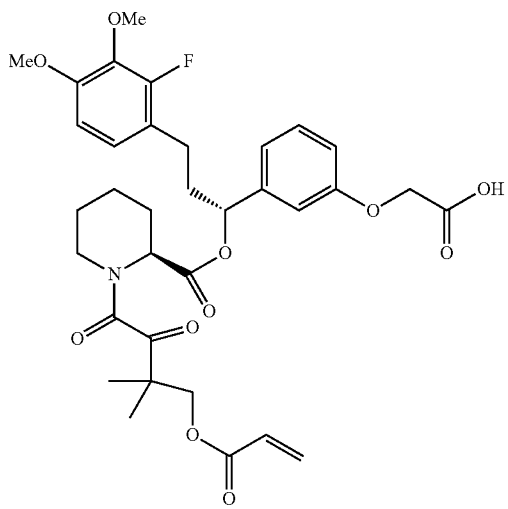 [SMILES: C=CC(=O)OCC(C)(C)C(=O)C(=O)N1CCCC[C@H]1C(=O)O[C@H](CCc1ccc(OC)c(OC)c1F)c1cccc(OCC(=O)O)c1] |
| Rae15 | 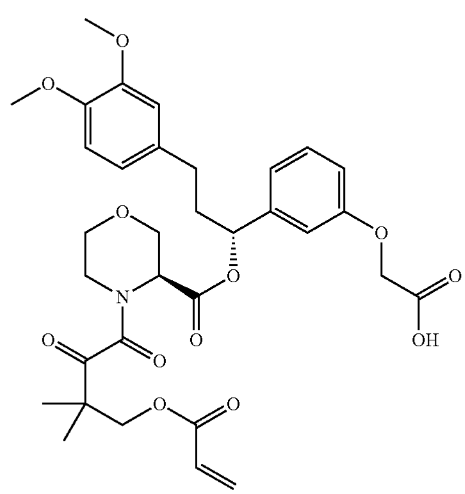 [SMILES: C=CC(=O)OCC(C)(C)C(=O)C(=O)N1CCOC[C@H]1C(=O)O[C@H](CCc1ccc(OC)c(OC)c1)c1cccc(OCC(=O)O)c1] |

TABLE 3-continued
The FKBD/linker moieties used in the present disclosure.
| FKBD identifier | Chemical Structure |
|---|---|
| Rae16 | 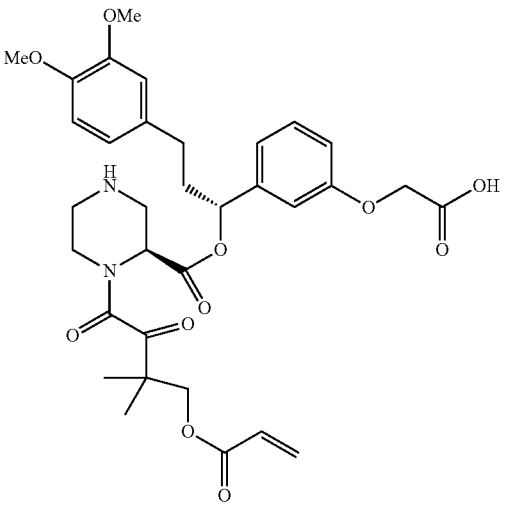 [SMILES: C=CC(=O)OCC(C)(C)C(=O)C(=O)N1CCNC[C@H]1C(=O)O[C@H](CCc1ccc(OC)c(OC)c1)c1cccc(OCC(=O)O)c1] |
| Rae17 | 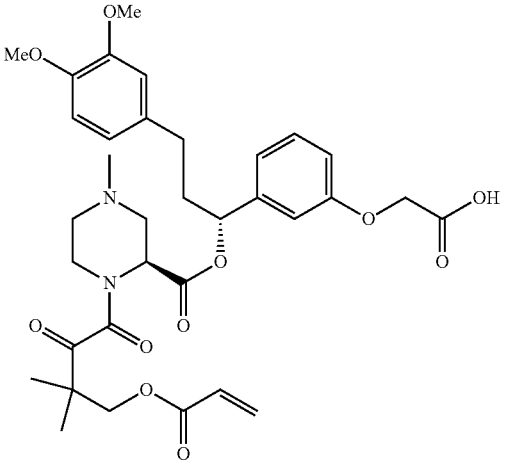 [SMILES: C=CC(=O)OCC(C)(C)C(=O)C(=O)N1CCN(C)C[C@H]1C(=O)O[C@H](CCc1ccc(OC)c(OC)c1)c1cccc(OCC(=O)O)c1] |
| Rae18 | 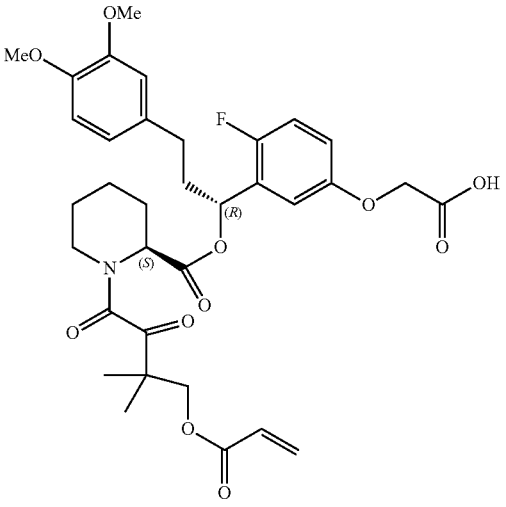 |

TABLE 3-continued
The FKBD/linker moieties used in the present disclosure.
| FKBD identifier | Chemical Structure |
|---|---|
| Rae19 | 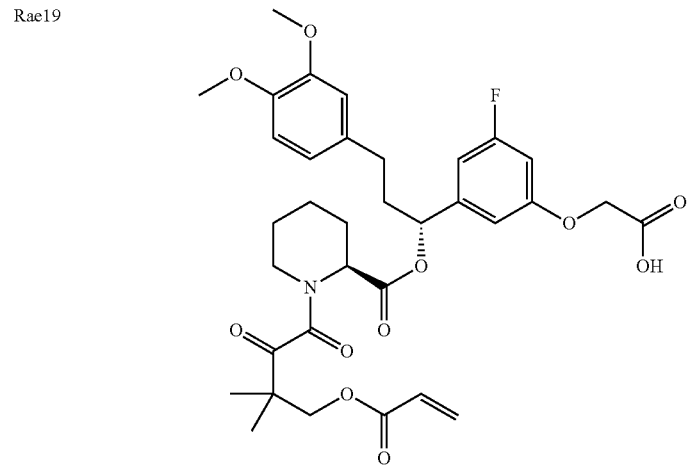 |
| Rae20 | 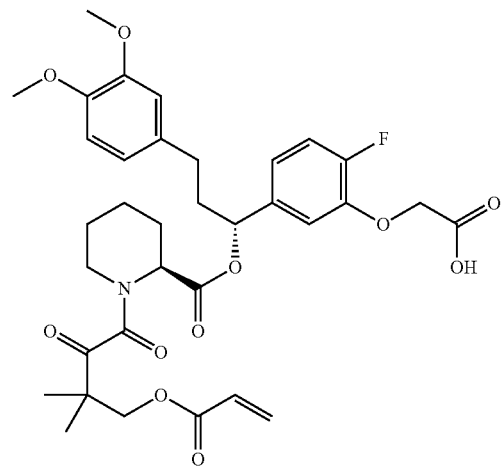 [SMILES: C=CC(=O)OCC(C)(C)C(=O)C(=O)N1CCCC[C@H]1C(=O)O[C@H](CCc1ccc(OC)c(OC)c1)c1ccc(F)c(OCC(=O)O)c1] |
| Rae21 | 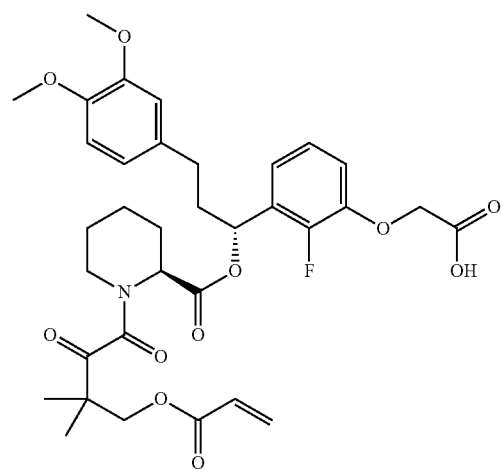 [SMILES: C=CC(=O)OCC(C)(C)C(=O)C(=O)N1CCCC[C@H]1C(=O)O[C@H](CCc1ccc(OC)c(OC)c1)c1cccc(OCC(=O)O)c1F] |

TABLE 3-continued
The FKBD/linker moieties used in the present disclosure.
| FKBD identifier | Chemical Structure |
|---|---|
| Rae22 | 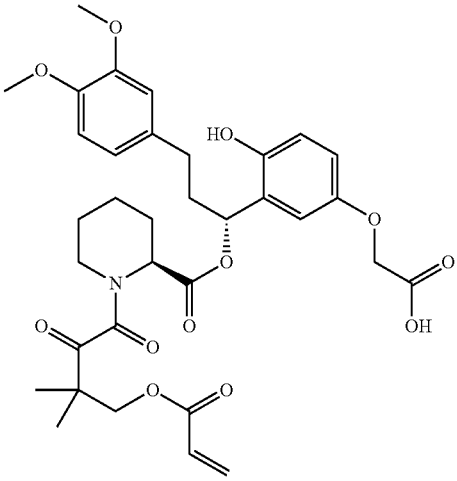 [SMILES: C=CC(=O)OCC(C)(C)C(=O)C(=O)N1CCCC[C@H]1C(=O)O[C@H](CCc1ccc(OC)c(OC)c1)c1cc(OCC(=O)O)ccc1O] |
| Rae23 | 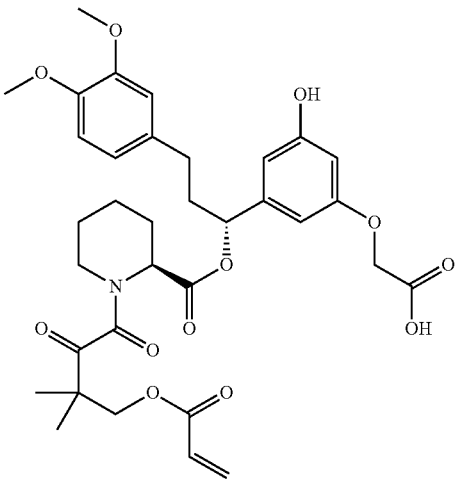 [SMILES: C=CC(=O)OCC(C)(C)C(=O)C(=O)N1CCCC[C@H]1C(=O)O[C@H](CCc1ccc(OC)c(OC)c1)c1cc(O)cc(OCC(=O)O)c1] |
| Rae24 | 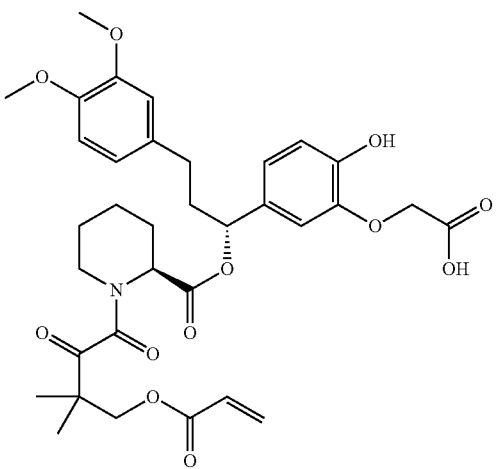 [SMILES: C=CC(=O)OCC(C)(C)C(=O)C(=O)N1CCCC[C@H]1C(=O)O[C@H](CCc1ccc(OC)c(OC)c1)c1ccc(O)c(OCC(=O)O)c1] |

TABLE 3-continued

The FKBD/linker moieties used in the present disclosure.

| FKBD identifier | Chemical Structure |
|---|---|
| Rae25 | 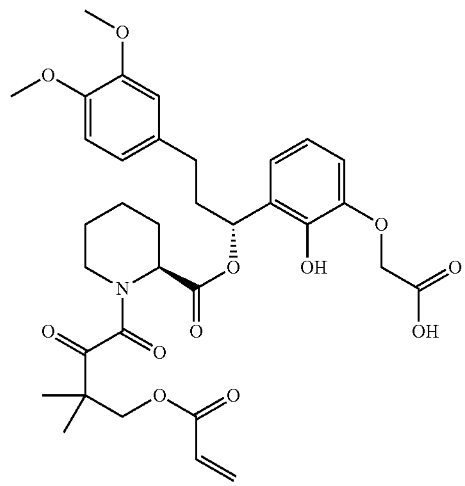 [SMILES: C=CC(=O)OCC(C)(C)C(=O)C(=O)N1CCCC[C@H]1C(=O)O[C@H](CCc1ccc(OC)c(OC)c1)c1cccc(OCC(=O)O)c1O] |
| Rae26 | 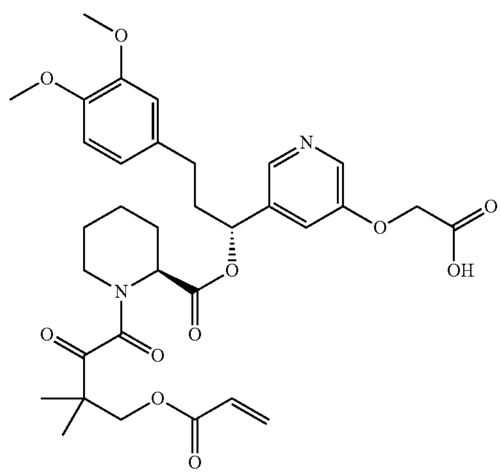 [SMILES: C=CC(=O)OCC(C)(C)C(=O)C(=O)N1CCCC[C@H]1C(=O)O[C@H](CCc1ccc(OC)c(OC)c1)c1cncc(OCC(=O)O)c1] |
| Rae27 | 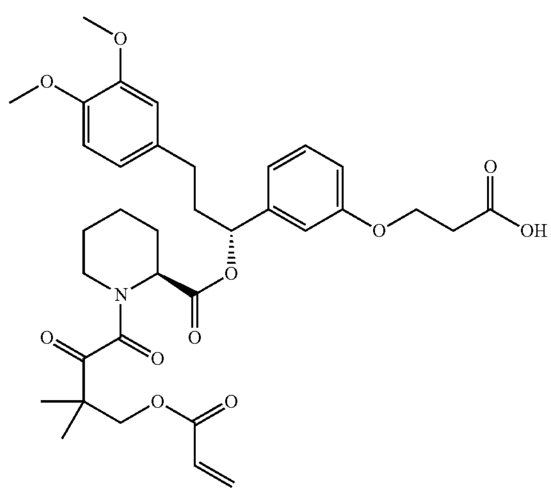 [SMILES: C=CC(=O)OCC(C)(C)C(=O)C(=O)N1CCCC[C@H]1C(=O)O[C@H](CCc1ccc(OC)c(OC)c1)c1cccc(OCCC(=O)O)c1] |

TABLE 3-continued
The FKBD/linker moieties used in the present disclosure.
| FKBD identifier | Chemical Structure |
|---|---|
| Rae28 | 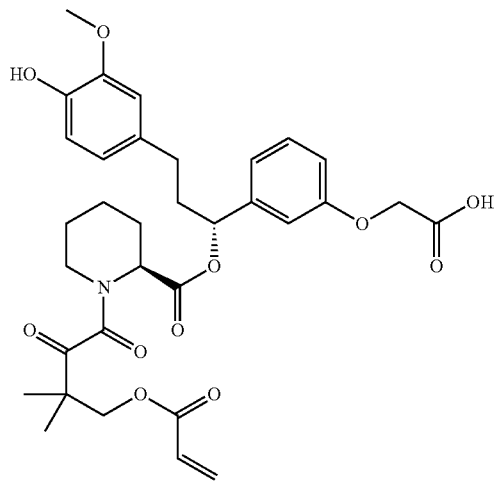 [SMILES: C=CC(=O)OCC(C)(C)C(=O)C(=O)N1CCCC[C@H]1C(=O)O[C@H](CCc1ccc(O)c(OC)c1)c1cccc(OCC(=O)O)c1] |
| Rae29 | 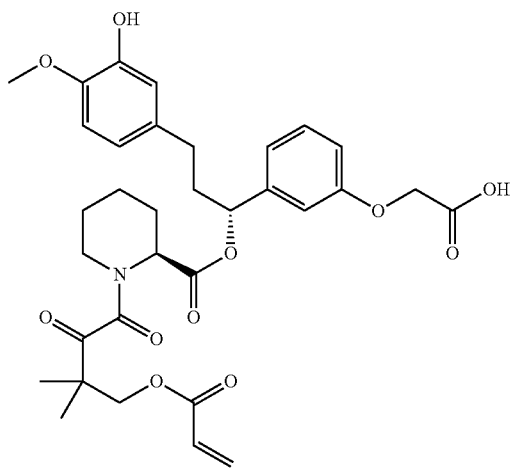 [SMILES: C=CC(=O)OCC(C)(C)C(=O)C(=O)N1CCCC[C@H]1C(=O)O[C@H](CCc1ccc(OC)c(O)c1)c1cccc(OCC(=O)O)c1] |
| Rae30 | 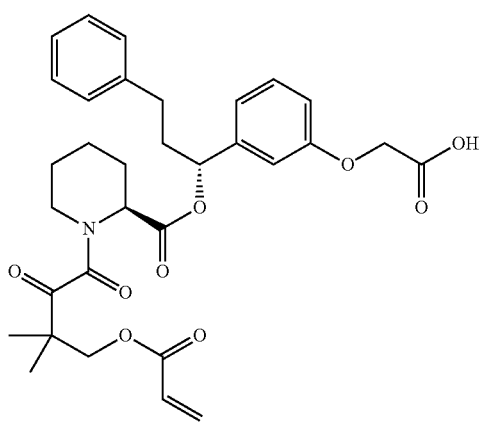 [SMILES: C=CC(=O)OCC(C)(C)C(=O)C(=O)N1CCCC[C@H]1C(=O)O[C@H](CCc1ccccc1)c1cccc(OCC(=O)O)c1] |

TABLE 3-continued
The FKBD/linker moieties used in the present disclosure.
| FKBD identifier | Chemical Structure |
|---|---|
| Rae31* | 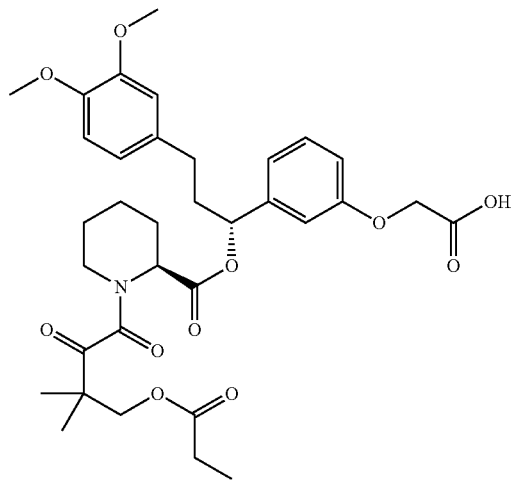 [SMILES: CCC(=O)OCC(C)(C)C(=O)C(=O)N1CCCC[C@H]1C(=O)O[C@H](CCc1ccc(OC)c(OC)c1)c1cccc(OCC(=O)O)c1] |
| Rae32 | 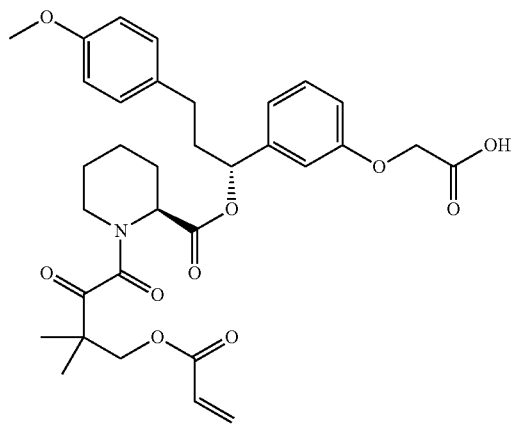 [SMILES: C=CC(=O)OCC(C)(C)C(=O)C(=O)N1CCCC[C@H]1C(=O)O[C@H](CCc1ccc(OC)cc1)c1cccc(OCC(=O)O)c1] |
| Rae33 | 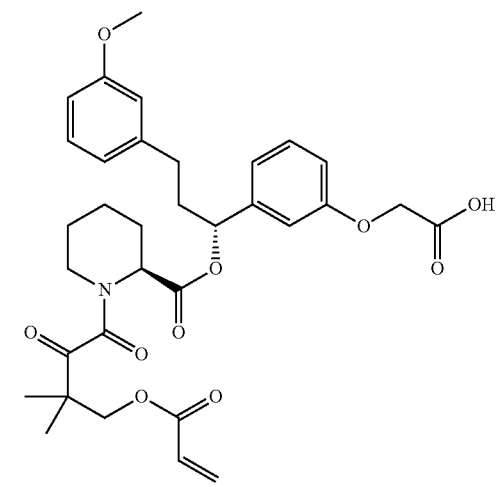 [SMILES: C=CC(=O)OCC(C)(C)C(=O)C(=O)N1CCCC[C@H]1C(=O)O[C@H](CCc1cccc(OC)c1)c1cccc(OCC(=O)O)c1] |

TABLE 3-continued
The FKBD/linker moieties used in the present disclosure.
| FKBD identifier | Chemical Structure |
|---|---|
| Rae34 | 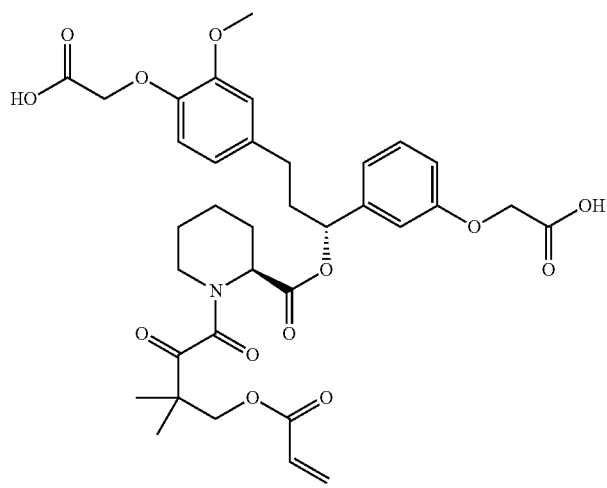 [SMILES: C=CC(=O)OCC(C)(C)C(=O)C(=O)N1CCCC[C@H]1C(=O)O[C@H](CCc1ccc(OCC(=O)O)c(OC)c1)c1cccc(OCC(=O)O)c1] |
| Rae35 | 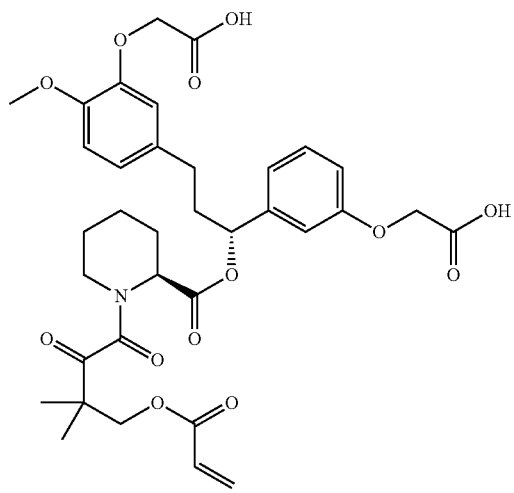 [SMILES: C=CC(=O)OCC(C)(C)C(=O)C(=O)N1CCCC[C@H]1C(=O)O[C@H](CCc1ccc(OC)c(OCC(=O)O)c1)c1cccc(OCC(=O)O)c1] |
| Rae36 | 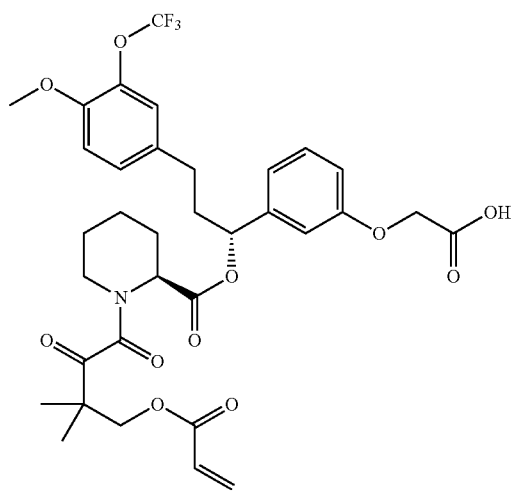 [SMILES: C=CC(=O)OCC(C)(C)C(=O)C(=O)N1CCCC[C@H]1C(=O)O[C@H](CCc1ccc(OC)c(OC(F)(F)F)c1)c1cccc(OCC(=O)O)c1] |

TABLE 3-continued

The FKBD/linker moieties used in the present disclosure.

| FKBD identifier | Chemical Structure |
|---|---|
| Rae37 | (structure) |
| Rae38 | (structure) |

*This FKBD is reduced and cyclized via lactamization.

Table 4 below shows the amino acid monomers used for the the Rapafucin macrocylic compounds synthesis in the present disclosure.

TABLE 4

The monomers used in the present disclosure.

| Entry No. | Monomer identifier | Chemical Structure |
|---|---|---|
| 1 | G | (glycine structure) |
| 2 | Sar | (sarcosine structure) |

TABLE 4-continued

The monomers used in the present disclosure.

| Entry No. | Monomer identifier | Chemical Structure |
|---|---|---|
| 3 | dA | D-Alanine |
| 4 | A | L-Alanine |
| 5 | bAla | β-Alanine |
| 6 | Dpr | 2,3-diaminopropionic acid |
| 7 | ra199 | N-methyl-D-alanine |
| 8 | mA | N-methyl-L-alanine |
| 9 | Aib | 2-aminoisobutyric acid |
| 10 | Abu | 2-aminobutyric acid |
| 11 | C | L-cysteine |
| 12 | dC | D-cysteine |
| 13 | SeC | L-selenocysteine |

TABLE 4-continued

The monomers used in the present disclosure.

| Entry No. | Monomer identifier | Chemical Structure |
|---|---|---|
| 14 | DSec | L-selenocysteine (HOOC-CH(NH2)-CH2-SeH, L-configuration) |
| 15 | dS | D-serine |
| 16 | S | L-serine |
| 17 | ra165 | (S)-azetidine-2-carboxylic acid |
| 18 | Aze | (R)-azetidine-2-carboxylic acid |
| 19 | ra126 | 1-aminocyclopropane-1-carboxylic acid |
| 20 | ra524 | azetidine-3-carboxylic acid |
| 21 | dP | D-proline |
| 22 | P | L-proline |
| 23 | ra132 | (S)-2-amino-2-cyclopropylacetic acid |

TABLE 4-continued

The monomers used in the present disclosure.

| Entry No. | Monomer identifier | Chemical Structure |
|---|---|---|
| 24 | SbPro | 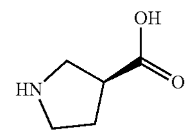 |
| 25 | RbPro | 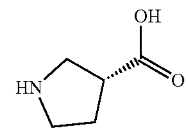 |
| 26 | ra603 | 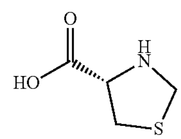 |
| 27 | Dab | 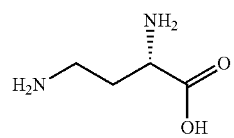 |
| 28 | ra484 | 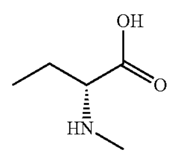 |
| 29 | ra203 | 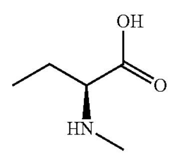 |
| 30 | ra201 | 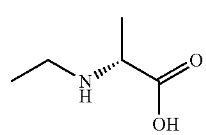 |
| 31 | ra202 | 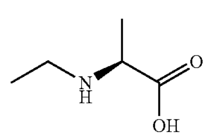 |
| 32 | isoV | 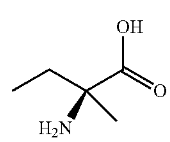 |
| 33 | ra130 | 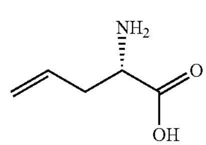 |

TABLE 4-continued

The monomers used in the present disclosure.

| Entry No. | Monomer identifier | Chemical Structure |
|---|---|---|
| 34 | Nva | ![structure] |
| 35 | ra131 | ![structure] |
| 36 | dV | ![structure] |
| 37 | V | ![structure] |
| 38 | bVal | ![structure] |
| 39 | Hcy | ![structure] |
| 40 | mC | ![structure] |
| 41 | dT | ![structure] |
| 42 | T | ![structure] |
| 43 | mS | ![structure] |

TABLE 4-continued

The monomers used in the present disclosure.

| Entry No. | Monomer identifier | Chemical Structure |
|---|---|---|
| 44 | Hse | (structure of homoserine) |
| 45 | Bux | (structure) |
| 46 | Om | (structure of ornithine) |
| 47 | dN | (structure) |
| 48 | N | (structure of asparagine) |
| 49 | RbAsn | (structure) |
| 50 | SbAsn | (structure) |
| 51 | RbAsp & dD | (structure) |
| 52 | D | (structure of aspartate) |
| 53 | ra344 | (structure) |

TABLE 4-continued
The monomers used in the present disclosure.
| Entry No. | Monomer identifier | Chemical Structure |
|---|---|---|
| 54 | mV | 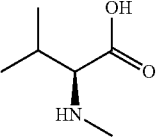 |
| 55 | ra345 | 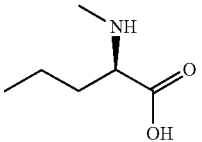 |
| 56 | ra379 | 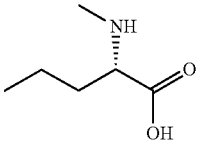 |
| 57 | ra359 | 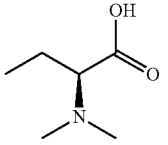 |
| 58 | Nle | 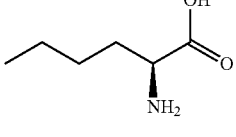 |
| 59 | Dl | 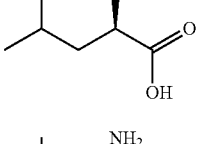 |
| 60 | L | 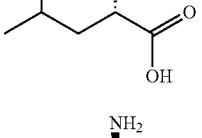 |
| 61 | dI | 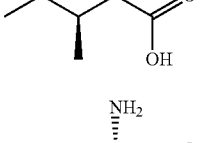 |
| 62 | I | 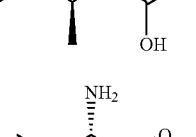 |
| 63 | Tle | 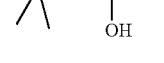 |

TABLE 4-continued

The monomers used in the present disclosure.

| Entry No. | Monomer identifier | Chemical Structure |
|---|---|---|
| 64 | RbIle | (structure: 3-amino-3-methylpentanoic acid, R configuration) |
| 65 | SbIle | (structure: 3-amino-3-methylpentanoic acid, S configuration) |
| 66 | SbLeu | (structure: β-homoleucine, S configuration) |
| 67 | RbLeu | (structure: β-homoleucine, R configuration) |
| 68 | ra74 | (structure: 4,4-difluoro-2-aminobutanoic acid) |
| 69 | RbMet | (structure: β-homomethionine, R configuration) |
| 70 | SbMet | (structure: β-homomethionine, S configuration) |
| 71 | M | (structure: L-methionine) |
| 72 | dM | (structure: D-methionine) |
| 73 | Pen | (structure: penicillamine) |
| 74 | ra371 | (structure: O-methyl threonine) |

TABLE 4-continued

The monomers used in the present disclosure.

| Entry No. | Monomer identifier | Chemical Structure |
|---|---|---|
| 75 | mT | (structure) |
| 76 | ra582 | (structure) |
| 77 | ra380 | (structure) |
| 78 | ra473 | (structure) |
| 79 | ra341 | (structure) |
| 80 | ra538 | (structure) |
| 81 | ra555 | (structure) |
| 82 | ra550 | (structure) |
| 83 | Spg | (structure) |

TABLE 4-continued

The monomers used in the present disclosure.

| Entry No. | Monomer identifier | Chemical Structure |
|---|---|---|
| 84 | ra144 | D-cyclopropylalanine |
| 85 | ra189 | L-cyclopropylalanine |
| 86 | ra330 | α-amino-cyclobutaneacetic acid |
| 87 | ra541 | (S)-piperidine-3-carboxylic acid |
| 88 | ra528 | (S)-2-(pyrrolidin-2-yl)acetic acid |
| 89 | ra168 | (2S,4S)-4-fluoropyrrolidine-2-carboxylic acid |
| 90 | ra532 | (2S,4S)-4-hydroxypyrrolidine-2-carboxylic acid |
| 91 | Roh4P | (2S,4R)-4-hydroxypyrrolidine-2-carboxylic acid |
| 92 | ra508 | (S)-morpholine-3-carboxylic acid |

TABLE 4-continued

The monomers used in the present disclosure.

| Entry No. | Monomer identifier | Chemical Structure |
|---|---|---|
| 93 | ra557 | 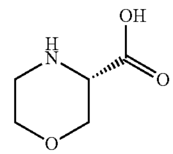 |
| 94 | ra576 | 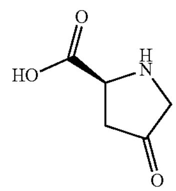 |
| 95 | Glp | 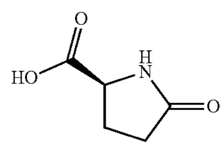 |
| 96 | ra505 | 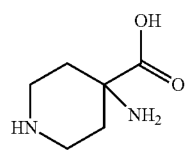 |
| 97 | ra518 | 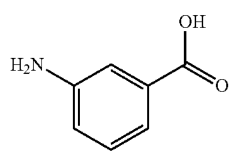 |
| 98 | ra584 | 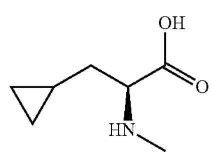 |
| 99 | ra372 | 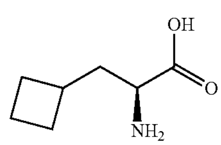 |
| 100 | ra83 | 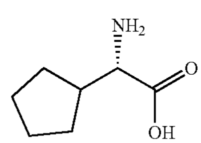 |
| 101 | ra162 | 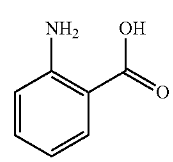 |

TABLE 4-continued

The monomers used in the present disclosure.

| Entry No. | Monomer identifier | Chemical Structure |
|---|---|---|
| 102 | ra169 | 4,4-difluoroproline |
| 103 | ra127 | (R)-2-amino-2-(thiophen-3-yl)acetic acid |
| 104 | ra76 | (S)-2-amino-2-(thiophen-3-yl)acetic acid |
| 105 | ra600 | (R)-2-amino-2-(thiophen-2-yl)acetic acid |
| 106 | ra128 | (S)-2-amino-2-(thiophen-2-yl)acetic acid |
| 107 | ra564 | (R)-5,5-dimethylthiazolidine-4-carboxylic acid |
| 108 | ra510 | 5,5-dimethylthiazolidine-4-carboxylic acid |
| 109 | ra464 | (2S,4S)-4-(methylthio)pyrrolidine-2-carboxylic acid |
| 110 | ra466 | (2S,4R)-4-(methylthio)pyrrolidine-2-carboxylic acid |
| 111 | ra543 | (S)-2,2-dimethylthiazolidine-4-carboxylic acid |

TABLE 4-continued

The monomers used in the present disclosure.

| Entry No. | Monomer identifier | Chemical Structure |
|---|---|---|
| 112 | ra170 | 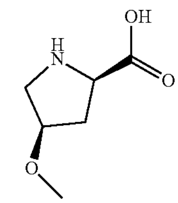 |
| 113 | m4oh3P | 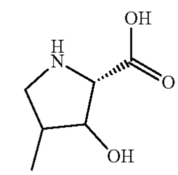 |
| 114 | dK | 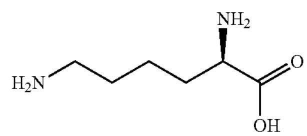 |
| 115 | K | 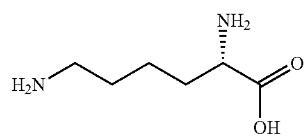 |
| 116 | SbLys | 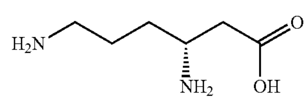 |
| 117 | RbLys | 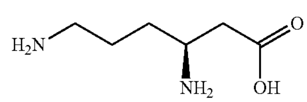 |
| 118 | mN | 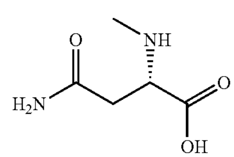 |
| 119 | dQ | 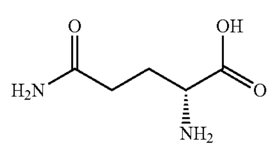 |
| 120 | Q | 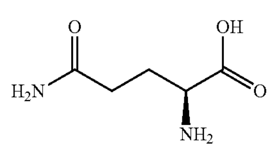 |
| 121 | RbGln | 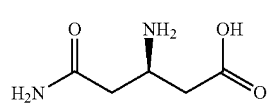 |
| 122 | SbGln | 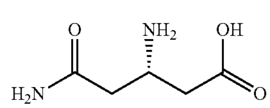 |

TABLE 4-continued

The monomers used in the present disclosure.

| Entry No. | Monomer identifier | Chemical Structure |
|---|---|---|
| 123 | mD | 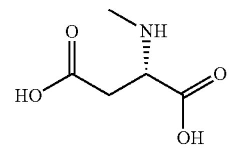 |
| 124 | dE | 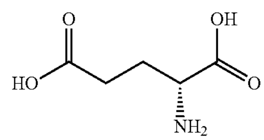 |
| 125 | E | 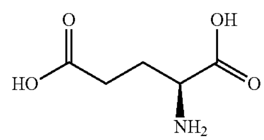 |
| 126 | ra206 | 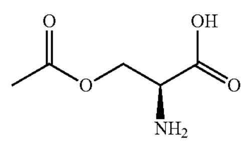 |
| 127 | RbGlu | 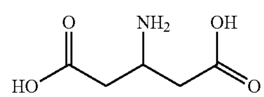 |
| 128 | mI | 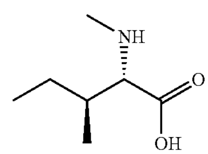 |
| 129 | ra352 | 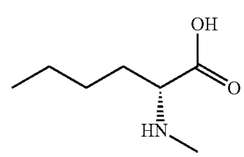 |
| 130 | ra147 | 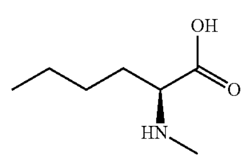 |
| 131 | ra207 | 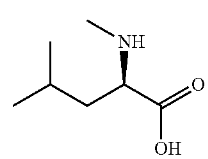 |
| 132 | mL | 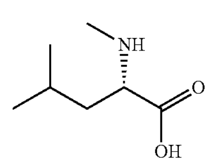 |

TABLE 4-continued

The monomers used in the present disclosure.

| Entry No. | Monomer identifier | Chemical Structure |
|---|---|---|
| 133 | ra530 | (L-tert-leucine derivative with neopentyl side chain, α-NH₂, COOH) |
| 134 | Elscy | (S-ethyl disulfide cysteine: HOOC-CH(NH₂)-CH₂-S-S-CH₂CH₃) |
| 135 | mM | (N-methyl methionine) |
| 136 | ra61 | (α-amino acid with -CH₂-CF₃ side chain; 4,4,4-trifluoro-homoalanine) |
| 137 | Cya | (cysteic acid: HOOC-CH(NH₂)-CH₂-SO₃H) |
| 138 | ra401 | (methionine sulfoxide) |
| 139 | mK | (N-methyl lysine) |
| 140 | oh5K | (5-hydroxy-6-amino lysine derivative) |
| 141 | mQ | (N-methyl glutamine) |
| 142 | mE | (N-methyl glutamic acid) |

TABLE 4-continued

The monomers used in the present disclosure.

| Entry No. | Monomer identifier | Chemical Structure |
|---|---|---|
| 143 | Aad | 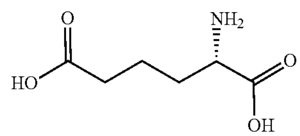 [SMILES: N[C@@H](CCCC(=O)O)C(=O)O] |
| 144 | ra458 | 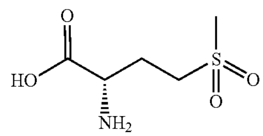 |
| 145 | ra459 | 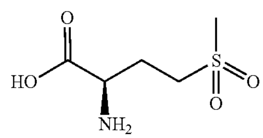 |
| 146 | ra583 | 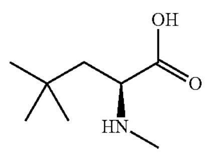 |
| 147 | ra310 | 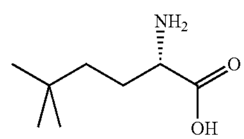 |
| 148 | ra563 | 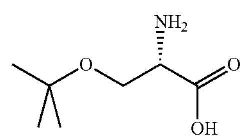 |
| 149 | Tza | 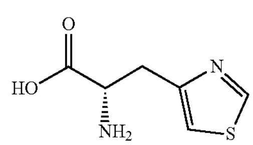 |
| 150 | ra301 | 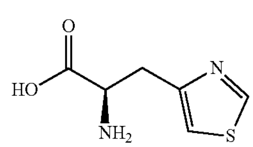 |
| 151 | ra507 | 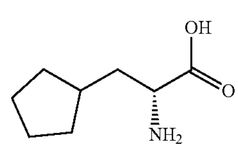 [SMILES: N[C@H](CC1CCCC1)C(=O)O] |
| 152 | ra509 | 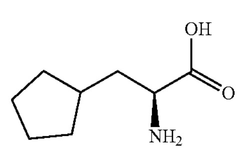 |

TABLE 4-continued

The monomers used in the present disclosure.

| Entry No. | Monomer identifier | Chemical Structure |
|---|---|---|
| 153 | ra602 | (phenylglycine, racemic) |
| 154 | ra601 | (R)-phenylglycine |
| 155 | Phg | (S)-phenylglycine |
| 156 | ra84 | (S)-2-amino-2-cyclohexylacetic acid |
| 157 | ra337 | 2-(2-aminophenyl)acetic acid |
| 158 | ra338 | 3-amino-5-bromobenzoic acid |
| 159 | ra363 | (R)-2-amino-3-(thiophen-3-yl)propanoic acid |
| 160 | ra364 | (S)-2-amino-3-(thiophen-3-yl)propanoic acid |
| 161 | Thl | (S)-2-amino-3-(thiophen-2-yl)propanoic acid |

TABLE 4-continued

The monomers used in the present disclosure.

| Entry No. | Monomer identifier | Chemical Structure |
|---|---|---|
| 162 | ra368 | (S)-2-amino-3-(thiophen-2-yl)propanoic acid |
| 163 | ra67 | (R)-2-amino-3-(furan-2-yl)propanoic acid |
| 164 | ra68 | (S)-2-amino-3-(furan-2-yl)propanoic acid |
| 165 | dH | D-histidine |
| 166 | H | L-histidine |
| 167 | SbHis | (S)-3-amino-3-(1H-imidazol-4-yl)propanoic acid |
| 168 | RbHis | (R)-3-amino-3-(1H-imidazol-4-yl)propanoic acid |
| 169 | ra405 | (R)-2-amino-3-(pyridin-3-yl)propanoic acid |
| 170 | ra90 | (S)-2-amino-3-(pyridin-3-yl)propanoic acid |
| 171 | ra406 | (R)-2-amino-3-(pyridin-4-yl)propanoic acid |

TABLE 4-continued

The monomers used in the present disclosure.

| Entry No. | Monomer identifier | Chemical Structure |
|---|---|---|
| 172 | ra89 | (structure) |
| 173 | ra91 | (structure) |
| 174 | ra176 | (structure) |
| 175 | ra462 | (structure) |
| 176 | ra461 | (structure) |
| 177 | ra565 | (structure) |
| 178 | ra122 | (structure) |
| 179 | dF | (structure) |

TABLE 4-continued

The monomers used in the present disclosure.

| Entry No. | Monomer identifier | Chemical Structure |
|---|---|---|
| 180 | F | L-Phenylalanine |
| 181 | ra527 | D-cyclohexylalanine |
| 182 | Cha | L-cyclohexylalanine |
| 183 | SbPhe | (S)-3-amino-3-phenylpropanoic acid |
| 184 | RbPhe | (R)-3-amino-3-phenylpropanoic acid |
| 185 | ra516 | (R)-2-amino-2-(4-chlorophenyl)acetic acid |
| 186 | ra325 | (R)-2-amino-2-(2-chlorophenyl)acetic acid |
| 187 | ra450 | (S)-2-amino-2-(3-hydroxyphenyl)acetic acid |
| 188 | ra522 | (S)-2-amino-2-(4-hydroxyphenyl)acetic acid |

TABLE 4-continued

The monomers used in the present disclosure.

| Entry No. | Monomer identifier | Chemical Structure |
|---|---|---|
| 189 | mH | 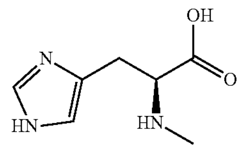 |
| 190 | Hhs | 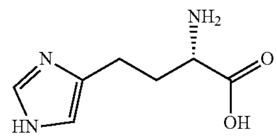 [SMILES: N[C@@H](CCc1c[nH]cn1)C(=O)O] |
| 191 | ra490 | 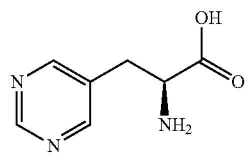 [SMILES: N[C@@H](Cc1cncnc1)C(=O)O] |
| 192 | ra609 | 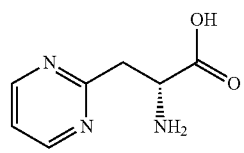 [SMILES: N[C@H](Cc1ncccn1)C(=O)O] |
| 193 | ra173 | 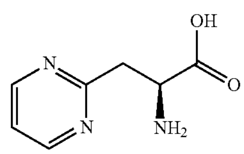 [SMILES: N[C@@H](Cc1ncccn1)C(=O)O] |
| 194 | ra102 | 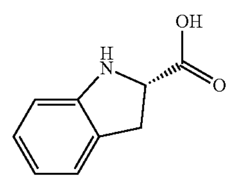 [SMILES: O=C(O)[C@@H]1Cc2ccccc2N1] |
| 195 | ra542 | 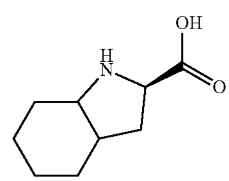 [SMILES: O=C(O)[C@H]1CC2CCCCC2N1] |
| 196 | Olc | 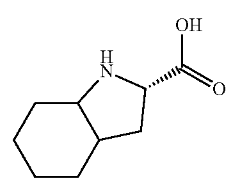 [SMILES: O=C(O)[C@@H]1CC2CCCCC2N1] |
| 197 | ra540 | 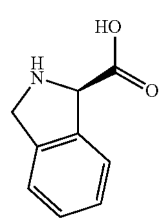 [SMILES: O=C(O)[C@@H]1NCc2ccccc21] |

TABLE 4-continued

The monomers used in the present disclosure.

| Entry No. | Monomer identifier | Chemical Structure |
|---|---|---|
| 198 | dR | (structure) |
| 199 | R | (structure) |
| 200 | RbArg | (structure) |
| 201 | SbArg | (structure) |
| 202 | Apm | (structure) |
| 203 | ra355 | (structure) |
| 204 | ra300 | (structure) |
| 205 | ra581 | (structure) |
| 206 | ra142 | (structure) |
| 207 | ra183 | (structure) |

TABLE 4-continued
The monomers used in the present disclosure.
| Entry No. | Monomer identifier | Chemical Structure |
|---|---|---|
| 208 | ra562 | 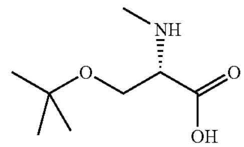 |
| 209 | Sta | 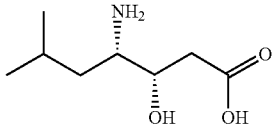 |
| 210 | Cit | 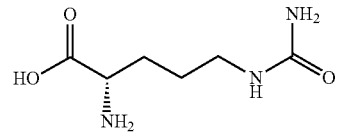 [SMILES: NC(=O)NCCC[C@H](N)C(=O)O] |
| 211 | mR | 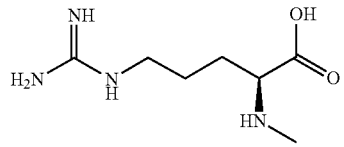 |
| 212 | Har | 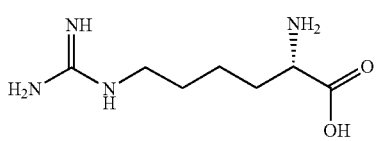 [SMILES: N=C(N)NCCCC[C@H](N)C(=O)O] |
| 213 | ra664 | 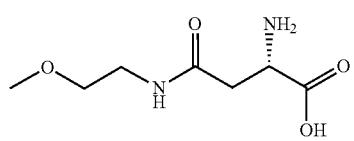 |
| 214 | Dpm | 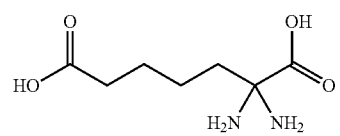 [SMILES: NC(N)(CCCCC(=O)O)C(=O)O] |
| 215 | m3K | 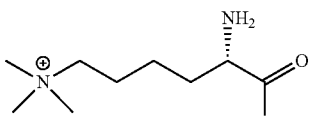 |
| 216 | Ra590 | 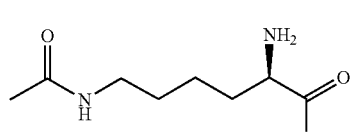 |
| 217 | ra307 | 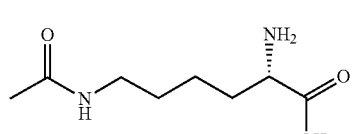 |

TABLE 4-continued

The monomers used in the present disclosure.

| Entry No. | Monomer identifier | Chemical Structure |
|---|---|---|
| 218 | ra547 | allyl ester of D-glutamic acid |
| 219 | Asu | L-2-aminosuberic acid |
| 220 | ra535 | D-aspartic acid β-tert-butyl ester |
| 221 | ra348 | L-aspartic acid β-tert-butyl ester |
| 222 | Aca | 2-aminodecanoic acid |
| 223 | Gla | γ-carboxyglutamic acid |
| 224 | ra80 | N-methyl-O-tert-butyl-threonine |
| 225 | ra545 | (R)-1,2,3,4-tetrahydroisoquinoline-3-carboxylic acid |
| 226 | Tic | (S)-1,2,3,4-tetrahydroisoquinoline-3-carboxylic acid |

TABLE 4-continued

The monomers used in the present disclosure.

| Entry No. | Monomer identifier | Chemical Structure |
|---|---|---|
| 227 | ra351 | 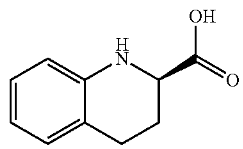 [SMILES: O=C(O)[C@H]1CCc2ccccc2N1] |
| 228 | ra350 | 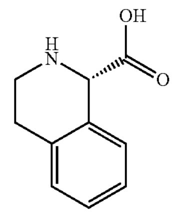 [SMILES: O=C(O)[C@H]1NCCc2ccccc21] |
| 229 | ra69 | 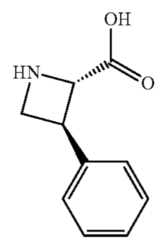 [SMILES: O=C(O)[C@H]1NC[C@@H]1c1ccccc1] |
| 230 | ra101 | 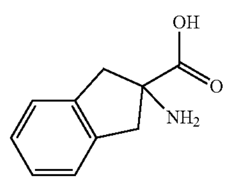 [SMILES: NC1(C(=O)O)Cc2ccccc2C1] |
| 231 | ra204 | 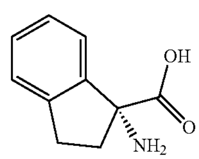 |
| 232 | ra521 | 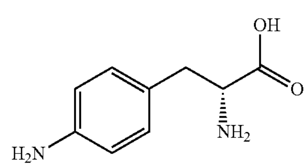 [SMILES: Nc1ccc(C[C@@H](N)C(=O)O)cc1] |
| 233 | ra523 | 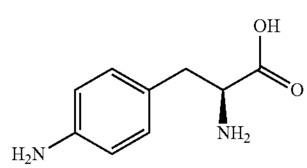 |
| 234 | ra172 | 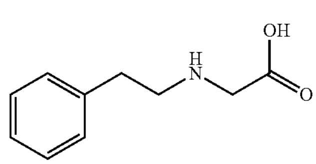 [SMILES: O=C(O)CNCCc1ccccc1] |

TABLE 4-continued

The monomers used in the present disclosure.

| Entry No. | Monomer identifier | Chemical Structure |
|---|---|---|
| 235 | ra195 | (D)-N-methyl phenylalanine |
| 236 | mF | (L)-N-methyl phenylalanine |
| 237 | ra558 | (L)-N-methyl cyclohexylalanine |
| 238 | ra120 | α-methyl phenylalanine |
| 239 | ra659 | (D)-homophenylalanine |
| 240 | ra134 | (L)-homophenylalanine |
| 241 | ra59 | (L)-homocyclohexylalanine |
| 242 | ra549 | (D)-homocyclohexylalanine |
| 243 | ra104 | (L)-3-methylphenylalanine |

TABLE 4-continued

The monomers used in the present disclosure.

| Entry No. | Monomer identifier | Chemical Structure |
|---|---|---|
| 244 | ra123 | 4-methyl-L-phenylalanine |
| 245 | ra87 | 2-methyl-L-phenylalanine |
| 246 | ra336 | (S)-2-amino-2-(2,6-dichlorophenyl)acetic acid |
| 247 | ra116 | 4-chloro-D-phenylalanine |
| 248 | ra665 | 4-chloro-L-phenylalanine |
| 249 | ra117 | 3-chloro-D-phenylalanine |
| 250 | ra115 | 2-chloro-D-phenylalanine |
| 251 | ral118 | 4-fluoro-D-phenylalanine |
| 252 | ra339 | 4-fluoro-L-phenylalanine |

TABLE 4-continued

The monomers used in the present disclosure.

| Entry No. | Monomer identifier | Chemical Structure |
|---|---|---|
| 253 | ra119 | (D)-3-fluorophenylalanine |
| 254 | ra666 | (L)-3-fluorophenylalanine |
| 255 | ra121 | (D)-2-fluorophenylalanine |
| 256 | ra551 | (D)-4-iodophenylalanine |
| 257 | ra539 | 4-tert-butoxy-pyrrolidine-2-carboxylic acid |
| 258 | ra381 | (R)-2-amino-2-(2-methoxyphenyl)acetic acid |
| 259 | dY | D-tyrosine |
| 260 | Y | L-tyrosine |
| 261 | ra469 | (R)-2-amino-2-(3-methoxyphenyl)acetic acid |

TABLE 4-continued

The monomers used in the present disclosure.

| Entry No. | Monomer identifier | Chemical Structure |
|---|---|---|
| 262 | ra400 | (S)-2-amino-2-(3-methoxyphenyl)acetic acid |
| 263 | ra106 | (2S,3R)-2-amino-3-hydroxy-3-phenylpropanoic acid |
| 264 | ra335 | (2S,3S)-2-amino-3-hydroxy-3-phenylpropanoic acid |
| 265 | ra513 | (S)-2-amino-3-(3-hydroxyphenyl)propanoic acid |
| 266 | ra329 | (R)-2-amino-2-(4-methoxyphenyl)acetic acid |
| 267 | SbTyr | (S)-3-amino-3-(4-hydroxyphenyl)propanoic acid |
| 268 | RbTyr | (R)-3-amino-3-(4-hydroxyphenyl)propanoic acid |
| 269 | ra658 | (S)-2-amino-4-morpholino-4-oxobutanoic acid |
| 270 | ra113 | (S)-2-amino-3-(2-cyanophenyl)propanoic acid |

TABLE 4-continued

The monomers used in the present disclosure.

| Entry No. | Monomer identifier | Chemical Structure |
|---|---|---|
| 271 | ra114 | 3-cyano-L-phenylalanine |
| 272 | ra596 | 4-(aminomethyl)-L-phenylalanine |
| 273 | ra112 | 4-cyano-L-phenylalanine |
| 274 | ra561 | 2,3-dimethyl-L-phenylalanine |
| 275 | ra208 | 2,6-dimethyl-L-phenylalanine |
| 276 | ra63 | 2,4-dimethyl-L-phenylalanine |
| 277 | ra66 | 3,4-dichloro-L-phenylalanine |
| 278 | ra55 | 3,4-dichloro-L-phenylalanine |
| 279 | ra62 | 2,4-dichloro-L-phenylalanine |

TABLE 4-continued

The monomers used in the present disclosure.

| Entry No. | Monomer identifier | Chemical Structure |
|---|---|---|
| 280 | ra56 | (S)-2-amino-3-(2,4-dichlorophenyl)propanoic acid |
| 281 | ra534 | (R)-2-amino-3-(2,5-dichlorophenyl)propanoic acid |
| 282 | ra387 | (R)-2-amino-3-(2,3-difluorophenyl)propanoic acid |
| 283 | ra386 | (S)-2-amino-3-(2,3-difluorophenyl)propanoic acid |
| 284 | ra374 | (R)-2-amino-3-(3,4-difluorophenyl)propanoic acid |
| 285 | ra360 | (S)-2-amino-3-(3,4-difluorophenyl)propanoic acid |
| 286 | ra64 | (S)-2-amino-3-(3,5-difluorophenyl)propanoic acid |

TABLE 4-continued

The monomers used in the present disclosure.

| Entry No. | Monomer identifier | Chemical Structure |
|---|---|---|
| 287 | ra65 | 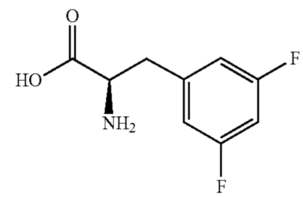 [SMILES: N[C@H](Cc1cc(F)cc(F)c1)C(=O)O] |
| 288 | ra382 | 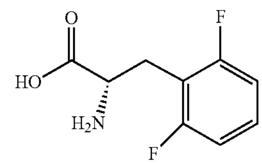 [SMILES: N[C@@H](Cc1c(F)cccc1F)C(=O)O] |
| 289 | ra537 | 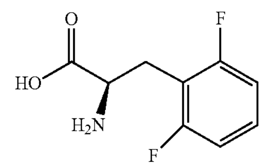 [SMILES: N[C@H](Cc1c(F)cccc1F)C(=O)O] |
| 290 | ra88 | 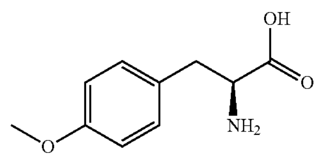 |
| 291 | ra209 | 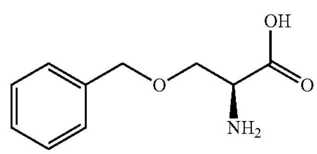 [SMILES: N[C@@H](COCc1ccccc1)C(=O)O] |
| 292 | ra497 | 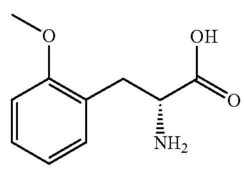 |
| 293 | ra185 | 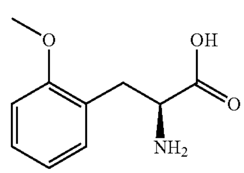 |
| 294 | mY | 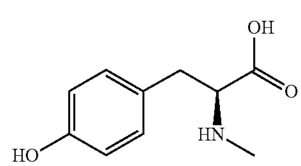 |
| 295 | ra133 | 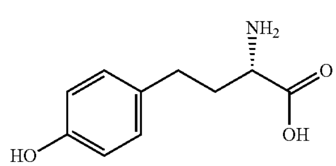 [SMILES: N[C@@H](CCc1ccc(O)cc1)C(=O)O] |

TABLE 4-continued

The monomers used in the present disclosure.

| Entry No. | Monomer identifier | Chemical Structure |
|---|---|---|
| 296 | ra667 | 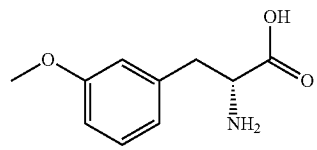 |
| 297 | ra124 | 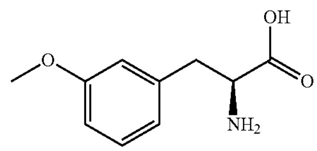 |
| 298 | Uraa1 | 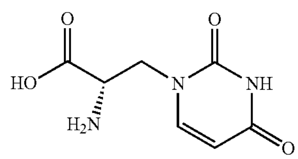 [SMILES: N[C@@H](Cn1ccc(=O)[nH]c1=O)C(=O)O] |
| 299 | ra594 | 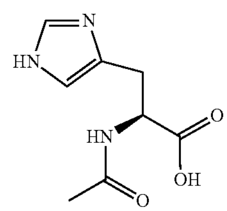 |
| 300 | Dsu | 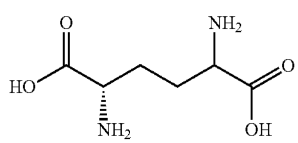 |
| 301 | ra456 | 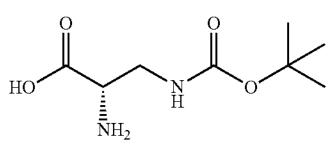 |
| 302 | ra457 | 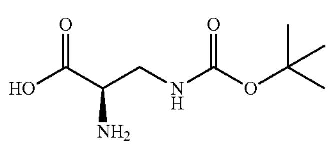 |
| 303 | ra589 | 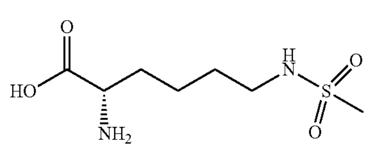 |
| 304 | ra559 | 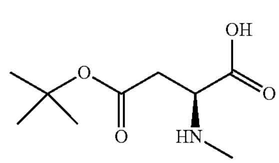 |

TABLE 4-continued

The monomers used in the present disclosure.

| Entry No. | Monomer identifier | Chemical Structure |
|---|---|---|
| 305 | ra536 | (L-glutamic acid γ-tert-butyl ester) |
| 306 | ra548 | (D-glutamic acid γ-tert-butyl ester) |
| 307 | ra573 | (5-phenylpyrrolidine-2-carboxylic acid) |
| 308 | ra86 | (3-phenylpyrrolidine-2-carboxylic acid) |
| 309 | ra574 | (4-phenylpyrrolidine-2-carboxylic acid) |
| 310 | ra533 | (2-amino-2-(2,3-dihydro-1H-inden-2-yl)acetic acid) |
| 311 | ra75 | (2-amino-2-(2,3-dihydro-1H-inden-2-yl)acetic acid) |
| 312 | ra105 | (7-hydroxy-1,2,3,4-tetrahydroisoquinoline-3-carboxylic acid) |

TABLE 4-continued

The monomers used in the present disclosure.

| Entry No. | Monomer identifier | Chemical Structure |
|---|---|---|
| 313 | ra136 | 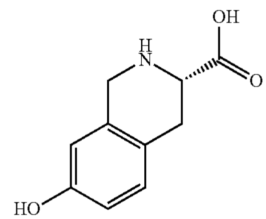 [SMILES: O=C(O)[C@@H]1Cc2ccc(O)cc2CN1] |
| 314 | ra454 | 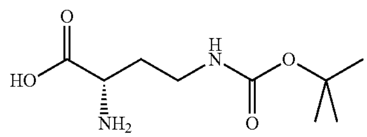 |
| 315 | ra321 | 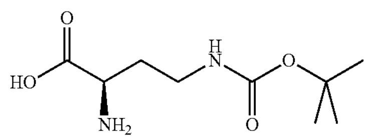 |
| 316 | ra588 | 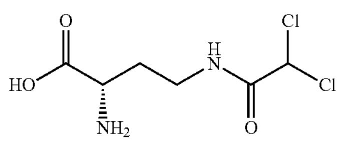 [SMILES: N[C@@H](CCNC(=O)C(Cl)Cl)C(=O)O] |
| 317 | ra560 | 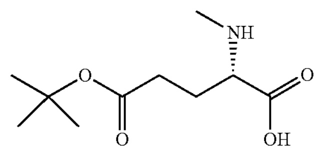 |
| 318 | ra517 | 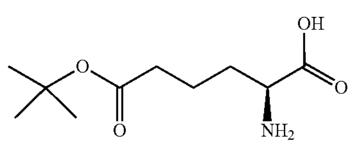 |
| 319 | ra648 | 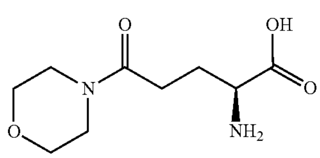 [SMILES: N[C@@H](CCC(=O)N1CCOCC1)C(=O)O] |
| 320 | ra317 | 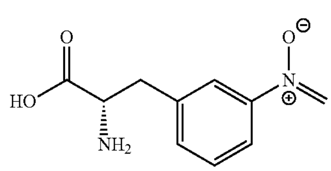 |
| 321 | ra302 | 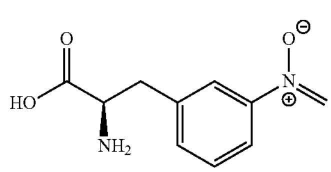 |

TABLE 4-continued

The monomers used in the present disclosure.

| Entry No. | Monomer identifier | Chemical Structure |
|---|---|---|
| 322 | ra660 | *cyclohexyl-NH-C(O)-CH2-CH(NH2)-COOH* |
| 323 | ra108 | *(S)-2-amino-3-(4-carbamoylphenyl)propanoic acid* |
| 324 | ra378 | *(R)-2-amino-3-(4-carbamoylphenyl)propanoic acid* |
| 325 | ra109 | *(S)-2-amino-3-(3-carbamoylphenyl)propanoic acid* |
| 326 | ra597 | *(R)-2-amino-3-(3-carbamoylphenyl)propanoic acid* |
| 327 | ra111 | *(S)-2-amino-3-(2-carbamoylphenyl)propanoic acid* |
| 328 | ra579 | *(S)-2-amino-3-(4-carboxyphenyl)propanoic acid* |
| 329 | App | *(3S,4S)-4-amino-3-hydroxy-5-phenylpentanoic acid* |

TABLE 4-continued

The monomers used in the present disclosure.

| Entry No. | Monomer identifier | Chemical Structure |
|---|---|---|
| 330 | Cap | 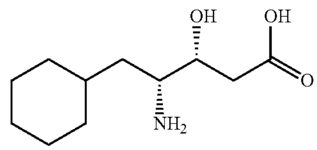 [SMILES: N[C@H](CC1CCCCC1)[C@H](O)CC(=O)O] |
| 331 | dW | 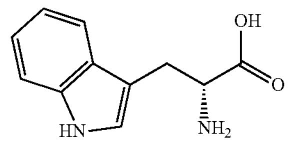 [SMILES: N[C@H](Cc1c[nH]c2ccccc12)C(=O)O] |
| 332 | W | 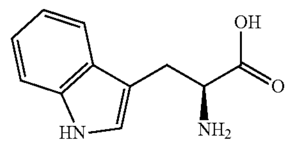 [SMILES: N[C@@H](Cc1c[nH]c2ccccc12)C(=O)O] |
| 333 | SbTrp | 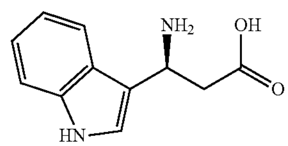 [SMILES: N[C@@H](CC(=O)O)c1c[nH]c2ccccc12] |
| 334 | RbTrp | 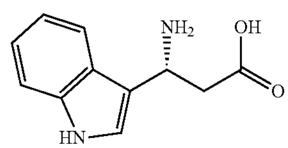 [SMILES: N[C@H](CC(=O)O)c1c[nH]c2ccccc12] |
| 335 | ra347 | 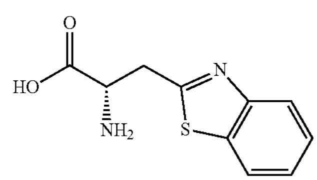 [SMILES: N[C@@H](Cc1nc2ccccc2s1)C(=O)O] |
| 336 | ra575 | 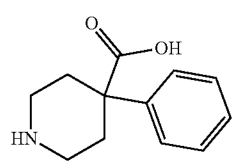 [SMILES: O=C(O)C1(c2ccccc2)CCNCC1] |
| 337 | ra404 | 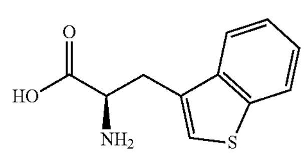 [SMILES: N[C@H](Cc1csc2ccccc12)C(=O)O] |
| 338 | ra407 | 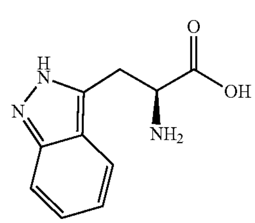 [SMILES: N[C@@H](Cc1[nH]nc2ccccc12)C(=O)O] |

TABLE 4-continued
The monomers used in the present disclosure.
| Entry No. | Monomer identifier | Chemical Structure |
|---|---|---|
| 339 | ra129 | 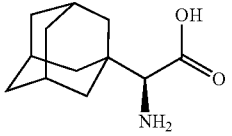 |
| 340 | ra608 | 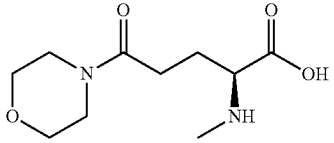 [SMILES: CN[C@@H](CCC(=O)N1CCOCC1)C(=O)O] |
| 341 | ra642 | 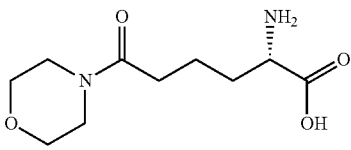 [SMILES: N[C@@H](CCCC(=O)N1CCOCC1)C(=O)O] |
| 342 | ra463 | 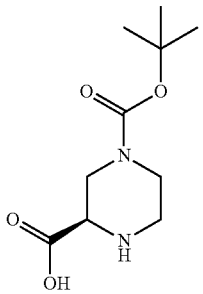 [SMILES: CC(C)(C)OC(=O)N1CCN[C@@H](C(=O)O)C1] |
| 343 | ra467 | 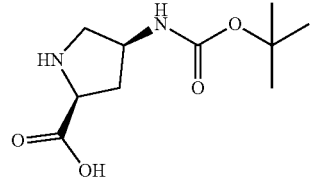 [SMILES: CC(C)(C)OC(=O)N[C@@H]1CN[C@H](C(=O)O)C1] |
| 344 | ra529 | 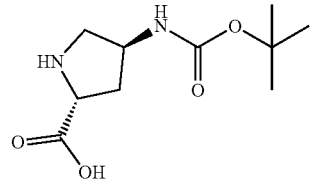 [SMILES: CC(C)(C)OC(=O)N[C@@H]1CN[C@@H](C(=O)O)C1] |
| 345 | ra468 | 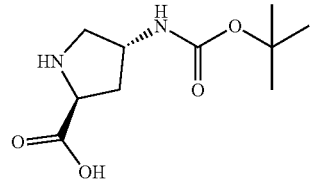 [SMILES: CC(C)(C)OC(=O)N[C@H]1CN[C@H](C(=O)O)C1] |
| 346 | ra140 | 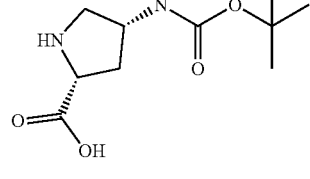 |

TABLE 4-continued

The monomers used in the present disclosure.

| Entry No. | Monomer identifier | Chemical Structure |
|---|---|---|
| 347 | ra141 | 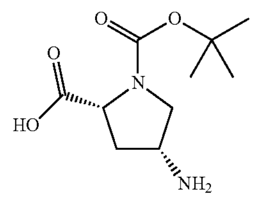 [SMILES: CC(C)(C)OC(=O)N1C[C@H](N)C[C@@H]1C(=O)O] |
| 348 | no22Y | 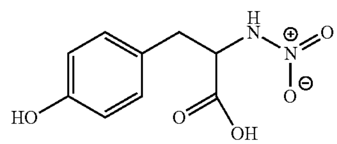 [SMILES: O=C(O)C(Cc1ccc(O)cc1)N[N+](=O)[O-]] |
| 349 | ra591 | 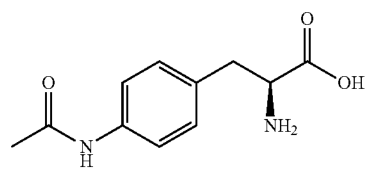 [SMILES: CC(=O)Nc1ccc(C[C@H](N)C(=O)O)cc1] |
| 350 | ra638 | 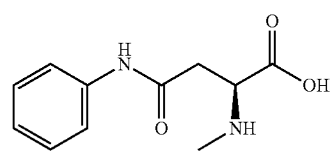 [SMILES: CN[C@@H](CC(=O)Nc1ccccc1)C(=O)O] |
| 351 | ra650 | 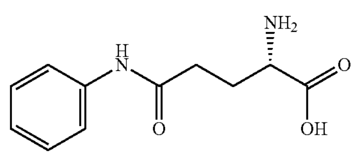 [SMILES: N[C@@H](CCC(=O)Nc1ccccc1)C(=O)O] |
| 352 | ra592 | 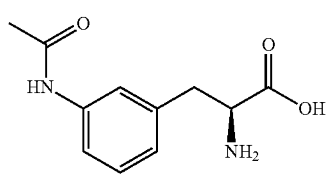 [SMILES: CC(=O)Nc1cccc(C[C@H](N)C(=O)O)c1] |
| 353 | ra578 | 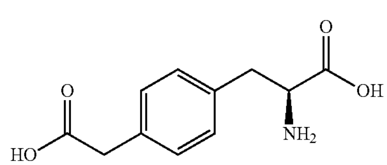 [SMILES: N[C@@H](Cc1ccc(CC(=O)O)cc1)C(=O)O] |
| 354 | ra604 | 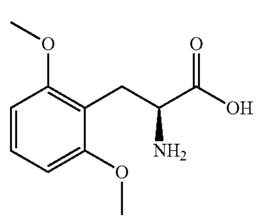 [SMILES: COc1cccc(OC)c1C[C@H](N)C(=O)O] |

TABLE 4-continued

The monomers used in the present disclosure.

| Entry No. | Monomer identifier | Chemical Structure |
|---|---|---|
| 355 | ra373 | 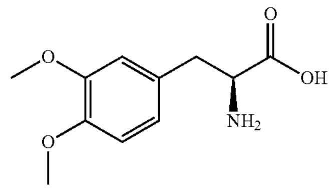 [SMILES: COc1ccc(C[C@H](N)C(=O)O)cc1OC] |
| 356 | ra171 | 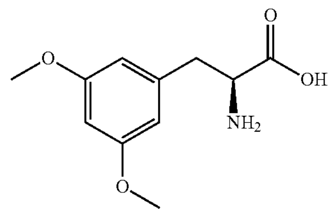 [SMILES: COc1cc(C[C@H](N)C(=O)O)cc(OC)c1] |
| 357 | ra110 | 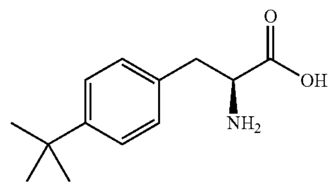 [SMILES: CC(C)(C)c1ccc(C[C@H](N)C(=O)O)cc1] |
| 358 | ra107 | 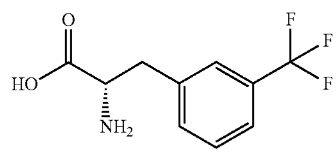 [SMILES: N[C@@H](Cc1cccc(C(F)(F)F)c1)C(=O)O] |
| 359 | ra93 | 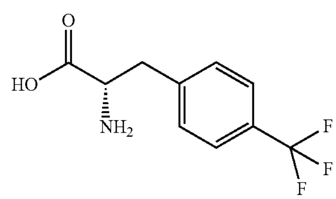 [SMILES: N[C@@H](Cc1ccc(C(F)(F)F)cc1)C(=O)O] |
| 360 | ra370 | 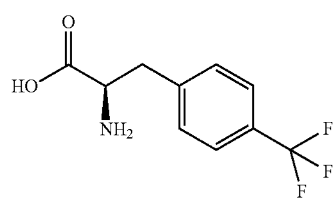 [SMILES: N[C@H](Cc1ccc(C(F)(F)F)cc1)C(=O)O] |
| 361 | ra92 | 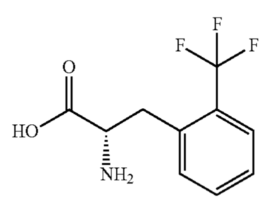 [SMILES: N[C@@H](Cc1ccccc1C(F)(F)F)C(=O)O] |
| 362 | ra79 | 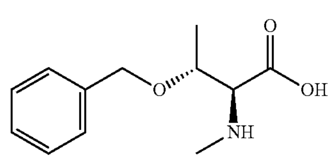 [SMILES: CN[C@H](C(=O)O)[C@@H](C)OCc1ccccc1] |

TABLE 4-continued

The monomers used in the present disclosure.

| Entry No. | Monomer identifier | Chemical Structure |
|---|---|---|
| 363 | ra639 | 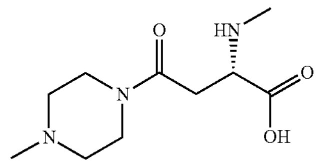 [SMILES: CN[C@@H](CC(=O)N1CCN(C)CC1)C(=O)O] |
| 364 | ra649 | 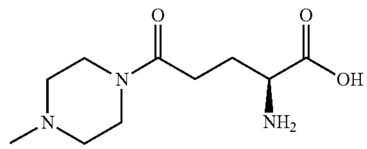 [SMILES: CN1CCN(C(=O)CC[C@H](N)C(=O)O)CC1] |
| 365 | ra546 | 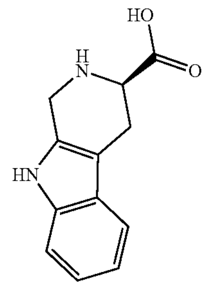 [SMILES: O=C(O)[C@H]1Cc2c([nH]c3ccccc23)CN1] |
| 366 | ra554 | 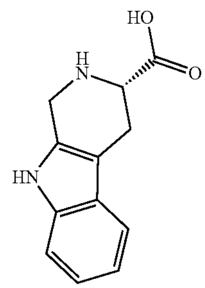 [SMILES: O=C(O)[C@@H]1Cc2c([nH]c3ccccc23)CN1] |
| 367 | mW | 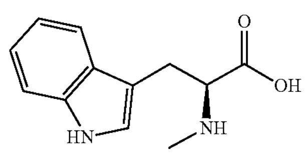 [SMILES: CN[C@@H](Cc1c[nH]c2ccccc12)C(=O)O] |
| 368 | ra324 | 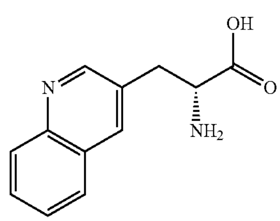 [SMILES: N[C@H](Cc1cnc2ccccc2c1)C(=O)O] |
| 369 | ra327 | 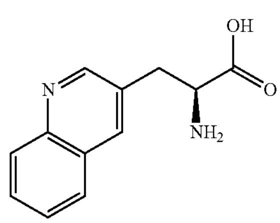 [SMILES: N[C@@H](Cc1cnc2ccccc2c1)C(=O)O] |

TABLE 4-continued

The monomers used in the present disclosure.

| Entry No. | Monomer identifier | Chemical Structure |
|---|---|---|
| 370 | ra605 | D-quinolin-6-yl-alanine |
| 371 | Ra385 | D-1-methyl-tryptophan |
| 372 | ra354 | L-1-methyl-tryptophan |
| 373 | ra58 | L-quinolin-2-yl-alanine |
| 374 | ra314 | L-(2-oxoindolin-3-yl)-alanine |
| 375 | ra486 | L-(2-oxoindolin-3-yl)-alanine |
| 376 | ra567 | D-2-naphthyl-alanine |
| 377 | napA | L-2-naphthyl-alanine |
| 378 | ra566 | D-1-naphthyl-alanine |

TABLE 4-continued
The monomers used in the present disclosure.
| Entry No. | Monomer identifier | Chemical Structure |
|---|---|---|
| 379 | ra148 | 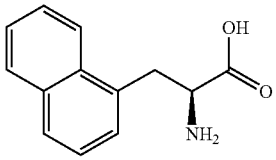 [SMILES: N[C@@H](Cc1cccc2ccccc12)C(=O)O] |
| 380 | ra167 & ra78 | 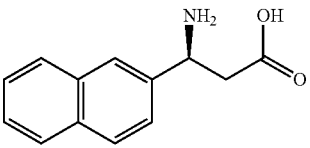 [SMILES: N[C@@H](CC(=O)O)c1ccc2ccccc2c1] |
| 381 | ra71 | 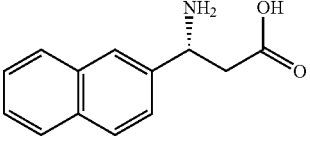 [SMILES: N[C@H](CC(=O)O)c1ccc2ccccc2c1] |
| 382 | ra334 & ra487 | 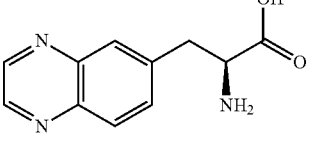 |
| 383 | ra333 | 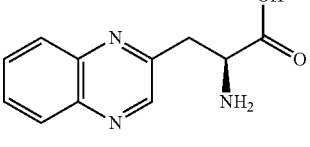 |
| 384 | ra452 | 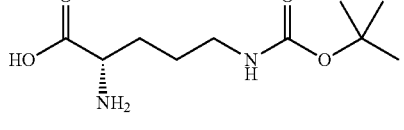 |
| 385 | ra306 | 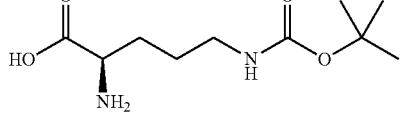 |
| 386 | ra637 | 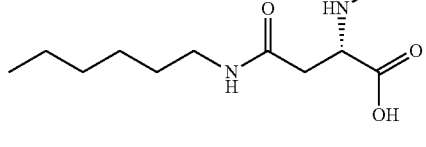 |
| 387 | ra587 | 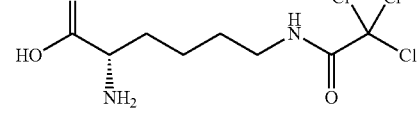 |

TABLE 4-continued

The monomers used in the present disclosure.

| Entry No. | Monomer identifier | Chemical Structure |
|---|---|---|
| 388 | ra586 | 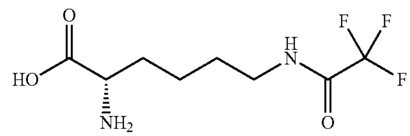 [SMILES: N[C@@H](CCCCNC(=O)C(F)(F)F)C(=O)O] |
| 389 | ra643 | 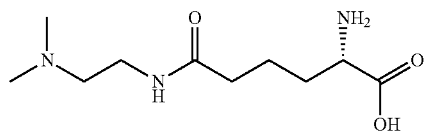 [SMILES: CN(C)CCNC(=O)CCC[C@H](N)C(=O)O] |
| 390 | ra453 | 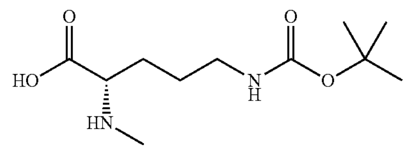 [SMILES: CN[C@@H](CCCNC(=O)OC(C)(C)C)C(=O)O] |
| 391 | ra308 | 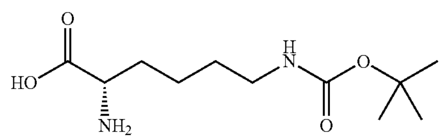 [SMILES: CC(C)(C)OC(=O)NCCCC[C@H](N)C(=O)O] |
| 392 | ra305 | 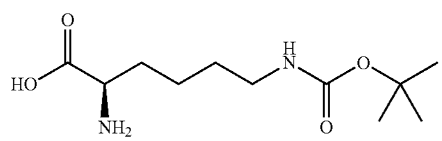 [SMILES: CC(C)(C)OC(=O)NCCCC[C@@H](N)C(=O)O] |
| 393 | ra661 | 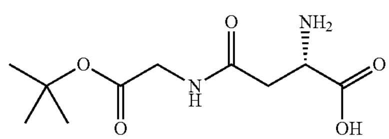 [SMILES: CC(C)(C)OC(=O)CNC(=O)C[C@H](N)C(=O)O] |
| 394 | ra647 | 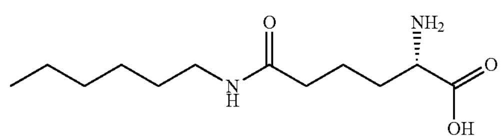 [SMILES: CCCCCCNC(=O)CCC[C@H](N)C(=O)O] |
| 395 | ra326 | 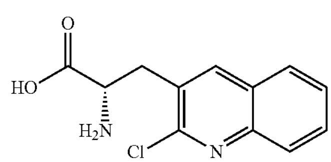 [SMILES: N[C@@H](Cc1cc2ccccc2nc1Cl)C(=O)O] |
| 396 | ra323 | 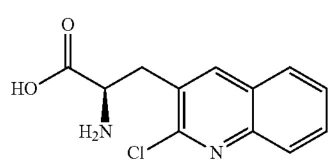 [SMILES: N[C@H](Cc1cc2ccccc2nc1Cl)C(=O)O] |
| 397 | ra342 | 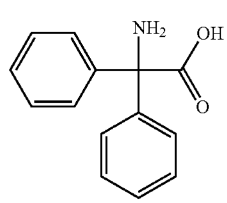 [SMILES: NC(C(=O)O)(c1ccccc1)c1ccccc1] |

TABLE 4-continued

The monomers used in the present disclosure.

| Entry No. | Monomer identifier | Chemical Structure |
|---|---|---|
| 398 | ra496 | 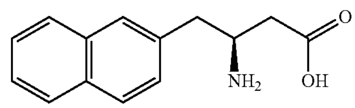 [SMILES: N[C@H](CC(=O)O)Cc1ccc2ccccc2c1] |
| 399 | ra332 | 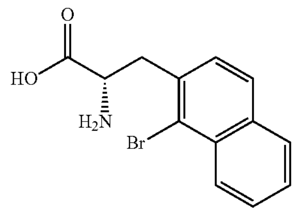 [SMILES: N[C@@H](Cc1ccc2ccccc2c1Br)C(=O)O] |
| 400 | ra593 | 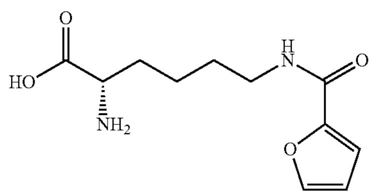 [SMILES: N[C@@H](CCCCNC(=O)c1ccco1)C(=O)O] |
| 401 | ra81 | 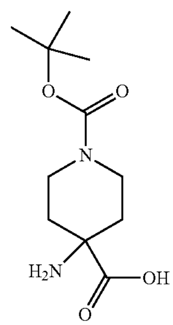 [SMILES: CC(C)(C)OC(=O)N1CCC(N)(C(=O)O)CC1] |
| 402 | ra663 | 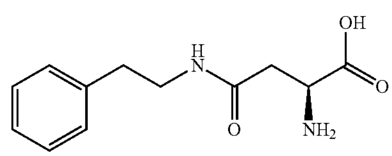 [SMILES: N[C@@H](CC(=O)NCCc1ccccc1)C(=O)O] |
| 403 | ra640 | 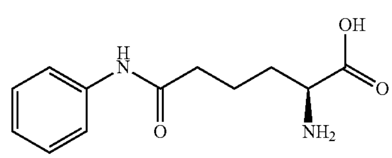 [SMILES: N[C@@H](CCCC(=O)Nc1ccccc1)C(=O)O] |
| 404 | ra646 | 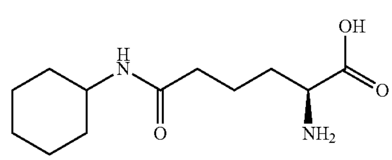 [SMILES: N[C@@H](CCCC(=O)NC1CCCCC1)C(=O)O] |
| 405 | ra636 | 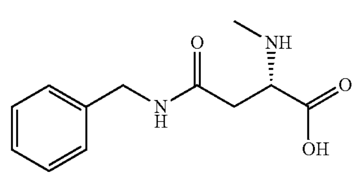 [SMILES: CN[C@@H](CC(=O)NCc1ccccc1)C(=O)O] |

TABLE 4-continued

The monomers used in the present disclosure.

| Entry No. | Monomer identifier | Chemical Structure |
|---|---|---|
| 406 | ra652 | 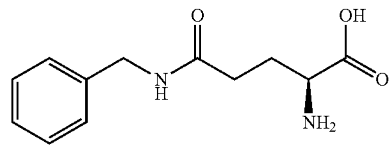 [SMILES: N[C@@H](CCC(=O)NCc1ccccc1)C(=O)O] |
| 407 | ra515 | 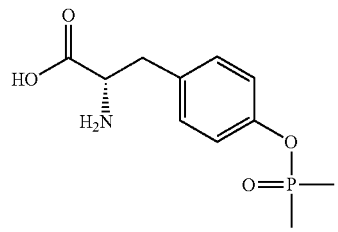 [SMILES: CP(C)(=O)Oc1ccc(C[C@H](N)C(=O)O)cc1] |
| 408 | ra520 | 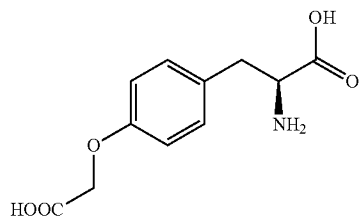 [SMILES: N[C@@H](Cc1ccc(OCC(=O)O)cc1)C(=O)O] |
| 409 | ra94 | 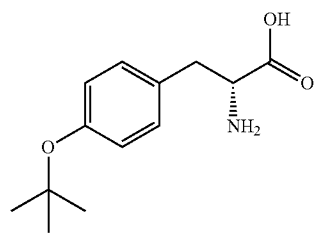 [SMILES: CC(C)(C)Oc1ccc(C[C@@H](N)C(=O)O)cc1] |
| 410 | ra137 | 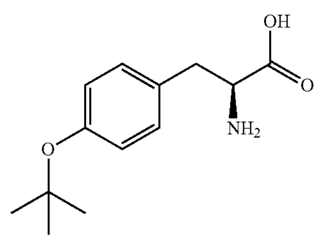 [SMILES: CC(C)(C)Oc1ccc(C[C@H](N)C(=O)O)cc1] |
| 411 | ra495 & ra531 | 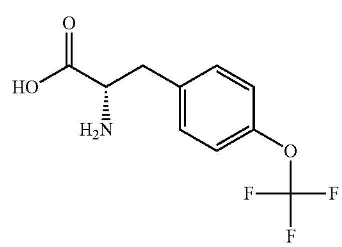 [SMILES: N[C@@H](Cc1ccc(OC(F)(F)F)cc1)C(=O)O] |
| 412 | ra641 | 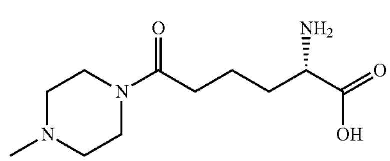 [SMILES: CN1CCN(C(=O)CCC[C@H](N)C(=O)O)CC1] |

TABLE 4-continued
The monomers used in the present disclosure.
| Entry No. | Monomer identifier | Chemical Structure |
|---|---|---|
| 413 | ra651 | 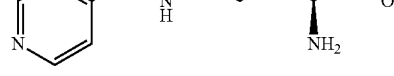 |
| 414 | ra612 | 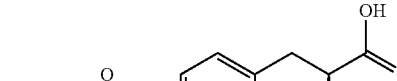 |
| 415 | ra500 | 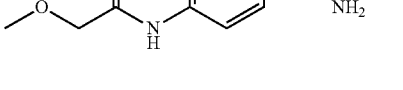 |
| 416 | ra644 | 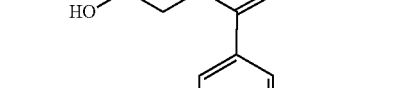 |
| 417 | ra399 | 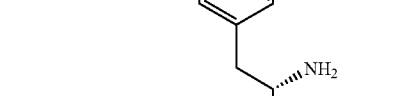 |
| 418 | ra98 | 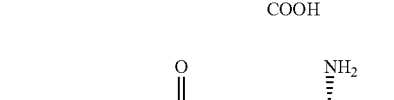 |
| 419 | ra645 | 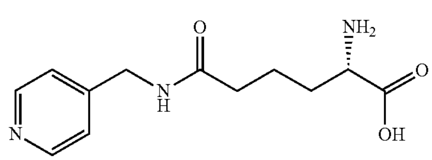 [SMILES: N[C@@H](CCCC(=O)NCc1ccncc1)C(=O)O] |

TABLE 4-continued

The monomers used in the present disclosure.

| Entry No. | Monomer identifier | Chemical Structure |
|---|---|---|
| 420 | Pyl | 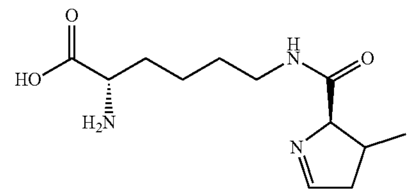 [SMILES: CC1CC=N[C@H]1C(=O)NCCCC[C@H](N)C(=O)O] |
| 421 | DPyl | 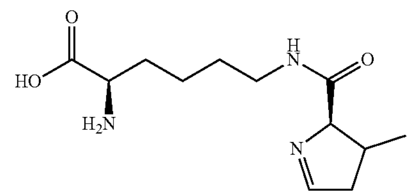 [SMILES: CC1CC=N[C@H]1C(=O)NCCCC[C@@H](N)C(=O)O] |
| 422 | ra662 | 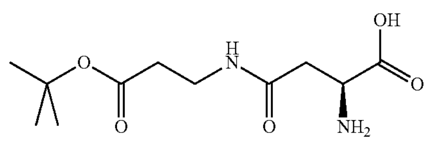 [SMILES: CC(C)(C)OC(=O)CCNC(=O)C[C@H](N)C(=O)O] |
| 423 | ra653 | 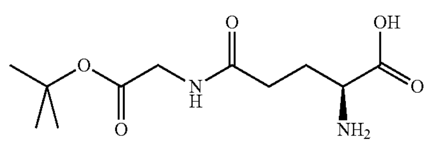 [SMILES: CC(C)(C)OC(=O)CNC(=O)CC[C@H](N)C(=O)O] |
| 424 | ra491 | 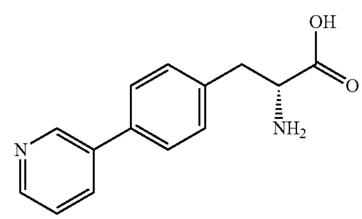 [SMILES: N[C@H](Cc1ccc(-c2cccnc2)cc1)C(=O)O] |
| 425 | ra577 | 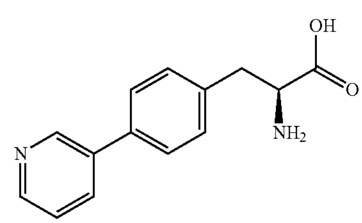 [SMILES: N[C@@H](Cc1ccc(-c2cccnc2)cc1)C(=O)O] |
| 426 | ra70 | 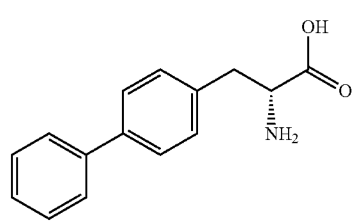 [SMILES: N[C@H](Cc1ccc(-c2ccccc2)cc1)C(=O)O] |

TABLE 4-continued

The monomers used in the present disclosure.

| Entry No. | Monomer identifier | Chemical Structure |
|---|---|---|
| 427 | ra95 | 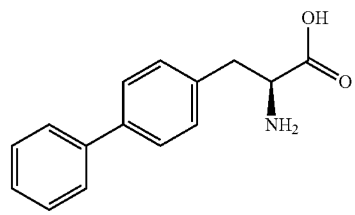 [SMILES: N[C@@H](Cc1ccc(-c2ccccc2)cc1)C(=O)O] |
| 428 | ra97 | 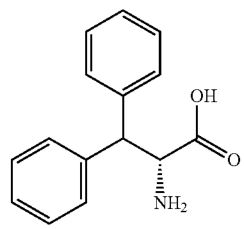 [SMILES: N[C@@H](C(=O)O)C(c1ccccc1)c1ccccc1] |
| 429 | ra136 | 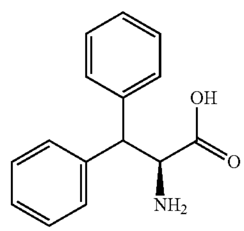 [SMILES: N[C@H](C(=O)O)C(c1ccccc1)c1ccccc1] |
| 430 | ra96 | 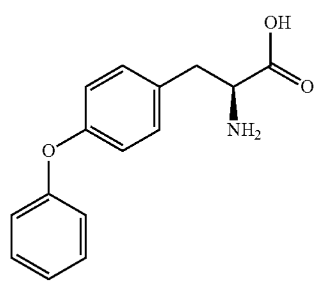 [SMILES: N[C@@H](Cc1ccc(Oc2ccccc2)cc1)C(=O)O] |
| 431 | ra514 | 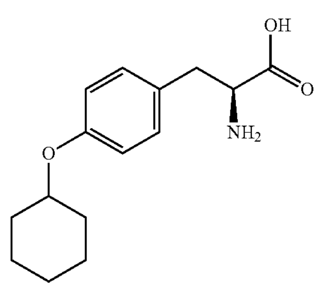 [SMILES: N[C@@H](Cc1ccc(OC2CCCCC2)cc1)C(=O)O] |
| 432 | ra654 | 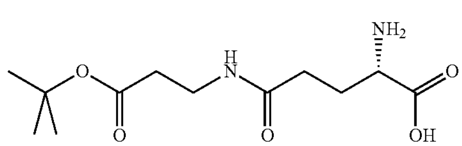 [SMILES: CC(C)(C)OC(=O)CCNC(=O)CC[C@H](N)C(=O)O] |

TABLE 4-continued

The monomers used in the present disclosure.

| Entry No. | Monomer identifier | Chemical Structure |
|---|---|---|
| 433 | ra657 | 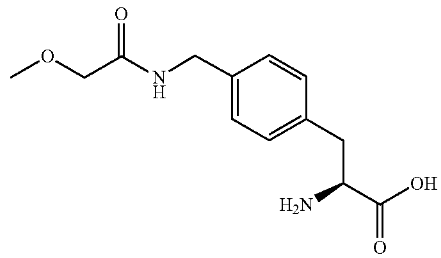 [SMILES: COCC(=O)NCc1ccc(C[C@H](N)C(=O)O)cc1] |
| 434 | ra511 | 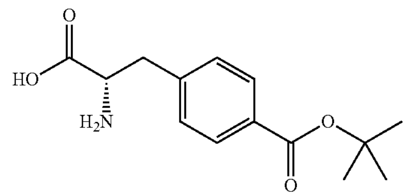 [SMILES: CC(C)(C)OC(=O)c1ccc(C[C@H](N)C(=O)O)cc1] |
| 435 | ra366 | 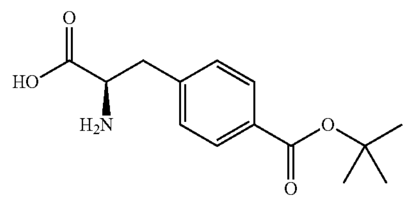 [SMILES: CC(C)(C)OC(=O)c1ccc(C[C@@H](N)C(=O)O)cc1] |
| 436 | pnaC | 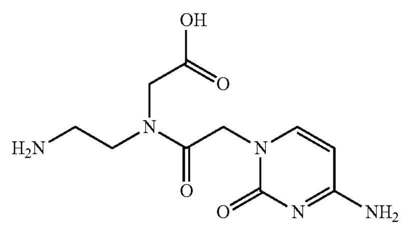 [SMILES: NCCN(CC(=O)O)C(=O)Cn1ccc(N)nc1=O] |
| 437 | ra615 | 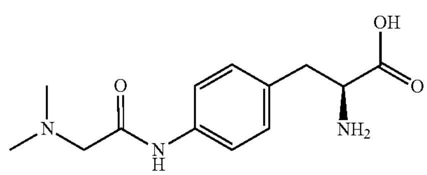 [SMILES: CN(C)CC(=O)Nc1ccc(C[C@H](N)C(=O)O)cc1] |
| 438 | pnaT | 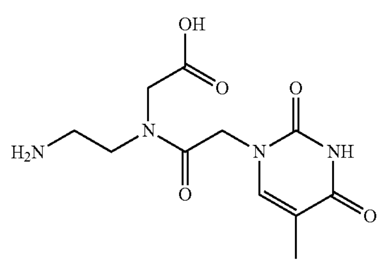 [SMILES: Cc1cn(CC(=O)N(CCN)CC(=O)O)c(=O)[nH]c1=O] |
| 439 | ra624 | 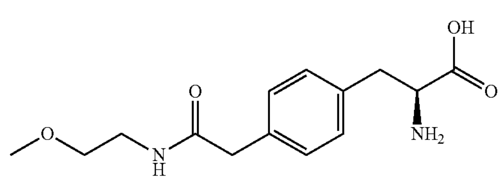 [SMILES: COCCNC(=O)Cc1ccc(C[C@H](N)C(=O)O)cc1] |

TABLE 4-continued

The monomers used in the present disclosure.

| Entry No. | Monomer identifier | Chemical Structure |
|---|---|---|
| 440 | ra526 | 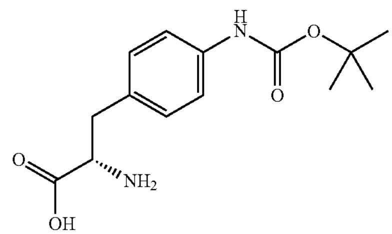 [SMILES: CC(C)(C)OC(=O)Nc1ccc(C[C@H](N)C(=O)O)cc1] |
| 441 | ra525 | 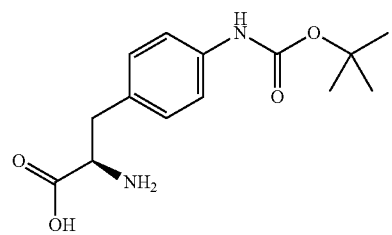 [SMILES: CC(C)(C)OC(=O)Nc1ccc(C[C@@H](N)C(=O)O)cc1] |
| 442 | ra471 | 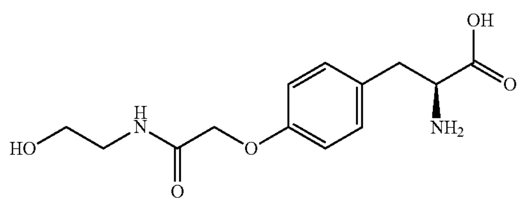 [SMILES: N[C@@H](Cc1ccc(OCC(=O)NCCO)cc1)C(=O)O] |
| 443 | ra613 | 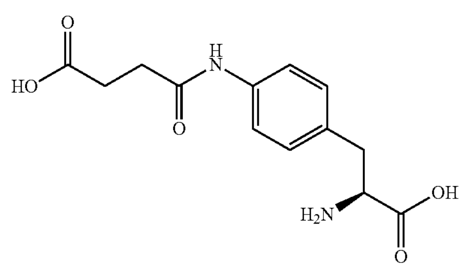 [SMILES: N[C@@H](Cc1ccc(NC(=O)CCC(=O)O)cc1)C(=O)O] |
| 444 | ra599 | 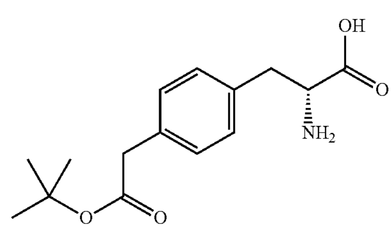 [SMILES: CC(C)(C)OC(=O)Cc1ccc(C[C@@H](N)C(=O)O)cc1] |
| 445 | ra553 | 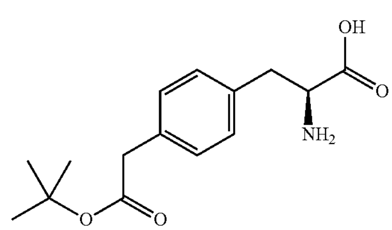 [SMILES: CC(C)(C)OC(=O)Cc1ccc(C[C@H](N)C(=O)O)cc1] |

TABLE 4-continued

The monomers used in the present disclosure.

| Entry No. | Monomer identifier | Chemical Structure |
|---|---|---|
| 446 | ra626 | 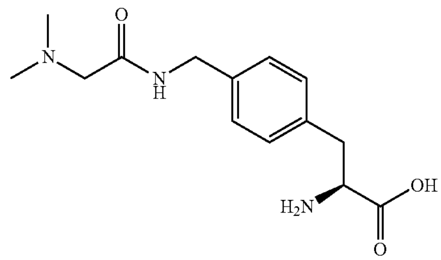 [SMILES: CN(C)CC(=O)NCc1ccc(C[C@H](N)C(=O)O)cc1] |
| 447 | ra633 | 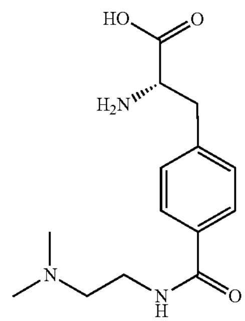 [SMILES: CN(C)CCNC(=O)c1ccc(C[C@H](N)C(=O)O)cc1] |
| 448 | ra628 | 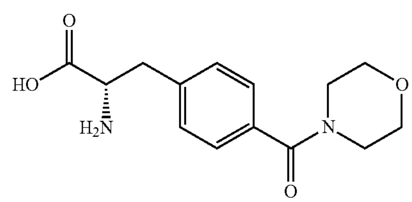 [SMILES: N[C@@H](Cc1ccc(C(=O)N2CCOCC2)cc1)C(=O)O] |
| 449 | ra60 | 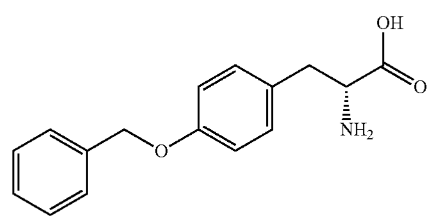 [SMILES: N[C@H](Cc1ccc(OCc2ccccc2)cc1)C(=O)O] |
| 450 | ra73 | 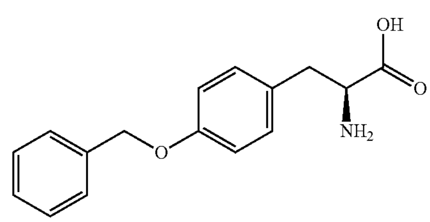 [SMILES: N[C@@H](Cc1ccc(OCc2ccccc2)cc1)C(=O)O] |
| 451 | ra175 | 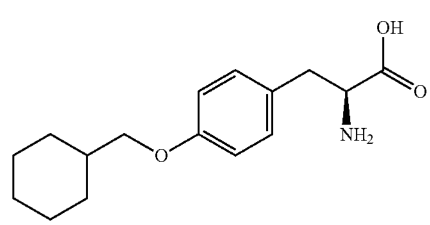 [SMILES: N[C@@H](Cc1ccc(OCC2CCCCC2)cc1)C(=O)O] |

TABLE 4-continued

The monomers used in the present disclosure.

| Entry No. | Monomer identifier | Chemical Structure |
|---|---|---|
| 452 | ra606 | 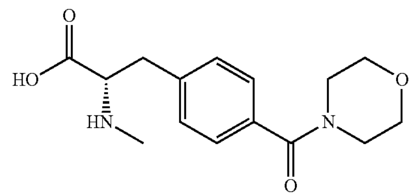 [SMILES: CN[C@@H](Cc1ccc(C(=O)N2CCOCC2)cc1)C(=O)O] |
| 453 | ra398 | 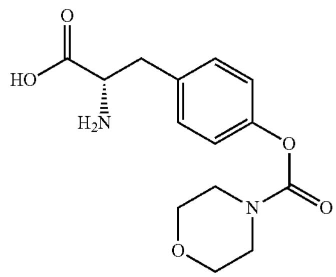 [SMILES: N[C@@H](Cc1ccc(OC(=O)N2CCOCC2)cc1)C(=O)O] |
| 454 | ra494 | 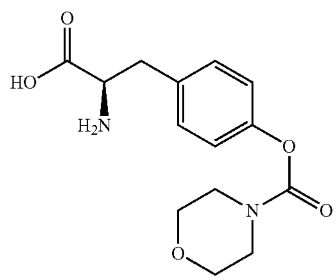 [SMILES: N[C@H](Cc1ccc(OC(=O)N2CCOCC2)cc1)C(=O)O] |
| 455 | ra501 | 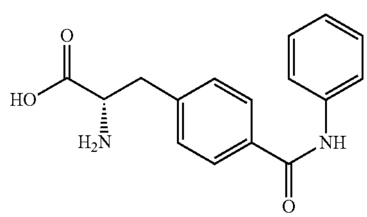 [SMILES: N[C@@H](Cc1ccc(C(=O)Nc2ccccc2)cc1)C(=O)O] |
| 456 | ra503 | 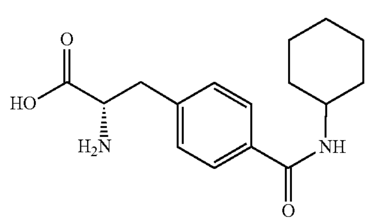 [SMILES: N[C@@H](Cc1ccc(C(=O)NC2CCCCC2)cc1)C(=O)O] |
| 457 | ra611 | 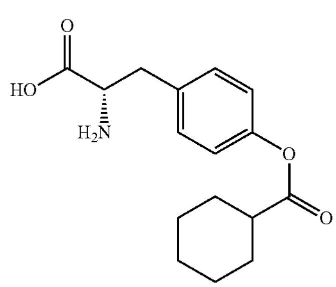 [SMILES: N[C@@H](Cc1ccc(OC(=O)C2CCCCC2)cc1)C(=O)O] |

TABLE 4-continued

The monomers used in the present disclosure.

| Entry No. | Monomer identifier | Chemical Structure |
|---|---|---|
| 458 | ra353 | 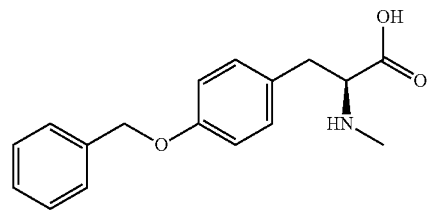 [SMILES: CN[C@@H](Cc1ccc(OCc2ccccc2)cc1)C(=O)O] |
| 459 | ra616 | 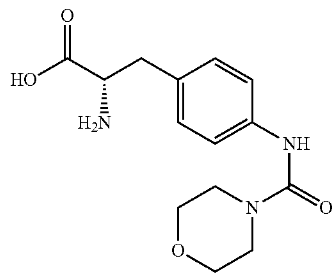 [SMILES: N[C@@H](Cc1ccc(NC(=O)N2CCOCC2)cc1)C(=O)O] |
| 460 | ra629 | 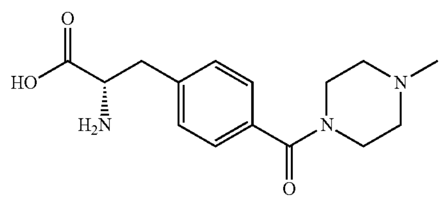 [SMILES: CN1CCN(C(=O)c2ccc(C[C@H](N)C(=O)O)cc2)CC1] |
| 461 | ra504 | 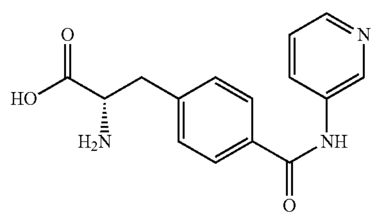 [SMILES: N[C@@H](Cc1ccc(C(=O)Nc2cccnc2)cc1)C(=O)O] |
| 462 | pnaA | 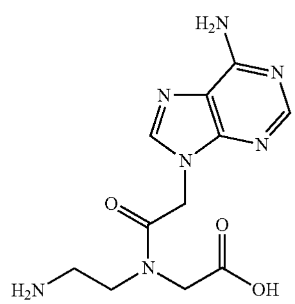 [SMILES: NCCN(CC(=O)O)C(=O)Cn1cnc2c(N)ncnc21] |
| 463 | ra318 | 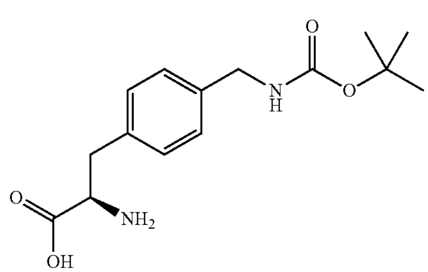 [SMILES: CC(C)(C)OC(=O)NCc1ccc(C[C@@H](N)C(=O)O)cc1] |

TABLE 4-continued

The monomers used in the present disclosure.

| Entry No. | Monomer identifier | Chemical Structure |
|---|---|---|
| 464 | ra614 | 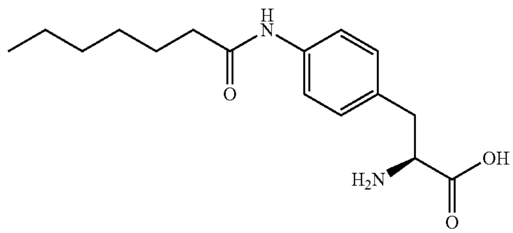 [SMILES: CCCCCCC(=O)Nc1ccc(C[C@H](N)C(=O)O)cc1] |
| 465 | ra630 | 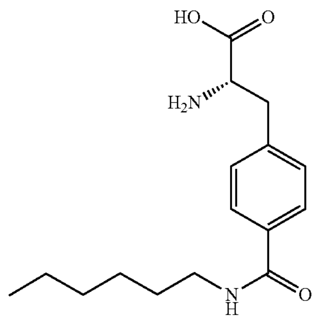 [SMILES: CCCCCCNC(=O)c1ccc(C[C@H](N)C(=O)O)cc1] |
| 466 | ra512 | 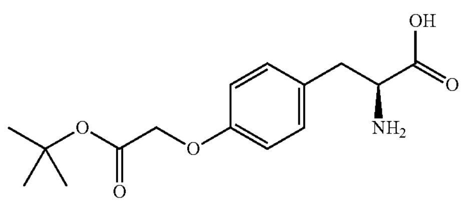 [SMILES: CC(C)(C)OC(=O)COc1ccc(C[C@H](N)C(=O)O)cc1] |
| 467 | ra319 | 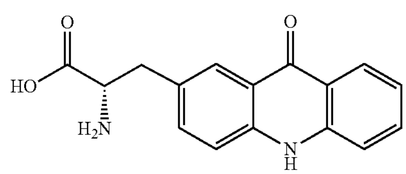 [SMILES: N[C@@H](Cc1ccc2[nH]c3ccccc3c(=O)c2c1)C(=O)O] |
| 468 | Pqa | 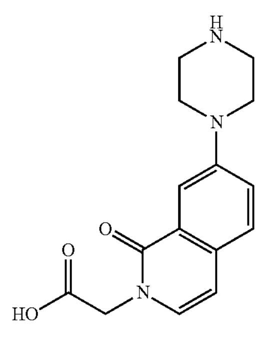 [SMILES: O=C(O)Cn1ccc2ccc(N3CCNCC3)cc2c1=O] |
| 469 | ra619 | 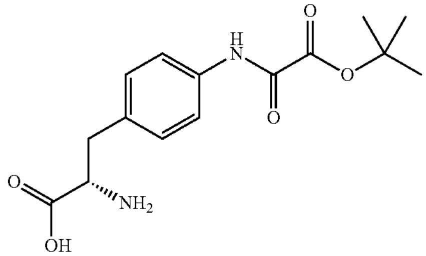 [SMILES: CC(C)(C)OC(=O)C(=O)Nc1ccc(C[C@H](N)C(=O)O)cc1] |

TABLE 4-continued
The monomers used in the present disclosure.
| Entry No. | Monomer identifier | Chemical Structure |
|---|---|---|
| 470 | ra627 | 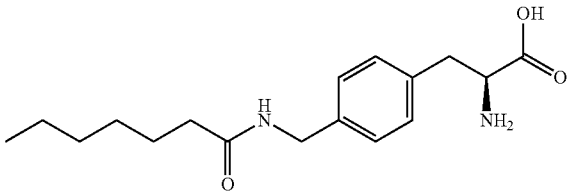 [SMILES: CCCCCCC(=O)NCc1ccc(C[C@H](N)C(=O)O)cc1] |
| 471 | ra623 | 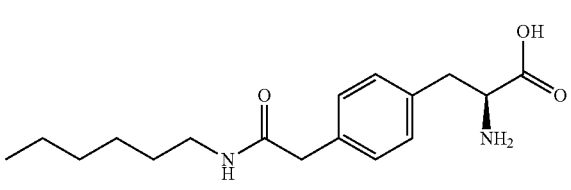 [SMILES: CCCCCCNC(=O)Cc1ccc(C[C@H](N)C(=O)O)cc1] |
| 472 | ra358 | 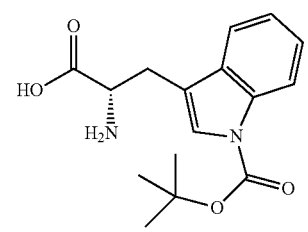 [SMILES: CC(C)(C)OC(=O)n1cc(C[C@H](N)C(=O)O)c2ccccc21] |
| 473 | ra346 | 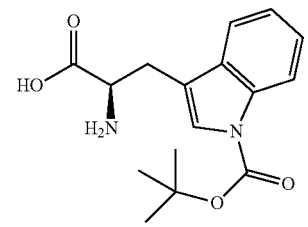 [SMILES: CC(C)(C)OC(=O)n1cc(C[C@@H](N)C(=O)O)c2ccccc21] |
| 474 | ra492 | 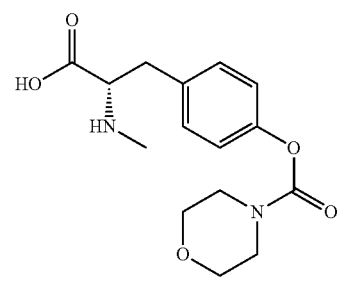 [SMILES: CN[C@@H](Cc1ccc(OC(=O)N2CCOCC2)cc1)C(=O)O] |
| 475 | ra493 | 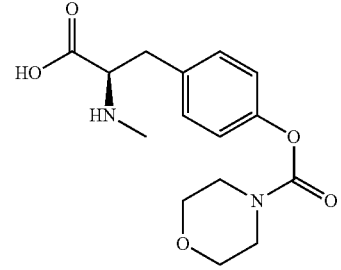 [SMILES: CN[C@H](Cc1ccc(OC(=O)N2CCOCC2)cc1)C(=O)O] |

TABLE 4-continued

The monomers used in the present disclosure.

| Entry No. | Monomer identifier | Chemical Structure |
|---|---|---|
| 476 | ra617 | 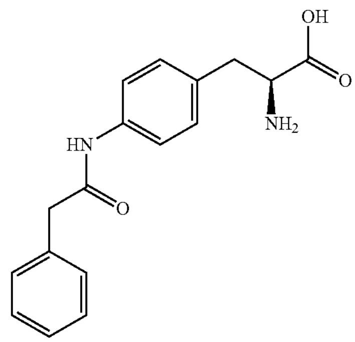 [SMILES: N[C@@H](Cc1ccc(NC(=O)Cc2ccccc2)cc1)C(=O)O] |
| 477 | ra622 | 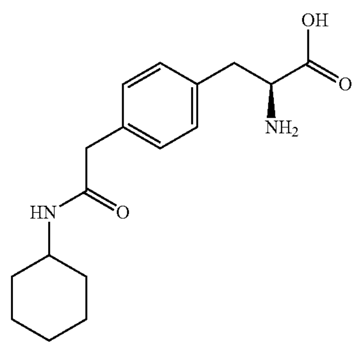 [SMILES: N[C@@H](Cc1ccc(CC(=O)NC2CCCCC2)cc1)C(=O)O] |
| 478 | ra502 | 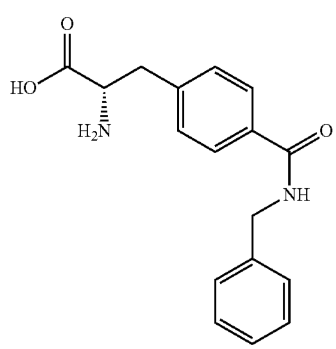 [SMILES: N[C@@H](Cc1ccc(C(=O)NCc2ccccc2)cc1)C(=O)O] |
| 479 | ra655 | 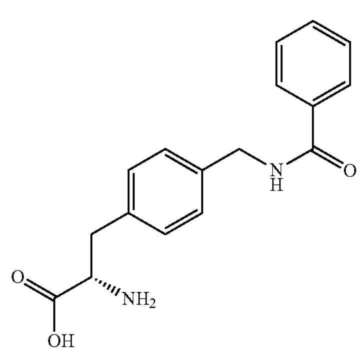 [SMILES: N[C@@H](Cc1ccc(CNC(=O)c2ccccc2)cc1)C(=O)O] |

TABLE 4-continued

The monomers used in the present disclosure.

| Entry No. | Monomer identifier | Chemical Structure |
|---|---|---|
| 480 | ra618 | 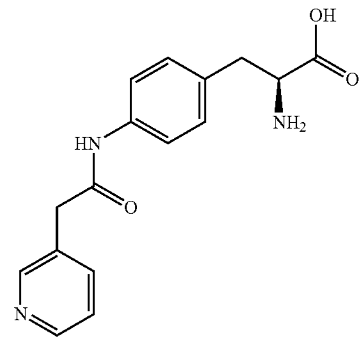 [SMILES: N[C@@H](Cc1ccc(NC(=O)Cc2cccnc2)cc1)C(=O)O] |
| 481 | ra625 | 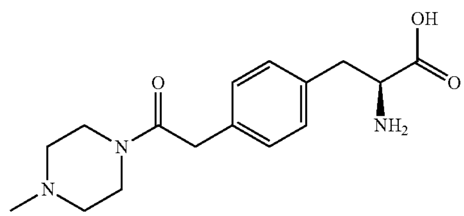 [SMILES: CN1CCN(C(=O)Cc2ccc(C[C@H](N)C(=O)O)cc2)CC1] |
| 482 | ra621 | 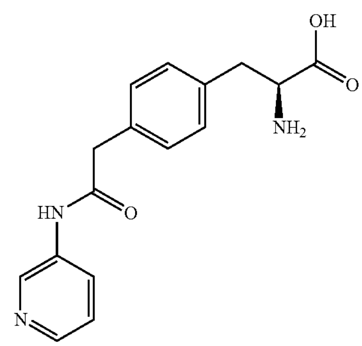 [SMILES: N[C@@H](Cc1ccc(CC(=O)Nc2cccnc2)cc1)C(=O)O] |
| 483 | ra631 | 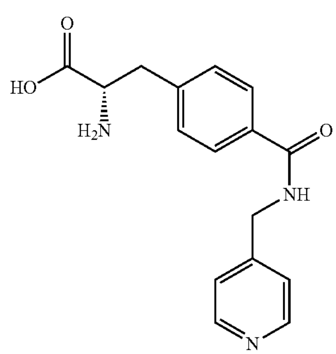 [SMILES: N[C@@H](Cc1ccc(C(=O)NCc2ccncc2)cc1)C(=O)O] |
| 484 | pnaG | 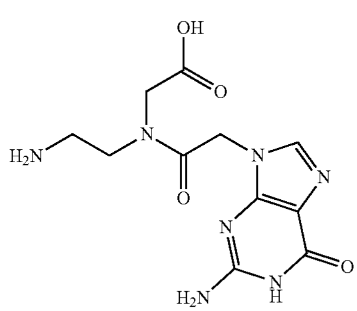 [SMILES: NCCN(CC(=O)O)C(=O)Cn1cnc2c(=O)[nH]c(N)nc21] |

TABLE 4-continued
The monomers used in the present disclosure.
| Entry No. | Monomer identifier | Chemical Structure |
|---|---|---|
| 485 | ra607 | 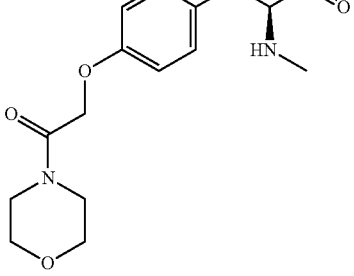 |
| 486 | ra656 | 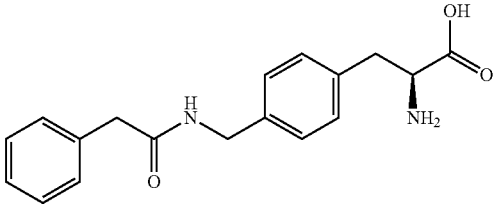 [SMILES: N[C@@H](Cc1ccc(CNC(=O)Cc2ccccc2)cc1)C(=O)O] |
| 487 | ra620 | 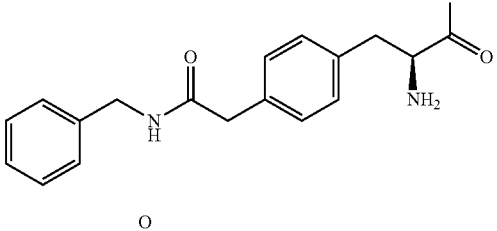 |
| 488 | ra668 | 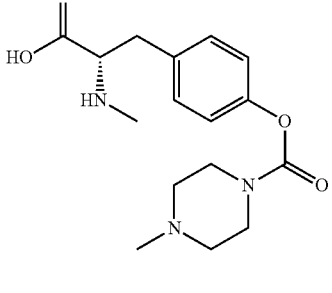 |
| 489 | ra635 | 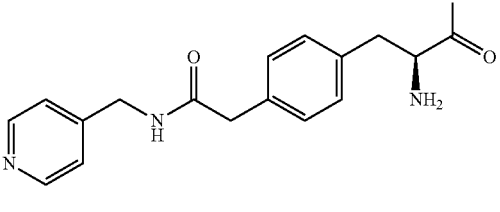 |
| 490 | ra472 | 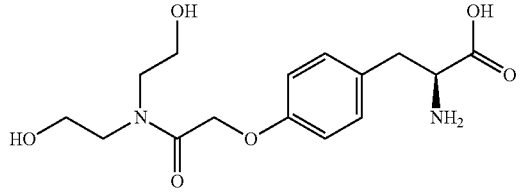 [SMILES: N[C@@H](Cc1ccc(OCC(=O)N(CCO)CCO)cc1)C(=O)O] |

TABLE 4-continued

The monomers used in the present disclosure.

| Entry No. | Monomer identifier | Chemical Structure |
|---|---|---|
| 491 | ra569 | 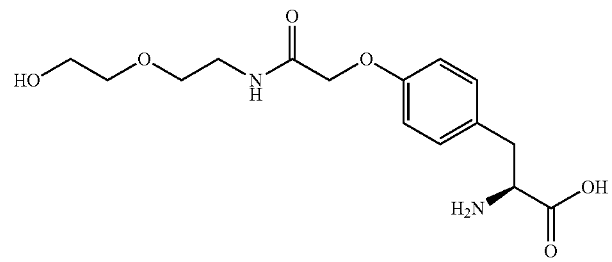 [SMILES: N[C@@H](Cc1ccc(OCC(=O)NCCOCCO)cc1)C(=O)O] |
| 492 | ra632 | 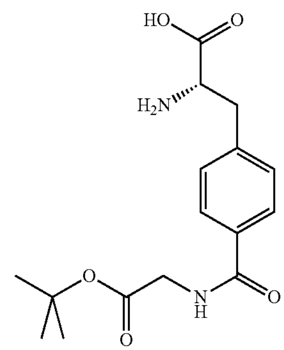 [SMILES: CC(C)(C)OC(=O)CNC(=O)c1ccc(C[C@H](N)C(=O)O)cc1] |
| 493 | ra634 | 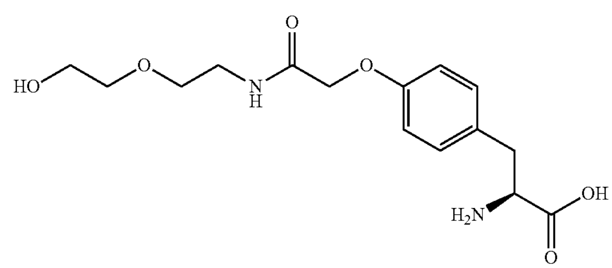 [SMILES: N[C@@H](Cc1ccc(OCC(=O)NCCOCCO)cc1)C(=O)O] |
| 494 | ra570 | 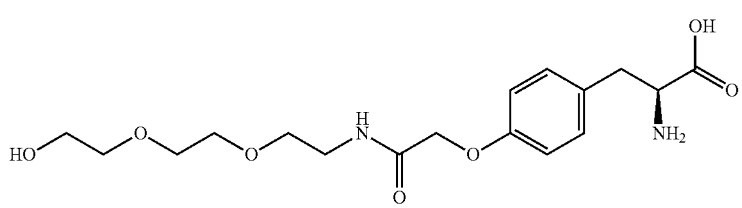 [SMILES: N[C@@H](Cc1ccc(OCC(=O)NCCOCCOCCO)cc1)C(=O)O] |
| 495 | ra595 | 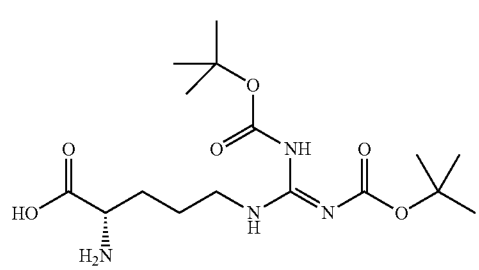 [SMILES: CC(C)(C)OC(=O)/N=C(/NCCC[C@H](N)C(=O)O)NC(=O)OC(C)(C)C] |

TABLE 4-continued

The monomers used in the present disclosure.

| Entry No. | Monomer identifier | Chemical Structure |
|---|---|---|
| 496 | ra311 | 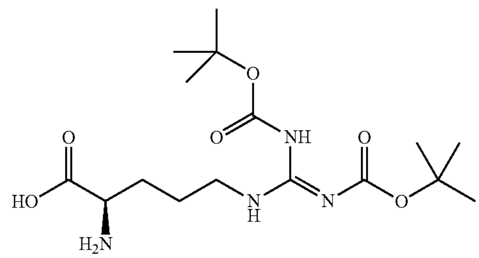 [SMILES: CC(C)(C)OC(=O)/N=C(/NCCC[C@@H](N)C(=O)O)NC(=O)OC(C)(C)C] |
| 497 | ra304 | 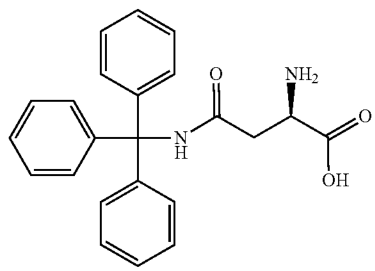 [SMILES: N[C@H](CC(=O)NC(c1ccccc1)(c1ccccc1)c1ccccc1)C(=O)O] |
| 498 | ra303 | 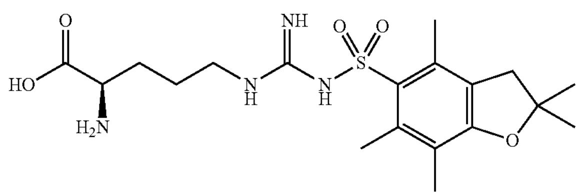 [SMILES: Cc1c(C)c(S(=O)(=O)NC(=N)NCCC[C@@H](N)C(=O)O)c(C)c2c1OC(C)(C)C2] |
| 499 | ra571 | 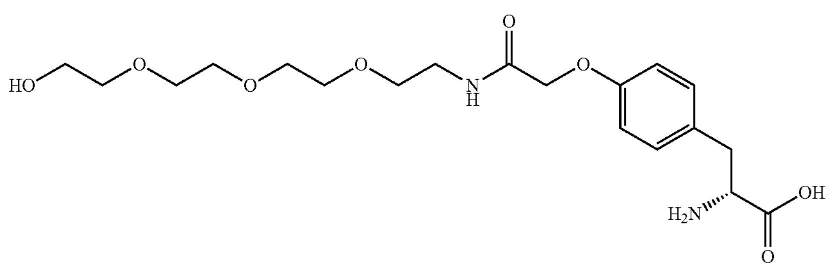 [SMILES: N[C@H](Cc1ccc(OCC(=O)NCCOCCOCCOCCO)cc1)C(=O)O] |
| 500 | ra309 | 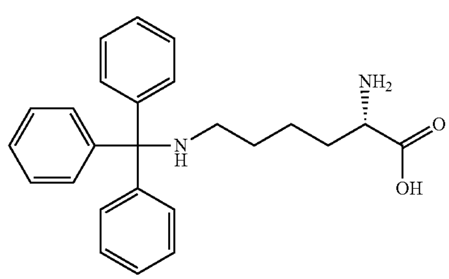 [SMILES: N[C@@H](CCCCNC(c1ccccc1)(c1ccccc1)c1ccccc1)C(=O)O] |
| 501 | ra402 | 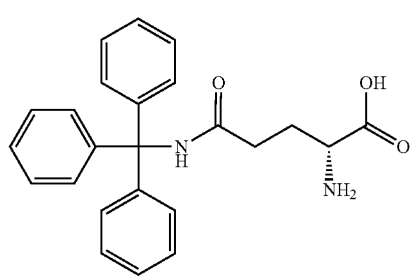 [SMILES: N[C@H](CCC(=O)NC(c1ccccc1)(c1ccccc1)c1ccccc1)C(=O)O] |

TABLE 4-continued

The monomers used in the present disclosure.

| Entry No. | Monomer identifier | Chemical Structure |
|---|---|---|
| 502 | ra322 | 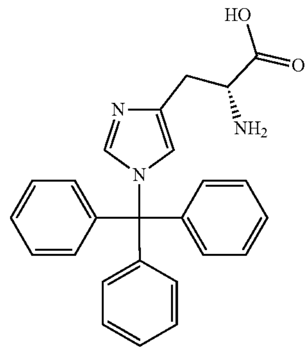 [SMILES: N[C@H](Cc1cn(C(c2ccccc2)(c2ccccc2)c2ccccc2)cn1)C(=O)O] |
| 503 | ra349 | 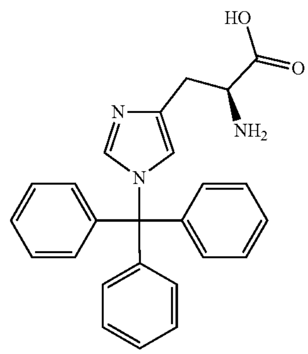 [SMILES: N[C@@H](Cc1cn(C(c2ccccc2)(c2ccccc2)c2ccccc2)cn1)C(=O)O] |
| 504 | ra408 | 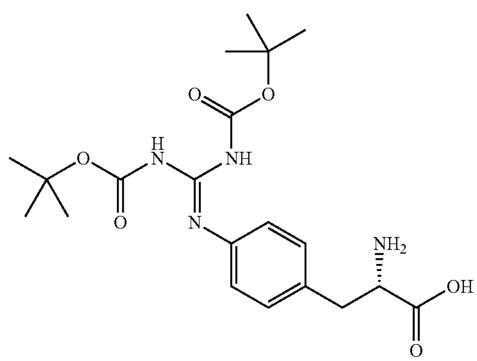 [SMILES: CC(C)(C)OC(=O)NC(=Nc1ccc(C[C@H](N)C(=O)O)cc1)NC(=O)OC(C)(C)C] |
| 505 | ra572 | 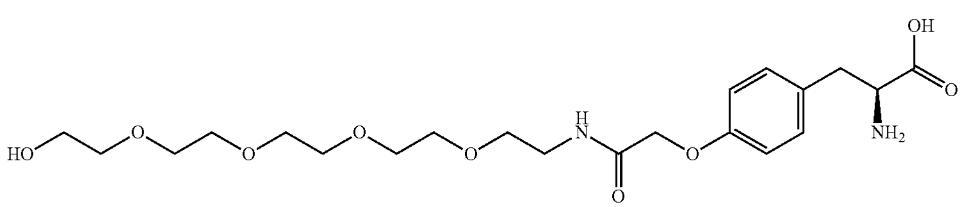 [SMILES: N[C@@H](Cc1ccc(OCC(=O)NCCOCCOCCOCCOCCO)cc1)C(=O)O] |
| 506 | ra580 | 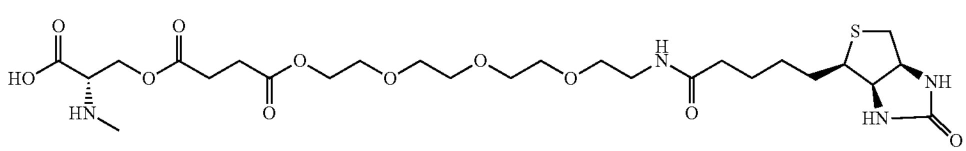 [SMILES: CN[C@@H](COC(=O)CCC(=O)OCCOCCOCCOCCNC(=O)CCCC[C@H]1SC[C@H]2NC(=O)N[C@H]21)C(=O)O] |

TABLE 4-continued

The monomers used in the present disclosure.

| Entry No. | Monomer identifier | Chemical Structure |
|---|---|---|
| 507 | Ala | *(L-alanine structure)* |
| 508 | mAla | *(N-methyl-L-alanine structure)* |
| 509 | dAla | *(D-alanine structure)* |
| 510 | ChA | *(cyclohexylalanine structure)* |
| 511 | Pro | *(L-proline structure)* |
| 512 | Val | *(L-valine structure)* |
| 513 | mVal | *(N-methyl-L-valine structure)* |
| 514 | Leu | *(L-leucine structure)* |
| 515 | dLeu | *(D-leucine structure)* |

TABLE 4-continued

The monomers used in the present disclosure.

| Entry No. | Monomer identifier | Chemical Structure |
|---|---|---|
| 516 | mLeu | 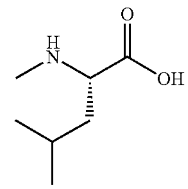 |
| 517 | mdLeu | 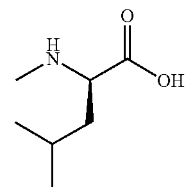 |
| 518 | mLeu | 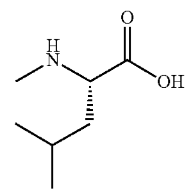 |
| 519 | HoSerMe | 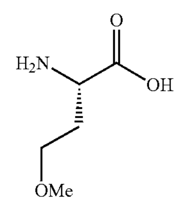 |
| 520 | Phe | 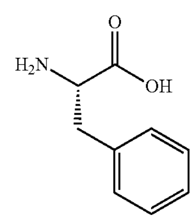 [SMILES: N[C@@H](Cc1ccccc1)C(=O)O] |
| 521 | Nal | 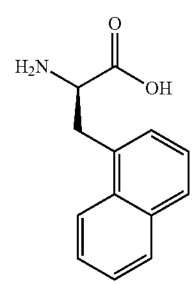 [SMILES: N[C@H](Cc1cccc2ccccc12)C(=O)O] |
| 522 | Nva | 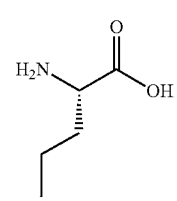 |

TABLE 4-continued

The monomers used in the present disclosure.

| Entry No. | Monomer identifier | Chemical Structure |
|---|---|---|
| 523 | PhF | 4-fluoro-L-phenylalanine |
| 524 | PhG | L-phenylglycine |
| 525 | dPhe | D-phenylalanine |
| 526 | mG | N-methylglycine (sarcosine) |
| 527 | mNle | N-methyl-L-norleucine |
| 528 | mPhe | N-methyl-L-phenylalanine |
| 529 | mSerBu | N-methyl-O-tert-butyl-L-serine |

TABLE 4-continued

The monomers used in the present disclosure.

| Entry No. | Monomer identifier | Chemical Structure |
|---|---|---|
| 530 | mdPhe | 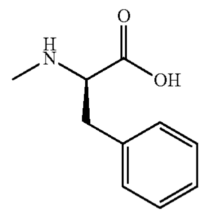 |
| 531 | mIle | 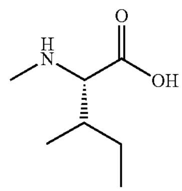 |

Scheme 2. The hydroxyl group used for peptide synthesis/connection in RbAsp, dD, D, and SbAsp.

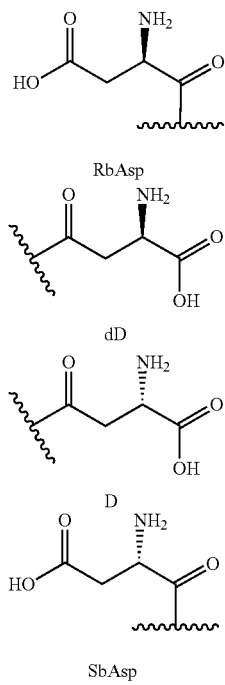

The monomers RbAsp, dD, D, and SbAsp have more than one hydroxyl groups. In some embodiments, the hydroxyl group that serves as a linkage point to the adjacent residues in each of these monomers is illustrated in Scheme 2 above. In some embodiments, the other hydroxyl group in these monomers can be used as a linkage point to the adjacent residues.

In some embodiments, disclosed herein is a compound of Formula VIII or a pharmaceutically acceptable salt or solvate thereof.

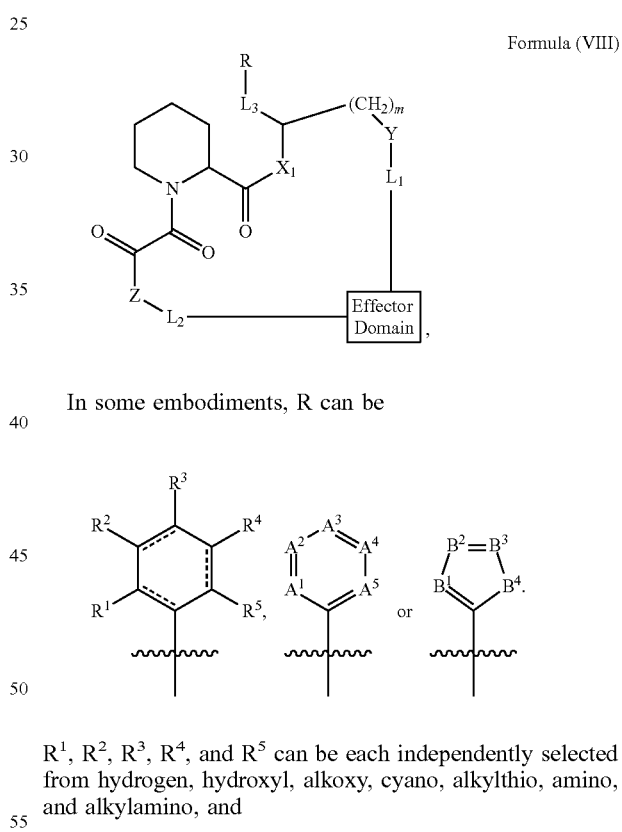

Formula (VIII)

In some embodiments, R can be $R^1$, $R^2$, $R^3$, $R^4$, and $R^5$ can be each independently selected from hydrogen, hydroxyl, alkoxy, cyano, alkylthio, amino, and alkylamino, and O—Linker—, wherein can be a resin; wherein one, two, three, or four of $A^1$, $A^2$, $A^3$, $A^4$, and $A^5$ can be N or P with the remaining being CH; wherein one, two, three, or four of $B^1$, $B^2$, $B^3$ and $B^4$ can be O, N, or S with the remaining being CH or $CH_2$ as appropriate; wherein ------ can be a single or double bond.

In some embodiments, $X_1$ can be O or $NR^6$; Y can be —C(O)— or

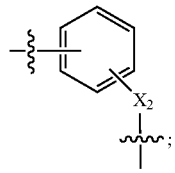

$X_2$ can be $(CH_2)_m$, O, OC(O), $NR^6$, $NR^6C(O)$; Z can be

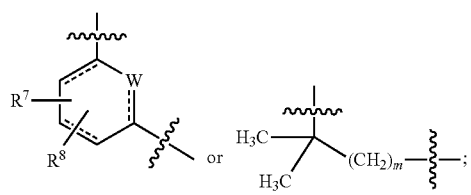

W can be O, CH, $CH_2$, $CR^9$, or $CR^{10}R^{11}$; can be $L_1$ and $L_2$ can be each independently a direct bond, substituted or unsubstituted —$(C_1-C_6)$alkyl-, substituted or unsubstituted —$(CH_2)_nO(C_1-C_6)$alkyl-, substituted or unsubstituted —$(CH_2)_nC(O)(C_1-C_6)$alkyl-, substituted or unsubstituted —$(CH_2)_nC(O)O(C_1-C_6)$alkyl-, substituted or unsubstituted —$(CH_2)_nOC(O)(C_1-C_6)$alkyl-, substituted or unsubstituted —$(CH_2)_nNH(C_1-C_6)$alkyl-, substituted or unsubstituted —$(CH_2)_nC(O)NH(C_1-C_6)$alkyl-, substituted or unsubstituted —$(CH_2)_nS(C_1-C_6)$alkyl-, substituted or unsubstituted —$(CH_2)_nC(O)(CH_2)_nS(C_1-C_6)$alkyl-, substituted or unsubstituted —$(C_2-C_6)$alkenyl-, substituted or unsubstituted —$(CH_2)_nO(C_2-C_6)$alkenyl-, substituted or unsubstituted —$(CH_2)_nC(O)(C_2-C_6)$alkenyl-, substituted or unsubstituted —$(CH_2)_nC(O)O(C_2-C_6)$alkenyl-, substituted or unsubstituted —$(CH_2)_nOC(O)(C_2-C_6)$alkenyl-, substituted or unsubstituted —$(CH_2)_nNH(C_2-C_6)$alkenyl-, substituted or unsubstituted —$(CH_2)_nC(O)NH(C_2-C_6)$alkenyl-, substituted or unsubstituted —$(CH_2)_nS(C_2-C_6)$alkenyl-, substituted or unsubstituted —$(CH_2)_nC(O)(CH_2)_nS(C_2-C_6)$alkenyl-, substituted or unsubstituted —$(C_2-C_6)$alkynyl-, substituted or unsubstituted —$(CH_2)_nO(C_2-C_6)$alkynyl-, substituted or unsubstituted —$(CH_2)_nC(O)(C_2-C_6)$alkynyl-, substituted or unsubstituted —$(CH_2)_nC(O)O(C_2-C_6)$alkynyl-, substituted or unsubstituted —$(CH_2)_nOC(O)(C_2-C_6)$alkynyl-, substituted or unsubstituted —$(CH_2)_nNH(C_2-C_6)$alkynyl-, substituted or unsubstituted —$(CH_2)_nC(O)NH(C_2-C_6)$alkynyl-, substituted or unsubstituted —$(CH_2)_nS(C_2-C_6)$alkynyl-, substituted or unsubstituted —$(CH_2)_nC(O)(CH_2)_nS(C_2-C_6)$alkynyl-, substituted or unsubstituted —$(C_1-C_6)$alkyl-$NR^{18}$—, substituted or unsubstituted —$(CH_2)_nO(C_1-C_6)$alkyl-$NR^{18}$—, substituted or unsubstituted —$(CH_2)_nC(O)(C_1-C_6)$alkyl-$NR^{18}$—, substituted or unsubstituted —$(CH_2)_nC(O)O(C_1-C_6)$alkyl-$NR^{18}$—, substituted or unsubstituted —$(CH_2)_nOC(O)(C_1-C_6)$alkyl-$NR^{18}$—, substituted or unsubstituted —$(CH_2)_nNH(C_1-C_6)$alkyl-$NR^{18}$—, substituted or unsubstituted —$(CH_2)_nC(O)NH(C_1-C_6)$alkyl-$NR^{18}$—, substituted or unsubstituted —$(CH_2)_nS(C_1-C_6)$alkyl-$NR^{18}$—, substituted or unsubstituted —$(CH_2)_nC(O)(CH_2)_nS(C_1-C_6)$alkyl-$NR^{18}$—, substituted or unsubstituted —$(C_2-C_6)$alkenyl-$NR^{18}$—, substituted or unsubstituted —$(CH_2)_nO(C_2-C_6)$alkenyl-$NR^{18}$—, substituted or unsubstituted —$(CH_2)_nC(O)(C_2-C_6)$alkenyl-$NR^{18}$—, substituted or unsubstituted —$(CH_2)_nC(O)O(C_2-C_6)$alkenyl-$NR^{18}$—, substituted or unsubstituted —$(CH_2)_nOC(O)(C_2-C_6)$alkenyl-$NR^{18}$—, substituted or unsubstituted —$(CH_2)_nNH(C_2-C_6)$alkenyl-$NR^{18}$—, substituted or unsubstituted —$(CH_2)_nC(O)NH(C_2-C_6)$alkenyl-$NR^{18}$—, substituted or unsubstituted —$(CH_2)_nS(C_2-C_6)$alkenyl-$NR^{18}$—, substituted or unsubstituted —$(CH_2)_nC(O)(CH_2)_nS(C_2-C_6)$alkenyl-$NR^{18}$—, substituted or unsubstituted —$(C_2-C_6)$alkynyl-$NR^{18}$—, substituted or unsubstituted —$(CH_2)_nO(C_2-C_6)$alkynyl-$NR^{18}$—, substituted or unsubstituted —$(CH_2)_nC(O)(C_2-C_6)$alkynyl-$NR^{18}$—, substituted or unsubstituted —$(CH_2)_nC(O)O(C_2-C_6)$alkynyl-$NR^{18}$—, substituted or unsubstituted —$(CH_2)_nOC(O)(C_2-C_6)$alkynyl-$NR^{18}$—, substituted or unsubstituted —$(CH_2)_nNH(C_2-C_6)$alkynyl-$NR^{18}$—, substituted or unsubstituted —$(CH_2)_nC(O)NH(C_2-C_6)$alkynyl-$NR^{18}$—, substituted or unsubstituted —$(CH_2)_nS(C_2-C_6)$alkynyl-$NR^{18}$—, substituted or unsubstituted —$(CH_2)_nC(O)(CH_2)_nS(C_2-C_6)$alkynyl-$NR^{18}$—, substituted or unsubstituted —$(C_1-C_6)$alkyl-C(O)—, substituted or unsubstituted —$(CH_2)_nO(C_1-C_6)$alkyl-C(O)—, substituted or unsubstituted —$(CH_2)_nC(O)(C_1-C_6)$alkyl-C(O)—, substituted or unsubstituted —$(CH_2)_nC(O)O(C_1-C_6)$alkyl-C(O)—, substituted or unsubstituted —$(CH_2)_nOC(O)(C_1-C_6)$alkyl-C(O)—, substituted or unsubstituted —$(CH_2)_nNH(C_1-C_6)$alkyl-C(O)—, substituted or unsubstituted —$(CH_2)_nC(O)NH(C_1-C_6)$alkyl-C(O)—, substituted or unsubstituted —$(CH_2)_nS(C_1-C_6)$alkyl-C(O)—, substituted or unsubstituted —$(CH_2)_nC(O)(CH_2)_nS(C_1-C_6)$alkyl-C(O)—, substituted or unsubstituted —$(C_2-C_6)$alkenyl-C(O)—, substituted or unsubstituted —$(CH_2)_nO(C_2-C_6)$alkenyl-C(O)—, substituted or unsubstituted —$(CH_2)_nC(O)(C_2-C_6)$alkenyl-C(O)—, substituted or unsubstituted —$(CH_2)_nC(O)O(C_2-C_6)$alkenyl-C(O)—, substituted or unsubstituted —$(CH_2)_nOC(O)(C_2-C_6)$alkenyl-C(O)—, substituted or unsubstituted —$(CH_2)_nNH(C_2-C_6)$alkenyl-C(O)—, substituted or unsubstituted —$(CH_2)_nC(O)NH(C_2-C_6)$alkenyl-C(O)—, substituted or unsubstituted —$(CH_2)_nS(C_2-C_6)$alkenyl-C(O)—, substituted or unsubstituted —$(CH_2)_nC(O)(CH_2)_nS(C_2-C_6)$alkenyl-C(O)—, substituted or unsubstituted —$(C_2-C_6)$alkynyl-C(O)—, substituted or unsubstituted —$(CH_2)_nO(C_2-C_6)$alkynyl-C(O)—, substituted or unsubstituted —$(CH_2)_nC(O)(C_2-C_6)$alkynyl-C(O)—, substituted or unsubstituted —$(CH_2)_nC(O)O(C_2-C_6)$alkynyl-C(O)—, substituted or unsubstituted —$(CH_2)_nOC(O)(C_2-C_6)$alkynyl-C(O)—, substituted or unsubstituted —$(CH_2)_nNH(C_2-C_6)$alkynyl-C(O)—, substituted or unsubstituted —$(CH_2)_nC(O)NH(C_2-C_6)$alkynyl-C(O)—, substituted or unsubstituted —$(CH_2)_nS(C_2-C_6)$alkynyl-C(O)—, substituted or unsubstituted —$(CH_2)_nC(O)(CH_2)_nS(C_2-C_6)$alkynyl-C(O)—, —O—, —NH—, —S—, —S(O)—, —$SO_2$—, —Si—, and —B—, wherein each alkyl, alkenyl, and alkynyl group may be optionally substituted with alkyl, alkoxy, amino, hydroxyl, sulfhydryl, halogen, carboxyl, oxo, cyano, nitro, or trifluoromethyl.

$L_3$ can be a direct bond, substituted or unsubstituted —$(C_1-C_6)$alkyl-, substituted or unsubstituted —$(CH_2)_nO(C_1-C_6)$alkyl-, substituted or unsubstituted —$(CH_2)_nC(O)(C_1-C_6)$alkyl-, substituted or unsubstituted —$(CH_2)_nC(O)O(C_1-C_6)$alkyl-, substituted or unsubstituted —$(CH_2)_nOC(O)(C_1-C_6)$alkyl-, substituted or unsubstituted —$(CH_2)_nNH(C_1-C_6)$alkyl-, substituted or unsubstituted —$(CH_2)_nC(O)NH(C_1-C_6)$alkyl-, substituted or unsubstituted —$(CH_2)_nS(C_1-$ $C_6$)alkyl-, substituted or unsubstituted —$(CH_2)_nC(O)(CH_2)_nS(C_1$-$C_6$)alkyl-, substituted or unsubstituted —$(C_2$-$C_6$)alkenyl-, substituted or unsubstituted —$(CH_2)_nO(C_2$-$C_6$)alkenyl-, substituted or unsubstituted —$(CH_2)_nC(O)(C_2$-$C_6$)alkenyl-, substituted or unsubstituted —$(CH_2)_nC(O)O(C_2$-$C_6$)alkenyl-, substituted or unsubstituted —$(CH_2)_nOC(O)(C_2$-$C_6$)alkenyl-, substituted or unsubstituted —$(CH_2)_nNH(C_2$-$C_6$)alkenyl-, substituted or unsubstituted —$(CH_2)_nC(O)NH(C_2$-$C_6$)alkenyl-, substituted or unsubstituted —$(CH_2)_nS(C_2$-$C_6$)alkenyl-, substituted or unsubstituted —$(CH_2)_nC(O)(CH_2)_nS(C_2$-$C_6$)alkenyl-, substituted or unsubstituted —$(C_2$-$C_6$)alkynyl-, substituted or unsubstituted —$(CH_2)_nO(C_2$-$C_6$)alkynyl-, substituted or unsubstituted —$(CH_2)_nC(O)(C_2$-$C_6$)alkynyl-, substituted or unsubstituted —$(CH_2)_nC(O)O(C_2$-$C_6$)alkynyl-, substituted or unsubstituted —$(CH_2)_nOC(O)(C_2$-$C_6$)alkynyl-, substituted or unsubstituted —$(CH_2)_nNH(C_2$-$C_6$)alkynyl-, substituted or unsubstituted —$(CH_2)_nC(O)NH(C_2$-$C_6$)alkynyl-, substituted or unsubstituted —$(CH_2)_nS(C_2$-$C_6$)alkynyl-, substituted or unsubstituted —$(CH_2)_nC(O)(CH_2)_nS(C_2$-$C_6$)alkynyl-, substituted or unsubstituted —$(C_1$-$C_6$)alky-$NR^{18}$—, substituted or unsubstituted —$(CH_2)_nO(C_1$-$C_6$)alky-$NR^{18}$—, substituted or unsubstituted —$(CH_2)_nC(O)(C_1$-$C_6$)alky-$NR^{18}$—, substituted or unsubstituted —$(CH_2)_nC(O)O(C_1$-$C_6$)alky-$NR^{18}$—, substituted or unsubstituted —$(CH_2)_nOC(O)(C_1$-$C_6$)alky-$NR^{18}$—, substituted or unsubstituted —$(CH_2)_nNH(C_1$-$C_6$)alky-$NR^{18}$—, substituted or unsubstituted —$(CH_2)_nC(O)NH(C_1$-$C_6$)alky-$NR^{18}$—, substituted or unsubstituted —$(CH_2)_nS(C_1$-$C_6$)alky-$NR^{18}$—, substituted or unsubstituted —$(CH_2)_nC(O)(CH_2)_nS(C_1$-$C_6$)alkyl-$NR^{18}$—, substituted or unsubstituted —$(C_2$-$C_6$)alkenyl-$NR^{18}$—, substituted or unsubstituted —$(CH_2)_nO(C_2$-$C_6$)alkenyl-$NR^{18}$—, substituted or unsubstituted —$(CH_2)_nC(O)(C_2$-$C_6$)alkenyl-$NR^{18}$—, substituted or unsubstituted —$(CH_2)_nC(O)O(C_2$-$C_6$)alkenyl-$NR^{18}$—, substituted or unsubstituted —$(CH_2)_nOC(O)(C_2$-$C_6$)alkenyl-$NR^{18}$—, substituted or unsubstituted —$(CH_2)_nNH(C_2$-$C_6$)alkenyl-$NR^{18}$—, substituted or unsubstituted —$(CH_2)_nC(O)NH(C_2$-$C_6$)alkenyl-$NR^{18}$—, substituted or unsubstituted —$(CH_2)_nS(C_2$-$C_6$)alkenyl-$NR^{18}$—, substituted or unsubstituted —$(CH_2)_nC(O)(CH_2)_nS(C_2$-$C_6$)alkenyl-$NR^{18}$—, substituted or unsubstituted —$(C_2$-$C_6$)alkynyl-$NR^{18}$—, substituted or unsubstituted —$(CH_2)_nO(C_2$-$C_6$)alkynyl-$NR^{18}$—, substituted or unsubstituted —$(CH_2)_nC(O)(C_2$-$C_6$)alkynyl-$NR^{18}$—, substituted or unsubstituted —$(CH_2)_nC(O)O(C_2$-$C_6$)alkynyl-$NR^{18}$—, substituted or unsubstituted —$(CH_2)_nOC(O)(C_2$-$C_6$)alkynyl-$NR^{18}$—, substituted or unsubstituted —$(CH_2)_nNH(C_2$-$C_6$)alkynyl-$NR^{18}$—, substituted or unsubstituted —$(CH_2)_nC(O)NH(C_2$-$C_6$)alkynyl-$NR^{18}$—, substituted or unsubstituted —$(CH_2)_nS(C_2$-$C_6$)alkynyl-$NR^{18}$—, substituted or unsubstituted —$(CH_2)_nC(O)(CH_2)_nS(C_2$-$C_6$)alkynyl-$NR^{18}$—, substituted or unsubstituted —$(C_1$-$C_6$)alkyl-$C(O)$—, substituted or unsubstituted —$(CH_2)_nO(C_1$-$C_6$)alkyl-$C(O)$—, substituted or unsubstituted —$(CH_2)_nC(O)(C_1$-$C_6$)alkyl-$C(O)$—, substituted or unsubstituted —$(CH_2)_nC(O)O(C_1$-$C_6$)alkyl-$C(O)$—, substituted or unsubstituted —$(CH_2)_nOC(O)(C_1$-$C_6$)alkyl-$C(O)$—, substituted or unsubstituted —$(CH_2)_nNH(C_1$-$C_6$)alkyl-$C(O)$—, substituted or unsubstituted —$(CH_2)_nC(O)NH(C_1$-$C_6$)alkyl-$C(O)$—, substituted or unsubstituted —$(CH_2)_nS(C_1$-$C_6$)alkyl-$C(O)$—, substituted or unsubstituted —$(CH_2)_nC(O)(CH_2)_nS(C_1$-$C_6$)alkyl-$C(O)$—, substituted or unsubstituted —$(C_2$-$C_6$)alkenyl-$C(O)$—, substituted or unsubstituted —$(CH_2)_nO(C_2$-$C_6$)alkenyl-$C(O)$—, substituted or unsubstituted —$(CH_2)_nC(O)(C_2$-$C_6$)alkenyl-$C(O)$—, substituted or unsubstituted —$(CH_2)_nC(O)O(C_2$-$C_6$)alkenyl-$C(O)$—, substituted or unsubstituted —$(CH_2)_nOC(O)(C_2$-$C_6$)alkenyl-$C(O)$—, substituted or unsubstituted —$(CH_2)_nNH(C_2$-$C_6$)alkenyl-$C(O)$—, substituted or unsubstituted —$(CH_2)_nC(O)NH(C_2$-$C_6$)alkenyl-$C(O)$—, substituted or unsubstituted —$(CH_2)_nS(C_2$-$C_6$)alkenyl-$C(O)$—, substituted or unsubstituted —$(CH_2)_nC(O)(CH_2)_nS(C_2$-$C_6$)alkenyl-$C(O)$—, substituted or unsubstituted —$(C_2$-$C_6$)alkynyl-$C(O)$—, substituted or unsubstituted —$(CH_2)_nO(C_2$-$C_6$)alkynyl-$C(O)$—, substituted or unsubstituted —$(CH_2)_nC(O)(C_2$-$C_6$)alkynyl-$C(O)$—, substituted or unsubstituted —$(CH_2)_nC(O)O(C_2$-$C_6$)alkynyl-$C(O)$—, substituted or unsubstituted —$(CH_2)_nOC(O)(C_2$-$C_6$)alkynyl-$C(O)$—, substituted or unsubstituted —$(CH_2)_nNH(C_2$-$C_6$)alkynyl-$C(O)$—, substituted or unsubstituted —$(CH_2)_nC(O)NH(C_2$-$C_6$)alkynyl-$C(O)$—, substituted or unsubstituted —$(CH_2)_nS(C_2$-$C_6$)alkynyl-$C(O)$—, substituted or unsubstituted —$(CH_2)_nC(O)(CH_2)_nS(C_2$-$C_6$)alkynyl-$C(O)$—, wherein each alkyl, alkenyl and alkynyl group may be optionally substituted with alkyl, alkoxy, amino, hydroxyl, sulfhydryl, halogen, carboxyl, oxo, cyano, nitro, or trifluoromethyl.

Each m can be independently an integer selected from 0, 1, 2, 3, 4, 5, and 6; each n is independently an integer selected from 0, 1, 2, 3, 4, 5, and 6; $R^6$ is hydrogen or alkyl; $R^7$ and $R^8$ are each independently selected from hydrogen, hydroxy, alkyl, alkoxy, cyano, alkylthio, amino, and alkylamino, and OPG, wherein OPG is a protecting group; $R^9$, $R^{10}$, and $R^{11}$ are each independently selected from hydrogen, hydroxy, alkyl, alkoxy, cyano, alkylthio, amino, and alkylamino, and OPG, wherein OPG is a protecting group.

The Effector Domain can have Formula (A):

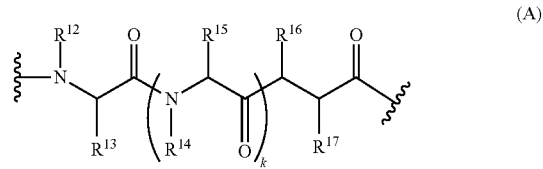

(A)

$R^{12}$, $R^{14}$, $R^{16}$, and $R^{18}$ can be each independently hydrogen, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, $(CH_2)_nCN$, $(CH_2)_nCF_3$, $(CH_2)_nC_2F_5$. $R^{13}$, $R^{15}$, and $R^{17}$ are each independently the sidechains of naturally occurring amino acids and their modified forms including but are not limited to D-amino acid configuration, or hydrogen, halogen, amino, cyano, nitro, trifluoromethyl, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, substituted or unsubstituted $(CH_2)_n$-aryl, substituted or unsubstituted $(CH_2)_n$-heteroaryl, $(CH_2)_nCN$, $(CH_2)_nCF_3$, $(CH_2)_nC_2F_5$, $(CH_2)_nOR^{19}$, $(CH_2)_nC(O)R^{19}$, $(CH_2)_nC(O)OR^{19}$, $(CH_2)_nOC(O)R^{19}$, $(CH_2)_nNR^{20}R^{21}$, $(CH_2)_nC(O)NR^{20}R^{21}$, $(CH_2)_nNR^{22}C(O)R^{19}$, $(CH_2)_nNR^{22}C(O)OR^{19}$, $(CH_2)_nNR^{22}C(O)NR^{20}R^{21}$, $(CH_2)_nSR^{19}$, $(CH_2)_nS(O)_jNR^{20}R^{21}$, $(CH_2)_nNR^{22}S(O)_jR^{19}$, or $-(CH_2)_nNR^{22}S(O)_jNR^{20}R^{21}$.

$R^{12}$ and $R^{13}$, $R^{14}$ and $R^{15}$, $R^{16}$ and $R^{17}$ can be covalently connected to form a substituted or unsubstituted 5-, 6-, or 7-membered heterocycle. Each k can be independently an integer selected from 0, 1, 2, 3, 4, 5, 6, 7, 8, 9, and 10. Each j can be independently an integer selected from 0, 1, and 2. $R^{19}$, $R^{20}$, $R^{21}$, and $R^{22}$ can be each independently hydrogen, halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, or heteroalkylaryl.

Or $R^{19}$ and $R^{22}$ are as described above, and $R^{20}$ and $R^{21}$, together with the N atom to which they are attached, form a substituted or unsubstituted 5-, 6-, or 7-membered heterocycloalkyl or a substituted or unsubstituted 5-membered heteroaryl, wherein each of the above groups listed for $R^{13}$, $R^{15}$, and $R^{17}$ may be optionally independently substituted with 1 to 3 groups selected from halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, heteroalkylaryl, $(CH_2)_nCN$, $(CH_2)_nCF_3$, $(CH_2)_nC_2F_5$, $(CH_2)_nOR^{19}$, $(CH_2)_nC(O)R^{19}$, $(CH_2)_nC(O)OR^{19}$, $(CH_2)_nOC(O)R^{19}$, $(CH_2)_nNR^{20}R^{21}$, $(CH_2)_nNR^{20}R^{21}$, $(CH_2)_nNR^{22}C(O)R^{19}$, $(CH_2)_nNR^{22}C(O)OR^{19}$, $(CH_2)_nNR^{22}C(O)NR^{20}R^{21}$, $(CH_2)_nSR^{19}$, $(CH_2)_nS(O)_jNR^{20}R^{21}$, $(CH_2)_nNR^{22}S(O)_jR^{19}$, or $-(CH_2)_nNR^{22}S(O)_jNR^{20}R^{21}$.

Or the Effector Domain can have Formula (B):

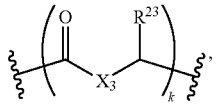

Formula (B)

Each k can be independently an integer selected from 0, 1, 2, 3, 4, 5, 6, 7, 8, 9, and 10; $R^{23}$ can be a hydrogen or alkyl; $X_3$ can be substituted or unsubstituted $-(C_1-C_{30})$alkyl-, alkenyl-, alkynyl- with each carbon individually assuming one of the following redox states: $CH_2$, CH—OH, C(O);

Or the Effector Domain can have Formula (C):

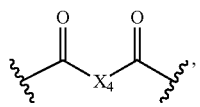

Formula (C)

$X_4$ can be substituted or unsubstituted $-(C_1-C_{30})$alkyl-, alkenyl-, alkynyl- with each carbon individually assuming one of the following redox states: $CH_2$, CH—OH, C(O).

Or the Effector Domain has Formula (D):

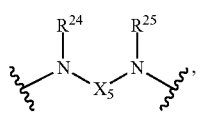

Formula (D)

$R^{24}$ and $R^{25}$ are each a hydrogen or alkyl; $X_5$ can be substituted or unsubstituted $-(C_1-C_{30})$alkyl-, alkenyl-, alkynyl- with each carbon individually assuming one of the following redox states: $CH_2$, CH—OH, C(O).

Or the Effector Domain can be Formula (E):

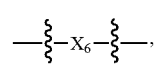

Formula (E)

$X_6$ can be substituted or unsubstituted $-(C_1-C_{30})$alkyl-, alkenyl-, alkynyl- with each carbon individually assuming one of the following redox states: $CH_2$, CH—OH, C(O).

In some embodiments, $L_3$ is not

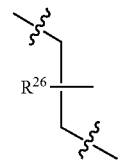

with $R^{26}$ being hydrogen or alkyl.

In some embodiments, R is not

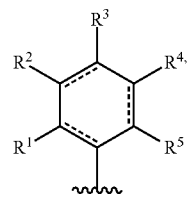

wherein $R^3$ is hydrogen, hydroxyl, or OPG, wherein PG is a protecting group, or

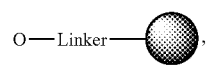

wherein

is a resin; wherein $R^2$ is hydrogen, hydroxyl, or alkoxy; and wherein $R^1$, $R^4$, and $R^5$ are each independently hydrogen or no substituent as dictated by chemical bonding; wherein ------- is a single or double bond.

In some embodiments, $L_1$ and $L_2$ not each independently direct bond, substituted or unsubstituted $-(C_1-C_6)$alkyl-, substituted or unsubstituted $-(CH_2)_nO(C_1-C_6)$alkyl-, substituted or unsubstituted $-(CH_2)_nC(O)-$, substituted or unsubstituted $-(CH_2)_nC(O)(C_1-C_6)$alkyl-, substituted or unsubstituted $-(CH_2)_nC(O)O(C_1-C_6)$alkyl-, substituted or unsubstituted $-(CH_2)_nNH(C_1-C_6)$alkyl-, substituted or unsubstituted $-(CH_2)_nC(O)NH(C_1-C_6)$alkyl-, substituted or unsubstituted $-(CH_2)_nS(C_1-C_6)$alkyl-, substituted or unsubstituted $-(CH_2)_nC(O)(CH_2)_nS(C_1-C_6)$alkyl-, substituted or unsubstituted $-(C_2-C_6)$alkenyl-, substituted or unsubstituted —$(CH_2)_nO(C_2-C_6)$alkenyl-, substituted or unsubstituted —$(CH_2)_nC(O)(C_2-C_6)$alkenyl-, substituted or unsubstituted —$(CH_2)_nC(O)O(C_2-C_6)$alkenyl-, substituted or unsubstituted —$(CH_2)_nNH(C_1-C_6)$alkenyl-, substituted or unsubstituted —$(CH_2)_nC(O)NH(C_2-C_6)$alkenyl-, substituted or unsubstituted —$(CH_2)_nS(C_2-C_6)$alkenyl-, substituted or unsubstituted —$(CH_2)_nC(O)(CH_2)_nS(C_2-C_6)$alkenyl-, substituted or unsubstituted —$(C_2-C_6)$alkynyl-, substituted or unsubstituted —$(CH_2)_nO(C_2-C_6)$alkynyl-, substituted or unsubstituted —$(CH_2)_nC(O)(C_2-C_6)$alkynyl-, substituted or unsubstituted —$(CH_2)_nC(O)O(C_2-C_6)$alkynyl-, substituted or unsubstituted —$(CH_2)_nNH(C_1-C_6)$alkynyl-, substituted or unsubstituted —$(CH_2)_nC(O)NH(C_2-C_6)$alkynyl-, substituted or unsubstituted —$(CH_2)_nS(C_2-C_6)$alkynyl-, substituted or unsubstituted —$(CH_2)_nC(O)(CH_2)_nS(C_2-C_6)$alkynyl-, wherein each alkyl, alkenyl, and alkynyl group may be optionally substituted with alkyl, alkoxy, amino, carboxyl, cyano, nitro, or trifluoromethyl.

In some embodiments, the Effector Domain is a compound of Formula (F)

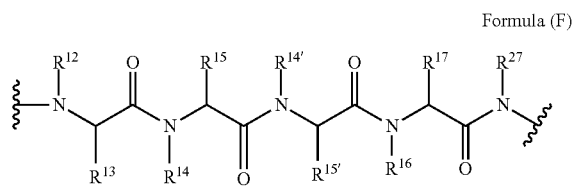

Formula (F)

$R^{12}$, $R^{14}$, $R^{14'}$, $R^{16}$, and $R^{27}$ are not each independently hydrogen or alkyl and $R^{13}$, $R^{14}$, $R^{14'}$, and $R^{16}$ are not each independently hydrogen, halogen, amino, cyano, nitro, trifluoromethyl, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, or unsubstituted heteroalkylaryl, $(CH_2)_nCN$, $(CH_2)_nCF_3$, $(CH_2)_nC_2F_5$, $(CH_2)_nOR^{19}$, $(CH_2)_nC(O)R^{19}$, $(CH_2)_nC(O)OR^{19}$, $(CH_2)_nOC(O)R^{19}$, $(CH_2)_nNR^{20}R^{21}$, $(CH_2)_nC(O)NR^{20}R^{21}$, $(CH_2)_nNR^{22}C(O)R^{19}$, $(CH_2)_nNR^{22}C(O)OR^{19}$, $(CH_2)_nNR^{22}C(O)NR^{20}R^{21}$, $(CH_2)_nS(O)_jNR^{20}R^{21}$, $(CH_2)_nNR^{22}S(O)_jR^{19}$, or —$(CH_2)_nNR^{22}S(O)_jNR^{20}R^{21}$; n is an integer selected from 0, 1, 2, 3, 4, 5, and 6; j is an integer selected from 0, 1, and 2.

$R^{19}$, $R^{20}$, $R^{21}$, and $R^{22}$ are each independently hydrogen, halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, or heteroalkylaryl, or $R^{19}$ and $R^{22}$ are as described above, and $R^{20}$ and $R^{21}$, together with the N atom to which they are attached, form a substituted or unsubstituted 5-, 6-, or 7-membered heterocycloalkyl or a substituted or unsubstituted 5-membered heteroaryl.

Each of the above groups listed for $R^{13}$, $R^{15}$, and $R^{17}$ may be optionally independently substituted with 1 to 3 groups selected from halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, heteroalkylaryl, $(CH_2)_nCN$, $(CH_2)_nCF_3$, $(CH_2)_nC_2F_5$, $(CH_2)_nOR^{19}$, $(CH_2)_nC(O)R^{19}$, $(CH_2)_nC(O)$ $(O)OR^{19}$, $(CH_2)_nOC(O)R^{19}$, $(CH_2)_nNR^{20}R^{21}$, $(CH_2)_nC(O)NR^{20}R^{21}$, $(CH_2)_nNR^{22}C(O)R^{19}$, $(CH_2)_nNR^{22}C(O)OR^{19}$, $(CH_2)_nNR^{22}C(O)NR^{20}R^{21}$, $(CH_2)_nSR^{19}$, $(CH_2)_nS(O)_jNR^{20}R^{21}$, $(CH_2)_nNR^{22}S(O)_jR^{19}$, or —$(CH_2)_nNR^{22}S(O)_jNR^{20}R^{21}$.

In some embodiments, $L_3$ in Formula (VII) is —$CH_2CH_2$—, R is

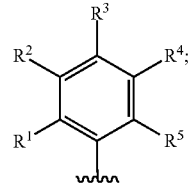

$R^1$, $R^4$, $R^5$ and W are each hydrogen; $R^2$ and $R^3$ are each methoxy; m=0; Y is

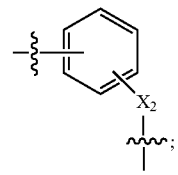

$X_2$ is O or $NR^6C(O)$; $L_1$ is —$CH_2$—$C(O)$— or —$(CH_2)_2C(O)$—; Z is

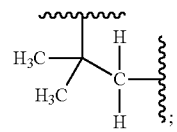 [SMILES: *CC(*)(C)C]

$L_2$ is —OCO—CH=CH—$(CH_2)_2N(Me)$-. In some embodiments, $X_2$ is O and Li is —$CH_2$—$C(O)$—. In some embodiments, $X_2$ is $NR^6C(O)$ and $L_1$ is —$(CH_2)_2C(O)$—.

In some embodiments, the effector domain can be Formula (G)

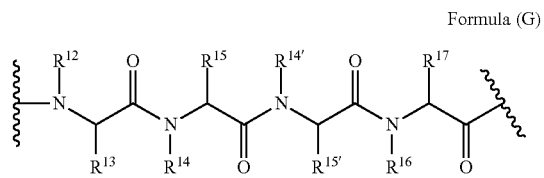

Formula (G)

Wherein $R^{12}$, $R^{14}$, $R^{14'}$, and $R^{16}$ are each independently hydrogen, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, $(CH_2)_nCN$, $(CH_2)_nCF_3$, $(CH_2)_nC_2F_5$.

$R^{13}$, $R^{15}$, $R^{15'}$ and $R^{17}$ are each independently the sidechains of naturally occurring amino acids and their modified forms including but are not limited to D-amino acid configuration, or hydrogen, halogen, amino, cyano, nitro, trifluoromethyl, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, substituted or unsubstituted $(CH_2)_n$-aryl, substituted or unsubstituted $(CH_2)_n$-heteroaryl, $(CH_2)_nCN$, $(CH_2)_nCF_3$, $(CH_2)_nC_2F_5$, $(CH_2)_nOR^{19}$, $(CH_2)_nC(O)R^{19}$, $(CH_2)_nC(O)OR^{19}$, $(CH_2)_nOC(O)R^{19}$, $(CH_2)_nNR^{20}R^{21}$, $(CH_2)_nC(O)NR^{20}R^{21}$, $(CH_2)_nNR^{22}C(O)R^{19}$, $(CH_2)_nNR^{22}C(O)OR^{19}$, $(CH_2)_nNR^{22}C(O)NR^{21}R^{21}$, $(CH_2)_nSR^{19}$, $(CH_2)_nS(O)_jNR^{20}R^{21}$, $(CH_2)_nNR^{22}S(O)_jR^{19}$, or $—(CH_2)_nNR^{22}S(O)_jNR^{20}R^{21}$. $R^{12}$ and $R^{13}$, $R^{14}$ and $R^{15}$, $R^{14'}$ and $R^{15'}$, $R^{16}$ and $R^{17}$ can be covalently connected to form a substituted or unsubstituted 5-, 6-, or 7-membered heterocycle.

In some embodiments, disclosed herein is a method of using a hybrid cyclic library based on the immunophilin ligand family of natural products FK506 and rapamycin, to screen for compounds for treating cancer. In some embodiments, disclosed herein is a method of using a hybrid cyclic library based on the immunophilin ligand family of natural products FK506 and rapamycin, to screen for compounds for treating autoimmune disease.

In some embodiments, the Rapafucin compounds in the present disclosure can have a structure according to Formula (IX) or Formula (X) or an optically pure stereoisomer or pharmaceutically acceptable salt thereof.

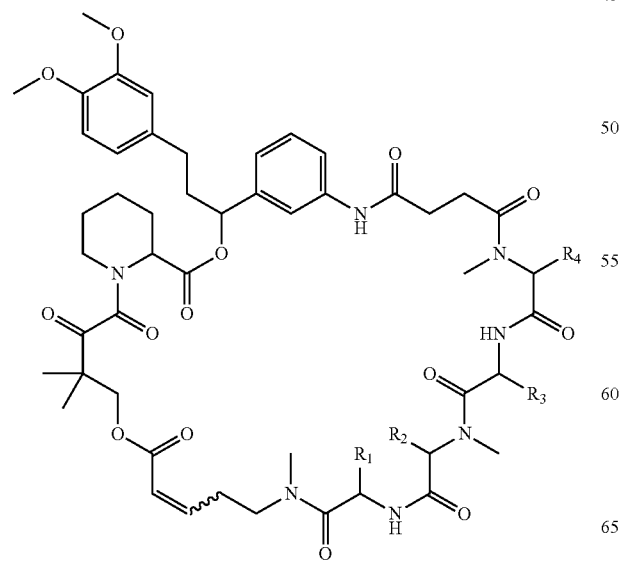

Formula (IX)

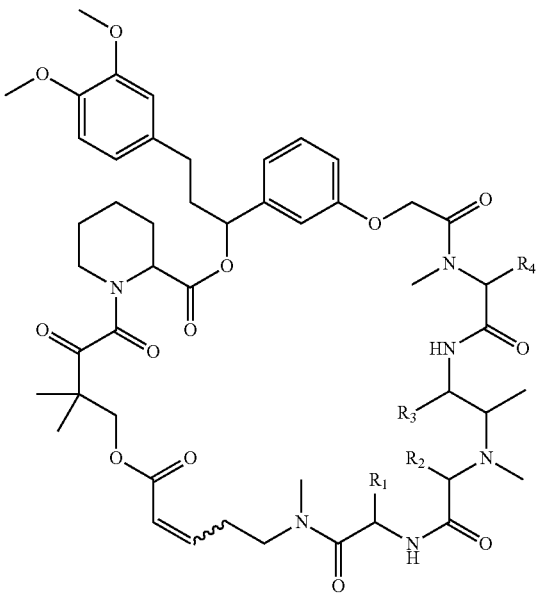

Formula (X)

The amino acid moieties with $R^1$, $R^2$, $R^3$, and $R^4$ can be selected from Table 2 below illustrating the amino acid monomers used for the present disclosure. In some embodiments, the amino acid moieties with $R^1$ and $R^3$ can be selected from the group consisting of

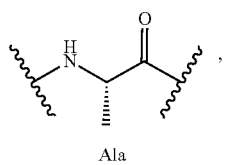

Ala

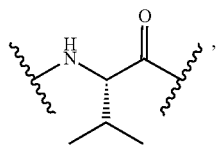

Val

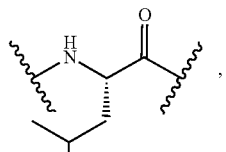

Leu

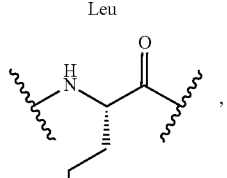

HoSerMe

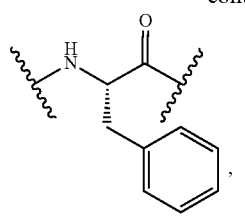
Phe
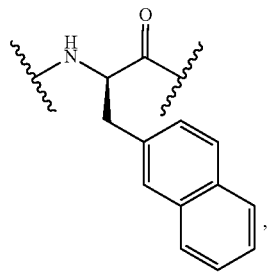
Nal
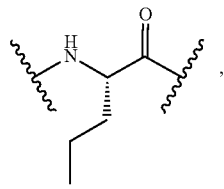
Nva
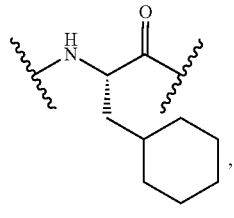
ChA
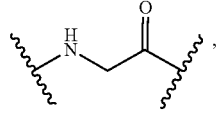
G
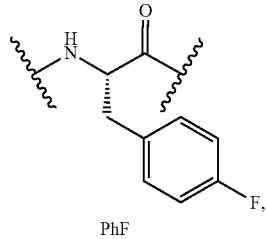
PhF
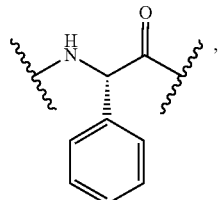
PhG
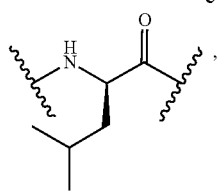
dLeu
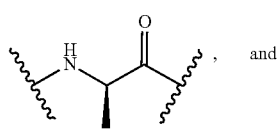
, and
dAla
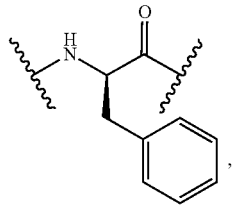
dPhe
or $R_1$ or $R_3$ together with nitrogen to form
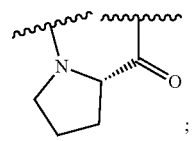
Pro
;
In some embodiments, the amino acid moieties with $R_2$ and $R^4$ can be selected from the group consisting of
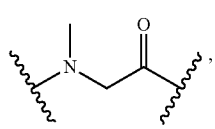
mG
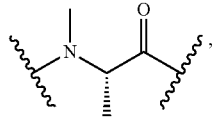
mAla
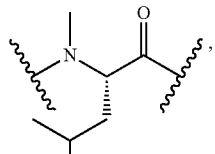
mLeu

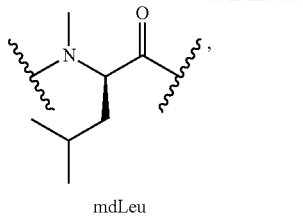

mdLeu

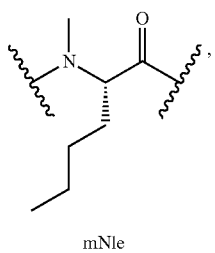

mNle

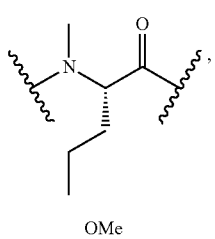

OMe

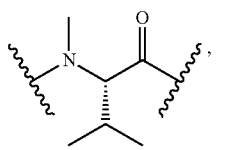

mVal

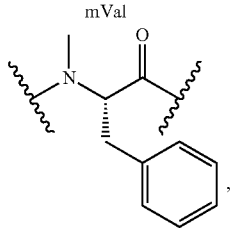

mPhe

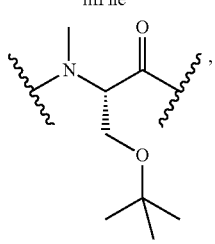

mSerBu

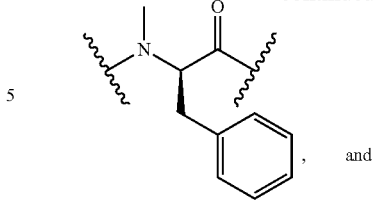

, and mdPhe

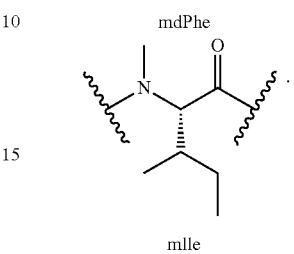

.

mIle

The macrocyclic natural products FK506 and rapamycin are approved immunosuppressive drugs with important biological activities. Both have been shown to inhibit T-cell activation, each with distinct mechanisms. In addition, rapamycin has been shown to have strong anti-proliferative activity. FK506 and rapamycin share an extraordinary mode of action; they act by recruiting an abundant and ubiquitously expressed cellular protein, the prolyl cis-trans isomerase FKBP, and the binary complexes subsequently bind to and allosterically inhibit their target proteins calcineurin and mTOR, respectively. Structurally, FK506 and rapamycin share a similar FKBP-binding domain but differ in their effector domains. In FK506 and rapamycin, nature has taught us that switching the effector domain of FK506 to that in rapamycin, it is possible to change the targets from calcineurin to mTOR. The generation of a rapafucin library of macrocyles that contain FK506 and rapamycin binding domains should have great potential as new leads for developing drugs to be used for treating diseases.

A variety of methods exist for the generation of compound libraries for developing and screening potentially useful compounds in treating diseases. One such method is the development of encoded libraries, and particularly libraries in which each compound includes an amplifiable tag. Such libraries include DNA-encoded libraries in which a DNA tag identifying a library member can be amplified using molecular biology techniques, such as the polymerase chain reaction (PCR). The use of such methods for producing libraries of rapafucin macrocyles that contain FK506-like and rapamycin-like binding domains has yet to be demonstrated. Thus, there remains a need for DNA-encoded rapafucin libraries of macrocyles that contain FK506-like and rapamycin-like binding domains.

In one aspect, provided herein is a tagged macrocyclic compound that comprises: an FK506 binding protein binding domain (FKBD); an effector domain; a first linking region; and a second linking region; wherein the FKBD, the effector domain, the first linking region, and the second linking region together form a macrocycle; and wherein at least one of the FKBD, the effector domain, the first linker, and the second linker can be operatively linked to one or more oligonucleotides (D) which can identify the structure of at least one of the FKBD, the effector domain, the first linker, and the second linker.

In certain embodiments, provided herein is a tagged macrocyclic compound of Formula (XI):

Formula (XI)

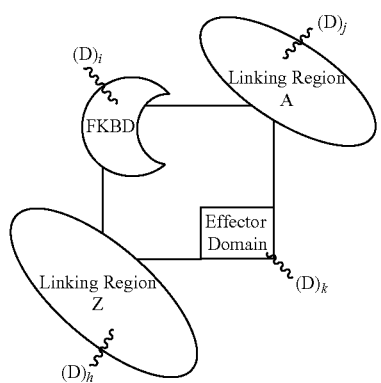

In some embodiments, h, i, j, and k are each independently an integer from 0-20, provided that at least one of h, i, j, and k is not 0; and D is an oligonucleotide that can identify at least one of the FKBD, the Effector Domain, the Linking Region A, or the Linking Region Z, where the solid lines linking the FKBD, the Effector Domain, the Linking Region A, and/or the Linking Region Z indicate an operative linkage and the squiggle lines indicate an operative linkage. In certain embodiments, oligonucleotide (D) can be operatively linked to at least one of the FKBD, the Effector Domain, the Linking Region A, or the Linking Region Z.

In some embodiments, provided herein is a tagged macrocyclic compound of Formula (XII) or a pharmaceutically acceptable salt, solvate, or stereoisomer thereof:

Formula (XII)

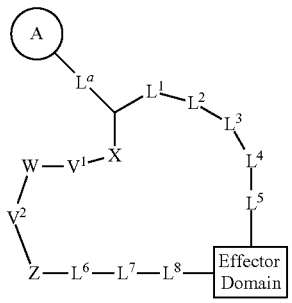

In some embodiments, Ring A is a 5-10 membered aryl, cycloalkyl, heteroaryl or heterocycloalkyl, optionally substituted with 1-17 substituents, each of which is independently selected from the group consisting of hydrogen, hydroxy, halo, alkyl, alkoxy, cyano, haloalkyl, haloalkoxy, alkylthio, oxo, amino, alkylamino, dialkylamino,

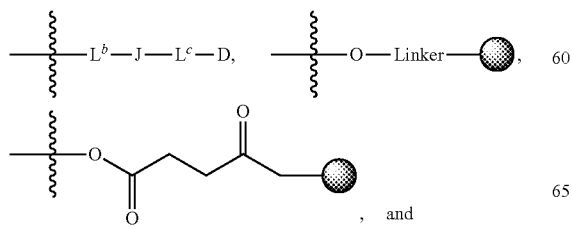

, and

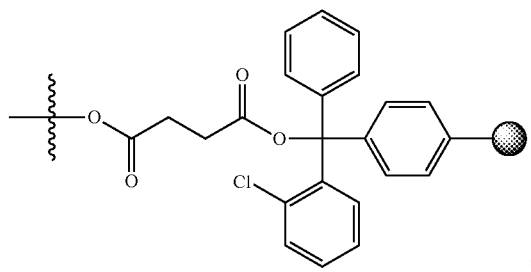

, wherein

is a resin; J is independently at each occurrence selected from the group consisting of —C(O)NR$^6$—.

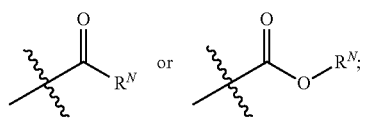

wherein R$^6$ is each hydrogen, alkyl, arylalkyl,

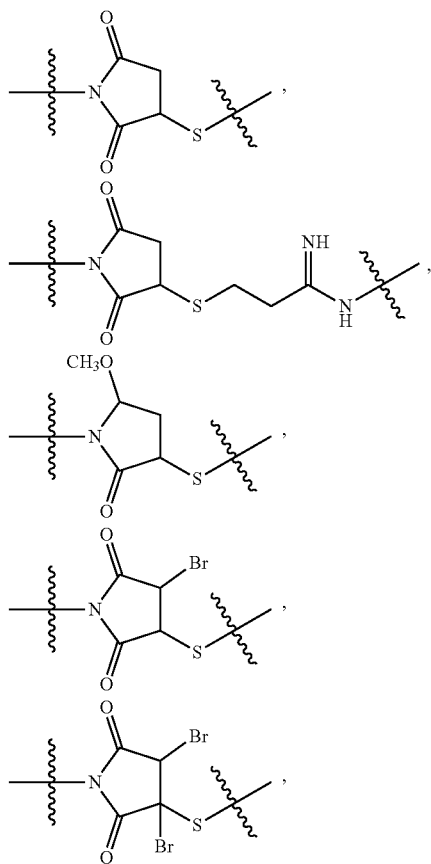

-continued
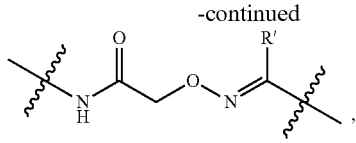
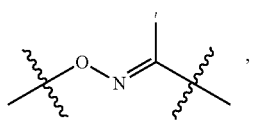
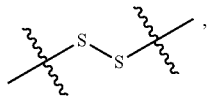
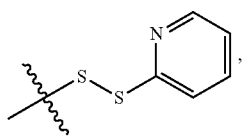
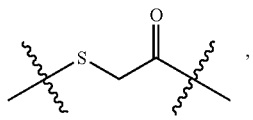
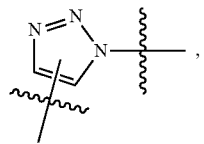
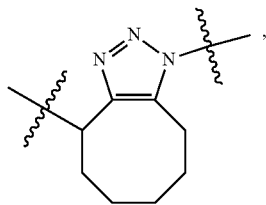
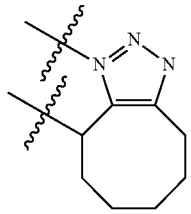
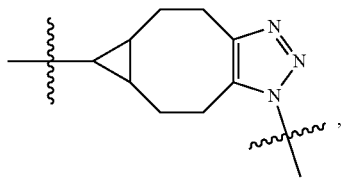
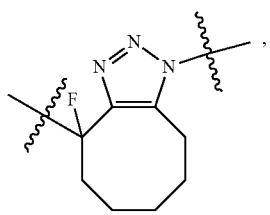
-continued
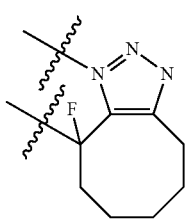
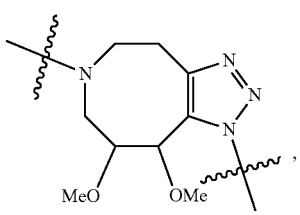
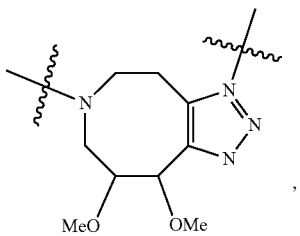
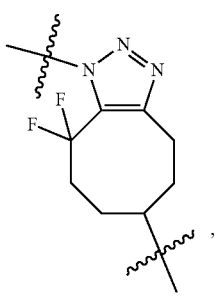
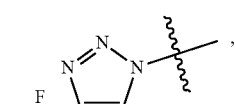
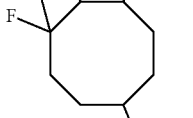
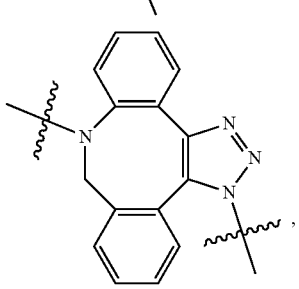

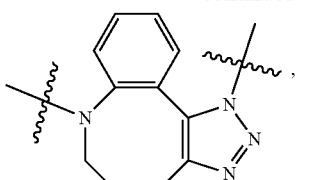,

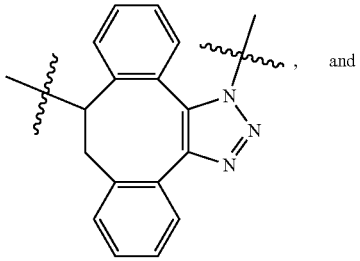, and

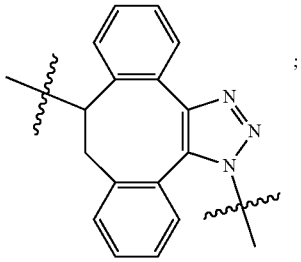;

wherein $R^N$ is aryl, alkyl, or arylalkyl; R' is hydrogen, alkyl, arylalkyl, or haloalkyl; D is independently at each occurrence an oligonucleotide; $L^b$ and $L^c$ are independently at each occurrence selected from the group consisting of bond, —O—, —S—, —OC(O)—, —C(O)O—, —(CH$_2$)$_n$C(O)—, —(CH$_2$)$_n$C(O)C(O)—, —(CH$_2$)$_n$NR$^5$C(O)C(O)—, —NR$^5$(CH$_2$)$_n$C(O)C(O)—, optionally substituted (CH$_2$)$_n$C$_{1-6}$ alkylene (CH$_2$)$_n$—, optionally substituted (CH$_2$)$_n$C(O)C$_{1-6}$ alkylene (CH$_2$)$_n$—, optionally substituted (CH$_2$)$_n$NR$^5$C$_{1-6}$ alkylene (CH$_2$)$_n$—, optionally substituted (CH$_2$)$_n$C(O)NR$^5$C$_{1-6}$ alkylene (CH$_2$)$_n$—, optionally substituted (CH$_2$)$_n$NR$^5$C(O)C$_{1-6}$ alkylene (CH$_2$)$_n$—, optionally substituted (CH$_2$)$_n$C(O)OC$_{1-6}$ alkylene (CH$_2$)$_n$—, optionally substituted (CH$_2$)$_n$OC(O)C$_{1-6}$ alkylene (CH$_2$)$_n$—, optionally substituted (CH$_2$)$_n$OC$_{1-6}$ alkylene (CH$_2$)$_n$—, optionally substituted (CH$_2$)$_n$NR$^5$C$_{1-6}$alkylene (CH$_2$)$_n$—, optionally substituted (CH$_2$)$_n$—S—C$_{1-6}$alkylene (CH$_2$)$_n$—, and optionally substituted (CH$_2$CH$_2$O)$_n$; wherein each alkylene is optionally substituted with 1 or 2 groups independently selected from the group consisting of of halo, hydroxy, haloalkyl, haloalkoxy, alkyl, alkoxy, amino, carboxyl, cyano, nitro, NHFmoc; wherein each $R^5$ is independently hydrogen, alkyl, arylalkyl,

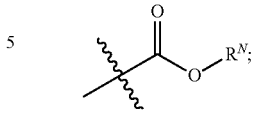

or and

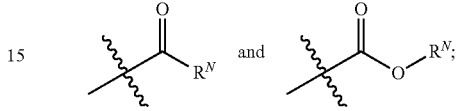

wherein $R^N$ is aryl, alkyl, or arylalkyl; X is O, S or NR$^8$, wherein R$^8$ is hydrogen, hydroxy, OR$^9$, NR$^{10}$R$^{11}$, alkyl, arylalkyl,

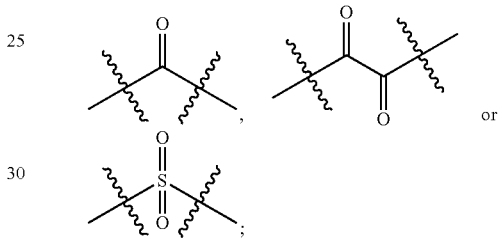

wherein $R^N$ is aryl, alkyl, or arylalkyl; wherein R$^9$, R$^{10}$ and R$^{11}$ are each independently hydrogen or alkyl; V$^1$ and V$^2$ are each independently

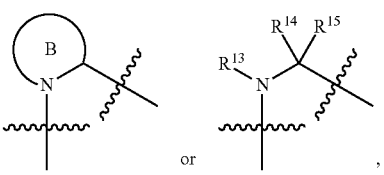

W is

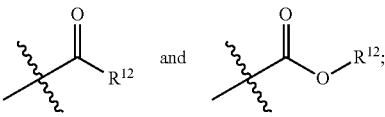

wherein Ring B is a 4-10 membered heterocycloalkyl, optionally substituted with 1-10 substituents, each of which is selected from the group consisting of hydrogen, hydroxy, halo, alkyl, alkoxy, cyano, haloalkyl, haloalkoxy, alkylthio, oxo, amino, alkylamino, dialkylamino, arylalkyl,

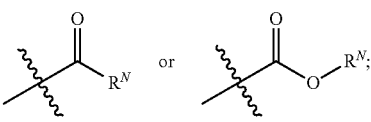

wherein R$^{12}$ is aryl, alkyl, or arylalkyl; wherein R$^{13}$ is hydrogen, hydroxy, OR$^{16}$, NR$^{17}$R$^{18}$, alkyl, arylalkyl, wherein $R^N$ is aryl, alkyl, or arylalkyl; $R^{14}$ and $R^{15}$ is each independently hydrogen, hydroxy, halo, alkyl, alkoxy, haloalkyl, haloalkoxy, aryl, arylalkyl, or heteroaryl; Z is bond,

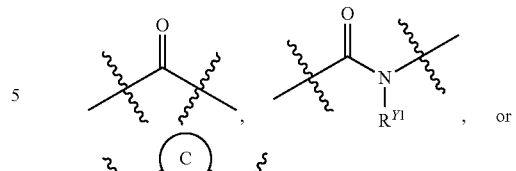

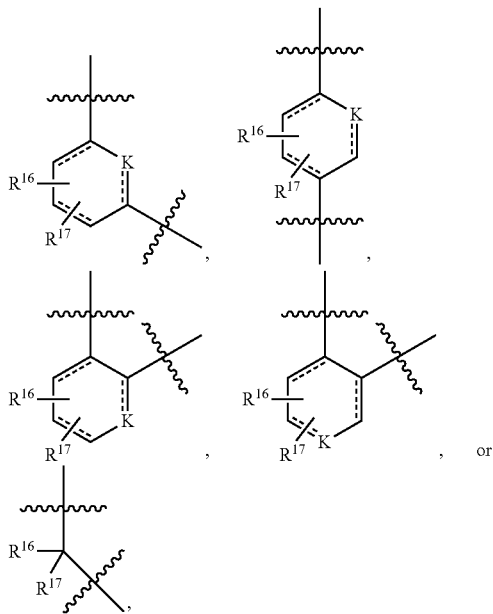

wherein $R^{16}$ and $R^{17}$ are each independently selected from the group consisting of of hydrogen, hydroxy, halo, alkyl, alkoxy, cycloalkyl, cyano, alkylthio, amino, alkylamino, and dialkylamino; K is O, $CHR^{18}$, $CR^{18}$, N, or and $NR^{18}$, wherein $R^{18}$ is hydrogen or alkyl;

$L^a$, $L^1$, $L^2$, $L^3$, $L^4$, $L^5$, $L^6$, $L^7$ and $L^8$ are each independently a bond, —O—, —$NR^{19}$—, —SO—, —$SO_2$—, $(CH_2)_n$—, or a linking group selected from Table 1; wherein Ring C is a 5-6 membered heteroaryl, optionally substituted with 1-4 substituents, each of which is independently selected from the group consisting of hydrogen, hydroxyl, halo, alkyl, alkoxy, haloalkyl, haloalkoxy, cyano, alkylthio, amino, alkylamino, dialkylamino and

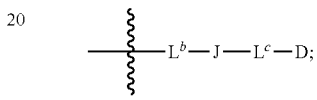

wherein each $R^{19}$, $R^{20}$, and $R^{21}$ is independently is selected from the group consisting of hydrogen, hydroxy, $OR^{22}$, $NR^{23}R^{24}$, alkyl, arylalkyl,

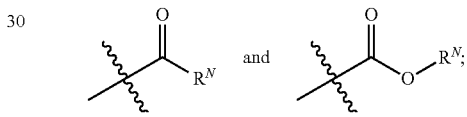

wherein $R^N$ is aryl, alkyl, or arylalkyl; wherein $R^{22}$, $R^{23}$, and $R^{24}$ are each independently hydrogen or alkyl;

n is 0, 1, 2, 3, 4, 5 or 6; wherein the Effector Domain has Formula (XIIa):

Formula (XIIa)

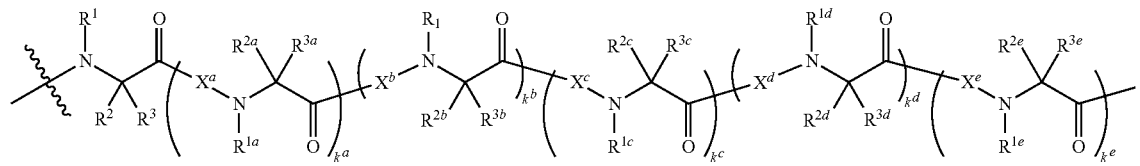

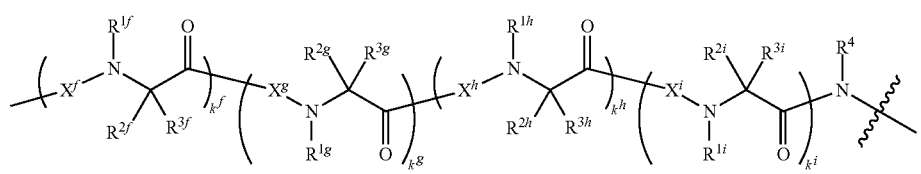

In some embodiments, each $k^a$, $k^b$, $k^c$, $k^d$, $k^e$, $k^f$, $k^g$, $k^h$, and $k^i$ is independently 0 or 1; each $X^a$, $X^b$, $X^c$, $X^d$, $X^e$, $X^f$, $X^g$, $X^h$, and $X^i$ is independently a bond, —S—, —S—S—, —S(O)—, —S(O)$_2$—, substituted or unsubstituted —(C$_1$-C$_3$) alkylene-, —(C$_2$-C$_4$) alkenylene-, —(C$_2$-C$_4$) alkynylene-, or

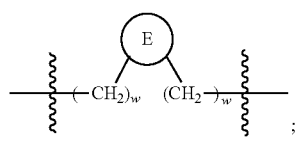

wherein Ring E is phenyl or a 5-6 heteroaryl or heterocycloalkyl; wherein each w is independently 0, 1, or 2; each $R^1$, $R^{1a}$, $R^{1b}$, $R^{1c}$, $R^{1d}$, $R^{1e}$, $R^{1f}$, $R^{1g}$, $R^{1h}$, $R^{1i}$ and $R^4$ is independently hydrogen, alkyl, arylalkyl or $NR^{25}$, wherein $R^{25}$ is hydrogen, hydroxy, $OR^{26}$, $NR^{27}R^{28}$, alkyl, arylalkyl,

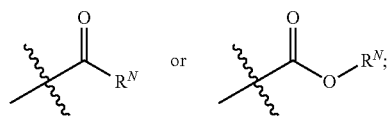

wherein $R^N$ is aryl, alkyl, or arylalkyl; wherein $R^{26}$, $R^{27}$, and $R^{28}$ are each independently hydrogen or alkyl; each $R^2$, $R^3$, $R^{2a}$, $R^{3a}$, $R^{2b}$, $R^{3b}$, $R^{2c}$, $R^{3c}$, $R^{2d}$, $R^{3d}$, $R^{2e}$, $R^{3e}$, $R^{2f}$, $R^{3f}$, $R^{2g}$, $R^{3g}$, $R^{2h}$, $R^{3h}$, $R^{2i}$, and $R^{3i}$ is independently selected from the group consisting of hydrogen, halo, amino, cyano, nitro, haloalkyl, optionally substituted alkyl, optionally substituted alkoxy, optionally substituted alkenyl, optionally substituted alkynyl, optionally substituted cycloalkyl, optionally substituted heterocycloalkyl, optionally substituted alkylamino, optionally substituted dialkylamino, optionally substituted aryl, optionally substituted heteroaryl, optionally substituted arylalkyl, optionally substituted heteroarylalkyl and

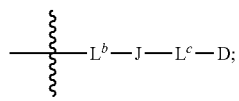

or wherein the Effector Domain has Formula (XIIb):

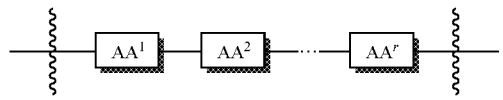

Formula (XIIb)

wherein each of $AA^1$, $AA^2$, ..., and $AA^r$ is an natural or unnatural amino acid residue; and r is 3, 4, 5, 6, 7, 8, 9, or 10;

or wherein the Effector Domain has Formula (XIIc):

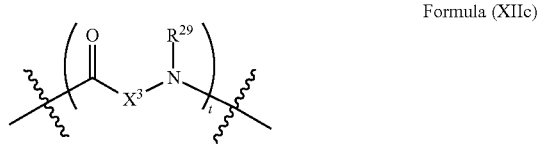

Formula (XIIc)

wherein each t is independently an integer selected from 0, 1, 2, 3, 4, 5, 6, 7, 8, 9, and 10; $R^{29}$ is a hydrogen, hydroxy, $OR^{30}$, $NR^{31}R^{32}$, alkyl, arylalkyl,

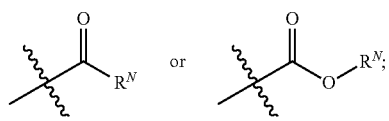

wherein $R^N$ is aryl, alkyl, or arylalkyl; wherein $R^{30}$, $R^{31}$, and $R^{32}$ are each independently hydrogen or alkyl; $X^3$ is substituted or unsubstituted —(C$_1$-C$_6$) alkylene-, —(C$_2$-C$_6$) alkenylene-, —(C$_2$-C$_6$) alkynylene-, or

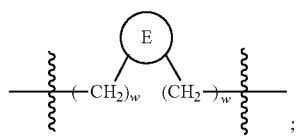

wherein Ring E is phenyl or a 5-6 heteroaryl or heterocycloalkyl; wherein each w is independently 0, 1, or 2;
or wherein the Effector Domain has Formula (XIId):

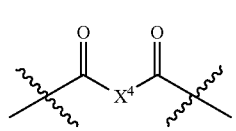

Formula (XIId)

wherein $X^4$ is substituted or unsubstituted —(C$_1$-C$_6$) alkylene-, —(C$_2$-C$_6$) alkenylene-, —(C$_2$-C$_6$) alkynylene-, or

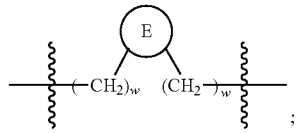

wherein Ring E is phenyl or a 5-6 heteroaryl or heterocycloalkyl; wherein each w is independently 0, 1, or 2;
or wherein the Effector Domain has Formula (XIIe):

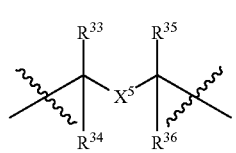

Formula (XIIe)

wherein $R^{33}$, $R^{34}$, $R^{35}$ and $R^{36}$ are each hydrogen or alkyl; $X^5$ is substituted or unsubstituted —$(C_1-C_6)$ alkylene-, —$(C_2-C_6)$ alkenylene-, —$(C_2-C_6)$ alkynylene-, or

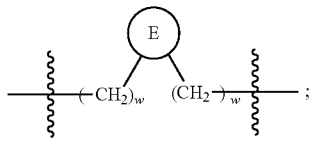

wherein Ring E is phenyl or a 5-6 heteroaryl or heterocycloalkyl; wherein each w is independently 0, 1, or 2;
or wherein the Effector Domain has Formula (XIIf):

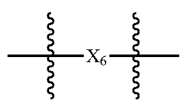

Formula (XIIf)

$X^6$ is substituted or unsubstituted —$(C_1-C_6)$ alkylene-, —$(C_2-C_6)$ alkenylene-, —$(C_2-C_6)$ alkynylene-, or

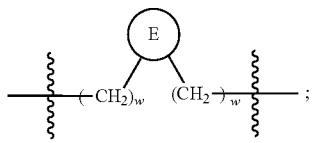

wherein Ring E is phenyl or a 5-6 heteroaryl or heterocycloalkyl; wherein each w is independently 0, 1, or 2; provided that when R is

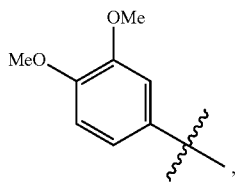 [SMILES: *c1ccc(OC)c(OC)c1]

L is ethylene, X is O, W is

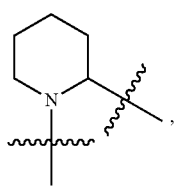 [SMILES: *C1CCCCN1*]

V is

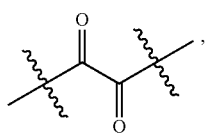 [SMILES: *C(=O)C(*)=O]

Z is

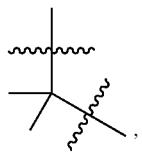 [SMILES: *C(*)(C)C]

$-L^6-L^7-L^8-$ is

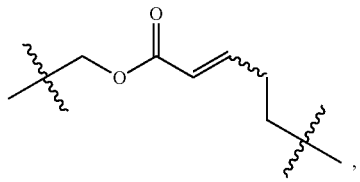 [SMILES: *CCC=CC(=O)OC*]

then $-L^1-L^2-L^3-L^4-L^5-$ is not

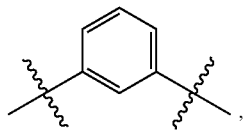 [SMILES: *c1cccc(*)c1]

and; wherein Ring A is substituted with at least one

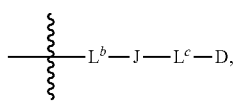

or at least one of $R^2$, $R^3$, $R^{2a}$, $R^{3a}$, $R^{2b}$, $R^{3b}$, $R^{2c}$, $R^{3c}$, $R^{2d}$, $R^{3d}$, $R^{2e}$, $R^{3e}$, $R^{2f}$, $R^{3f}$, $R^{2g}$, $R^{3g}$, $R^{2h}$, $R^{3h}$, $R^{2i}$, and $R^{3i}$ is

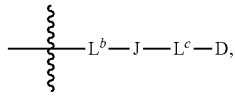

or at least one of $L^a$, $L^1$, $L^2$, $L^3$, $L^4$, $L^5$, $L^6$, $L^7$ and $L^8$ is Ring C substituted with at least one

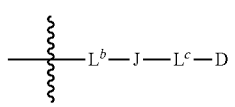

or wherein at least one of the linking groups selected from Table 1 is substituted with at least one

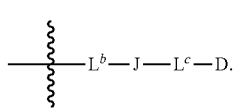

In another aspect, provided herein is a compound library that comprises a plurality of distinct tagged macrocyclic compounds according to any of the above. In certain embodiments, provided herein is a compound library that comprises at least about $10^2$ distinct tagged macrocyclic compounds according to any of the above. In certain embodiments, provided herein is a compound library that comprises from about $10^2$ to about $10^{10}$ distinct tagged macrocyclic compounds according to any of the above.

In a further aspect, provided herein is a method of making a library of tagged macrocyclic compounds as disclosed herein, the method comprising synthesizing a plurality of distinct tagged macrocyclic compounds according to any of the above.

In a still further aspect, provided herein is a method of making a tagged macrocyclic compound as disclosed herein, the method comprising operatively linking at least one oligonucleotide (D) to at least one of an FKBD, an effector domain, a first linking region, and a second linking region, and forming a macrocyclic ring comprising the FKBD, the effector domain, the first linking region, and the second linking region.

In certain embodiments, provided herein is a method of making a tagged macrocyclic compound as disclosed herein, the method comprising macrocyclic compound to at least one oligonucleotide (D), the macrocyclic compound comprising an FKBD, an effector domain, a first linking region, and a second linking region, wherein the FKBD, the effector domain, the first linking region, and the second linking region together form a macrocycle; and wherein the at least one oligonucleotide (D) can identify the structure of at least one of the FKBD, the effector domain, the first linking region, and the second linking region.

In yet a further aspect, the method of making a tagged macrocyclic compound comprises: operatively linking a compound of Formula (XIII):

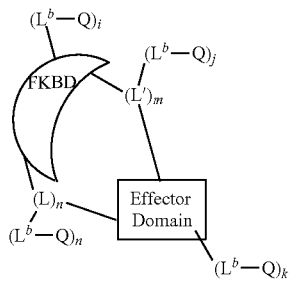

Formula (XIII)

to a compound of Formula (XIV):

Q'-L$^c$-D          Formula (XIV)

In some embodiments, $\mathcal{L}$ and $\mathcal{L}'$ are independently at each occurrence: a bond, —O—, —NR$^{19}$—, —SO—, —SO$_2$—, —(CH$_2$)$_n$—,

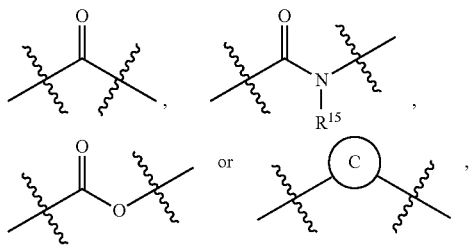

or a linking group selected from Table 1 wherein Ring C is a 5-6 membered heteroaryl, optionally substituted with 1-4 substituents, each of which is independently selected from the group consisting of hydrogen, hydroxy, halo, alkyl, alkoxy, haloalkyl, haloalkoxy, cyano, alkylthio, amino, alkylamino, dialkylamino; wherein R$^{19}$ is selected from the group consisting of hydrogen, hydroxy, OR$^{22}$, NR$^{23}$R$^{24}$, alkyl, arylalkyl,  : wherein R$^N$ is aryl, alkyl, or arylalkyl; wherein R$^{22}$, R$^{23}$, and R$^{24}$ are each independently hydrogen or alkyl; Q and Q' are each independently selected from the group consisting of N$_3$, —C≡CH, NR$^6$R$^7$, —COOH, —ONH$_2$, —SH, —NH$_2$,

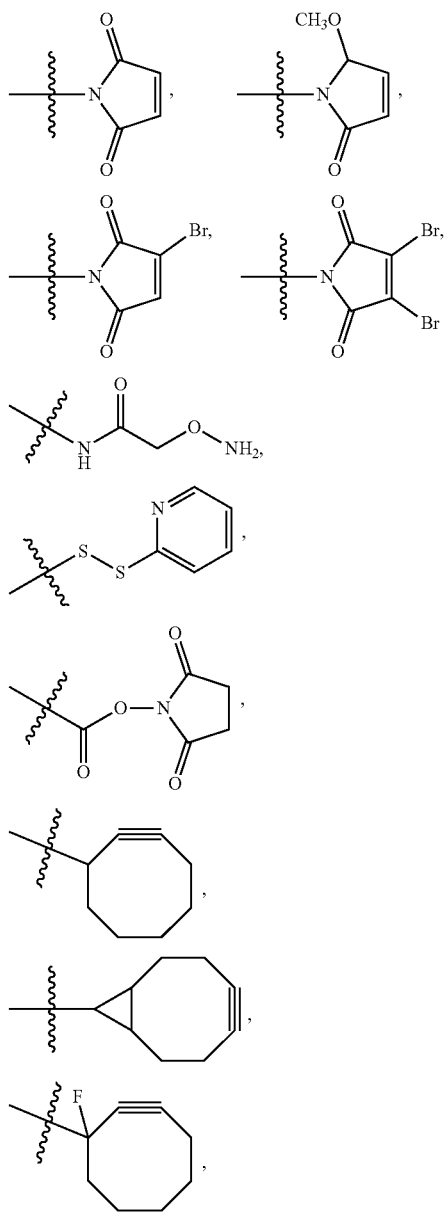

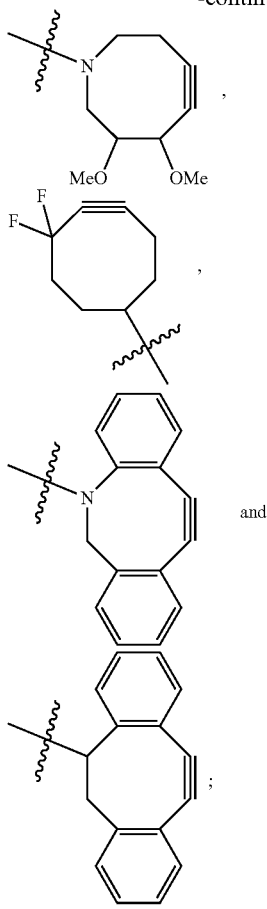

wherein $R^6$ and $R^7$ is each independently hydrogen, alkyl, arylalkyl,

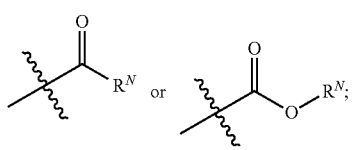

wherein $R^N$ is aryl, alkyl, or arylalkyl; and R' is hydrogen, alkyl, arylalkyl, or haloalkyl; $L^b$ and $L^c$ are independently at each occurrence selected from the group consisting of a bond, —O—, —S—, —OC(O)—, —C(O)O—, —(CH$_2$)$_n$C(O)—, —(CH$_2$)$_n$C(O)C(O)—, —(CH$_2$)$_n$NR$^5$C(O)C(O)—, —NR$^5$(CH$_2$)$_n$C(O)C(O)—, optionally substituted (CH$_2$)$_n$C$_{1-6}$ alkylene-(CH$_2$)$_n$—, optionally substituted (CH$_2$)$_n$C(O)C$_{1-6}$ alkylene-(CH$_2$)$_n$—, optionally substituted (CH$_2$)$_n$NR$^5$C$_{1-6}$ alkylene-(CH$_2$)$_n$—, optionally substituted (CH$_2$)$_n$C(O)NR$^5$C$_{1-6}$ alkylene-(CH$_2$)$_n$—, optionally substituted (CH$_2$)$_n$NR$^5$C(O)C$_{1-6}$ alkylene-(CH$_2$)$_n$—, optionally substituted (CH$_2$)$_n$C(O)OC$_{1-6}$ alkylene-(CH$_2$)$_n$—, optionally substituted (CH$_2$)$_n$OC(O)C$_{1-6}$ alkylene-(CH$_2$)$_n$—, optionally substituted (CH$_2$)$_n$OC$_{1-6}$ alkylene-(CH$_2$)$_n$—, optionally substituted (CH$_2$)$_n$NR$^5$C$_{1-6}$ alkylene-(CH$_2$)$_n$—, optionally substituted (CH$_2$)$_n$—S—C$_{1-6}$ alkylene-(CH$_2$)$_n$—, and optionally substituted (CH$_2$CH$_2$O)$_n$; wherein each alkylene is optionally substituted with 1 or 2 groups independently selected from the group consisting of of halo, hydroxy, haloalkyl, haloalkoxy, alkyl, alkoxy, amino, carboxyl, cyano, nitro, NHFmoc; wherein each $R^5$ is independently hydrogen, alkyl, arylalkyl,

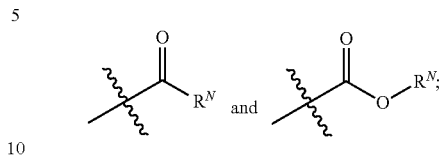

wherein $R^N$ is aryl, alkyl, or arylalkyl;

D is an oligonucleotide; h, i, j, and k are each independently an integer from 0-20, provided that at least one of h, i, j, and k is not 0; n is an integer from 1-5; m is an integer from 1-5.

In another aspect, provided herein is a method of making a tagged macrocyclic compound, the method comprising operatively linking a compound of Formula (XII):

Formula (XII)

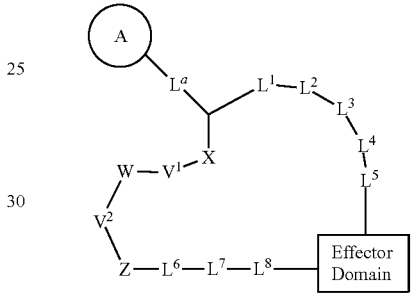

with a compound of Formula (XIV):

Q'-L$^c$-D          Formula (XIV)

Ring A is a 5-10 membered aryl, cycloalkyl, heteroaryl or heterocycloalkyl, optionally substituted with 1-17 substituents, each of which is independently selected from the group consisting of hydrogen, hydroxy, halo, alkyl, alkoxy, cyano, haloalkyl, haloalkoxy, alkylthio, oxo, amino, alkylamino, dialkylamino,

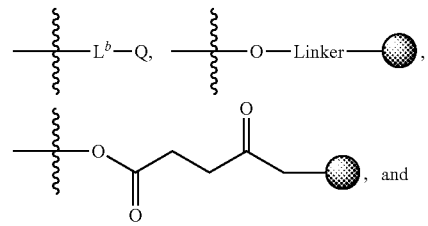

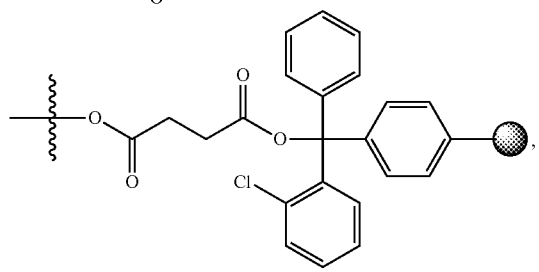

wherein

is a resin;

$L^b$ and $L^c$ are independently selected from the group consisting of a bond, —O—, —S—, —OC(O)—, —C(O)O—, —(CH$_2$)$_n$C(O)—, —(CH$_2$)$_n$C(O)C(O)—, —(CH$_2$)$_n$NR$^5$C(O)C(O)—, —NR$^5$(CH$_2$)$_n$C(O)C(O)—, optionally substituted (CH$_2$)$_n$C$_{1-6}$ alkylene-(CH$_2$)$_n$—, optionally substituted (CH$_2$)$_n$C(O)C$_{1-6}$ alkylene-(CH$_2$)$_n$—, optionally substituted (CH$_2$)$_n$NR$^5$C$_{1-6}$ alkylene-(CH$_2$)$_n$—, optionally substituted (CH$_2$)$_n$C(O)NR$^5$C$_{1-6}$ alkylene-(CH$_2$)$_n$—, optionally substituted (CH$_2$)$_n$NR$^5$C(O)C$_{1-6}$ alkylene-(CH$_2$)$_n$—, optionally substituted (CH$_2$)$_n$C(O)OC$_{1-6}$ alkylene-(CH$_2$)$_n$—, optionally substituted (CH$_2$)$_n$OC(O)C$_{1-6}$ alkylene-(CH$_2$)$_n$—, optionally substituted (CH$_2$)$_n$OC$_{1-6}$ alkylene-(CH$_2$)$_n$—, optionally substituted (CH$_2$)$_n$NR$^5$C$_{1-6}$ alkylene-(CH$_2$)$_n$—, optionally substituted (CH$_2$)$_n$—S—C$_{1-6}$alkylene-(CH$_2$)$_n$—, and optionally substituted (CH$_2$CH$_2$O)$_n$; wherein each alkylene is optionally substituted with 1 or 2 groups independently selected from the group consisting of of halo, hydroxy, haloalkyl, haloalkoxy, alkyl, alkoxy, amino, carboxyl, cyano, nitro, NHFmoc; wherein each R$^5$ is independently hydrogen, alkyl, arylalkyl,

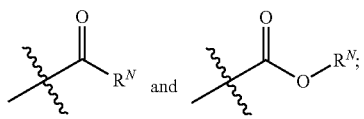

wherein R$^N$ is aryl, alkyl, or arylalkyl;

Q and Q' are independently selected from the group consisting of —N$_3$, —C≡CH, NR$^6$R$^7$, —COOH, —ONH$_2$, —SH, —NH$_2$,

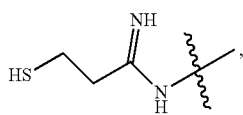

—(C=O)R',

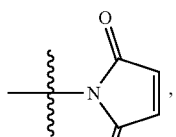 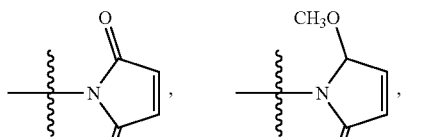

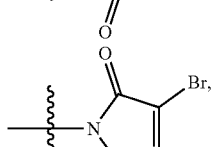

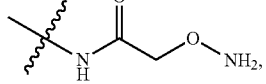

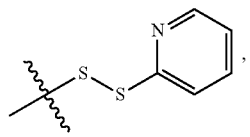

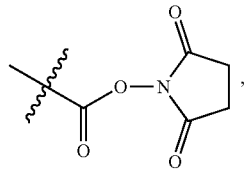

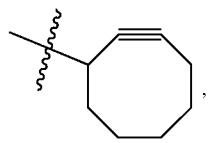

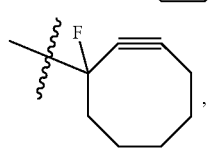

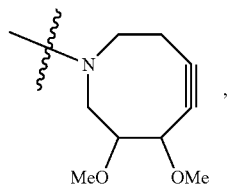

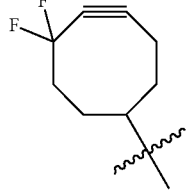

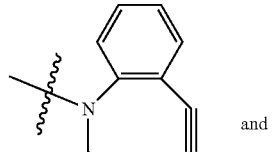

and

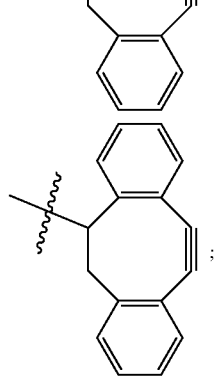

;

wherein R$^6$ and R$^7$ is each independently hydrogen, alkyl, arylalkyl,

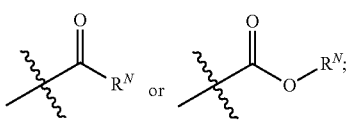

wherein $R^N$ is aryl, alkyl, or arylalkyl; and R' is hydrogen, alkyl, arylalkyl, or haloalkyl; X is O, S or $NR^8$, wherein $R^8$ is hydrogen, hydroxy, $OR^9$, $NR^{10}R^{11}$, alkyl, arylalkyl,

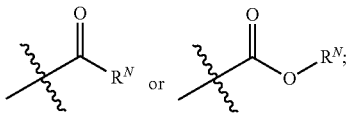

wherein $R^N$ is aryl, alkyl, or arylalkyl; wherein $R^9$, $R^{10}$ and $R^{11}$ are each independently hydrogen or alkyl; $V^1$ and $V^2$ are each independently

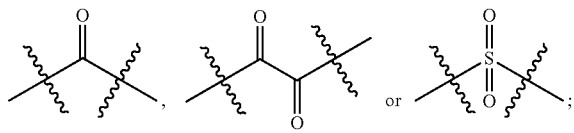

W is

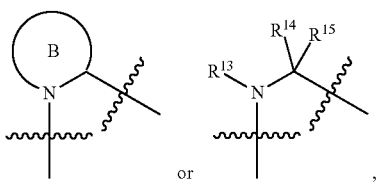

wherein Ring B is a 4-10 membered heterocycloalkyl, optionally substituted with 1-10 substituents, each of which is selected from the group consisting of hydrogen, hydroxy, halo, alkyl, alkoxy, cyano, haloalkyl, haloalkoxy, alkylthio, oxo, amino, alkylamino, dialkylamino, arylalkyl,

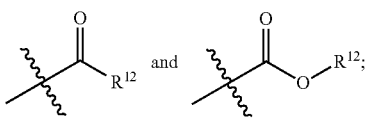

wherein $R^{12}$ is aryl, alkyl, or arylalkyl; wherein $R^{13}$ is hydrogen, hydroxy, $OR^{16}$, $NR^{17}R^{18}$, alkyl, arylalkyl,

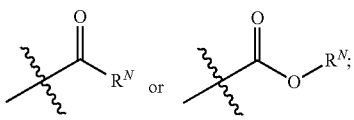

wherein $R^N$ is aryl, alkyl, or arylalkyl; $R^{14}$ and $R^{15}$ is each independently hydrogen, hydroxy, halo, alkyl, alkoxy, haloalkyl, haloalkoxy, aryl, arylalkyl, or heteroaryl;

Z is bond,

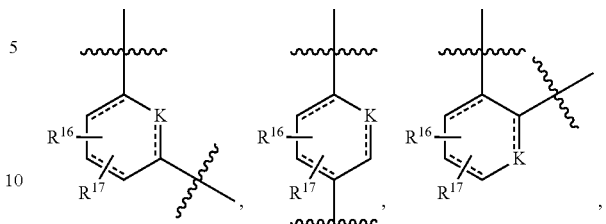

wherein $R^{16}$ and $R^{17}$ are each independently selected from the group consisting of of hydrogen, hydroxy, halo, alkyl, alkoxy, cycloalkyl, cyano, alkylthio, amino, alkylamino, and dialkylamino; K is O, $CHR^{18}$, $CHR^{18}$, $CR^{18}$, N, and $NR^{18}$, wherein $R^{18}$ is hydrogen or alkyl;

$L^a$, $L^1$, $L^2$, $L^3$, $L^4$, $L^5$, $L^6$, $L^7$ and $L^8$ are each independently a bond, —O—, —$NR^{19}$—, —SO—, —$SO_2$—, —$(CH_2)_n$—,

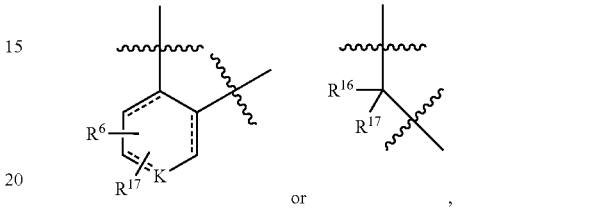

or a linking group selected from Table 1; wherein Ring C is a 5-6 membered heteroaryl, optionally substituted with 1-4 substituents, each of which is independently selected from the group consisting of hydrogen, hydroxy, halo, alkyl, alkoxy, haloalkyl, haloalkoxy, cyano, alkylthio, amino, alkylamino, dialkylamino and

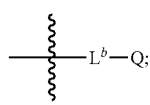

wherein $R^{19}$ is selected from the group consisting of hydrogen, hydroxy, $OR^{22}$, $NR^{23}R^{24}$, alkyl, arylalkyl,

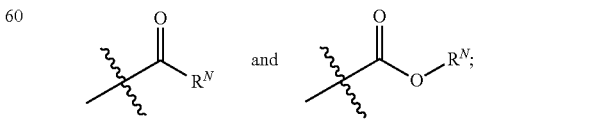

wherein $R^N$ is aryl, alkyl, or arylalkyl; wherein $R^{22}$, $R^{23}$, and $R^{24}$ are each independently hydrogen or alkyl;

n is 0, 1, 2, 3, 4, 5 or 6; wherein the Effector Domain has Formula (XIIa):

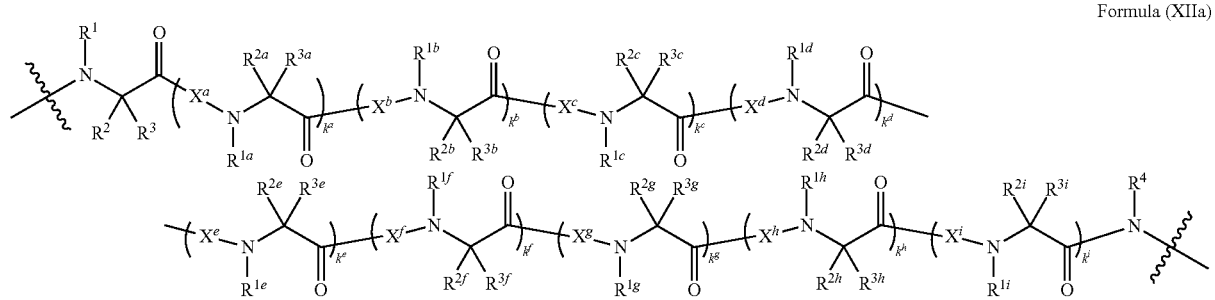

Formula (XIIa)

each $k^a$, $k^b$, $k^c$, $k^d$, $k^e$, $k^f$, $k^g$, $k^h$, and $k^i$ is independently 0 or 1; each $X^a$, $X^b$, $X^c$, $X^d$, $X^e$, $X^f$, $X^g$, $X^h$, and $X^i$ is independently a bond, —S—, —S—S—, —S(O)—, —S(O)$_2$—, substituted or unsubstituted —(C$_1$-C$_3$) alkylene-, —(C$_2$-C$_4$) alkenylene-, —(C$_2$-C$_4$) alkynylene-, or

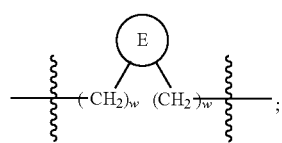

wherein Ring E is phenyl or a 5-6 heteroaryl or heterocycloalkyl; wherein each w is independently 0, 1, or 2; each $R^1$, $R^{1a}$, $R^{1b}$, $R^{1c}$, $R^{1d}$, $R^{1e}$, $R^{1e}$, $R^{1f}$, $R^{1g}$, $R^{1h}$, $R^{1i}$, and $R^4$ is independently hydrogen, alkyl, arylalkyl or $NR^{25}$, wherein $R^{25}$ is hydrogen, hydroxy, $OR^{26}$, $NR^{27}R^{28}$, alkyl, arylalkyl,

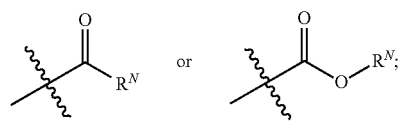

wherein $R^N$ is aryl, alkyl, or arylalkyl; wherein $R^{26}$, $R^{27}$, and $R^{28}$ are each independently hydrogen or alkyl; each $R^2$, $R^3$, $R^{2a}$, $R^{3a}$, $R^{2b}$, $R^{3b}$, $R^{2c}$, $R^{3c}$, $R^{2d}$, $R^{3d}$, $R^{2e}$, $R^{3e}$, $R^{2f}$, $R^{3f}$, $R^{2g}$, $R^{3g}$, $R^{2h}$, $R^{3h}$, $R^{2i}$, and $R^{3i}$ is independently selected from the group consisting of hydrogen, halo, amino, cyano, nitro, haloalkyl, optionally substituted alkyl, optionally substituted alkoxy, optionally substituted alkenyl, optionally substituted alkynyl, optionally substituted cycloalkyl, optionally substituted heterocycloalkyl, optionally substituted alkylamino, optionally substituted dialkylamino, optionally substituted aryl, optionally substituted heteroaryl, optionally substituted arylalkyl, optionally substituted heteroarylalkyl, and

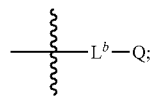

or wherein the Effector Domain has Formula (XIIb):

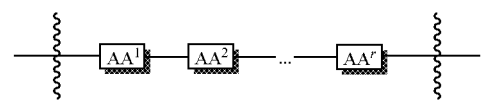

Formula (XIIb)

wherein each of $AA^1$, $AA^2$, . . . , and $AA^r$ is an natural or unnatural amino acid residue; and r is 3, 4, 5, 6, 7, 8, 9, or 10;

or wherein the Effector Domain has Formula (XIIc):

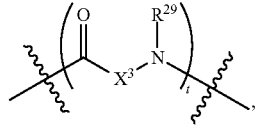

Formula (XIIc)

each t is independently an integer selected from 0, 1, 2, 3, 4, 5, 6, 7, 8, 9, and 10; $R^{29}$ is hydrogen, hydroxy, $OR^{30}$, $NR^{31}R^{32}$, alkyl, arylalkyl,

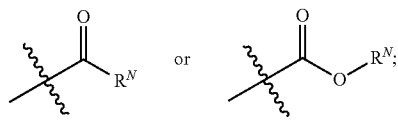

wherein $R^N$ is aryl, alkyl, or arylalkyl; wherein $R^{30}$, $R^{31}$, and $R^{32}$ are each independently hydrogen or alkyl; $X^3$ is substituted or unsubstituted —(C$_1$-C$_6$) alkylene-, —(C$_2$-C$_6$) alkenylene-, —(C$_2$-C$_6$) alkynylene-, or

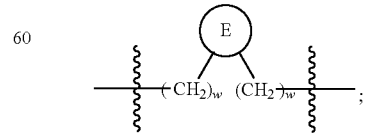

wherein Ring E is phenyl or a 5-6 heteroaryl or heterocycloalkyl; wherein each w is independently 0, 1, or 2;

or wherein the Effector Domain has Formula (XIId):

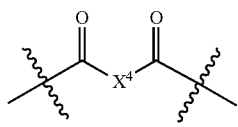

Formula (XIId)

$X^4$ is substituted or unsubstituted —($C_1$-$C_6$) alkylene-, —($C_2$-$C_6$) alkenylene-, —($C_2$-$C_6$) alkynylene-, or

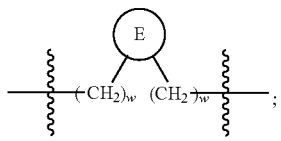

wherein Ring E is phenyl or a 5-6 heteroaryl or heterocycloalkyl; wherein each w is independently 0, 1, or 2;
or wherein the Effector Domain has Formula (XIIe):

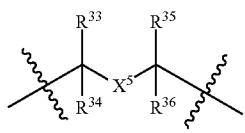

Formuls (XIIe)

$R^{33}$, $R^{34}$, $R^{35}$ and $R^{36}$ are each hydrogen or alkyl; $X^5$ is substituted or unsubstituted —($C_1$-$C_6$) alkylene-, —($C_2$-$C_6$) alkenylene-, —($C_2$-$C_6$) alkynylene-, or

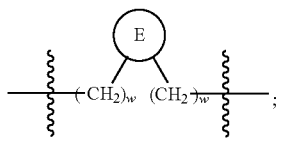

wherein Ring E is phenyl or a 5-6 heteroaryl or heterocycloalkyl; wherein each w is independently 0, 1, or 2;
or wherein the Effector Domain has Formula (XIIf):

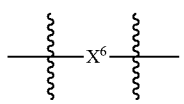

Formula (XIIf)

$X^6$ is substituted or unsubstituted —($C_1$-$C_6$) alkylene-, —($C_2$-$C_6$) alkenylene-, —($C_2$-$C_6$) alkynylene-, or

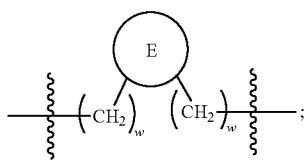

wherein Ring E is phenyl or a 5-6 heteroaryl or heterocycloalkyl; wherein each w is independently 0, 1, or 2; and provided that when Ring A is

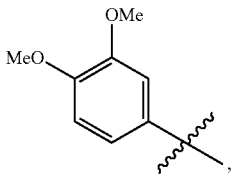

, $L^a$ is ethylene, X is O, W is

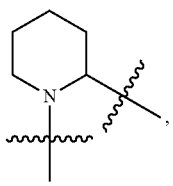

, $V^1$ is

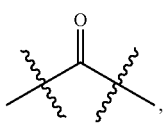 [SMILES: *C(*)=O]

, $V^2$ is

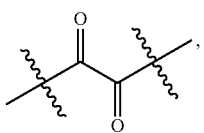 [SMILES: *C(=O)C(*)=O]

,

Z is

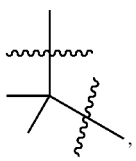 [SMILES: *C(*)(C)C]

,

-$L^6$-$L^7$-$L^8$- is

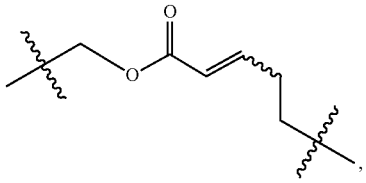 [SMILES: *CCC=CC(=O)OC*]

,

305 and -L$^1$-L$^2$-L$^3$-L$^4$-L$^5$- is not

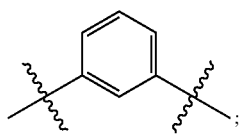 [SMILES: *c1cccc(*)c1]
;

D is an oligonucleotide; wherein Ring A is substituted with at least one

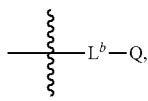

or at least one of R$^2$, R$^3$, R$^{2a}$, R$^{3a}$, R$^{2b}$, R$^{3b}$, R$^{2c}$, R$^{3c}$, R$^{2d}$, R$^{3d}$, R$^{2e}$, R$^{3e}$, R$^{2f}$, R$^{3f}$, R$^{2g}$, R$^{3g}$, R$^{2h}$, R$^{3h}$, R$^{2i}$, and R$^{3i}$ is

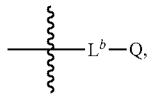

or at least one of L$^a$, L$^1$, L$^2$, L$^3$, L$^4$, L$^5$, L$^6$, L$^7$ and L$^8$ is Ring C substituted with at least one

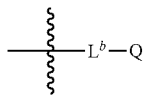

or wherein at least one of the linking groups selected from Table 1 is substituted with at least one

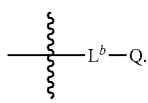

In yet another aspect, provided herein is a method for identifying one or more compounds that bind to a biological target the method comprising: (a) incubating the biological target with at least a portion of the plurality of distinct tagged macrocyclic compounds of the compound library of claim 2 to make at least one bound compound and at least one unbound compound of the plurality of distinct tagged macrocyclic compounds; (b) removing the at least one unbound compound; and (c) sequencing each of the oligonucleotides (D) of the at least one bound compound.

In certain embodiments, the DNA-encoded library can be a single pharmacophore library, wherein only one chemical moiety can be attached to a single strand of DNA, as described in, e.g., Neri & Lerner, *Annu. Rev. Biochem.* (2018) 87:5.1-5.24, which is hereby incorporated by reference in its entirety. In certain embodiments, the DNA-encoded library can be a dual pharmacophore library, wherein two independent molecules can be attached to the double strands of DNA, as described in, e.g., Id; Mannocci et al., *Chem. Commun.* (2011) 47:12747-53, which is hereby incorporated by reference in its entirety.

306

In a further aspect, provided herein is a method of making a library of tagged macrocyclic compounds, the method comprising synthesizing a plurality of distinct tagged macrocyclic compounds. In certain embodiments, each tagged macrocyclic compound of the plurality of distinct tagged macrocyclic compounds comprising a macrocyclic compound operatively linked to at least one oligonucleotide (D). In certain embodiments, each compound of the plurality of distinct tagged macrocyclic compounds of the compound library comprises a macrocyclic compound operatively linked to at least one oligonucleotide (D). In certain embodiments, the macrocyclic compound comprising an FKBD, an effector domain, a first linking region, and a second linking region. In certain embodiments, the FKBD, the effector domain, the first linking region, and the second linking region together form a macrocycle. In certain embodiments, each of the at least one oligonucleotide (D) can identify at least one of the FKBD, the effector domain, the first linking region, and the second linking region of each of the plurality of distinct tagged macrocyclic compounds. In certain embodiments, each compound of the plurality of distinct tagged macrocyclic compounds of the compound library comprises a compound of Formula (A) (as above-defined). In certain embodiments, each compound of the plurality of distinct tagged macrocyclic compounds of the compound library comprises a compound of Formula (I) (as above-defined herein). In certain embodiments, each compound of the plurality of distinct tagged macrocyclic compounds of the compound library can be a reaction product of operatively linking a compound of Formula (B) (as above-defined herein) with a compound of Formula (C) (as above-defined herein). In certain embodiments, each compound of the plurality of distinct tagged macrocyclic compounds of the compound library can be a reaction product of operatively linking a compound of Formula (B') (as above-defined herein) with a compound of Formula (C) (as above-defined herein).

In certain embodiments, the method of synthesizing a library of compounds can be selected from the group consisting of the split-and-pool method, DNA-templated library synthesis (DTS), encoded self-assembling chemical (ESAC) library synthesis, DNA-recorded library synthesis, DNA-directed library synthesis, DNA-routing, and 3-D proximity-based library synthesis (YoctoReactor). As a person of ordinary skill in the art would be aware, various techniques for synthesizing the library of tagged macrocyclic compounds are described in, e.g., Neri & Lerner, *Annu. Rev. Biochem.* (2018) 87:5.1-5.24; Roman et al., *SLAS Discov.* (2018) 23(5):387-396; Lim, *C&EN*, (2017) 95 (29):10-10; Halford, *C&EN*, (2017) 95(25): 28-33; Estevez, *Tetrahedron: Asymmetry.* (2017) 28:837-842; Neri, *Chembiochem.* (2017) 4; 18(9):827-828; Yuen & Franzini, *Chembiochem.* (2017) 4; 18(9):829-836; Skopic et al., *Chem Sci.* (2017) 1; 8(5):3356-3361; Shi et al.; *Bioorg Med Chem Lett.* (2017) 1; 27(3):361-69; Zimmermann & Neri, *Drug Discov Today.* (2016) 21(11):1828-1834; Satz et al., *Bioconjug Chem.* (2015) 19; 26(8):1623-32; Ding et al., *ACS Comb Sci.* (2016) 10; 18(10):625-629; Arico-Muendel, *MedChemComm*, (2016) 7(10): 1898-1909; Skopic, *MedChemComm*, (2016) 7(10): 1957-1965; Satz, *CS Comb. Sci.* (2016) 18 (7):415-424; Tian et al., *MedChemComm*, (2016) 7(7): 1316-1322; Salamon et al., *ACS Chem Biol.* (2016) 19; 11(2):296-307; Satz et al., *Bioconjug Chem.* (2015) 19; 26(8):1623-32; Connors et al., *Curr Opin Chem Biol.* (2015) 26:42-7; Blakskjaer et al., *Curr Opin Chem Biol.* (2015) 26:62-71; Scheuermann & Neri, *Curr Opin Chem Biol.* (2015) 26:99-103; Franzini et al., *Angew Chem Int Ed Engl.*

(2015) 23; 54(13):3927-31; Franzini et al., *Bioconjug Chem.* (2014) 20; 25(8):1453-61; Franzini, Neri & Scheuermann, *Acc Chem Res.* (2014) 15; 47(4):1247-55; Mannocci et al., *Chem. Commun.* (2011) 47:12747-53; Kleiner et al., *Chem Soc Rev.* (2011) 40(12): 5707-17; Clark, *Curr Opin Chem Biol.* (2010) 14(3):396-403; Mannocci et al., *Proc Natl Acad Sci USA.* (2008) 18; 105(46):17670-75; Buller et al., *Bioorg Med Chem Lett.* (2008) 18(22):5926-31; Scheuermann et al., *Bioconjugate Chem.* (2008) 19:778-85; Zimmerman et al., *ChemBioChem* (2017) 18(9):853-57, and Cuozzo et al., *ChemBioChem* (2017), 18(9):864-71, each of which is hereby incorporated by reference in its entirety.

In some embodiments, the method of synthesizing a library of tagged macrocyclic compounds comprises DNA-recorded library synthesis, in which encoding and library synthesis take place separately, as described in, e.g., Shi et al., Bioorg Med Chem Lett. (2017) 1; 27(3):361-369; Kleiner et al., Chem Soc Rev. (2011) 40(12): 5707-17. In certain embodiments, the DNA-recorded library synthesis c comprises split-and-pool methods, which are described in, e.g., Krall, Scheuermann & Neri, *Angew Chem. Int. Ed Engl.* (2013) 28; 52(5):1384-402; Mannocci et al., *Chem. Commun.* (2011) 47:12747-53; and U.S. Pat. No. 7,989,395 to Morgan et al., each of which is hereby incorporated by reference in its entirety. In certain embodiments, the split-and-pool method comprises successive chemical ligation of oligonucleotide tags to an initial oligonucleotide (or headpiece), which can be covalently linked to a chemically generated entity by successive split-and-pool steps. In certain embodiments, during each split step, a chemical synthesis step can be performed along with an oligonucleotide ligation step.

In some embodiments, the library can be synthesized by a sequence of split-and-pool cycles, wherein an initial oligonucleotide (or headpiece) can be reacted with a first set of building blocks (e.g., a plurality of FKBD building blocks). For each building block of the first set of building blocks (e.g., each FKBD building block), an oligonucleotide (D) can be appended to the initial oligonucleotide (or headpiece) and the resulting product can be pooled (or mixed), and subsequently split into separate reactions. Subsequently, in certain embodiments, a second set of building blocks (e.g., a plurality of effector domain building blocks) can be added, and an oligonucleotide (D) can be appended to each building block of the second set of building blocks. In certain embodiments, each oligonucleotide (D) identifies a distinct building block.

In some embodiments, the method of synthesizing a library of tagged macrocyclic compounds comprises DNA-directed library synthesis, in which DNA both encodes and templates library synthesis as described in, e.g., Kleiner et al., *Bioconjugate Chem.* (2010) 21, 1836-41; and Shi et al., Bioorg Med Chem Lett. (2017) 1; 27(3):361-369, each of which is hereby incorporated by reference in its entirety. In certain embodiments, the DNA-directed library synthesis comprises the DNA-templated synthesis (DTS) method as described in, e.g., Mannocci et al., *Chem. Commun.* (2011) 47:12747-53, Franzini, Neri & Scheuermann, *Acc Chem Res.* (2014) 15; 47(4):1247-55; and Mannocci et al., *Chem. Commun.* (2011) 47:12747-53, each of which are hereby incorporated by reference in its entirety. In certain embodiments, the DTS method comprises DNA oligonucleotides that not only encode but also direct the construction of the library. See Buller et al., *Bioconjugate Chem.* (2010) 21, 1571-80, which is hereby incorporated by reference in its entirety. In certain embodiments different building blocks can be incorporated into molecules using DNA-linked reagents that can be forced into proximity by base pairing between their DNA tags. See Gartner et al., *Science* (2004) 305:1601-05, which is hereby incorporated by reference in its entirety. In certain embodiments, a library of long oligonucleotides can be synthesized first as a template for the DNA-encoded library. In certain embodiments, the oligonucleotides can be subjected to sequence-specific chemical reactions through immobilization on resin tagged with complementary DNA sequences. See Wrenn & Harbury, *Annu. Rev. Biochem.* (2007) 76:331-49, which is hereby incorporated by reference in its entirety.

In certain embodiments, the DNA-directed library synthesis comprises 3-D proximity-based library synthesis, also known as YoctoReactor technology, which is described in, e.g., Blakskjaer et al., *Curr Opin Chem Biol.* (2015) 26:62-7, which is hereby incorporated by reference in its entirety.

In certain embodiments, the method of synthesizing a library of tagged macrocyclic compounds comprises encoded self-assembling chemical (ESAC) library synthesis, also known as double-pharmacophore DNA-encoded chemical libraries, as described in, e.g., Mannocci et al., *Chem. Commun.* (2011) 47:12747-53; Melkko et al., *Nat. Biotechnol.* (2004) 22(5):568-74; Scheuermann et al., *Bioconjugate Chem.* (2008) 19:778-85; and U.S. Pat. No. 8,642, 215 to Neri et al. each of which is hereby incorporated by reference in its entirety. In certain embodiments, synthesizing a library of tagged macrocyclic compounds by ESAC synthesis comprises, for example, non-covalent combinatorial assembly of complementary oligonucleotide sub-libraries, in which each sub-library can include a first oligonucleotide appended to a first building block, wherein the first oligonucleotide comprises a coding domain that identifies the first building block, and a hybridization domain, which self-assembles to a second oligonucleotide appended to a second building block, second oligonucleotide comprising a coding domain that identifies the second building block, and a hybridization domain that self-assembles to the first oligonucleotide.

In some embodiments, the method of synthesizing a library of tagged macrocyclic compounds comprises DNA-routing, as described in, e.g., Clark, *Curr Opin Chem Biol.* (2010) 14(3):396-403, which is hereby incorporated by reference in its entirety.

In certain embodiments, oligonucleotide ligation can utilize one of several methods that would be appreciated be a person of ordinary skill in the art, described, for example, in Zimmermann & Neri, *Drug Discov. Today*. (2016) 21(11): 1828-1834; and Keefe et al., *Curr Opin Chem Biol.* (2015) 26:80-88, each of which are hereby incorporated by reference in its entirety. In certain embodiments, the oligonucleotide ligation can be an enzymatic ligation. In certain embodiments, the oligonucleotide ligation can be a chemical ligation.

In certain embodiments, the ligation comprises base-pairing a short, complementary "adapter" oligonucleotide to single-stranded oligonucleotides to either end of the ligation site, allowing ligation of single-stranded DNA tags in each cycle. See Clark et al., *Nat. Chem. Biol.* (2009) 5:647-54, which is hereby incorporated by reference in its entirety. In certain embodiments, the oligonucleotide ligation comprises utilizing 2-base overhangs at the 3' end of the headpiece and of each building block's DNA tag to form sticky ends for ligation. In certain embodiments, the sequences of the overhangs can depend on the cycle but not on the building block, so that any DNA tag can be ligated to any DNA tag from the previous cycle, but not to a truncated sequence. See id. In certain embodiments, the oligonucleotide ligation step can utilize oligonucleotides of opposite sense for subsequent cycles, with a small region of overlap in which the two oligonucleotides are complementary. In certain embodiments, in lieu of ligation, DNA polymerase can be used to fill in the rest of the complementary sequences, creating a double-strand oligonucleotide comprising both tags. In certain embodiments, the oligonucleotide ligation can be chemical. While not wishing to be bound by theory, it is thought that chemical ligation may permit greater flexibility with regard to solution conditions and may reduce the buffer exchange steps necessary. See Keefe et al., *Curr Opin Chem Biol.* (2015) 26:80-88, which is hereby incorporated by reference in its entirety.

In certain embodiments, provided herein is a method for identifying one or more compounds that bind to a biological target, the method comprising: (a) incubating the biological target with at least a portion of a plurality of distinct tagged macrocyclic compounds of a compound library to make at least one bound compound and at least one unbound compound of the plurality of distinct tagged macrocyclic compounds; (b) removing the at least one unbound compound; (c) sequencing each of the at least one oligonucleotide (D) of the at least one bound compound. In certain embodiments, each compound of the plurality of distinct tagged macrocyclic compounds of the compound library comprises a macrocyclic compound operatively linked to at least one oligonucleotide (D). In certain embodiments, the macrocyclic compound comprises an FKBD, an effector domain, a first linking region, and a second linking region. In certain embodiments, the FKBD, the effector domain, the first linking region, and the second linking region together form a macrocycle. In certain embodiments, each at least one oligonucleotide (D) can identify at least one of the FKBD, the effector domain, the first linking region, and the second linking region of each of the plurality of distinct tagged macrocyclic compounds. In certain embodiments, each compound of the plurality of distinct tagged macrocyclic compounds of the compound library comprises a compound of Formula (A) (as above-defined). In certain embodiments, each compound of the plurality of distinct tagged macrocyclic compounds of the compound library comprises a compound of Formula (I) (as above-defined). As a person of ordinary skill in the art would be aware, various techniques for synthesizing the library of tagged macrocyclic compounds are described in, e.g., Kuai et al., *SLAS Discov.* (2018) 23(5):405-416; Brown et al., *Annu. Rev. Biochem.* (2018) 87:5.1-5.24; Roman et al., *SLAS Discov.* (2018) 23(5):387-396; Amigo et al., *SLAS Discov.* (2018) 23(5): 397-404; Shi et al., *Bioconjug Chem.* (2017) 20; 28(9):2293-2301; Machutta et al., *Nat Commun.* (2017) 8:16081; Li et al., *Chembiochem.* (2017) 4; 18(9):848-852; Satz et al., *ACS Comb Sci.* (2017) 10; 19(4):234-238; Denton & Krusemark, *MedChemComm*, (2016) 7(10): 2020-2027; Eidam & Satz, *MedChemComm*, (2016) 7(7): 1323-1331; Bao et al., *Anal. Chem.*, (2016) 88 (10):5498-5506; Decurtins et al., *Nat Protoc.* (2016) 11(4):764-80; Harris et al., *J. Med. Chem.* (2016) 59 (5):2163-78; Satz, *ACS Chem Biol.* (2016) 16; 10(10):2237-45; Chan et al., *Curr Opin Chem Biol.* (2015) 26:55-61; Franzini et al., *Chem Commun.* (2015) 11; 51(38): 8014-16; and Buller et al., *Bioorg Med Chem Lett.* (2010) 15; 20(14):4188-92, each of which is hereby incorporated by reference in its entirety.

In certain embodiments, the incubating step can be performed under conditions suitable for at least one of the plurality of distinct tagged macrocyclic compounds of the compound library to bind to the biological target. A person of ordinary skill in the art would understand what conditions would be considered suitable for at least one of the plurality of distinct tagged macrocyclic compounds of the compound library to bind to the biological target.

In certain embodiments, the identifying one or more compounds that bind to a biological target comprises a bind-wash-elute procedure for molecule selection as described in, e.g., Ding et al., *ACS Med. Chem. Lett.* (2015) 7; 6(8):888-93, which is hereby incorporated by reference in its entirety. In certain embodiments, the incubating step (a comprises contacting the plurality of tagged compounds in the compound library with a target protein, wherein the target protein can be immobilized on a substrate (e.g., resin). In certain embodiments, the removing step (b) comprises washing the substrate to remove the at least one unbound compound. In certain embodiments, the sequencing step (c) comprises sequencing the at least one oligonucleotide (D) to identify which of the plurality of tagged compounds bound to the target protein.

In certain embodiments, the identifying one or more compounds that bind to a biological target comprises utilizing unmodified, non-immobilized target protein. Such methods, which can utilize a a ligate-crosslink-purify strategy are described in, e.g., Shi et al., *Bioconjug. Chem.* (2017) 20; 28(9):2293-2301, which is hereby incorporated by reference in its entirety. In certain embodiments, other methods for identifying the one or more compounds that bind to the biological target can be utilized. Such methods would be apparently to a person of ordinary skill in the art, and examples of such methods are described in, e.g., Machutta et al., *Nat. Commun.* (2017) 8:16081; Chan et al., *Curr. Opin. Chem. Biol.* (2015) 26:55-61; Lim, *C&EN*, (2017) 95 (29):10; Amigo et al., *SLAS Discov.* (2018) 23(5):397-404; Tian et al., *MedChemComm.* (2016) 7(7): 1316-1322; See Satz, *CS Comb. Sci.* (2016) 18 (7):415-424 each of which is hereby incorporated by reference in its entirety.

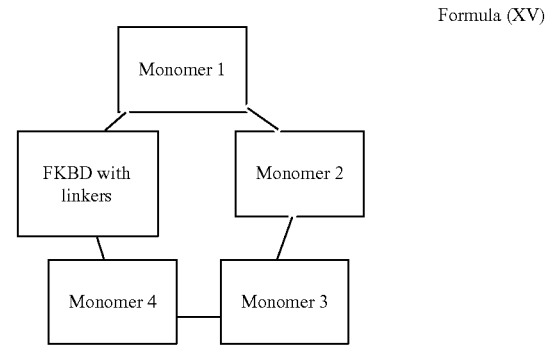

Formula (XV)

Tables 5-7 below show all the Rapafucin molecules in the present disclosure, the structural moieties are shown according to Formula (XV) An example of the chemical structure generated from Formula (XV) for compound 1 is shown below. In the case of amino acid monomers and FKBDs, a dehydration reaction occurs resulting in a peptide bond. Examples that do not designate a monomer 4 are Rapafucins composed of an FKBD with linker and only 3 monomers.

FKBD is:
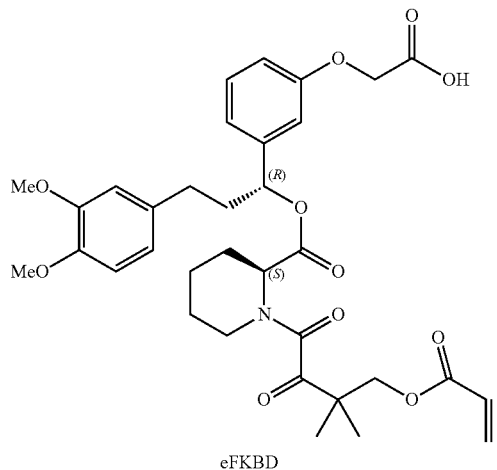
eFKBD
Linker is:
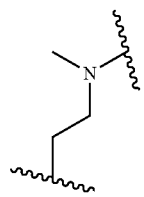
| Monomer 1 | Monomer 2 | Monomer 3 | Monomer 4 |
|---|---|---|---|
| ra147 | ra567 | ra562 | g |
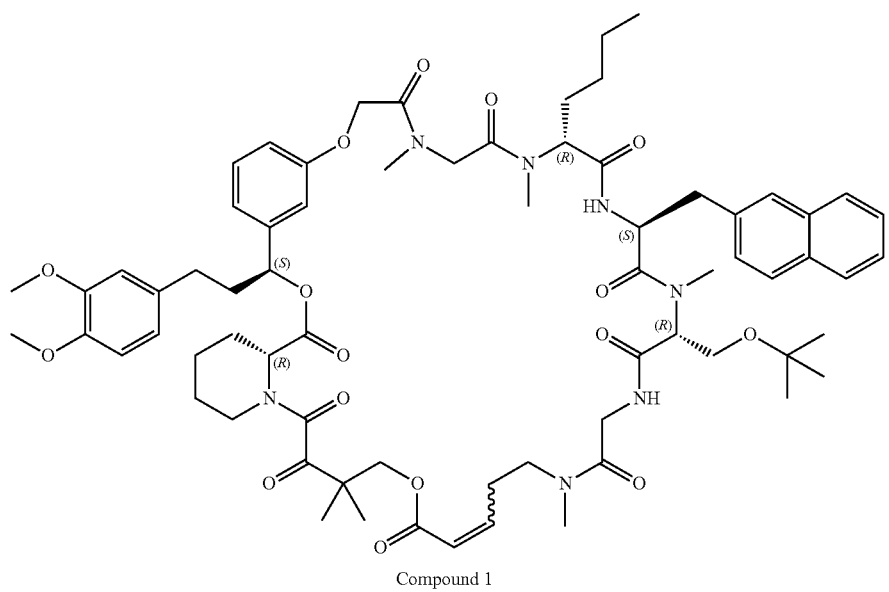
Compound 1

TABLE 5

Rapafucin compound 1 to compound 578 in this Disclosure.

| Compound No. | FKBD with linkers | Monomer 1 | Monomer 2 | Monomer 3 | Monomer 4 | Retention Time | Rel. Prolif., A549 |
|---|---|---|---|---|---|---|---|
| 1 | eFKBD | ra147 | ra567 | ra562 | g | 4.33 | low |
| 2 | eFKBD | ra147 | ra566 | ra562 | g | 4.35 | low |
| 3 | eFKBD | ra147 | ra58 | ra562 | g | 4.37 | low |
| 4 | eFKBD | ra147 | ra512 | ra562 | g | 4.32 | low |
| 5 | eFKBD | ra147 | ra71 | ra562 | g | 4.19 | low |
| 6 | eFKBD | ra147 | ra135 | ra562 | g | 4.40 | low |
| 7 | eFKBD | ra147 | ra97 | ra562 | g | 4.41 | low |
| 8 | eFKBD | ra147 | y | ra562 | g | 3.81 | low |
| 9 | eFKBD | ma | napA | ra562 | g | 4.71 | low |
| 10 | eFKBD | ra147 | ra94 | ra562 | g | 4.39 | low |
| 11 | eFKBD | ra147 | ra137 | ra562 | g | 4.38 | low |
| 12 | eFKBD | ra147 | ra98 | ra562 | g | 4.48 | low |
| 13 | eFKBD | ra147 | ra73 | ra562 | g | 4.40 | low |
| 14 | eFKBD | ra147 | ra60 | ra562 | g | 4.43 | low |
| 15 | eFKBD | ra147 | ra353 | ra562 | g | 4.53 | low |
| 16 | eFKBD | ra147 | ra133 | ra562 | g | 3.91 | low |
| 17 | eFKBD | ra147 | ra96 | ra562 | g | 4.47 | low |
| 18 | eFKBD | ra147 | ra95 | ra562 | g | 4.45 | low |
| 19 | eFKBD | ra147 | ra70 | ra562 | g | 4.48 | low |
| 20 | eFKBD | ra147 | ra91 | ra562 | g | 3.51 | low |
| 21 | eFKBD | ra147 | ra90 | ra562 | g | 3.44 | low |
| 22 | eFKBD | ra147 | ra89 | ra562 | g | 3.38 | low |
| 23 | eFKBD | ra147 | ra301 | ra562 | g | 3.89 | low |
| 24 | eFKBD | ra147 | ra68 | ra562 | g | 4.12 | low |
| 25 | eFKBD | ra147 | ra67 | ra562 | g | 4.13 | low |
| 26 | eFKBD | ra147 | ra189 | ra562 | g | 4.11 | low |
| 27 | eFKBD | ra147 | ra144 | ra562 | g | 4.19 | low |
| 28 | eFKBD | ra147 | ra530 | ra562 | g | 4.31 | low |
| 29 | eFKBD | ra147 | cha | ra562 | g | 4.48 | low |
| 30 | eFKBD | ra147 | ra527 | ra562 | g | 4.55 | low |
| 31 | eFKBD | ra147 | ra549 | ra562 | g | 4.59 | low |
| 32 | eFKBD | ra147 | ra59 | ra562 | g | 4.66 | low |
| 33 | eFKBD | ra147 | tle | ra562 | g | 4.23 | low |
| 34 | eFKBD | ra147 | ra83 | ra562 | g | 4.31 | low |
| 35 | eFKBD | ra147 | ra533 | ra562 | g | 4.39 | low |
| 36 | eFKBD | ra147 | ra84 | ra562 | g | 4.40 | low |
| 37 | eFKBD | ra147 | ra129 | ra562 | g | 4.69 | low |
| 38 | eFKBD | ra147 | ra602 | ra562 | g | 4.28 | low |
| 39 | eFKBD | ra147 | ra122 | ra562 | g | 4.41 | low |
| 40 | eFKBD | ra147 | ra128 | ra562 | g | 4.29 | low |
| 41 | eFKBD | ra147 | ra600 | ra562 | g | 4.29 | low |
| 42 | eFKBD | ra147 | df | ra562 | g | 4.30 | low |
| 43 | eFKBD | ra147 | ra134 | ra562 | g | 4.39 | low |
| 44 | eFKBD | ra147 | mf | ra562 | g | 4.45 | low |
| 45 | eFKBD | ra147 | ra185 | ra562 | g | 4.31 | low |
| 46 | eFKBD | ra147 | ra124 | ra562 | g | 4.25 | low |
| 47 | eFKBD | ra147 | ra113 | ra562 | g | 4.22 | low |
| 48 | eFKBD | ra147 | ra114 | ra562 | g | 4.17 | low |
| 49 | eFKBD | ra147 | ra112 | ra562 | g | 4.14 | low |
| 50 | eFKBD | ra147 | ra87 | ra562 | g | 4.38 | low |
| 51 | eFKBD | ra147 | ra104 | ra562 | g | 4.42 | low |
| 52 | eFKBD | ra147 | ra63 | ra562 | g | 4.43 | low |
| 53 | eFKBD | ma | ra107 | ra562 | g | 4.51 | medium |
| 54 | eFKBD | ma | ra110 | ra209 | g | 4.22 | high |
| 55 | eFKBD | ra147 | ra119 | ra562 | g | 4.26 | low |
| 56 | eFKBD | ra147 | ra118 | ra562 | g | 4.24 | low |
| 57 | eFKBD | ma | ra110 | ra562 | g | 4.32 | high |
| 58 | eFKBD | ra147 | ra65 | ra562 | g | 4.34 | low |
| 59 | eFKBD | ra147 | ra115 | ra562 | g | 4.34 | low |
| 60 | eFKBD | ra147 | ra117 | ra562 | g | 4.40 | low |
| 61 | eFKBD | ra147 | ra116 | ra562 | g | 4.35 | low |
| 62 | eFKBD | ra147 | ra62 | ra562 | g | 4.49 | low |
| 63 | eFKBD | ra147 | ra56 | ra562 | g | 4.54 | low |
| 64 | eFKBD | ra147 | ra55 | ra562 | g | 4.52 | low |
| 65 | eFKBD | ra147 | ra366 | ra562 | g | 4.47 | low |
| 66 | eFKBD | ma | ra111 | ra562 | g | 3.57 | low |
| 67 | eFKBD | ra147 | ra109 | ra562 | g | 3.75 | low |
| 68 | eFKBD | ra147 | ra525 | ra562 | g | 4.34 | low |
| 69 | eFKBD | ra147 | ra526 | ra562 | g | 4.37 | low |
| 70 | eFKBD | ra147 | ra523 | ra562 | g | 4.93 | low |
| 71 | eFKBD | ra147 | ra521 | ra562 | g | 4.90 | low |
| 72 | eFKBD | ra147 | oic | ra562 | g | 4.34 | low |
| 73 | eFKBD | ra147 | ra102 | ra562 | g | 4.33 | low |
| 74 | eFKBD | ra147 | tic | ra562 | g | 4.26 | low |

TABLE 5-continued

Rapafucin compound 1 to compound 578 in this Disclosure.

| Compound No. | FKBD with linkers | Monomer 1 | Monomer 2 | Monomer 3 | Monomer 4 | Retention Time | Rel. Prolif., A549 |
|---|---|---|---|---|---|---|---|
| 75 | eFKBD | ma | ra121 | ra562 | g | 3.96 | high |
| 76 | eFKBD | ra147 | ra105 | ra562 | g | 4.00 | low |
| 77 | eFKBD | ma | ra123 | ra562 | g | 4.47 | low |
| 78 | eFKBD | ma | ra567 | ra562 | g | 4.58 | low |
| 79 | eFKBD | ma | ra566 | ra562 | g | 4.63 | low |
| 80 | eFKBD | ma | ra167 | ra562 | g | 4.43 | low |
| 81 | eFKBD | ma | ra71 | ra562 | g | 4.40 | low |
| 82 | eFKBD | ma | ra78 | ra562 | g | 4.42 | low |
| 83 | eFKBD | ma | ra327 | ra562 | g | 3.66 | low |
| 84 | eFKBD | ma | ra324 | ra562 | g | 3.62 | low |
| 85 | eFKBD | ma | rbphe | ra562 | g | 4.22 | low |
| 86 | eFKBD | ma | ra135 | ra562 | g | 4.69 | low |
| 87 | eFKBD | ma | ra97 | ra562 | g | 4.66 | low |
| 88 | eFKBD | ma | y | ra562 | g | 3.89 | low |
| 89 | eFKBD | ma | ra127 | ra562 | g | 4.21 | low |
| 90 | eFKBD | ma | ra171 | ra562 | g | 4.33 | low |
| 91 | eFKBD | ma | ra175 | ra562 | g | 5.39 | low |
| 92 | eFKBD | ma | ra137 | ra562 | g | 4.65 | low |
| 93 | eFKBD | ma | ra94 | ra562 | g | 4.65 | low |
| 94 | eFKBD | ma | ra98 | ra562 | g | 4.86 | low |
| 95 | eFKBD | ma | ra73 | ra562 | g | 4.70 | low |
| 96 | eFKBD | ma | ra60 | ra562 | g | 4.71 | low |
| 97 | eFKBD | ma | ra353 | ra562 | g | 4.90 | low |
| 98 | eFKBD | ma | ra133 | ra562 | g | 3.92 | low |
| 99 | eFKBD | ma | ra96 | ra562 | g | 4.74 | low |
| 100 | eFKBD | ma | ra95 | ra562 | g | 4.73 | low |
| 101 | eFKBD | ma | ra70 | ra562 | g | 4.74 | low |
| 102 | eFKBD | ma | ra491 | ra562 | g | 3.47 | low |
| 103 | eFKBD | ma | ra91 | ra562 | g | 3.51 | low |
| 104 | eFKBD | ma | ra90 | ra562 | g | 3.41 | low |
| 105 | eFKBD | ma | ra89 | ra562 | g | 3.34 | low |
| 106 | eFKBD | ma | ra301 | ra562 | g | 3.90 | low |
| 107 | eFKBD | ma | ra68 | ra562 | g | 4.19 | low |
| 108 | eFKBD | ma | ra67 | ra562 | g | 4.19 | low |
| 109 | eFKBD | ma | ra347 | ra562 | g | 4.35 | low |
| 110 | eFKBD | ma | ra189 | ra562 | g | 4.19 | low |
| 111 | eFKBD | ma | ra144 | ra562 | g | 4.21 | low |
| 112 | eFKBD | ma | ra530 | ra562 | g | 4.40 | low |
| 113 | eFKBD | ma | ra509 | ra562 | g | 4.52 | low |
| 114 | eFKBD | ma | ra507 | ra562 | g | 4.56 | low |
| 115 | eFKBD | ma | cha | ra562 | g | 4.67 | low |
| 116 | eFKBD | ma | ra527 | ra562 | g | 4.72 | low |
| 117 | eFKBD | ma | ra549 | ra562 | g | 4.88 | low |
| 118 | eFKBD | ma | ra59 | ra562 | g | 4.94 | low |
| 119 | eFKBD | ma | tle | ra562 | g | 4.34 | low |
| 120 | eFKBD | ma | ra83 | ra562 | g | 4.40 | low |
| 121 | eFKBD | ma | ra75 | ra562 | g | 4.53 | low |
| 122 | eFKBD | ma | ra533 | ra562 | g | 4.54 | low |
| 123 | eFKBD | ma | ra84 | ra562 | g | 4.51 | low |
| 124 | eFKBD | ma | ra129 | ra562 | g | 4.89 | low |
| 125 | eFKBD | ma | ra602 | ra562 | g | 4.24 | low |
| 126 | eFKBD | ma | ra122 | ra562 | g | 4.41 | low |
| 127 | eFKBD | ma | ra450 | ra562 | g | 3.95 | low |
| 128 | eFKBD | ma | ra522 | ra562 | g | 3.83 | low |
| 129 | eFKBD | ma | ra128 | ra562 | g | 4.20 | low |
| 130 | eFKBD | ma | ra600 | ra562 | g | 4.21 | low |
| 131 | eFKBD | ma | ra76 | ra562 | g | 4.20 | low |
| 132 | eFKBD | ma | df | ra562 | g | 4.34 | low |
| 133 | eFKBD | ma | ra134 | ra562 | g | 4.41 | low |
| 134 | eFKBD | ma | mf | ra562 | g | 4.58 | low |
| 135 | eFKBD | ma | ra185 | ra562 | g | 4.37 | low |
| 136 | eFKBD | ma | ra124 | ra562 | g | 4.34 | low |
| 137 | eFKBD | ma | ra513 | ra562 | g | 3.99 | low |
| 138 | eFKBD | ma | ra113 | ra562 | g | 4.27 | low |
| 139 | eFKBD | ma | ra114 | ra562 | g | 4.24 | low |
| 140 | eFKBD | ma | ra112 | ra562 | g | 4.20 | low |
| 141 | eFKBD | ma | ra87 | ra562 | g | 4.49 | low |
| 142 | eFKBD | ma | ra104 | ra562 | g | 4.50 | low |
| 143 | eFKBD | ma | ra148 | ra562 | g | 4.13 | low |
| 144 | eFKBD | ma | ra63 | ra562 | g | 4.64 | low |
| 145 | eFKBD | ma | ra561 | ra562 | g | 4.62 | low |
| 146 | eFKBD | ma | ra208 | ra562 | g | 4.64 | low |
| 147 | eFKBD | ma | ra382 | ra562 | g | 4.39 | low |
| 148 | eFKBD | ma | ra495 | ra562 | g | 4.64 | low |

TABLE 5-continued

Rapafucin compound 1 to compound 578 in this Disclosure.

| Compound No. | FKBD with linkers | Monomer 1 | Monomer 2 | Monomer 3 | Monomer 4 | Retention Time | Rel. Prolif., A549 |
|---|---|---|---|---|---|---|---|
| 149 | eFKBD | ma | ra64 | ra562 | g | 4.46 | low |
| 150 | eFKBD | ma | ra119 | ra562 | g | 4.39 | low |
| 151 | eFKBD | ma | ra118 | ra562 | g | 4.37 | low |
| 152 | eFKBD | ma | ra65 | ra562 | g | 4.44 | low |
| 153 | eFKBD | ma | ra66 | ra562 | g | 4.73 | low |
| 154 | eFKBD | ma | ra115 | ra562 | g | 4.49 | low |
| 155 | eFKBD | ma | ra117 | ra562 | g | 4.55 | low |
| 156 | eFKBD | ma | ra116 | ra562 | g | 4.54 | low |
| 157 | eFKBD | ma | ra62 | ra562 | g | 4.76 | low |
| 158 | eFKBD | ma | ra56 | ra562 | g | 4.76 | low |
| 159 | eFKBD | ma | ra534 | ra562 | g | 4.72 | medium |
| 160 | eFKBD | ma | ra88 | ra562 | g | 4.28 | low |
| 161 | eFKBD | ma | ra55 | ra562 | g | 4.73 | low |
| 162 | eFKBD | ma | ra366 | ra562 | g | 4.77 | low |
| 163 | eFKBD | ra199 | napA | ra562 | g | 4.11 | low |
| 164 | eFKBD | ma | ra92 | ra562 | g | 4.56 | low |
| 165 | eFKBD | ra202 | napA | ra562 | g | 4.17 | low |
| 166 | eFKBD | ra484 | napA | ra562 | g | 4.21 | low |
| 167 | eFKBD | ma | ra93 | ra144 | g | 3.90 | medium |
| 168 | eFKBD | ml | ra167 | ra562 | g | 4.32 | low |
| 169 | eFKBD | ra207 | ra167 | ra562 | g | 4.28 | low |
| 170 | eFKBD | ra565 | ra167 | ra562 | g | 4.21 | low |
| 171 | eFKBD | ra172 | ra167 | ra562 | g | 4.24 | low |
| 172 | eFKBD | ra562 | ra167 | ra562 | g | 4.33 | low |
| 173 | eFKBD | ra209 | ra167 | ra562 | g | 4.28 | low |
| 174 | eFKBD | ra61 | ra167 | ra562 | g | 4.17 | low |
| 175 | eFKBD | ra74 | ra167 | ra562 | g | 4.08 | low |
| 176 | eFKBD | ra147 | ra332 | ra562 | g | 4.54 | low |
| 177 | eFKBD | ma | ra332 | ra562 | g | 4.24 | low |
| 178 | eFKBD | ra199 | ra332 | ra562 | g | 4.22 | low |
| 179 | eFKBD | ra201 | ra332 | ra562 | g | 4.30 | low |
| 180 | eFKBD | ra202 | ra332 | ra562 | g | 4.30 | low |
| 181 | eFKBD | ra203 | ra332 | ra562 | g | 4.32 | low |
| 182 | eFKBD | ra484 | ra332 | ra562 | g | 4.30 | low |
| 183 | eFKBD | ra379 | ra332 | ra562 | g | 4.41 | low |
| 184 | eFKBD | ml | ra109 | ra562 | g | 3.69 | low |
| 185 | eFKBD | ra207 | ra109 | ra562 | g | 3.67 | low |
| 186 | eFKBD | ra565 | ra109 | ra562 | g | 3.60 | low |
| 187 | eFKBD | ra562 | ra109 | ra562 | g | 3.72 | low |
| 188 | eFKBD | ra209 | ra109 | ra562 | g | 3.71 | low |
| 189 | eFKBD | ra61 | ra109 | ra562 | g | 3.59 | low |
| 190 | eFKBD | ra74 | ra109 | ra562 | g | 3.48 | low |
| 191 | eFKBD | ma | ra108 | ra562 | g | 3.21 | low |
| 192 | eFKBD | ra199 | ra108 | ra562 | g | 3.23 | low |
| 193 | eFKBD | ra201 | ra108 | ra562 | g | 3.31 | low |
| 194 | eFKBD | ra202 | ra108 | ra562 | g | 3.33 | low |
| 195 | eFKBD | ra203 | ra108 | ra562 | g | 3.36 | low |
| 196 | eFKBD | ra484 | ra108 | ra562 | g | 3.36 | low |
| 197 | eFKBD | ra379 | ra108 | ra562 | g | 3.47 | low |
| 198 | eFKBD | ml | oic | ra562 | g | 4.25 | low |
| 199 | eFKBD | ra207 | oic | ra562 | g | 4.29 | low |
| 200 | eFKBD | ra565 | oic | ra562 | g | 4.21 | low |
| 201 | eFKBD | ra172 | oic | ra562 | g | 4.23 | low |
| 202 | eFKBD | ra562 | oic | ra562 | g | 4.23 | low |
| 203 | eFKBD | ra209 | oic | ra562 | g | 4.27 | low |
| 204 | eFKBD | ra61 | oic | ra562 | g | 4.14 | low |
| 205 | eFKBD | ra74 | oic | ra562 | g | 4.07 | low |
| 206 | eFKBD | ra147 | ra542 | ra562 | g | 4.25 | low |
| 207 | eFKBD | ma | ra542 | ra562 | g | 3.92 | low |
| 208 | eFKBD | ra199 | ra542 | ra562 | g | 3.91 | low |
| 209 | eFKBD | ra201 | ra542 | ra562 | g | 4.00 | low |
| 210 | eFKBD | ra202 | ra542 | ra562 | g | 3.99 | low |
| 211 | eFKBD | ra203 | ra542 | ra562 | g | 3.98 | low |
| 212 | eFKBD | ra484 | ra542 | ra562 | g | 4.01 | low |
| 213 | eFKBD | ra379 | ra542 | ra562 | g | 4.13 | low |
| 214 | eFKBD | ml | tic | ra562 | g | 4.19 | low |
| 215 | eFKBD | ra207 | tic | ra562 | g | 4.26 | low |
| 216 | eFKBD | ra565 | tic | ra562 | g | 4.14 | low |
| 217 | eFKBD | ra172 | tic | ra562 | g | 4.16 | low |
| 218 | eFKBD | ra562 | tic | ra562 | g | 4.17 | low |
| 219 | eFKBD | ra209 | tic | ra562 | g | 4.20 | low |
| 220 | eFKBD | ra61 | tic | ra562 | g | 4.06 | low |
| 221 | eFKBD | ra74 | tic | ra562 | g | 4.02 | low |
| 222 | eFKBD | ma | ra93 | ra209 | g | 4.06 | medium |

TABLE 5-continued

Rapafucin compound 1 to compound 578 in this Disclosure.

| Compound No. | FKBD with linkers | Monomer 1 | Monomer 2 | Monomer 3 | Monomer 4 | Retention Time | Rel. Prolif., A549 |
|---|---|---|---|---|---|---|---|
| 223 | eFKBD | ma | ra136 | ra562 | g | 3.54 | low |
| 224 | eFKBD | ra199 | ra136 | ra562 | g | 3.57 | low |
| 225 | eFKBD | ra201 | ra136 | ra562 | g | 3.62 | low |
| 226 | eFKBD | ra202 | ra136 | ra562 | g | 3.64 | low |
| 227 | eFKBD | ra203 | ra136 | ra562 | g | 3.66 | low |
| 228 | eFKBD | ra484 | ra136 | ra562 | g | 3.64 | low |
| 229 | eFKBD | ra379 | ra136 | ra562 | g | 3.78 | low |
| 230 | eFKBD | ml | ra545 | ra562 | g | 4.19 | low |
| 231 | eFKBD | ra207 | ra545 | ra562 | g | 4.12 | low |
| 232 | eFKBD | ra565 | ra545 | ra562 | g | 4.10 | low |
| 233 | eFKBD | ra172 | ra545 | ra562 | g | 4.11 | low |
| 234 | eFKBD | ra562 | ra545 | ra562 | g | 4.15 | low |
| 235 | eFKBD | ra209 | ra545 | ra562 | g | 4.18 | low |
| 236 | eFKBD | ra61 | ra545 | ra562 | g | 4.08 | medium |
| 237 | eFKBD | ra74 | ra545 | ra562 | g | 4.02 | low |
| 238 | eFKBD | ra147 | ra350 | ra562 | g | 4.18 | low |
| 239 | eFKBD | ma | ra350 | ra562 | g | 3.87 | low |
| 240 | eFKBD | ra199 | ra350 | ra562 | g | 3.93 | low |
| 241 | eFKBD | ra201 | ra350 | ra562 | g | 3.96 | low |
| 242 | eFKBD | ra202 | ra350 | ra562 | g | 3.97 | low |
| 243 | eFKBD | ra203 | ra350 | ra562 | g | 3.97 | low |
| 244 | eFKBD | ra484 | ra350 | ra562 | g | 4.05 | low |
| 245 | eFKBD | ra379 | ra350 | ra562 | g | 4.17 | low |
| 246 | eFKBD | ml | ra351 | ra562 | g | 4.31 | low |
| 247 | eFKBD | ra207 | ra351 | ra562 | g | 4.14 | low |
| 248 | eFKBD | ra565 | ra351 | ra562 | g | 4.16 | low |
| 249 | eFKBD | ra172 | ra351 | ra562 | g | 4.19 | low |
| 250 | eFKBD | ra562 | ra351 | ra562 | g | 4.25 | low |
| 251 | eFKBD | ra209 | ra351 | ra562 | g | 4.27 | low |
| 252 | eFKBD | ra61 | ra351 | ra562 | g | 4.18 | low |
| 253 | eFKBD | ra74 | ra351 | ra562 | g | 4.02 | low |
| 254 | eFKBD | ma | ra93 | ra562 | g | 4.58 | low |
| 255 | eFKBD | ml | ra93 | ra562 | g | 4.96 | low |
| 256 | eFKBD | ra344 | ra102 | ra562 | g | 4.48 | low |
| 257 | eFKBD | ra209 | ra102 | ra562 | g | 3.24 | low |
| 258 | eFKBD | ra147 | ra554 | ra562 | g | 4.96 | low |
| 259 | eFKBD | ma | ra554 | ra562 | g | 4.49 | low |
| 260 | eFKBD | ra201 | ra554 | ra562 | g | 4.57 | low |
| 261 | eFKBD | ra203 | ra554 | ra562 | g | 4.65 | low |
| 262 | eFKBD | ra344 | ra546 | ra562 | g | 4.60 | low |
| 263 | eFKBD | ml | ra546 | ra562 | g | 4.86 | low |
| 264 | eFKBD | ra565 | ra546 | ra562 | g | 4.63 | low |
| 265 | eFKBD | ra209 | ra546 | ra562 | g | 4.78 | low |
| 266 | eFKBD | ra147 | mw | ra562 | g | 4.68 | low |
| 267 | eFKBD | ma | mw | ra562 | g | 4.37 | low |
| 268 | eFKBD | ra201 | mw | ra562 | g | 4.44 | low |
| 269 | eFKBD | ra203 | mw | ra562 | g | 4.44 | low |
| 270 | eFKBD | ra344 | ra354 | ra562 | g | 4.68 | low |
| 271 | eFKBD | ml | ra354 | ra562 | g | 4.83 | low |
| 272 | eFKBD | ra565 | ra354 | ra562 | g | 4.67 | low |
| 273 | eFKBD | ra209 | ra354 | ra562 | g | 4.80 | low |
| 274 | eFKBD | ra147 | ra385 | ra562 | g | 4.89 | low |
| 275 | eFKBD | ma | ra385 | ra562 | g | 4.45 | low |
| 276 | eFKBD | ra201 | ra385 | ra562 | g | 4.54 | low |
| 277 | eFKBD | ra203 | ra385 | ra562 | g | 4.57 | low |
| 278 | eFKBD | ra344 | ra486 | ra562 | g | 5.86 | low |
| 279 | eFKBD | ml | ra486 | ra562 | g | 5.40 | low |
| 280 | eFKBD | ra565 | ra486 | ra562 | g | 5.26 | low |
| 281 | eFKBD | ra209 | ra486 | ra562 | g | 4.29 | low |
| 282 | eFKBD | ra147 | ra487 | ra562 | g | 4.34 | low |
| 283 | eFKBD | ma | ra487 | ra562 | g | 3.94 | low |
| 284 | eFKBD | ra201 | ra487 | ra562 | g | 4.03 | low |
| 285 | eFKBD | ra203 | ra487 | ra562 | g | 4.07 | low |
| 286 | eFKBD | ma | ra323 | ra562 | g | 3.20 | low |
| 287 | eFKBD | ra201 | ra323 | ra562 | g | 5.30 | low |
| 288 | eFKBD | ra203 | ra323 | ra562 | g | 5.27 | low |
| 289 | eFKBD | ra344 | ra347 | ra562 | g | 4.56 | low |
| 290 | eFKBD | ml | ra347 | ra562 | g | 4.71 | low |
| 291 | eFKBD | ra565 | ra347 | ra562 | g | 4.55 | low |
| 292 | eFKBD | ra209 | ra347 | ra562 | g | 4.69 | low |
| 293 | eFKBD | ra147 | napa | ra209 | g | 4.29 | medium |
| 294 | eFKBD | ra201 | ra88 | ra562 | g | 4.35 | low |
| 295 | eFKBD | ra203 | ra88 | ra562 | g | 4.39 | low |
| 296 | eFKBD | ra344 | ra137 | ra562 | g | 4.90 | low |

TABLE 5-continued

Rapafucin compound 1 to compound 578 in this Disclosure.

| Compound No. | FKBD with linkers | Monomer 1 | Monomer 2 | Monomer 3 | Monomer 4 | Retention Time | Rel. Prolif., A549 |
|---|---|---|---|---|---|---|---|
| 297 | eFKBD | ml | ra137 | ra562 | g | 5.06 | low |
| 298 | eFKBD | ra565 | ra137 | ra562 | g | 4.89 | low |
| 299 | eFKBD | ra209 | ra137 | ra562 | g | 5.03 | low |
| 300 | eFKBD | ra147 | ra495 | ra562 | g | 5.05 | low |
| 301 | eFKBD | ra201 | ra495 | ra562 | g | 4.72 | low |
| 302 | eFKBD | ra203 | ra495 | ra562 | g | 4.76 | low |
| 303 | eFKBD | ra344 | ra171 | ra562 | g | 4.53 | low |
| 304 | eFKBD | ml | ra171 | ra562 | g | 4.69 | low |
| 305 | eFKBD | ra565 | ra171 | ra562 | g | 4.53 | low |
| 306 | eFKBD | ra209 | ra171 | ra562 | g | 4.66 | low |
| 307 | eFKBD | ra201 | ra123 | ra562 | g | 4.56 | low |
| 308 | eFKBD | ra203 | ra123 | ra562 | g | 4.59 | low |
| 309 | eFKBD | ra344 | ra93 | ra562 | g | 4.81 | low |
| 310 | eFKBD | ra565 | ra93 | ra562 | g | 4.77 | low |
| 311 | eFKBD | ra209 | ra93 | ra562 | g | 4.91 | low |
| 312 | eFKBD | ra147 | ra107 | ra549 | g | 4.57 | medium |
| 313 | eFKBD | ra201 | ra64 | ra562 | g | 4.52 | low |
| 314 | eFKBD | ra203 | ra64 | ra562 | g | 4.57 | low |
| 315 | eFKBD | ra344 | ra116 | ra562 | g | 4.78 | low |
| 316 | eFKBD | ml | ra116 | ra562 | g | 4.91 | low |
| 317 | eFKBD | ra565 | ra116 | ra562 | g | 4.82 | low |
| 318 | eFKBD | ra209 | ra116 | ra562 | g | 4.92 | low |
| 319 | eFKBD | ra147 | ra107 | ra562 | g | 4.44 | low |
| 320 | eFKBD | ra201 | ra66 | ra562 | g | 4.82 | low |
| 321 | eFKBD | ra203 | ra66 | ra562 | g | 4.88 | low |
| 322 | eFKBD | ra344 | ra75 | ra562 | g | 4.89 | low |
| 323 | eFKBD | ml | ra75 | ra562 | g | 5.04 | low |
| 324 | eFKBD | ra565 | ra75 | ra562 | g | 4.83 | low |
| 325 | eFKBD | ra209 | ra75 | ra562 | g | 4.87 | low |
| 326 | eFKBD | ra147 | ra108 | ra562 | g | 3.68 | low |
| 327 | eFKBD | ra201 | ra127 | ra562 | g | 4.31 | low |
| 328 | eFKBD | ra203 | ra127 | ra562 | g | 4.34 | low |
| 329 | eFKBD | ra344 | ra113 | ra562 | g | 4.46 | low |
| 330 | eFKBD | ml | ra113 | ra562 | g | 4.60 | low |
| 331 | eFKBD | ra565 | ra113 | ra562 | g | 4.48 | low |
| 332 | eFKBD | ra209 | ra113 | ra562 | g | 4.61 | low |
| 333 | eFKBD | ra147 | ra497 | ra562 | g | 4.24 | low |
| 334 | eFKBD | ra147 | ra148 | ra562 | g | 4.39 | medium |
| 335 | eFKBD | ra147 | ra110 | ra562 | g | 4.61 | medium |
| 336 | eFKBD | ra147 | ra111 | ra562 | g | 3.86 | low |
| 337 | eFKBD | ra147 | ra121 | ra549 | g | 4.41 | medium |
| 338 | eFKBD | ra147 | ra121 | ra562 | g | 4.25 | low |
| 339 | eFKBD | ra147 | napa | ra206 | g | 4.05 | medium |
| 340 | eFKBD | ra147 | ra497 | ra206 | g | 3.91 | medium |
| 341 | eFKBD | ra147 | ra93 | ra206 | g | 4.08 | medium |
| 342 | eFKBD | ra147 | ra204 | ra206 | g | 3.91 | medium |
| 343 | eFKBD | ra147 | ra148 | ra206 | g | 4.06 | medium |
| 344 | eFKBD | ra147 | ra121 | ra206 | g | 3.88 | medium |
| 345 | eFKBD | ra147 | ra107 | ra206 | g | 4.07 | medium |
| 346 | eFKBD | ra147 | ra110 | ra206 | g | 4.26 | medium |
| 347 | eFKBD | ra147 | ra88 | ra206 | g | 3.85 | medium |
| 348 | eFKBD | ra147 | ra92 | ra206 | g | 4.02 | medium |
| 349 | eFKBD | ra147 | ra111 | ra206 | g | 3.61 | medium |
| 350 | eFKBD | ra147 | ra123 | ra562 | g | 4.28 | low |
| 351 | eFKBD | ra147 | ra93 | ra209 | g | 4.33 | medium |
| 352 | eFKBD | ra147 | ra204 | ra209 | g | 4.17 | low |
| 353 | eFKBD | ra147 | ra148 | ra209 | g | 4.31 | medium |
| 354 | eFKBD | ra147 | ra121 | ra209 | g | 4.17 | medium |
| 355 | eFKBD | ra147 | ra107 | ra209 | g | 4.33 | medium |
| 356 | eFKBD | ra147 | ra110 | ra209 | g | 4.49 | medium |
| 357 | eFKBD | ra147 | ra88 | ra209 | g | 4.11 | low |
| 358 | eFKBD | ra147 | ra92 | ra209 | g | 4.28 | medium |
| 359 | eFKBD | ra147 | ra111 | ra209 | g | 3.86 | low |
| 360 | eFKBD | ra147 | napa | ra106 | g | 4.16 | low |
| 361 | eFKBD | ra147 | ra497 | ra106 | g | 4.06 | low |
| 362 | eFKBD | ra147 | ra93 | ra106 | g | 4.20 | low |
| 363 | eFKBD | ra147 | ra204 | ra106 | g | 4.06 | low |
| 364 | eFKBD | ra147 | ra148 | ra106 | g | 4.17 | low |
| 365 | eFKBD | ra147 | ra121 | ra106 | g | 4.02 | low |
| 366 | eFKBD | ra147 | ra107 | ra106 | g | 4.19 | low |
| 367 | eFKBD | ra147 | ra110 | ra106 | g | 4.36 | low |
| 368 | eFKBD | ra147 | ra88 | ra106 | g | 3.97 | low |
| 369 | eFKBD | ra147 | ra92 | ra106 | g | 4.15 | low |
| 370 | eFKBD | ra147 | ra111 | ra106 | g | 3.74 | low |

TABLE 5-continued

Rapafucin compound 1 to compound 578 in this Disclosure.

| Compound No. | FKBD with linkers | Monomer 1 | Monomer 2 | Monomer 3 | Monomer 4 | Retention Time | Rel. Prolif., A549 |
|---|---|---|---|---|---|---|---|
| 371 | eFKBD | ra147 | napa | ra189 | g | 4.17 | low |
| 372 | eFKBD | ra147 | ra497 | ra189 | g | 4.06 | low |
| 373 | eFKBD | ra147 | ra93 | ra189 | g | 4.20 | low |
| 374 | eFKBD | ra147 | ra204 | ra189 | g | 4.06 | low |
| 375 | eFKBD | ra147 | ra148 | ra189 | g | 4.18 | low |
| 376 | eFKBD | ra147 | ra121 | ra189 | g | 4.02 | low |
| 377 | eFKBD | ra147 | ra107 | ra189 | g | 4.20 | low |
| 378 | eFKBD | ra147 | ra110 | ra189 | g | 4.36 | low |
| 379 | eFKBD | ra147 | ra88 | ra189 | g | 3.98 | low |
| 380 | eFKBD | ra147 | ra92 | ra189 | g | 4.16 | low |
| 381 | eFKBD | ra147 | ra111 | ra189 | g | 3.74 | low |
| 382 | eFKBD | ra147 | napa | ra144 | g | 4.17 | low |
| 383 | eFKBD | ra147 | ra497 | ra144 | g | 4.03 | low |
| 384 | eFKBD | ra147 | ra93 | ra144 | g | 4.19 | low |
| 385 | eFKBD | ra147 | ra204 | ra144 | g | 4.07 | low |
| 386 | eFKBD | ra147 | ra121 | ra144 | g | 4.03 | medium |
| 387 | eFKBD | ra147 | ra107 | ra144 | g | 4.19 | low |
| 388 | eFKBD | ra147 | ra110 | ra144 | g | 4.39 | medium |
| 389 | eFKBD | ra147 | ra88 | ra144 | g | 3.96 | low |
| 390 | eFKBD | ra147 | ra92 | ra144 | g | 4.16 | medium |
| 391 | eFKBD | ra147 | ra111 | ra144 | g | 3.73 | low |
| 392 | eFKBD | ra147 | napa | ra126 | g | 4.00 | low |
| 393 | eFKBD | ra147 | ra497 | ra126 | g | 3.84 | low |
| 394 | eFKBD | ra147 | ra93 | ra126 | g | 4.03 | low |
| 395 | eFKBD | ra147 | ra511 | ra126 | g | 4.03 | low |
| 396 | eFKBD | ra147 | ra204 | ra126 | g | 3.87 | low |
| 397 | eFKBD | ra147 | ra148 | ra126 | g | 4.00 | low |
| 398 | eFKBD | ra147 | ra121 | ra126 | g | 3.83 | low |
| 399 | eFKBD | ra147 | ra107 | ra126 | g | 4.03 | low |
| 400 | eFKBD | ra147 | ra110 | ra126 | g | 4.18 | low |
| 401 | eFKBD | ra147 | ra88 | ra126 | g | 3.77 | low |
| 402 | eFKBD | ra147 | ra92 | ra126 | g | 3.98 | low |
| 403 | eFKBD | ra147 | ra111 | ra126 | g | 3.51 | low |
| 404 | eFKBD | ra147 | napa | ra549 | g | 4.54 | low |
| 405 | eFKBD | ra147 | ra127 | ra562 | g | 4.22 | low |
| 406 | eFKBD | ra147 | ra93 | ra549 | g | 4.58 | low |
| 407 | eFKBD | ra147 | ra204 | ra549 | g | 4.43 | low |
| 408 | eFKBD | ra147 | ra148 | ra549 | g | 4.55 | medium |
| 409 | eFKBD | ra147 | ra136 | ra562 | g | 4.00 | low |
| 410 | eFKBD | ra147 | ra110 | ra549 | g | 4.78 | medium |
| 411 | eFKBD | ra147 | ra88 | ra549 | g | 4.34 | medium |
| 412 | eFKBD | ra147 | ra92 | ra549 | g | 4.53 | medium |
| 413 | eFKBD | ra147 | ra111 | ra549 | g | 4.15 | low |
| 414 | eFKBD | ma | ra497 | ra562 | g | 3.94 | low |
| 415 | eFKBD | ra147 | ra148 | ra144 | g | 4.18 | medium |
| 416 | eFKBD | ra147 | ra497 | ra209 | g | 4.17 | medium |
| 417 | eFKBD | ra147 | ra497 | ra549 | g | 4.43 | medium |
| 418 | eFKBD | ra147 | ra64 | ra562 | g | 4.32 | low |
| 419 | eFKBD | ma | ra497 | ra206 | g | 3.57 | low |
| 420 | eFKBD | ma | ra93 | ra206 | g | 3.80 | low |
| 421 | eFKBD | ma | ra204 | ra206 | g | 3.57 | low |
| 422 | eFKBD | ma | ra148 | ra206 | g | 3.74 | low |
| 423 | eFKBD | ma | ra121 | ra206 | g | 3.53 | low |
| 424 | eFKBD | ma | ra107 | ra206 | g | 3.79 | low |
| 425 | eFKBD | ma | ra110 | ra206 | g | 3.96 | low |
| 426 | eFKBD | ma | ra88 | ra206 | g | 3.49 | low |
| 427 | eFKBD | ma | ra92 | ra206 | g | 3.72 | low |
| 428 | eFKBD | ma | napa | ra209 | g | 4.04 | low |
| 429 | eFKBD | ma | ra497 | ra209 | g | 3.91 | medium |
| 430 | eFKBD | ma | ra204 | ra209 | g | 3.91 | low |
| 431 | eFKBD | ma | ra148 | ra209 | g | 4.04 | low |
| 432 | eFKBD | ma | ra107 | ra209 | g | 4.06 | low |
| 433 | eFKBD | ra147 | ra66 | ra562 | g | 4.49 | low |
| 434 | eFKBD | ma | ra88 | ra209 | g | 3.83 | medium |
| 435 | eFKBD | ma | napa | ra106 | g | 3.90 | low |
| 436 | eFKBD | ma | ra497 | ra106 | g | 3.75 | low |
| 437 | eFKBD | ma | ra93 | ra106 | g | 3.93 | low |
| 438 | eFKBD | ma | ra204 | ra106 | g | 3.74 | low |
| 439 | eFKBD | ma | ra148 | ra106 | g | 3.91 | low |
| 440 | eFKBD | ma | ra121 | ra106 | g | 3.72 | low |
| 441 | eFKBD | ma | ra107 | ra106 | g | 3.93 | low |
| 442 | eFKBD | ma | ra110 | ra106 | g | 4.10 | low |
| 443 | eFKBD | ma | ra88 | ra106 | g | 3.66 | low |
| 444 | eFKBD | ma | ra92 | ra106 | g | 3.90 | low |

TABLE 5-continued

Rapafucin compound 1 to compound 578 in this Disclosure.

| Compound No. | FKBD with linkers | Monomer 1 | Monomer 2 | Monomer 3 | Monomer 4 | Retention Time | Rel. Prolif., A549 |
|---|---|---|---|---|---|---|---|
| 445 | eFKBD | ma | ra111 | ra106 | g | 3.35 | low |
| 446 | eFKBD | ma | napa | ra189 | g | 3.86 | low |
| 447 | eFKBD | ma | ra497 | ra189 | g | 3.71 | low |
| 448 | eFKBD | ma | ra93 | ra189 | g | 3.90 | low |
| 449 | eFKBD | ma | ra204 | ra189 | g | 3.72 | low |
| 450 | eFKBD | ma | ra148 | ra189 | g | 3.86 | low |
| 451 | eFKBD | ma | ra121 | ra189 | g | 3.67 | low |
| 452 | eFKBD | ma | ra107 | ra189 | g | 3.90 | low |
| 453 | eFKBD | ma | ra110 | ra189 | g | 4.07 | low |
| 454 | eFKBD | ma | ra88 | ra189 | g | 3.65 | low |
| 455 | eFKBD | ma | ra92 | ra189 | g | 3.85 | low |
| 456 | eFKBD | ma | ra111 | ra189 | g | 3.33 | low |
| 457 | eFKBD | ma | napa | ra144 | g | 3.87 | low |
| 458 | eFKBD | ma | ra497 | ra144 | g | 3.70 | medium |
| 459 | eFKBD | ma | ra204 | ra144 | g | 3.69 | low |
| 460 | eFKBD | ma | ra148 | ra144 | g | 3.88 | low |
| 461 | eFKBD | ma | ra121 | ra144 | g | 3.70 | medium |
| 462 | eFKBD | ma | ra107 | ra144 | g | 3.91 | low |
| 463 | eFKBD | ma | ra110 | ra144 | g | 4.08 | medium |
| 464 | eFKBD | ma | ra88 | ra144 | g | 3.63 | low |
| 465 | eFKBD | ma | ra92 | ra144 | g | 3.87 | low |
| 466 | eFKBD | ma | ra111 | ra144 | g | 3.30 | low |
| 467 | eFKBD | ma | ra497 | ra126 | g | 3.46 | low |
| 468 | eFKBD | ma | ra148 | ra126 | g | 3.67 | low |
| 469 | eFKBD | ma | ra121 | ra126 | g | 3.44 | low |
| 470 | eFKBD | ma | ra107 | ra126 | g | 3.72 | low |
| 471 | eFKBD | ma | ra110 | ra126 | g | 3.89 | low |
| 472 | eFKBD | ma | ra92 | ra126 | g | 3.69 | low |
| 473 | eFKBD | ma | ra111 | ra126 | g | 3.04 | low |
| 474 | eFKBD | ma | napa | ra549 | g | 4.29 | low |
| 475 | eFKBD | ma | ra497 | ra549 | g | 4.16 | low |
| 476 | eFKBD | ma | ra93 | ra549 | g | 4.31 | low |
| 477 | eFKBD | ma | ra204 | ra549 | g | 4.14 | low |
| 478 | eFKBD | ma | ra148 | ra549 | g | 4.31 | low |
| 479 | eFKBD | ma | ra121 | ra549 | g | 4.15 | low |
| 480 | eFKBD | ma | ra107 | ra549 | g | 4.32 | low |
| 481 | eFKBD | ma | ra110 | ra549 | g | 4.51 | low |
| 482 | eFKBD | ma | ra88 | ra549 | g | 4.09 | low |
| 483 | eFKBD | ma | ra92 | ra549 | g | 4.29 | low |
| 484 | eFKBD | ma | ra111 | ra549 | g | 3.86 | low |
| 485 | eFKBD | ra147 | ra88 | ra562 | g | 4.13 | low |
| 486 | eFKBD | ml | napa | ra549 | g | 5.13 | low |
| 487 | eFKBD | ml | napa | ra144 | g | 4.53 | low |
| 488 | eFKBD | mi | napa | ra562 | g | 4.85 | low |
| 489 | eFKBD | mi | napa | ra549 | g | 5.10 | low |
| 490 | eFKBD | mv | napa | ra209 | g | 4.56 | low |
| 491 | eFKBD | ra379 | napa | ra549 | g | 4.96 | low |
| 492 | eFKBD | ra379 | napa | ra144 | g | 4.40 | low |
| 493 | eFKBD | ra203 | ra185 | ra209 | g | 4.31 | low |
| 494 | eFKBD | ra202 | ra185 | ra209 | g | 4.48 | low |
| 495 | eFKBD | ra310 | ra185 | ra209 | g | 4.68 | low |
| 496 | eFKBD | ra203 | ra110 | ra562 | g | 4.95 | low |
| 497 | eFKBD | ra202 | ra110 | ra562 | g | 4.91 | low |
| 498 | eFKBD | ra310 | ra110 | ra562 | g | 5.32 | low |
| 499 | eFKBD | ra203 | ra93 | ra209 | g | 4.46 | low |
| 500 | eFKBD | ra202 | ra93 | ra209 | g | 4.47 | low |
| 501 | eFKBD | ra310 | ra93 | ra209 | g | 4.80 | low |
| 502 | eFKBD | ra147 | ra92 | ra562 | g | 4.41 | low |
| 503 | eFKBD | mi | ra497 | ra209 | g | 4.54 | low |
| 504 | eFKBD | mi | ra497 | ra549 | g | 4.93 | low |
| 505 | eFKBD | mi | ra497 | ra144 | g | 4.32 | low |
| 506 | eFKBD | ra379 | ra497 | ra562 | g | 4.48 | low |
| 507 | eFKBD | ra379 | ra497 | ra209 | g | 4.40 | low |
| 508 | eFKBD | ra379 | ra497 | ra549 | g | 4.78 | low |
| 509 | eFKBD | ra379 | ra497 | ra144 | g | 4.20 | low |
| 510 | eFKBD | ra147 | ra93 | ra562 | g | 4.44 | low |
| 511 | eFKBD | ml | ra93 | ra549 | g | 5.05 | low |
| 512 | eFKBD | ra201 | napA | ra562 | g | 4.15 | low |
| 513 | eFKBD | mi | ra93 | ra562 | g | 4.83 | low |
| 514 | eFKBD | mi | ra93 | ra209 | g | 4.66 | low |
| 515 | eFKBD | mi | ra93 | ra549 | g | 5.06 | low |
| 516 | eFKBD | mi | ra93 | ra144 | g | 4.47 | low |
| 517 | eFKBD | ra379 | ra93 | ra562 | g | 4.70 | low |
| 518 | eFKBD | ra379 | ra93 | ra209 | g | 4.56 | low |

TABLE 5-continued

Rapafucin compound 1 to compound 578 in this Disclosure.

| Compound No. | FKBD with linkers | Monomer 1 | Monomer 2 | Monomer 3 | Monomer 4 | Retention Time | Rel. Prolif., A549 |
|---|---|---|---|---|---|---|---|
| 519 | eFKBD | ra379 | ra93 | ra549 | g | 4.91 | low |
| 520 | eFKBD | ra379 | ra93 | ra144 | g | 4.37 | low |
| 521 | eFKBD | ml | ra148 | ra562 | g | 4.91 | low |
| 522 | eFKBD | ml | ra148 | ra209 | g | 4.73 | low |
| 523 | eFKBD | ml | ra148 | ra549 | g | 5.17 | low |
| 524 | eFKBD | mi | ra148 | ra562 | g | 4.86 | low |
| 525 | eFKBD | mi | ra148 | ra209 | g | 4.69 | low |
| 526 | eFKBD | mi | ra148 | ra549 | g | 5.12 | low |
| 527 | eFKBD | mi | ra148 | ra144 | g | 4.51 | low |
| 528 | eFKBD | ra379 | ra148 | ra562 | g | 4.74 | low |
| 529 | eFKBD | ra379 | ra148 | ra209 | g | 4.59 | low |
| 530 | eFKBD | ra379 | ra148 | ra549 | g | 4.98 | low |
| 531 | eFKBD | ra379 | ra148 | ra144 | g | 4.40 | low |
| 532 | eFKBD | ra203 | napA | ra562 | g | 4.18 | low |
| 533 | eFKBD | ml | ra107 | ra209 | g | 4.72 | low |
| 534 | eFKBD | ml | ra107 | ra144 | g | 4.52 | low |
| 535 | eFKBD | mi | ra107 | ra562 | g | 4.83 | low |
| 536 | eFKBD | mi | ra107 | ra209 | g | 4.69 | low |
| 537 | eFKBD | mi | ra107 | ra549 | g | 5.09 | low |
| 538 | eFKBD | mi | ra107 | ra144 | g | 4.49 | low |
| 539 | eFKBD | ra379 | ra107 | ra562 | g | 4.73 | low |
| 540 | eFKBD | ra379 | ra107 | ra209 | g | 4.57 | low |
| 541 | eFKBD | ra379 | ra107 | ra549 | g | 4.94 | low |
| 542 | eFKBD | ra379 | ra107 | ra144 | g | 4.40 | low |
| 543 | eFKBD | ml | ra121 | ra562 | g | 4.64 | low |
| 544 | eFKBD | ml | ra121 | ra209 | g | 4.49 | low |
| 545 | eFKBD | ra379 | napA | ra562 | g | 4.30 | low |
| 546 | eFKBD | ml | ra121 | ra144 | g | 4.33 | low |
| 547 | eFKBD | mi | ra121 | ra562 | g | 4.60 | low |
| 548 | eFKBD | mi | ra121 | ra209 | g | 4.48 | low |
| 549 | eFKBD | mi | ra121 | ra549 | g | 4.86 | low |
| 550 | eFKBD | mi | ra121 | ra144 | g | 4.30 | low |
| 551 | eFKBD | ra379 | ra121 | ra562 | g | 4.48 | low |
| 552 | eFKBD | ra379 | ra121 | ra209 | g | 4.35 | low |
| 553 | eFKBD | ra379 | ra121 | ra549 | g | 4.71 | low |
| 554 | eFKBD | ra379 | ra121 | ra144 | g | 4.18 | low |
| 555 | eFKBD | ra347 | ra110 | ra144 | g | 4.98 | low |
| 556 | eFKBD | ra319 | ra110 | ra562 | g | 4.78 | low |
| 557 | eFKBD | ra319 | ra110 | ra209 | g | 4.59 | low |
| 558 | eFKBD | ra319 | ra110 | ra549 | g | 4.94 | low |
| 559 | eFKBD | ra319 | ra110 | ra144 | g | 4.44 | low |
| 560 | rae1 | ra147 | napA | ra562 | g | 5.56 | medium |
| 561 | rae2 | ra147 | napA | ra562 | g | 5.63 | medium |
| 562 | rae3 | ra147 | napA | ra562 | g | 5.48 | medium |
| 563 | rae4 | ra147 | napA | ra562 | g | 5.47 | low |
| 564 | rae5 | ra147 | napA | ra562 | g | 5.48 | low |
| 565 | rae9 | ra147 | napA | ra562 | g | 5.35 | medium |
| 566 | rae10 | ra147 | napA | ra562 | g | 5.10 | medium |
| 567 | rae11 | ra147 | napA | ra562 | g | 5.11 | medium |
| 568 | rae12 | ra147 | napA | ra562 | g | 5.74 | medium |
| 569 | rae13 | ra147 | napA | ra562 | g | 5.27 | medium |
| 570 | rae14 | ra147 | napA | ra562 | g | 5.72 | medium |
| 571 | rae16 | ra147 | napA | ra562 | g | 5.93 | low |
| 572 | rae17 | ra147 | napA | ra562 | g | 4.41 | medium |
| 573 | rae18 | ra147 | napA | ra562 | g | 5.49 | low |
| 574 | rae19 | ra147 | napA | ra562 | g | 5.60 | low |
| 575 | eFKBD | ra147 | napA | ra562 | g | 5.44 | low |
| 576 | rae20 | ra147 | napA | ra562 | g | 5.56 | medium |
| 577 | eFKBD | 2-Nal | mSerBu | Gly | | 6.45 | low |
| 578 | eFKBD | 2-Nal | mNle | Gly | | 6.44 | low |

TABLE 6

Rapafucin compound 579 to compound 877.

| Compound No. | FKBD with linkers | Monomer 1 | Monomer 2 | Monomer 3 | Monomer 4 | Retention Time | Rel. Prolif., NCI-H929 |
|---|---|---|---|---|---|---|---|
| 579 | eFKBD | mf | dF | sar | dF | 4.105 | low |
| 580 | eFKBD | ra208 | dF | sar | dF | 4.158 | low |

TABLE 6-continued

Rapafucin compound 579 to compound 877.

| Compound No. | FKBD with linkers | Monomer 1 | Monomer 2 | Monomer 3 | Monomer 4 | Retention Time | Rel. Prolif., NCI-H929 |
|---|---|---|---|---|---|---|---|
| 581 | eFKBD | ra561 | dF | sar | dF | 4.189 | low |
| 582 | eFKBD | ra531 | dF | sar | dF | 4.252 | low |
| 583 | eFKBD | ra382 | dF | sar | dF | 4.055 | low |
| 584 | eFKBD | ra537 | dF | sar | dF | 4.042 | low |
| 585 | eFKBD | ra577 | dF | sar | dF | 3.342 | low |
| 586 | eFKBD | ra450 | dF | sar | dF | 3.767 | low |
| 587 | eFKBD | ra522 | dF | sar | dF | 3.671 | low |
| 588 | eFKBD | ra513 | dF | sar | dF | 3.769 | low |
| 589 | eFKBD | ra509 | dF | sar | dF | 4.171 | low |
| 590 | eFKBD | ra507 | dF | sar | dF | 4.143 | low |
| 591 | eFKBD | ra534 | dF | sar | dF | 4.221 | low |
| 592 | eFKBD | ra578 | dF | sar | dF | 3.71 | low |
| 593 | eFKBD | ra523 | dF | sar | dF | 3.198 | low |
| 594 | eFKBD | ra521 | dF | sar | dF | 3.308 | low |
| 595 | eFKBD | ra520 | dF | sar | dF | 3.646 | low |
| 596 | eFKBD | ra549 | dF | sar | dF | 4.392 | low |
| 597 | eFKBD | ra600 | dF | sar | dF | 3.969 | low |
| 598 | eFKBD | ra551 | dF | sar | dF | 4.233 | low |
| 599 | eFKBD | ra518 | dF | sar | dF | 3.876 | low |
| 600 | eFKBD | cha | dF | sar | dF | 4.264 | high |
| 601 | eFKBD | ra527 | dF | sar | dF | 4.257 | high |
| 602 | eFKBD | ra566 | dF | sar | dF | 4.215 | low |
| 603 | eFKBD | ra567 | dF | sar | dF | 4.189 | low |
| 604 | eFKBD | ra533 | dF | sar | dF | 4.135 | low |
| 605 | eFKBD | ra530 | dF | sar | dF | 4.111 | low |
| 606 | eFKBD | ra579 | dF | sar | dF | 3.649 | low |
| 607 | eFKBD | ra55 | dF | sar | dF | 4.26 | low |
| 608 | eFKBD | ra56 | dF | sar | dF | 4.259 | low |
| 609 | eFKBD | tza | dF | sar | dF | 3.759 | low |
| 610 | eFKBD | ra58 | dF | sar | dF | 3.607 | low |
| 611 | eFKBD | ra59 | dF | sar | dF | 4.367 | low |
| 612 | eFKBD | ra60 | dF | sar | dF | 5.05 | low |
| 613 | eFKBD | ra61 | dF | sar | dF | 4.001 | low |
| 614 | eFKBD | ra62 | dF | sar | dF | 4.283 | low |
| 615 | eFKBD | ra63 | dF | sar | dF | 4.23 | low |
| 616 | eFKBD | ra64 | dF | sar | dF | 4.87 | low |
| 617 | eFKBD | ra65 | dF | sar | dF | 4.156 | low |
| 618 | eFKBD | ra66 | dF | sar | dF | 4.303 | low |
| 619 | eFKBD | ra67 | dF | sar | dF | 3.968 | low |
| 620 | eFKBD | ra68 | dF | sar | dF | 3.983 | low |
| 621 | eFKBD | ra69 | dF | sar | dF | 4.076 | low |
| 622 | eFKBD | ra70 | dF | sar | dF | 4.286 | low |
| 623 | eFKBD | ra71 | dF | sar | dF | 4.111 | low |
| 624 | eFKBD | ra73 | dF | sar | dF | 4.283 | low |
| 625 | eFKBD | ra74 | dF | sar | dF | 3.899 | low |
| 626 | eFKBD | ra75 | dF | sar | dF | 4.16 | low |
| 627 | eFKBD | ra76 | dF | sar | dF | 4.616 | low |
| 628 | eFKBD | ra511 | dF | sar | dF | 4.289 | low |
| 629 | eFKBD | ra78 | dF | sar | dF | 4.119 | low |
| 630 | eFKBD | ra79 | dF | sar | dF | 4.255 | low |
| 631 | eFKBD | ra83 | dF | sar | dF | 4.065 | low |
| 632 | eFKBD | ra84 | dF | sar | dF | 4.155 | low |
| 633 | eFKBD | ra87 | dF | sar | dF | 4.123 | low |
| 634 | eFKBD | ra88 | dF | sar | dF | 4.023 | low |
| 635 | eFKBD | ra89 | dF | sar | dF | 3.242 | low |
| 636 | eFKBD | ra90 | dF | sar | dF | 3.298 | low |
| 637 | eFKBD | ra91 | dF | sar | dF | 3.418 | low |
| 638 | eFKBD | ra92 | dF | sar | dF | 4.206 | low |
| 639 | eFKBD | ra93 | dF | sar | dF | 4.232 | low |
| 640 | eFKBD | ra94 | dF | sar | dF | 4.245 | low |
| 641 | eFKBD | ra95 | dF | sar | dF | 4.3 | low |
| 642 | eFKBD | ra96 | dF | sar | dF | 4.3 | low |
| 643 | eFKBD | ra97 | dF | sar | dF | 4.231 | low |
| 644 | eFKBD | ra98 | dF | sar | dF | 4.33 | low |
| 645 | eFKBD | ra353 | dF | sar | dF | 4.358 | low |
| 646 | eFKBD | ra104 | dF | sar | dF | 4.133 | low |
| 647 | eFKBD | ra106 | dF | sar | dF | 3.942 | low |
| 648 | eFKBD | ra107 | dF | sar | dF | 4.228 | low |
| 649 | eFKBD | ra108 | dF | sar | dF | 3.467 | low |
| 650 | eFKBD | ra110 | dF | sar | dF | 4.368 | low |
| 651 | eFKBD | ra111 | dF | sar | dF | 3.74 | low |
| 652 | eFKBD | ra112 | dF | sar | dF | 3.984 | low |
| 653 | eFKBD | ra113 | dF | sar | dF | 4.007 | low |
| 654 | eFKBD | ra114 | dF | sar | dF | 3.994 | low |

TABLE 6-continued

Rapafucin compound 579 to compound 877.

| Compound No. | FKBD with linkers | Monomer 1 | Monomer 2 | Monomer 3 | Monomer 4 | Retention Time | Rel. Prolif., NCI-H929 |
|---|---|---|---|---|---|---|---|
| 655 | eFKBD | ra115 | dF | sar | dF | 4.161 | low |
| 656 | eFKBD | ra116 | dF | sar | dF | 4.194 | low |
| 657 | eFKBD | ra117 | dF | sar | dF | 4.201 | low |
| 658 | eFKBD | ra119 | dF | sar | dF | 4.101 | low |
| 659 | eFKBD | ra120 | dF | sar | dF | 4.164 | low |
| 660 | eFKBD | ra121 | dF | sar | dF | 4.091 | low |
| 661 | eFKBD | ra123 | dF | sar | dF | 1.825 | low |
| 662 | eFKBD | ra124 | dF | sar | dF | 4.07 | low |
| 663 | eFKBD | ra126 | dF | sar | dF | 3.797 | low |
| 664 | eFKBD | ra127 | dF | sar | dF | 4.014 | low |
| 665 | eFKBD | ra128 | dF | sar | dF | 4.012 | low |
| 666 | eFKBD | ra132 | dF | sar | dF | 3.863 | low |
| 667 | eFKBD | ra135 | dF | sar | dF | 4.226 | low |
| 668 | eFKBD | ra144 | dF | sar | dF | 4.573 | low |
| 669 | eFKBD | ra148 | dF | sar | dF | 4.164 | low |
| 670 | eFKBD | ra171 | dF | sar | dF | 4.013 | low |
| 671 | eFKBD | ra173 | dF | sar | dF | 3.614 | low |
| 672 | eFKBD | ra175 | dF | sar | dF | 4.582 | low |
| 673 | eFKBD | ra176 | dF | sar | dF | 3.334 | medium |
| 674 | eFKBD | ra185 | dF | sar | dF | 4.055 | low |
| 675 | eFKBD | mf | ra537 | sar | dF | 4.129 | low |
| 676 | eFKBD | ra561 | ra537 | sar | dF | 4.139 | low |
| 677 | eFKBD | ra63 | ra537 | sar | dF | 4.182 | low |
| 678 | eFKBD | ra526 | ra537 | sar | dF | 4.129 | low |
| 679 | eFKBD | cha | ra537 | sar | dF | 4.239 | low |
| 680 | eFKBD | ra75 | ra537 | sar | dF | 4.145 | low |
| 681 | eFKBD | mf | ra507 | sar | dF | 4.218 | low |
| 682 | eFKBD | ra521 | ra507 | sar | dF | 3.257 | low |
| 683 | eFKBD | ra347 | ra507 | sar | dF | 4.142 | low |
| 684 | eFKBD | ra354 | ra507 | sar | dF | 4.188 | low |
| 685 | eFKBD | ra64 | ra507 | sar | dF | 4.202 | low |
| 686 | eFKBD | ra89 | ra507 | sar | dF | 0.393 | low |
| 687 | eFKBD | mf | ra521 | sar | dF | 3.353 | medium |
| 688 | eFKBD | ra561 | ra521 | sar | dF | 3.51 | low |
| 689 | eFKBD | ra382 | ra521 | sar | dF | 3.329 | low |
| 690 | eFKBD | ra513 | ra521 | sar | dF | 3.096 | low |
| 691 | eFKBD | ra75 | ra521 | sar | dF | 3.423 | low |
| 692 | eFKBD | tza | ra521 | sar | dF | 2.97 | low |
| 693 | eFKBD | mf | ra527 | sar | dF | 4.32 | low |
| 694 | eFKBD | napa | ra527 | sar | dF | 4.386 | low |
| 695 | eFKBD | cha | ra527 | sar | dF | 4.496 | low |
| 696 | eFKBD | ra107 | ra527 | sar | dF | 4.399 | low |
| 697 | eFKBD | ra63 | ra527 | sar | dF | 4.425 | low |
| 698 | eFKBD | ra171 | ra527 | sar | dF | 4.191 | low |
| 699 | eFKBD | mf | ra566 | sar | dF | 4.256 | low |
| 700 | eFKBD | ra521 | ra566 | sar | dF | 3.42 | low |
| 701 | eFKBD | ra347 | ra566 | sar | dF | 4.179 | low |
| 702 | eFKBD | ra107 | ra566 | sar | dF | 4.331 | low |
| 703 | eFKBD | ra64 | ra566 | sar | dF | 4.102 | low |
| 704 | eFKBD | tza | ra566 | sar | dF | 3.929 | low |
| 705 | eFKBD | mf | napa | sar | dF | 4.254 | low |
| 706 | eFKBD | napa | napa | sar | dF | 4.311 | low |
| 707 | eFKBD | cha | napa | sar | dF | 4.383 | low |
| 708 | eFKBD | ra354 | napa | sar | dF | 4.232 | low |
| 709 | eFKBD | ra171 | napa | sar | dF | 4.167 | low |
| 710 | eFKBD | ra89 | napa | sar | dF | 3.46 | low |
| 711 | eFKBD | mf | ra55 | sar | dF | 4.326 | low |
| 712 | eFKBD | ra561 | ra55 | sar | dF | 4.363 | low |
| 713 | eFKBD | ra526 | ra55 | sar | dF | 4.283 | low |
| 714 | eFKBD | ra63 | ra55 | sar | dF | 4.37 | low |
| 715 | eFKBD | ra171 | ra55 | sar | dF | 4.159 | low |
| 716 | eFKBD | ra89 | ra55 | sar | dF | 3.451 | low |
| 717 | eFKBD | mf | ra56 | sar | dF | 4.261 | low |
| 718 | eFKBD | ra561 | ra56 | sar | dF | 4.343 | low |
| 719 | eFKBD | ra513 | ra56 | sar | dF | 3.919 | low |
| 720 | eFKBD | ra347 | ra56 | sar | dF | 4.202 | low |
| 721 | eFKBD | ra75 | ra56 | sar | dF | 4.305 | low |
| 722 | eFKBD | ra173 | ra56 | sar | dF | 3.822 | low |
| 723 | eFKBD | mf | ra59 | sar | dF | 4.381 | low |
| 724 | eFKBD | ra526 | ra59 | sar | dF | 4.353 | low |
| 725 | eFKBD | cha | ra59 | sar | dF | 4.598 | low |
| 726 | eFKBD | ra107 | ra59 | sar | dF | 4.514 | low |
| 727 | eFKBD | ra75 | ra59 | sar | dF | 4.487 | low |
| 728 | eFKBD | tza | ra59 | sar | dF | 4.06 | low |

TABLE 6-continued

Rapafucin compound 579 to compound 877.

| Compound No. | FKBD with linkers | Monomer 1 | Monomer 2 | Monomer 3 | Monomer 4 | Retention Time | Rel. Prolif., NCI-H929 |
|---|---|---|---|---|---|---|---|
| 729 | eFKBD | mf | ra60 | sar | dF | 4.373 | low |
| 730 | eFKBD | napa | ra60 | sar | dF | 4.444 | low |
| 731 | eFKBD | ra382 | ra60 | sar | dF | 4.338 | low |
| 732 | eFKBD | ra107 | ra60 | sar | dF | 4.46 | low |
| 733 | eFKBD | ra64 | ra60 | sar | dF | 4.358 | low |
| 734 | eFKBD | ra89 | ra60 | sar | dF | 3.661 | low |
| 735 | eFKBD | mf | ra65 | sar | dF | 4.229 | low |
| 736 | eFKBD | ra561 | ra65 | sar | dF | 4.288 | low |
| 737 | eFKBD | ra347 | ra65 | sar | dF | 4.142 | low |
| 738 | eFKBD | ra354 | ra65 | sar | dF | 4.185 | low |
| 739 | eFKBD | ra171 | ra65 | sar | dF | 4.12 | low |
| 740 | eFKBD | ra173 | ra65 | sar | dF | 3.776 | low |
| 741 | eFKBD | mf | ra67 | sar | dF | 4.046 | low |
| 742 | eFKBD | napa | ra67 | sar | dF | 4.144 | low |
| 743 | eFKBD | ra513 | ra67 | sar | dF | 3.696 | low |
| 744 | eFKBD | ra382 | ra67 | sar | dF | 4.009 | low |
| 745 | eFKBD | ra171 | ra67 | sar | dF | 3.991 | low |
| 746 | eFKBD | ra173 | ra67 | sar | dF | 3.56 | low |
| 747 | eFKBD | mf | ra70 | sar | dF | 4.417 | low |
| 748 | eFKBD | ra513 | ra70 | sar | dF | 4.104 | low |
| 749 | eFKBD | ra63 | ra70 | sar | dF | 4.504 | low |
| 750 | eFKBD | ra107 | ra70 | sar | dF | 4.477 | low |
| 751 | eFKBD | ra75 | ra70 | sar | dF | 4.461 | low |
| 752 | eFKBD | ra354 | ra70 | sar | dF | 4.461 | low |
| 753 | eFKBD | mf | ra144 | sar | dF | 4.082 | low |
| 754 | eFKBD | napa | ra144 | sar | dF | 4.215 | low |
| 755 | eFKBD | ra173 | ra144 | sar | dF | 3.611 | low |
| 756 | eFKBD | cha | ra144 | sar | dF | 4.216 | low |
| 757 | eFKBD | ra354 | ra144 | sar | dF | 4.111 | low |
| 758 | eFKBD | mf | ra354 | sar | dF | 4.315 | low |
| 759 | eFKBD | ra513 | ra354 | sar | dF | 3.942 | low |
| 760 | eFKBD | ra382 | ra354 | sar | dF | 4.351 | low |
| 761 | eFKBD | ra64 | ra354 | sar | dF | 4.354 | low |
| 762 | eFKBD | ra63 | ra354 | sar | dF | 4.485 | low |
| 763 | eFKBD | ra89 | ra354 | sar | dF | 3.554 | low |
| 764 | eFKBD | mf | ra533 | sar | dF | 4.273 | low |
| 765 | eFKBD | ra347 | ra533 | sar | dF | 4.204 | low |
| 766 | eFKBD | ra382 | ra533 | sar | dF | 4.252 | low |
| 767 | eFKBD | ra173 | ra533 | sar | dF | 3.845 | low |
| 768 | eFKBD | ra64 | ra533 | sar | dF | 4.325 | low |
| 769 | eFKBD | mf | ra567 | sar | ra60 | 5.28 | low |
| 770 | eFKBD | mf | ra537 | sar | ra525 | 4.74 | low |
| 771 | eFKBD | mf | ra527 | sar | ra537 | 4.993 | low |
| 772 | eFKBD | mf | ra537 | sar | ra566 | 4.871 | low |
| 773 | eFKBD | mf | ra567 | sar | ra537 | 4.881 | low |
| 774 | eFKBD | mf | ra537 | sar | ra533 | 4.765 | low |
| 775 | eFKBD | mf | ra59 | sar | ra537 | 5.226 | low |
| 776 | eFKBD | mf | ra537 | sar | ra60 | 4.989 | low |
| 777 | eFKBD | mf | ra537 | sar | ra67 | 4.5 | low |
| 778 | eFKBD | mf | ra70 | sar | ra537 | 5.023 | low |
| 779 | eFKBD | mf | ra537 | sar | ra144 | 4.505 | low |
| 780 | eFKBD | mf | ra354 | sar | ra537 | 4.749 | low |
| 781 | eFKBD | mf | ra507 | sar | ra525 | 4.948 | low |
| 782 | eFKBD | mf | ra507 | sar | ra566 | 5.088 | low |
| 783 | eFKBD | mf | ra567 | sar | ra507 | 5.034 | low |
| 784 | eFKBD | mf | ra507 | sar | ra533 | 4.97 | low |
| 785 | eFKBD | mf | ra55 | sar | ra507 | 5.175 | low |
| 786 | eFKBD | mf | ra507 | sar | ra56 | 5.191 | low |
| 787 | eflcbd | mf | ra59 | sar | ra507 | 5.424 | low |
| 788 | eFKBD | mf | ra507 | sar | ra60 | 5.184 | low |
| 789 | eFKBD | mf | ra65 | sar | ra507 | 4.886 | low |
| 790 | eFKBD | mf | ra67 | sar | ra507 | 4.656 | low |
| 791 | eFKBD | mf | ra70 | sar | ra507 | 5.206 | low |
| 792 | eFKBD | mf | ra507 | sar | ra144 | 4.666 | low |
| 793 | eFKBD | mf | ra354 | sar | ra507 | 4.898 | low |
| 794 | eFKBD | mf | ra566 | sar | ra521 | 3.993 | low |
| 795 | eFKBD | mf | ra533 | sar | ra525 | 4.247 | low |
| 796 | eFKBD | mf | ra56 | sar | ra521 | 4.04 | low |
| 797 | eFKBD | mf | ra60 | sar | ra537 | 5.01 | low |
| 798 | eFKBD | mf | ra67 | sar | ra537 | 4.523 | low |
| 799 | eFKBD | mf | ra537 | sar | ra70 | 4.998 | low |
| 800 | eFKBD | mf | ra144 | sar | ra537 | 4.516 | low |
| 801 | eFKBD | mf | ra537 | sar | ra354 | 4.732 | low |
| 802 | eFKBD | mf | ra566 | sar | ra527 | 5.259 | low |

TABLE 6-continued

Rapafucin compound 579 to compound 877.

| Compound No. | FKBD with linkers | Monomer 1 | Monomer 2 | Monomer 3 | Monomer 4 | Retention Time | Rel. Prolif., NCI-H929 |
|---|---|---|---|---|---|---|---|
| 803 | eFKBD | mf | ra527 | sar | ra567 | 5.237 | low |
| 804 | eFKBD | mf | ra527 | sar | ra55 | 5.356 | low |
| 805 | eFKBD | mf | ra56 | sar | ra527 | 5.375 | low |
| 806 | eFKBD | mf | ra527 | sar | ra59 | 5.647 | low |
| 807 | eFKBD | mf | ra60 | sar | ra527 | 5.345 | low |
| 808 | eFKBD | mf | ra527 | sar | ra65 | 5.033 | low |
| 809 | eFKBD | mf | ra67 | sar | ra527 | 4.798 | low |
| 810 | eFKBD | mf | ra70 | sar | ra533 | 5.155 | low |
| 811 | eFKBD | mf | ra527 | sar | ra354 | 5.076 | low |
| 812 | eFKBD | mf | ra567 | sar | ra566 | 5.11 | low |
| 813 | eFKBD | mf | ra59 | sar | ra566 | 5.479 | low |
| 814 | eFKBD | mf | ra566 | sar | ra60 | 5.242 | low |
| 815 | eFKBD | mf | ra65 | sar | ra566 | 4.932 | low |
| 816 | eFKBD | mf | ra566 | sar | ra67 | 4.716 | low |
| 817 | eFKBD | mf | ra70 | sar | ra566 | 5.298 | low |
| 818 | eFKBD | mf | ra566 | sar | ra144 | 4.729 | low |
| 819 | eFKBD | mf | ra354 | sar | ra566 | 4.968 | low |
| 820 | eFKBD | mf | ra566 | sar | ra533 | 5.027 | low |
| 821 | eFKBD | mf | ra59 | sar | ra567 | 5.461 | low |
| 822 | eFKBD | mf | ra65 | sar | ra567 | 4.938 | low |
| 823 | eFKBD | mf | ra567 | sar | ra67 | 4.706 | low |
| 824 | eFKBD | mf | ra70 | sar | ra567 | 5.267 | low |
| 825 | eFKBD | mf | ra55 | sar | ra533 | 5.146 | low |
| 826 | eFKBD | mf | ra59 | sar | ra533 | 5.378 | low |
| 827 | eFKBD | mf | ra533 | sar | ra60 | 5.166 | low |
| 828 | eFKBD | mf | ra65 | sar | ra533 | 4.851 | low |
| 829 | eFKBD | mf | ra533 | sar | ra67 | 4.65 | low |
| 830 | eFKBD | mf | ra533 | sar | ra144 | 4.659 | low |
| 831 | eFKBD | mf | ra354 | sar | ra533 | 4.889 | low |
| 832 | eFKBD | mf | ra59 | sar | ra55 | 5.603 | low |
| 833 | eFKBD | mf | ra55 | sar | ra60 | 5.352 | low |
| 834 | eFKBD | mf | ra65 | sar | ra55 | 5.028 | low |
| 835 | eFKBD | mf | ra67 | sar | ra55 | 4.798 | low |
| 836 | eFKBD | mf | ra70 | sar | ra55 | 5.382 | low |
| 837 | eFKBD | mf | ra55 | sar | ra144 | 4.811 | low |
| 838 | eFKBD | mf | ra59 | sar | ra56 | 5.631 | low |
| 839 | eFKBD | mf | ra56 | sar | ra60 | 5.367 | low |
| 840 | eFKBD | mf | ra65 | sar | ra56 | 5.049 | low |
| 841 | eFKBD | mf | ra56 | sar | ra67 | 4.82 | low |
| 842 | eFKBD | mf | ra70 | sar | ra56 | 5.411 | low |
| 843 | eFKBD | mf | ra354 | sar | ra56 | 5.079 | low |
| 844 | eFKBD | mf | ra59 | sar | ra60 | 5.553 | low |
| 845 | eFKBD | mf | ra65 | sar | ra59 | 5.23 | low |
| 846 | eFKBD | mf | ra70 | sar | ra59 | 5.602 | low |
| 847 | eFKBD | mf | ra59 | sar | ra144 | 4.976 | low |
| 848 | eFKBD | mf | ra354 | sar | ra59 | 5.25 | low |
| 849 | eFKBD | mf | ra60 | sar | ra65 | 5.031 | low |
| 850 | eFKBD | mf | ra67 | sar | ra60 | 4.813 | low |
| 851 | eFKBD | mf | ra60 | sar | ra70 | 5.349 | low |
| 852 | eFKBD | mf | ra67 | sar | ra65 | 4.54 | low |
| 853 | eFKBD | mf | ra65 | sar | ra70 | 5.053 | low |
| 854 | eFKBD | mf | ra144 | sar | ra65 | 4.54 | low |
| 855 | eFKBD | mf | ra65 | sar | ra354 | 4.771 | low |
| 856 | eFKBD | mf | ra144 | sar | ra55 | 4.77 | low |
| 857 | eFKBD | mf | ra354 | sar | ra55 | 5.049 | low |
| 858 | eFKBD | mf | ra70 | sar | ra144 | 4.834 | low |
| 859 | eFKBD | mf | ra354 | sar | ra70 | 5.081 | low |
| 860 | eFKBD | mf | ra144 | sar | ra354 | 4.574 | low |
| 861 | eFKBD | mf | ra527 | sar | ra507 | 5.191 | low |
| 862 | efkbd | ra606 | df | sar | df | 5.285 | high |
| 863 | rae21 | ra98 | df | sar | df | 4.281 | low |
| 864 | rae19 | ra98 | df | sar | df | 4.22 | low |
| 865 | aFKBD | ra98 | df | sar | df | 4.098 | low |
| 866 | eflcbd | ra607 | df | sar | df | 5.077 | high |
| 867 | rae21 | ra492 | df | sar | df | 5.75 | low |
| 868 | rae19 | ra492 | df | sar | df | 5.54 | low |
| 869 | aFKBD | ra492 | df | sar | df | 5.403 | low |
| 870 | efkbd | ra608 | df | sar | df | 4.948 | low |
| 871 | rae34 | mf | df | sar | df | 3.854 | low |
| 872 | rae35 | mf | df | sar | df | 4.434 | low |
| 873 | raa19 | mf | df | sar | df | 4.871 | low |
| 874 | raa20 | mf | df | sar | df | 4.622 | low |

TABLE 6-continued

Rapafucin compound 579 to compound 877.

| Compound No. | FKBD with linkers | Monomer 1 | Monomer 2 | Monomer 3 | Monomer 4 | Retention Time | Rel. Prolif., NCI-H929 |
|---|---|---|---|---|---|---|---|
| 875 | rae36 | mf | df | sar | df | 5.43 | low |
| 876 | rae27 | mf | df | sar | df | 4.962 | low |
| 877 | rae37 | ra398 | df | sar | df | 4.181 | kmv |

TABLE 7

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 878 | aFKBD | ra104 | mf | dp | ml | 5.14 | low |
| 879 | aFKBD | ml | p | ra195 | f | 4.22 | low |
| 880 | aFKBD | ml | p | mf | f | 4.24 | low |
| 881 | aFKBD | ml | dp | ra195 | f | 4.33 | low |
| 882 | aFKBD | ra207 | p | ra195 | f | 4.33 | low |
| 883 | aFKBD | ml | dp | mf | f | 4.33 | low |
| 884 | aFKBD | ra207 | p | mf | f | 4.16 | low |
| 885 | aFKBD | ra207 | dp | ra195 | f | 4.10 | low |
| 886 | aFKBD | f | ra195 | p | ml | 4.14 | low |
| 887 | aFKBD | f | ra195 | p | ra207 | 4.18 | low |
| 888 | aFKBD | f | ra195 | dp | ml | 4.13 | low |
| 889 | aFKBD | f | mf | P | ml | 4.05 | low |
| 890 | aFKBD | dF | ra195 | p | ml | 4.06 | low |
| 891 | aFKBD | f | mf | dp | ml | 4.14 | low |
| 892 | aFKBD | dF | ra195 | dp | ml | 4.11 | low |
| 893 | aFKBD | dF | mf | p | ml | 4.11 | low |
| 894 | aFKBD | ra381 | mf | dp | ml | 4.15 | low |
| 895 | aFKBD | ra400 | mf | dp | ml | 4.13 | medium |
| 896 | aFKBD | ra329 | mf | dp | ml | 4.10 | medium |
| 897 | aFKBD | ra325 | mf | dp | ml | 4.17 | medium |
| 898 | aFKBD | ra516 | mf | dp | ml | 4.27 | high |
| 899 | aFKBD | ra381 | f | dp | ml | 4.06 | low |
| 900 | aFKBD | ra400 | f | dp | ml | 4.06 | low |
| 901 | aFKBD | ra329 | f | dp | ml | 4.03 | low |
| 902 | aFKBD | ra325 | f | dp | ml | 4.11 | low |
| 903 | aFKBD | ra516 | f | dp | ml | 4.17 | high |
| 904 | aFKBD | ra522 | f | dp | ml | 3.78 | low |
| 905 | aFKBD | ra450 | f | dp | ml | 3.89 | high |
| 906 | aFKBD | ra602 | f | dp | ml | 4.04 | high |
| 907 | aFKBD | ra381 | dF | dp | ml | 4.07 | medium |
| 908 | aFKBD | ra400 | dF | dp | ml | 4.08 | low |
| 909 | aFKBD | ra329 | dF | dp | ml | 4.05 | medium |
| 910 | aFKBD | ra325 | dF | dp | ml | 4.18 | medium |
| 911 | aFKBD | ra516 | dF | dp | ml | 4.29 | low |
| 912 | aFKBD | ra522 | dF | dp | ml | 3.87 | low |
| 913 | aFKBD | ra450 | dF | dp | ml | 3.93 | low |
| 914 | aFKBD | ra602 | dF | dp | ml | 4.11 | low |
| 915 | aFKBD | ra381 | ra195 | dp | ml | 4.10 | low |
| 916 | aFKBD | ra400 | ra195 | dp | ml | 4.12 | low |
| 917 | aFKBD | ra329 | ra195 | dp | ml | 4.08 | low |
| 918 | aFKBD | ra325 | ra195 | dp | ml | 4.18 | low |
| 919 | aFKBD | ra516 | ra195 | dp | ml | 4.26 | low |
| 920 | aFKBD | ra522 | ra195 | dp | ml | 3.82 | low |
| 921 | aFKBD | ra450 | ra195 | dp | ml | 3.91 | low |
| 922 | aFKBD | ra602 | ra195 | dp | ml | 4.11 | low |
| 923 | aFKBD | ra381 | y | dp | ml | 3.79 | low |
| 924 | aFKBD | ra400 | y | dp | ml | 3.78 | low |
| 925 | aFKBD | ra329 | y | dp | ml | 3.76 | low |
| 926 | aFKBD | ra325 | y | dp | ml | 3.82 | low |
| 927 | aFKBD | ra516 | y | dp | ml | 3.89 | high |
| 928 | aFKBD | ra602 | ra577 | dp | ml | 3.45 | low |
| 929 | aFKBD | ra602 | ra173 | dp | ml | 3.60 | low |
| 930 | aFKBD | ra602 | ra66 | dp | ml | 4.29 | medium |
| 931 | aFKBD | ra602 | ra56 | dp | ml | 4.30 | low |
| 932 | aFKBD | ra602 | ra64 | dp | ml | 4.13 | high |
| 933 | aFKBD | ra602 | ra171 | dp | ml | 4.08 | high |
| 934 | aFKBD | ra602 | ra63 | dp | ml | 4.27 | low |
| 935 | aFKBD | ra577 | mf | dp | ml | 3.55 | low |
| 936 | aFKBD | ra173 | mf | dp | ml | 3.77 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 937 | aFKBD | ra66 | mf | dp | ml | 4.44 | low |
| 938 | aFKBD | ra56 | mf | dp | ml | 4.43 | low |
| 939 | aFKBD | ra64 | mf | dp | ml | 4.27 | low |
| 940 | aFKBD | ra171 | mf | dp | ml | 4.20 | low |
| 941 | aFKBD | ra63 | mf | dp | ml | 4.38 | low |
| 942 | aFKBD | ra577 | y | dp | ml | 3.23 | low |
| 943 | aFKBD | ra173 | y | dp | ml | 3.41 | low |
| 944 | aFKBD | ra66 | y | dp | ml | 4.06 | high |
| 945 | aFKBD | ra56 | y | dp | ml | 4.06 | high |
| 946 | aFKBD | ra64 | y | dp | ml | 3.93 | low |
| 947 | aFKBD | ra171 | y | dp | ml | 3.86 | low |
| 948 | aFKBD | ra63 | y | dp | ml | 4.01 | low |
| 949 | aFKBD | ra122 | mf | dp | ml | 4.13 | low |
| 950 | aFKBD | f | ra512 | dp | ml | 4.32 | low |
| 951 | aFKBD | y | ra512 | dp | ml | 4.08 | low |
| 952 | aFKBD | mf | ra512 | dp | ml | 4.44 | low |
| 953 | aFKBD | ra522 | ra512 | dp | ml | 4.04 | low |
| 954 | aFKBD | ra450 | ra512 | dp | ml | 4.12 | medium |
| 955 | aFKBD | ra602 | ra348 | dp | ml | 4.09 | high |
| 956 | aFKBD | ra602 | ra547 | dp | ml | 3.96 | high |
| 957 | aFKBD | ra602 | ra381 | dp | ml | 4.01 | medium |
| 958 | aFKBD | ra602 | ra400 | dp | ml | 4.04 | low |
| 959 | aFKBD | ra602 | ra329 | dp | ml | 4.03 | medium |
| 960 | aFKBD | ra602 | ra325 | dp | ml | 4.09 | low |
| 961 | aFKBD | ra602 | ra516 | dp | ml | 4.19 | low |
| 962 | aFKBD | ra602 | mf | dp | ra348 | 4.15 | low |
| 963 | aFKBD | ra602 | mf | dp | ra547 | 3.99 | low |
| 964 | aFKBD | ra602 | mf | dp | sar | 3.70 | low |
| 965 | aFKBD | ra602 | mf | dp | ra147 | 4.16 | high |
| 966 | aFKBD | ra602 | y | dp | ra348 | 3.73 | low |
| 967 | aFKBD | ra602 | y | dp | ra547 | 3.60 | low |
| 968 | aFKBD | ra602 | y | dp | sar | 3.17 | low |
| 969 | aFKBD | ra602 | y | dp | ra147 | 3.78 | low |
| 970 | aFKBD | ra602 | y | dp | mi | 3.74 | medium |
| 971 | aFKBD | ra512 | mf | dp | ml | 4.36 | low |
| 972 | aFKBD | ra602 | mf | dp | cha | 4.32 | low |
| 973 | aFKBD | ra602 | mf | dp | ra84 | 4.24 | low |
| 974 | aFKBD | ra602 | mf | dp | ra206 | 3.88 | low |
| 975 | aFKBD | ra602 | mf | dp | ra209 | 4.21 | low |
| 976 | aFKBD | ra602 | mf | dp | ra80 | 4.21 | low |
| 977 | aFKBD | ra602 | mf | dp | ra549 | 4.57 | low |
| 978 | aFKBD | ra602 | mf | dp | ra189 | 4.08 | medium |
| 979 | aFKBD | ra602 | mf | dp | ra132 | 3.96 | low |
| 980 | aFKBD | ra602 | mf | dp | mv | 4.07 | medium |
| 981 | aFKBD | ra602 | mf | dp | ra176 | 3.52 | low |
| 982 | aFKBD | ra602 | mf | dp | ra301 | 3.86 | low |
| 983 | aFKBD | ra602 | mf | dp | ra81 | 4.12 | low |
| 984 | aFKBD | ra602 | mf | dp | ra350 | 4.10 | low |
| 985 | aFKBD | ra602 | mf | dp | ra575 | 4.17 | low |
| 986 | aFKBD | ra602 | mf | dp | ra307 | 3.74 | low |
| 987 | aFKBD | ra602 | mf | dp | ra347 | 4.20 | low |
| 988 | aFKBD | ra602 | mf | dp | ra554 | 4.17 | low |
| 989 | aFKBD | ra602 | mf | dp | ra546 | 4.22 | low |
| 990 | aFKBD | ra602 | mf | dp | ra175 | 4.89 | low |
| 991 | aFKBD | ra512 | y | dp | ml | 4.06 | low |
| 992 | aFKBD | ra602 | y | dp | cha | 4.00 | low |
| 993 | aFKBD | ra602 | y | dp | ra84 | 4.52 | low |
| 994 | aFKBD | ra602 | y | dp | ra206 | 4.73 | low |
| 995 | aFKBD | ra602 | y | dp | ra209 | 4.12 | low |
| 996 | aFKBD | ra602 | y | dp | ra80 | 3.91 | low |
| 997 | aFKBD | ra602 | y | dp | ra549 | 4.16 | low |
| 998 | aFKBD | ra602 | y | dp | ra189 | 3.68 | low |
| 999 | aFKBD | ra602 | y | dp | ra132 | 3.53 | low |
| 1000 | aFKBD | ra602 | y | dp | mv | 3.70 | low |
| 1001 | aFKBD | ra602 | y | dp | ra176 | 3.26 | low |
| 1002 | aFKBD | ra602 | y | dp | ra301 | 3.38 | low |
| 1003 | aFKBD | ra602 | y | dp | ra81 | 3.77 | low |
| 1004 | aFKBD | ra602 | y | dp | ra350 | 3.83 | low |
| 1005 | aFKBD | ra602 | y | dp | ra575 | 3.85 | low |
| 1006 | aFKBD | ra602 | y | dp | ra307 | 3.25 | low |
| 1007 | aFKBD | ra602 | y | dp | ra347 | 3.83 | low |
| 1008 | aFKBD | ra602 | y | dp | ra554 | 4.09 | low |
| 1009 | aFKBD | ra602 | y | dp | ra546 | 4.74 | low |
| 1010 | aFKBD | ra602 | y | dp | ra175 | 4.79 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1011 | aFKBD | ra602 | mf | ra564 | ml | 4.97 | high |
| 1012 | aFKBD | ra602 | mf | ra510 | ml | 4.85 | medium |
| 1013 | aFKBD | ra602 | mf | ra508 | ml | 4.49 | high |
| 1014 | aFKBD | ra602 | mf | ra557 | ml | 4.43 | low |
| 1015 | aFKBD | ra602 | mf | ra575 | ml | 4.90 | low |
| 1016 | aFKBD | ra602 | mf | ra81 | ml | 4.29 | low |
| 1017 | aFKBD | ra602 | mf | ra554 | ml | 4.79 | low |
| 1018 | aFKBD | ra602 | mf | ra546 | ml | 4.84 | low |
| 1019 | aFKBD | ra602 | y | ra564 | ml | 4.48 | medium |
| 1020 | aFKBD | ra602 | y | ra510 | ml | 4.26 | high |
| 1021 | aFKBD | ra602 | y | ra508 | ml | 4.03 | high |
| 1022 | aFKBD | ra602 | y | ra557 | ml | 3.93 | low |
| 1023 | aFKBD | ra602 | y | ra575 | ml | 4.82 | medium |
| 1024 | aFKBD | ra602 | y | ra81 | ml | 5.04 | low |
| 1025 | aFKBD | ra602 | y | ra554 | ml | 4.31 | low |
| 1026 | aFKBD | ra602 | y | ra546 | ml | 4.43 | low |
| 1027 | aFKBD | ra602 | ra347 | dp | ml | 4.41 | high |
| 1028 | aFKBD | ra602 | ra554 | dp | ml | 4.54 | medium |
| 1029 | aFKBD | ra602 | ra546 | dp | ml | 4.61 | low |
| 1030 | aFKBD | ra602 | ra175 | dp | ml | 5.45 | low |
| 1031 | aFKBD | ra602 | ra307 | dp | ml | 3.86 | medium |
| 1032 | aFKBD | ra602 | ra522 | dp | ml | 4.07 | high |
| 1033 | aFKBD | ra602 | ra206 | dp | ml | 4.12 | high |
| 1034 | aFKBD | ra602 | ra450 | dp | ml | 4.15 | low |
| 1035 | aFKBD | ra602 | ra209 | dp | ml | 4.51 | medium |
| 1036 | aFKBD | ra602 | ra350 | dp | ml | 4.46 | low |
| 1037 | aFKBD | ra602 | ra176 | dp | ml | 3.88 | low |
| 1038 | aFKBD | ra602 | ra301 | dp | ml | 4.03 | low |
| 1039 | aFKBD | ra602 | ra81 | dp | ml | 4.38 | high |
| 1040 | aFKBD | ra602 | ra549 | dp | ml | 4.94 | medium |
| 1041 | aFKBD | ra602 | mv | dp | ml | 4.44 | high |
| 1042 | aFKBD | ra602 | ra575 | dp | ml | 4.60 | low |
| 1043 | aFKBD | ra602 | ra575 | dp | ml | 4.47 | low |
| 1044 | aFKBD | ra301 | mf | dp | ml | 4.19 | low |
| 1045 | aFKBD | ra347 | mf | dp | ml | 4.63 | low |
| 1046 | aFKBD | ra554 | mf | dp | ml | 4.69 | low |
| 1047 | aFKBD | ra546 | mf | dp | ml | 4.73 | low |
| 1048 | aFKBD | ra175 | mf | dp | ml | 5.81 | low |
| 1049 | aFKBD | ra522 | mf | dp | ml | 4.18 | low |
| 1050 | aFKBD | ra450 | mf | dp | ml | 4.31 | high |
| 1051 | aFKBD | ra549 | mf | dp | ml | 5.17 | low |
| 1052 | aFKBD | ra176 | mf | dp | ml | 3.85 | low |
| 1053 | aFKBD | ra350 | mf | dp | ml | 4.67 | low |
| 1054 | aFKBD | ra575 | mf | dp | ml | 4.15 | low |
| 1055 | aFKBD | ra347 | y | dp | ml | 4.16 | low |
| 1056 | aFKBD | ra554 | y | dp | ml | 4.27 | low |
| 1057 | aFKBD | ra546 | y | dp | ml | 4.46 | low |
| 1058 | aFKBD | ra175 | y | dp | ml | 4.94 | low |
| 1059 | aFKBD | ra522 | y | dp | ml | 3.80 | low |
| 1060 | aFKBD | ra450 | y | dp | ml | 3.91 | high |
| 1061 | aFKBD | ra301 | y | dp | ml | 3.80 | low |
| 1062 | aFKBD | ra176 | y | dp | ml | 3.57 | low |
| 1063 | aFKBD | ra350 | y | dp | ml | 4.20 | low |
| 1064 | aFKBD | ra575 | y | dp | ml | 4.16 | low |
| 1065 | aFKBD | ra513 | mf | dp | ml | 4.59 | high |
| 1066 | aFKBD | ra602 | ra559 | dp | ml | 4.07 | high |
| 1067 | aFKBD | ra602 | ra548 | dp | ml | 4.02 | high |
| 1068 | aFKBD | ra602 | ra536 | dp | ml | 4.07 | low |
| 1069 | aFKBD | ra602 | ra576 | dp | ml | 3.63 | high |
| 1070 | aFKBD | ra602 | dQ | dp | ml | 3.33 | low |
| 1071 | aFKBD | ra602 | ra517 | dp | ml | 4.06 | low |
| 1072 | aFKBD | ra602 | dN | dp | ml | 3.32 | low |
| 1073 | aFKBD | ra602 | N | dp | ml | 3.35 | low |
| 1074 | aFKBD | ra602 | Q | dp | ml | 3.35 | medium |
| 1075 | aFKBD | ra602 | ra560 | dp | ml | 4.09 | high |
| 1076 | aFKBD | ra602 | ra561 | dp | ml | 4.13 | low |
| 1077 | aFKBD | ra602 | ra534 | dp | ml | 4.15 | low |
| 1078 | aFKBD | ra602 | ra382 | dp | ml | 3.98 | low |
| 1079 | aFKBD | ra602 | ra531 | dp | ml | 4.19 | low |
| 1080 | aFKBD | ra602 | ra318 | dp | ml | 4.06 | high |
| 1081 | aFKBD | ra602 | ra553 | dp | ml | 4.24 | medium |
| 1082 | aFKBD | ra602 | ra73 | dp | ml | 4.22 | low |
| 1083 | aFKBD | ra602 | ra535 | dp | ml | 4.00 | low |
| 1084 | aFKBD | ra602 | Aca | dp | ml | 4.42 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1085 | aFKBD | ra602 | ra558 | dp | ml | 4.30 | medium |
| 1086 | aFKBD | ra602 | ra529 | dp | ml | 3.91 | low |
| 1087 | aFKBD | ra602 | ra140 | dp | ml | 3.92 | low |
| 1088 | aFKBD | ra348 | mf | dp | ml | 4.11 | low |
| 1089 | aFKBD | ra559 | mf | dp | ml | 4.25 | low |
| 1090 | aFKBD | ra548 | mf | dp | ml | 4.14 | low |
| 1091 | aFKBD | ra536 | mf | dp | ml | 4.14 | low |
| 1092 | aFKBD | ra576 | mf | dp | ml | 3.82 | low |
| 1093 | aFKBD | dQ | mf | dp | ml | 3.43 | low |
| 1094 | aFKBD | ra517 | mf | dp | ml | 4.18 | low |
| 1095 | aFKBD | dN | mf | dp | ml | 3.44 | low |
| 1096 | aFKBD | N | mf | dp | ml | 3.45 | low |
| 1097 | aFKBD | Q | mf | dp | ml | 3.46 | low |
| 1098 | aFKBD | ra560 | mf | dp | ml | 4.24 | low |
| 1099 | aFKBD | ra561 | mf | dp | ml | 4.24 | low |
| 1100 | aFKBD | ra534 | mf | dp | ml | 4.28 | low |
| 1101 | aFKBD | ra382 | mf | dp | ml | 4.10 | low |
| 1102 | aFKBD | ra531 | mf | dp | ml | 4.30 | low |
| 1103 | aFKBD | ra318 | mf | dp | ml | 4.16 | low |
| 1104 | aFKBD | ra553 | mf | dp | ml | 4.33 | low |
| 1105 | aFKBD | ra73 | mf | dp | ml | 4.32 | low |
| 1106 | aFKBD | ra535 | mf | dp | ml | 4.12 | low |
| 1107 | aFKBD | Aca | mf | dp | ml | 4.53 | low |
| 1108 | aFKBD | ra558 | mf | dp | ml | 4.46 | low |
| 1109 | aFKBD | ra529 | mf | dp | ml | 4.01 | low |
| 1110 | aFKBD | ra140 | mf | dp | ml | 4.04 | low |
| 1111 | aFKBD | ra348 | y | dp | ml | 3.77 | low |
| 1112 | aFKBD | ra559 | y | dp | ml | 3.88 | low |
| 1113 | aFKBD | ra548 | y | dp | ml | 3.80 | low |
| 1114 | aFKBD | ra536 | y | dp | ml | 3.78 | low |
| 1115 | aFKBD | ra576 | y | dp | ml | 3.45 | low |
| 1116 | aFKBD | dQ | y | dp | ml | 3.08 | low |
| 1117 | aFKBD | ra517 | y | dp | ml | 3.83 | low |
| 1118 | aFKBD | dN | y | dp | ml | 3.10 | low |
| 1119 | aFKBD | N | y | dp | ml | 3.10 | low |
| 1120 | aFKBD | Q | y | dp | ml | 3.12 | low |
| 1121 | aFKBD | ra560 | y | dp | ml | 3.91 | low |
| 1122 | aFKBD | ra561 | y | dp | ml | 3.88 | low |
| 1123 | aFKBD | ra534 | y | dp | ml | 3.94 | low |
| 1124 | aFKBD | ra382 | y | dp | ml | 3.77 | low |
| 1125 | aFKBD | ra531 | y | dp | ml | 3.98 | low |
| 1126 | aFKBD | ra318 | y | dp | ml | 3.88 | low |
| 1127 | aFKBD | ra553 | y | dp | ml | 4.01 | low |
| 1128 | aFKBD | ra73 | y | dp | ml | 4.00 | low |
| 1129 | aFKBD | ra535 | y | dp | ml | 3.77 | low |
| 1130 | aFKBD | Aca | y | dp | ml | 4.14 | low |
| 1131 | aFKBD | ra558 | y | dp | ml | 4.07 | low |
| 1132 | aFKBD | ra529 | y | dp | ml | 3.71 | low |
| 1133 | aFKBD | ra140 | y | dp | ml | 3.70 | low |
| 1134 | aFKBD | ra602 | mf | ra576 | ml | 4.00 | low |
| 1135 | aFKBD | ra602 | mf | ra535 | ml | 4.36 | low |
| 1136 | aFKBD | ra602 | mf | dN | ml | 3.66 | low |
| 1137 | aFKBD | ra602 | mf | dQ | ml | 3.68 | high |
| 1138 | aFKBD | ra602 | mf | ra536 | ml | 4.37 | low |
| 1139 | aFKBD | ra602 | y | ra576 | ml | 3.50 | low |
| 1140 | aFKBD | ra602 | y | ra535 | ml | 3.95 | low |
| 1141 | aFKBD | ra602 | y | dN | ml | 3.18 | low |
| 1142 | aFKBD | ra602 | y | dQ | ml | 3.23 | low |
| 1143 | aFKBD | ra602 | y | ra536 | ml | 3.95 | low |
| 1144 | aFKBD | ra602 | mf | dp | ra559 | 4.06 | low |
| 1145 | aFKBD | ra602 | mf | dp | ra548 | 4.13 | low |
| 1146 | aFKBD | ra602 | mf | dp | ra517 | 4.14 | low |
| 1147 | aFKBD | ra602 | mf | dp | N | 3.46 | low |
| 1148 | aFKBD | ra602 | mf | dp | Q | 3.48 | low |
| 1149 | aFKBD | ra602 | mf | dp | ra560 | 4.09 | low |
| 1150 | aFKBD | ra602 | mf | dp | Aca | 4.53 | low |
| 1151 | aFKBD | ra602 | mf | dp | ra558 | 4.27 | low |
| 1152 | aFKBD | ra602 | y | dp | ra559 | 3.66 | low |
| 1153 | aFKBD | ra602 | y | dp | ra548 | 3.69 | low |
| 1154 | aFKBD | ra602 | y | dp | ra517 | 3.73 | low |
| 1155 | aFKBD | ra602 | y | dp | N | 2.42 | low |
| 1156 | aFKBD | ra602 | y | dp | Q | 2.57 | low |
| 1157 | aFKBD | ra602 | y | dp | ra560 | 3.71 | low |
| 1158 | aFKBD | ra602 | y | dp | Aca | 4.07 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1159 | aFKBD | ra602 | y | dp | ra558 | 3.91 | low |
| 1160 | aFKBD | ra602 | mf | ra545 | ml | 4.42 | high |
| 1161 | aFKBD | ra602 | mf | ra102 | ml | 4.21 | medium |
| 1162 | aFKBD | ra602 | mf | ra351 | ml | 4.36 | low |
| 1163 | aFKBD | ra602 | mf | aze | ml | 3.93 | low |
| 1164 | aFKBD | ra602 | mf | ra529 | ml | 4.33 | low |
| 1165 | aFKBD | ra602 | mf | ra140 | ml | 4.24 | medium |
| 1166 | aFKBD | ra602 | mf | ra538 | ml | 4.27 | low |
| 1167 | aFKBD | ra602 | mf | ra603 | ml | 4.15 | medium |
| 1168 | aFKBD | ra602 | mf | ra528 | ml | 4.06 | medium |
| 1169 | aFKBD | ra602 | mf | ra532 | ml | 3.88 | low |
| 1170 | aFKBD | ra602 | mf | ra539 | ml | 4.33 | high |
| 1171 | aFKBD | ra602 | mf | ra168 | ml | 4.09 | low |
| 1172 | aFKBD | ra602 | mf | ra169 | ml | 4.19 | low |
| 1173 | aFKBD | ra602 | mf | ra170 | ml | 3.96 | low |
| 1174 | aFKBD | ra602 | mf | ra542 | ml | 4.38 | low |
| 1175 | aFKBD | ra602 | mf | oic | ml | 4.19 | low |
| 1176 | aFKBD | ra602 | mf | ra524 | ml | 3.94 | low |
| 1177 | aFKBD | ra602 | mf | ra165 | ml | 4.03 | medium |
| 1178 | aFKBD | ra602 | mf | ra69 | ml | 4.19 | low |
| 1179 | aFKBD | ra602 | mf | ra573 | ml | 4.49 | low |
| 1180 | aFKBD | ra602 | mf | ra574 | ml | 30728.60 | low |
| 1181 | aFKBD | ra602 | y | ra545 | ml | 3.96 | high |
| 1182 | aFKBD | ra602 | y | ra102 | ml | 3.88 | low |
| 1183 | aFKBD | ra602 | y | ra351 | ml | 4.01 | medium |
| 1184 | aFKBD | ra602 | y | aze | ml | 3.48 | low |
| 1185 | aFKBD | ra602 | y | ra529 | ml | 3.97 | low |
| 1186 | aFKBD | ra602 | y | ra140 | ml | 3.89 | medium |
| 1187 | aFKBD | ra602 | y | ra538 | ml | 3.89 | medium |
| 1188 | aFKBD | ra602 | y | ra603 | ml | 3.77 | high |
| 1189 | aFKBD | ra602 | y | ra528 | ml | 3.67 | low |
| 1190 | aFKBD | ra602 | y | ra532 | ml | 3.52 | low |
| 1191 | aFKBD | ra602 | y | ra539 | ml | 3.98 | high |
| 1192 | aFKBD | ra602 | y | ra168 | ml | 3.71 | medium |
| 1193 | aFKBD | ra602 | y | ra169 | ml | 3.82 | high |
| 1194 | aFKBD | ra602 | y | ra170 | ml | 3.52 | low |
| 1195 | aFKBD | ra602 | y | ra542 | ml | 4.03 | high |
| 1196 | aFKBD | ra602 | y | oic | ml | 3.84 | low |
| 1197 | aFKBD | ra602 | y | ra524 | ml | 3.51 | low |
| 1198 | aFKBD | ra602 | y | ra165 | ml | 3.60 | medium |
| 1199 | aFKBD | ra602 | y | ra69 | ml | 3.82 | low |
| 1200 | aFKBD | ra602 | y | ra573 | ml | 4.03 | low |
| 1201 | aFKBD | ra602 | y | ra574 | ml | 3.87 | low |
| 1202 | aFKBD | ra69 | mf | dp | ml | 4.06 | low |
| 1203 | aFKBD | ra351 | mf | dp | ml | 4.21 | low |
| 1204 | aFKBD | ra102 | mf | dp | ml | 4.08 | low |
| 1205 | aFKBD | oic | mf | dp | ml | 4.22 | low |
| 1206 | aFKBD | ra542 | mf | dp | ml | 4.24 | low |
| 1207 | aFKBD | ra574 | mf | dp | ml | 4.21 | low |
| 1208 | aFKBD | ra573 | mf | dp | ml | 4.30 | low |
| 1209 | aFKBD | ra351 | y | dp | ml | 3.83 | low |
| 1210 | aFKBD | ra102 | y | dp | ml | 3.73 | low |
| 1211 | aFKBD | oic | y | dp | ml | 3.78 | low |
| 1212 | aFKBD | ra542 | y | dp | ml | 3.81 | low |
| 1213 | aFKBD | ra574 | y | dp | ml | 3.84 | low |
| 1214 | aFKBD | ra545 | y | dp | ml | 3.83 | low |
| 1215 | aFKBD | ra573 | y | dp | ml | 3.88 | low |
| 1216 | aFKBD | ra602 | ra545 | dp | ml | 4.03 | low |
| 1217 | aFKBD | ra602 | ra351 | dp | ml | 4.89 | low |
| 1218 | aFKBD | ra602 | ra69 | dp | ml | 4.10 | low |
| 1219 | aFKBD | ra602 | ra102 | dp | ml | 3.95 | low |
| 1220 | aFKBD | ra602 | y | dp | mf | 3.71 | low |
| 1221 | aFKBD | ra602 | mf | dp | mf | 4.07 | low |
| 1222 | aFKBD | ra602 | mf | dp | ra524 | 3.60 | low |
| 1223 | aFKBD | ra540 | mf | dp | ml | 4.11 | low |
| 1224 | aFKBD | ra602 | y | dp | ra562 | 3.72 | low |
| 1225 | aFKBD | ra602 | mf | dp | ra562 | 4.07 | low |
| 1226 | aFKBD | ra602 | mf | dp | y | 3.72 | low |
| 1227 | aFKBD | ra602 | y | dp | ra542 | 3.65 | low |
| 1228 | aFKBD | ra602 | mf | dp | ra573 | 4.15 | low |
| 1229 | aFKBD | ra602 | y | dp | ra573 | 3.71 | low |
| 1230 | aFKBD | ra602 | mf | dp | ra574 | 4.03 | low |
| 1231 | aFKBD | ra602 | rbphe | dp | ml | 3.97 | low |
| 1232 | aFKBD | ra602 | ra461 | dp | ml | 3.97 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1233 | aFKBD | ra602 | ra462 | dp | ml | 4.01 | low |
| 1234 | aFKBD | ra602 | m | dp | ml | 3.88 | high |
| 1235 | aFKBD | ra602 | dm | dp | ml | 3.91 | low |
| 1236 | aFKBD | ra602 | ra458 | dp | ml | 3.65 | medium |
| 1237 | aFKBD | ra602 | ra459 | dp | ml | 3.63 | medium |
| 1238 | aFKBD | ra602 | ra456 | dp | ml | 3.96 | high |
| 1239 | aFKBD | ra602 | ra457 | dp | ml | 4.03 | low |
| 1240 | aFKBD | ra602 | ra454 | dp | ml | 4.00 | high |
| 1241 | aFKBD | ra602 | ra321 | dp | ml | 4.01 | low |
| 1242 | aFKBD | ra602 | ra452 | dp | ml | 3.97 | medium |
| 1243 | aFKBD | ra602 | ra306 | dp | ml | 4.02 | low |
| 1244 | aFKBD | ra602 | ra310 | dp | ml | 4.18 | low |
| 1245 | aFKBD | ra602 | ra463 | dp | ml | 4.04 | low |
| 1246 | aFKBD | ra602 | ra464 | dp | ml | 3.89 | low |
| 1247 | aFKBD | ra602 | ra466 | dp | ml | 3.88 | low |
| 1248 | aFKBD | ra602 | ra467 | dp | ml | 4.01 | low |
| 1249 | aFKBD | ra602 | ra468 | dp | ml | 3.94 | low |
| 1250 | aFKBD | rbphe | mf | dp | ml | 4.02 | low |
| 1251 | aFKBD | ra461 | mf | dp | ml | 4.07 | low |
| 1252 | aFKBD | ra462 | mf | dp | ml | 4.07 | low |
| 1253 | aFKBD | m | mf | dp | ml | 4.00 | high |
| 1254 | aFKBD | dm | mf | dp | ml | 4.00 | low |
| 1255 | aFKBD | ra458 | mf | dp | ml | 3.75 | low |
| 1256 | aFKBD | ra459 | mf | dp | ml | 3.72 | low |
| 1257 | aFKBD | ra456 | mf | dp | ml | 4.08 | low |
| 1258 | aFKBD | ra457 | mf | dp | ml | 4.09 | low |
| 1259 | aFKBD | ra454 | mf | dp | ml | 4.10 | low |
| 1260 | aFKBD | ra321 | mf | dp | ml | 4.07 | low |
| 1261 | aFKBD | ra452 | mf | dp | ml | 4.08 | low |
| 1262 | aFKBD | ra306 | mf | dp | ml | 4.07 | low |
| 1263 | aFKBD | ra453 | mf | dp | ml | 4.16 | low |
| 1264 | aFKBD | ra310 | mf | dp | ml | 4.29 | low |
| 1265 | aFKBD | ra463 | mf | dp | ml | 4.21 | low |
| 1266 | aFKBD | ra464 | mf | dp | ml | 4.01 | low |
| 1267 | aFKBD | ra466 | mf | dp | ml | 4.01 | low |
| 1268 | aFKBD | ra467 | mf | dp | ml | 4.13 | low |
| 1269 | aFKBD | ra468 | mf | dp | ml | 4.10 | low |
| 1270 | aFKBD | rbphe | y | dp | ml | 3.69 | low |
| 1271 | aFKBD | ra461 | y | dp | ml | 3.71 | low |
| 1272 | aFKBD | ra462 | y | dp | ml | 3.73 | low |
| 1273 | aFKBD | m | y | dp | ml | 3.64 | high |
| 1274 | aFKBD | dm | y | dp | ml | 3.64 | low |
| 1275 | aFKBD | ra458 | y | dp | ml | 3.43 | low |
| 1276 | aFKBD | ra459 | y | dp | ml | 3.42 | low |
| 1277 | aFKBD | ra456 | y | dp | ml | 3.77 | low |
| 1278 | aFKBD | ra457 | y | dp | ml | 3.77 | low |
| 1279 | aFKBD | ra454 | y | dp | ml | 3.76 | low |
| 1280 | aFKBD | ra321 | y | dp | ml | 3.75 | low |
| 1281 | aFKBD | ra452 | y | dp | ml | 3.77 | low |
| 1282 | aFKBD | ra306 | y | dp | ml | 3.77 | low |
| 1283 | aFKBD | ra453 | y | dp | ml | 3.86 | low |
| 1284 | aFKBD | ra310 | y | dp | ml | 3.91 | low |
| 1285 | aFKBD | ra463 | y | dp | ml | 3.85 | low |
| 1286 | aFKBD | ra464 | y | dp | ml | 3.65 | low |
| 1287 | aFKBD | ra466 | y | dp | ml | 3.69 | low |
| 1288 | aFKBD | ra467 | y | dp | ml | 3.83 | low |
| 1289 | aFKBD | ra468 | y | dp | ml | 3.80 | low |
| 1290 | aFKBD | phg | mf | dp | rbphe | 3.86 | low |
| 1291 | aFKBD | phg | mf | dp | ra461 | 3.95 | low |
| 1292 | aFKBD | ra602 | mf | dp | ra462 | 3.97 | low |
| 1293 | aFKBD | ra602 | mf | dp | m | 3.96 | low |
| 1294 | aFKBD | ra602 | mf | dp | ra458 | 3.73 | low |
| 1295 | aFKBD | ra602 | mf | dp | ra456 | 4.12 | low |
| 1296 | aFKBD | ra602 | mf | dp | ra454 | 4.07 | low |
| 1297 | aFKBD | ra602 | mf | dp | ra452 | 4.06 | low |
| 1298 | aFKBD | ra602 | mf | dp | ra453 | 4.00 | high |
| 1299 | aFKBD | ra602 | mf | dp | ra310 | 4.32 | low |
| 1300 | aFKBD | ra602 | mf | dp | ra463 | 3.98 | low |
| 1301 | aFKBD | ra602 | y | dp | rbphe | 3.54 | low |
| 1302 | aFKBD | ra602 | y | dp | ra461 | 3.56 | low |
| 1303 | aFKBD | ra602 | y | dp | ra462 | 3.55 | low |
| 1304 | aFKBD | ra602 | y | dp | m | 3.51 | low |
| 1305 | aFKBD | ra602 | y | dp | ra458 | 3.21 | low |
| 1306 | aFKBD | ra602 | y | dp | ra456 | 3.64 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1307 | aFKBD | ra602 | y | dp | ra454 | 3.64 | low |
| 1308 | aFKBD | ra602 | y | dp | ra452 | 3.65 | low |
| 1309 | aFKBD | ra602 | y | dp | ra453 | 3.66 | low |
| 1310 | aFKBD | ra602 | y | dp | ra310 | 3.86 | low |
| 1311 | aFKBD | ra602 | y | dp | ra463 | 3.66 | low |
| 1312 | aFKBD | ra602 | mf | dm | ml | 4.23 | high |
| 1313 | aFKBD | ra602 | mf | ra459 | ml | 3.92 | high |
| 1314 | aFKBD | ra602 | mf | ra457 | ml | 4.27 | low |
| 1315 | aFKBD | ra602 | mf | ra321 | ml | 4.26 | low |
| 1316 | aFKBD | ra602 | mf | ra306 | ml | 4.26 | medium |
| 1317 | aFKBD | ra602 | mf | ra463 | ml | 4.25 | low |
| 1318 | aFKBD | ra602 | y | dm | ml | 3.79 | low |
| 1319 | aFKBD | ra602 | y | ra459 | ml | 3.50 | medium |
| 1320 | aFKBD | ra602 | y | ra457 | ml | 3.90 | low |
| 1321 | aFKBD | ra602 | y | ra321 | ml | 3.90 | low |
| 1322 | aFKBD | ra602 | y | ra306 | ml | 3.89 | low |
| 1323 | aFKBD | ra602 | y | ra463 | ml | 3.91 | low |
| 1324 | aFKBD | ra602 | ra110 | dp | ml | 4.30 | low |
| 1325 | aFKBD | ra602 | ra115 | dp | ml | 4.02 | medium |
| 1326 | aFKBD | ra602 | ra117 | dp | ml | 4.08 | high |
| 1327 | aFKBD | ra602 | ra116 | dp | ml | 4.08 | medium |
| 1328 | aFKBD | ra602 | ra113 | dp | ml | 3.90 | medium |
| 1329 | aFKBD | ra602 | ra114 | dp | ml | 3.87 | high |
| 1330 | aFKBD | ra602 | ra112 | dp | ml | 3.85 | high |
| 1331 | aFKBD | ra602 | ra111 | dp | ml | 3.56 | low |
| 1332 | aFKBD | ra602 | mf | dp | mi | 4.13 | medium |
| 1333 | aFKBD | ra602 | ra148 | dp | ml | 4.13 | medium |
| 1334 | aFKBD | ra602 | napA | dp | ml | 4.10 | medium |
| 1335 | aFKBD | ra602 | tic | dp | ml | 3.95 | low |
| 1336 | aFKBD | ra602 | ra136 | dp | ml | 3.67 | low |
| 1337 | aFKBD | ra602 | ra105 | dp | ml | 3.67 | low |
| 1338 | aFKBD | ra602 | ra137 | dp | ml | 4.14 | medium |
| 1339 | aFKBD | ra602 | ra101 | dp | ml | 3.89 | low |
| 1340 | aFKBD | ra602 | ra540 | dp | ml | 4.04 | low |
| 1341 | aFKBD | ra602 | ra86 | dp | ml | 4.04 | low |
| 1342 | aFKBD | ra602 | ra204 | dp | ml | 4.04 | low |
| 1343 | aFKBD | ra602 | ra134 | dp | ml | 4.04 | high |
| 1344 | aFKBD | ra602 | ra135 | dp | ml | 4.20 | low |
| 1345 | aFKBD | ra602 | ra525 | dp | ml | 4.12 | low |
| 1346 | aFKBD | ra602 | ra122 | dp | ml | 4.00 | medium |
| 1347 | aFKBD | ra122 | ra122 | dp | ml | 4.10 | low |
| 1348 | aFKBD | ra122 | y | dp | ml | 3.76 | low |
| 1349 | aFKBD | ra110 | mf | dp | ml | 4.41 | low |
| 1350 | aFKBD | ra115 | mf | dp | ml | 4.14 | low |
| 1351 | aFKBD | ra117 | mf | dp | ml | 4.20 | low |
| 1352 | aFKBD | ra116 | mf | dp | ml | 4.18 | low |
| 1353 | aFKBD | ra113 | mf | dp | ml | 4.00 | low |
| 1354 | aFKBD | ra114 | mf | dp | ml | 4.00 | low |
| 1355 | aFKBD | ra112 | mf | dp | ml | 3.96 | low |
| 1356 | aFKBD | ra111 | mf | dp | ml | 3.72 | low |
| 1357 | aFKBD | ra109 | mf | dp | ml | 3.60 | low |
| 1358 | aFKBD | ra108 | mf | dp | ml | 3.55 | low |
| 1359 | aFKBD | ra148 | mf | dp | ml | 4.24 | low |
| 1360 | aFKBD | napA | mf | dp | ml | 4.24 | low |
| 1361 | aFKBD | ra602 | mf | dp | ml | 4.05 | high |
| 1362 | aFKBD | ra136 | mf | dp | ml | 3.79 | low |
| 1363 | aFKBD | ra105 | mf | dp | ml | 3.81 | low |
| 1364 | aFKBD | ra137 | mf | dp | ml | 4.27 | low |
| 1365 | aFKBD | ra101 | mf | dp | ml | 4.08 | low |
| 1366 | aFKBD | ra86 | mf | dp | ml | 4.39 | low |
| 1367 | aFKBD | ra134 | mf | dp | ml | 4.11 | low |
| 1368 | aFKBD | ra135 | mf | dp | ml | 4.26 | low |
| 1369 | aFKBD | ra525 | mf | dp | ml | 4.17 | low |
| 1370 | aFKBD | ra110 | y | dp | ml | 4.05 | low |
| 1371 | aFKBD | ra115 | y | dp | ml | 3.79 | low |
| 1372 | aFKBD | ra117 | y | dp | ml | 3.83 | low |
| 1373 | aFKBD | ra116 | y | dp | ml | 3.84 | medium |
| 1374 | aFKBD | ra113 | y | dp | ml | 3.68 | low |
| 1375 | aFKBD | ra114 | y | dp | ml | 3.66 | low |
| 1376 | aFKBD | ra112 | y | dp | ml | 3.64 | low |
| 1377 | aFKBD | ra111 | y | dp | ml | 3.40 | low |
| 1378 | aFKBD | ra109 | y | dp | ml | 3.26 | low |
| 1379 | aFKBD | ra108 | y | dp | ml | 3.20 | low |
| 1380 | aFKBD | ra148 | y | dp | ml | 3.87 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1381 | aFKBD | napA | y | dp | ml | 3.88 | low |
| 1382 | aFKBD | ra136 | y | dp | ml | 3.50 | low |
| 1383 | aFKBD | ra105 | y | dp | ml | 3.43 | low |
| 1384 | aFKBD | ra540 | y | dp | ml | 3.77 | low |
| 1385 | aFKBD | ra86 | y | dp | ml | 3.74 | low |
| 1386 | aFKBD | ra204 | y | dp | ml | 3.70 | low |
| 1387 | aFKBD | ra134 | y | dp | ml | 3.76 | low |
| 1388 | aFKBD | ra135 | y | dp | ml | 3.94 | low |
| 1389 | aFKBD | ra525 | y | dp | ml | 3.86 | low |
| 1390 | aFKBD | ra602 | mf | ra540 | ml | 4.23 | medium |
| 1391 | aFKBD | ra602 | y | ra540 | ml | 3.75 | low |
| 1392 | aFKBD | ra602 | y | ra86 | ml | 4.16 | low |
| 1393 | aFKBD | ra602 | mf | tic | ml | 4.15 | low |
| 1394 | aFKBD | ra602 | y | tic | ml | 3.75 | low |
| 1395 | aFKBD | ra602 | mf | ra105 | ml | 3.95 | high |
| 1396 | aFKBD | ra602 | y | ra105 | ml | 3.63 | high |
| 1397 | aFKBD | ra602 | mf | ra136 | ml | 3.87 | low |
| 1398 | aFKBD | ra602 | y | ra136 | ml | 3.54 | low |
| 1399 | aFKBD | ra602 | ra513 | dp | ml | 5.67 | high |
| 1400 | aFKBD | ra602 | ra120 | dp | ml | 4.88 | low |
| 1401 | aFKBD | ra602 | ra92 | dp | ml | 5.10 | low |
| 1402 | aFKBD | ra602 | ra107 | dp | ml | 5.14 | high |
| 1403 | aFKBD | ra602 | ra93 | dp | ml | 5.14 | medium |
| 1404 | aFKBD | ra602 | ra95 | dp | ml | 5.28 | low |
| 1405 | aFKBD | ra602 | ra96 | dp | ml | 5.23 | medium |
| 1406 | aFKBD | ra602 | ra87 | dp | ml | 4.91 | medium |
| 1407 | aFKBD | ra602 | ra104 | dp | ml | 4.91 | high |
| 1408 | aFKBD | ra602 | ra123 | dp | ml | 4.90 | high |
| 1409 | aFKBD | ra602 | ra89 | dp | ml | 3.55 | high |
| 1410 | aFKBD | ra602 | ra90 | dp | ml | 3.67 | medium |
| 1411 | aFKBD | ra602 | ra91 | dp | ml | 4.02 | medium |
| 1412 | aFKBD | ra602 | ra97 | dp | ml | 5.25 | low |
| 1413 | aFKBD | ra602 | ra94 | dp | ml | 5.29 | low |
| 1414 | aFKBD | ra602 | ra353 | dp | ml | 5.43 | medium |
| 1415 | aFKBD | ra602 | ra88 | dp | ml | 4.80 | high |
| 1416 | aFKBD | ra602 | ra185 | dp | ml | 4.92 | high |
| 1417 | aFKBD | ra602 | ra124 | dp | ml | 4.81 | high |
| 1418 | aFKBD | ra602 | ra526 | dp | ml | 5.07 | high |
| 1419 | aFKBD | ra602 | ra121 | dp | ml | 4.86 | high |
| 1420 | aFKBD | ra602 | ra339 | dp | ml | 4.91 | high |
| 1421 | aFKBD | ra602 | ra106 | dp | ml | 4.59 | high |
| 1422 | aFKBD | ra602 | my | dp | ml | 4.58 | high |
| 1423 | aFKBD | ra602 | ra133 | dp | ml | 4.40 | high |
| 1424 | aFKBD | ra602 | mf | dp | ra83 | 4.16 | low |
| 1425 | aFKBD | ra92 | mf | dp | ml | 5.26 | low |
| 1426 | aFKBD | ra107 | mf | dp | ml | 5.27 | low |
| 1427 | aFKBD | ra93 | mf | dp | ml | 5.32 | low |
| 1428 | aFKBD | ra95 | mf | dp | ml | 5.43 | low |
| 1429 | aFKBD | ra96 | mf | dp | ml | 5.44 | low |
| 1430 | aFKBD | Ra87 | mf | dp | ml | 5.15 | low |
| 1431 | aFKBD | ra602 | ra108 | dp | ml | 3.46 | high |
| 1432 | aFKBD | ra123 | mf | dp | ml | 5.15 | low |
| 1433 | aFKBD | ra89 | mf | dp | ml | 3.58 | low |
| 1434 | aFKBD | ra90 | mf | dp | ml | 3.66 | low |
| 1435 | aFKBD | ra97 | mf | dp | ml | 5.45 | low |
| 1436 | aFKBD | ra94 | mf | dp | ml | 5.38 | low |
| 1437 | aFKBD | ra353 | mf | dp | ml | 5.60 | low |
| 1438 | aFKBD | ra88 | mf | dp | ml | 4.94 | low |
| 1439 | aFKBD | ra185 | mf | dp | ml | 5.06 | low |
| 1440 | aFKBD | ra124 | mf | dp | ml | 5.00 | low |
| 1441 | aFKBD | ra526 | mf | dp | ml | 5.21 | low |
| 1442 | aFKBD | ra121 | mf | dp | ml | 5.02 | low |
| 1443 | aFKBD | ra119 | mf | dp | ml | 5.06 | low |
| 1444 | aFKBD | ra339 | mf | dp | ml | 5.05 | low |
| 1445 | aFKBD | ra106 | mf | dp | ml | 4.79 | low |
| 1446 | aFKBD | my | mf | dp | ml | 4.63 | low |
| 1447 | aFKBD | ra133 | mf | dp | ml | 4.55 | low |
| 1448 | aFKBD | ra513 | y | dp | ml | 4.10 | high |
| 1449 | aFKBD | ra120 | y | dp | ml | 4.51 | high |
| 1450 | aFKBD | ra92 | y | dp | ml | 4.72 | low |
| 1451 | aFKBD | ra107 | y | dp | ml | 4.79 | low |
| 1452 | aFKBD | ra93 | y | dp | ml | 4.80 | low |
| 1453 | aFKBD | ra95 | y | dp | ml | 4.91 | low |
| 1454 | aFKBD | ra96 | y | dp | ml | 4.92 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1455 | aFKBD | Ra87 | y | dp | ml | 4.58 | low |
| 1456 | aFKBD | ra104 | y | dp | ml | 4.59 | low |
| 1457 | aFKBD | ra123 | y | dp | ml | 4.58 | low |
| 1458 | aFKBD | ra89 | y | dp | ml | 3.06 | low |
| 1459 | aFKBD | ra90 | y | dp | ml | 3.24 | low |
| 1460 | aFKBD | ra91 | y | dp | ml | 3.20 | low |
| 1461 | aFKBD | ra97 | y | dp | ml | 4.77 | low |
| 1462 | aFKBD | ra94 | y | dp | ml | 4.76 | low |
| 1463 | aFKBD | ra353 | y | dp | ml | 5.14 | low |
| 1464 | aFKBD | ra88 | y | dp | ml | 4.42 | low |
| 1465 | aFKBD | ra185 | y | dp | ml | 4.49 | low |
| 1466 | aFKBD | ra124 | y | dp | ml | 4.44 | low |
| 1467 | aFKBD | ra526 | y | dp | ml | 4.75 | low |
| 1468 | aFKBD | ra121 | y | dp | ml | 4.47 | low |
| 1469 | aFKBD | ra119 | y | dp | ml | 4.50 | low |
| 1470 | aFKBD | ra339 | y | dp | ml | 4.49 | medium |
| 1471 | aFKBD | ra106 | y | dp | ml | 4.25 | low |
| 1472 | aFKBD | my | y | dp | ml | 4.16 | low |
| 1473 | aFKBD | ra133 | y | dp | ml | 4.03 | low |
| 1474 | raa26 | ra602 | mf | dp | ml | 6.14 | high |
| 1475 | raa26 | ra602 | y | dp | ml | 5.89 | high |
| 1476 | raa21 | ra602 | y | dp | ml | 3.91 | high |
| 1477 | raa21 | ra602 | mf | dp | ml | 5.99 | high |
| 1478 | raa7 | ra602 | mf | dp | ml | 5.15 | medium |
| 1479 | raa7 | ra602 | y | dp | ml | 4.08 | low |
| 1480 | raa6 | ra602 | mf | dp | ml | 6.33 | high |
| 1481 | raa6 | ra602 | y | dp | ml | 6.38 | high |
| 1482 | raa1 | ra602 | mf | dp | ml | 4.47 | high |
| 1483 | raa1 | ra602 | y | dp | ml | 4.47 | low |
| 1484 | raa25 | ra602 | mf | dp | ml | 5.90 | high |
| 1485 | raa14 | ra602 | mf | dp | ml | 7.44 | low |
| 1486 | raa14 | ra602 | y | dp | ml | 6.60 | low |
| 1487 | raa16 | ra602 | mf | dp | ml | 7.30 | low |
| 1488 | raa16 | ra602 | y | dp | ml | 6.52 | low |
| 1489 | raa12 | ra602 | mf | dp | ml | 6.10 | high |
| 1490 | raa12 | ra602 | y | dp | ml | 5.51 | high |
| 1491 | raa3 | ra602 | mf | dp | ml | 5.88 | low |
| 1492 | raa3 | ra602 | y | dp | ml | 5.28 | low |
| 1493 | aFKBD | ra602 | ra109 | dp | ml | 3.50 | high |
| 1494 | raa13 | ra602 | y | dp | ml | 6.65 | low |
| 1495 | raa11 | ra602 | mf | dp | ml | 6.29 | high |
| 1496 | raa11 | ra602 | y | dp | ml | 4.66 | high |
| 1497 | raa15 | ra602 | mf | dp | ml | 5.17 | low |
| 1498 | raa15 | ra602 | y | dp | ml | 4.70 | low |
| 1499 | raa4 | ra602 | mf | dp | ml | 4.69 | low |
| 1500 | raa4 | ra602 | y | dp | ml | 5.39 | low |
| 1501 | raa31 | ra602 | mf | dp | ml | 5.00 | medium |
| 1502 | raa29 | ra602 | mf | dp | ml | 5.22 | high |
| 1503 | raa29 | ra602 | y | dp | ml | 4.59 | medium |
| 1504 | raa32 | ra602 | mf | dp | ml | 5.66 | medium |
| 1505 | raa8 | ra602 | mf | dp | ml | 4.71 | high |
| 1506 | raa10 | ra602 | mf | dp | ml | 4.91 | high |
| 1507 | raa8 | ra602 | y | dp | ml | 5.15 | medium |
| 1508 | raa10 | ra602 | y | dp | ml | 4.19 | low |
| 1509 | raa2 | ra602 | mf | dp | ml | 4.76 | medium |
| 1510 | raa2 | ra602 | y | dp | ml | 5.91 | low |
| 1511 | raa5 | ra602 | mf | dp | ml | 5.26 | low |
| 1512 | raa5 | ra602 | y | dp | ml | 4.60 | low |
| 1513 | aFKBD | ra602 | ra119 | dp | ml | 4.91 | high |
| 1514 | aFKBD | ra602 | ra520 | dp | ml | 4.31 | high |
| 1515 | aFKBD | ra602 | ra569 | dp | ml | 4.10 | medium |
| 1516 | aFKBD | ra602 | ra570 | dp | ml | 4.01 | low |
| 1517 | aFKBD | ra602 | ra571 | dp | ml | 4.01 | low |
| 1518 | aFKBD | ra602 | ra572 | dp | ml | 3.95 | low |
| 1519 | aFKBD | ra602 | ra399 | dp | ml | 4.71 | low |
| 1520 | aFKBD | ra602 | ra515 | dp | ml | 5.34 | low |
| 1521 | aFKBD | ra602 | ra398 | dp | ml | 6.89 | low |
| 1522 | aFKBD | ra602 | y | dp | ml | 3.65 | high |
| 1523 | raa9 | ra602 | mf | dp | ml | 4.02 | low |
| 1524 | aFKBD | ra132 | mf | dp | ml | 5.76 | low |
| 1525 | aFKBD | ra127 | mf | dp | ml | 5.46 | high |
| 1526 | aFKBD | ra126 | mf | dp | ml | 5.39 | low |
| 1527 | aFKBD | ra189 | mf | dp | ml | 5.91 | medium |
| 1528 | aFKBD | ra84 | mf | dp | ml | 5.19 | high |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1529 | aFKBD | ra83 | mf | dp | ml | 5.92 | medium |
| 1530 | aFKBD | ra130 | mf | dp | ml | 6.01 | low |
| 1531 | aFKBD | ra600 | mf | dp | ml | 5.88 | high |
| 1532 | aFKBD | ra565 | mf | dp | ml | 5.97 | low |
| 1533 | aFKBD | ra602 | y | dp | ra83 | 4.44 | low |
| 1534 | aFKBD | tic | mf | dp | ml | 4.10 | low |
| 1535 | aFKBD | ra147 | mf | dp | ml | 6.18 | low |
| 1536 | aFKBD | ra563 | mf | dp | ml | 6.14 | low |
| 1537 | aFKBD | ra602 | mf | dp | ml | 5.83 | low |
| 1538 | raal3 | ra602 | mf | dp | ml | 7.41 | low |
| 1539 | raal9 | ra602 | mf | dp | ml | 5.46 | low |
| 1540 | raal9 | ra602 | y | dp | ml | 4.75 | low |
| 1541 | raa20 | ra602 | mf | dp | ml | 6.31 | low |
| 1542 | raa22 | ra602 | ra471 | dp | ml | 3.31 | medium |
| 1543 | aFKBD | ra602 | ra472 | dp | ml | 3.70 | high |
| 1544 | aFKBD | ra602 | ra471 | dp | ml | 5.26 | high |
| 1545 | aFKBD | ra602 | mf | ra473 | ml | 6.57 | low |
| 1546 | aFKBD | ra602 | y | ra473 | ml | 3.07 | low |
| 1547 | aFKBD | ra602 | ra512 | ra105 | ml | 6.45 | high |
| 1548 | aFKBD | ra513 | ra512 | ra105 | ml | 6.06 | medium |
| 1549 | aFKBD | ra513 | mf | ra105 | ml | 5.84 | medium |
| 1550 | raa20 | ra602 | y | dp | ml | 5.78 | low |
| 1551 | aFKBD | ra513 | ra512 | dp | ml | 6.23 | low |
| 1552 | aFKBD | ra602 | ra511 | dp | ml | 6.59 | medium |
| 1553 | aFKBD | ra513 | ra520 | dp | ml | 5.13 | medium |
| 1554 | aFKBD | ra513 | ra520 | ra105 | ml | 4.13 | high |
| 1555 | raa18 | ra602 | mf | dp | ml | 4.39 | high |
| 1556 | rae27 | ra602 | mf | dp | ml | 5.02 | low |
| 1557 | raa17 | ra602 | mf | dp | ml | 4.37 | high |
| 1558 | afkbd | phg | ra500 | dp | ml | 3.81 | high |
| 1559 | afkbd | phg | ra501 | dp | ml | 3.86 | medium |
| 1560 | afkbd | phg | ra502 | dp | ml | 3.83 | low |
| 1561 | afkbd | phg | ra503 | dp | ml | 3.19 | low |
| 1562 | afkbd | phg | ra504 | dp | ml | 3.22 | low |
| 1563 | rae21 | ra147 | napA | ra562 | g | 6.94 | high |
| 1564 | rae29 | ra147 | napA | ra562 | g | 6.67 | high |
| 1565 | rae26 | ra147 | napA | ra562 | g |  | low |
| 1566 | rae1 | my | df | sar | df |  | medium |
| 1567 | rae10 | my | df | sar | df |  | medium |
| 1568 | rae11 | my | df | sar | df |  | low |
| 1569 | rae12 | my | df | sar | df |  | low |
| 1570 | rae13 | my | df | sar | df |  | medium |
| 1571 | rae14 | my | df | sar | df |  | low |
| 1572 | rae16 | my | df | sar | df |  | low |
| 1573 | rae16a | my | df | sar | df |  | low |
| 1574 | rae17 | my | df | sar | df |  | low |
| 1575 | rae18 | my | df | sar | df |  | low |
| 1576 | rae19 | my | df | sar | df |  | medium |
| 1577 | rae2 | my | df | sar | df |  | medium |
| 1578 | rae20 | my | df | sar | df |  | low |
| 1579 | rae21 | my | df | sar | df |  | medium |
| 1580 | rae26 | my | df | sar | df |  | low |
| 1581 | rae3 | my | df | sar | df |  | medium |
| 1582 | rae4 | my | df | sar | df |  | low |
| 1583 | rae5 | my | df | sar | df |  | low |
| 1584 | rae9 | my | df | sar | df |  | low |
| 1585 | afkbd | phg | ra655 | dp | ml | 3.72 | High |
| 1586 | afkbd | phg | ra656 | dp | ml | 3.74 | Med |
| 1587 | afkbd | phg | ra626 | dp | ml | 3.15 | Low |
| 1588 | afkbd | phg | ra592 | dp | ml | 3.44 | High |
| 1589 | afkbd | phg | ra618 | dp | ml | 3.10 | Low |
| 1590 | afkbd | phg | ra655 | dp | ml | 3.72 | High |
| 1591 | afkbd | phg | ra656 | dp | ml | 3.74 | Med |
| 1592 | afkbd | phg | ra626 | dp | ml | 3.15 | Low |
| 1593 | afkbd | phg | ra592 | dp | ml | 3.44 | High |
| 1594 | afkbd | phg | ra618 | dp | ml | 3.10 | Low |
| 1595 | afkbd | phg | ra620 | dp | ml | 3.92 | Low |
| 1596 | afkbd | phg | ra623 | dp | ml | 3.96 | Low |
| 1597 | afkbd | ml | df | mi | g | 6.48 | High |
| 1598 | aFKBD | Ra602 | Ra503 | dp | ml | 5.09 | high |
| 1599 | aFKBD | mf | dp | ml |  | 5.83 | low |
| 1600 | aFKBD | Ra602 | mf | ml |  | 4.01 | low |
| 1601 | aFKBD | Ra602 | y | ml |  | 3.53 | low |
| 1602 | aFKBD | y | dp | ml |  | 3.57 | low |

TABLE 7-continued

Rapafucin compound 878 to compound 1604.

| Compound No. | FKBD with linkers | Monomer 1 | Monomer 2 | Monomer 3 | Monomer 4 | Retention Time | Rel. Uptake, 293T |
|---|---|---|---|---|---|---|---|
| 1603 | aFKBD | Ra195 | dp | ml | | 4.02 | low |
| 1604 | aFKBD | mf | dp | ml | | 4.49 | low |

TABLE 8

Rapafucin compound 1605 to compound 1627.

| Compound No. | RA1 | RA2 | RA3 | RA4 | RA5 | Hill-slope | Uptake, IC50 (nM) |
|---|---|---|---|---|---|---|---|
| 1605 | aFKBD | Gly | dmPhe | Pro | mVal | −0.9753 | 27.95 |
| 1606 | aFKBD | Ala | dmPhe | Pro | mVal | −1.164 | 23.73 |
| 1607 | aFKBD | Nva | dmPhe | Pro | mVal | −1.112 | 18 |
| 1608 | aFKBD | Leu | dmPhe | Pro | mVal | −1.105 | 54.14 |
| 1609 | aFKBD | Phe | dmPhe | Pro | mVal | −1.191 | 54.99 |
| 1610 | aFKBD | Phg | dmPhe | Pro | mVal | −0.8952 | 16.51 |
| 1611 | eFKBD | Gly | dmPhe | Pro | mVal | −1.024 | 48.88 |
| 1612 | eFKBD | Ala | dmPhe | Pro | mVal | −1.125 | 33.54 |
| 1613 | eFKBD | HoSMe | dmPhe | Pro | mVal | −0.8614 | 59.46 |
| 1614 | aFKBD | Ala | dmPhe | Pro | mIle | −0.6276 | 34.4 |
| 1615 | aFKBD | Nva | dmPhe | Pro | mIle | −0.87 | 12.19 |
| 1616 | aFKBD | Phg | dmPhe | Pro | mIle | −0.9138 | 100.1 |
| 1617 | eFKBD | Ala | dmPhe | Pro | mIle | −1.212 | 34.15 |
| 1618 | eFKBD | Nva | dmPhe | Pro | mIle | −1.195 | 173.1 |
| 1619 | eFKBD | Ala | dmPhe | Pro | mAla | −1.134 | 66.71 |
| 1620 | eFKBD | Gly | dmPhe | Pro | mNle | −1.007 | 13.91 |
| 1621 | eFKBD | Ala | dmPhe | Pro | mNle | −1.017 | 9.76 |
| 1622 | eFKBD | Gly | dmPhe | Pro | mLeu | −1.494 | 28.54 |
| 1623 | eFKBD | Ala | dmPhe | Pro | mLeu | −0.741 | 10.53 |
| 1624 | aFKBD | Ala | dmPhe | Pro | mLeu | −0.3876 | 31.45 |
| 1625 | eFKBD | Gly | dmPhe | Pro | mNva | −1.363 | 42.27 |
| 1626 | eFKBD | Gly | dmPhe | Pro | dmAla | −1.314 | 154.9 |
| 1627 | eFKBD | Gly | dmPhe | Pro | Ach | −1.236 | 261.9 |

In treatment, the dose of agent optionally ranges from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other embodiments the dose ranges from about 100 mg/kg to about 5 g/kg, about 500 mg/kg to about 2 mg/kg and about 750 mg/kg to about 1.5 g/kg of the subject's body weight. For example, depending on the type and severity of the disease, about 1 µg/kg to 15 mg/kg (e.g., 0.1-20 mg/kg) of agent is a candidate dosage for administration to the patient, whether, for example, by one or more separate administrations, or by continuous infusion. A typical daily dosage is in the range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit doses can be in the range, for instance of about 5 mg to 500 mg, such as 50 mg, 100 mg, 150 mg, 200 mg, 250 mg and 300 mg. The progress of therapy is monitored by conventional techniques and assays.

In some embodiments, an agent is administered to a human patient at an effective amount (or dose) of less than about 1 µg/kg, for instance, about 0.35 to about 0.75 µg/kg or about 0.40 to about 0.60 µg/kg. In some embodiments, the dose of an agent is about 0.35 µg/kg, or about 0.40 µg/kg, or about 0.45 µg/kg, or about 0.50 µg/kg, or about 0.55 µg/kg, or about 0.60 µg/kg, or about 0.65 µg/kg, or about 0.70 µg/kg, or about 0.75 µg/kg, or about 0.80 µg/kg, or about 0.85 µg/kg, or about 0.90 µg/kg, or about 0.95 µg/kg or about 1 µg/kg. In various embodiments, the absolute dose of an agent is about 2 µg/subject to about 45 µg/subject, or about 5 to about 40, or about 10 to about 30, or about 15 to about 25 µg/subject. In some embodiments, the absolute dose of an agent is about 20 µg, or about 30 µg, or about 40 µg.

In various embodiments, the dose of an agent may be determined by the human patient's body weight. For example, an absolute dose of an agent of about 2 µg for a pediatric human patient of about 0 to about 5 kg (e.g., about 0, or about 1, or about 2, or about 3, or about 4, or about 5 kg); or about 3 µg for a pediatric human patient of about 6 to about 8 kg (e.g., about 6, or about 7, or about 8 kg), or about 5 µg for a pediatric human patient of about 9 to about 13 kg (e.g., 9, or about 10, or about 11, or about 12, or about 13 kg); or about 8 µg for a pediatric human patient of about 14 to about 20 kg (e.g., about 14, or about 16, or about 18, or about 20 kg), or about 12 µg for a pediatric human patient of about 21 to about 30 kg (e.g., about 21, or about 23, or about 25, or about 27, or about 30 kg), or about 13 µg for a pediatric human patient of about 31 to about 33 kg (e.g., about 31, or about 32, or about 33 kg), or about 20 µg for an adult human patient of about 34 to about 50 kg (e.g., about 34, or about 36, or about 38, or about 40, or about 42, or about 44, or about 46, or about 48, or about 50 kg), or about 30 µg for an adult human patient of about 51 to about 75 kg (e.g., about 51, or about 55, or about 60, or about 65, or about 70, or about 75 kg), or about 45 µg for an adult human patient of greater than about 114 kg (e.g., about 114, or about 120, or about 130, or about 140, or about 150 kg).

In certain embodiments, an agent in accordance with the methods provided herein is administered subcutaneously (s.c.), intraveneously (i.v.), intramuscularly (i.m.), intranasally or topically. Administration of an agent described herein can, independently, be one to four times daily or one to four times per month or one to six times per year or once every two, three, four or five years. Administration can be for the duration of one day or one month, two months, three months, six months, one year, two years, three years, and may even be for the life of the human patient. The dosage may be administered as a single dose or divided into multiple doses. In some embodiments, an agent is administered about 1 to about 3 times (e.g., 1, or 2 or 3 times).

The following example is provided to further illustrate the advantages and features of the present disclosure, but it is not intended to limit the scope of the disclosure. While this example is typical of those that might be used, other procedures, methodologies, or techniques known to those skilled in the art may alternatively be used.

EXAMPLES

General experimental for synthesis. Syntheti reagents. Piperidine, N,N-diisopropylethylamine (DIPEA) were purchased from Alfa Aesar. Anhydrous pyridine was purchased from Acros. Solid support resin with 2-chlorotrityl chloride (Cat #: 03498) was purchased from Chem-Impex. HATU was purchased from ChemImpex. Fmoc protected amino acid building blocks were purchased from ChemImpex, Novabiochem or GL Biochem. Dichloromethane (DCM or $CH_2Cl_2$), methanol (MeOH), hexanes, ethyl acetate (EtOAc), 1,2-dichloroethane (DCE, anhydrous), N,N'-dimethylformamide (DMF, anhydrous), Hoveyda-Grubbs catalyst 2nd generation and all the other chemical reagents were purchased from Sigma-Aldrich.

Instruments for synthesis and purification. NMR spectra were recorded with Burker-400 and -500. High performance liquid chromatographic analyses were performed with Agilent LC-MS system (Agilent 1260 series, mass detector 6120 quadrupole). Orbital shaking for solid-phase reactions was performed on a Mettler-Toledo Bohdan MiniBlock system for 96 tubes (30-200 mg resin in SiliCycle tubes) or a VWR Mini Shaker (0.2-2 g resin in a plastic syringe with a fritted disc). Reagents were added with an adjustable Rainin 8-channel pipette for the MiniBlock system. Microwave reactions were performed with a Biotage Initiator Plus or Multiwave Pro with silicon carbide 24-well blocks from Anton Parr. Compound purification at 0.05-50 g scale was performed with Teledyne Isco CombiFlash Rf 200 or Biotage Isolera One systems followed by a Heidolph rotary evaporator. Purification at 1-50 mg scale was performed with Agilent HPLC system. Mixture of Rapafucins in the 45,000-compound library are purified in a high-throughput manner by SPE cartridges (Biotage, 460-0200-C, ISOLUTE, SI 2 g/6 mL) on vacuum manifold (Sigma-Aldrich, Visiprep™ SPE Vacuum Manifold, Disposable Liner, 12-port) followed by overnight drying with a custom-designed box (50 cm×50 cm×15 cm) that allows air flowing rapidly inside to remove the solvent. The high-throughput weighing of the compounds in the library was done by a Mettler-Toledo analytical balance that linked (Sartorious Entris line with RS232 port) to a computer with custom-coded electronic spreadsheet.

FKBD Example 1

4-((3-((R)-1-(((S)-1-(4-(acryloyloxy)-3,3-dimethyl-2-oxobutanoyl)piperidine-2-carbonyl)oxy)-3-(3,4-dimethoxyphenyl)propyl)phenyl)amino)-4-oxobutanoic acid (aFKBD)

Scheme 3. Synthesis of intermediate 5 ((S)-1-(4-(acryloyloxy)-3,3-dimethyl-2-oxobutanoyl)piperidine-2-carboxylic acid).

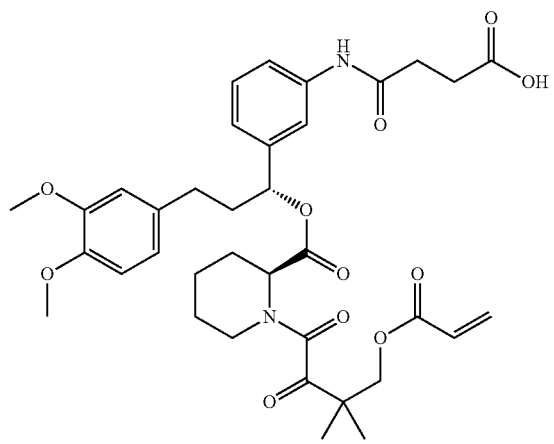

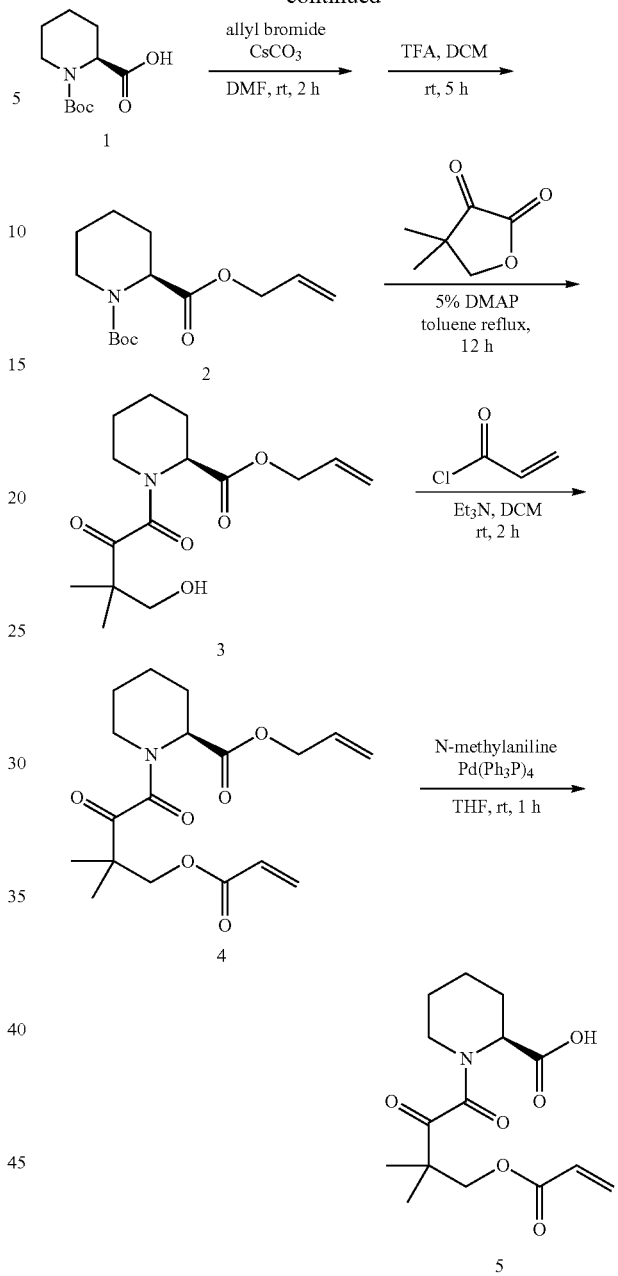

2-allyl 1-(tert-butyl) (S)-piperidine-1,2-dicarboxylate (2). To a solution of N-Boc homoproline 1 (6.30 g) in DMF (40 mL), $Cs_2CO_3$ (2.90 g) was added. The resulting suspension was stirred at RT for 5 min before the addition of allyl bromide (6.3 g). After stirring at RT for 2 h, the suspension was filtered through a pad of celite, rinsed with EtOAc (50 mL), and washed with HCl (1M, 50 mL×3). The organic layer was dried over $Na_2SO_4$ and co-evaporated with toluene (30 mL×2). Crude product (8.10 g) was collected as a yellow oil and was pure enough for the next step without further purification. The crude product (8.10 g) and TFA (4.3 g) were mixed well in dichloromethane (20 mL) and stirred at RT for 0.5 h. 2-allyl 1-(tert-butyl) (S)-piperidine-1,2-dicarboxylate 2 (3.00 g) was collected as a yellow oil and was pure enough for the next step without further purification.

allyl (S)-1-(4-hydroxy-3,3-dimethyl-2-oxobutanoyl)piperidine-2-carboxylate (3). Compound 2 (3.0 g), dihydro-4, 4-dimethyl-2,3-furandione (2.1 g) and DMAP (20 mg) were dissolved in toluene (20 mL) and the reaction was refluxed with an oil bath (120° C.) for 14 h. After the solvent was removed, the residue was purified by column chromatography (80-200 mesh) with EtOAc/hexane (1/3). 3 (3.50 g) was collected as a yellow oil. $^1$H NMR (500 MHz, CDCl$_3$) δ 6.04-5.80 (m, 1H), 5.36 (d, J=17 Hz, 1H), 5.31-5.25 (m, 2H), 4.68 (s, 2H), 3.76-3.56 (m, 2H), 3.50 (d, J=13 Hz, 1H), 3.40 (s, 1H), 3.20 (t, J=13 Hz, 1H), 2.37 (d, J=13 Hz, 1H), 1.84-1.61 (m, 3H), 1.61-1.34 (m, 2H), 1.24 (s, 6H). $^{13}$C NMR (126 MHz, CDCl$_3$) δ 205.9, 170.1, 168.1, 131.4, 119.2, 69.3, 66.3, 51.6, 49.5, 44.2, 26.3, 24.8, 21.3, 21.2, 21.0.

allyl (S)-1-(4-(acryloyloxy)-3,3-dimethyl-2-oxobutanoyl)piperidine-2-carboxylate (4) Acryloyl chloride (0.78 g) in dry CH$_2$Cl$_2$ (20 mL) was added dropwise to a mixture of compound 3 (3.50 g) and N,N-diisopropylethylamine (2.0 mL) in 50 mL CH$_2$Cl$_2$ with ice-batch over 30 min. After addition, the reaction was allowed to stir at RT for 30 min before quenched with saturated NaHCO$_3$ solution (20 mL). The organic phase was washed with water, dried over Na$_2$SO$_4$, concentrated and purified by column (EtOAc:Hexans=1:5) to afford product 4 (2.21 g) as a yellow oil. $^1$H NMR (500 MHz, CDCl$_3$) δ 6.39 (dd, J=17, 1.5 Hz, 1H), 6.08 (dd, J=17, 11 Hz, 1H), 5.91 (ddt, J=17, 11, 6 Hz, 1H), 5.84 (dd, J=11, 1.5 Hz, 1H), 5.35 (ddd, J=17, 2.5, 1.5 Hz, 1H), 5.28-5.25 (m, 1H), 5.26 (ddd, J=11, 2.5, 1.5 Hz, 1H), 4.66 (ddd, J=6, 4, 2.5 Hz, 2H), 4.37 (d, J=11 Hz, 1H), 4.27 (d, J=11 Hz, 1H), 3.52 (dd, J=13, 1.5 Hz, 1H), 3.23 (td, J=13, 3 Hz, 1H), 2.34 (d, J=14 Hz, 1H), 1.84-1.76 (m, 1H), 1.76-1.67 (m, 1H), 1.67-1.60 (m, 1H), 1.59-1.47 (m, 1H), 1.47-1.38 (m, 1H), 1.36 (s, 3H), 1.35 (s, 3H). $^{13}$C NMR (126 MHz, CDCl$_3$) δ 204.8, 169.8, 166.7, 165.5, 131.5, 131.2, 128.0, 118.9, 69.5, 69.3, 66.0, 51.3, 46.7, 43.9, 26.4, 24.9, 22.2, 21.5, 21.1. HRMS for [M+H]+ C18H25NO6, calculated: 352.1760, observed: 352.1753.

(S)-1-(4-(acryloyloxy)-3,3-dimethyl-2-oxobutanoyl)piperidine-2-carboxylic acid (5). compound 4 (4.2 g), Pd(PPh3)4 (230 mg), N-methylaniline (2.5 mL) were dissolved in THF (40 mL) and stirred at RT for 6 h. The reaction mixture was then diluted with EtOAc (80 mL) and washed with HCl (1M, 50 mL×3). The organic phase was separated, dried over Na$_2$SO$_4$, filtered and concentrated. The crude product was purified using column chromatography (200-400 mesh), where the byproduct can be eluted with 2% MeOH in dichloromethane, followed by the desired product with 3% MeOH and 0.1% AcOH in dichloromethane. 5 (2.55 g) was collected as a white solid (66%). $^1$H NMR (500 MHz, CDCl$_3$) δ 9.96 (s, 1H), 6.39 (d, J=17 Hz, 1H), 6.08 (dd, J=17, 10 Hz, 1H), 5.85 (d, J=10 Hz, 1H), 5.30 (s, 1H), 4.55-4.30 (m, 1H), 4.32 (d, J=6 Hz, 2H), 3.53 (d, J=12 Hz, 1H), 3.24 (t, J=12 Hz, 1H), 2.35 (d, J=13 Hz, 1H), 1.91-1.60 (m, 2H), 1.60-1.42 (m, 2H), 1.36 (s, 3H), 1.34 (s, 3H). $^{13}$C NMR (126 MHz, CDCl$_3$) δ 204.7, 175.3, 166.8, 165.7, 131.4, 127.8, 69.6, 69.5, 51.2, 46.7, 44.0, 26.2, 24.9, 22.1, 21.8, 21.1. HRMS for [M+H]+ C15H21NO6, calculated: 312.1447, observed: 312.1444.

Scheme 4. Synthesis of aFKBD.

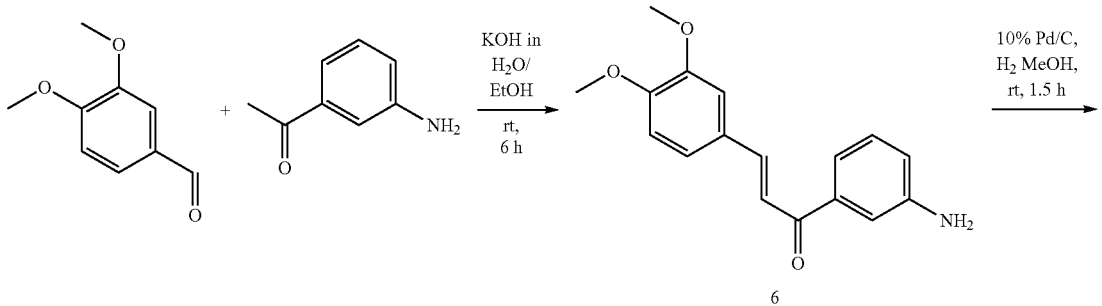

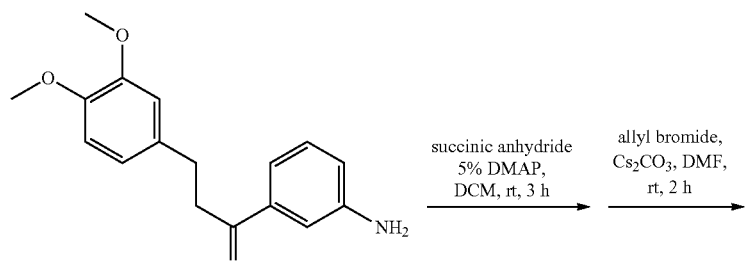

-continued
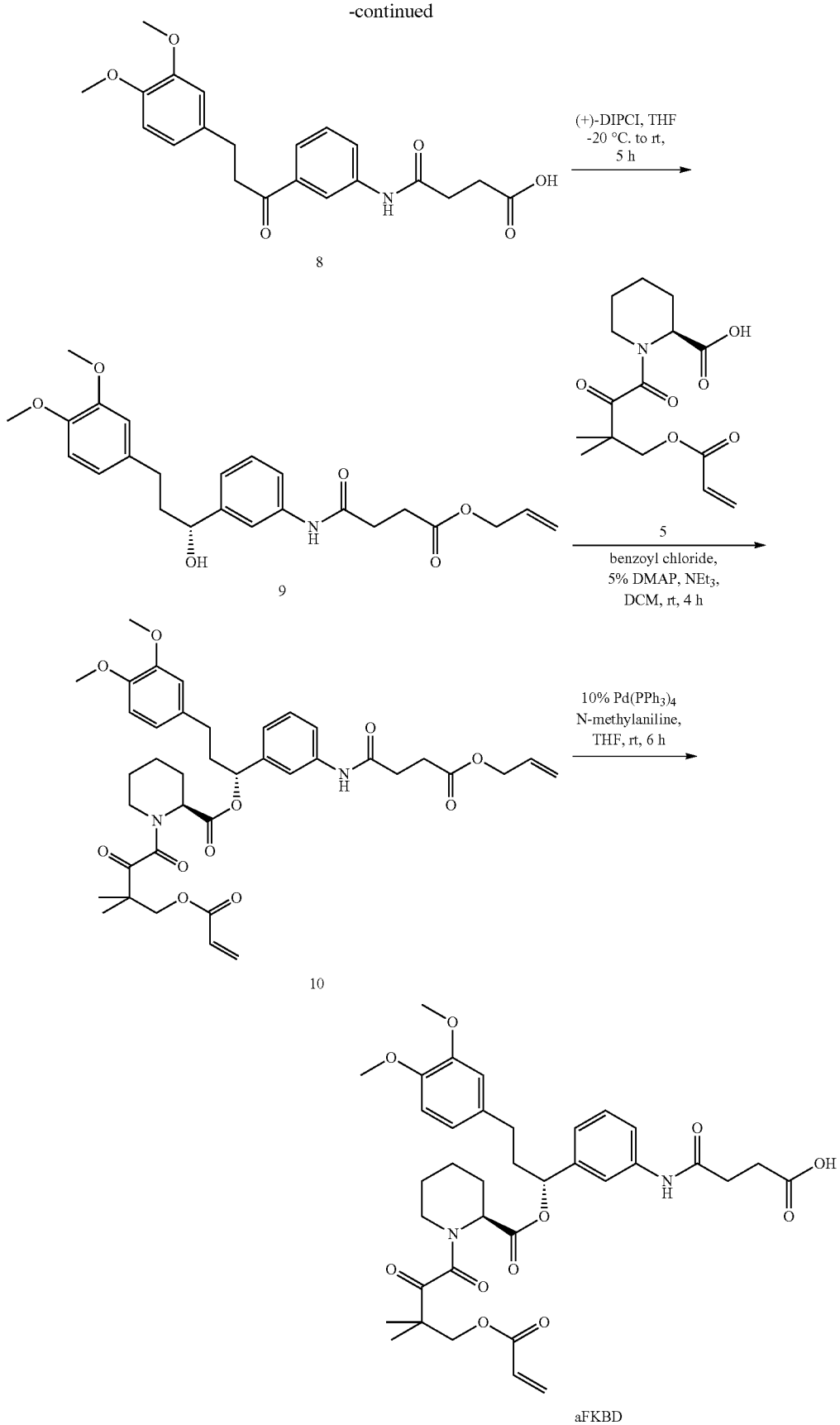

(E)-1-(3-aminophenyl)-3-(3,4-dimethoxyphenyl)prop-2-en-1-one (6). To a solution of 3,4-dimethoxybenzaldehyde (5.10 g) and 3-amino acetophenone (4.15 g) mixture in EtOH (20 mL, 95%), NaOH (0.2 g in 2 mL water) was added. The reaction mixture was stirred at RT for 6 h and a slurry of yellow precipitate was formed. The reaction mixture was then diluted with EtOAc (40 mL) and washed with water (30 mL×3). Upon concentrated, the crude product 6 (9.0 g) is pure enough for the next step.

1-(3-aminophenyl)-3-(3,4-dimethoxyphenyl)propan-1-one (7). To a solution of α,β-unsaturated ketone 6 (crude, 9.0 g) in MeOH (20 mL), Pd/C (10%, 1.61 g) was added. The reaction vessel was flushed with hydrogen gas repetitively by using a balloon of hydrogen and high vacuum. The reaction mixture was stirred at RT for 1 h before filtered through a pad of celite. Longer reaction time would render the reaction to generate undesired byproducts. The filtrate was concentrated and subject to column chromatography (50 g silica gel) and eluted with EtOAc/CH$_2$Cl$_2$/hexane (1/3/3 to 1/1/1). 7 (2.48 g) was collected as a yellow oil. $^1$H NMR (500 MHz, CDCl$_3$) δ 7.36-7.16 (m, 3H, ar), 6.92-6.71 (m, 4H, ar), 3.86 (s, 3H, OCH$_3$), 3.85 (s, 3H, OCH3), 3.81 (s, 2H, NH2), 3.23 (t, J=7.5 Hz, 2H, COCH2), 2.99 (t, J=7.4 Hz, 2H, ArCH2). $^{13}$C NMR (126 MHz, CDCl$_3$) δ 199.66 (C=O), 148.90 (ar), 147.38 (ar), 146.82 (ar), 138.03 (ar), 134.03 (ar), 129.49 (ar), 120.19 (ar), 119.61 (ar), 118.44 (ar), 113.91 (ar), 111.87 (ar), 111.35 (ar), 55.98 (OCH$_3$), 55.87 (OCH3), 40.80 (COCH2), 29.91 (ArCH2). HRMS for [M+H]+ C17H19NO$_3$, calculated: 286.1443, observed: 286.1436.

4-((3-(3-(3,4-dimethoxyphenyl)propanoyl)phenyl)amino)-4-oxobutanoic acid (9). Aniline 7 (3.50 g), succinic anhydride (1.0 g) and DMAP (61 mg) were mixed in dichloromethane (30 mL). After stirring at RT for 3 h, the reaction mixture was washed with HCl (1M, 30 mL×4). Crude product (3.80 g) was collected as a white solid and was used directly in the next step without further purification. Cs$_2$CO$_3$ (1.86 g) was added into a solution of the above crude product (3.80 g) in DMF (20 mL). The resulting suspension was stirred at RT for 10 min before allyl bromide (1.50 mL) was added. The reaction mixture was stirred for an extra 2 h. The white precipitate was filtered off with a pad of celite. The filtrate was added with EtOAc (40 mL) and H$_2$O (40 mL). Upon stirring for 10 min, the product precipitated. Product 9 (2.11 g) was obtained by filtration, air-dried as an off-white solid, and used in the next step without further purification.

(R)-1-(3-(4-(allyloxy)-4-oxobutanamido)phenyl)-3-(3,4-dimethoxyphenyl)propyl (S)-1-(4-(acryloyloxy)-3,3-dimethyl-2-oxobutanoyl)piperidine-2-carboxylate (10). Alcohol 9 (1.65 g) and carboxylic acid 5 (1.26 g, for synthesis see FKBD EXAMPLE 1) were dissolved in a mixture of THF (anhydrous, 5 mL) and dichloromethane (anhydrous, 10 mL). Benzoyl chloride (0.60 mL), Et3N (1.0 mL) and DMAP (18 mg) were added in order and the resulting suspension was stirred at RT for 2 h. Without further treatment, the mixture was subject to column chromatography (80-200 mesh) with EtOAc/hexane (1/2à1/1). 10 (2.50 g) was collected as a yellow foam. 1H NMR (500 MHz, CDCl3) δ 8.08 (s, 1H), 7.65 (d, J=8 Hz, 1H), 7.46 (s, 1H), 7.28 (t, J=8 Hz, 1H), 7.01 (d, J=8 Hz, 1H), 6.77 (d, J=9 Hz, 1H), 6.69 (d, J=5 Hz, 1H), 6.67 (s, 1H), 6.39 (dd, J=17, 1.5 Hz, 1H), 6.06 (dd, J=17, 10.5 Hz, 1H), 5.90 (ddt, J=17, 10.5, 6 Hz, 1H), 5.83 (dd, J=10.5, 1.5 Hz, 1H), 5.79 (ddd, J=10.5, 8, 3.5 Hz, 1H), 5.31 (dd, J=17, 1.5 Hz, 2H), 5.31 (d, J=6 Hz, 1H), 5.22 (dd, J=10.5, 1.5 Hz, 1H), 4.60 (dt, J=6, 1.5 Hz, 2H), 4.33 (d, J=0.7 Hz, 2H), 3.86 (s, 3H), 3.85 (s, 3H), 3.46 (d, J=14 Hz, 1H), 3.09 (dd, J=18, 8 Hz, 1H), 2.78 (t, J=6 Hz, 2H), 2.70 (t, J=6 Hz, 2H), 2.62-2.48 (m, 2H), 2.36 (d, J=14 Hz, 1H), 2.30-2.16 (m, 1H), 2.13-2.00 (m, 1H), 1.74 (d, J=10.5 Hz, 2H), 1.62 (d, J=12 Hz, 1H), 1.42 (d, J=12.6 Hz, 1H), 1.36 (s, 6H). 13C NMR (126 MHz, CDCl3) δ 205.6, 172.6, 169.8, 169.3, 166.2, 165.6, 148.9, 147.3, 140.7, 138.6, 133.5, 132.0, 131.5, 129.2, 127.8, 122.0, 120.2, 119.3, 118.4, 117.2, 111.7, 111.3, 76.5, 69.2, 65.5, 55.9, 55.9, 51.3, 46.8, 44.1, 38.1, 31.9, 31.1, 29.3, 26.1, 25.1, 22.0, 21.9, 20.9.

4-((3-((R)-1-(((S)-1-(4-(acryloyloxy)-3,3-dimethyl-2-oxobutanoyl)piperidine-2-carbonyl)oxy)-3-(3,4-dimethoxyphenyl)propyl)phenyl)amino)-4-oxobutanoic acid (aFKBD). 10 (2.50 g), Pd(PPh3)4 (100 mg), N-methylaniline (1.0 mL) were mixed well in THF (20 mL) at RT for 5 h. The reaction mixture was then diluted with EtOAc (50 mL) and washed with HCl (1M, 50 mL×3). The organic phase was dried over Na2SO4, filtered and concentrated. The crude product was purified by column chromatography (200-400 mesh), where the byproduct can be eluted with 2% MeOH in dichloromethane, followed by the desired product with 3% MeOH and 0.05% AcOH in dichloromethane. aFKBD (2.25 g) was collected as an off-white foam. $^1$H NMR (500 MHz, CDCl$_3$) δ 8.40 (s, 1H), 7.62 (s, 1H), 7.48 (s, 1H), 7.26 (t, J=7.5 Hz, 1H), 7.01 (d, J=7.5 Hz, 1H), 6.97 (dd, J=16, 7 Hz, 1H), 6.86-6.74 (m, 1H), 6.74-6.58 (m, 2H), 5.85-5.68 (m, 2H), 5.39-5.24 (m, 1H), 4.29 (q, J=11 Hz, 2H), 3.86 (s, 3H), 3.84 (s, 3H), 3.46 (d, J=13 Hz, 1H), 3.13 (t, J=13 Hz, 1H), 2.74 (d, J=5.5 Hz, 2H), 2.69 (d, J=5.5 Hz, 2H), 2.63-2.48 (m, 2H), 2.36 (d, J=13 Hz, 1H), 2.30-2.15 (m, 1H), 2.15-1.99 (m, 1H), 1.85 (d, J=6 Hz, 1H), 1.75 (d, J=12 Hz, 1H), 1.63 (d, J=13 Hz, 1H), 1.55-1.38 (m, 2H), 1.34 (s, 6H). $^{13}$C NMR (126 MHz, CDCl$_3$) δ 205.6, 176.8, 170.4, 169.4, 166.4, 166.1, 148.9, 147.3, 145.9, 140.7, 138.5, 133.5, 129.2, 122.1, 121.9, 120.2, 119.5, 117.4, 111.8, 111.4, 76.6, 69.0, 55.9, 55.8, 51.4, 46.8, 44.1, 38.1, 31.6, 31.1, 29.3, 26.2, 25.0, 21.8, 20.9, 18.1. HRMS for [M+H]+ C36H44O2N11, calculated: 681.3023, observed: 681.3018.

FKBD Example 2
2-(3-((R)-1-(((S)-1-(4-(acryloyloxy)-3,3-dimethyl-2-oxobutanoyl)piperidine-2-carbonyl)oxy)-3-(3,4-dimethoxyphenyl)propyl)phenoxy)acetic acid (eFKBD)
Scheme 5. Synthesis of eFKBD.
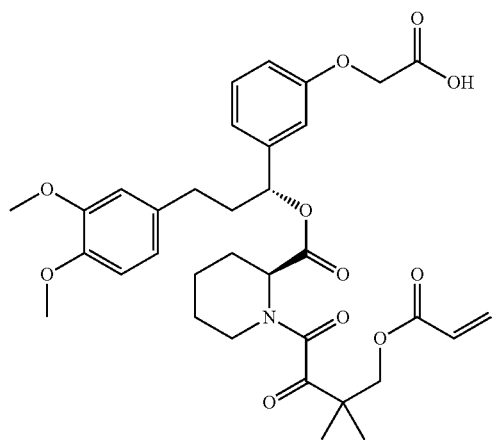
5
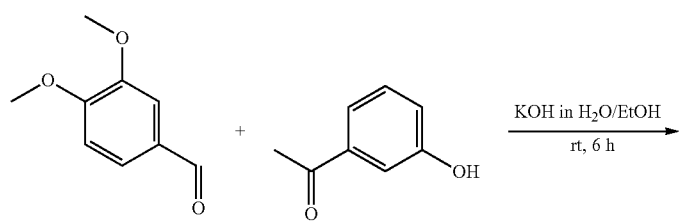
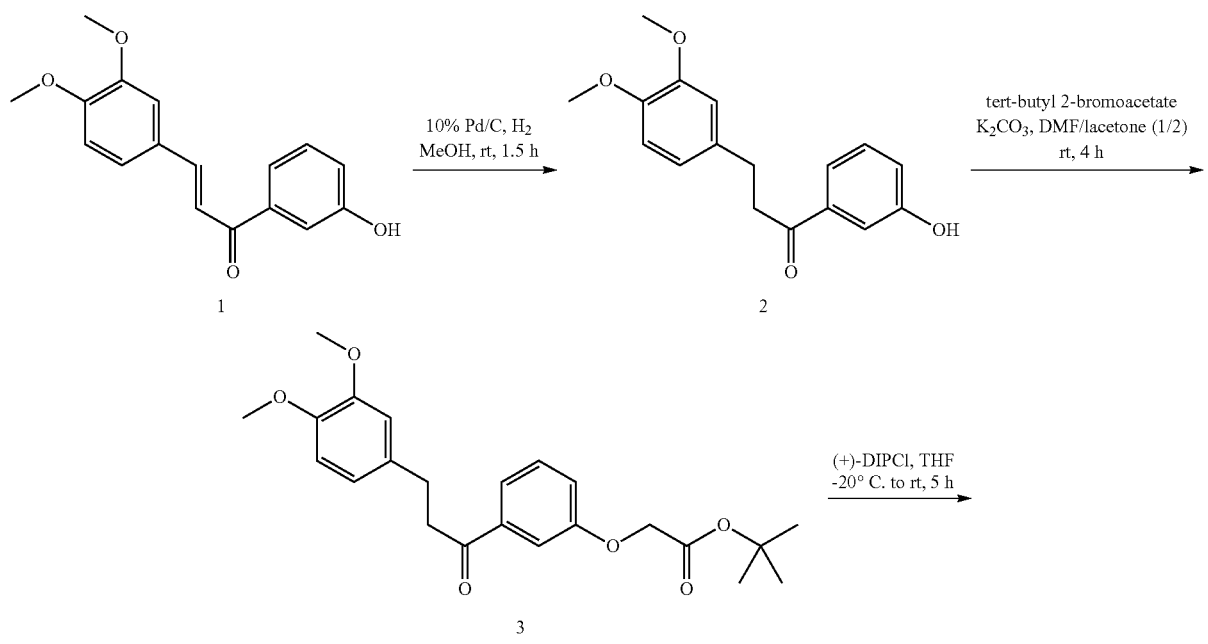

-continued
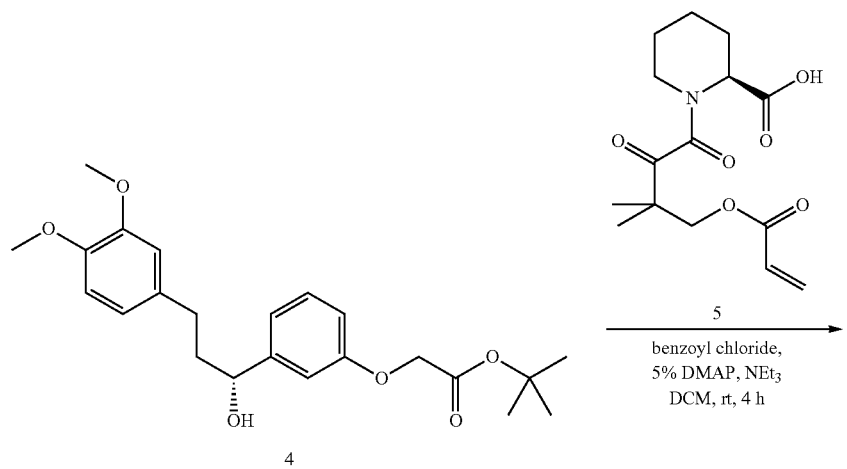
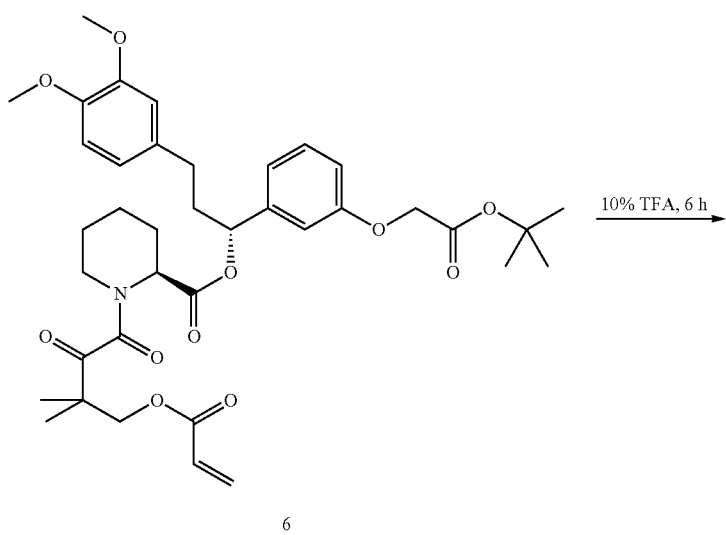
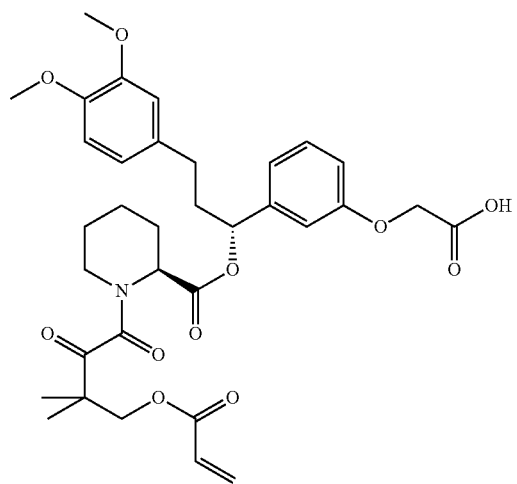
eFKBD (R)-1-(3-(2-(tert-butoxy)-2-oxoethoxy)phenyl)-3-(3,4-dimethoxyphenyl)propyl (S)-1-(4-(acryloyloxy)-3,3-dimethyl-2-oxobutanoyl)piperidine-2-carboxylate (6). Alcohol 4 (3.8 g, 1.0 eq. For its synthesis see Liu et al. (2014) *Angew. Chem. Int. Ed.* 53:10049-55), carboxylic acid 5 (4.1 g, 1.2 eq. for synthesis see FKBD EXAMPLE 1) and DMAP (134 mg, 0.1 eq.) were dissolved in a mixture of THF (anhydrous, 35 mL) and dichloromethane (anhydrous, 35 mL) in a round bottom 42 flask under argon protection. Et3N (4.7 mL) and benzoyl chloride (2.17 mL, 2.62 g, 1.7 eq.) were added dropwise through syringes in order and the resulting suspension was stirred at RT for 2 h. Reaction was monitored through TLC. When full conversion is achieved, the reaction mixture was diluted with 500 Ml EtOAc, washed with 5% HCl and saturated $NaHCO_3$. Organic phase was washed with brine and dried over $Na_2SO_4$. Then solvents were removed and product was purified by column chromatography (80-200 mesh) with EtOAc/hexane (1/10 to 1/3). 6 (5.3 g, 69%) was collected as a light yellow foam. $^1$H NMR (500 MHz, $CDCl_3$) δ 7.26 (d, J=8 Hz, 1H), 6.97 (d, J=8.5 Hz, 1H), 6.93-6.89 (m, 1H), 6.86-6.81 (m, 1H), 6.78 (d, J=8.5 Hz, 1H), 6.71-6.64 (m, 2H), 6.38 (dd, J=17, 1.5 Hz, 1H), 6.06 (dd, J=17, 10.5 Hz, 1H), 5.82 (dd, J=10.5, 1.5 Hz, 1H), 5.78 (dd, J=8, 6 Hz, 1H), 5.29 (d, J=5 Hz, 1H), 4.53 (s, 2H), 4.36 (d, J=11 Hz, 1H), 4.27 (d, J=11 Hz, 1H), 3.86 (s, 3H), 3.84 (s, 3H), 3.48 (d, J=13 Hz, 1H), 3.17 (td, J=13, 3.0 Hz, 1H), 2.67-2.44 (m, 2H), 2.37 (d, J=14 Hz, 1H), 2.32-2.18 (m, 1H), 2.14-1.99 (m, 1H), 1.83-1.65 (m, 2H), 1.65-1.56 (m, 1H), 1.50-1.43 (m, 2H), 1.48 (s, 9H), 1.35 (s, 3H), 1.35 (s, 3H). $^{13}$C NMR (126 MHz, $CDCl_3$) δ 204.8, 169.4, 167.8, 166.4, 165.4, 158.1, 148.9, 147.3, 141.3, 133.4, 131.2, 129.7, 127.9, 120.2, 119.8, 114.2, 113.2, 111.7, 111.3, 82.3, 76.7, 69.2, 65.7, 55.9, 55.8, 51.4, 46.6, 44.0, 37.9, 31.2, 28.0, 26.4, 25.0, 22.1, 21.6, 21.1. HRMS for [M+H]+ C38H49NO11, calculated: 696.3384, observed: 696.3386.

2-(3-((R)-1-(((S)-1-(4-(acryloyloxy)-3,3-dimethyl-2-oxobutanoyl)piperidine-2-carbonyl)oxy)-3-(3,4-dimethoxyphenyl)propyl)phenoxy)acetic acid (eFKBD). Compound 6 (5.3 g, 1.0 eq.) was dissolved in 60 mL of dichloromethane in a round-bottom flask under Ar protection. Then TFA (17 mL, 11.4 g, 13 eq.) was added through a syringe in 3 portions during 3.5 h while stirring at room temperature. The reaction was monitored through TLC. When full conversion was achieved, solvents and TFA were removed under vacuum. Product was purified by column chromatography (80-200 mesh) with EtOAc/hexane (1/5à1/1). eFKBD (4.6 g, 96%) was collected as a light yellow foam. $^1$H NMR (500 MHz, $CDCl_3$) δ 7.28 (dd, J=3.5 Hz, 3.5 Hz, 1H), 6.88 (d, J=8.5 Hz, 1H), 6.83-6.81 (m, 2H), 6.80-6.78 (m, 1H), 6.69-6.67 (m, 2H), 6.37 (d, J=8.5 Hz, 1H), 6.05-6.02 (m, 1H), 5.83-5.72 (m, 2H), 5.30-5.28 (dd, J=10, 5 Hz, 1H), 4.67 (dd, J=10, 5 Hz, 1H), 4.17 (dd, J=10, 6 Hz, 2H), 3.48-3.45 (m, 1H), 3.24-3.22 (m, 1H), 2.61-2.55 (m, 2H), 2.38 (m, 1H), 2.23 (m, 1H), 2.04 (m, 1H), 1.79 (m, 1H), 1.62 (m, 1H), 1.33 (m, 1H), 1.30 (m, 1H), 1.25 (s, 3H), 1.24 (s, 3H). $^{13}$C NMR (126 MHz, $CDCl_3$) δ 204.6, 169.2, 166.7, 165.7, 157.9, 149.0, 147.5, 141.7, 131.4, 129.9, 127.9, 120.0, 115.4, 111.8, 111.4, 111.1, 69.3, 65.2, 60.5, 55.9, 51.7, 44.1, 38.0, 31.4, 22.1, 21.1, 14.2. HRMS for [M+H]+ C34H42NO11, calculated: 640.2758, observed: 640.2761.

FKBD Example 3

4-(3-((R)-1-((S)-1-(4-(acryloyloxy)-3,3-dimethyl-2-oxobutanoyl)piperidine-2-carbonyloxy)-3-morpholinopropyl)phenylamino)-4-oxobutanoic acid (Raa1)

Scheme 6. Synthesis of Raa1 FKBD moiety.

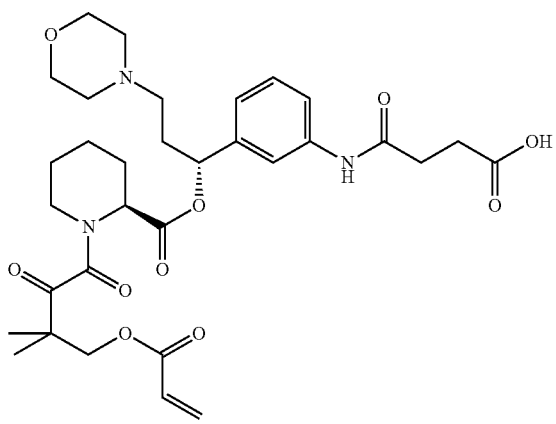

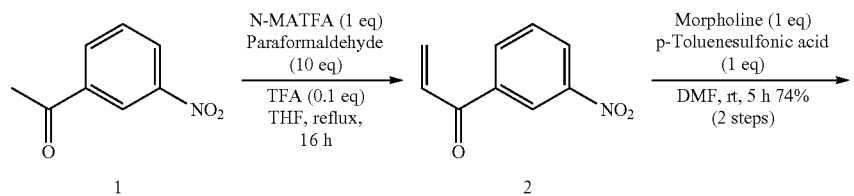

-continued
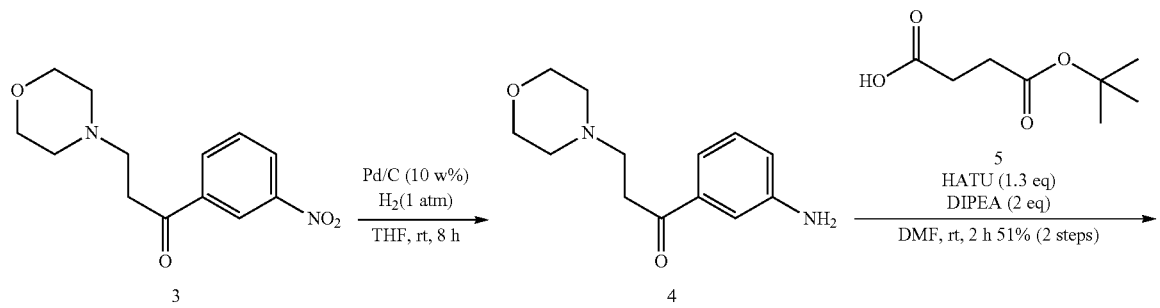
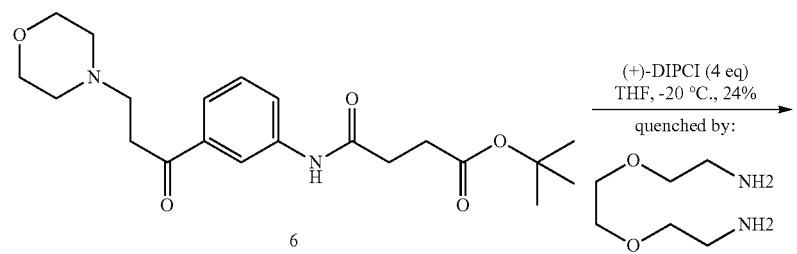
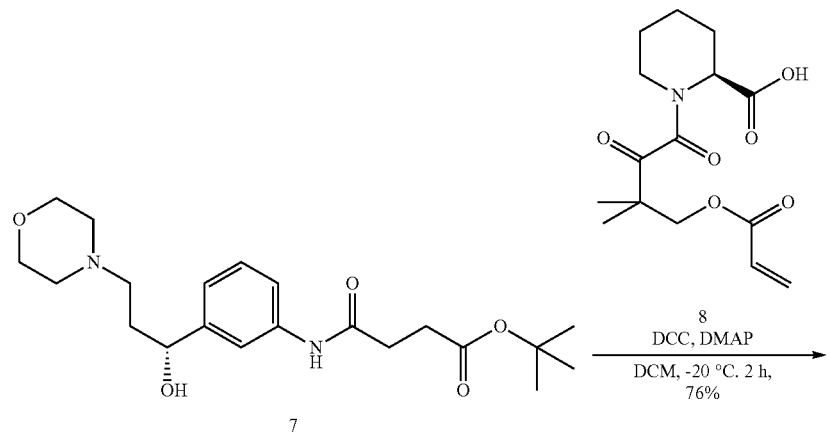
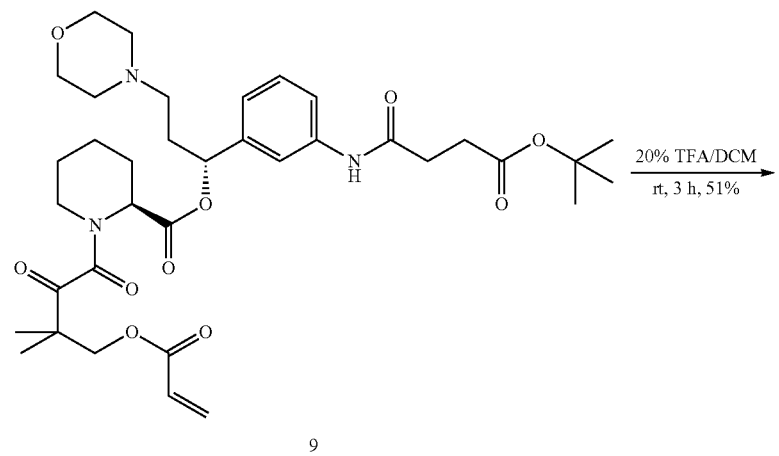

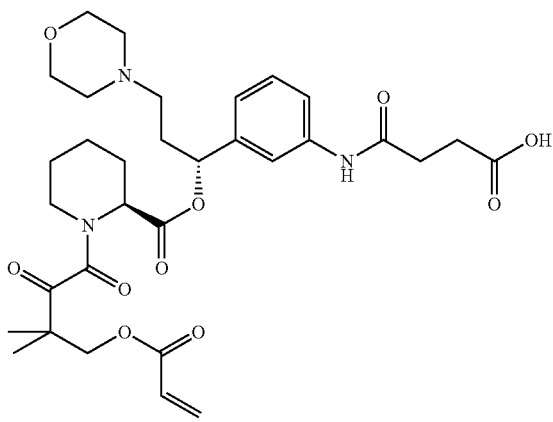

Raa1

1-(3-nitrophenyl)prop-2-en-1-one (2). Paraformaldehyde (36 g, 120 mmol) was added to a stirred solution of 1-(3-nitrophenyl)ethanone 1 (20 g, 120 mmol), N-methylanilinium trifluoroacetate (26.8 g, 120 mmol) and TFA (1.4 g, 12 mmol) in THF (300 mL) at rt, the resultant reaction was heated to reflux for 16 h. The solvent was removed in vacuo, the residue was diluted with water (100 mL) and EA (200 mL). The organic extracts were dried over $Na_2SO_4$ and concentrated in vacuo to afford compound 2 as a yellow solid (14.2 g, crude) used for next step directly without purification. $[M+H]^+=178.1$.

3-morpholino-1-(3-nitrophenyl)propan-1-one (3). To a solution of 2 (12 g, 33.9 mmol, crude) in DMF (30 mL) was added Morpholine (2.95 g, 33.9 mmol), followed by 4-methylbenzenesulfonic acid (5.83 g, 33.9 mmol). After stirring at room temperature for 5 h, quenched the reaction with $H_2O$ (50 mL), extracted with EA (100 mL×3). The organic extracts were dried over $Na_2SO_4$ and concentrated in vacuo to give a crude product which was further purified by column ($SiO_2$, Methanol/DCM=0-10% as eluent) to afford compound 3 (6.6 g, 74%) as a yellow oil. $[M+H]^+=265.2$ 1-(3-aminophenyl)-3-morpholinopropan-1-one (4). To a solution of 3 (4.2 g, 15.9 mmol) in THF (20 mL) was added 10% Pd/C (wet, 840 mg) at rt. The resulting reaction mixture was hydrogenated with $H_2$ (g) at rt for 8 h. The reaction mixture was then filtered and concentrated in vacuo to afford crude compound 4 (3.46 g, crude) as a yellow oil used for next step directly. $[M+H]^+=235.1$ tert-butyl 4-(3-(3-morpholinopropanoyl)phenylamino)-4-oxobutanoate (6). To a solution of 4 (5.05 g, 21.5 mmol) and 4-tert-butoxy-4-oxobutanoic acid 5 (4.86 g, 27.95 mmol) in DMF (20 mL) was added DIPEA (5.55 g, 43 mmol) followed by HATU (10.62 g, 27.95 mmol) at rt. The resulting reaction mixture was stirred at rt for 2 h. Quenched the reaction with $H_2O$ (50 mL), extracted with EA (100 mL×3). The organic extracts were dried over $Na_2SO_4$ and concentrated in vacuo to give a crude product which was further purified by column ($SiO_2$, Methanol/DCM=0-5% as eluent) to afford compound 6 (4.3 g, 51%) as a yellow solid. $[M+H]^+=391.0$ (R)-tert-butyl 4-(3-(1-hydroxy-3-morpholinopropyl)phenylamino)-4-oxobutanoate (7). To a solution of ketone 6 (4.1 g, 10.5 mmol) in anhydrous THF (40 mL) was added (+)DIPChloride (42 mmol) in heptane (1.7 M, 24.7 mL) at −20° C. The resulting reaction mixture was stirred at −20° C. until complete conversion of 6, the quenched with 2,2'-(ethane-1,2-diylbis(oxy))diethanamine (7 g, 47.25 mmol) by forming an insoluble complex. After stirring at rt for another 30 min, the suspension was filtered through a pad of celite and concentrated in vacuo to give a crude product which was further purified by column ($SiO_2$, $CH_3OH$/EA=0-5% as eluent) to afford compound 7 (1.0 g, 24%) as an off white solid. $[M+H]^+=393.0$ (S)—((R)-1-(3-(4-tert-butoxy-4-oxobutanamido)phenyl)-3-morpholinopropyl) 1-(4-(acryloyloxy)-3,3-dimethyl-2-oxobutanoyl)piperidine-2-carboxylate (9). A solution of 7 (1.0 g, 2.55 mmol) and 8 (952 mg, 3.06 mmol) in anhydrous DCM (25 mL) was cooled to −20° C. before a solution of DCC (630 mg, 3.06 mmol) in anhydrous DCM (2 mL) was added, followed by the addition of a solution of 4-(dimethylamino)pyridine (DMAP, 31 mg, 0.255 mmol) under argon atmosphere. The resulting white suspension was stirred at −20° C. for 2 h. The reaction mixture was then filtered and the filtrate were dried over $Na_2SO_4$ and concentrated in vacuo to give a crude product which was further purified by column ($SiO_2$, $CH_3OH$/DCM=0-5% as eluent) to afford compound 9 (1.3 g, 76%) as a white solid. $[M+H]^+=686.0$ 4-(3-((R)-1-((S)-1-(4-(acryloyloxy)-3,3-dimethyl-2-oxobutanoyl)piperidine-2-carbonyloxy)-3-morpholinopropyl)phenylamino)-4-oxobutanoic acid (RAa-1). To a solution of 9 (1.3 g, 1.9 mmol) in DCM (10 mL) was added TFA (2 mL) at rt. The resulting mixture was stirred at rt for 3 h. The reaction mixture was charged to silica-gel flash column directly ($CH_3OH$/DCM=0-5% as eluent) to afford RAa-1 as a white solid (620 mg, 51%).

FKBD Example 4
4-(3-((R)-1-((S)-1-(4-(acryloyloxy)-3,3-dimethyl-2-oxobutanoyl)piperidine-2-carbonyloxy)-4-morpholinobutyl)phenylamino)-4-oxobutanoic acid (Raa2)
Scheme 7. Synthesis of Raa2 FKBD moiety.
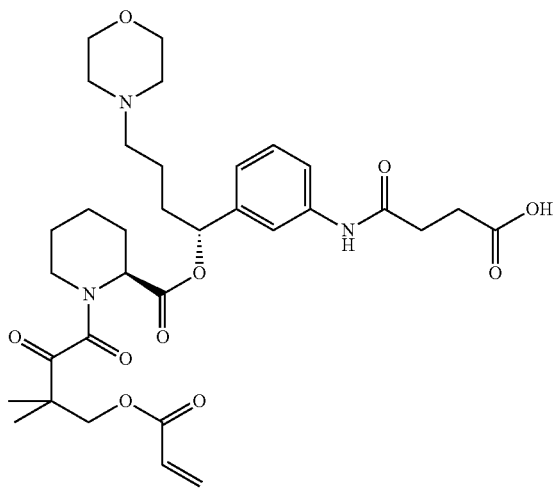
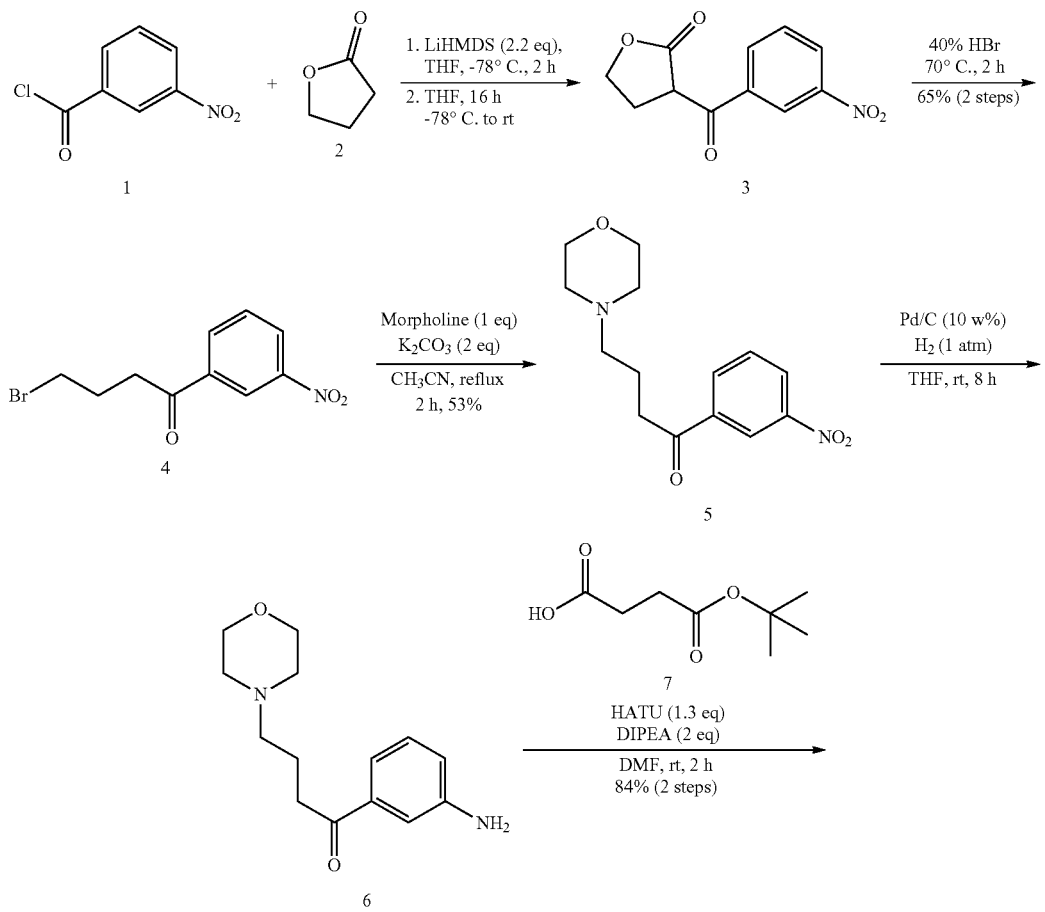

-continued
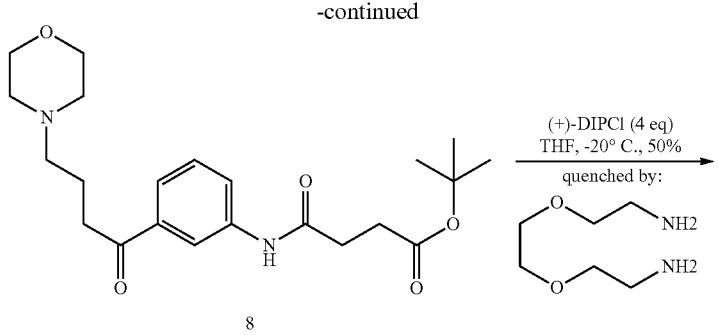
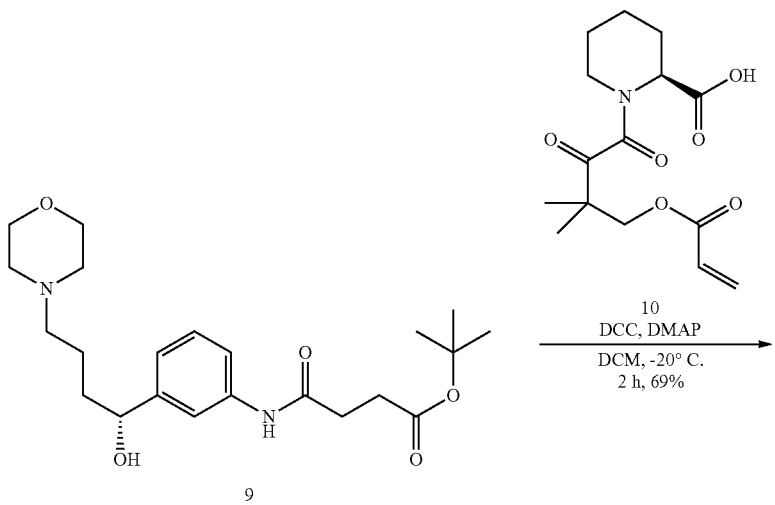
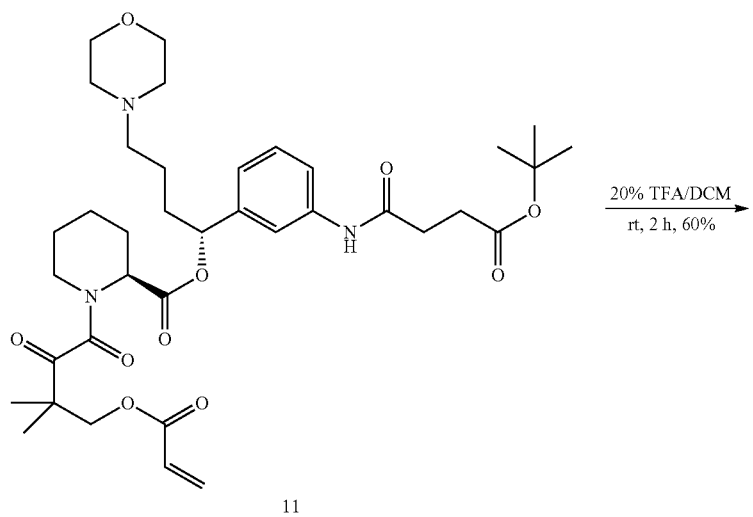

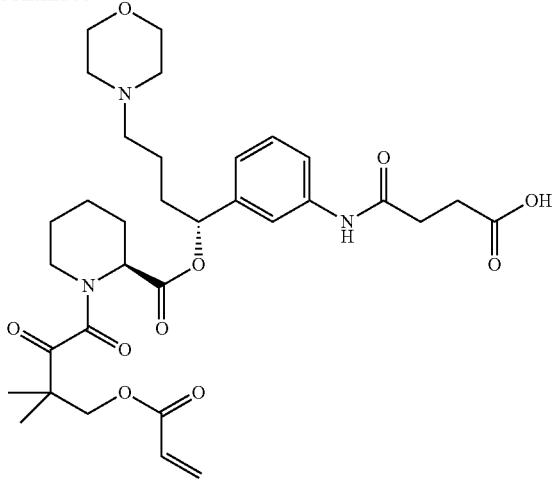

Raa2

3-(3-nitrobenzoyl)-dihydrofuran-2(3H)-one (3). To a stirred solution of dihydrofuran-2(3H)-one 2 (6.02 g, 70 mmol) in anhydrous THF (60 mL) was added LiHMDS (1M in THF, 77 mL, 77 mmol) at −78° C. and stirred for 2 h under argon atmosphere. Then the solution of 3-nitrobenzoyl chloride 1 (6.5 g, 35 mmol) in anhydrous THF (10 mL) was added at −78° C. The resultant reaction mixture was slowly warmed to rt and stirred at rt for 16 h. Quenched the reaction with saturated $NH_4Cl_{aq}$ (20 mL), extracted with EA (100 mL×3). The organic extracts were dried over $Na_2SO_4$ and concentrated in vacuo to afford compound 3 (8.5 g, crude) as a yellow oil used for next step directly without purification. $[M+H]^+$=236.1

4-bromo-1-(3-nitrophenyl)butan-1-one (4). A solution of 3 (25.9 g, 110 mmol, crude) in 40% HBr (150 mL) was heated to 70° C. for 2 h. The reaction mixture was cooled to rt and adjusted the pH to 5-6 with saturated $NaHCO_3{}_{aq}$, extracted with EA (200 mL×3). The organic extracts were dried over $Na_2SO_4$ and concentrated in vacuo to give a crude product which was further purified by column ($SiO_2$, EA/PE=0-10% as eluent) to afford compound 4 (18.5 g, 74% for 2 steps) as a yellow oil.

4-morpholino-1-(3-nitrophenyl)butan-1-one (5). To a solution of 4 (8.5 g, 31.25 mmol) and Morpholine (2.72 g, 31.25 mmol) in $CH_3CN$ (100 mL) was added $K_2CO_3$ (8.64 g, 62.5 mmol) at rt. The resulting reaction mixture was heated to reflux for 2 h. The reaction mixture was then filtered and concentrated in vacuo to give a crude product which was further purified by column ($SiO_2$, Methanol/DCM=0-5% as eluent) to afford compound 5 (4.6 g, 53%) as a yellow oil. $[M+H]^+$=279.2

1-(3-aminophenyl)-4-morpholinobutan-1-one (6). A solution of 5 (5.9 g, 21.2 mmol) in THF (60 mL) was added 10% Pd/C (wet, 1.18 g) at rt. The resulting reaction mixture was hydrogenated with $H_2$ (g) at rt for 10 h. The reaction mixture was then filtered and concentrated in vacuo to afford crude compound 6 (4.8 g, crude) as a yellow solid used for next step directly. $[M+H]^+$=249.0

To a solution of 6 (4.8 g, 19.35 mmol) and 4-tert-butoxy-4-oxobutanoic acid 7 (4.86 g, 27.95 mmol) in DMF (15 mL) was added DIPEA (5.0 g, 38.7 mmol) followed by HATU (9.56 g, 25.15 mmol) at rt. The resulting reaction mixture was stirred at rt for 2 h. Quenched the reaction with $H_2O$ (50 mL), extracted with EA (100 mL×3). The organic extracts were dried over $Na_2SO_4$ and concentrated in vacuo to give a crude product which was further purified by column ($SiO_2$, Methanol/DCM=0-5% as eluent) to afford compound 8 (6.6 g, 84%) as a yellow solid. $[M+H]^+$=405.0

(R)-tert-butyl 4-(3-(1-hydroxy-4-morpholinobutyl)phenylamino)-4-oxobutanoate (9). To a solution of ketone 8 (5.0 g, 12.4 mmol) in anhydrous THF (20 mL) was added (+)DIPChloride (49.6 mmol) in heptane (1.7 M, 29 mL) at −20° C. The resulting reaction mixture was stirred at −20° C. until complete conversion of 8, then quenched with 2,2'-(ethane-1,2-diylbis(oxy))diethanamine (8.3 g, 55.8 mmol) by forming an insoluble complex. After stirring at rt for another 30 min, the suspension was filtered through a pad of celite and concentrated in vacuo to give a crude product which was further purified by column ($SiO_2$, $CH_3OH$/EA=0-5% as eluent) to afford compound 9 as an off white solid (2.5 g, 50%). $[M+H]^+$=407.3

(S)—((R)-1-(3-(4-tert-butoxy-4-oxobutanamido)phenyl)-4-morpholinobutyl)1-(4-(acryloyloxy)-3,3-dimethyl-2-oxobutanoyl)piperidine-2-carboxylate (11). A solution of 9 (2.45 g, 6.05 mmol) and 10 (2.29 g, 7.38 mmol) in anhydrous DCM (40 mL) was cooled to −20° C. before a solution of DCC (1.52 g, 7.38 mmol) in anhydrous DCM (5 mL) was added, followed by the addition of a solution of 4-(dimethylamino)pyridine (DMAP, 75 mg, 0.615 mmol) in anhydrous DCM (1 mL) under argon atmosphere. The resulting white suspension was stirred at −20° C. for 2 h. The reaction mixture was then filtered and the filtrate were dried over $Na_2SO_4$ and concentrated in vacuo to give a crude product which was further purified by column ($SiO_2$, $CH_3OH$/DCM=0-5% as eluent) to afford compound 11 as a white solid (3 g, 69%). $[M+H]^+$=700.0

4-(3-((R)-1-((S)-1-(4-(acryloyloxy)-3,3-dimethyl-2-oxobutanoyl)piperidine-2-carbonyloxy)-4-morpholinobutyl)phenylamino)-4-oxobutanoic acid (Raa2). To a solution of 11(1.0 g, 1.42 mmol) in DCM (10 mL) was added TFA (2 mL) at rt. The resulting mixture was stirred at rt for 2 h. The reaction mixture was charged to silica-gel flash column directly ($CH_3OH$/DCM=0-5% as eluent) to afford Raa2 (550 mg, 60%) as a white solid.

FKBD Example 5
4-(3-((R)-3-(4-(((9H-fluoren-9-yl)methoxy)carbonyl)piperazin-1-yl)-1-((S)-1-(4-(acryloyloxy)-3,3-dimethyl-2-oxobutanoyl)piperidine-2-carbonyloxy)propyl)phenylamino)-4-oxobutanoic acid (Raa3)
Scheme 8. Synthesis of Raa3 FKBD moiety.
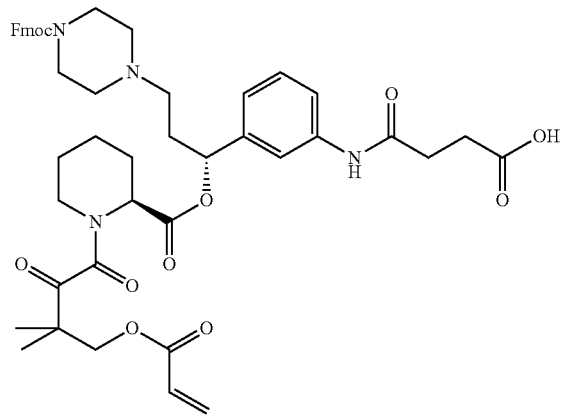
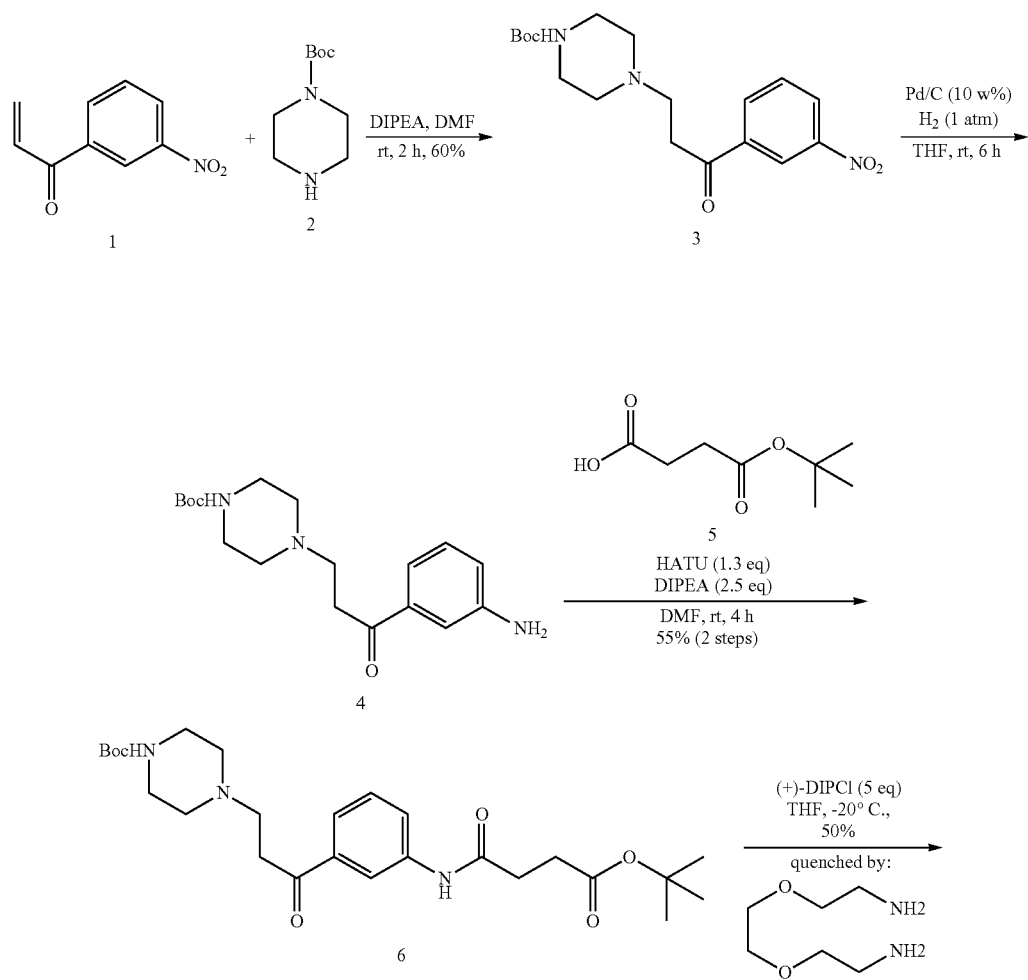

-continued
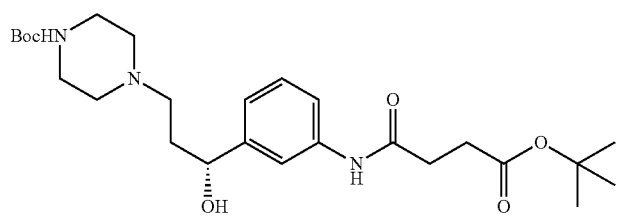
7
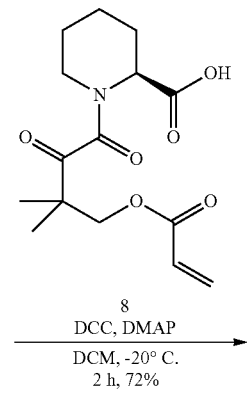
8
DCC, DMAP
DCM, -20° C.
2 h, 72%
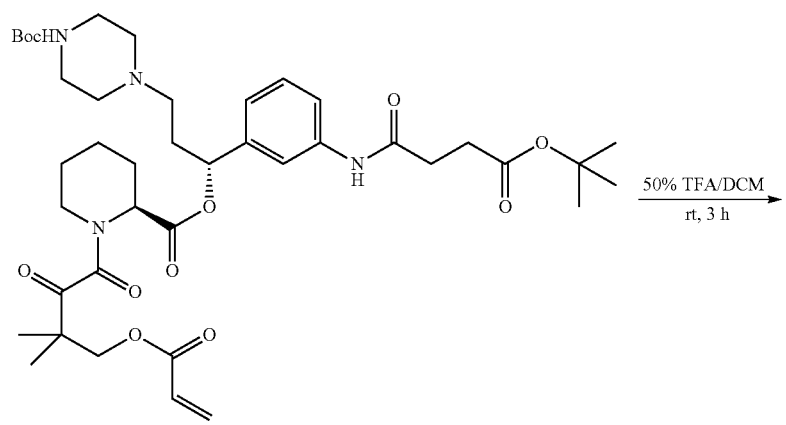
9
50% TFA/DCM
rt, 3 h
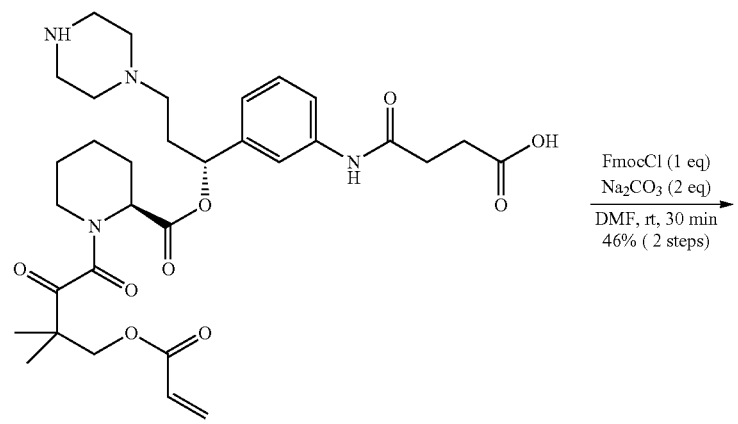
10
FmocCl (1 eq)
Na₂CO₃ (2 eq)
DMF, rt, 30 min
46% (2 steps)

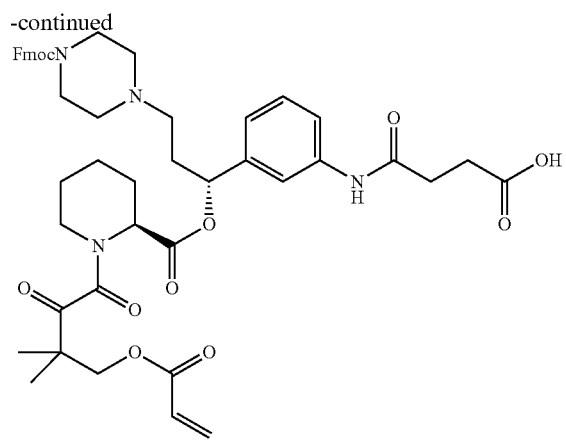

Raa3 tert-butyl 4-(3-(3-nitrophenyl)-3-oxopropyl)piperazine-1-carboxylate (3). To a solution of 1 (10 g, 28.2 mmol, crude) in DMF (20 mL) was added DIPEA (3.64 g, 28.2 mmol), followed by 2 (5.24 g, 28.2 mmol). After stirring at room temperature for 2 h, quenched the reaction with $H_2O$ (100 mL), extracted with EA (100 mL×3). The organic extracts were dried over $Na_2SO_4$ and concentrated in vacuo to give a crude product which was further purified by column ($SiO_2$, Methanol/DCM=0-10% as eluent) to afford compound 3 as a yellow oil (6.1 g, 60%). $[M+H]^+=364.2$ tert-butyl 4-(3-(3-aminophenyl)-3-oxopropyl)piperazine-1-carboxylate (4). A solution of 3 (6.1 g, 15.9 mmol) in THF (50 mL) was added 10% Pd/C (wet, 1.22 g) at rt. The resulting reaction mixture was hydrogenated with $H_2$ (g) at rt for 8 h. The reaction mixture was then filtered and concentrated in vacuo to afford crude compound 4 as a brown solid (5.5 g, crude) used for next step directly. $[M+H]^+=334.3$ tert-butyl 4-(3-(3-(4-tert-butoxy-4-oxobutanamido)phenyl)-3-oxopropyl)piperazine-1-carboxylate (6). To a solution of 4 (5.2 g, 15.6 mmol) and 4-tert-butoxy-4-oxobutanoic acid 5 (3.53 g, 20.27 mmol) in DMF (35 mL) was added DIPEA (5.04 g, 38.99 mmol) followed by HATU (7.71 g, 20.27 mmol) at rt. The resulting reaction mixture was stirred at rt for 4 h. Quenched the reaction with $H_2O$ (50 mL), extracted with EA (100 mL×3). The organic extracts were dried over $Na_2SO_4$ and concentrated in vacuo to give a crude product which was further purified by column ($SiO_2$, PE/EA=0-50% as eluent) to afford compound 6 (4.3 g, 56%) as a yellow solid. $[M+H]^+=490.4$ (R)-tert-butyl 4-(3-(3-(4-tert-butoxy-4-oxobutanamido) phenyl)-3-hydroxypropyl)piperazine-1-carboxylate (7). To a solution of ketone 6 (3.8 g, 7.76 mmol) in anhydrous THF (30 mL) was added (+)DIPChloride (38.8 mmol) in heptane (1.7 M, 23 mL) at −20° C. The resulting reaction mixture was stirred at −20° C. until complete conversion of 6, the quenched with 2,2'-(ethane-1,2-diylbis(oxy))diethanamine (6.32 g, 42.68 mmol) by forming an insoluble complex. After stirring at rt for another 30 min, the suspension was filtered through a pad of celite and concentrated in vacuo to give a crude product which was further purified by column ($SiO_2$, $CH_3OH$/EA=0-5% as eluent) to afford compound 7 as an off white solid (1.9 g, 51%). $[M+H]^+=492.3$ tert-butyl 4-((R)-3-((S)-1-(4-(acryloyloxy)-3,3-dimethyl-2-oxobutanoyl)piperidine-2-carbonyloxy)-3-(3-(4-tert-butoxy-4-oxobutanamido)phenyl)propyl)piperazine-1-carboxylate (9). A solution of 7 (1.03 g, 2.1 mmol) and 8 (784 mg, 2.52 mmol) in anhydrous DCM (20 mL) was cooled to −20° C. before a solution of DCC (865 mg, 4.2 mmol) in anhydrous DCM (2 mL) was added, followed by the addition of a solution of 4-(dimethylamino)pyridine (DMAP, 26 mg, 0.21 mmol) under argon atmosphere. The resulting white suspension was stirred at −20° C. for 2 h. The reaction mixture was then filtered and the filtrate were dried over $Na_2SO_4$ and concentrated in vacuo to give a crude product which was further purified by column ($SiO_2$, $CH_3OH$/DCM=0-5% as eluent) to afford compound 9 as a yellow solid (1.2 g, 72%). $[M+H]^+=784.9$ 4-(3-((R)-1-((S)-1-(4-(acryloyloxy)-3,3-dimethyl-2-oxobutanoyl)piperidine-2-carbonyloxy)-3-(piperazin-1-yl) propyl)phenylamino)-4-oxobutanoic acid (10). To a solution of 9 (1.2 g, 1.9 mmol) in DCM (6 mL) was added TFA (3 mL) at rt. The resulting mixture was stirred at rt for 3 h. The reaction mixture was concentrated in vacuo to afford compound 10 (1.1 g, crude) as a yellow solid. $[M+H]^+=628.9$ 4-(3-((R)-3-(4-(((9H-fluoren-9-yl)methoxy)carbonyl)piperazin-1-yl)-1-((S)-1-(4-(acryloyloxy)-3,3-dimethyl-2-oxobutanoyl)piperidine-2-carbonyloxy)propyl)phenylamino)-4-oxobutanoic acid (Raa3). To a solution of 10 (1.1 g, 1.74 mmol) in DMF (4 mL) was added $Na_2CO_3$ (369 mg, 3.48 mmol) followed by FmocChloride (450 mg, 1.74 mmol) at rt. The resulting reaction mixture was stirred at rt for 30 min. Quenched the reaction with $H_2O$ (10 mL), extracted with EA (30 mL×3). The organic extracts were dried over $Na_2SO_4$ and concentrated in vacuo to give a crude product which was further purified by column ($SiO_2$, Methanol/DCM=0-5% as eluent) to afford Raa3 (680 mg, 46%) as a white solid.

FKBD Example 6
4-(3-((R)-4-(4-(((9H-fluoren-9-yl)methoxy)carbonyl)piperazin-1-yl)-1-((S)-1-(4-(acryloyloxy)-3,3-dimethyl-2-oxobutanoyl)piperidine-2-carbonyloxy)butyl)phenylamino)-4-oxobutanoic acid (Raa4)
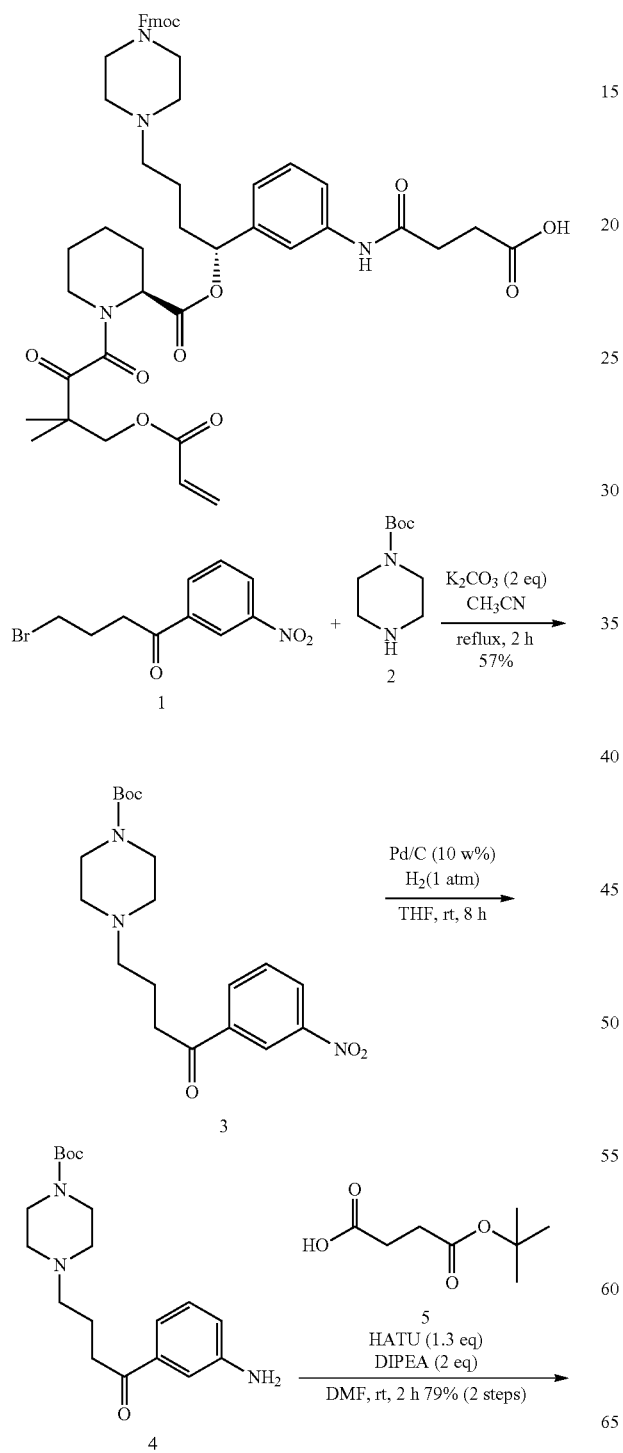
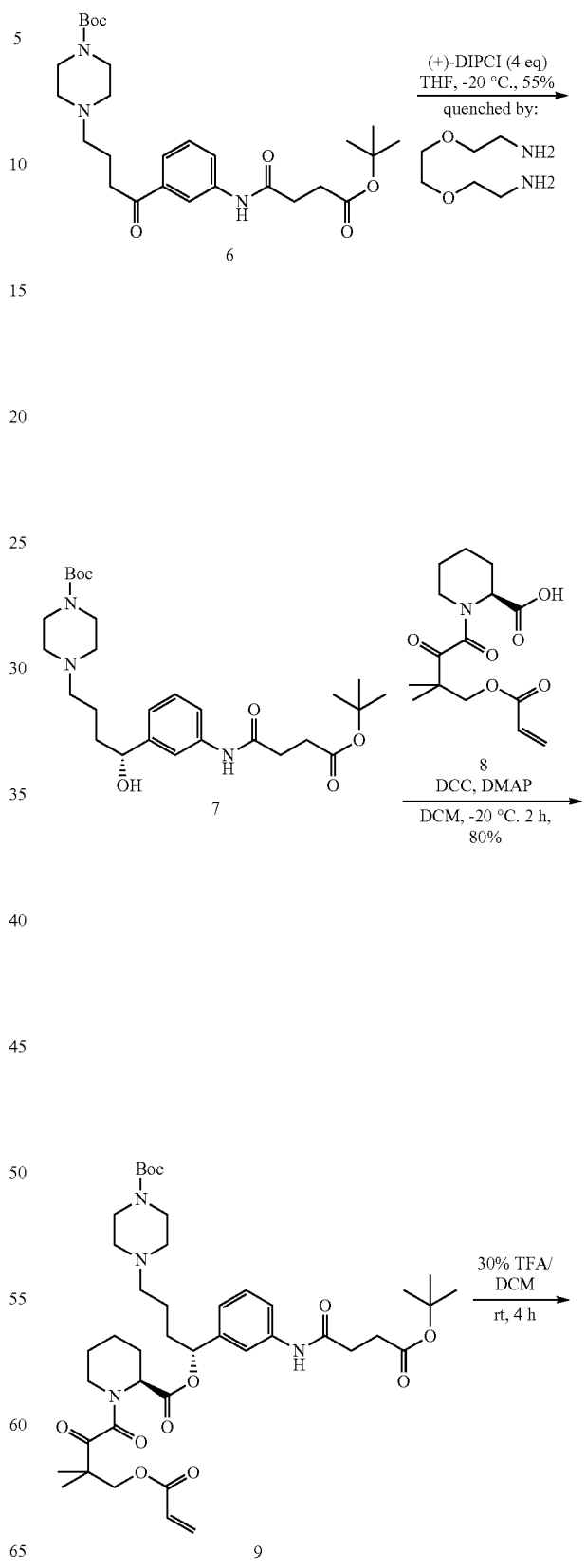

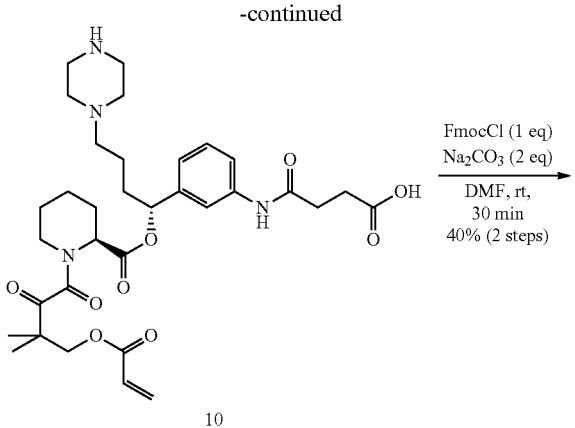

10

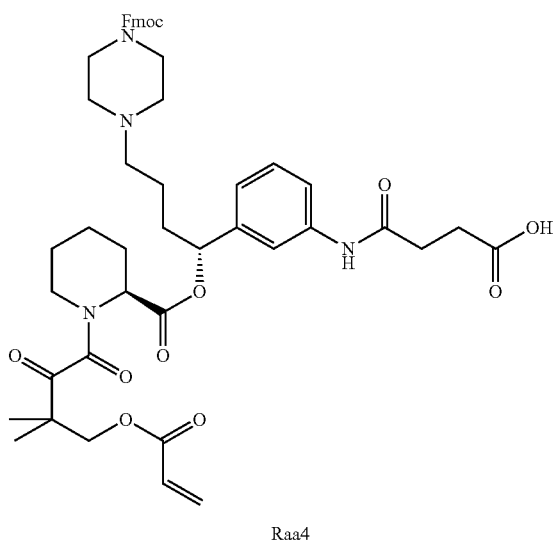

Raa4 tert-butyl 4-(4-(3-nitrophenyl)-4-oxobutyl)piperazine-1-carboxylate (3). To a solution of 1(10.5 g, 38.6 mmol) and 2 (7.2 g, 38.6 mmol) in CH$_3$CN (100 mL) was added K$_2$CO$_3$ (10.7 g, 77.2 mmol) at rt. The resulting reaction mixture was heated to reflux for 2 h. The reaction mixture was then filtered and concentrated in vacuo to give a crude product which was further purified by column (SiO$_2$, Methanol/DCM=0-5% as eluent) to afford compound 3 (8.3 g, 57%) as a yellow solid. [M+H]$^+$=378.0 tert-butyl 4-(4-(3-aminophenyl)-4-oxobutyl)piperazine-1-carboxylate (4). A solution of 3 (8.3 g, 22 mmol) in THF (60 mL) was added 10% Pd/C (wet, 1.66 g) at rt. The resulting reaction mixture was hydrogenated with H$_2$ (g) at rt for 10 h. The reaction mixture was then filtered and concentrated in vacuo to afford crude compound 4 (7.4 g, crude) as a yellow solid used for next step directly. [M+H]$^+$=348.3 tert-butyl 4-(3-(4-morpholinobutanoyl)phenylamino)-4-oxobutanoate (6). To a solution of 4 (7.4 g, 21.3 mmol) and 4-tert-butoxy-4-oxobutanoic acid 5 (4.82 g, 27.6 mmol) in DMF (15 mL) was added DIPEA (5.5 g, 42.6 mmol) followed by HATU (10.5 g, 27.69 mmol) at rt. The resulting reaction mixture was stirred at rt for 2 h. Quenched the reaction with H$_2$O (50 mL), extracted with EA (100 mL×3). The organic extracts were dried over Na$_2$SO$_4$ and concentrated in vacuo to give a crude product which was further purified by column (SiO$_2$, Methanol/DCM=0-5% as eluent) to afford compound 6 (8.5 g, 79%) as a yellow solid. [M+H]$^+$=504.0

(R)-tert-butyl 4-(4-(3-(4-tert-butoxy-4-oxobutanamido)phenyl)-4-hydroxybutyl)piperazine-1-carboxylate (7). To a solution of ketone 6 (4.5 g, 8.9 mmol) in anhydrous THF (20 mL) was added (+)DIPChloride (35.6 mmol) in heptane (1.7 M, 21 mL) at −20° C. The resulting reaction mixture was stirred at −20° C. until complete conversion of 6, then quenched with 2,2'-(ethane-1,2-diylbis(oxy))diethanamine (5.9 g, 40.0 mmol) by forming an insoluble complex. After stirring at rt for another 30 min, the suspension was filtered through a pad of celite and concentrated in vacuo to give a crude product which was further purified by column (SiO$_2$, Methanol/EA=0-5% as eluent) to afford compound 7 as an off white solid (2.5 g, 55%). [M+H]$^+$=506.0 tert-butyl 4-((R)-4-((S)-1-(4-(acryloyloxy)-3,3-dimethyl-2-oxobutanoyl)piperidine-2-carbonyloxy)-4-(3-(4-tert-butoxy-4-oxobutanamido)phenyl)butyl)piperazine-1-carboxylate (9). A solution of 7 (2.3 g, 4.5 mmol) and 8 (1.68 g, 5.4 mmol) in anhydrous DCM (30 mL) was cooled to −20° C. before a solution of DCC (1.11 g, 5.4 mmol) in anhydrous DCM (5 mL) was added, followed by the addition of a solution of 4-(dimethylamino)pyridine (DMAP, 55 mg, 0.615 mmol) in anhydrous DCM (1 mL) under argon atmosphere. The resulting white suspension was stirred at −20° C. for 2 h. The reaction mixture was then filtered and the filtrate were dried over Na$_2$SO$_4$ and concentrated in vacuo to give a crude product which was further purified by column (SiO$_2$, Methanol/DCM=0-5% as eluent) to afford compound 9 as a white solid (2.9 g, 80%). [M+H]$^+$=799.5

4-(3-((R)-1-((S)-1-(4-(acryloyloxy)-3,3-dimethyl-2-oxobutanoyl)piperidine-2-carbonyloxy)-4-(piperazin-1-yl)butyl)phenylamino)-4-oxobutanoic acid (10). To a solution of 9 (2.9 g, 3.6 mmol) in DCM (10 mL) was added TFA (3 mL) at rt. The resulting mixture was stirred at rt for 4 h. The reaction mixture was charged to silica-gel flash column directly (CH$_3$OH/DCM=0-5% as eluent) to afford compound 10 (2.6 g, crude) as a yellow solid used for next step directly. [M+H]$^+$=643.4

4-(3-((R)-4-(4-(((9H-fluoren-9-yl)methoxy)carbonyl)piperazin-1-yl)-1-((S)-1-(4-(acryloyloxy)-3,3-dimethyl-2-oxobutanoyl)piperidine-2-carbonyloxy)butyl)phenylamino)-4-oxobutanoic acid (Raa4). To a solution of 10 (1.2 g, 1.62 mmol) in DMF (2 mL) was added Na$_2$CO$_3$ (343 mg, 3.24 mmol) followed by FmocChloride (419 mg, 1.62 mmol) at rt. The resulting reaction mixture was stirred at rt for 30 min. Quenched the reaction with H$_2$O (10 mL), extracted with EA (30 mL×3). The organic extracts were dried over Na$_2$SO$_4$ and concentrated in vacuo to give a crude product which was further purified by column (SiO$_2$, Methanol/DCM=0-5% as eluent) to afford Raa4 (570 mg, 40%) as a white solid.

FKBD Example 7
4-(5-((R)-1-((S)-1-(4-(acryloyloxy)-3,3-dimethyl-2-oxobutanoyl)piperidine-2-carbonyloxy)-3-(3,4-dimethoxyphenyl)propyl)pyridin-3-ylamino)-4-oxobutanoic acid (Raa5)
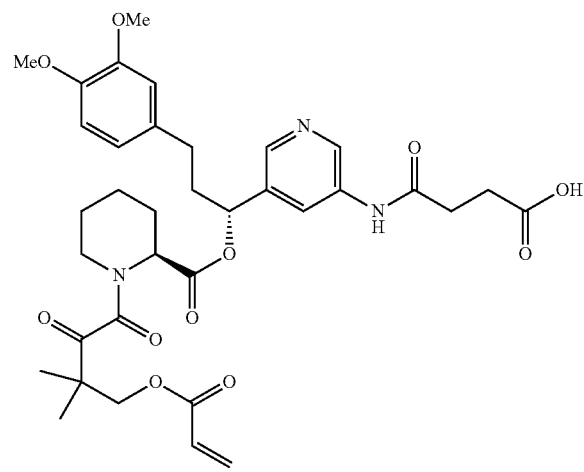
Scheme 10. Synthesis of Raa5 FKBD moiety.
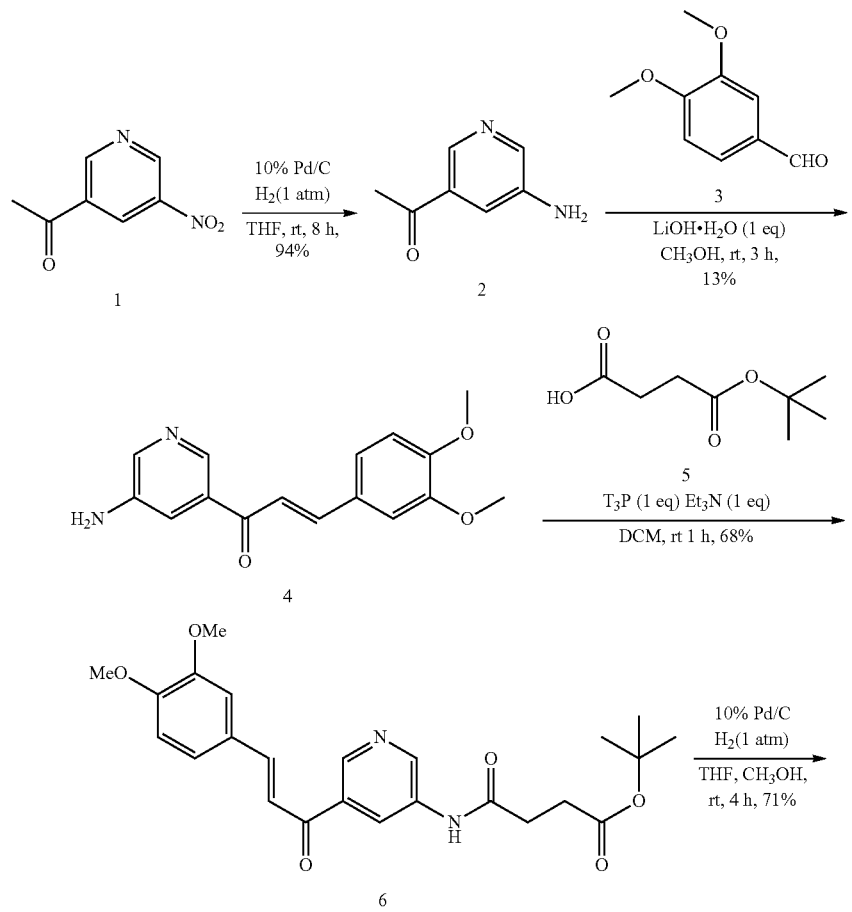

-continued
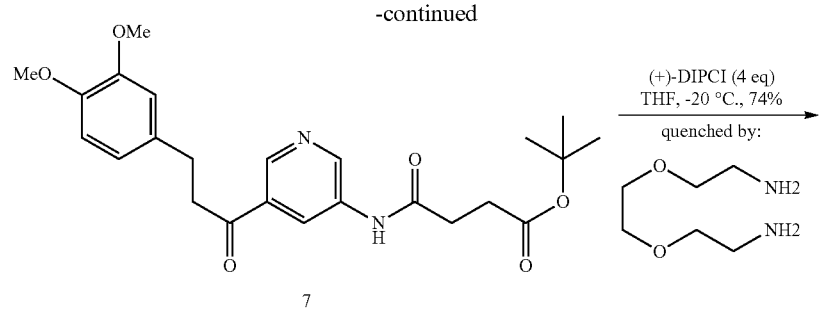
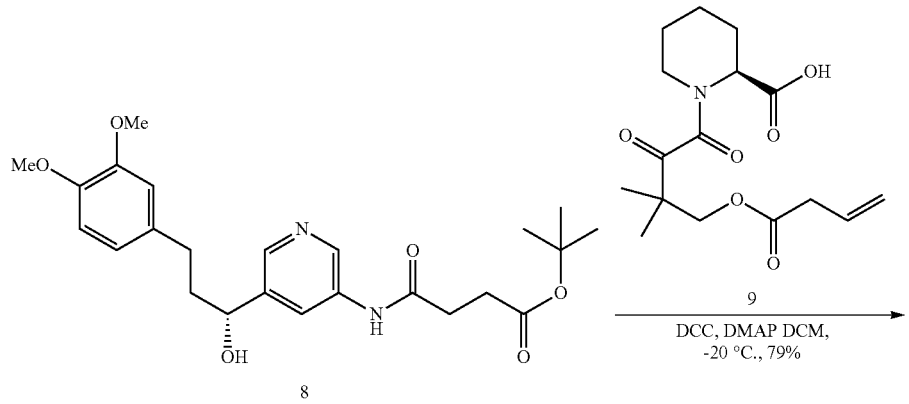
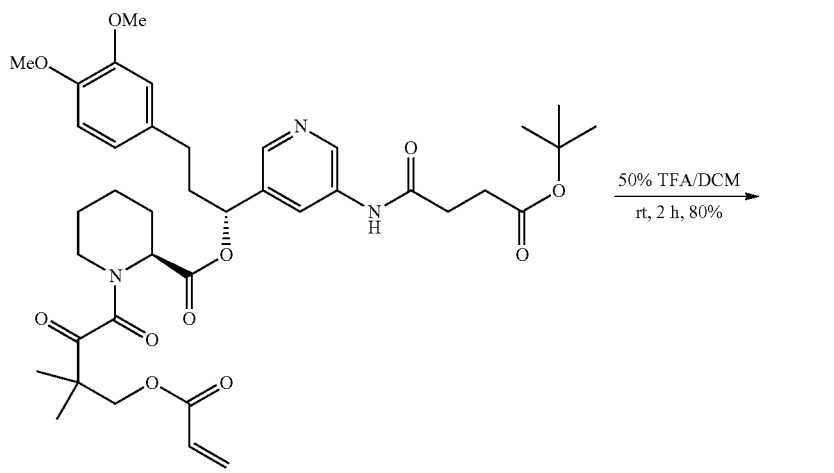
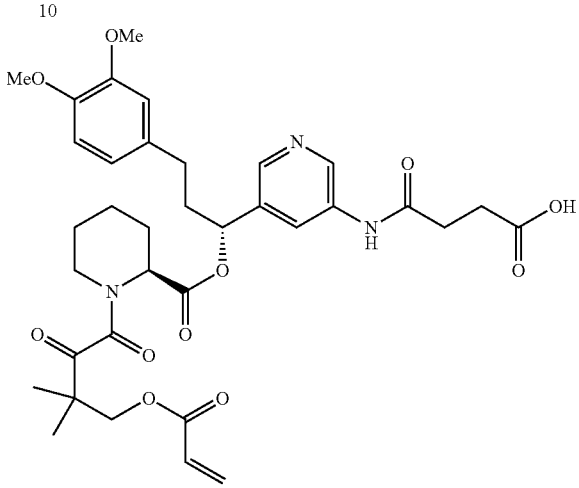

1-(5-aminopyridin-3-yl)ethanone (2). To a solution of 1 (13 g, 78.3 mmol) in THF (100 mL) was added 10% Pd/C (wet, 8.0 g) at rt. The resulting reaction mixture was stirred at rt for 10 h under $H_2$ (g). The reaction mixture was then filtered and concentrated in vacuo to give a crude product which was further purified by column ($SiO_2$, Methanol/DCM=0-5% as eluent) to afford compound 2 (10 g, 94%) as a yellow solid. $[M+H]^+=137.0$ (E)-1-(5-aminopyridin-3-yl)-3-(3,4-dimethoxyphenyl)prop-2-en-1-one (4). To a solution of 2 (6.5 g, 47.8 mmol) and 3 (7.9 g, 47.8 mmol) in $CH_3OH$ (60 mL) was added LiOH·$H_2O$ (2 g, 47.8 mmol) at 0° C. The resulting reaction mixture was stirred at rt for 3 h. The solvent was removed in vacuo and the residue was diluted with DCM and $H_2O$. The organic extracts were dried over $Na_2SO_4$ and concentrated in vacuo to give a crude product which was further purified by column ($SiO_2$, Methanol/DCM=0-5% as eluent) to afford compound 4 (1.8 g, 13%) as a yellow solid. $[M+H]^+=285.0$ (E)-tert-butyl 4-(5-(3-(3,4-dimethoxyphenyl)acryloyl)pyridin-3-ylamino)-4-oxobutanoate (6). To a solution of 4 (1.8 g, 6.3 mmol) and 4-tert-butoxy-4-oxobutanoic acid 5 (1.1 g, 6.3 mmol) in DCM (35 mL) was added $Et_3N$ (12.7 g, 12.6 mmol) followed by $T_3P$ (50% in EtOAc, 8.0 g, 12.6 mmol) at rt. The resulting reaction mixture was stirred at rt for 1 h. Quenched the reaction with $H_2O$ (20 mL), extracted with DCM (40 mL×2). The organic extracts were dried over $Na_2SO_4$ and concentrated in vacuo to give a crude product which was further purified by column ($SiO_2$, Methanol/DCM=0-5% as eluent) to afford compound 6 (1.88 g, 68%) as a yellow solid. $[M+H]^+=440.9$ tert-butyl 4-(5-(3-(3,4-dimethoxyphenyl)propanoyl)pyridin-3-ylamino)-4-oxobutanoate (7). A solution of 6 (1.88 g, 4.27 mmol) in THF (50 mL) and Methanol (5 mL) was added 10% Pd/C (wet, 380 mg) at rt. The resulting reaction mixture was hydrogenated with $H_2$ (g) at rt for 4 h. The reaction mixture was then filtered and concentrated in vacuo to give a crude product which was further purified by column ($SiO_2$, Methanol/DCM=0-5% as eluent) to afford compound 7 (1.34 g, 71%) as a brown solid. $[M+H]^+=442.9$ (R)-tert-butyl 4-(5-(3-(3,4-dimethoxyphenyl)-1-hydroxypropyl)pyridin-3-ylamino)-4-oxobutanoate (8). To a solution of ketone 7 (1.34 g, 3.0 mmol) in anhydrous THF (20 mL) was added (+)DIPChloride (12.0 mmol) in heptane (1.7 M, 7.05 mL) at −20° C. The resulting reaction mixture was stirred at −20° C. until complete conversion of 7, then quenched with 2,2'-(ethane-1,2-diylbis(oxy))diethanamine (2.0 g, 13.5 mmol) by forming an insoluble complex. After stirring at rt for another 30 min, the suspension was filtered through a pad of celite and concentrated in vacuo to give a crude product which was further purified by column ($SiO_2$, $CH_3OH$/EA=0-5% as eluent) to afford compound 8 (0.99 g, 74%) as a white solid. $[M+H]^+=445.0$ (S)—((R)-1-(5-(4-tert-butoxy-4-oxobutanamido)pyridin-3-yl)-3-(3,4-dimethoxyphenyl)propyl) 1-(4-(acryloyloxy)-3,3-dimethyl-2-oxobutanoyl)piperidine-2-carboxylate (10). A solution of 8 (990 mg, 2.22 mmol) and 9 (827 mg, 2.66 mmol) in anhydrous DCM (20 mL) was cooled to −20° C. before a solution of DCC (548 mg, 2.66 mmol) in anhydrous DCM (2 mL) was added, followed by the addition of a solution of 4-(dimethylamino)pyridine (DMAP, 27 mg, 0.22 mmol) in anhydrous DCM (1 mL) under argon atmosphere. The resulting white suspension was stirred at −20° C. for 2 h. The reaction mixture was then filtered and the filtrate were dried over $Na_2SO_4$ and concentrated in vacuo to give a crude product which was further purified by column ($SiO_2$, $CH_3OH$/DCM=0-5% as eluent) to afford compound 10 (1.3 g, 79%) as a white solid. $[M+H]^+=738.0$ 4-(5-((R)-1-((S)-1-(4-(acryloyloxy)-3,3-dimethyl-2-oxobutanoyl)piperidine-2-carbonyloxy)-3-(3,4-dimethoxyphenyl)propyl)pyridin-3-ylamino)-4-oxobutanoic acid (Raa5). To a solution of 10 (1.3 g, 1.76 mmol) in DCM (10 mL) was added TFA (5 mL) at rt. The resulting mixture was stirred at rt for 2 h. The reaction mixture was charged to silica-gel flash column directly ($CH_3OH$/DCM=0-5% as eluent) to afford Raa5 (960 mg, 80%) as a white solid.

FKBD Example 8

4-(6-((R)-1-((S)-1-(4-(acryloyloxy)-3,3-dimethyl-2-oxobutanoyl)piperidine-2-carbonyloxy)-3-(3,4-dimethoxyphenyl)propyl)pyridin-2-ylamino)-4-oxobutanoic acid (Raa6)

Scheme 11. Synthesis of Raa6 FKBD moiety.

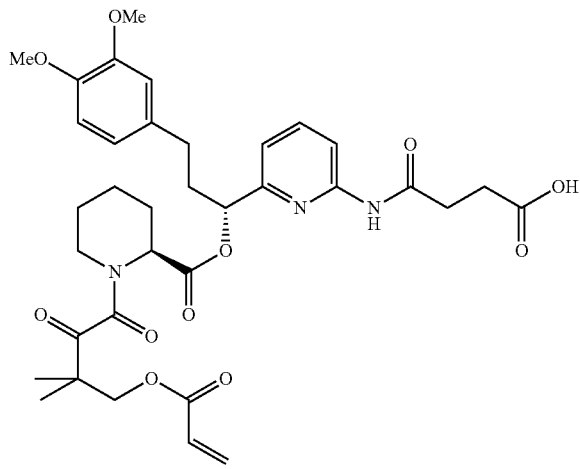

-continued
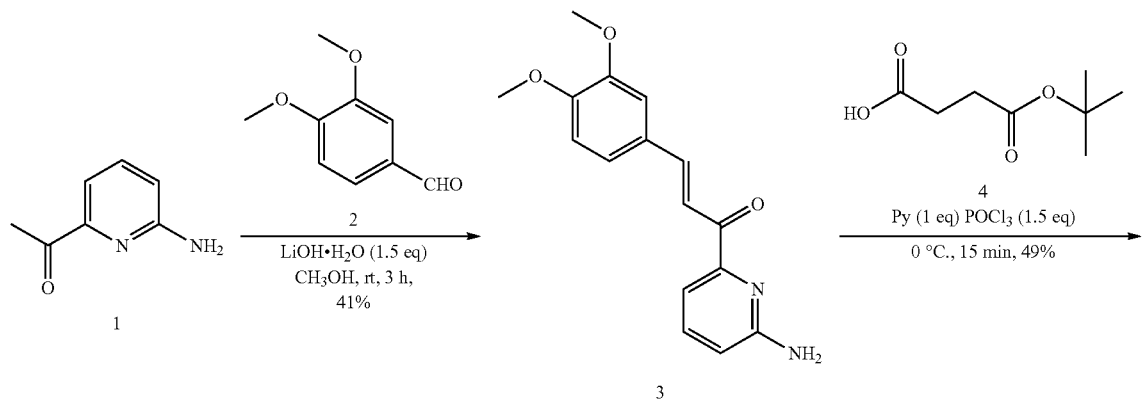
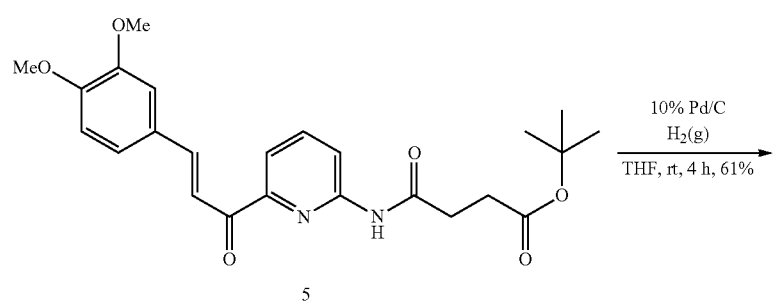
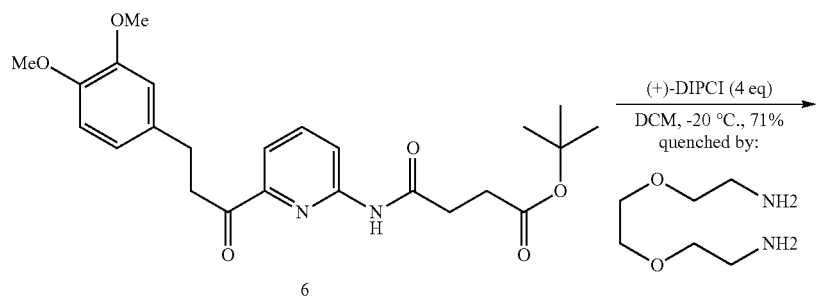
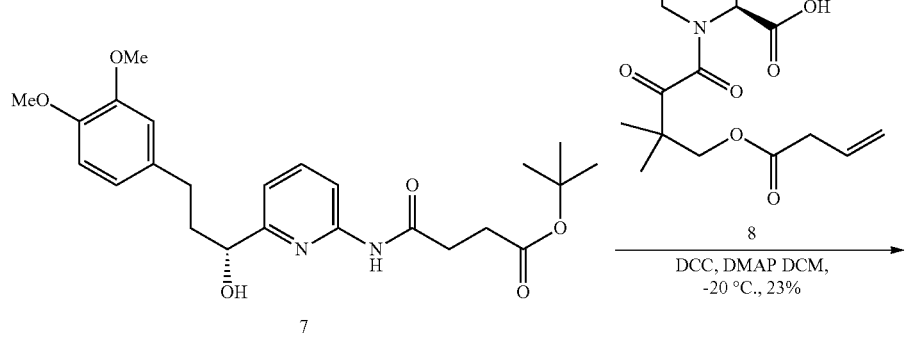

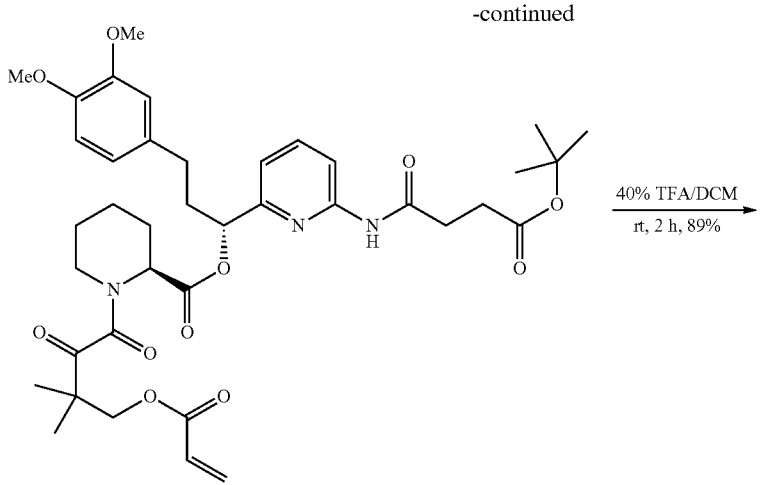

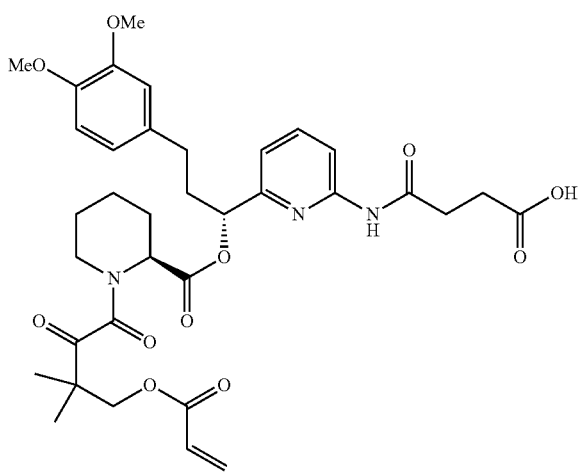

(E)-1-(6-aminopyridin-2-yl)-3-(3,4-dimethoxyphenyl)prop-2-en-1-one (3). To a solution of 1 (3.75 g, 27.57 mmol) and 2 (4.58 g, 27.57 mmol) in CH₃OH (40 mL) was added LiOH·H₂O (1.74 g, 41.35 mmol) at rt. The resulting reaction mixture was stirred at rt for 3 h. The solvent was removed in vacuo and the residue was diluted with DCM and H₂O. The organic extracts were dried over Na₂SO₄ and concentrated in vacuo to give a crude product which was further purified by column (SiO₂, Methanol/DCM=0-5% as eluent) to afford compound 3 (3.2 g, 41%) as a yellow solid. [M+H]⁺=285.0

(E)-tert-butyl 4-(6-(3-(3,4-dimethoxyphenyl)acryloyl)pyridin-2-ylamino)-4-oxobutanoate (5). To a solution of 3 (3.2 g, 11.26 mmol) and 4-tert-butoxy-4-oxobutanoic acid 4 (2.35 g, 13.5 mmol) in Pyridine (10 mL) was added POCl₃ (2.58 g, 16.89 mmol) at 0° C. The resulting reaction mixture was stirred at 0° C. for 15 min. Quenched the reaction with H₂O (20 mL), extracted with EA (30 mL×3). The organic extracts were dried over Na₂SO₄ and concentrated in vacuo to give a crude product which was further purified by column (SiO₂, Methanol/DCM=0-5% as eluent) to afford compound 5 (2.45 g, 49%) as a yellow solid. [M+H]⁺=440.9 tert-butyl 4-(6-(3-(3,4-dimethoxyphenyl)propanoyl)pyridin-2-ylamino)-4-oxobutanoate (6). A solution of 5 (2.45 g, 5.56 mmol) in THF (30 mL) was added 10% Pd/C (wet, 500 mg) at rt. The resulting reaction mixture was hydrogenated with H₂ (g) at rt for 4 h. The reaction mixture was then filtered and concentrated in vacuo to give a crude product which was further purified by column (SiO₂, Methanol/DCM=0-5% as eluent) to afford compound 6 (1.5 g, 61%) as a yellow solid. [M+H]⁺=443.3

(R)-tert-butyl 4-(6-(3-(3,4-dimethoxyphenyl)-1-hydroxypropyl)pyridin-2-ylamino)-4-oxobutanoate (7). To a solution of ketone 6 (1.4 g, 3.16 mmol) in anhydrous DCM (20 mL) was added (+)DIPChloride (12.64 mmol) in heptane (1.7 M, 7.5 mL) at −20° C. The resulting reaction mixture was stirred at −20° C. until complete conversion of 7, then quenched with 2,2'-(ethane-1,2-diylbis(oxy))diethanamine (2.1 g, 14.22 mmol) by forming an insoluble complex. After stirring at rt for another 30 min, the suspension was filtered through a pad of celite and concentrated in vacuo to give a crude product which was further purified by column (SiO₂, CH₃OH/EA=0-5% as eluent) to afford compound 7 (1.0 g, 71%) as a white solid. [M+H]⁺=445.3

(S)—((R)-1-(6-(4-tert-butoxy-4-oxobutanamido)pyridin-2-yl)-3-(3,4-dimethoxyphenyl)propyl) 1-(4-(acryloyloxy)-3,3-dimethyl-2-oxobutanoyl)piperidine-2-carboxylate (9). A solution of 7 (1.0 g, 2.24 mmol) and 8 (836 mg, 2.69 mmol) in anhydrous DCM (20 mL) was cooled to −20° C. before a solution of DCC (554 mg, 2.69 mmol) in anhydrous DCM (2 mL) was added, followed by the addition of a solution of 4-(dimethylamino)pyridine (DMAP, 27 mg, 0.22 mmol) in anhydrous DCM (1 mL) under argon atmosphere. The resulting white suspension was stirred at −20° C. for 2 h. The reaction mixture was then filtered and the filtrate were dried over Na$_2$SO$_4$ and concentrated in vacuo to give a crude product which was further purified by column (SiO$_2$, CH$_3$OH/DCM=0-5% as eluent) to afford compound 9 (0.38 g, 23%) as a white solid. [M+H]$^+$=738.4

4-(6-((R)-1-((S)-1-(4-(acryloyloxy)-3,3-dimethyl-2-oxobutanoyl)piperidine-2-carbonyloxy)-3-(3,4-dimethoxyphenyl)propyl)pyridin-2-ylamino)-4-oxobutanoic acid (Raa6). To a solution of 9 (0.38 g, 1.76 mmol) in DCM (5 mL) was added TFA (2 mL) at rt. The resulting mixture was stirred at rt for 2 h. The reaction mixture was charged to silica-gel flash column directly (CH$_3$OH/DCM=0-5% as eluent) to afford Raa6 (310 mg, 89%) as a white solid.

FKBD Example 9

4-((6-((R)—(((S)-1-(4-(acryloyloxy)-3,3-dimethyl-2-oxobutanoyl)piperidine-2-carbonyl)oxy)-3-(3,4-dimethoxyphenyl)propyl)pyrazin-2-yl)amino)-4-oxobutanoic acid (Raa7)

Scheme 12. Synthesis of Raa7 FKBD moiety.

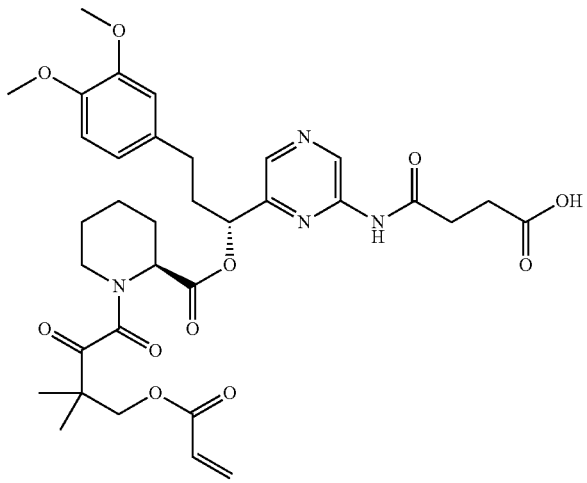

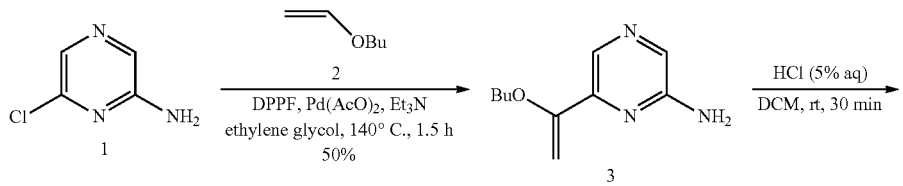

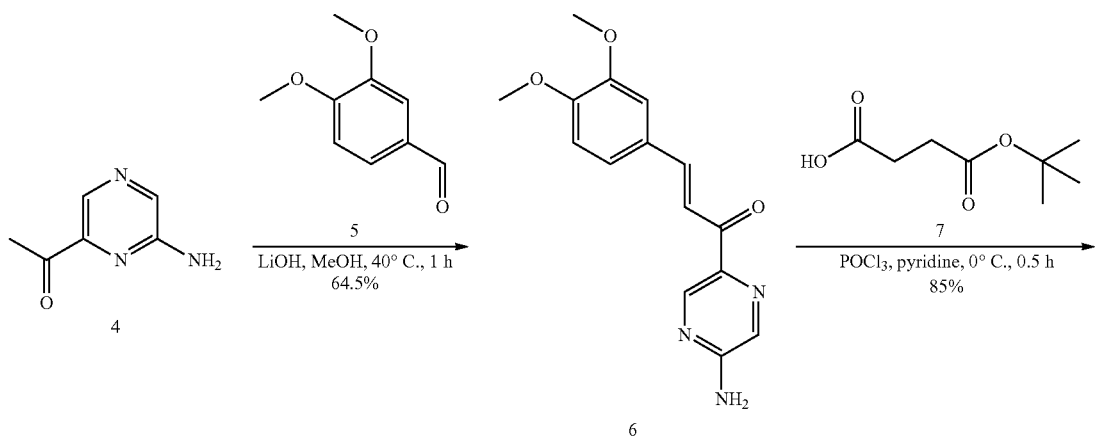

-continued
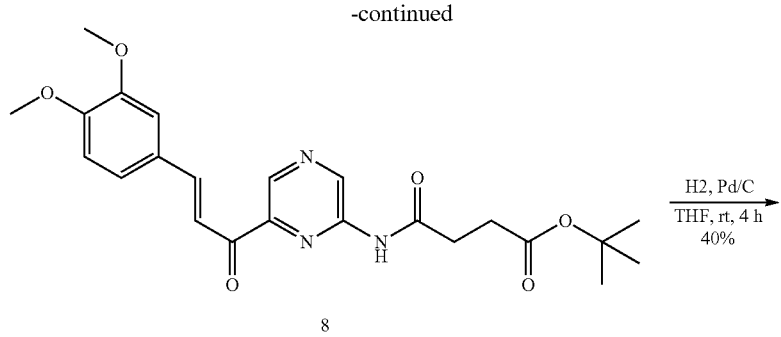
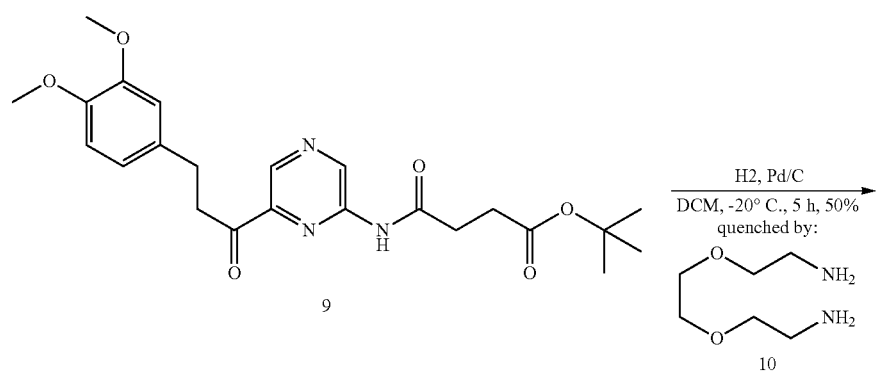
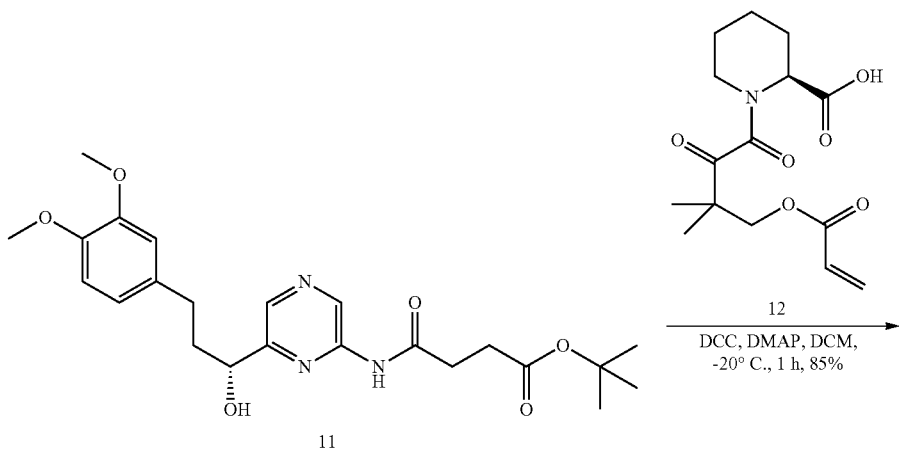
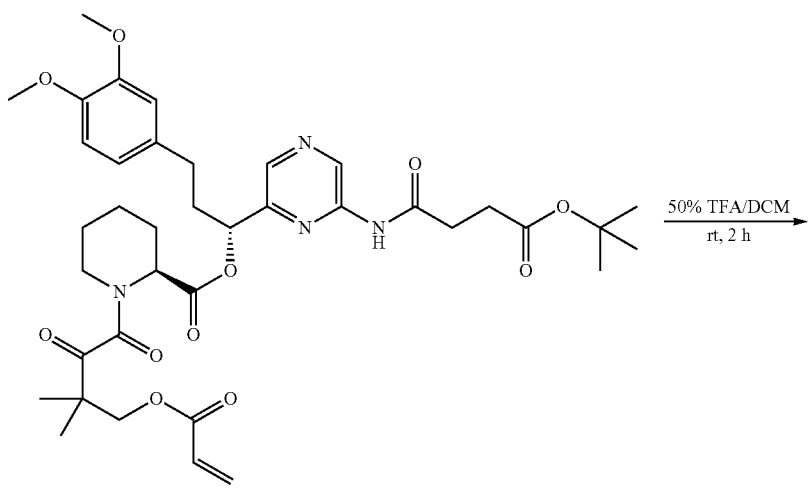

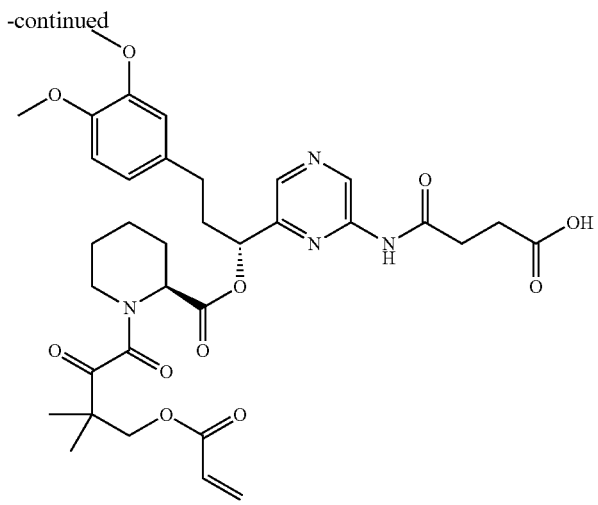

Raa7

6-(1-butoxyvinyl)pyrazin-2-amine (3). To a solution of 1(16 g, 124 mmol) in ethylene glycol (150 mL) was added Pd(AcO)$_2$ (0.8 g, 3.7 mmol) and DPPF (4.12 g, 7.4 mmol) at rt. Degassed by Ar2, and then 2 and Et$_3$N was injected sequentially. The reaction mixture was heated to reflux and reacted for 1.5 h. The product mixture was poured into water (300 ml), extracted with DCM (100 ml*3). Combined the organic phase and washed with brine (100 ml*3). Filtered and concentrated to get 3 (12 g, 50%) as white solid. [M+H]$^+$=194

1-(6-aminopyrazin-2-yl)ethan-1-one (4). To a solution of 3 (12 g, 62 mmol) in DCM (50 ml) was added 5% HCl (20 ml). The reaction mixture was stirred at rt for 0.5 h. Poured the product mixture into water (200 ml), adjusted pH to 8-9 with K$_2$CO$_3$ (aq). Extracted with DCM (50 ml*6), combined the organic phase and concentrated to get the crude. Purified by silica gel chromatography (PE/EA=20-30% as eluent) to give product 4 (2.9 g, 34%) as yellow solid. [M+H]$^+$=138

(E)-1-(5-amiopyrazin-2-yl)-3-(3,4-dimethoxyphenyl)prop-2-en-1-one (6). To a solution of 4 (2.9 g, 21 mmol) in MeOH (20 ml) was added LiOH (1.74 g, 42 mol) and 5 (3.43 g, 21 mmol). The reaction mixture was stirred at 40° C. for 1 h. Poured the product mixture into water (200 ml), filtered until no more precipitation, washed the solid cake with water, and then little MeOH. Dried to get product 6 (3.8 g, 64.5%) as yellow solid. [M+H]$^+$=286 tert-butyl(E)-4-((6-(3-(3,4-dimethoxyphenyl)acryloyl)pyrazin-2-yl)amino-4-oxobutanoate (8). To a solution of 8 (3.8 g, 133 mmol) and 7 (4.64 g, 266 mmol) in pyridine (100 ml) was added POCl$_3$ (6.12 g, 400 mmol) at 0° C. The reaction mixture was stirred at 0° C. for 30 min. Poured the product mixture into water (300 ml), extracted with DCM (100 ml*3), combined the organic phase and washed with brine (100 ml*5). Dried over Na$_2$SO$_4$, filtered and concentrated to get the crude. Purified by silica gel chromatography (MeOH/DCM=1-2% as eluent) to give product 8 (5 g, 68%) as yellow solid. [M+H]$^+$=442 tert-butyl 4-((6-(3-(3,4-dimethoxyphenyl)propannoyl)pyrazin-2-yl)amino)-4-oxobutanoate (9). To a solution of 8 (5.0 g, 113 mmol) in THF was added Pd/C (500 mg, 10%), the reaction mixture was degassed with H$_2$*5, stirred at rt for 4 h. Filtered and concentrated the filtrate to get the crude. Purified by silica gel chromatography (MeOH/DCM=1-2% as eluent) to give product 9 (2.0 g, 40%) as yellow solid. [M+H]$^+$=444 tert-butyl (R)4-((6-(3-(3,4-dimethoxyphenyl)-1-hydroxyphenyl)pyrazin-2-yl)amino)-4-oxobutanoate (11). To a solution of 9 (2.0 g, 45 mmol) in DCM (50 ml) was added DIPCl (14.5 g, 450 mmol) at −20° C., degassed with Ar$_2$. The reaction mixture was stirred at −20° C. for 5 h. Quenched with 10 (6.75 g, 455 mmol). The product mixture was concentrated directly, and the brown residue was purified by silica gel chromatography (MeOH/DCM=2-5% as eluent) to give product 11 (1.0 g, 50%) as yellow solid. [M+H]$^+$=446

(R)-1-(6-(4-tert-butoxy)-4-oxobutanamido)pyrazin-2-yl)-3-(3,4-dimethoxyphenyl(S)-1(4-(acryloyloxy)-3,3-dimethyl-2-oxobutanoyl)piperidine-2-carboxylate (13). To a solution of 11 (1.0 g, 22 mmol) in DCM (30 ml) was added 12 (1.05 g, 34 mmol) at −20° C., and degassed with Ar$_2$, then DCC (0.7 g, 34 mmol) and DMAP (0.03 g, 2.2 mmol) in DCM was injected sequentially. The reaction mixture was stirred at −20° C. for 1 h. Filtered and washed the solid cake with DCM (20 ml), the filtrate was combined and evaporated to get the crude. Purified by silica gel chromatography (MeOH/DCM=1-2% as eluent) to give product 13 (1.8 g, 85%) as yellow solid. [M+H]$^+$=739

4-((6-((R)—(((S)-1-(4-(acryloyloxy)-3,3-dimethyl-2-oxobutanoyl)piperidine-2-carbonyl)oxy)-3-(3,4-dimethoxyphenyl)propyl)pyrazin-2-yl)amino)-4-oxobutanoic acid (Raa7). To a solution of 13 (1.8 g, 24 mmol) in DCM (20 ml) was added TFA (20 ml). The reaction mixture was stirred at rt for 2 h. Concentrated the product mixture directly, the yellow residue was purified by silica gel chromatography (MeOH/DCM=1-2% as eluent) to give product Raa7 (500 mg, 30%) as light yellow solid.

FKBD Example 10
4-((3-((R)-1-(((S)-4-(4-(acryloyloxy)-3,3-dimethyl-2-oxobutanoyl)morpholine-3-carbonyl)oxy)-3-(3,4-dimethoxyphenyl)propyl)phenyl)amino)-4-oxobutanoic acid (Raa8)
Scheme 13. Synthesis of Raa8 FKBD moiety.
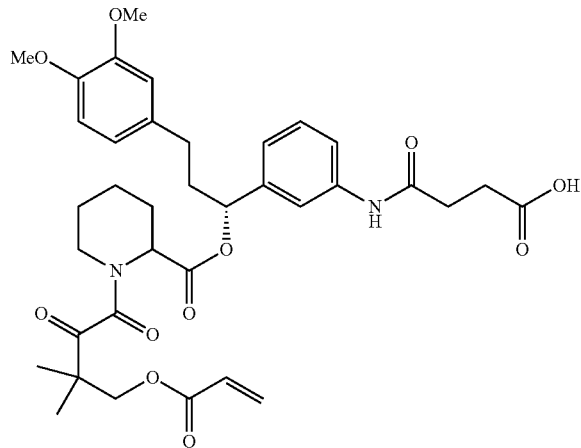
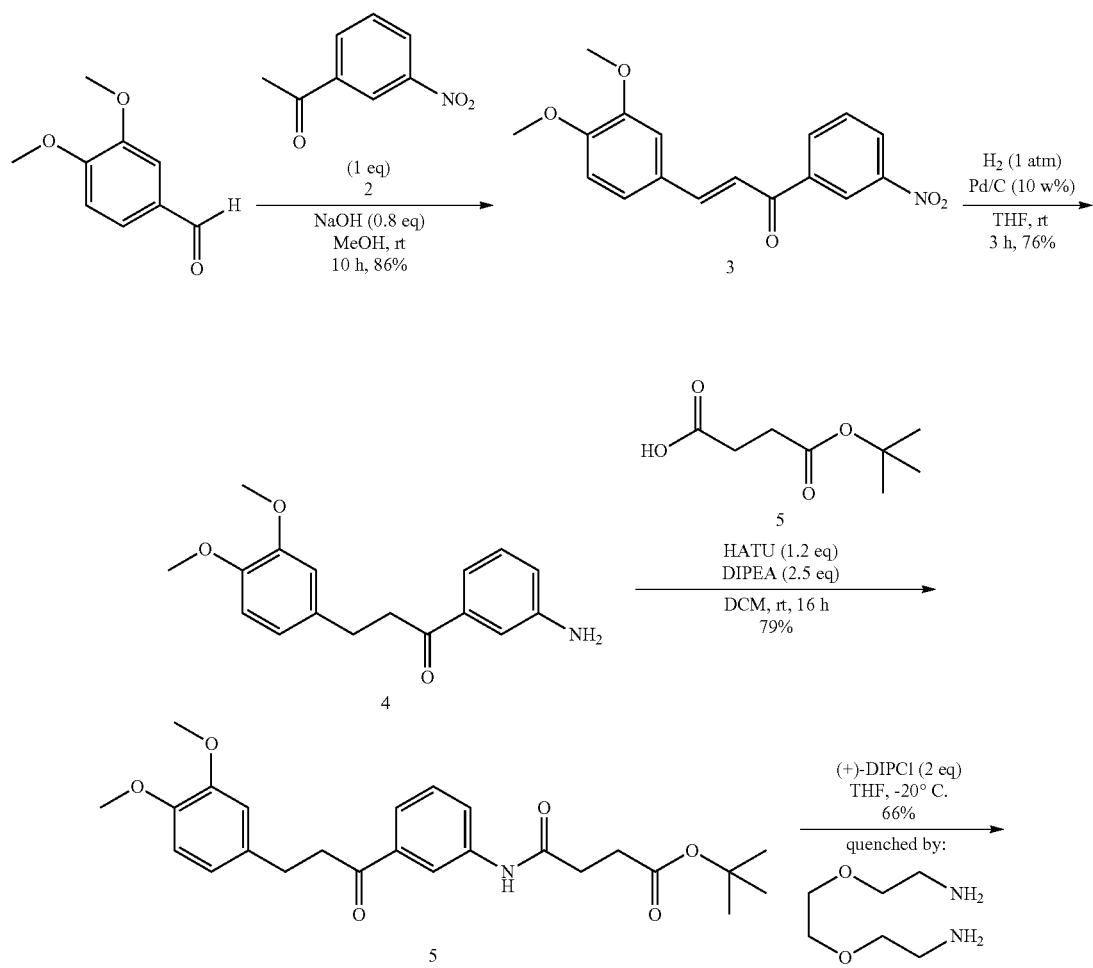

-continued
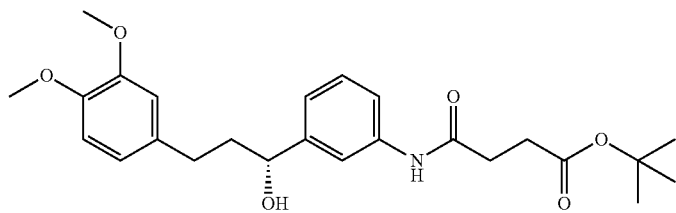
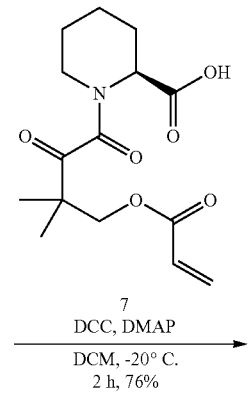
7
DCC, DMAP
———————→
DCM, -20° C.
2 h, 76%
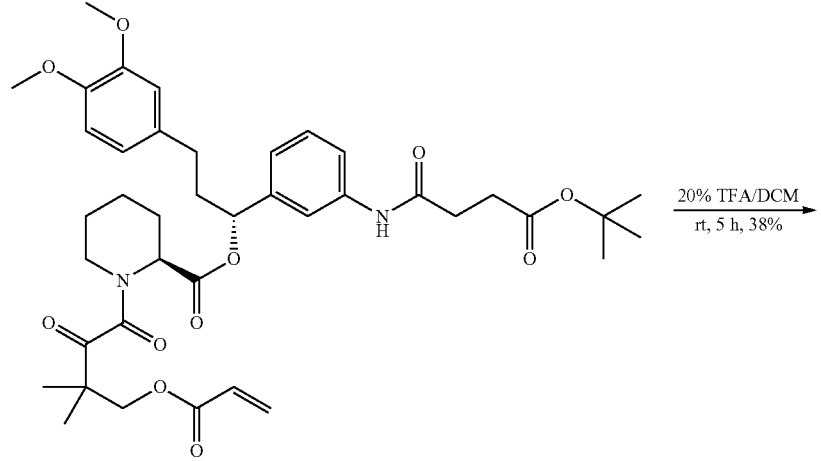
20% TFA/DCM
———————→
rt, 5 h, 38%
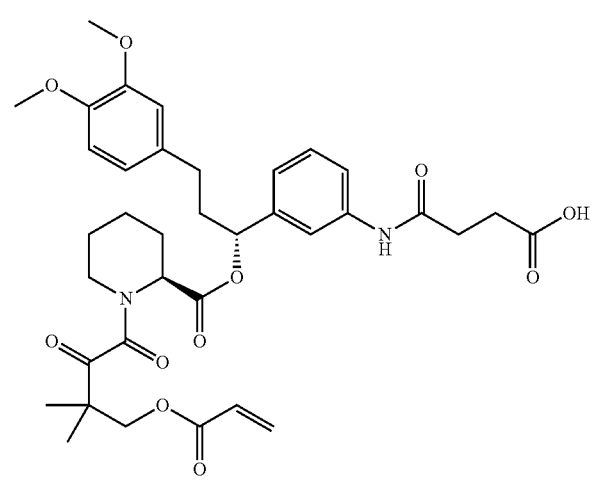
Raa8

(E)-3-(3,4-dimethoxyphenyl)-1-(3-nitrophenyl)prop-2-en-1-one (3). To the solution of 3,4-dimethoxybenzaldehyde 1 (60 g, 360 mmol) and 1-(3-nitrophenyl)ethan-1-one 2 (59.6 g, 360 mmol) in MeOH (1100 mL) was added NaOH (15 g) at 0° C. The resulting solution was stirred at rt for 10 h. The precipitate was collected to give compound 3 as a yellow solid (97 g, 86%). [M+Na]$^+$=336.1

1-(3-aminophenyl)-3-(3,4-dimethoxyphenyl)propan-1-one (4). A solution of 3 (32 g, 110 mmol) and 10% Pd/C (10 g) in THF (120 mL) was hydrogenated with H$_2$ for 8 h at room temperature. The reaction mixture was then filtered and concentrated. The residue was purified by silica-gel flash column chromatography (AcOEt/PE 1:3) to give compound 4 as a white solid (24 g, 76%). [M+H]$^+$=286.2 tert-butyl 4-((3-(3-(3,4-dimethoxyphenyl)propanoyl)phenyl)amino)-4-oxobutanoate (5). To a solution of 4 (12.0 g, 42 mmol) in DCM (30 mL) was added 4-tert-butoxy-4-oxobutanoic acid (8.8 g, 50 mmol), DIPEA (13.6 g, 105 mmol) and HATU (19.2 g, 50 mmol). The mixture was stirred at rt for 16 h. The product was purified by silica-gel flash column chromatography (AcOEt/PE 1:2) to give compound 5 as a white solid (16 g, 79%). [M+Na]$^+$=464.0 tert-butyl (R)-4-((3-(3-(3,4-dimethoxyphenyl)-1-hydroxypropyl)phenyl)amino)-4-oxobutanoate (6). A solution of ketone 5 (11.9 g, 26.9 mmol) in dry THF (120 mL) at −20° C. was treated with a solution of (+)-DIPChloride (135 mmol) in heptane (1.7 M, 79 mL) at −20° C. The resulting mixture was reacted at −20° C. until complete conversion of 5, then quenched with 2,2'-(ethylenedioxy)diethylamine (20 g) by forming an insoluble complex. After stirring at RT for another 30 min, the suspension was filtered through a pad of celite and concentrated. The crude compound was purified by silica-gel flash column chromatography (AcOEt/PE 3:1) to give compound 6 as a light yellow oil (7.9 g, 66%, ee 97%). [M+Na]$^+$=466.3

(R)-1-(3-(4-(tert-butoxy)-4-oxobutanamido)phenyl)-3-(3,4-dimethoxyphenyl)propyl (S)-4-(4-(acryloyloxy)-3,3-dimethyl-2-oxobutanoyl)morpholine-3-carboxylate (8). A solution of 6 (2.36 g, 5.32 mmol) and 7 (2 g, 6.38 mmol) in CH$_2$Cl$_2$ (10 mL) was cooled to −20° C. before a solution of DCC (1.65 g, 7.98 mmol) in CH$_2$Cl$_2$ (5 mL) was added, followed by the addition of a solution of 4-(dimethylamino)pyridine (DMAP, 65 mg, 0.53 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 2:1) to give compound 8 as a light yellow oil (2.5 g, 64%). [M+Na]$^+$=761.4

4-((3-((R)-1-(((S)-4-(4-(acryloyloxy)-3,3-dimethyl-2-oxobutanoyl)morpholine-3-carbonyl)oxy)-3-(3,4-dimethoxyphenyl)propyl)phenyl)amino)-4-oxobutanoic acid (Raab). A solution of 8 (2.5 g, 3.45 mmol) in CH$_2$Cl$_2$ (12 mL) was treated with a solution of 40% TFA in CH$_2$Cl$_2$ (12 mL) at 0° C. The mixture was allowed to react at room temperature until complete conversion. The reaction mixture was charged to silica-gel flash column directly (AcOEt/PE/AcOH 1:2:0.5%) to afford Raab (815 mg, 38%) as a pale yellow solid.

FKBD Example 11

4-((3-((R)-1-(((S)-4-(((9H-fluoren-9-yl)methoxy)carbonyl)-1-(4-(acryloyloxy)-3,3-dimethyl-2-oxobutanoyl)piperazine-2-carbonyl)oxy)-3-(3,4-dimethoxyphenyl)propyl)phenyl)amino)-4-oxobutanoic acid (Raa9)

Scheme 14. Synthesis of Raa9 FKBD moiety.

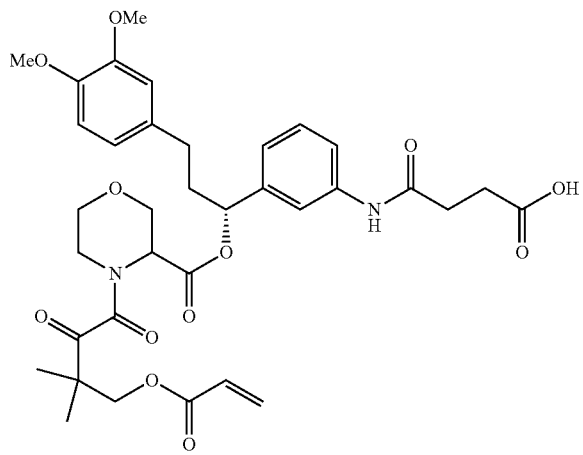

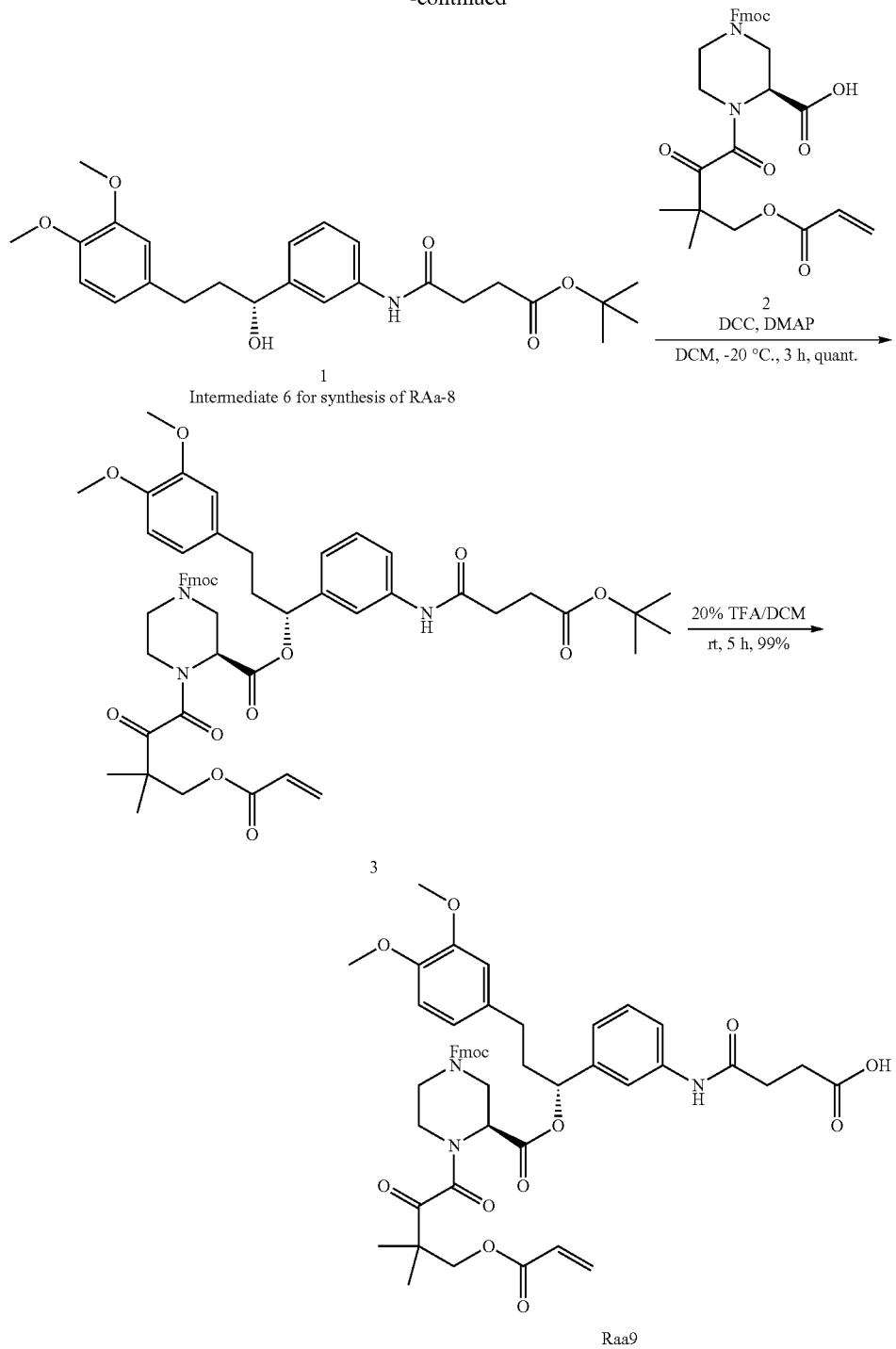

1-((9H-fluoren-9-yl)methyl) 3-((R)-1-(3-(4-(tert-butoxy)-4-oxobutanamido)phenyl)-3-(3,4-dimethoxyphenyl)propyl) (S)-4-(4-(acryloyloxy)-3,3-dimethyl-2-oxobutanoyl)piperazine-1,3-dicarboxylate (3). A solution of 1(1.35 g, 3.04 mmol) and 2 (1.95 g, 3.65 mmol) in CH$_2$Cl$_2$ (10 mL) was cooled to −20° C. before a solution of DCC (940 mg, 4.56 mmol) in CH$_2$Cl$_2$ (5 mL) was added, followed by the addition of a solution of 4-(dimethylamino)pyridine (DMAP, 37 mg, 0.3 mmol) in CH$_2$Cl$_2$ (2 mL) under argon atmosphere. The resulting white suspension was allowed to stir at −20° C. for 3 h. The reaction mixture was then filtered, evaporated, and the crude compound was purified by silica-gel flash column chromatography (DCM/MeOH 96:4) to give compound 3 as a white solid (3.0 g, quant.). [M+Na]$^+$= 981.6

4-((3-((R)-1-(((S)-4-(((9H-fluoren-9-yl)methoxy)carbonyl)-1-(4-(acryloyloxy)-3,3-dimethyl-2-oxobutanoyl)piperazine-2-carbonyl)oxy)-3-(3,4-dimethoxyphenyl)propyl)phenyl)amino)-4-oxobutanoic acid (Raa9). A solution of 3 (1.5 g, 1.56 mmol) in CH$_2$Cl$_2$ (12 mL) was treated with a solution of 40% TFA in $CH_2Cl_2$ (12 mL) at 0° C. The mixture was allowed to react at room temperature until complete conversion. The reaction mixture was charged to silica-gel flash column directly (AcOEt/PE/AcOH 1:2:0.5%) to afford Raa9 (1.4 g, 99%) as a white solid.

FKBD Example 12

(S)—((R)-1-(3-(4-tert-butoxy-4-oxobutanamido) phenyl)-3-(3,4-dimethoxyphenyl)propyl) 1-(4-(acry-loyloxy)-3,3-dimethyl-2-oxobutanoyl)-4-methylpip-erazine-2-carboxylate (Raa10)

Scheme 15. Synthesis of Raa10 FKBD moiety.

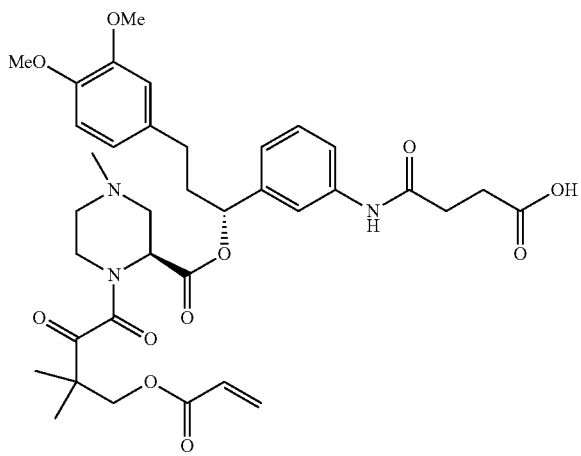

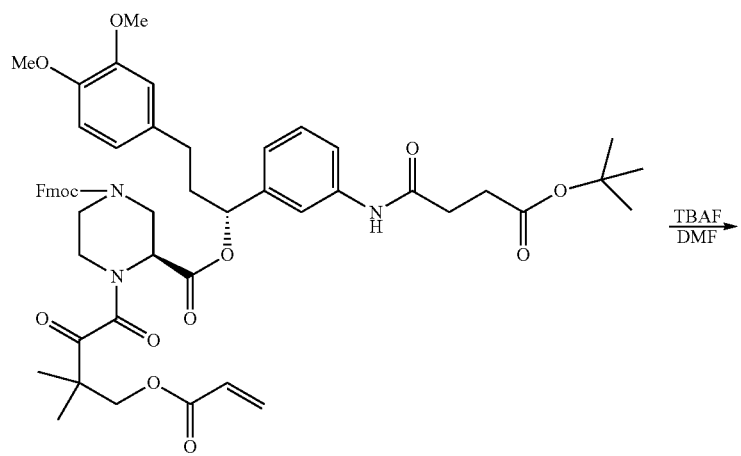

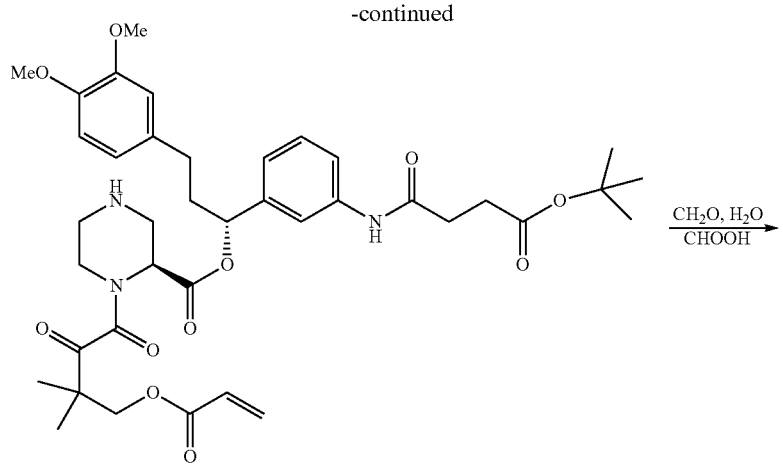

2

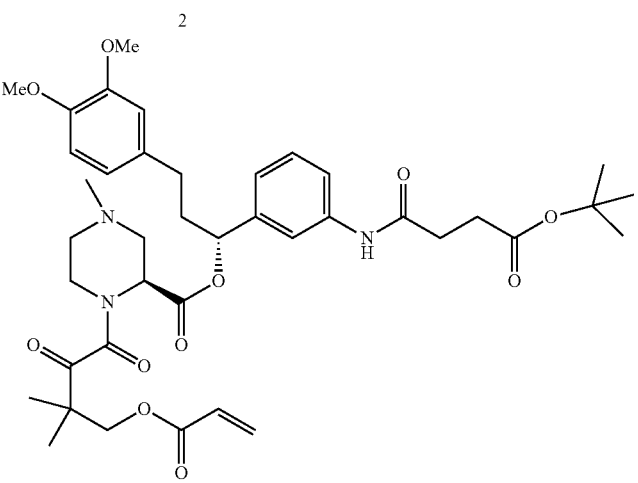

Raa10

(S)-1-(9H-fluoren-9-yl)methyl 3-((R)-1-(3-(4-tert-butoxy-4-oxobutanamido)phenyl)-3-(3,4-dimethoxyphenyl)propyl) 4-(4-(acryloyloxy)-3,3-dimethyl-2-oxobutanoyl)piperazine-1,3-dicarboxylate (2). To the solution of 1(1.3 g, 1.35 mmol) in DMF (5 mL) was added TBAF (3.2 ml, 1.0 M, 3.18 mmol) at 0° C. The resulting solution was heated to room temperature for 5 h. After this time the reaction mixture was washed with NaHCO$_3$ (aq., 50 ml*3) and NaCl (aq., 50 ml*3). The organic phase was concentrated. The reaction mixture was purified on silica with DCM/MEOH=50/1 to give 2 (800 mg, 80%) as a colourless oil. [M+H]$^+$=738.4

(S)—((R)-1-(3-(4-tert-butoxy-4-oxobutanamido)phenyl)-3-(3,4-dimethoxyphenyl)propyl) 1-(4-(acryloyloxy)-3,3-dimethyl-2-oxobutanoyl)-4-methylpiperazine-2-carboxylate (Raa10). A solution of 2 (800 mg, 1.08 mmol) in CHOOH (1.6 mL) was treated with an aqueous solution of formaldehyde (37% in water, 0.8 ml, 1.3 mmol) and allowed to stir at 50° C. for 1 h. After this time the reaction mixture was purified with DCM/MeOH=100/1 give 3 (400 mg, 50%) as a colorless oil. [M+H]$^+$=751.9

FKBD Example 13

(S)-4-(3-((R)-1-((S)-1-(4-(acryloyloxy)-3,3-dimethyl-2-oxobutanoyl)piperidine-2-carbonyloxy)-3-(3,4-dimethoxyphenyl)propyl)phenylamino)-3-hydroxy-4-oxobutanoic acid (Raa11)

Scheme 16. Synthesis of Raa11 FKBD moiety.

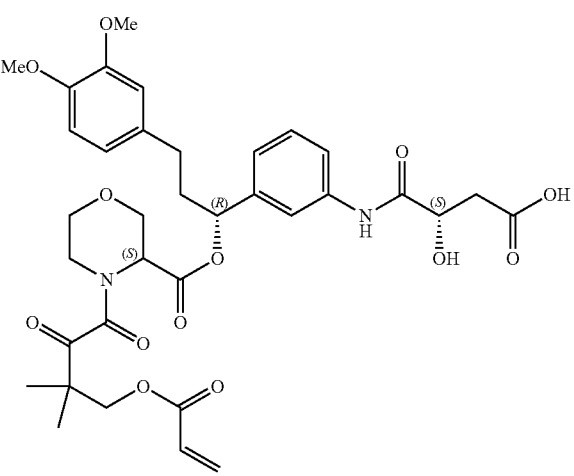

421

-continued

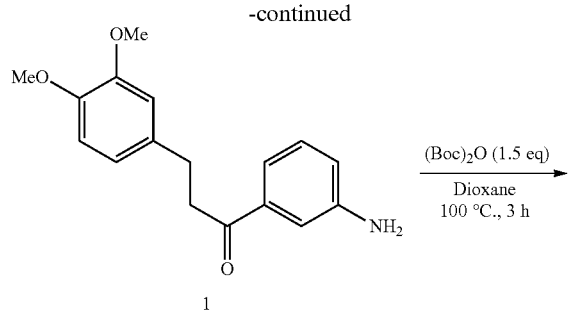

1

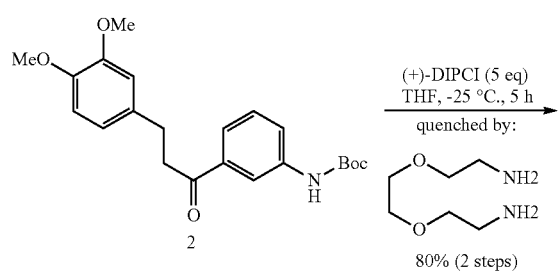

2

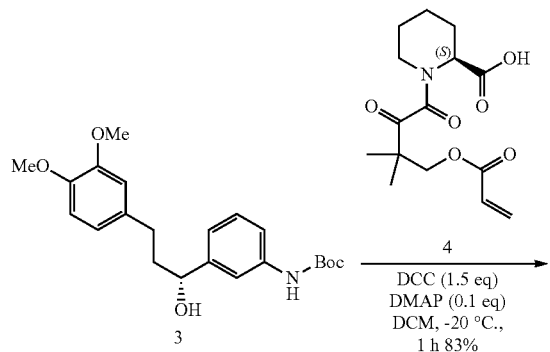

3

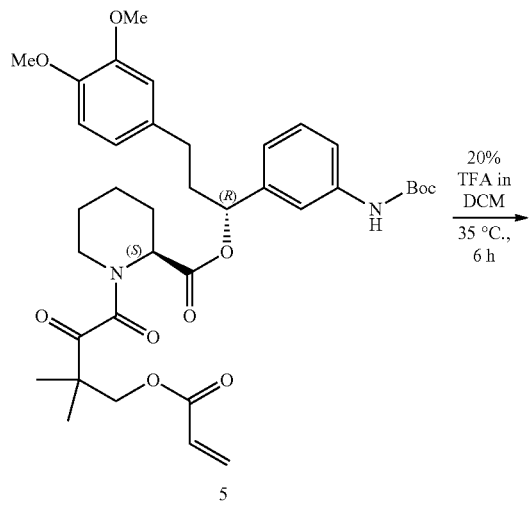

5

422

-continued

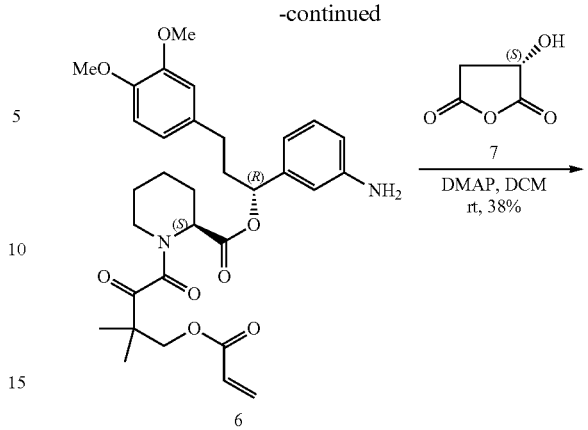

6

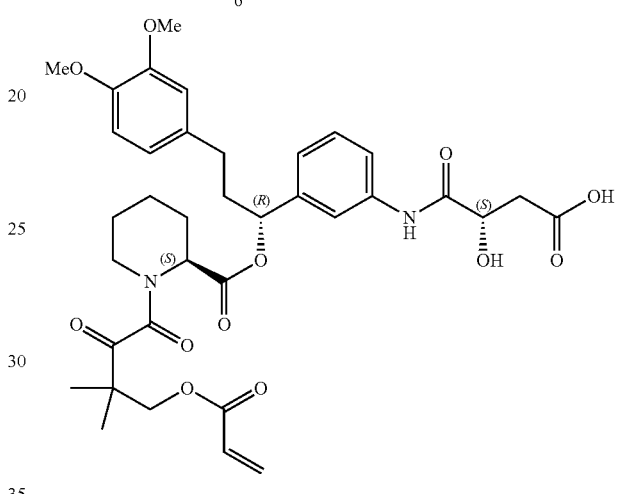

Raa12 tert-butyl 3-(3-(3,4-dimethoxyphenyl)propanoyl)phenyl-carbamate (2). To the solution of 1-(3-aminophenyl)-3-(3,4-dimethoxyphenyl)propan-1-one 1 (8.5 g, 29.79 mmol) in 1,4-dioxane (85 mL) was added (Boc)$_2$O (9.75 g, 44.68 mmol). The resulting solution was heated to 100° C. for 3 h. The solvent was evaporated and the residue (10.3 g, crude) was used directly for the next step without purification. [M+Na]$^+$=408

(R)-tert-butyl 3-(3-(3,4-dimethoxyphenyl)-1-hydroxypropyl)phenylcarbamate (3). A solution of ketone 2 (10 g, crude) in dry THF (200 mL) at −20° C. was treated with a solution of (+)-DIPChloride in heptane (1.7 M, 76.2 mL) at −20° C. The resulting mixture was reacted at −20° C. until complete conversion of 2, then quenched with 2,2'-(ethylenedioxy)diethylamine (23.1 g) by forming an insoluble complex. After stirring at RT for another 30 min, the suspension was filtered through a pad of celite and concentrated. The crude compound was purified by silica-gel flash column chromatography (AcOEt/PE 1:3) to give compound 3 as a light yellow oil (8.3 g, 80%). [M+Na]$^+$=410

(S)—((R)-1-(3-(tert-butoxycarbonylamino)phenyl)-3-(3,4-dimethoxyphenyl)propyl) 1-(4-(acryloyloxy)-3,3-dimethyl-2-oxobutanoyl)piperidine-2-carboxylate (5). A solution of 3 (8.3 g, 21.42 mmol) and 4 (8 g, 25.7 mmol) in CH$_2$Cl$_2$ (100 mL) was cooled to −20° C. before a solution of DCC (5.3 g, 25.7 mmol) in CH$_2$Cl$_2$ (5 mL) was added, followed by the addition of a solution of 4-(dimethylamino)pyridine (DMAP, 318 mg, 2.6 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:3) to give compound 5 as a light yellow oil (12 g, 83%). [M+Na]⁺=703.3

(S)—((R)-1-(3-aminophenyl)-3-(3,4-dimethoxyphenyl) propyl) 1-(4-(acryloyloxy)-3,3-dimethyl-2-oxobutanoyl)piperidine-2-carboxylate (6). To a solution of 5 (5 g, 7.34 mmol) in DCM (30 ml) was added TFA (6 ml). The mixture was stirred at 35° C. for 6 h. The solvent was evaporated and the residue (5.0 g, crude) was used directly for the next step without purification. [M+H]⁺=580.8

(S)-4-(3-((R)-1-((S)-1-(4-(acryloyloxy)-3,3-dimethyl-2-oxobutanoyl)piperidine-2-carbonyloxy)-3-(3,4-dimethoxyphenyl)propyl)phenylamino)-3-hydroxy-4-oxobutanoic acid (Raa11). A solution of 6 (1.0 g, crude) in DCM (20 mL) was added 7 (400 mg, 3.4 mmol) and DMAP (25 mg, 0.2 mmol). The mixture was allowed to react at room temperature until complete conversion. The reaction mixture was charged to silica-gel flash column directly (DCM/MeOH=10:1) to afford Raa11 (450 mg, 38%) as a white solid.

FKBD Example 14

(S)-4-(3-((R)-1-((S)-1-(4-(acryloyloxy)-3,3-dimethyl-2-oxobutanoyl)piperidine-2-carbonyloxy)-3-(3,4-dimethoxyphenyl)propyl)phenylamino)-2-hydroxy-4-oxobutanoic acid (Raa12)

Scheme 17. Synthesis of Raa12 FKBD moiety.

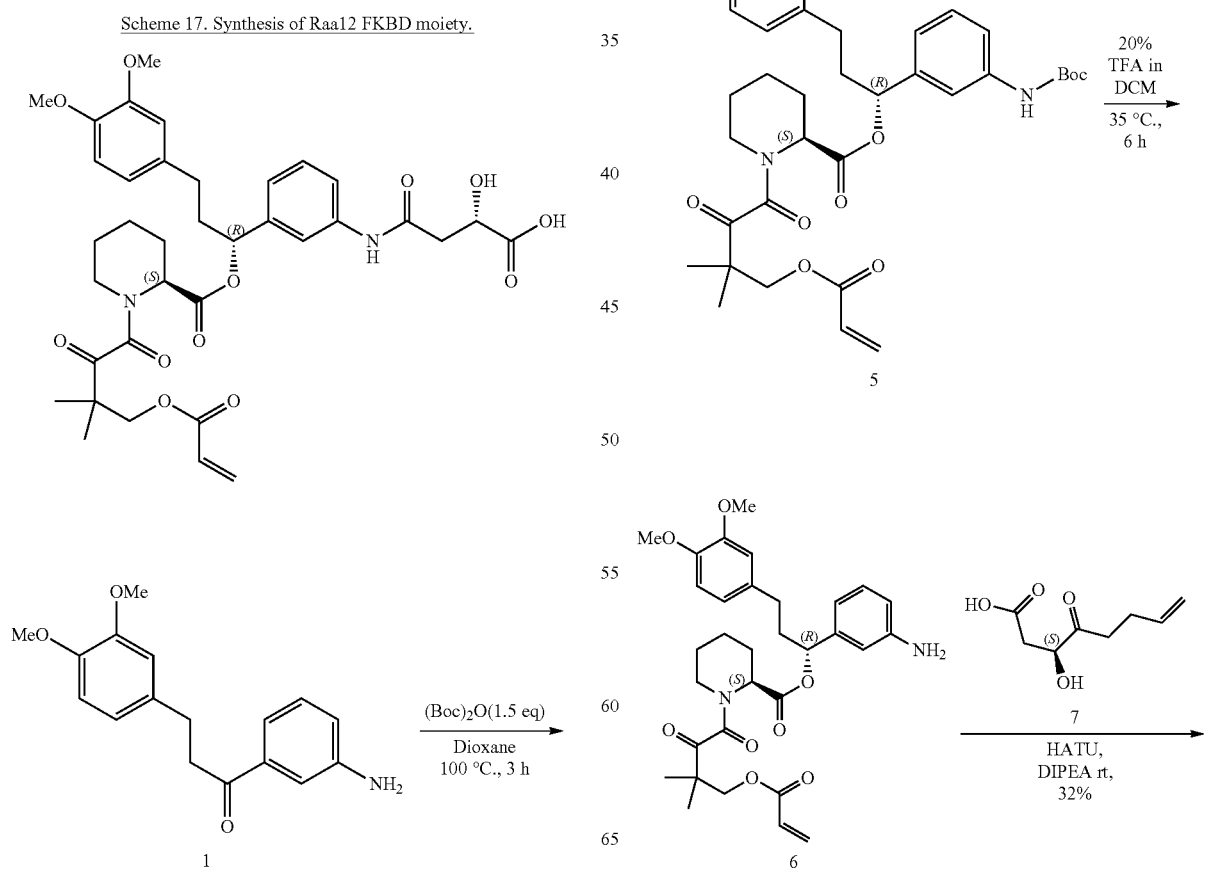

425

-continued

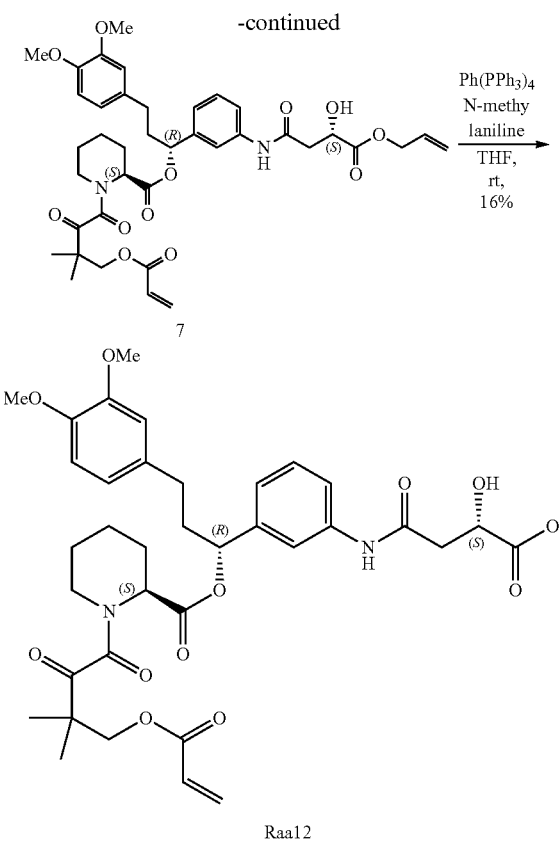

The synthesis of 6 is the same as Raa11.

(S)—((R)-1-(3-((S)-4-(allyloxy)-3-hydroxy-4-oxobutanamido)phenyl)-3-(3,4-dimethoxyphenyl)propyl) 1-(4-(acryloyloxy)-3,3-dimethyl-2-oxobutanoyl)piperidine-2-carboxylate (8). To a solution of 6 (2 g, 3.44 mmol) in DMF (30 ml) was added 7 (1.2 g, 6.9 mmol) DIPEA (1.33 g, 0.32 mmol) and HATU (1.96 g, 5.16 mmol). The mixture was stirred at rt for 3 h before being diluted with EtOAc. The organic layer was washed by brine, dried over $Na_2SO_4$ and concentrated in vacuo. The residue was purified by silica-gel column (DCM/MeOH 10:1) to give product 8 as a yellow oil (800 mg, 32%). $[M+H]^+=737$.

(S)-4-(3-((R)-1-((S)-1-(4-(acryloyloxy)-3,3-dimethyl-2-oxobutanoyl)piperidine-2-carbonyloxy)-3-(3,4-dimethoxyphenyl)propyl)phenylamino)-2-hydroxy-4-oxobutanoic acid (Raa12). A solution of 8 (800 mg, 1.09 mmol) in THF (100 mL) was added N-Methylaniline (232 mg, 2.17 mmol) and $Pd(PPh_3)_4$ (115 mg, 0.1 mmol). The mixture was allowed to react at room temperature under $N_2$ atmosphere until complete conversion. The reaction mixture was charged to silica-gel flash column directly (DCM/MeOH 10:1) to afford Raa12 (120 mg, 16%) as a white solid.

FKBD Example 15

(S)-3-(((9H-fluoren-9-yl)methoxy)carbonylamino)-4-(3-((R)-1-((S)-1-(4-(acryloyloxy)-3,3-dimethyl-2-oxobutanoyl)piperidine-2-carbonyloxy)-3-(3,4-dimethoxyphenyl)propyl)phenylamino)-4-oxobutanoic acid (Raa13)

Scheme 18. Synthesis of Raa13 FKBD moiety.

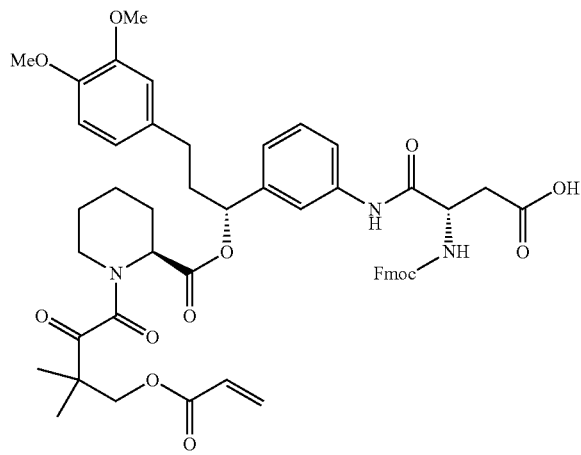

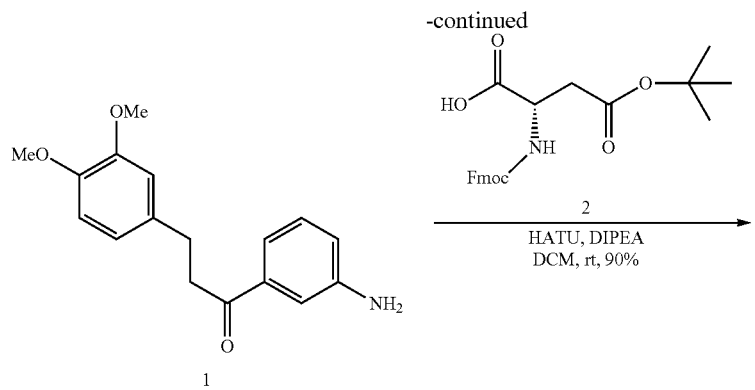
intermediate 4 for the synthesis of RAa-8
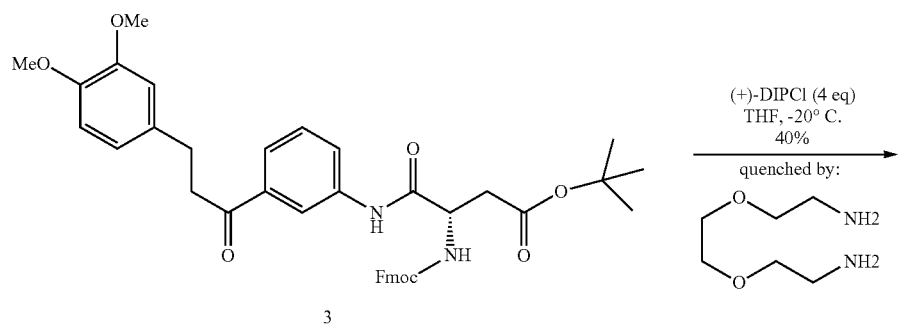
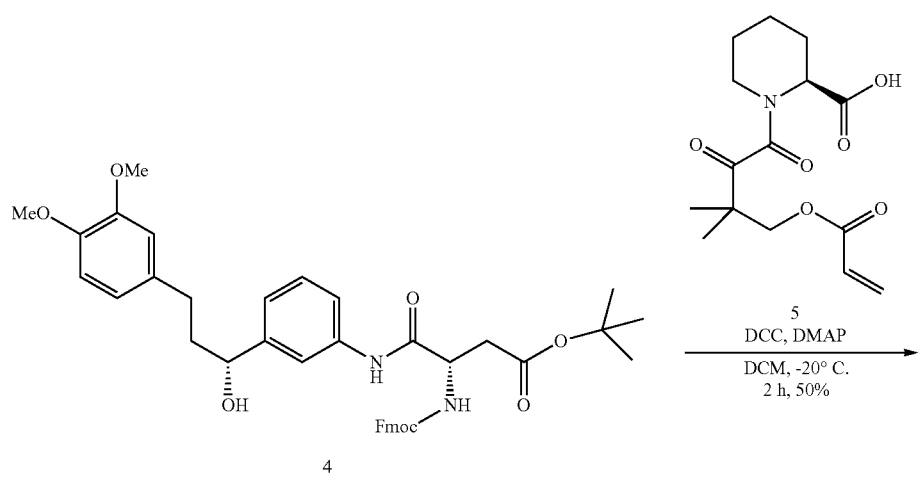

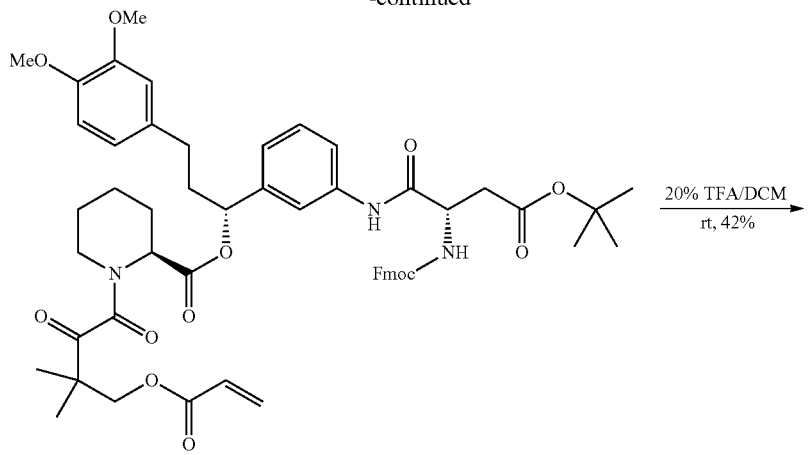

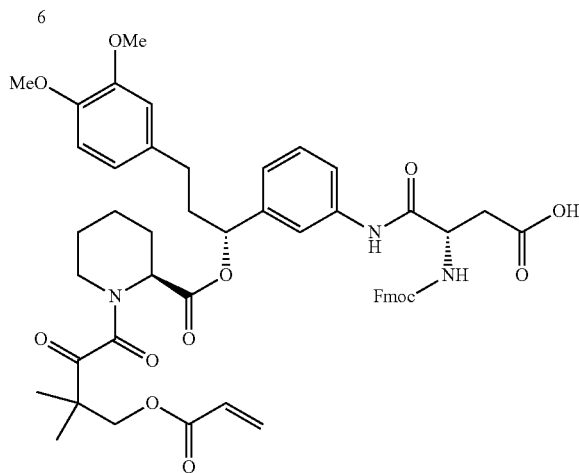

Raa13

(S)-tert-butyl 3-(((9H-fluoren-9-yl)methoxy)carbonylamino)-4-(3-(3-(3,4-dimethoxyphenyl)propanoyl)phenylamino)-4-oxobutanoate (3). A solution of 1 (4.0 g, 14.03 mmol), 2 (7.0 g, 16.8 mmol) in DCM (150 mL) was treated with DIPEA (8 ml, 42.1 mmol) and HATU (8.0 g, 21.1 mmol) at 0° C. and allowed to stir at room temperature for 15 h. After this time the reaction mixture was washed with H$_2$O and extracted with AcOEt (50 ml*3). The organic phase was dried over Na$_2$SO$_4$ and concentrated. The residue was purified by silica-gel flash column chromatography (AcOEt/PE 1:10) to give compound 3 as a brown oil (9 g, 90%). [M+Na]$^+$=700.9

(S)-tert-butyl 3-(((9H-fluoren-9-yl)methoxy)carbonylamino)-4-(3-((R)-3-(3,4-dimethoxyphenyl)-1-hydroxypropyl)phenylamino)-4-oxobutanoate (4). A solution of ketone 3 (4.7 g, 6.9 mmol) in dry THF (130 mL) at −20° C. was treated with a solution of (+)-DIPChloride (27.7 mmol) in heptane (1.7 M, 16.3 mL) at −20° C. The resulting mixture was reacted at −20° C. until complete conversion of 3, then quenched with 2,2'-(ethylenedioxy)diethylamine (2.8 mL) by forming an insoluble complex. After stirring at RT for another 30 min, the suspension was filtered through a pad of celite and concentrated. The crude compound was purified by silica-gel flash column chromatography (AcOEt/PE 1:10) to give compound 4 as a light yellow oil (1.7 g, 40%). [M+Na]$^+$=702.8

(S)—((R)-1-(3-((S)-2-(((9H-fluoren-9-yl)methoxy)carbonylamino)-4-tert-butoxy-4 oxobutanamido) phenyl)-3-(3,4-dimethoxyphenyl)propyl) 1-(4-(acryloyloxy)-3,3-dimethyl-2-oxobutanoyl)piperidine-2-carboxylate (6). A solution of 4 (1.7 g, 2.5 mmol) and 5 (1.2 g, 3.75 mmol) in CH$_2$Cl$_2$ (50 mL) was cooled to −20° C. before a solution of DCC (0.78 g, 3.75 mmol) in CH$_2$Cl$_2$ (5 mL) was added, followed by the addition of a solution of 4-(dimethylamino) pyridine (DMAP, 30 mg, 0.25 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:5) to give compound 6 as a light yellow oil (1.0 g, 50%).

(S)-3-(((9H-fluoren-9-yl)methoxy)carbonylamino)-4-(3-((R)-1-((S)-1-(4-(acryloyloxy)-3,3-dimethyl-2-oxobutanoyl)piperidine-2-carbonyloxy)-3-(3,4-dimethoxyphenyl) propyl)phenylamino)-4-oxobutanoic acid (Raa13). A solution of 6 (1.0 g, 1.02 mmol) in CH$_2$Cl$_2$ (10 mL) was treated with a solution of 40% TFA in CH$_2$Cl$_2$ (10 mL) at 0° C. The mixture was allowed to react at room temperature until complete conversion. The reaction mixture was charged to silica-gel flash column directly (DCM/MeOH=50/1) to afford Raa13 (401 mg, 42%) as a white solid.

FKBD Example 16
(S)-2-(((9H-fluoren-9-yl)methoxy)carbonylamino)-4-(3-((R)-1-((S)-1-(4-(acryloyloxy)-3,3-dimethyl-2-oxobutanoyl)piperidine-2-carbonyloxy)-3-(3,4-dimethoxyphenyl)propyl)phenylamino)-4-oxobutanoic acid (Raa14)
Scheme 19. Synthesis of Raa14 FKBD moiety.
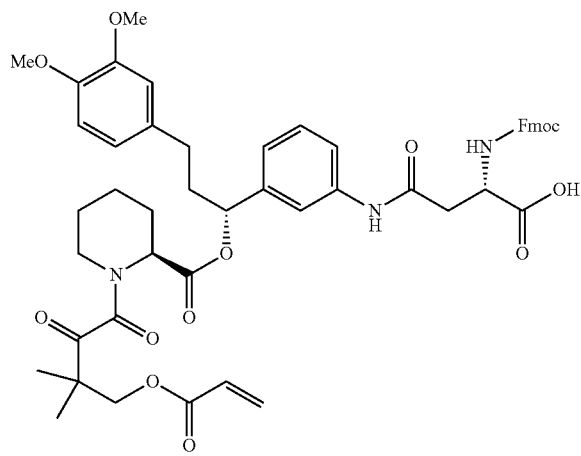
5
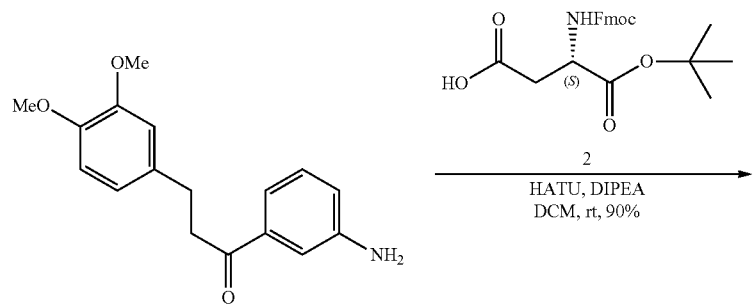
1
intermediate 4 for the synthesis of RAa-8
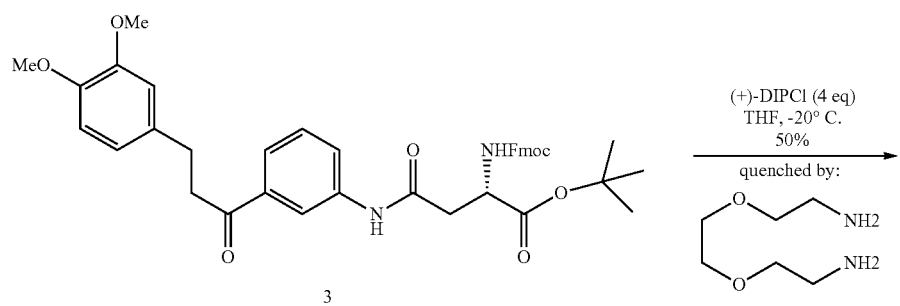
3

-continued
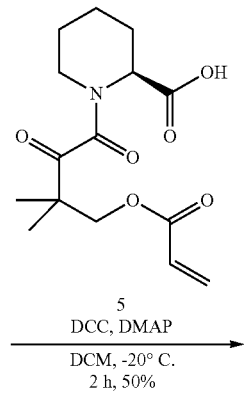
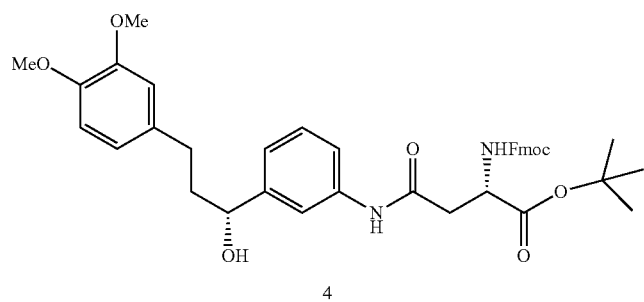
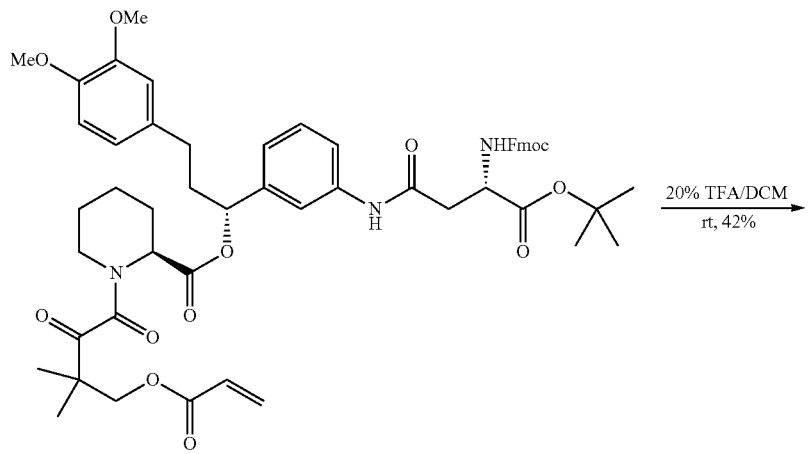
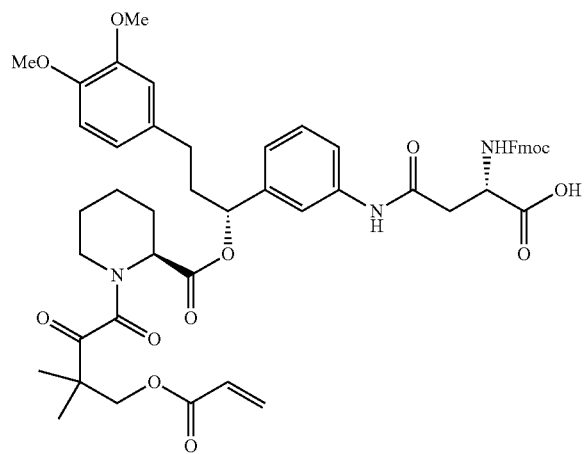
Raa14

(S)-tert-butyl 2-(((9H-fluoren-9-yl)methoxy)carbonylamino)-4-(3-(3-(3,4-dimethoxyphenyl)propanoyl)phenylamino)-4-oxobutanoate (3). A solution of 1 (4.0 g, 14.03 mmol), 2 (7.0 g, 16.8 mmol) in DCM (150 mL) was treated with DIPEA (8 ml, 42.1 mmol) and HATU (8.0 g, 21.1 mmol) at 0° C. and allowed to stir at room temperature for 15 h. After this time the reaction mixture was washed with H$_2$O and extracted with AcOEt (50 ml*3). The organic phase was dried over Na$_2$SO$_4$ and concentrated. The residue was purified by silica-gel flash column chromatography (AcOEt/PE 1:10) to give compound 3 as a brown oil (9 g, 90%). [M+Na]$^+$=700.9

(S)-tert-butyl 2-(((9H-fluoren-9-yl)methoxy)carbonylamino)-4-(3-((S)-3-(3,4-dimethoxyphenyl)-1-hydroxypropyl)phenylamino)-4-oxobutanoate (4). A solution of ketone 3 (4.0 g, 5.9 mmol) in dry THF (80 mL) at −20° C. was treated with a solution of (+)-DIPChloride (23.6 mmol) in heptane (1.7 M, 14.0 mL) at −20° C. The resulting mixture was reacted at −20° C. until complete conversion of 3, then quenched with 2,2'-(ethylenedioxy)diethylamine (2.8 mL) by forming an insoluble complex. After stirring at RT for another 30 min, the suspension was filtered through a pad of celite and concentrated. The crude compound was purified by silica-gel flash column chromatography (AcOEt/PE 1:10) to give compound 4 as a light yellow oil (2.0 g, 50%). [M+Na]$^+$=702.8

(S)—(R)-1-(3-((S)-3-(((9H-fluoren-9-yl)methoxy)carbonylamino)-4-tert-butoxy-4-oxobutanamido)phenyl)-3-(3,4-dimethoxyphenyl)propyl) 1-(4-(acryloyloxy)-3,3-dimethyl-2-oxobutanoyl)piperidine-2-carboxylate (6). A solution of 4 (2.0 g, 2.9 mmol) and 5 (1.2 g, 3.82 mmol) in CH$_2$Cl$_2$ (50 mL) was cooled to −20° C. before a solution of DCC (0.91 g, 4.11 mmol) in CH$_2$Cl$_2$ (5 mL) was added, followed by the addition of a solution of 4-(dimethylamino)pyridine (DMAP, 35 mg, 0.29 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:5) to give compound 6 as a light yellow oil (1.0 g, 50%).

(S)-2-(((9H-fluoren-9-yl)methoxy)carbonylamino)-4-(3-((R)-1-((S)-1-(4-(acryloyloxy)-3,3-dimethyl-2-oxobutanoyl)piperidine-2-carbonyloxy)-3-(3,4-dimethoxyphenyl)propyl)phenylamino)-4-oxobutanoic acid (Raa14). A solution of 6 (1.0 g, 1.02 mmol) in CH$_2$Cl$_2$ (10 mL) was treated with a solution of 40% TFA in CH$_2$Cl$_2$ (10 mL) at 0° C. The mixture was allowed to react at room temperature until complete conversion. The reaction mixture was charged to silica-gel flash column directly (DCM/MeOH=50/1) to afford Raa14 (367 mg, 42%) as a white solid.

FKBD Example 17

(2S,3S)-4-((3-((R)-1-(((S)-1-(4-(acryloyloxy)-3,3-dimethyl-2-oxobutanoyl)piperidine-2-carbonyl)oxy)-3-(3,4-dimethoxyphenyl)propyl)phenyl)amino)-2,3-dihydroxy-4-oxobutanoic acid (Raa15)

Scheme 20. Synthesis of Raa15 FKBD moiety.

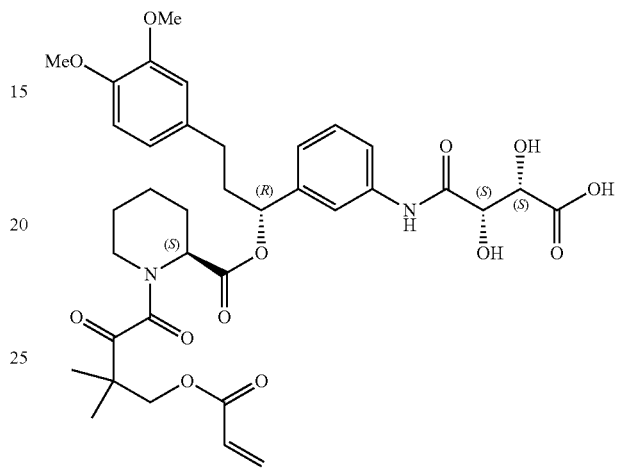

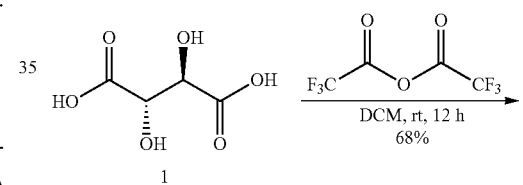

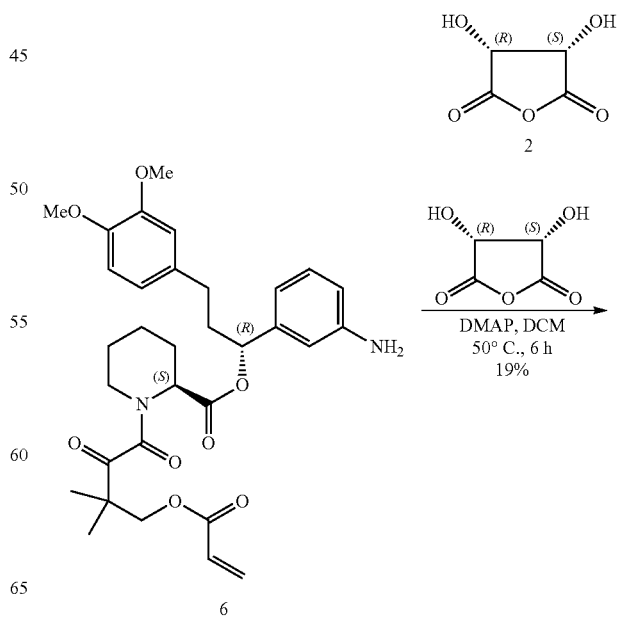

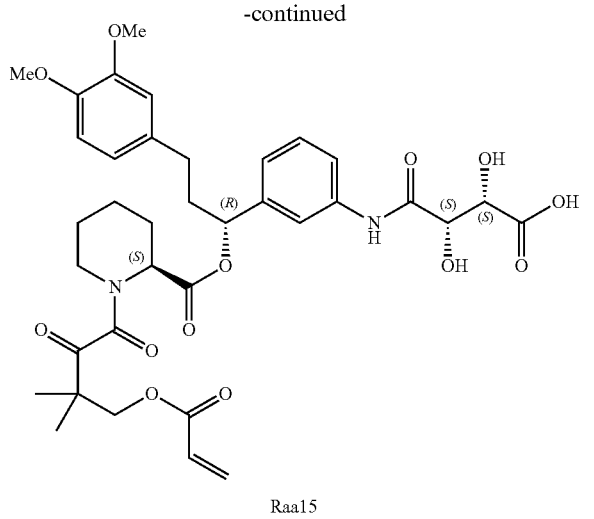

Raa15

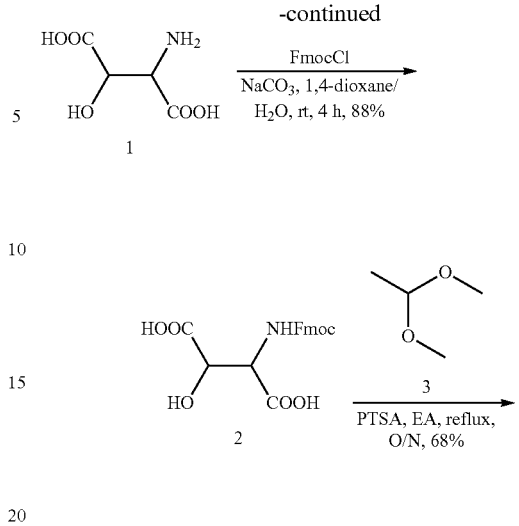

(3R,4S)-3,4-dihydroxydihydrofuran-2,5-dione (2). To the solution of (2R,3S)-2,3-dihydroxysuccinic acid 1 (10 g, 66.6 mmol) in DCM (100 mL) was added 2,2,2-trifluoroacetic anhydride (27.9 g, 133.2 mmol) at 25° C. The resulting solution was stirred at room temperature for 12 h. The mixture was concentrated in vacuum. The crude product was washed with petroleum ether (100 mL) to afford 2 (6 g, 68%) as a white solid.

(2S,3S)-4-((3-((R)-1-(((S)-1-(4-(acryloyloxy)-3,3-dimethyl-2-oxobutanoyl)piperidine-2-carbonyl)oxy)-3-(3,4-dimethoxyphenyl)propyl)phenyl)amino)-2,3-dihydroxy-4-oxobutanoic acid (Raa15). A mixture of 6 (2 g, 3.4 mmol), 2 (0.896 g, 6.8 mmol) and DMAP (80 mg, 0.68 mmol) in THF (60 mL) were stirred at 50° C. for 6 h. The mixture was filtered and concentrated in vacuum. The resulting residue was purified by prep-HPLC to afford Raa15 (476 mg, 19%) as a white solid.

FKBD Example 18

3-(((((9H-fluoren-9-yl)methoxy)amino)-4-((3-((R)-1-(((S)-1-(4-(acryloyloxy)-3,3-dimethyl-2-oxobutanoyl)piperidine-2-carbonyl)oxy)-3-(3,4-dimethoxyphenyl)propyl)phenyl)amino)-2-hydroxy-4-oxobutanoic acid (Raa16)

Scheme 21. Synthesis of Raa16 FKBD moiety.

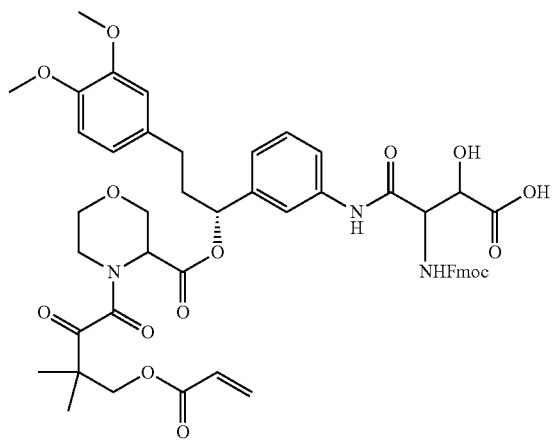

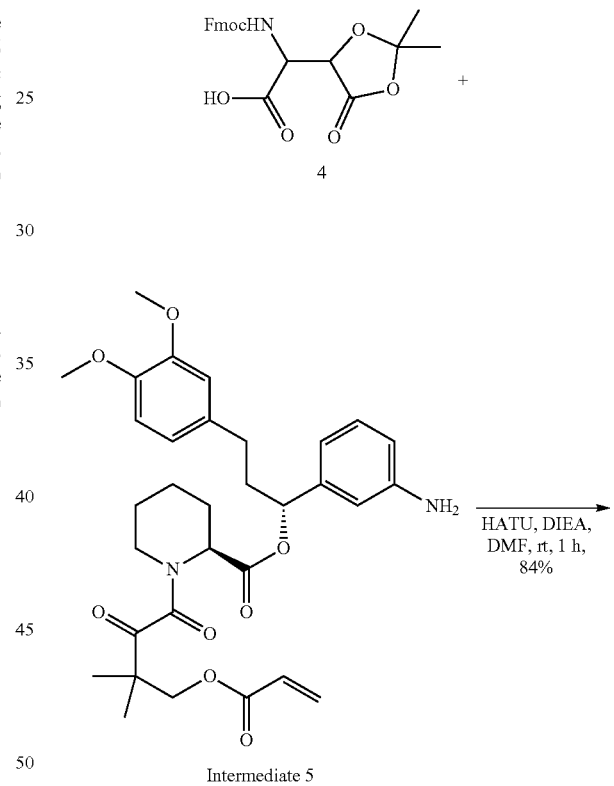

Intermediate 5
for the synthesis of RAa-11

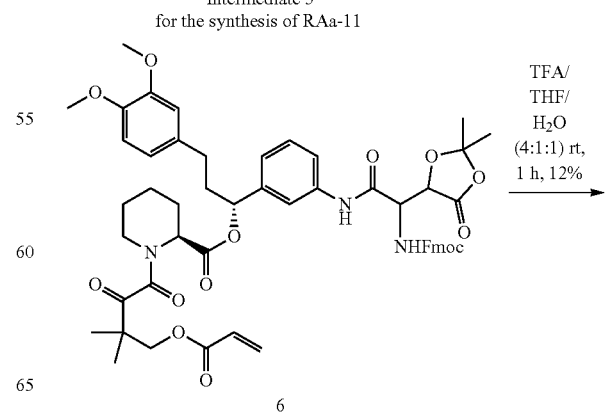

6

-continued

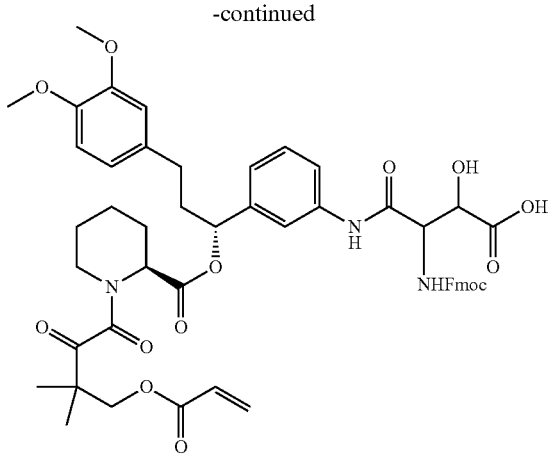

Raa16

2-((((9H-fluoren-9-yl)methoxy)carbonyl)amino)-3-hydroxysuccinic acid (2). To a solution of 1(10 g, 67.1 mmol) in 1,4-dioxane (150 ml) was added 10% NaCO$_3$(aq) 250 ml, and then FmocCl in 1,4-dioxane (150 ml) was dropwisely added at 0° C. The reaction mixture was stirred at 0° C. for 10 min, and then raised to rt and stirred for another 4 h. The product mixture was poured into water (500 ml), extracted with EA (200 ml) 3 times. Adjusted the hydrous layer to pH=2-3 by 2M HCl, and then extracted with DCM (200 ml) 3 times, combined the organic layer, washed with brine (200 ml) 3 times, dried over Na$_2$SO$_4$, filtered and concentrated to get product 2 (22 g, 88%) as white solid. [M+Na]$^+$=394

2-((((9H-fluoren-9-yl)methoxy)carbonyl)amino)-2-(2,2-dimethyl-5-oxo-1,3-dioxolan-4-yl)acetic acid (4). To a solution of 2 (5 g, 13.5 mmol) in EA (50 ml) was added 3 (14 g, 135 mmol) and PTSA (0.46 g 2.7 mmol). The reaction mixture was refluxed for 16 h. The product mixture was concentrated directly, and the brown residue was purified by silica gel chromatography (EA/PE=10-50% as eluent) to give 4 (3.8 g, 68.6%) as white solid. [M+Na]$^+$=434

(1R)-1-(3-(2-((((9H-fluoren-9-yl)methoxy)carbonyl)amino)-2-(2,2-dimethyl-5-oxo-1,3-dioxolan-4-yl)acetamido)phenyl)-3-(3,4-dimethoxyphenyl(2S)-1-(4-(acryloyloxy)-3,3-dimethyl-2-oxobutanoyl)piperidine-2-carboxylate (6). To a solution of 4 (2.2 g, 5.4 mmol) in DMF (150 ml) was added HATU (3 g, 8 mmol) and DIEA (1.38 g, 10.8 mmol). 5 (2.6 g 4.5 mmol) was added at last. The reaction mixture was stirred at rt for 1 h. Poured the product mixture into water (300 ml), extracted with DCM (100 ml*3), combined the organic phase and washed with brine (100 ml*5). Dried over Na$_2$SO$_4$, filtered and concentrated to get the crude. Purified by silica gel chromatography (Methanol/DCM=0-2% as eluent) to give compound 6 (3.7 g, 71%) as white solid. [M+Na]$^+$=996

3-(((9H-fluoren-9-yl)methoxy)amino)-4-((3-((R)-1-(((S)-1-(4-(acryloyloxy)-3,3-dimethyl-2-oxobutanoyl)piperidine-2-carbonyl)oxy)-3-(3,4-dimethoxyphenyl)propyl)phenyl)amino)-2-hydroxy-4-oxobutanoic acid (Raa16). To a solution of 6 (3.7 g, 38 mmol) in THF/H$_2$O (10 ml/10 ml) was added THF (40 ml). The reaction mixture was stirred at rt for 1 h. The product mixture was evaporated directly, and the residue was purified by silica gel chromatography (HCOOH/DCM=0-5% as eluent) to give compound Raa16 (500 mg, 14%) as light yellow solid.

FKBD Example 19

2-(3-((R)-1-(((S)-1-(4-(acryloyloxy)-3,3-dimethyl-2-oxobutanoyl)piperidine-2-carbonyl)oxy)-3-(3,4,5-trimethoxyphenyl)propyl)phenoxy)acetic acid (Rae1)

Scheme 22. Synthesis of Rae1 FKBD moiety.

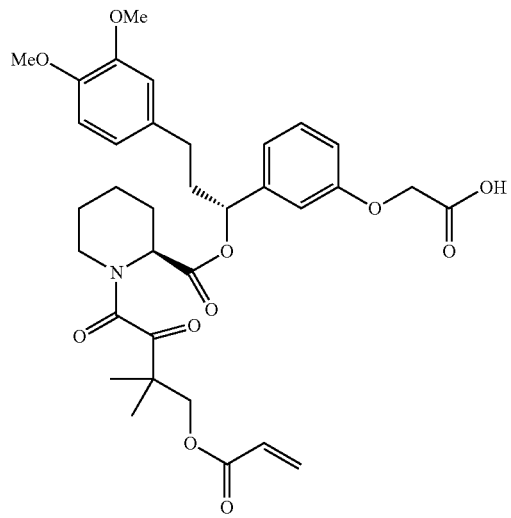

-continued
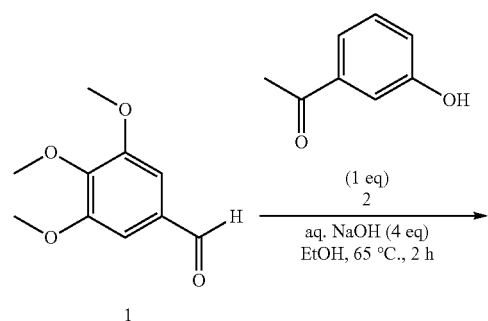
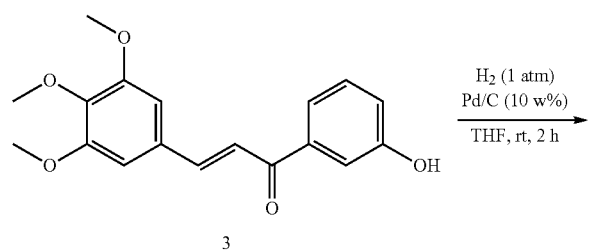
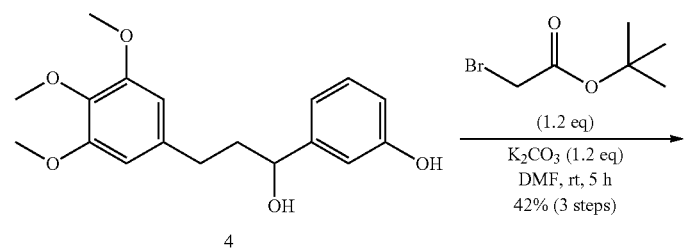
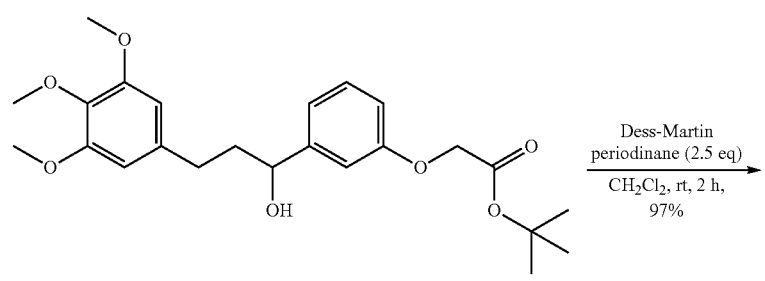
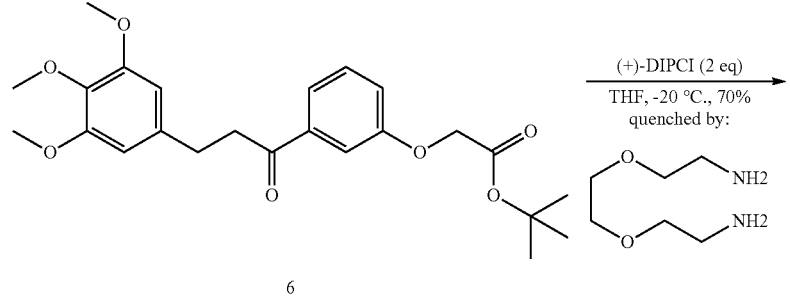

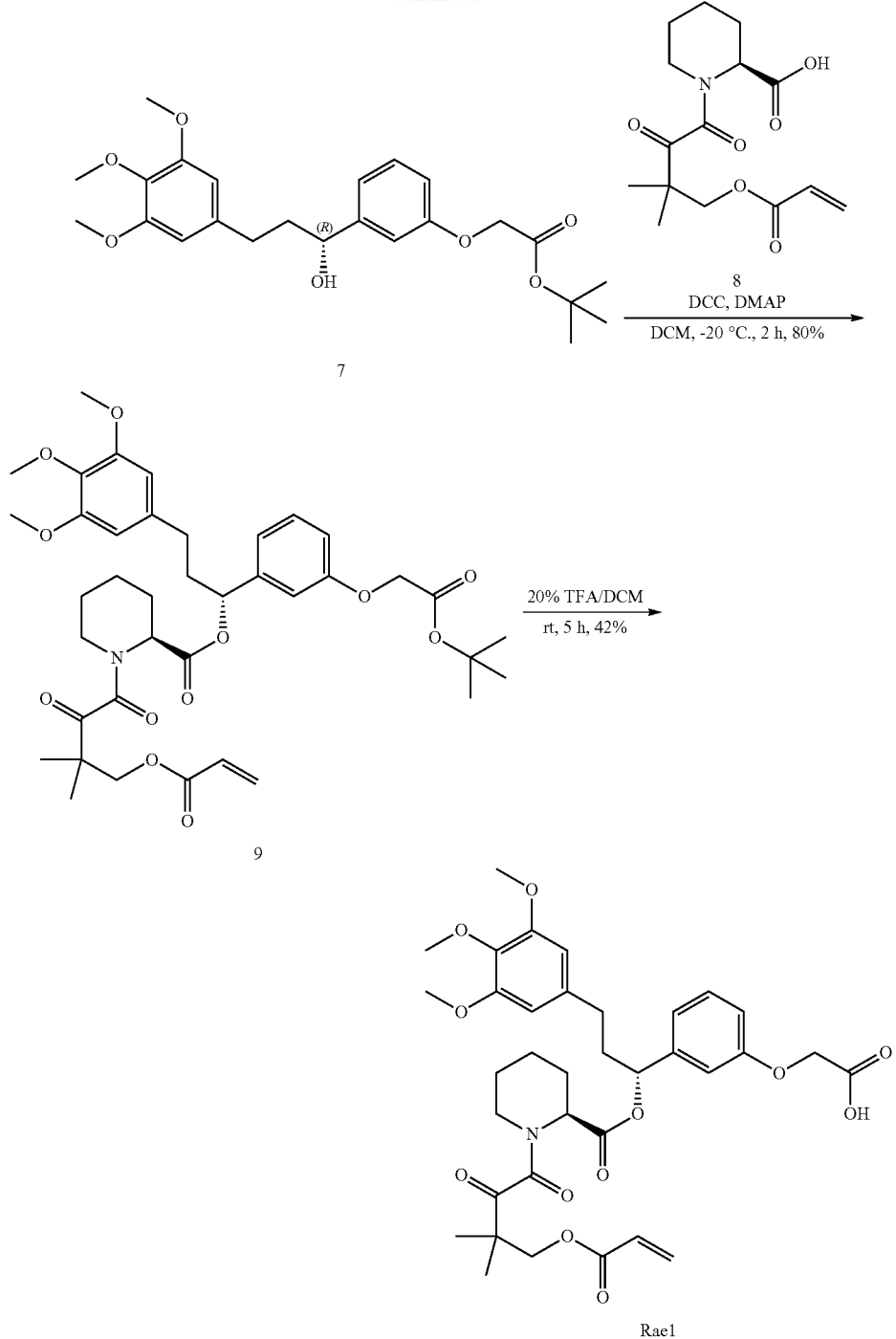

(E)-1-(3-hydroxyphenyl)-3-(3,4,5-trimethoxyphenyl) prop-2-en-1-one (3). To the solution of 3,4,5-trimethoxybenzaldehyde 1 (5 g, 25.5 mmol) and 3'-hydroxyacetophenone 2 (3.47 g, 25.5 mmol) in EtOH (50 mL) was added a solution of 10% aqueous NaOH (41 mL, 4.1 g, 101.9 mmol) at 0° C. The resulting solution was heated to 65° C. for 2 h. The solvent was evaporated and the residue (5.5 g, crude) was used directly for the next step without purification. [M+H]$^+$=314.9.

3-(1-hydroxy-3-(3,4,5-trimethoxyphenyl)propyl)phenol (4). A solution of 3 (5.5 g, crude) and 10% Pd/C (2 g) in THF (40 mL) was hydrogenated with $H_2$ for 4 h at room temperature. The reaction mixture was then filtered and concentrated to a solid (5.96 g, crude). [M+H—$H_2O$]$^+$=300.9 tert-butyl 2-(3-(1-hydroxy-3-(3,4,5-trimethoxyphenyl) propyl)phenoxy)acetate (5). A solution of 4 (5.96 g, 18.8 mmol, crude) and $K_2CO_3$ (3.12 g, 22.6 mmol) in DMF (30 mL) was treated with tert-butyl bromoacetate (3.68 g, 18.8 mmol) and allowed to stir at room temperature for 5 h. After this time the reaction mixture was poured into ice, yellow solid was precipitated. The crude product was purified by prep-HPLC to give 5 (4.65 g, 42% (3 steps)) as a yellow solid. [M+Na]⁺=454.8 tert-butyl 2-(3-(3-(3,4,5-trimethoxyphenyl)propanoyl)phenoxy)acetate (6). A solution of 5 (4.65 g, 10.75 mmol) in $CH_2Cl_2$ (110 mL) was treated with Dess-Martin periodinane (11.4 g, 26.88 mmol) and allowed to stir at room temperature for 3 h before being quenched with a solution of 10% aqueous $NaS_2O_3$. The solution was extracted with $CH_2Cl_2$ twice. The combined organic layers were washed by sat. $NaHCO_3$, brine, dried over $Na_2SO_4$ and concentrated in vacuo. The crude compound was purified by silica-gel flash column chromatography (AcOEt/PE 1:3) to give compound 6 as a white solid (4.5 g, 97%). [M+Na]⁺=453.2 tert-butyl (R)-2-(3-(1-hydroxy-3-(3,4,5-trimethoxyphenyl)propyl)phenoxy)acetate (7). A solution of ketone 6 (3.98 g, 9.25 mmol) in dry THF (40 mL) at −20° C. was treated with a solution of (+)-DIPChloride (18.5 mmol) in heptane (1.7 M, 10.88 mL) at −20° C. The resulting mixture was reacted at −20° C. until complete conversion of 6, then quenched with 2,2'-(ethylenedioxy)diethylamine (2.8 mL) by forming an insoluble complex. After stirring at RT for another 30 min, the suspension was filtered through a pad of celite and concentrated. The crude compound was purified by silica-gel flash column chromatography (AcOEt/PE 1:3) to give compound 7 as a light yellow oil (2.8 g, 70%, ee>99%). [M+Na]⁺=455.2

(R)-1-(3-(2-(tert-butoxy)-2-oxoethoxy)phenyl)-3-(3,4,5-trimethoxyphenyl)propyl (S)-1-(4-(acryloyloxy)-3,3-dimethyl-2-oxobutanoyl)piperidine-2-carboxylate (9). A solution of 7 (1.85 g, 4.3 mmol) and 8 (2 g, 6.4 mmol) in $CH_2Cl_2$ (15 mL) was cooled to −20° C. before a solution of DCC (1.3 g, 6.4 mmol) in $CH_2Cl_2$ (5 mL) was added, followed by the addition of a solution of 4-(dimethylamino)pyridine (DMAP, 52.3 mg, 0.43 mmol) in $CH_2Cl_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:2) to give compound 9 as a light yellow oil (2.5 g, 80%). [M+Na]⁺=748.4

2-(3-((R)-1-(((S)-1-(4-(acryloyloxy)-3,3-dimethyl-2-oxobutanoyl)piperidine-2-carbonyl)oxy)-3-(3,4,5-trimethoxyphenyl)propyl)phenoxy)acetic acid (Rae1). A solution of 9 (2.5 g, 3.44 mmol) in $CH_2Cl_2$ (11.5 mL) was treated with a solution of 40% TFA in $CH_2Cl_2$ (11.5 mL) at 0° C. The mixture was allowed to react at room temperature until complete conversion. The reaction mixture was charged to silica-gel flash column directly (AcOEt/PE/AcOH 1:2:0.5%) to afford Rae1 (969 mg, 42%) as a white solid.

FKBD Example 20

2-(3-((R)-1-(((S)-1-(4-(acryloyloxy)-3,3-dimethyl-2-oxobutanoyl)piperidine-2-carbonyl)oxy)-3-(2,3,4-trimethoxyphenyl)propyl)phenoxy)acetic acid (Rae2)

Scheme 23. Synthesis of Rae2 FKBD moiety.

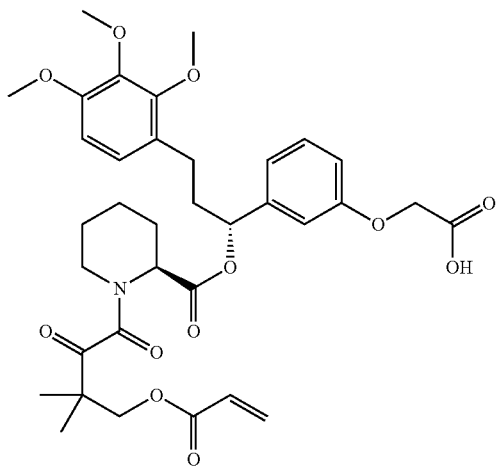

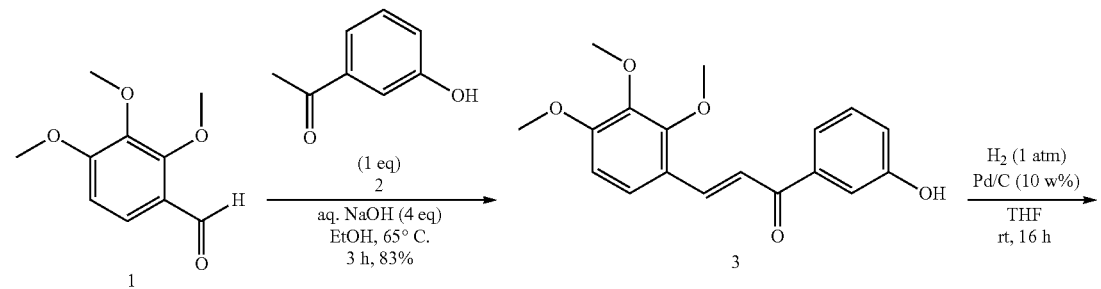

-continued
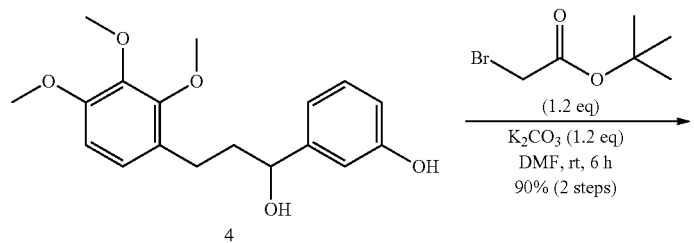
4
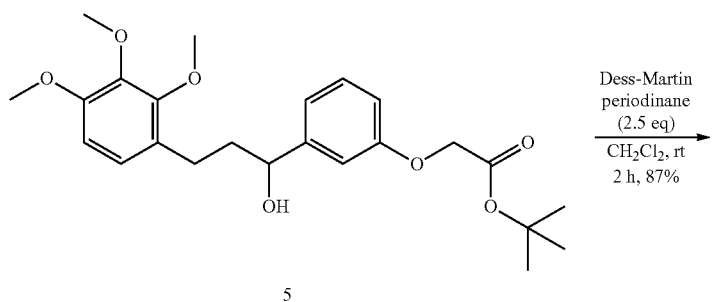
5
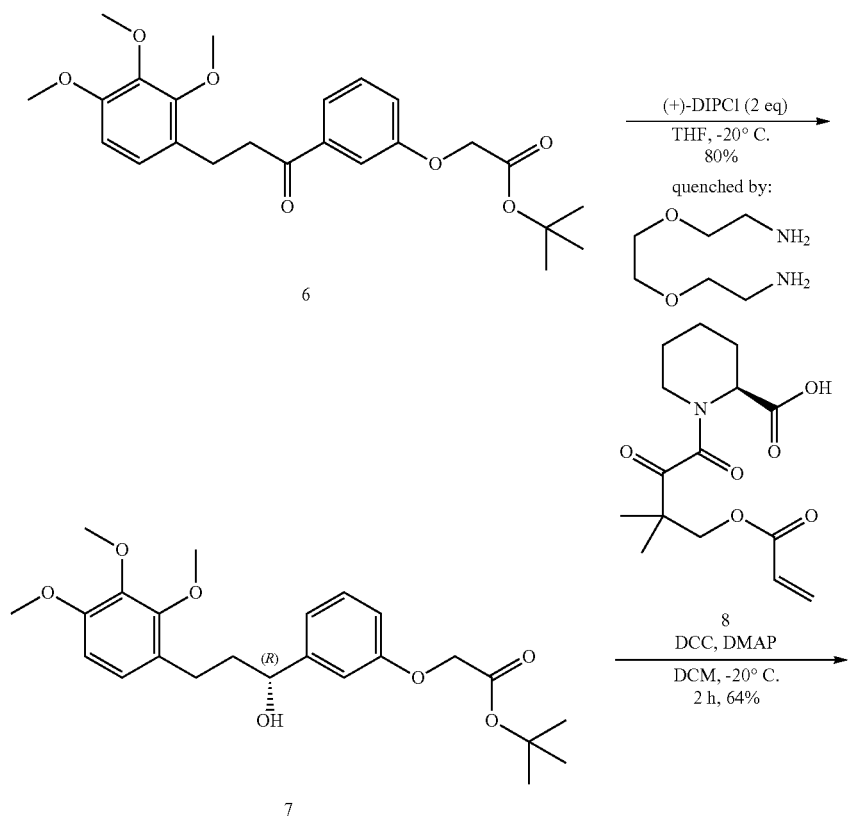

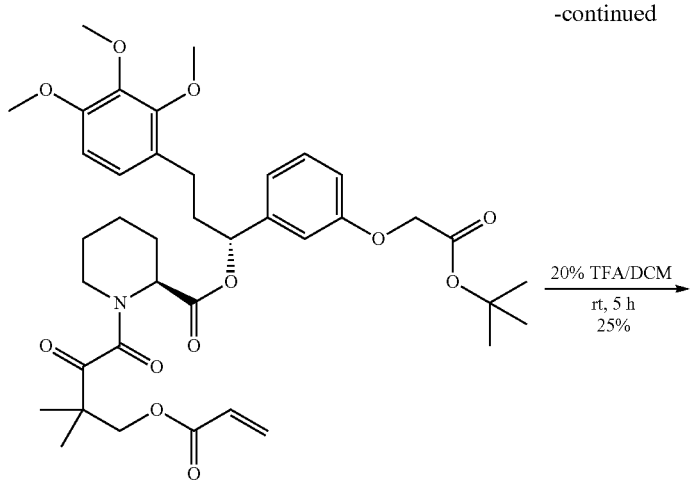 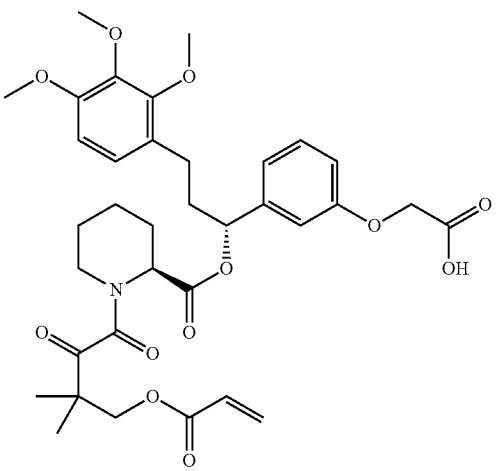

(E)-1-(3-hydroxyphenyl)-3-(2,3,4-trimethoxyphenyl)prop-2-en-1-one (3). To the solution of 2,3,4-trimethoxybenzaldehyde 1 (5 g, 25.5 mmol) and 3'-hydroxyacetophenone 2 (3.47 g, 25.5 mmol) in EtOH (30 mL) was added a solution of 10% aqueous NaOH (41 mL, 4.1 g, 101.9 mmol) at 0° C. The resulting solution was heated to 65° C. for 3 h. The solvent was evaporated and the residue was purified by silica-gel flash column chromatography (AcOEt/PE 1:5) to give compound 3 as a yellow oil (6.6 g, 83%). $[M+H]^+=314.9$ 3-(1-hydroxy-3-(2,3,4-trimethoxyphenyl)propyl)phenol (4). A solution of 3 (6.6 g, 21 mmol) and 10% Pd/C (3 g) in THF (30 mL) was hydrogenated with $H_2$ for 16 h at room temperature. The reaction mixture was then filtered and concentrated to a colorless oil (8 g, crude). $[M+H-H_2O]^+=301.0$ tert-butyl 2-(3-(1-hydroxy-3-(2,3,4-trimethoxyphenyl)propyl)phenoxy)acetate (5). A solution of 4 (8 g, 25 mmol, crude) and $K_2CO_3$ (4.19 g, 30 mmol) in DMF (30 mL) was treated with tert-butyl bromoacetate (5.92 g, 30 mmol) and allowed to stir at room temperature for 6 h. After this time the reaction mixture was quenched by $H_2O$ and extracted with EtOAc twice. The combined organic layers were washed by brine, dried over $Na_2SO_4$ and concentrated in vacuo. The crude compound was purified by silica-gel flash column chromatography (AcOEt/PE 1:3) to give compound 6 as a colorless oil (8.2 g, 90% (2 steps)). $[M+H-H_2O-tBu]^+=358.8$ tert-butyl 2-(3-(3-(2,3,4-trimethoxyphenyl)propanoyl)phenoxy)acetate (6). A solution of 5 (5.75 g, 13.29 mmol) in $CH_2Cl_2$ (30 mL) was treated with Dess-Martin periodinane (11.28 g, 26.59 mmol) and allowed to stir at room temperature for 2 h before being quenched with a solution of 10% aqueous $NaS_2O_3$. The solution was extracted with $CH_2Cl_2$ twice. The combined organic layers were washed by sat. $NaHCO_3$, brine, dried over $Na_2SO_4$ and concentrated in vacuo. The crude compound was purified by silica-gel flash column chromatography (AcOEt/PE 1:3) to give compound 6 as a yellow oil (5 g, 87%).

tert-butyl (R)-2-(3-(1-hydroxy-3-(2,3,4-trimethoxyphenyl)propyl)phenoxy)acetate (7). A solution of ketone 6 (5 g, 11.61 mmol) in dry THF (50 mL) at −20° C. was treated with a solution of (+)-DIPChloride (23.23 mmol) in heptane (1.7 M, 13.66 mL) at −20° C. The resulting mixture was reacted at −20° C. until complete conversion of 6, then quenched with 2,2'-(ethylenedioxy)diethylamine (3.4 mL) by forming an insoluble complex. After stirring at RT for another 30 min, the suspension was filtered through a pad of celite and concentrated. The crude compound was purified by silica-gel flash column chromatography (AcOEt/PE 1:3) to give compound 7 as a light yellow oil (4 g, 80%, ee 83%). $[M+H-H_2O-tBu]^+=358.9$ (R)-1-(3-(2-(tert-butoxy)-2-oxoethoxy)phenyl)-3-(3,4,5-trimethoxyphenyl)propyl (S)-1-(4-(acryloyloxy)-3,3-dimethyl-2-oxobutanoyl)piperidine-2-carboxylate (9). A solution of 7 (2 g, 4.62 mmol) and 8 (2.16 g, 6.93 mmol) in $CH_2Cl_2$ (23 mL) was cooled to −20° C. before a solution of DCC (1.43 g, 6.93 mmol) in $CH_2Cl_2$ (5 mL) was added, followed by the addition of a solution of 4-(dimethylamino)pyridine (DMAP, 57 mg, 0.46 mmol) in $CH_2Cl_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:2) to give compound 9 as a light yellow oil (2.13 g, 64%). $[M+Na]^+=748.4$ 2-(3-((R)-1-(((S)-1-(4-(acryloyloxy)-3,3-dimethyl-2-oxobutanoyl)piperidine-2-carbonyl)oxy)-3-(2,3,4-trimethoxyphenyl)propyl)phenoxy)acetic acid (Rae2). A solution of 9 (2.13 g, 2.93 mmol) in $CH_2Cl_2$ (12 mL) was treated with a solution of 40% TFA in $CH_2Cl_2$ (12 mL) at 0° C. The mixture was allowed to react at room temperature until complete conversion. The reaction mixture was charged to silica-gel flash column directly (AcOEt/PE/AcOH 1:2:0.5%) to afford Rae2 (508 mg, 25%) as a pale yellow solid.

FKBD Example 21
2-(3-((R)-1-(((S)-1-(4-(acryloyloxy)-3,3-dimethyl-2-oxobutanoyl)piperidine-2-carbonyl)oxy)-3-(2,4,5-trimethoxyphenyl)propyl)phenoxy)acetic acid (Rae3)
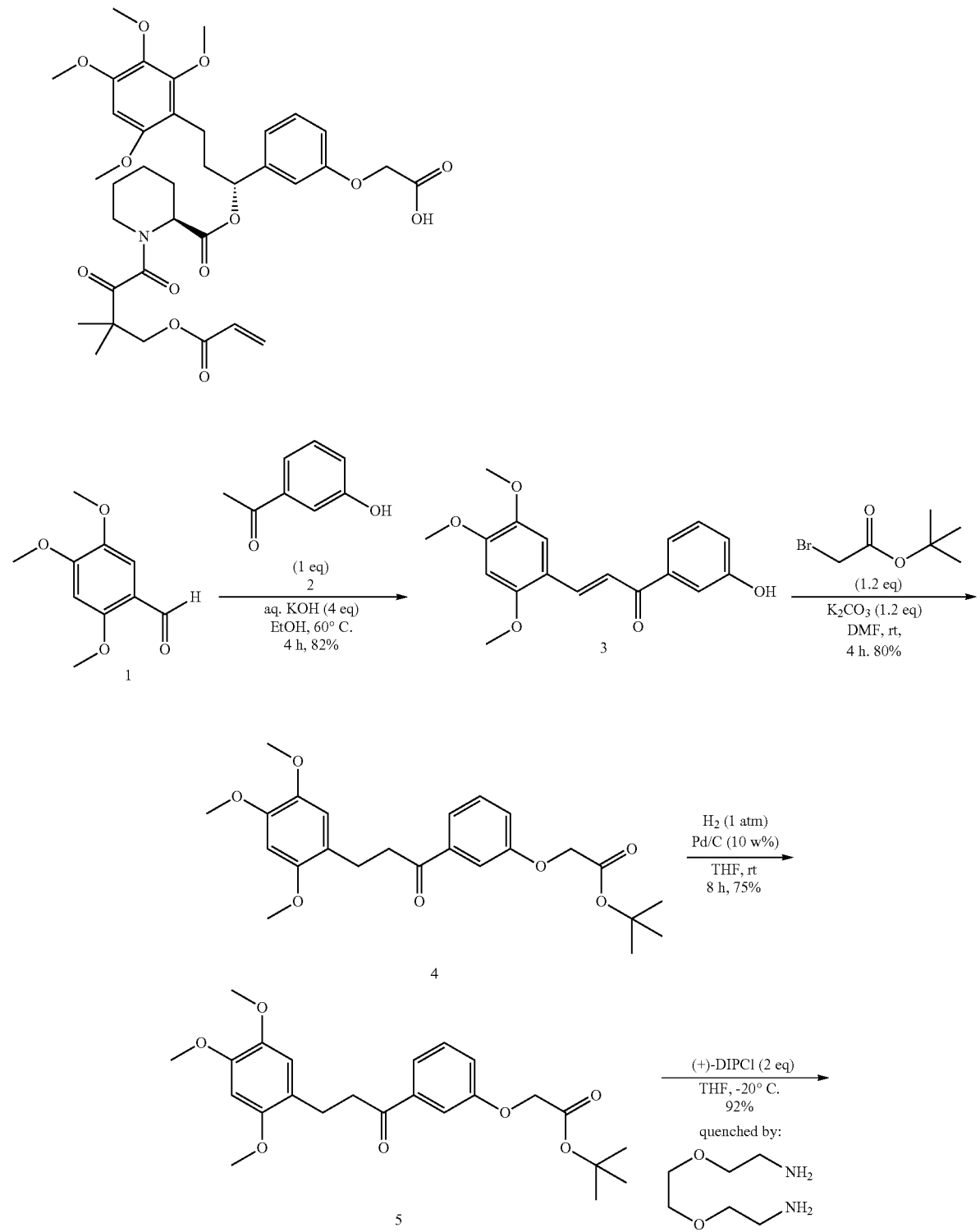
Scheme 24. Synthesis of Rae3 FKBD moiety.

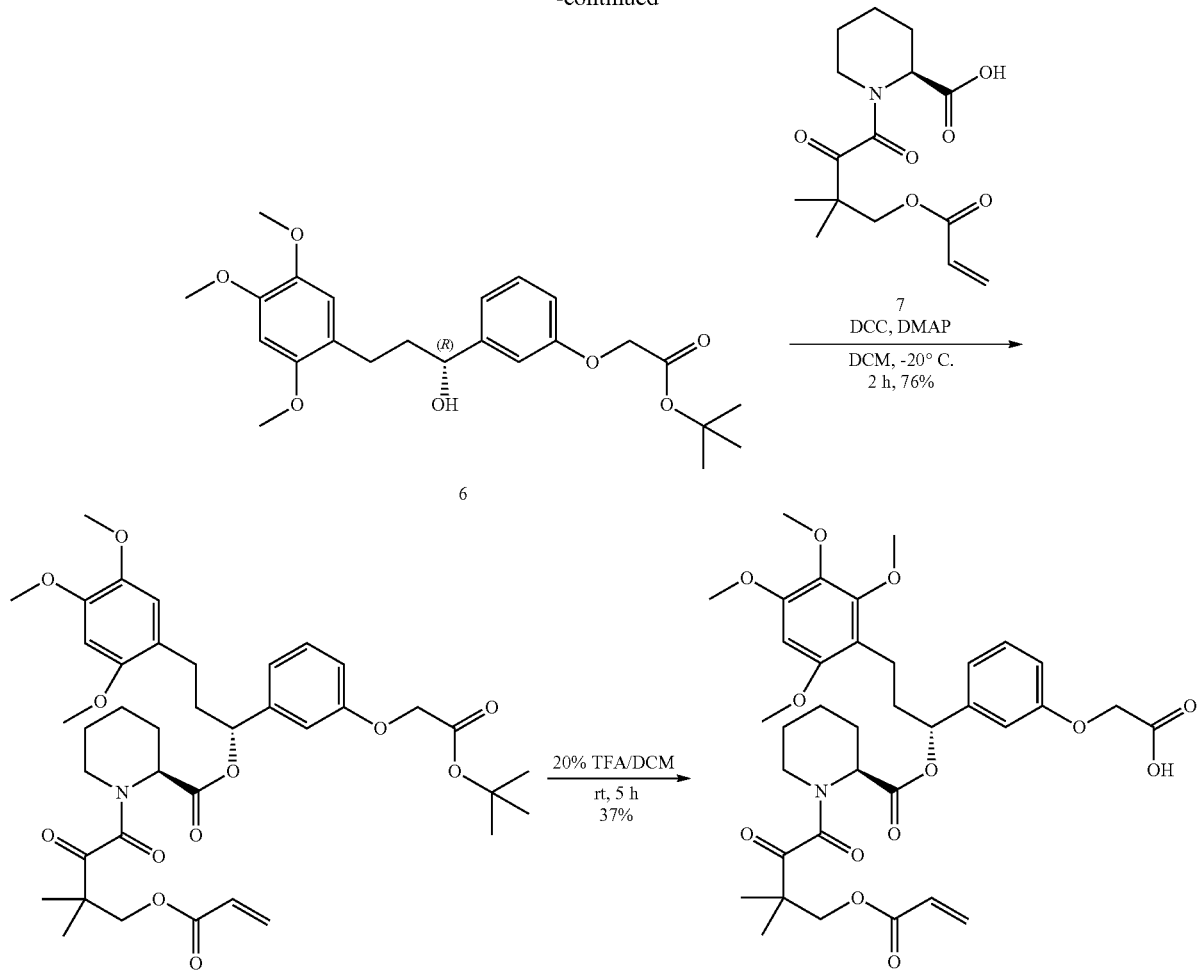

(E)-1-(3-hydroxyphenyl)-3-(2,4,5-trimethoxyphenyl) prop-2-en-1-one (3). To the solution of 2,4,5-trimethoxybenzaldehyde 1 (4.5 g, 22.96 mmol) and 3'-hydroxyacetophenone 2 (3.1 g, 22.96 mmol) in EtOH (50 mL) was added a solution of 10% aqueous KOH (15 mL, 5.1 g, 91.84 mmol) at 0° C. The resulting solution was heated to 60° C. for 4 h. The solvent was evaporated and the residue was purified by silica-gel flash column chromatography (AcOEt/PE 1:3) to give compound 3 as a yellow oil (5.9 g, 82%). [M+H]$^+$= 315.1 tert-butyl (E)-2-(3-(3-(2,4,5-trimethoxyphenyl)acryloyl) phenoxy)acetate (4). A solution of 3 (7.4 g, 23.6 mmol) and K$_2$CO$_3$ (3.9 g, 28.3 mmol) in DMF (200 mL) was treated with tert-butyl bromoacetate (5.5 g, 28.3 mmol) and allowed to stir at room temperature for 4 h. After this time the reaction mixture was quenched by H$_2$O and extracted with EtOAc twice. The combined organic layers were washed by brine, dried over Na$_2$SO$_4$ and concentrated in vacuo. The crude compound was purified by silica-gel flash column chromatography (AcOEt/PE 1:3) to give compound 4 as a colorless oil (8 g, 80%). [M+H]$^+$=429.3 tert-butyl 2-(3-(3-(2,4,5-trimethoxyphenyl)propanoyl) phenoxy)acetate (5). A solution of 4 (8 g, 18.69 mmol) and 10% Pd/C (1 g) in THF (200 mL) was hydrogenated with H$_2$ for 8 h at room temperature. The reaction mixture was then filtered and concentrated. The residue was purified by silica-gel flash column chromatography (AcOEt/PE 1:3) to give compound 5 as a colorless oil (6 g, 75%). [M+Na]$^+$=453.2 tert-butyl (R)-2-(3-(1-hydroxy-3-(2,4,5-trimethoxyphenyl)propyl)phenoxy)acetate (6). A solution of ketone 5 (6 g, 13.95 mmol) in dry THF (60 mL) at −20° C. was treated with a solution of (+)-DIPChloride (41.86 mmol) in heptane (1.7 M, 24.6 mL) at −20° C. The resulting mixture was reacted at −20° C. until complete conversion of 5, then quenched with 2,2'-(ethylenedioxy)diethylamine (5.9 mL) by forming an insoluble complex. After stirring at RT for another 30 min, the suspension was filtered through a pad of celite and concentrated. The crude compound was purified by silica-gel flash column chromatography (AcOEt/PE 1:1) to give compound 6 as a light yellow oil (5.5 g, 92%, ee>99%).). [M+Na]$^+$=455.2

(R)-1-(3-(2-(tert-butoxy)-2-oxoethoxy)phenyl)-3-(2,4,5-trimethoxyphenyl)propyl (S)-1-(4-(acryloyloxy)-3,3-dimethyl-2-oxobutanoyl)piperidine-2-carboxylate (8). A solution of 6 (1.85 g, 4.28 mmol) and 7 (2 g, 6.42 mmol) in CH$_2$Cl$_2$ (10 mL) was cooled to −20° C. before a solution of DCC (1.33 g, 6.42 mmol) in CH$_2$Cl$_2$ (5 mL) was added, followed by the addition of a solution of 4-(dimethylamino) pyridine (DMAP, 52 mg, 0.43 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:1) to give compound 8 as a light yellow oil (2.35 g, 76%). [M+Na]$^+$=747.9

2-(3-((R)-1-(((S)-1-(4-(acryloyloxy)-3,3-dimethyl-2-oxobutanoyl)piperidine-2-carbonyl)oxy)-3-(2,4,5-trimethoxyphenyl)propyl)phenoxy)acetic acid (Rae3). A solution of 8 (2.35 g, 3.24 mmol) in CH$_2$Cl$_2$ (12 mL) was treated with a solution of 40% TFA in CH$_2$Cl$_2$ (12 mL) at 0° C. The mixture was allowed to react at room temperature until complete conversion. The reaction mixture was charged to silica-gel flash column directly (AcOEt/PE/AcOH 1:2:0.5%) to afford Rae3 (815 mg, 37%) as a pale yellow solid.

FKBD Example 22

2-(3-((R)-1-(((S)-1-(4-(acryloyloxy)-3,3-dimethyl-2-oxobutanoyl)piperidine-2-carbonyl)oxy)-3-(2,3,5-trimethoxyphenyl)propyl)phenoxy)acetic acid (Rae4)

Scheme 25. Synthesis of Rae4 FKBD moiety.

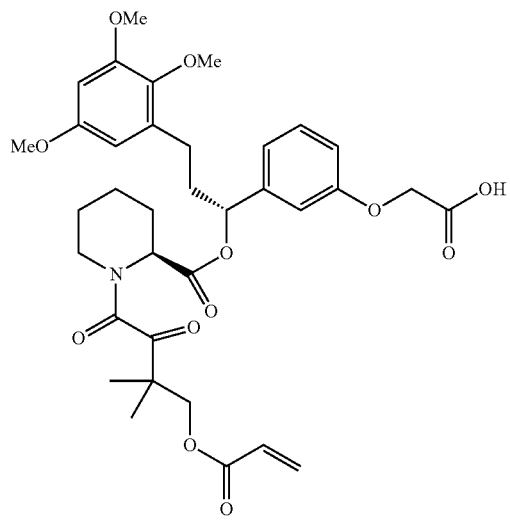

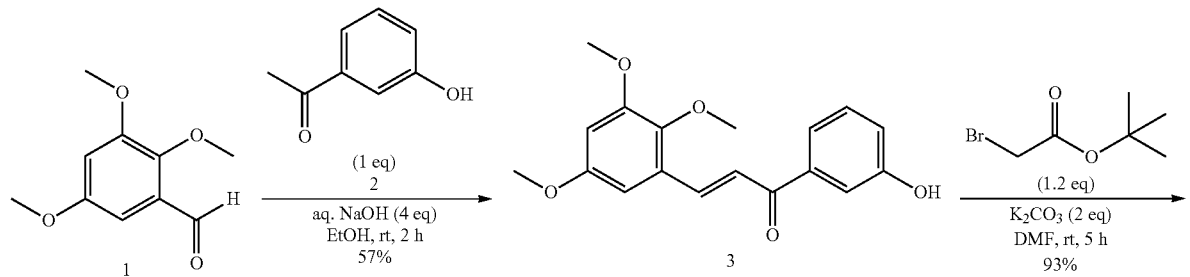

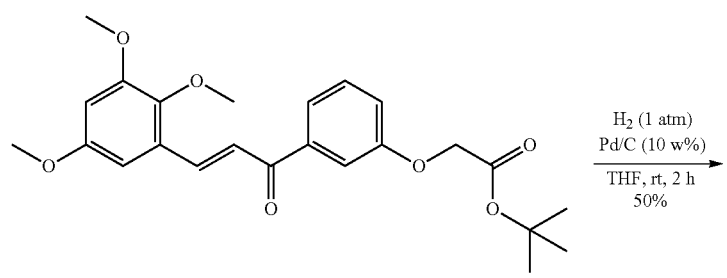

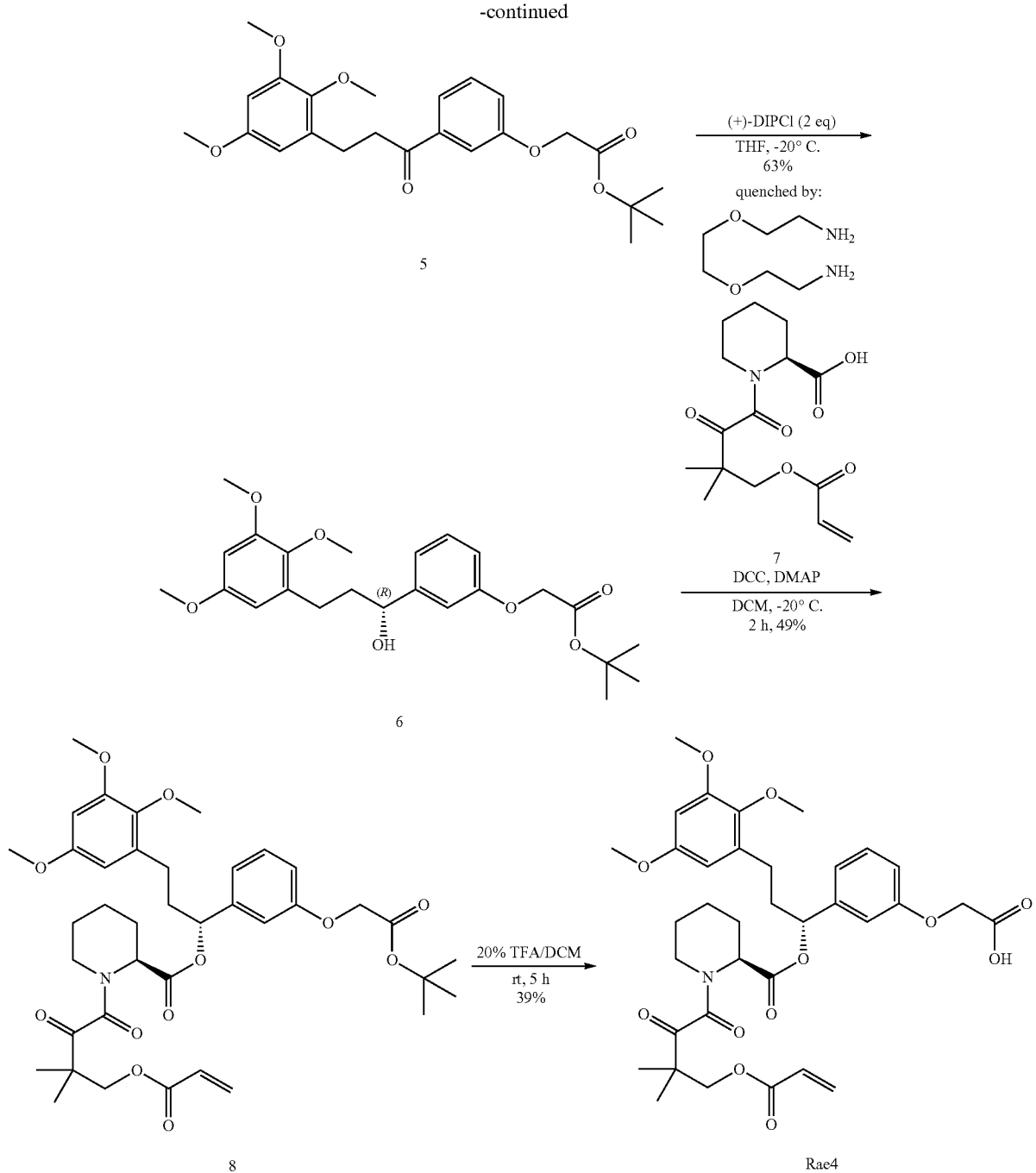

(E)-1-(3-hydroxyphenyl)-3-(2,3,5-trimethoxyphenyl) prop-2-en-1-one (3). To the solution of 2,3,5-trimethoxybenzaldehyde 1 (6 g, 30.6 mmol) and 1-(3-hydroxyphenyl) ethan-1-one 2 (4.2 g, 30.6 mmol) in EtOH (50 mL) was added a solution of 10% aqueous NaOH (50 mL, 122.4 mmol) at 0° C. The resulting solution was stirred at room temperature for 12 h. The solution was adjusted to pH 4 by added 4M aqueous HCl dropwise at 0° C., generated a large of yellow solid. Then the mixture was filtered and the solid was washed with water (50 mL) to afford 3 (5.5 g, 57%) as a yellow solid. [M+H]$^+$=315.2.

tert-butyl (E)-2-(3-(3-(2,3,5-trimethoxyphenyl)acryloyl) phenoxy) acetate (4). A solution of 3 (5.5 g, 17.4 mmol) and K$_2$CO$_3$ (4.82 g, 34.9 mmol) in DMF (40 mL) was treated with tert-butyl bromoacetate (4.06 g, 20.9 mmol) and allowed to stir at room temperature for 12 h. After this time the reaction mixture was poured into ice, yellow solid was precipitated. The mixture was filtered and the solid was washed with water (30 mL). The crude product was washed with petroleum ether (50 mL) to give 4 (7 g, 93%) as a yellow solid. [M+H]$^+$=428.8 tert-butyl 2-(3-(3-(2,3,5-trimethoxyphenyl)propanoyl) phenoxy)acetate (5). A solution of 4 (7 g, 11.68 mmol) and 10% Pd/C (1 g) in THF (100 mL) was hydrogenated with H$_2$ for 4 h at room temperature. The reaction mixture was then filtered and concentrated. The crude product was purified by column chromatography on silica gel to give 5 (3.5 g, 50%) as a yellow oil. [M+Na]⁺=452.9.

tert-butyl (R)-2-(3-(1-hydroxy-3-(2,3,5-trimethoxyphenyl)propyl)phenoxy)acetate (6). A solution of ketone 5 (3.5 g, 8.14 mmol) in dry THF (30 mL) at −20° C. was treated with a solution of (+)-DIPChloride (16.2 mmol) in heptane (1.7 M, 9.5 mL) at −20° C. The resulting mixture was reacted at −20° C. until complete conversion of 6, then quenched with 2,2'-(ethylenedioxy)diethylamine (2.4 g) by forming an insoluble complex. After stirring at room temperature for another 30 min, the suspension was filtered through a pad of celite and concentrated. The crude compound was purified by silica-gel flash column chromatography (AcOEt/PE 1:4) to give compound 6 (2.2 g, 63%, ee 97% vs racemate) as a light yellow oil. [M+Na]⁺=454.9

(R)-1-(3-(2-(tert-butoxy)-2-oxoethoxy)phenyl)-3-(2,3,5-trimethoxyphenyl)propyl (S)-1-(4-(acryloyloxy)-3,3-dimethyl-2-oxobutanoyl)piperidine-2-carboxylate (8). A solution of 6 (2.2 g, 5.09 mmol) and 8 (1.89 g, 6.1 mmol) in CH₂Cl₂ (15 mL) was cooled to −20° C. before a solution of DCC (1.36 g, 6.6 mmol) in CH₂Cl₂ (5 mL) was added, followed by the addition of a solution of 4-(dimethylamino)pyridine (62 mg, 0.5 mmol) in CH₂Cl₂ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:2) to give compound 8 (1.8 g, 49%) as a light yellow oil. [M+Na]⁺=748.4

2-(3-((R)-1-(((S)-1-(4-(acryloyloxy)-3,3-dimethyl-2-oxobutanoyl)piperidine-2-carbonyl)oxy)-3-(2,3,5-trimethoxyphenyl)propyl)phenoxy)acetic acid (Rae4). A solution of 8 (1.8 g, 2.48 mmol) in CH₂Cl₂ (10 mL) was treated with a solution of 40% TFA in CH₂Cl₂ (10 mL) at 0° C. The mixture was allowed to react at room temperature until complete conversion. The reaction mixture was charged to silica-gel flash column directly (AcOEt/PE/AcOH 1:3:0.5%) to afford Rae4 (652 mg, 39%) as a faint yellow solid.

FKBD Example 23

2-(3-((R)-1-(((S)-1-(4-(acryloyloxy)-3,3-dimethyl-2-oxobutanoyl)piperidine-2-carbonyl)oxy)-3-(2,3,6-trimethoxyphenyl)propyl)phenoxy)acetic acid (Rae5)

Scheme 26. Synthesis of Rae5 FKBD moiety.

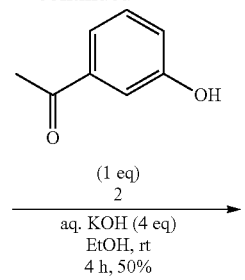
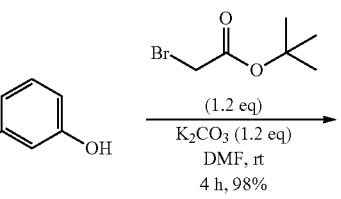
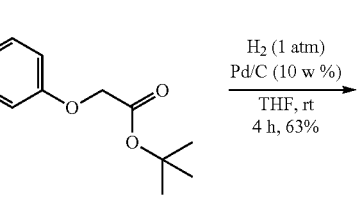

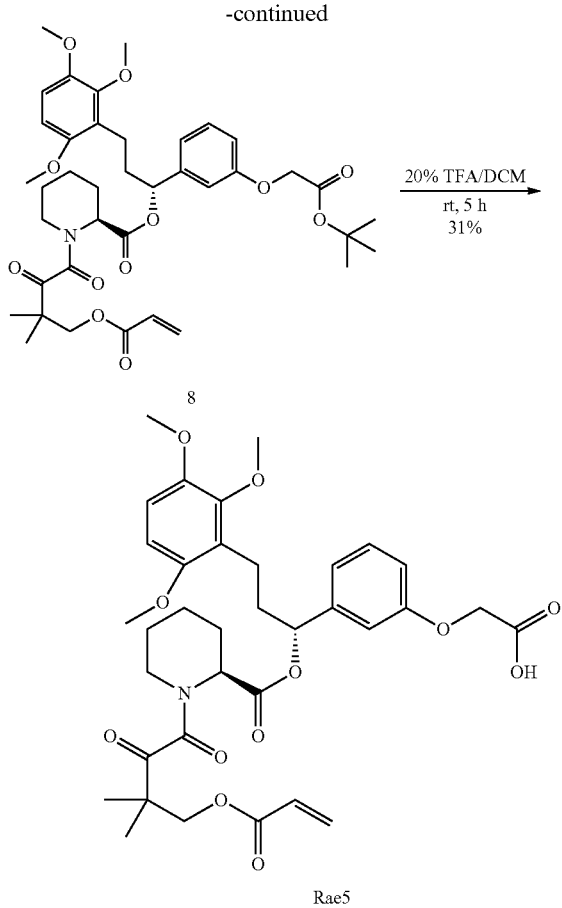

(E)-1-(3-hydroxyphenyl)-3-(2,3,6-trimethoxyphenyl) prop-2-en-1-one (3). To the solution of 2,3,6-trimethoxybenzaldehyde 1 (5 g, 25.48 mmol) and 3'-hydroxyacetophenone 2 (3.47 g, 25.48 mmol) in EtOH (40 mL) was added a solution of 40% aqueous KOH (15 mL, 5.7 g, 101.92 mmol) at 0° C. The resulting solution was reacted at room temperature for 4 h. The solvent was evaporated and the residue was purified by silica-gel flash column chromatography (AcOEt/PE 1:2) to give compound 3 as a yellow oil (4 g, 50%). [M+H]$^+$=315.2 tert-butyl (E)-2-(3-(3-(2,3,6-trimethoxyphenyl)acryloyl) phenoxy)acetate (4). A solution of 3 (3.5 g, 11.15 mmol) and K$_2$CO$_3$ (1.85 g, 13.37 mmol) in DMF (60 mL) was treated with tert-butyl bromoacetate (2.6 g, 13.37 mmol) and allowed to stir at room temperature for 4 h. After this time the reaction mixture was quenched by H$_2$O and extracted with EtOAc twice. The combined organic layers were washed by brine, dried over Na$_2$SO$_4$ and concentrated in vacuo. The crude compound was purified by silica-gel flash column chromatography (AcOEt/PE 1:4) to give compound 4 as a yellow oil (4.7 g, 98%). [M+H]$^+$=429.0 tert-butyl 2-(3-(3-(2,3,6-trimethoxyphenyl)propanoyl) phenoxy)acetate (5). A solution of 4 (4.6 g, 10.75 mmol) and 10% Pd/C (0.5 g) in THF (70 mL) was hydrogenated with H$_2$ for 4 h at room temperature. The reaction mixture was then filtered and concentrated. The residue was purified by silica-gel flash column chromatography (AcOEt/PE 1:3) to give compound 5 as a colorless oil (2.9 g, 63%). [M+Na]$^+$= 453.3 tert-butyl (R)-2-(3-(1-hydroxy-3-(2,3,6-trimethoxyphenyl)propyl)phenoxy)acetate (6). A solution of ketone 5 (2.9 g, 6.7 mmol) in dry THF (30 mL) at −20° C. was treated with a solution of (+)-DIPChloride (13.48 mmol) in heptane (1.7 M, 7.9 mL) at −20° C. The resulting mixture was reacted at −20° C. until complete conversion of 5, then quenched with 2,2'-(ethylenedioxy)diethylamine (1.96 mL) by forming an insoluble complex. After stirring at RT for another 30 min, the suspension was filtered through a pad of celite and concentrated. The crude compound was purified by silica-gel flash column chromatography (AcOEt/PE 1:5) to give compound 6 as a light yellow oil (2.4 g, 83%, ee>99%). [M+Na]$^+$=454.9

(R)-1-(3-(2-(tert-butoxy)-2-oxoethoxy)phenyl)-3-(2,3,6-trimethoxyphenyl)propyl (S)-1-(4-(acryloyloxy)-3,3-dimethyl-2-oxobutanoyl)piperidine 2-carboxylate (8). A solution of 6 (1.46 g, 3.45 mmol) and 7 (1.6 g, 5.17 mmol) in CH$_2$Cl$_2$ (18 mL) was cooled to −20° C. before a solution of DCC (1.065 g, 5.17 mmol) in CH$_2$Cl$_2$ (5 mL) was added, followed by the addition of a solution of 4-(dimethylamino) pyridine (DMAP, 43 mg, 0.35 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:1) to give compound 8 as a light yellow oil (1.7 g, 68%).

2-(3-((R)-1-(((S)-1-(4-(acryloyloxy)-3,3-dimethyl-2-oxobutanoyl)piperidine-2-carbonyl)oxy)-3-(2,3,6-trimethoxyphenyl)propyl)phenoxy)acetic acid (Rae5). A solution of 8 (1.7 g, 2.34 mmol) in CH$_2$Cl$_2$ (12 mL) was treated with a solution of 40% TFA in CH$_2$Cl$_2$ (12 mL) at 0° C. The mixture was allowed to react at room temperature until complete conversion. The reaction mixture was charged to silica-gel flash column directly (AcOEt/PE/ AcOH 1:2:0.5%) to afford Rae5 (494 mg, 31%) as a pale yellow solid.

FKBD Example 24

2-(3-((R)-1-(((S)-1-(4-(acryloyloxy)-3,3-dimethyl-2-oxobutanoyl)piperidine-2-carbonyl)oxy)-3-(2-hydroxy-3,4-dimethoxyphenyl)propyl)phenoxy)acetic acid (Rae9)

Scheme 27. Synthesis of Rae9 FKBD moiety.

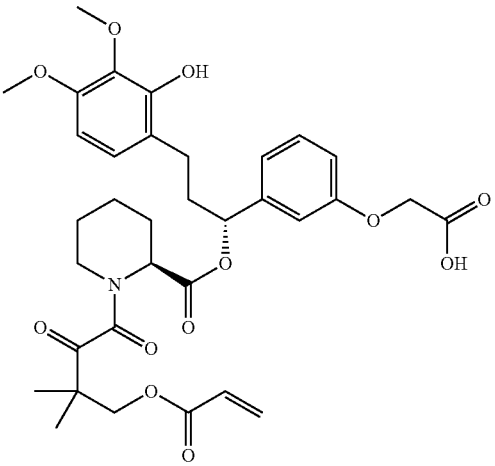

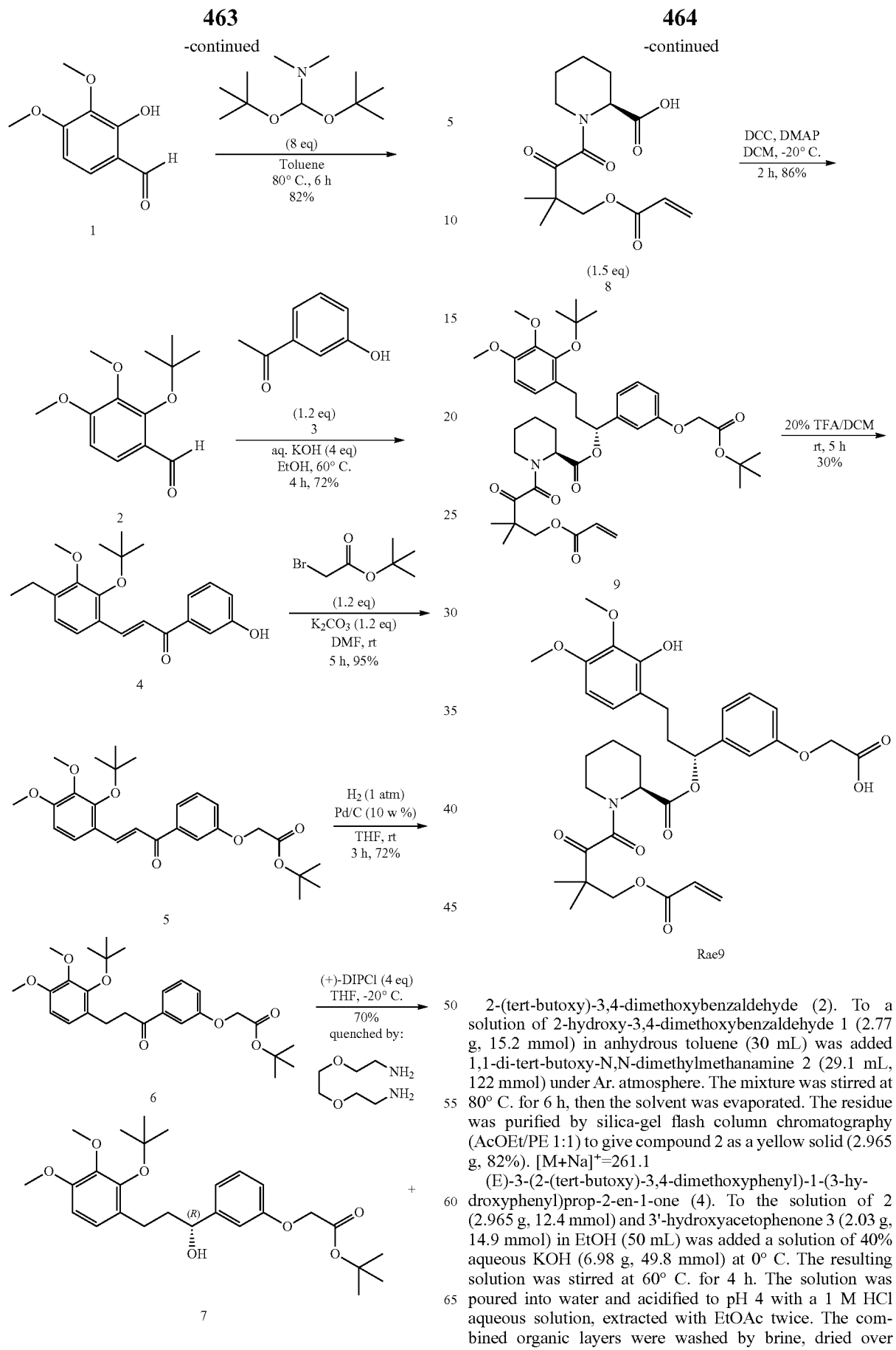

2-(tert-butoxy)-3,4-dimethoxybenzaldehyde (2). To a solution of 2-hydroxy-3,4-dimethoxybenzaldehyde 1 (2.77 g, 15.2 mmol) in anhydrous toluene (30 mL) was added 1,1-di-tert-butoxy-N,N-dimethylmethanamine 2 (29.1 mL, 122 mmol) under Ar. atmosphere. The mixture was stirred at 80° C. for 6 h, then the solvent was evaporated. The residue was purified by silica-gel flash column chromatography (AcOEt/PE 1:1) to give compound 2 as a yellow solid (2.965 g, 82%). [M+Na]$^+$=261.1

(E)-3-(2-(tert-butoxy)-3,4-dimethoxyphenyl)-1-(3-hydroxyphenyl)prop-2-en-1-one (4). To the solution of 2 (2.965 g, 12.4 mmol) and 3'-hydroxyacetophenone 3 (2.03 g, 14.9 mmol) in EtOH (50 mL) was added a solution of 40% aqueous KOH (6.98 g, 49.8 mmol) at 0° C. The resulting solution was stirred at 60° C. for 4 h. The solution was poured into water and acidified to pH 4 with a 1 M HCl aqueous solution, extracted with EtOAc twice. The combined organic layers were washed by brine, dried over Na₂SO₄ and concentrated in vacuo. The crude compound was purified by silica-gel flash column chromatography (AcOEt/PE 1:1) to give compound 4 as a yellow oil (3.2 g, 72%). [M+Na]⁺=378.9 tert-butyl (E)-2-(3-(3-(2-(tert-butoxy)-3,4-dimethoxyphenyl)acryloyl)phenoxy)acetate (5). A solution of 4 (3.2 g, 9 mmol) and K₂CO₃ (1.49 g, 10.8 mmol) in DMF (30 mL) was treated with tert-butyl bromoacetate (1.58 mL, 10.8 mmol) and allowed to stir at room temperature for 5 h. After this time the reaction mixture was quenched by H₂O and extracted with EtOAc twice. The combined organic layers were washed by brine, dried over Na₂SO₄ and concentrated in vacuo. The crude compound was purified by silica-gel flash column chromatography (AcOEt/PE 1:4) to give compound 5 as a yellow oil (4 g, 95%). [M+Na]⁺=493.3 tert-butyl 2-(3-(3-(2-(tert-butoxy)-3,4-dimethoxyphenyl)propanoyl)phenoxy)acetate (6). A solution of 5 (4 g, 8.5 mmol) and 10% Pd/C (0.8 g) in THF (50 mL) was hydrogenated with H₂ for 3 h at room temperature. The reaction mixture was then filtered and concentrated. The residue was purified by silica-gel flash column chromatography (AcOEt/PE 1:3) to give compound 6 as a colorless oil (2.878 g, 72%). [M+Na]⁺=495.3 tert-butyl (R)-2-(3-(3-(3-(tert-butoxy)-4,5-dimethoxyphenyl)-1-hydroxypropyl)phenoxy)acetate (7). A solution of ketone 6 (2.878 g, 6.1 mmol) in dry THF (30 mL) at −20° C. was treated with a solution of (+)-DIPChloride (24.4 mmol) in heptane (1.7 M, 14.3 mL) at −20° C. The resulting mixture was reacted at −20° C. until complete conversion of 6, then quenched with 2,2'-(ethylenedioxy)diethylamine (3.6 mL) by forming an insoluble complex. After stirring at RT for another 30 min, the suspension was filtered through a pad of celite and concentrated. The crude compound was purified by silica-gel flash column chromatography (AcOEt/PE 1:3) to give compound 7 as a light yellow oil (2 g, 70%, ee>99%). [M+Na]⁺=497.0

(R)-1-(3-(2-(tert-butoxy)-2-oxoethoxy)phenyl)-3-(2-(tert-butoxy)-3,4-dimethoxyphenyl)propyl (S)-1-(4-(acryloyloxy)-3,3-dimethyl-2-oxobutanoyl)piperidine-2-carboxylate (9). A solution of 7 (1.8 g, 3.793 mmol) and 8 (1.77 g, 5.69 mmol) in CH₂Cl₂ (13 mL) was cooled to −20° C. before a solution of DCC (1.17 g, 5.69 mmol) in CH₂Cl₂ (5 mL) was added, followed by the addition of a solution of 4-(dimethylamino)pyridine (DMAP, 46 mg, 0.379 mmol) in CH₂Cl₂ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:3) to give compound 9 as a light yellow oil (2.5 g, 86%). [M+Na]⁺=790.4

2-(3-((R)-1-(((S)-1-(4-(acryloyloxy)-3,3-dimethyl-2-oxobutanoyl)piperidine-2-carbonyl)oxy)-3-(2-hydroxy-3,4-dimethoxyphenyl)propyl)phenoxy)acetic acid (Rae9): A solution of 9 (2.5 g, 3.26 mmol) in CH₂Cl₂ (12 mL) was treated with a solution of 40% TFA in CH₂Cl₂ (12 mL) at 0° C. The mixture was allowed to react at room temperature until complete conversion. The reaction mixture was charged to silica-gel flash column directly (AcOEt/PE/AcOH 1:2:0.5) to afford Rae9 (636 mg, 30%) as a pale yellow solid.

FKBD Example 25

2-(3-((R)-1-(((S)-1-(4-(acryloyloxy)-3,3-dimethyl-2-oxobutanoyl)piperidine-2-carbonyl)oxy)-3-(3-hydroxy-4,5-dimethoxyphenyl)propyl)phenoxy)acetic acid (Rae10)

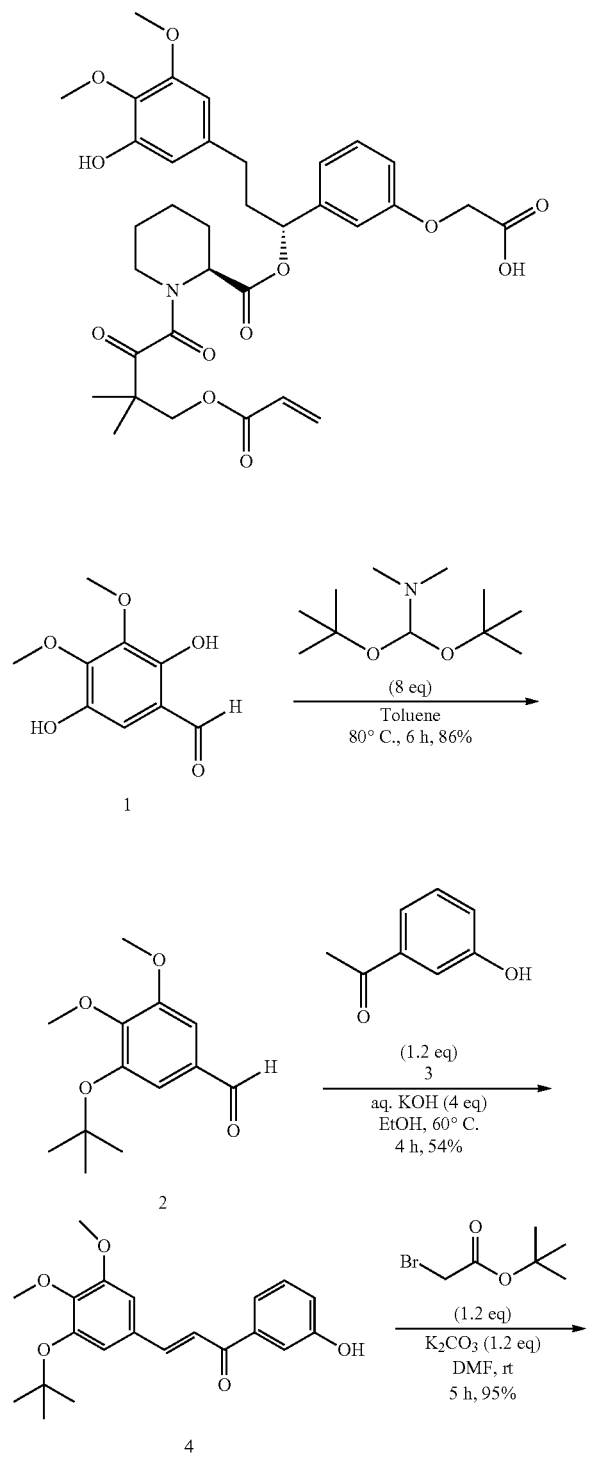

Scheme 28. Synthesis of Rae10 FKBD moiety.

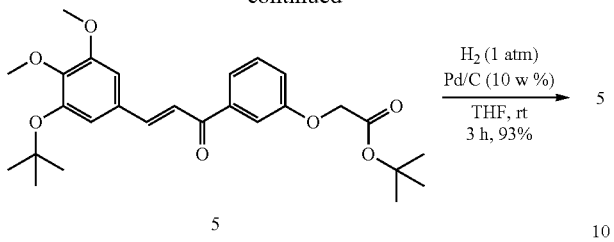

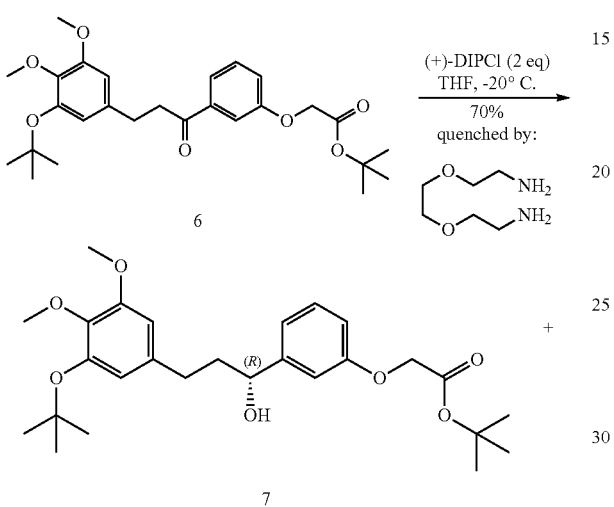

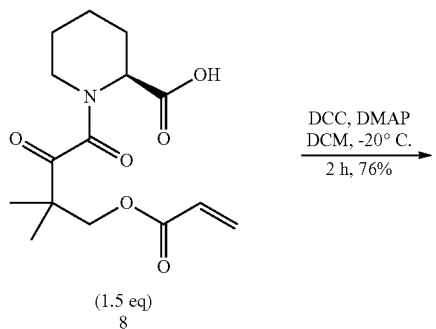

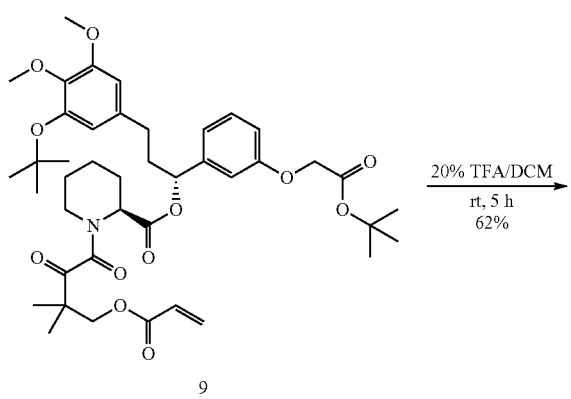

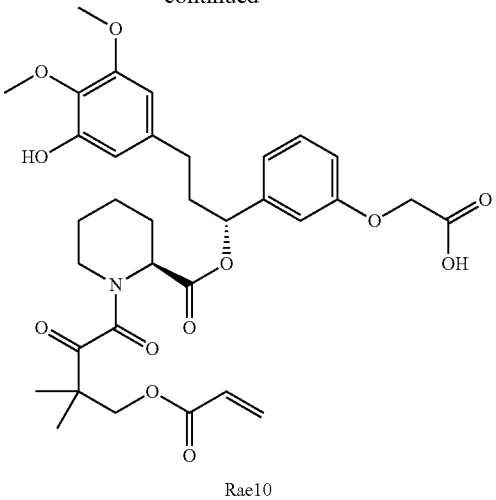

Rae10

3-(tert-butoxy)-4,5-dimethoxybenzaldehyde (2). To a solution of 3-hydroxy-4,5-dimethoxybenzaldehyde 1 (2.77 g, 15.2 mmol) in anhydrous toluene (30 mL) was added 1,1-di-tert-butoxy-N,N-dimethylmethanamine 2 (29.1 mL, 122 mmol) under Ar. atmosphere. The mixture was stirred at 80° C. for 6 h, then the solvent was evaporated. The residue was purified by silica-gel flash column chromatography (AcOEt/PE 1:1) to give compound 2 as a yellow solid (3.126 g, 86%). [M+H]$^+$=239.0

(E)-3-(3-(tert-butoxy)-4,5-dimethoxyphenyl)-1-(3-hydroxyphenyl)prop-2-en-1-one (4). To the solution of 2 (3.126 g, 13 mmol) and 3'-hydroxyacetophenone 3 (2.14 g, 15.7 mmol) in EtOH (30 mL) was added a solution of 40% aqueous KOH (7.36 g, 52 mmol) at 0° C. The resulting solution was stirred at 60° C. for 4 h. The solution was poured into water and acidified to pH 4 with a 1 M HCl aqueous solution, extracted with EtOAc twice. The combined organic layers were washed by brine, dried over Na$_2$SO$_4$ and concentrated in vacuo. The crude compound was purified by silica-gel flash column chromatography (AcOEt/PE 1:1) to give compound 4 as a yellow oil (2.489 g, 54%). [M+H]$^+$=357.0 tert-butyl (E)-2-(3-(3-(3-(tert-butoxy)-4,5-dimethoxyphenyl)acryloyl)phenoxy)acetate (5). A solution of 4 (2.489 g, 6.98 mmol) and K$_2$CO$_3$ (1.16 g, 8.38 mmol) in DMF (30 mL) was treated with tert-butyl bromoacetate (1.2 mL, 8.38 mmol) and allowed to stir at room temperature for 5 h. After this time the reaction mixture was quenched by H$_2$O and extracted with EtOAc twice. The combined organic layers were washed by brine, dried over Na$_2$SO$_4$ and concentrated in vacuo. The crude compound was purified by silica-gel flash column chromatography (AcOEt/PE 1:4) to give compound 5 as a yellow oil (3.1 g, 95%). [M+H]$^+$=471.0 tert-butyl 2-(3-(3-(3-(tert-butoxy)-4,5-dimethoxyphenyl) propanoyl)phenoxy)acetate (6). A solution of 5 (3.1 g, 6.59 mmol) and 10% Pd/C (0.5 g) in THF (50 mL) was hydrogenated with H$_2$ for 3 h at room temperature. The reaction mixture was then filtered and concentrated. The residue was purified by silica-gel flash column chromatography (AcOEt/PE 1:3) to give compound 6 as a colorless oil (2.88 g, 93%). [M+Na]$^+$=495.3 tert-butyl (R)-2-(3-(3-(3-(tert-butoxy)-4,5-dimethoxyphenyl)-1-hydroxypropyl)phenoxy)acetate (7). A solution of ketone 6 (2.868 g, 6.07 mmol) in dry THF (30 mL) at −20° C. was treated with a solution of (+)-DIPChloride (12.1 mmol) in heptane (1.7 M, 7.1 mL) at −20° C. The resulting mixture was reacted at −20° C. until complete conversion of 6, then quenched with 2,2'-(ethylenedioxy)diethylamine (3.6 mL) by forming an insoluble complex. After stirring at RT for another 30 min, the suspension was filtered through a pad of celite and concentrated. The crude compound was purified by silica-gel flash column chromatography (AcOEt/PE 1:3) to give compound 7 as a light yellow oil (2.03 g, 70%, ee>99% vs racemate). [M+Na]⁺=497.3

(R)-1-(3-(3-(tert-butoxy)-2-oxoethoxy)phenyl)-3-(2-(tert-butoxy)-4,5-dimethoxyphenyl)propyl (S)-1-(4-(acryloyloxy)-3,3-dimethyl-2-oxobutanoyl)piperidine-2-carboxylate (9). A solution of 7 (2.03 g, 4.3 mmol) and 8 (2 g, 6.4 mmol) in CH₂Cl₂ (43 mL) was cooled to −20° C. before a solution of DCC (1.3 g, 6.4 mmol) in CH₂Cl₂ (5 mL) was added, followed by the addition of a solution of 4-(dimethylamino)pyridine (DMAP, 52.3 mg, 0.43 mmol) in CH₂Cl₂ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:3) to give compound 9 as a light yellow oil (2.5 g, 76%). [M+Na]⁺=790.3

2-(3-((R)-1-(((S)-1-(4-(acryloyloxy)-3,3-dimethyl-2-oxobutanoyl)piperidine-2-carbonyl)oxy)-3-(3-hydroxy-4,5-dimethoxyphenyl)propyl)phenoxy)acetic acid (Rae10). A solution of 9 (2.5 g, 3.26 mmol) in CH₂Cl₂ (12 mL) was treated with a solution of 40% TFA in CH₂Cl₂ (12 mL) at 0° C. The mixture was allowed to react at room temperature until complete conversion. The reaction mixture was charged to silica-gel flash column directly (AcOEt/PE/AcOH 1:2:0.5%) to afford Rae10 (1.334 g, 62%) as a pale yellow solid.

FKBD Example 26

2-(3-((R)-1-(((S)-1-(4-(acryloyloxy)-3,3-dimethyl-2-oxobutanoyl)piperidine-2-carbonyl)oxy)-3-(2-hydroxy-4,5-dimethoxyphenyl)propyl)phenoxy)acetic acid (Rae11)

Scheme 29. Synthesis of Rae11 FKBD moiety.

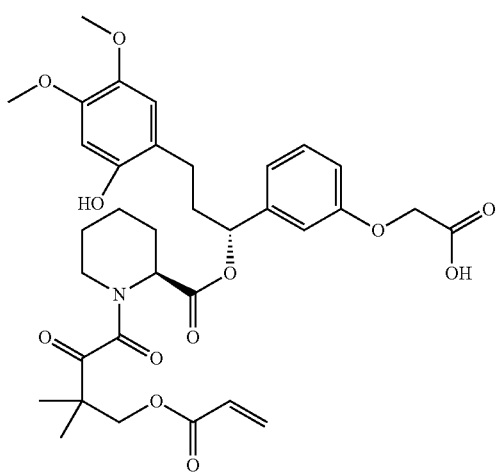

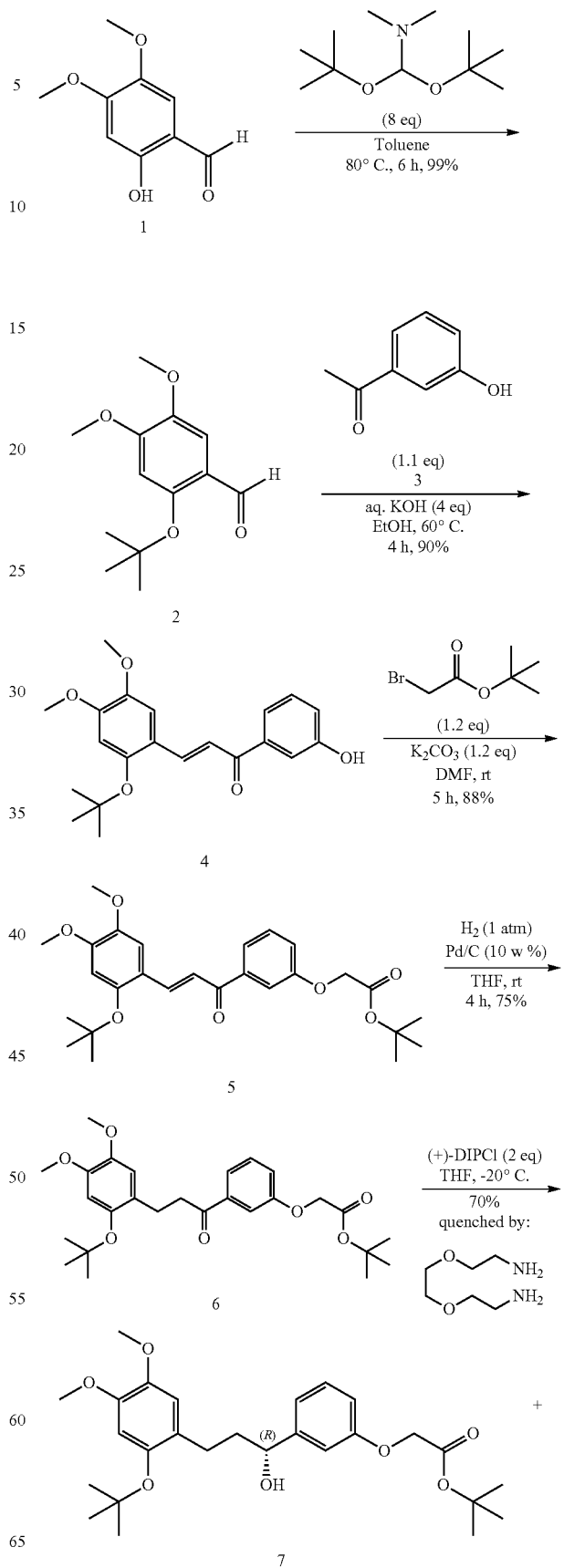

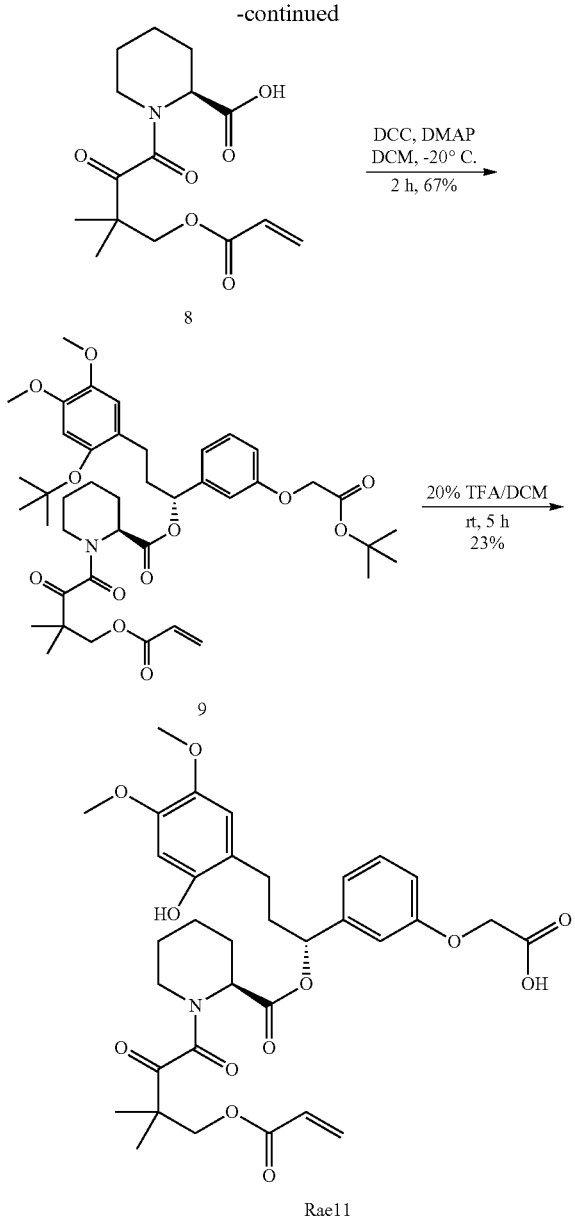

2-(tert-butoxy)-4,5-dimethoxybenzaldehyde (2). To a solution of 2-hydroxy-4,5-dimethoxybenzaldehyde 1 (3 g, 16.5 mmol) in anhydrous toluene (15 mL) was added 1,1-di-tert-butoxy-N,N-dimethylmethanamine 2 (31.6 mL, 132 mmol) under Ar. atmosphere. The mixture was stirred at 80° C. for 6 h, then the solvent was evaporated. The residue was purified by silica-gel flash column chromatography (AcOEt/PE 1:1) to give compound 2 as a yellow solid (3.875 g, 99%). $[M+Na]^+=261.2$ (E)-3-(2-(tert-butoxy)-4,5-dimethoxyphenyl)-1-(3-hydroxyphenyl)prop-2-en-1-one (4). To the solution of 2 (3.875 g, 16.3 mmol) and 3'-hydroxyacetophenone 3 (2.436 g, 17.9 mmol) in EtOH (50 mL) was added a solution of 40% aqueous KOH (8.5 mL, 3.65 g, 65.2 mmol) at 0° C. The resulting solution was stirred at 60° C. for 4 h. The solution was poured into water and acidified to pH 4 with a 1M HCl aqueous solution, extracted with EtOAc twice. The combined organic layers were washed by brine, dried over $Na_2SO_4$ and concentrated in vacuo. The crude compound was purified by silica-gel flash column chromatography (AcOEt/PE 1:1) to give compound 4 as a yellow oil (5.2 g, 90%). $[M+H]^+=357.2$ tert-butyl (E)-2-(3-(3-(2-(tert-butoxy)-4,5-dimethoxyphenyl)acryloyl)phenoxy)acetate (5). A solution of 4 (5.2 g, 14.59 mmol) and $K_2CO_3$ (2.4 g, 17.5 mmol) in DMF (50 mL) was treated with tert-butyl bromoacetate (2.55 mL, 17.5 mmol) and allowed to stir at room temperature for 5 h. After this time the reaction mixture was quenched by $H_2O$ and extracted with EtOAc twice. The combined organic layers were washed by brine, dried over $Na_2SO_4$ and concentrated in vacuo. The crude compound was purified by silica-gel flash column chromatography (AcOEt/PE 1:4) to give compound 5 as a yellow oil (6 g, 88%). $[M+H]^+=471.0$ tert-butyl 2-(3-(3-(2-(tert-butoxy)-4,5-dimethoxyphenyl)propanoyl)phenoxy)acetate (6). A solution of 5 (6 g, 12.75 mmol) and 10% Pd/C (1 g) in THF (70 mL) was hydrogenated with $H_2$ for 4 h at room temperature. The reaction mixture was then filtered and concentrated. The residue was purified by silica-gel flash column chromatography (AcOEt/PE 1:3) to give compound 6 as a colorless oil (4.5 g, 75%). $[M+Na]^+=495.3$ tert-butyl (R)-2-(3-(3-(2-(tert-butoxy)-4,5-dimethoxyphenyl)-1-hydroxypropyl)phenoxy)acetate (7). A solution of ketone 6 (4.5 g, 9.5 mmol) in dry THF (45 mL) at −20° C. was treated with a solution of (+)-DIPChloride (19 mmol) in heptane (1.7 M, 11.2 mL) at −20° C. The resulting mixture was reacted at −20° C. until complete conversion of 6, then quenched with 2,2'-(ethylenedioxy)diethylamine (2.8 mL) by forming an insoluble complex. After stirring at RT for another 30 min, the suspension was filtered through a pad of celite and concentrated. The crude compound was purified by silica-gel flash column chromatography (AcOEt/PE 1:3) to give compound 7 as a light yellow oil (3.2 g, 70%, ee>99% vs racemate). $[M+Na]^+=496.7$ (R)-1-(3-(2-(tert-butoxy)-2-oxoethoxy)phenyl)-3-(2-(tert-butoxy)-4,5-dimethoxyphenyl)propyl (S)-1-(4-(acryloyloxy)-3,3-dimethyl-2-oxobutanoyl)piperidine-2-carboxylate (9). A solution of 7 (1.93 g, 4.07 mmol) and 8 (1.9 g, 6.103 mmol) in $CH_2Cl_2$ (43 mL) was cooled to −20° C. before a solution of DCC (1.26 g, 6.103 mmol) in $CH_2Cl_2$ (5 mL) was added, followed by the addition of a solution of 4-(dimethylamino)pyridine (DMAP, 50 mg, 0.407 mmol) in $CH_2Cl_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:3) to give compound 9 as a light yellow oil (2.1 g, 67%). $[M+Na]^+=790.4$ 2-(3-((R)-1-(((S)-1-(4-(acryloyloxy)-3,3-dimethyl-2-oxobutanoyl)piperidine-2-carbonyl)oxy)-3-(2-hydroxy-4,5-dimethoxyphenyl)propyl)phenoxy)acetic acid (Rae11). A solution of 9 (2.1 g, 2.73 mmol) in $CH_2Cl_2$ (12 mL) was treated with a solution of 40% TFA in $CH_2Cl_2$ (12 mL) at 0° C. The mixture was allowed to react at room temperature until complete conversion. The reaction mixture was charged to silica-gel flash column directly (AcOEt/PE/AcOH 1:2:0.5%) to afford Rae11 (638 mg, 23%) as a pale yellow solid.

FKBD Example 27
2-(3-((R)-1-(((S)-1-(4-(acryloyloxy)-3,3-dimethyl-2-oxobutanoyl)piperidine-2-carbonyl)oxy)-3-(3-fluoro-4,5-dimethoxyphenyl)propyl)phenoxy)acetic acid (Rae12)
Scheme 30. Synthesis of Rae12 FKBD moiety.
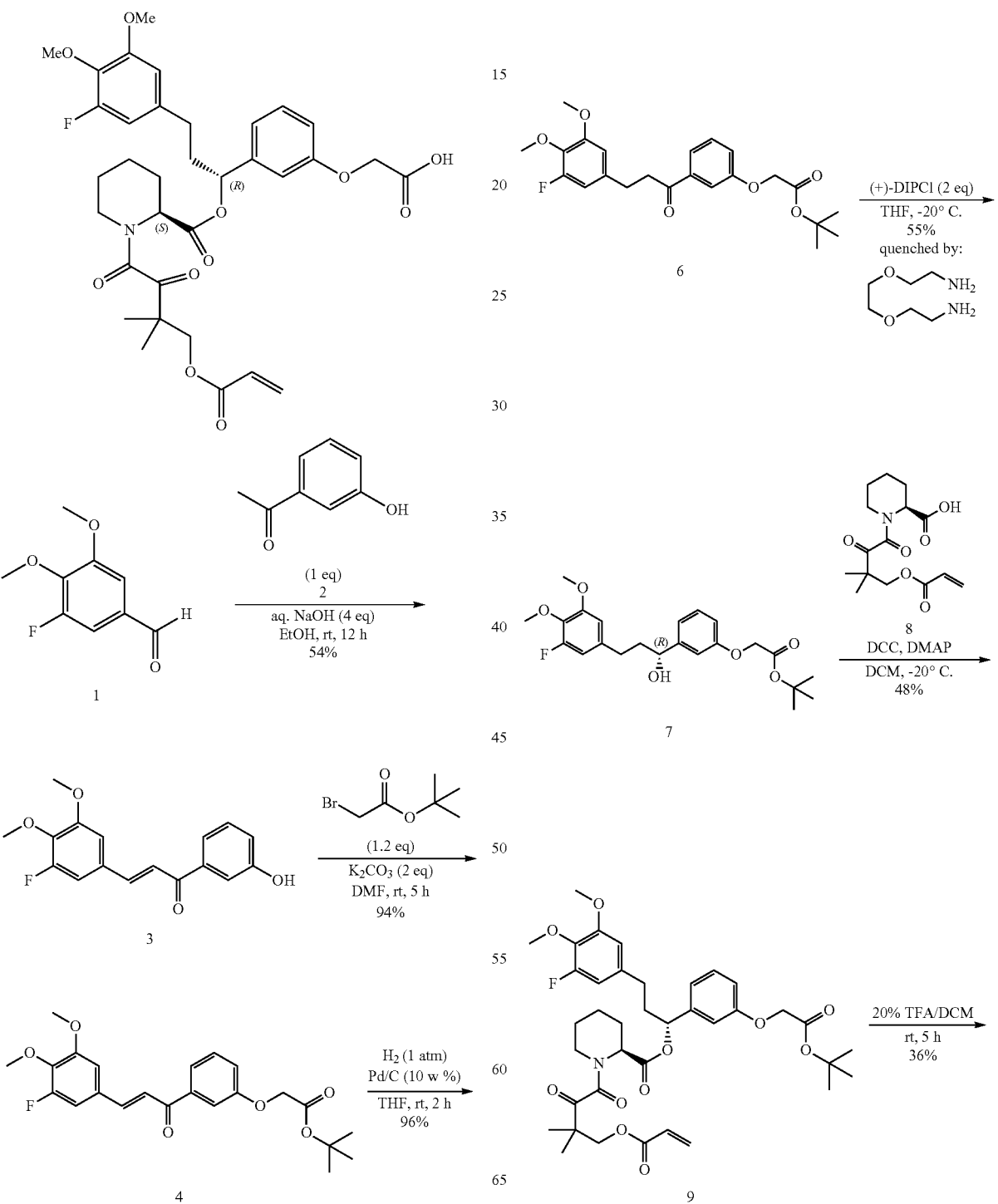

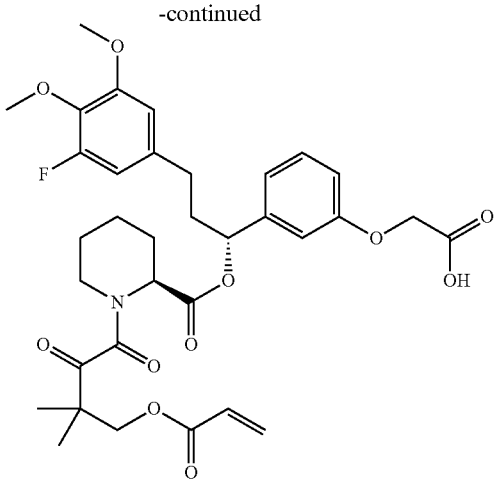

Rae12

(E)-3-(3-fluoro-4,5-dimethoxyphenyl)-1-(3-hydroxyphenyl)prop-2-en-1-one (3). To the solution of 3-fluoro-4,5-dimethoxybenzaldehyde 1 (4.5 g, 24.4 mmol) and 1-(3-hydroxyphenyl)ethan-1-one 2 (3.3 g, 24.4 mmol) in EtOH (60 mL) was added a solution of 10% aqueous NaOH (40 mL, 97.6 mmol) at 0° C. The resulting solution was stirred at room temperature for 12 h. The solution was adjusted to pH 4 by added 4M aqueous HCl dropwise at 0° C., generated a large of yellow solid. Then the mixture was filtered and the solid was washed with water (50 mL) to afford 3 (4 g, 54%) as a yellow solid. [M+H]$^+$=303.1 tert-butyl (E)-2-(3-(3-(3-fluoro-4,5-dimethoxyphenyl)acryloyl)phenoxy)acetate (4). A solution of 3 (4 g, 13.2 mmol) and K$_2$CO$_3$ (3.65 g, 26.4 mmol) in DMF (30 mL) was treated with tert-butyl bromoacetate (3.08 g, 15.8 mmol) and allowed to stir at room temperature for 5 h. After this time the reaction mixture was poured into ice, yellow solid was precipitated. The mixture was filtered and the solid was washed with water (30 mL). The crude product was purified by column chromatography on silica gel (AcOEt/PE 1:4) to give 4 (5.2 g, 94%) as a yellow solid. [M+Na]$^+$=438.7 tert-butyl 2-(3-(3-(3-fluoro-4,5-dimethoxyphenyl)-1-hydroxypropyl)phenoxy)acetate (5). A solution of 4 (5.2 g, 12.5 mmol) and 10% Pd/C (1 g) in THF (100 mL) was hydrogenated with H$_2$ for 2 h at room temperature. The reaction mixture was then filtered and concentrated. The crude product was purified by column chromatography on silica gel to give 5 (5 g, 96%) as a yellow oil. [M+Na]$^+$= 443.2 tert-butyl 2-(3-(3-(3-fluoro-4,5-dimethoxyphenyl)propanoyl)phenoxy)acetate (6). A solution of 5 (5 g, 11.9 mmol) in CH$_2$Cl$_2$ (100 mL) was treated with Dess-Martin periodinane (15.2 g, 36 mmol) and allowed to stir at room temperature for 2 h before being quenched with a solution of 10% aqueous NaS$_2$O$_3$. The solution was extracted with CH$_2$Cl$_2$ twice. The combined organic layers were washed by sat. NaHCO$_3$, brine, dried over Na$_2$SO$_4$ and concentrated in vacuo. The crude compound was purified by silica-gel flash column chromatography (AcOEt/PE 1:3) to give compound 6 as a white solid (4 g, 80%). [M+Na]$^+$=441.2 tert-butyl (R)-2-(3-(3-(3-fluoro-4,5-dimethoxyphenyl)-1-hydroxypropyl)phenoxy)acetate (7). A solution of ketone 6 (4 g, 9.56 mmol) in dry THF (30 mL) at –20° C. was treated with a solution of (+)-DIPChloride (19.1 mmol) in heptane (1.7 M, 11.2 mL) at –20° C. The resulting mixture was reacted at –20° C. until complete conversion of 6, then quenched with 2,2'-(ethylenedioxy)diethylamine (2.8 g) by forming an insoluble complex. After stirring at room temperature for another 30 min, the suspension was filtered through a pad of celite and concentrated. The crude compound was purified by silica-gel flash column chromatography (AcOEt/PE 1:4) to give compound 6 (2.2 g, 55%, ee>99%) as a light yellow oil. [M+Na]$^+$=442.7

(R)-1-(3-(2-(tert-butoxy)-2-oxoethoxy)phenyl)-3-(3-fluoro-4,5-dimethoxyphenyl)propyl (S)-1-(4-(acryloyloxy)-3,3-dimethyl-2-oxobutanoyl)piperidine-2-carboxylate (9). A solution of 7 (2.2 g, 5.23 mmol) and 8 (1.80 g, 5.76 mmol) in CH$_2$Cl$_2$ (20 mL) was cooled to –20° C. before a solution of DCC (1.4 g, 6.79 mmol) in CH$_2$Cl$_2$ (10 mL) was added, followed by the addition of a solution of 4-(dimethylamino)pyridine (63 mg, 0.52 mmol) in CH$_2$Cl$_2$ (2 mL) under argon atmosphere. The resulting white suspension was allowed to stir at –20° C. for 2 h. The reaction mixture was then filtered, evaporated, and the crude compound was purified by silica-gel flash column chromatography (AcOEt/PE 1:3) to give compound 9 (1.8 g, 48%) as a light yellow oil. [M+Na]$^+$= 736.4

2-(3-((R)-1-(((S)-1-(4-(acryloyloxy)-3,3-dimethyl-2-oxobutanoyl)piperidine-2-carbonyl)oxy)-3-(3-fluoro-4,5-dimethoxyphenyl)propyl)phenoxy)acetic acid (Rae12). A solution of 9 (1.8 g, 2.52 mmol) in CH$_2$Cl$_2$ (10 mL) was treated with a solution of 40% TFA in CH$_2$Cl$_2$ (10 mL) at 0° C. The mixture was allowed to react at room temperature until complete conversion. The reaction mixture was charged to silica-gel flash column directly (AcOEt/PE/AcOH 1:3:0.5%) to afford Rae12 (590 mg, 35%) as a faint yellow solid.

FKBD Example 28

2-(3-((R)-1-(((S)-1-(4-(acryloyloxy)-3,3-dimethyl-2-oxobutanoyl)piperidine-2-carbonyl)oxy)-3-(2-fluoro-4,5-dimethoxyphenyl)propyl)phenoxy)acetic acid (Rae13)

Scheme 31. Synthesis of Rae13 FKBD moiety.

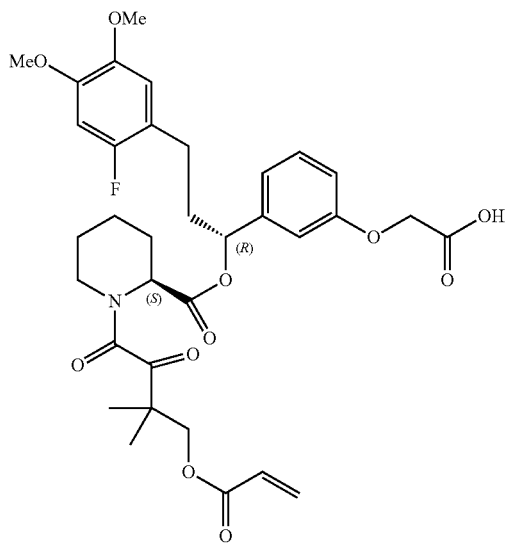

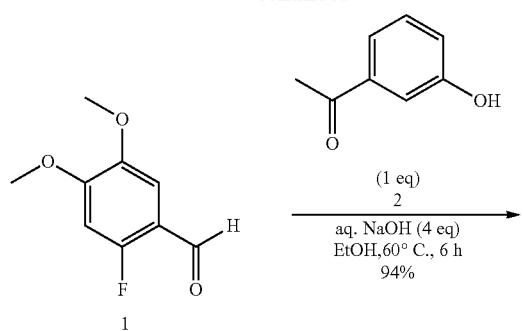

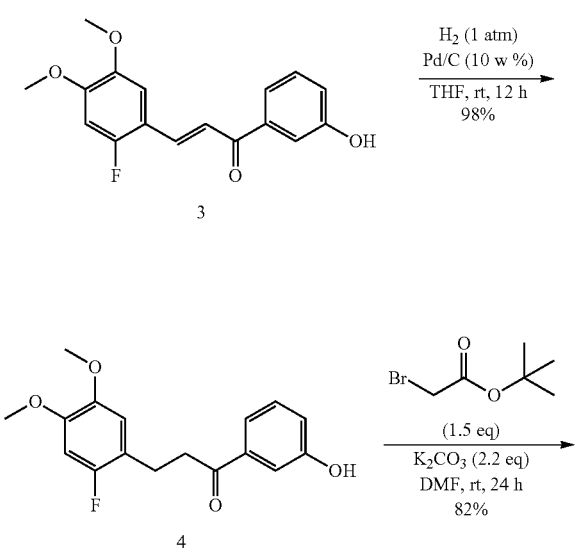

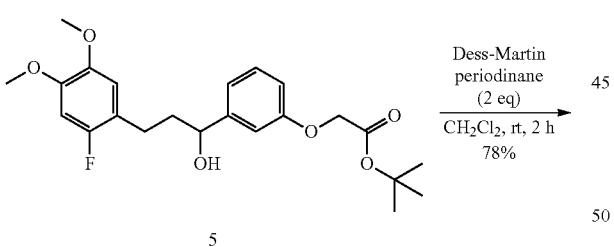

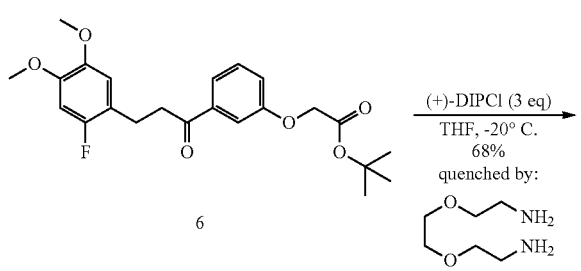

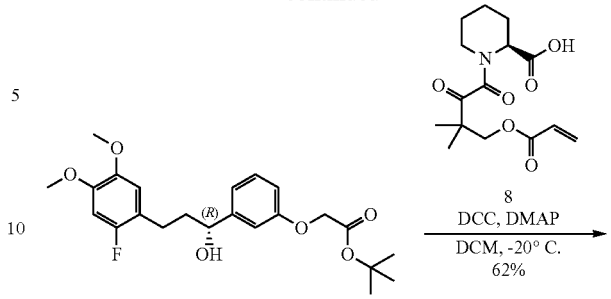

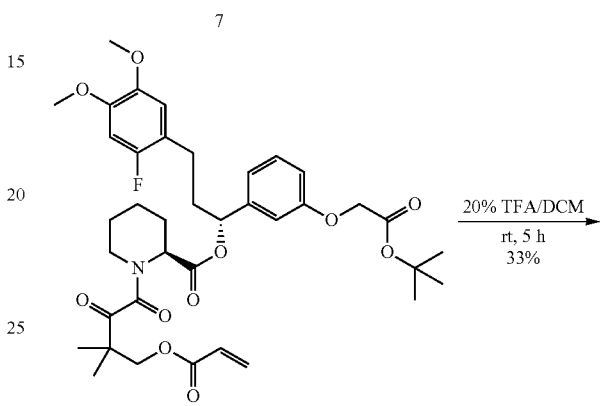

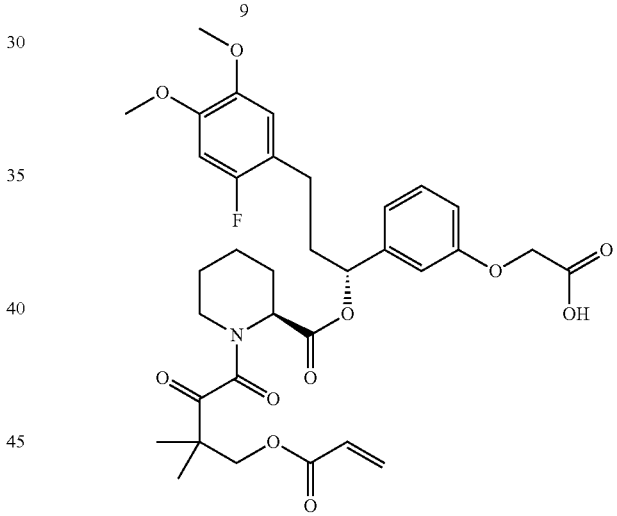

(E)-3-(2-fluoro-4,5-dimethoxyphenyl)-1-(3-hydroxyphenyl)prop-2-en-1-one (3). To the solution of 2-fluoro-4,5-dimethoxybenzaldehyde 1 (4.5 g, 24.4 mmol) and 1-(3-hydroxyphenyl)ethan-1-one 2 (3.3 g, 24.4 mmol) in EtOH (60 mL) was added a solution of 10% aqueous NaOH (40 mL, 97.6 mmol) at 0° C. The resulting solution was stirred at 65° C. for 6 h. The solution was adjusted to pH 4 by added 4M aqueous HCl dropwise at 0° C., generated a large of yellow solid. Then the mixture was filtered and the solid was washed with water (50 mL) to afford 3 (7 g, 94%) as a yellow solid. [M+H]$^+$=302.8

3-(3-(2-fluoro-4,5-dimethoxyphenyl)-1-hydroxypropyl)phenol (4). A solution of 3 (7 g, 23.1 mmol) and 10% Pd/C (2 g) in THF (150 mL) was hydrogenated with H$_2$ for 12 h at room temperature. The reaction mixture was then filtered and concentrated. The crude product was purified by column chromatography on silica gel to give 4 (7 g, 98%) as a yellow oil. [M+Na]$^+$=328.8 tert-butyl 2-(3-(3-(2-fluoro-4,5-dimethoxyphenyl)-1-hydroxypropyl)phenoxy)acetate (5). A solution of 4 (7 g, 23.1 mmol) and K$_2$CO$_3$ (7 g, 50.6 mmol) in DMF (200 mL) was treated with tert-butyl bromoacetate (6.7 g, 34.5 mmol) and allowed to stir at room temperature for 24 h. After this time the reaction mixture was poured into ice, yellow solid was precipitated. The mixture was filtered and the solid was washed with water (300 mL). The crude product was purified by column chromatography on silica gel (AcOEt/PE 1:6) to give 5 (8 g, 82%) as a yellow solid. [M+Na]$^+$=443.2 tert-butyl 2-(3-(3-(2-fluoro-4,5-dimethoxyphenyl)propanoyl)phenoxy)acetate (6). A solution of 5 (8 g, 19 mmol) in CH$_2$Cl$_2$ (100 mL) was treated with Dess-Martin periodinane (16 g, 38 mmol) and allowed to stir at room temperature for 2 h before being quenched with a solution of 10% aqueous NaS$_2$O$_3$. The solution was extracted with CH$_2$Cl$_2$ twice. The combined organic layers were washed by sat. NaHCO$_3$, brine, dried over Na$_2$SO$_4$ and concentrated in vacuo. The crude compound was purified by silica-gel flash column chromatography (AcOEt/PE 1:3) to give compound 6 as a yellow solid (6.3 g, 78%). [M+Na]$^+$=440.7 tert-butyl (R)-2-(3-(3-(2-fluoro-4,5-dimethoxyphenyl)-1-hydroxypropyl)phenoxy)acetate (7). A solution of ketone 6 (6.3 g, 15.07 mmol) in dry THF (60 mL) at −20° C. was treated with a solution of (+)-DIPChloride (45.2 mmol) in heptane (1.7 M, 26.5 mL) at −20° C. The resulting mixture was reacted at −20° C. until complete conversion of 6, then quenched with 2,2'-(ethylenedioxy)diethylamine (6.6 g) by forming an insoluble complex. After stirring at room temperature for another 30 min, the suspension was filtered through a pad of celite and concentrated. The crude compound was purified by silica-gel flash column chromatography (AcOEt/PE 1:3) to give compound 7 (4.3 g, 68%, ee>99%) as a light yellow oil. [M+Na]$^+$=443.2

(R)-1-(3-(2-(tert-butoxy)-2-oxoethoxy)phenyl)-3-(2-fluoro-4,5-dimethoxyphenyl)propyl (S)-1-(4-(acryloyloxy)-3,3-dimethyl-2-oxobutanoyl)piperidine-2-carboxylate (9). A solution of 7 (1.6 g, 3.81 mmol) and 8 (1.77 g, 5.71 mmol) in CH$_2$Cl$_2$ (20 mL) was cooled to −20° C. before a solution of DCC (1.17 g, 5.71 mmol) in CH$_2$Cl$_2$ (10 mL) was added, followed by the addition of a solution of 4-(dimethylamino)pyridine (50 mg, 0.38 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:2) to give compound 9 (1.7 g, 62%) as a light yellow oil. [M+Na]$^+$=736.4

2-(3-((R)-1-(((S)-1-(4-(acryloyloxy)-3,3-dimethyl-2-oxobutanoyl)piperidine-2-carbonyl)oxy)-3-(2-fluoro-4,5-dimethoxyphenyl)propyl)phenoxy)acetic acid (Rae13). A solution of 9 (1.7 g, 2.38 mmol) in CH$_2$Cl$_2$ (10 mL) was treated with a solution of 40% TFA in CH$_2$Cl$_2$ (10 mL) at 0° C. The mixture was allowed to react at room temperature until complete conversion. The reaction mixture was charged to silica-gel flash column directly (AcOEt/PE/AcOH 1:3:0.5%) to afford Rae13 (520 mg, 33%) as a faint yellow solid.

FKBD Example 29

2-(3-((R)-1-(((S)-1-(4-(acryloyloxy)-3,3-dimethyl-2-oxobutanoyl)piperidine-2-carbonyl)oxy)-3-(2-fluoro-3,4-dimethoxyphenyl)propyl)phenoxy)acetic acid (Rae14)

Scheme 32. Synthesis of Rae14 FKBD moiety.

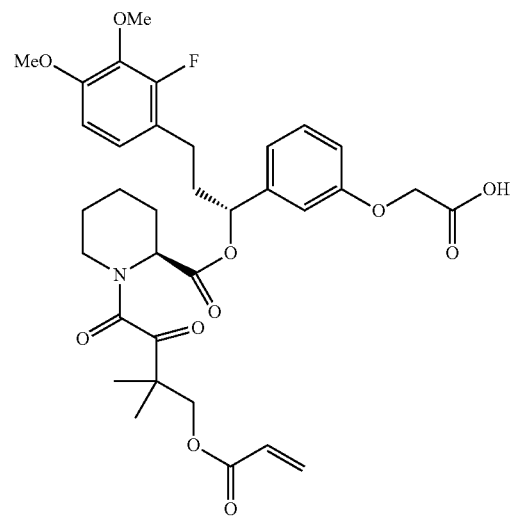

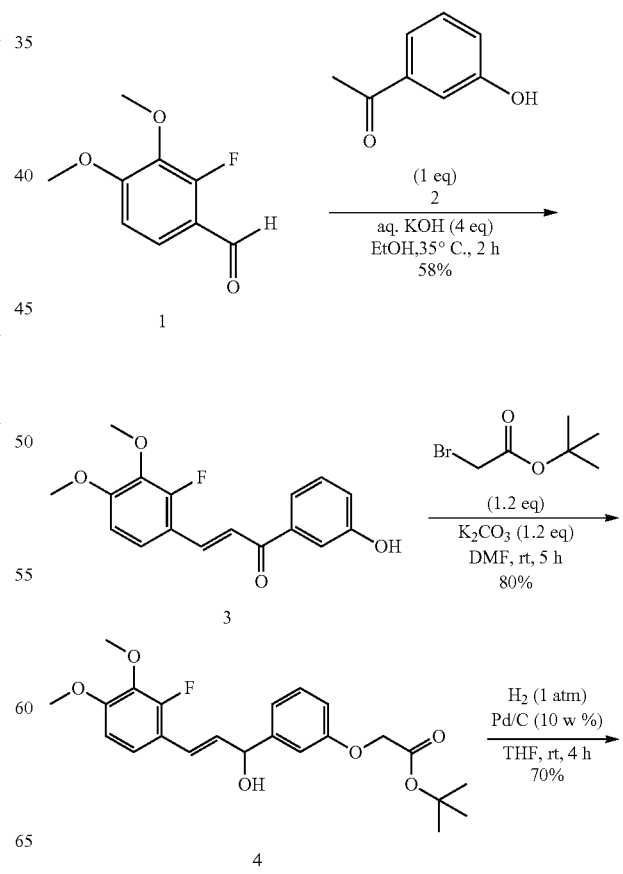

-continued

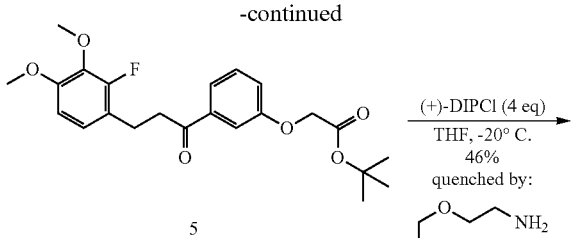

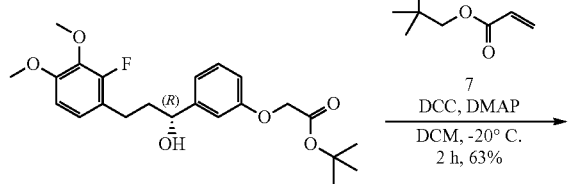

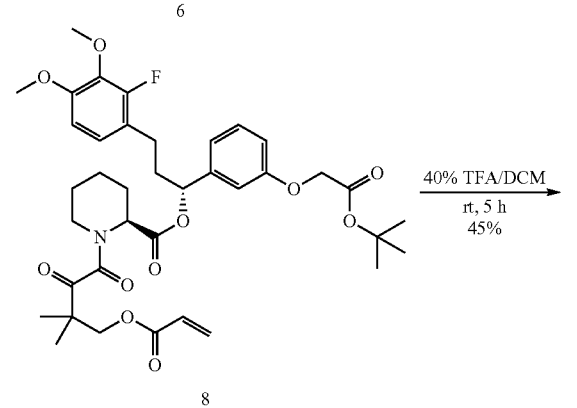

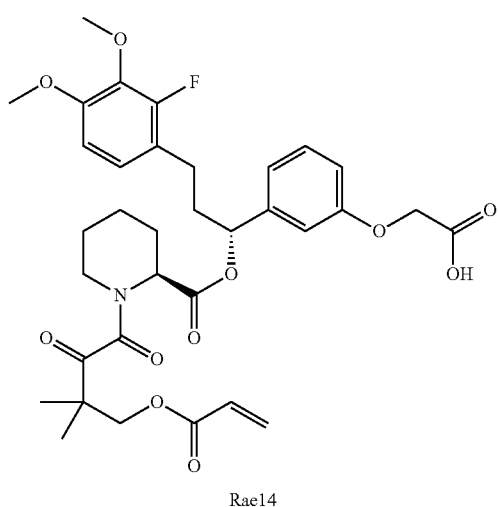

(E)-3-(2-fluoro-3,4-dimethoxyphenyl)-1-(3-hydroxyphenyl)prop-2-en-1-one (3). To the solution of 1(5.0 g, 27.17 mmol) and 2 (4.10 g, 29.89 mmol) in EtOH (150 mL) was added a solution of 40% aqueous KOH (15.22 g, 108.70 mmol) at 0° C. The resulting solution was heated to 35° C. for 2 h. The solvent was evaporated and the residue (4.8 g 58%) was used directly for the next step without purification. [M+H]$^+$=303.0

(E)-tert-butyl 2-(3-(3-(2-fluoro-3,4-dimethoxyphenyl)acryloyl)phenoxy)acetate (4). A solution of 3 (5.0 g, 16.55 mmol, crude) and K$_2$CO$_3$ (2.74 g, 19.87 mmol) in DMF (40 mL) was treated with tert-butyl bromoacetate (3.9 g, 19.87 mmol) and allowed to stir at room temperature for 5 h. After this time the reaction mixture was poured into ice, yellow solid was precipitated. The mixture was filtered and the solid was washed with water (30 mL). The crude product was purified by column chromatography on silica gel to give 4 (6.0 g, 80%) as a yellow solid. [M+Na]$^+$=439.2 tert-butyl 2-(3-(3-(2-fluoro-3,4-dimethoxyphenyl)propanoyl)phenoxy)acetate (5). A solution of 4 (4.0 g, 9.62 mmol) and 10% Pd/C (1.0 g) in THF (150 mL) was hydrogenated with H$_2$ for 4 h at room temperature. The reaction mixture was then filtered and concentrated. The crude product was purified by column chromatography on silica gel to give 5 (2.8 g, 70%) as a yellow oil. [M+Na]$^+$=440.8 tert-butyl (R)-2-(3-(3-(2-fluoro-3,4-dimethoxyphenyl)-1-hydroxypropyl)phenoxy)acetate (6). A solution of ketone 5 (2.8 g, 6.7 mmol) in dry THF (30 mL) at −20° C. was treated with a solution of (+)-DIPChloride (26.8 mmol) in heptane (1.7 M, 15.7 mL) at −20° C. The resulting mixture was reacted at −20° C. until complete conversion of 6, then quenched with 2,2′-(ethylenedioxy)diethylamine (3.96 g) by forming an insoluble complex. After stirring at room temperature for another 30 min, the suspension was filtered through a pad of celite and concentrated. The crude compound was purified by silica-gel flash column chromatography (AcOEt/PE 1:4) to give compound 6 (1.3 g, 46%, ee>99%) as a light yellow oil. [M+Na]$^+$=442.7

(R)-1-(3-(2-(tert-butoxy)-2-oxoethoxy)phenyl)-3-(2-fluoro-3,4-dimethoxyphenyl)propyl (S)-1-(4-(acryloyloxy)-3,3-dimethyl-2-oxobutanoyl)piperidine-2-carboxylate (8). A solution of 6 (1.3 g, 3.09 mmol) and 7 (1.25 g, 4.02 mmol) in CH$_2$Cl$_2$ (15 mL) was cooled to −20° C. before a solution of DCC (0.83 g, 4.02 mmol) in CH$_2$Cl$_2$ (5 mL) was added, followed by the addition of a solution of 4-(dimethylamino)pyridine (40 mg, 0.31 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:2) to give compound 8 (1.4 g, 63%) as a light yellow oil. [M+Na]$^+$=736.3

2-(3-((R)-1-(((S)-1-(4-(acryloyloxy)-3,3-dimethyl-2-oxobutanoyl)piperidine-2-carbonyl)oxy)-3-(2-fluoro-3,4-dimethoxyphenyl)propyl)phenoxy)acetic acid (Rae14). A solution of 8 (1.4 g, 1.96 mmol) in CH$_2$Cl$_2$ (10 mL) was treated with a solution of 40% TFA in CH$_2$Cl$_2$ (10 mL) at 0° C. The mixture was allowed to react at room temperature until complete conversion. The reaction mixture was charged to silica-gel flash column directly (AcOEt/PE/AcOH 1:3:0.5%) to afford Rae14 (585 mg, 45%) as a faint yellow solid.

FKBD Example 30
2-(3-((R)-1-(((S)-4-(((9H-fluoren-9-yl)methoxy)carbonyl)-1-(4-(acryloyloxy)-3,3-dimethyl-2-oxobutanoyl)piperazine-2-carbonyl)oxy)-3-(3,4-dimethoxyphenyl)propyl)phenoxy)acetic acid (Rae16)
5
Scheme 33. Synthesis of Rae16 FKBD moiety.
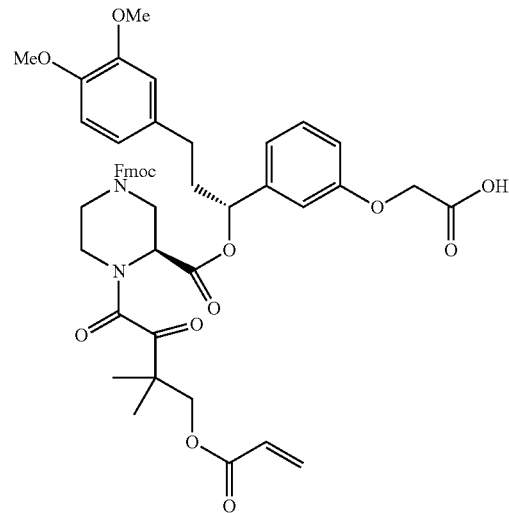
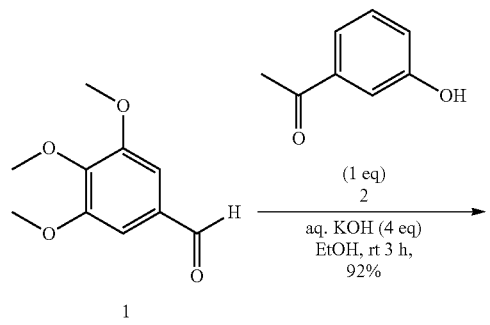
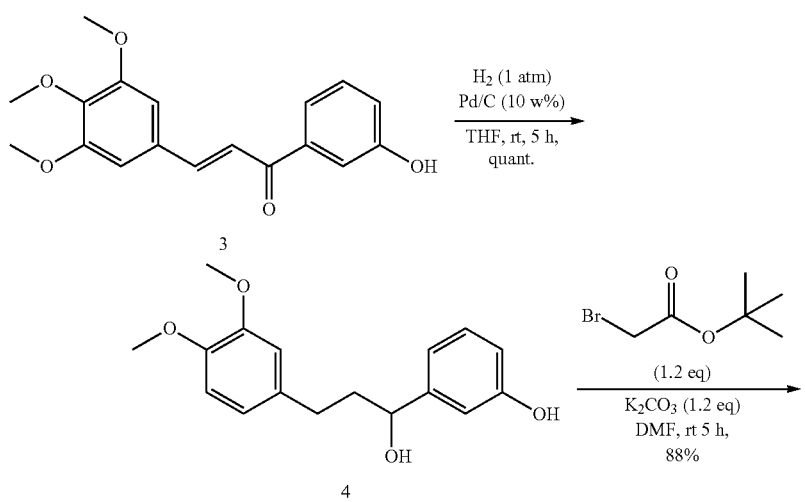

-continued
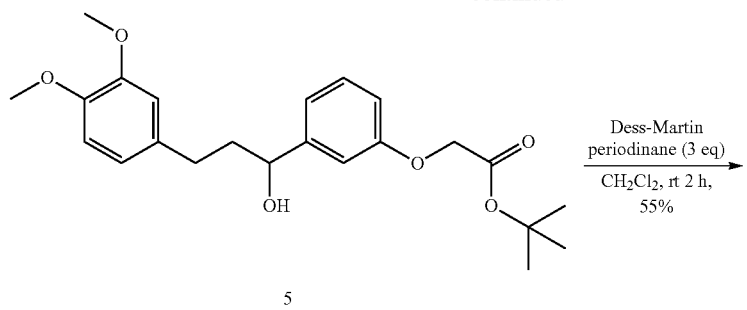
5
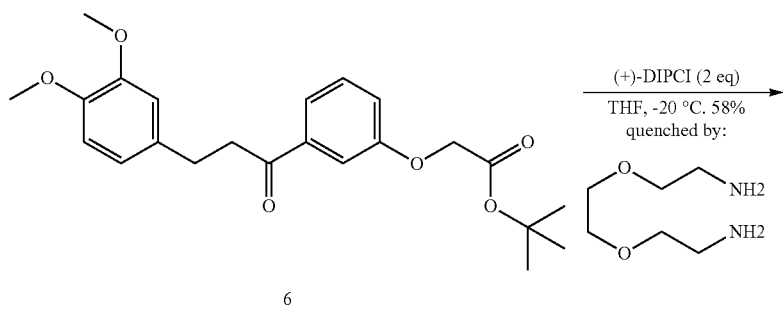
6
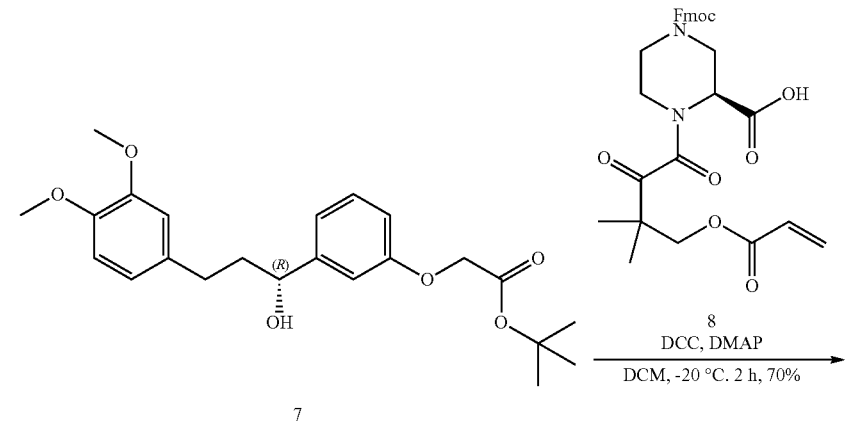
7
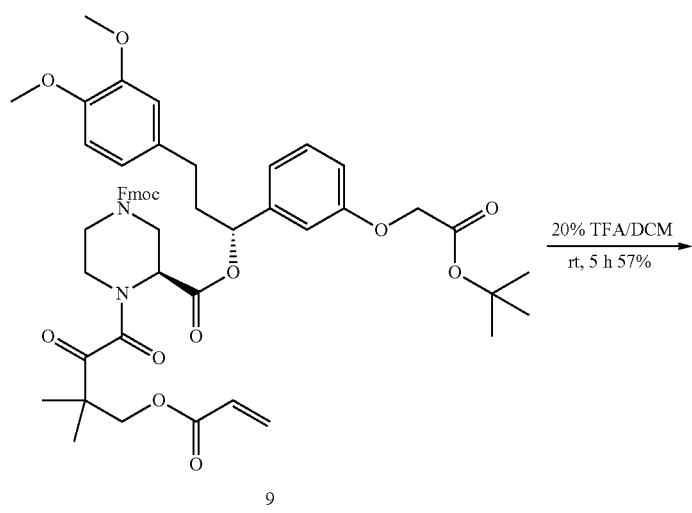
9

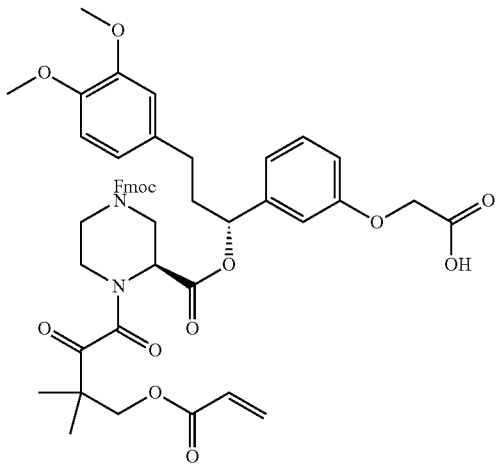

Rae16

(E)-3-(3,4-dimethoxyphenyl)-1-(3-hydroxyphenyl)prop-2-en-1-one (3). To the solution of 3,4-dimethoxybenzaldehyde 1 (17.6 g, 105.8 mmol) and 3'-hydroxyacetophenone 2 (12 g, 88.2 mmol) in EtOH (160 mL) was added a solution of 40% aqueous KOH (44 mL, 20 g, 352.8 mmol) at 0° C. The resulting solution was stirred at rt for 2 h, before being poured into ice-$H_2O$, the solution was acidified with 1M HCl solution and extracted with EtOAc. The combined organic layers were dried over $Na_2SO_4$ and concentrated in vacuo. The residue was recrystallized from EtOAc-PE to give the pale yellow powder (23 g, 92%). $[M+H]^+$=285.2

3-(3-(3,4-dimethoxyphenyl)-1-hydroxypropyl)phenol (4). A solution of 3 (16 g, 56.3 mmol) and 10% Pd/C (1.6 g) in THF (150 mL) was hydrogenated with $H_2$ for 4 h at room temperature. The reaction mixture was then filtered and concentrated to a solid (16.3 g, quant.). $[M+Na]^+$=311.2 tert-butyl 2-(3-(3-(3,4-dimethoxyphenyl)-1-hydroxypropyl)phenoxy)acetate (5). A solution of 4 (16.3 g, 56.53 mmol) and $K_2CO_3$ (9.4 g, 67.83 mmol) in DMF (150 mL) was treated with tert-butyl bromoacetate (9.9 mL, 67.83 mmol) and allowed to stir at room temperature for 5 h. After this time the reaction mixture was poured into ice, yellow solid was precipitated (20 g, 88%). $[M+Na]^+$=424.9.

tert-butyl 2-(3-(3-(3,4-dimethoxyphenyl)propanoyl)phenoxy)acetate (6). A solution of 5 (20 g, 49.7 mmol) in $CH_2Cl_2$ (400 mL) was treated with Dess-Martin periodinane (63 g, 149 mmol) and allowed to stir at room temperature for 3 h before being quenched with a solution of 10% aqueous $NaS_2O_3$. The solution was extracted with $CH_2Cl_2$ twice. The combined organic layers were washed by sat. $NaHCO_3$, brine, dried over $Na_2SO_4$ and concentrated in vacuo. The crude compound was purified by silica-gel flash column chromatography (AcOEt/PE 1:3) to give compound 6 as a white solid (11 g, 55%). $[M+Na]^+$=423.3.

tert-butyl (R)-2-(3-(3-(3,4-dimethoxyphenyl)-1-hydroxypropyl)phenoxy)acetate (7). A solution of ketone 6 (11.156 g, 27.9 mmol) in dry THF (100 mL) at −20° C. was treated with a solution of (+)-DIPChloride (83.6 mmol) in heptane (1.7 M, 49 mL) at −20° C. The resulting mixture was reacted at −20° C. until complete conversion of 6, then quenched with 2,2'-(ethylenedioxy)diethylamine (11.5 mL) by forming an insoluble complex. After stirring at RT for another 30 min, the suspension was filtered through a pad of celite and concentrated. The crude compound was purified by silica-gel flash column chromatography (AcOEt/PE 1:3) to give compound 7 as a light yellow oil (6.3 g, 58%, ee>99%). $[M+Na]^+$=425.3.

1-((9H-fluoren-9-yl)methyl) 3-((R)-1-(3-(2-(tert-butoxy)-2-oxoethoxy)phenyl)-3-(3,4-dimethoxyphenyl)propyl) (S)-4-(4-(acryloyloxy)-3,3-dimethyl-2-oxobutanoyl)piperazine-1,3-dicarboxylate (9). A solution of 7 (1.224 g, 3 mmol) and 8 (2.44 g, 4.56 mmol) in $CH_2Cl_2$ (10 mL) was cooled to −20° C. before a solution of DCC (0.94 g, 4.56 mmol) in $CH_2Cl_2$ (5 mL) was added, followed by the addition of a solution of 4-(dimethylamino)pyridine (DMAP, 37 mg, 0.3 mmol) in $CH_2Cl_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:2) to give compound 9 as a light yellow oil (1.8 g, 70%). $[M+Na]^+$=940.7.

2-(3-((R)-1-(((S)-4-(((9H-fluoren-9-yl)methoxy)carbonyl)-1-(4-(acryloyloxy)-3,3-dimethyl-2-oxobutanoyl)piperazine-2-carbonyl)oxy)-3-(3,4-dimethoxyphenyl)propyl)phenoxy)acetic acid (Rae16). A solution of 9 (1.8 g, 1.96 mmol) in $CH_2Cl_2$ (11.5 mL) was treated with a solution of 40% TFA in $CH_2Cl_2$ (11.5 mL) at 0° C. The mixture was allowed to react at room temperature until complete conversion. The reaction mixture was charged to silica-gel flash column directly (AcOEt/PE/AcOH 1:2:0.5%) to afford Rae16 (964 mg, 57%) as a white solid.

FKBD Example 31

2-(3-((R)-1-(((S)-1-(4-(acryloyloxy)-3,3-dimethyl-2-oxobutanoyl)-4-methylpiperazine-2-carbonyl)oxy)-3-(3,4-dimethoxyphenyl)propyl)phenoxy)acetic acid (Rae17)

Scheme 34. Synthesis of Rae17 FKBD moiety.

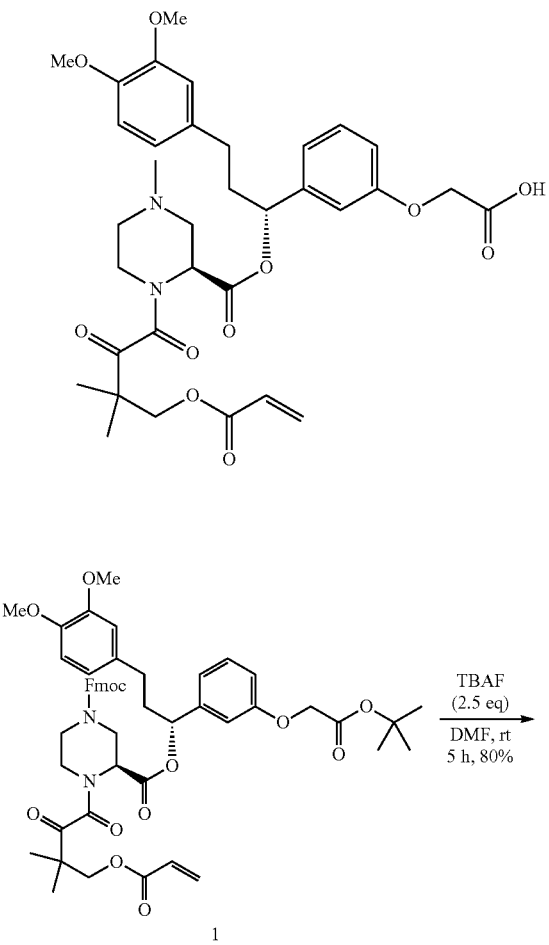

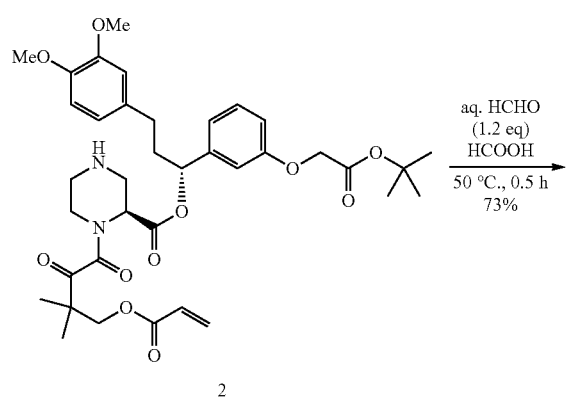

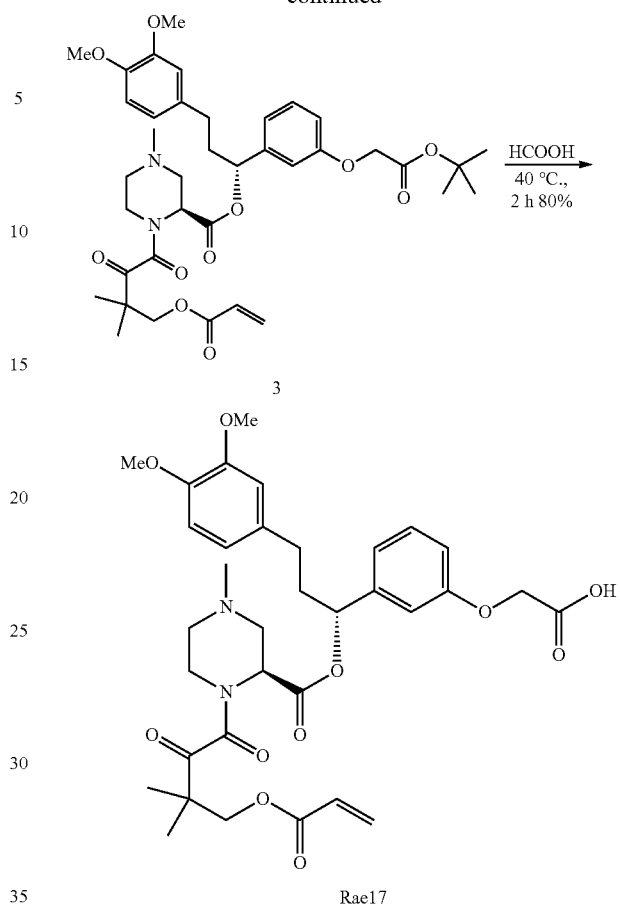

Rae17

(R)-1-(3-(2-(tert-butoxy)-2-oxoethoxy)phenyl)-3-(3,4-dimethoxyphenyl)propyl (S)-1-(4-(acryloyloxy)-3,3-dimethyl-2-oxobutanoyl)piperazine-2-carboxylate (2). To the solution of 1(1.0 g, 1.09 mmol) in DMF (5 mL) was added TBAF (2.5 ml, 1.0 M, 2.55 mmol) at 0° C. The resulting solution was warmed to room temperature for 5 h. After this time the reaction mixture was diluted with DCM and washed with sat. NaHCO$_3$ aqueous solution and brine. The organic layer was concentrated in vacuo, the residue was purified by silica-gel flash column chromatography (DCM/MeOH 50:1) to give compound 2 as a colorless oil (670 mg, 80%). [M+H]$^+$=696.9

(R)-1-(3-(2-(tert-butoxy)-2-oxoethoxy)phenyl)-3-(3,4-dimethoxyphenyl)propyl (S)-1-(4-(acryloyloxy)-3,3-dimethyl-2-oxobutanoyl)-4-methylpiperazine-2-carboxylate (3). A solution of 2 (670 mg, 0.96 mmol) in CHOOH (1.5 mL) was treated with an aqueous solution of formaldehyde (37% in water, 0.77 ml, 1.15 mmol) and allowed to stir at 50° C. for 1 h. After this time the reaction mixture was purified with DCM/MeOH/AcOH=100/1/0.5% to give 3 (500 mg, 73%) as a colorless oil. [M+H]$^+$=710.9

2-(3-((R)-1-(((S)-1-(4-(acryloyloxy)-3,3-dimethyl-2-oxobutanoyl)-4-methylpiperazine-2-carbonyl)oxy)-3-(3,4-dimethoxyphenyl)propyl)phenoxy)acetic acid (Rae17). A solution of 9 (0.5 g, 0.7 mmol) in HCOOH (40 mL) was heated to 40° C. for 2 h. The reaction mixture was charged to silica-gel flash column directly (AcOEt/PE/AcOH 1:2: 0.5%) to afford Rae17 (368.7 mg, 80%) as a white solid.

FKBD Example 32
2-(3-((R)-1-(((S)-1-(4-(acryloyloxy)-3,3-dimethyl-2-oxobutanoyl)piperidine-2-carbonyl)oxy)-3-(3,4-dimethoxyphenyl)propyl)-4-fluorophenoxy)acetic acid (Rae18)
Scheme 35. Synthesis of Rae18 FKBD moiety.
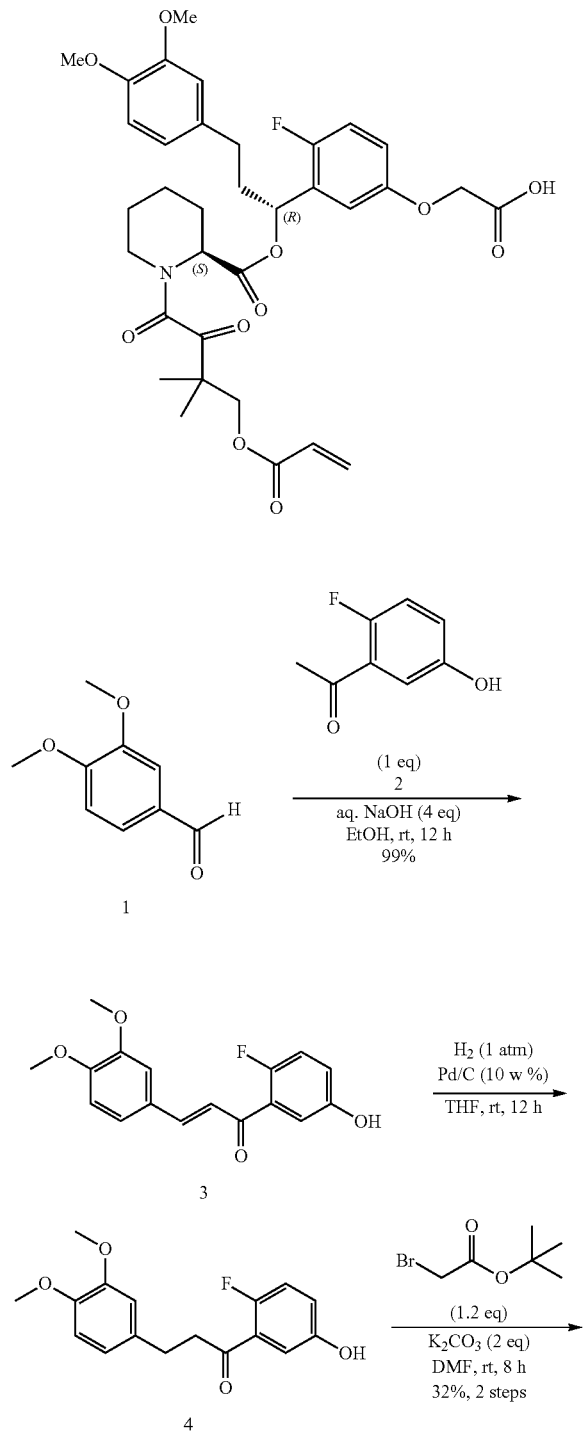
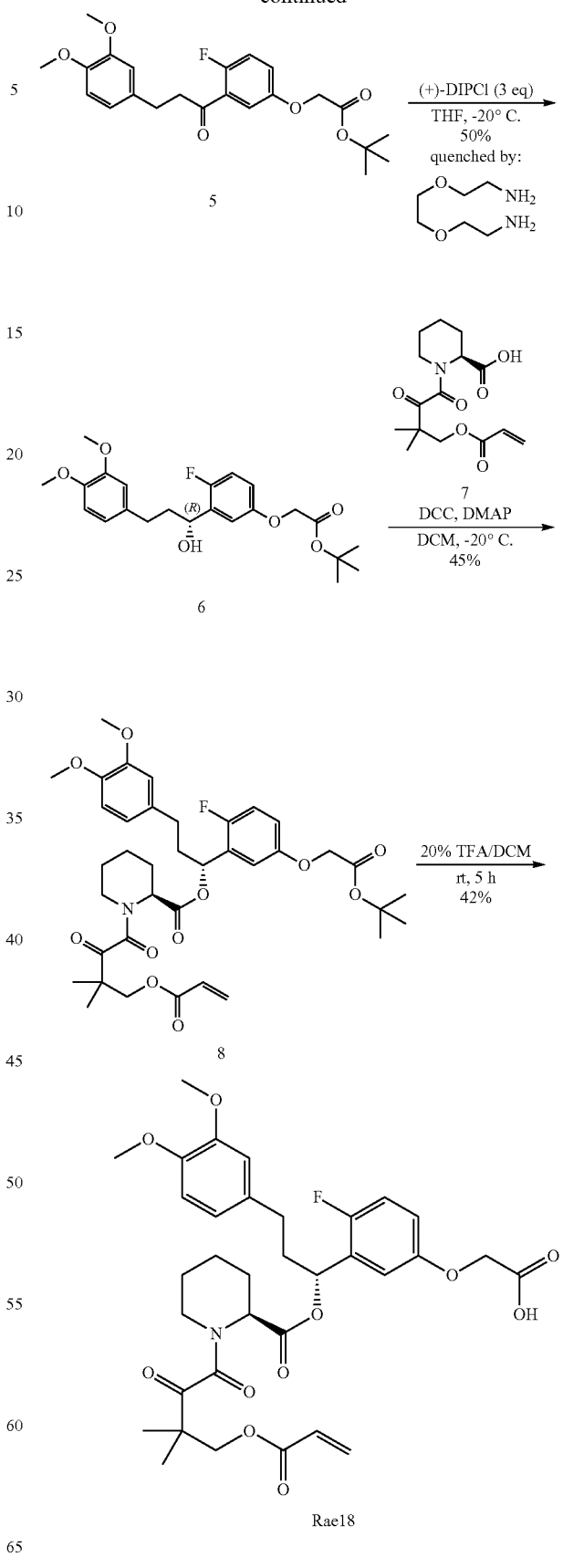

(E)-3-(3,4-dimethoxyphenyl)-1-(2-fluoro-5-hydroxyphenyl)prop-2-en-1-one (3). To the solution of 3,4-dimethoxybenzaldehyde 1 (5 g, 30.1 mmol) and 1-(2-fluoro-5-hydroxyphenyl)ethan-1-one 2 (4.6 g, 30.1 mmol) in EtOH (60 mL) was added a solution of 10% aqueous NaOH (50 mL, 120.4 mmol) at 0° C. The resulting solution was stirred at room temperature for 12 h. The solution was adjusted to pH 4 by added 4M aqueous HCl dropwise at 0° C., generated a large of yellow solid. Then the mixture was filtered and the solid was washed with water (50 mL) to afford 3 (9 g, 99%) as a yellow solid. [M+H]$^+$=303.2

3-(3,4-dimethoxyphenyl)-1-(2-fluoro-5-hydroxyphenyl)propan-1-one (4). A solution of 3 (9 g, 29.8 mmol) and 10% Pd/C (2 g) in THF (200 mL) was hydrogenated with H$_2$ for 12 h at room temperature. The reaction mixture was then filtered and concentrated. The crude product was used to the next step without any further purification. [M+H]$^+$=304.8 tert-butyl 2-(3-(3-(3,4-dimethoxyphenyl)propanoyl)-4-fluorophenoxy)acetate (5). A solution of 4 (10 g, 32.8 mmol) and K$_2$CO$_3$ (9 g, 65.6 mmol) in DMF (200 mL) was treated with tert-butyl bromoacetate (7.7 g, 39.3 mmol) and allowed to stir at room temperature for 8 h. After this time the reaction mixture was poured into ice, yellow solid was precipitated. The mixture was filtered and the solid was washed with water (300 mL). The crude product was purified by column chromatography on silica gel (AcOEt/PE 1:6) to give 5 (4 g, 32%, 2 steps) as a yellow oil. [M+Na]$^+$=441.0 tert-butyl (R)-2-(3-(3-(3,4-dimethoxyphenyl)-1-hydroxypropyl)-4-fluorophenoxy)acetate (6). A solution of ketone 5 (4 g, 9.56 mmol) in dry THF (30 mL) at −20° C. was treated with a solution of (+)-DIPChloride (28.68 mmol) in heptane (1.7 M, 16.8 mL) at −20° C. The resulting mixture was reacted at −20° C. until complete conversion of 6, then quenched with 2,2'-(ethylenedioxy)diethylamine (4.2 g) by forming an insoluble complex. After stirring at room temperature for another 30 min, the suspension was filtered through a pad of celite and concentrated. The crude compound was purified by silica-gel flash column chromatography (AcOEt/PE 1:3) to give compound 6 (2 g, 50%, ee 93%) as a light yellow oil. [M+Na]$^+$=442.7

(R)-1-(5-(2-(tert-butoxy)-2-oxoethoxy)-2-fluorophenyl)-3-(3,4-dimethoxyphenyl)propyl (S)-1-(4-(acryloyloxy)-3,3-dimethyl-2-oxobutanoyl)piperidine-2-carboxylate (8). A solution of 6 (2 g, 4.76 mmol) and 7 (2.22 g, 7.14 mmol) in CH$_2$Cl$_2$ (20 mL) was cooled to −20° C. before a solution of DCC (1.47 g, 7.14 mmol) in CH$_2$Cl$_2$ (10 mL) was added, followed by the addition of a solution of 4-(dimethylamino)pyridine (60 mg, 0.47 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:2) to give compound 8 (1.8 g, 45%) as a light yellow oil. [M+Na]$^+$=736.3

2-(3-((R)-1-(((S)-1-(4-(acryloyloxy)-3,3-dimethyl-2-oxobutanoyl)piperidine-2-carbonyl)oxy)-3-(3,4-dimethoxyphenyl)propyl)-4-fluorophenoxy)acetic acid (Rae18). A solution of 8 (1.7 g, 2.52 mmol) in CH$_2$Cl$_2$ (10 mL) was treated with a solution of 40% TFA in CH$_2$Cl$_2$ (10 mL) at 0° C. The mixture was allowed to react at room temperature until complete conversion. The reaction mixture was charged to silica-gel flash column directly (AcOEt/PE/AcOH 1:3:0.5%) to afford Rae18 (705 mg, 42%) as a white solid.

FKBD Example 33

2-(3-((R)-1-(((S)-1-(4-(acryloyloxy)-3,3-dimethyl-2-oxobutanoyl)piperidine-2-carbonyl)oxy)-3-(3,4-dimethoxyphenyl)propyl)-5-fluorophenoxy)acetic acid (Rae-19)

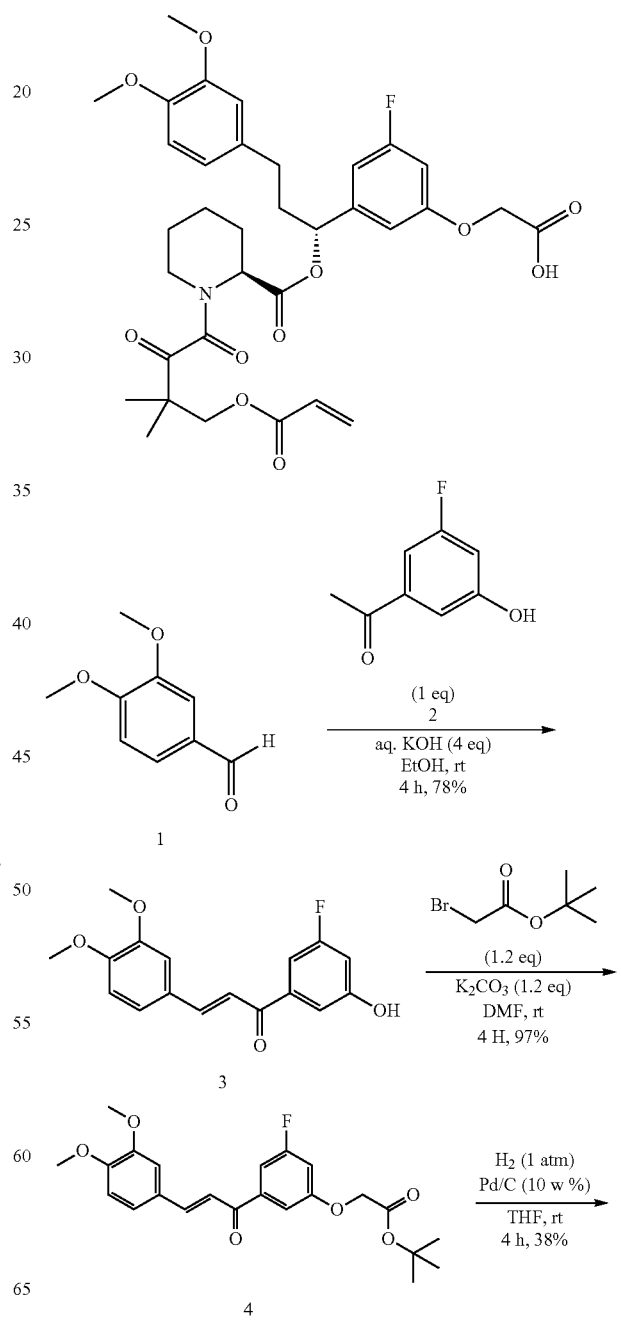

Scheme 36. Synthesis of Rae19 FKBD moiety.

-continued

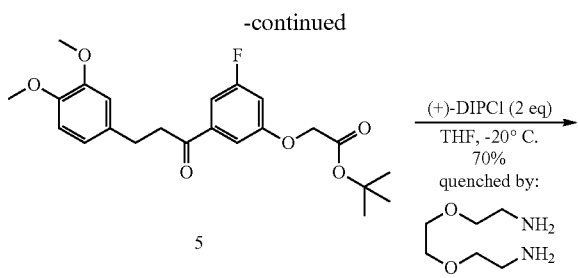

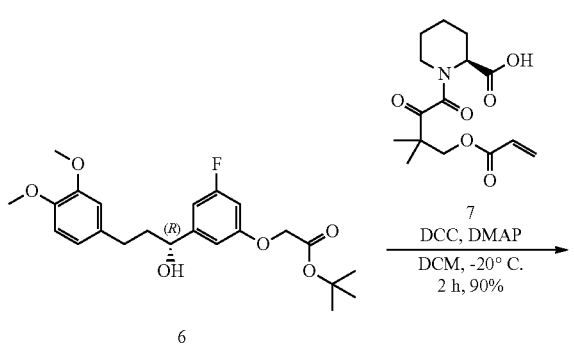

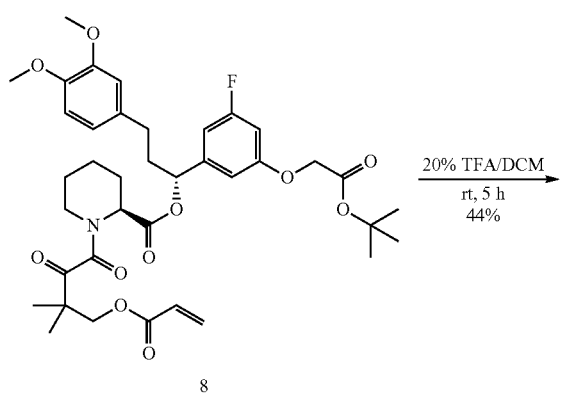

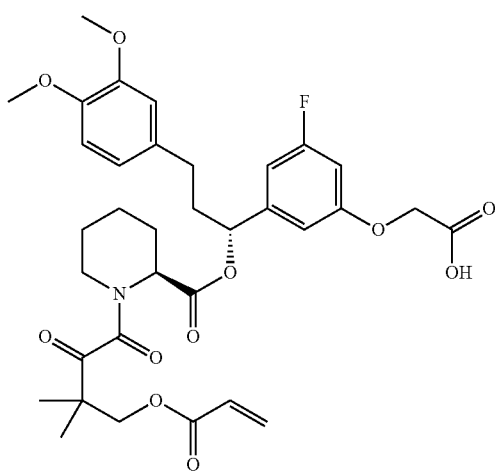

(E)-3-(3,4-dimethoxyphenyl)-1-(3-fluoro-5-hydroxyphenyl)prop-2-en-1-one (3). To the solution of 3,4-dimethoxybenzaldehyde 1 (6.391 g, 38.5 mmol) and 1-(3-fluoro-5-hydroxyphenyl)ethan-1-one 2 (5.39 g, 35 mmol) in EtOH (70 mL) was added a solution of 40% aqueous KOH (19.6 g, 140 mmol) at 0° C. The resulting solution was reacted at room temperature for 4 h. The yellow solid was filtrated to give compound 3 (8.3 g, 78%). [M+H]$^+$=303.0 tert-butyl (E)-2-(3-(3-(3,4-dimethoxyphenyl)acryloyl)-5-fluorophenoxy)acetate (4). A solution of 3 (8.3 g, 27.5 mmol) and K$_2$CO$_3$ (4.55 g, 32.9 mmol) in DMF (80 mL) was treated with tert-butyl bromoacetate (6.4 g, 32.9 mmol) and allowed to stir at room temperature for 4 h. After this time the reaction mixture was quenched by H$_2$O and extracted with EtOAc twice. The combined organic layers were concentrated in vacuo, which was used for the next step without purification (11.11 g, 97%). [M+Na]$^+$=439.2 tert-butyl 2-(3-(3-(3,4-dimethoxyphenyl)propanoyl)-5-fluorophenoxy)acetate (5). A solution of 4 (11.11 g, 26.7 mmol) and 10% Pd/C (1.11 g) in THF (200 mL) was hydrogenated with H$_2$ for 4 h at room temperature. The reaction mixture was then filtered and concentrated. The residue was purified by silica-gel flash column chromatography (AcOEt/PE 1:1) to give compound 5 as a colorless oil (4.2 g, 38%). [M+Na]$^+$=440.7 tert-butyl (R)-2-(3-(3-(3,4-dimethoxyphenyl)-1-hydroxypropyl)-5-fluorophenoxy)acetate (6). A solution of ketone 5 (4.2 g, 10 mmol) in dry THF (40 mL) at −20° C. was treated with a solution of (+)-DIPChloride (20 mmol) in heptane (1.7 M, 11.8 mL) at −20° C. The resulting mixture was reacted at −20° C. until complete conversion of 5, then quenched with 2,2'-(ethylenedioxy)diethylamine (2.9 mL) by forming an insoluble complex. After stirring at RT for another 30 min, the suspension was filtered through a pad of celite and concentrated. The crude compound was purified by silica-gel flash column chromatography (AcOEt/PE 1:5) to give compound 6 as a light yellow oil (2.94 g, 70%, ee 98% vs racemate). [M+Na]$^+$=443.0

(R)-1-(3-(2-(tert-butoxy)-2-oxoethoxy)-5-fluorophenyl)-3-(3,4-dimethoxyphenyl)propyl (S)-1-(4-(acryloyloxy)-3,3-dimethyl-2-oxobutanoyl)piperidine-2-carboxylate (8). A solution of 6 (1.8 g, 4.28 mmol) and 7 (2 g, 6.42 mmol) in CH$_2$Cl$_2$ (18 mL) was cooled to −20° C. before a solution of DCC (1.33 g, 6.42 mmol) in CH$_2$Cl$_2$ (5 mL) was added, followed by the addition of a solution of 4-(dimethylamino)pyridine (DMAP, 52 mg, 0.43 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:1) to give compound 8 as a light yellow oil (2.7 g, 90%). [M+Na]$^+$=735.9

2-(3-((R)-1-(((S)-1-(4-(acryloyloxy)-3,3-dimethyl-2-oxobutanoyl)piperidine-2-carbonyl)oxy)-3-(3,4-dimethoxyphenyl)propyl)-5-fluorophenoxy)acetic acid (Rae19). A solution of 8 (2.7 g, 4.11 mmol) in CH$_2$Cl$_2$ (12 mL) was treated with a solution of 40% TFA in CH$_2$Cl$_2$ (12 mL) at 0° C. The mixture was allowed to react at room temperature until complete conversion. The reaction mixture was charged to silica-gel flash column directly (AcOEt/PE/AcOH 1:2:0.5%) to afford Rae19 (1.094 g, 44%) as a pale yellow solid.

FKBD Example 34
2-(5-((R)-1-(((S)-1-(4-(acryloyloxy)-3,3-dimethyl-2-oxobutanoyl)piperidine-2-carbonyl)oxy)-3-(3,4-dimethoxyphenyl)propyl)-2-fluorophenoxy)acetic acid (Rae20)
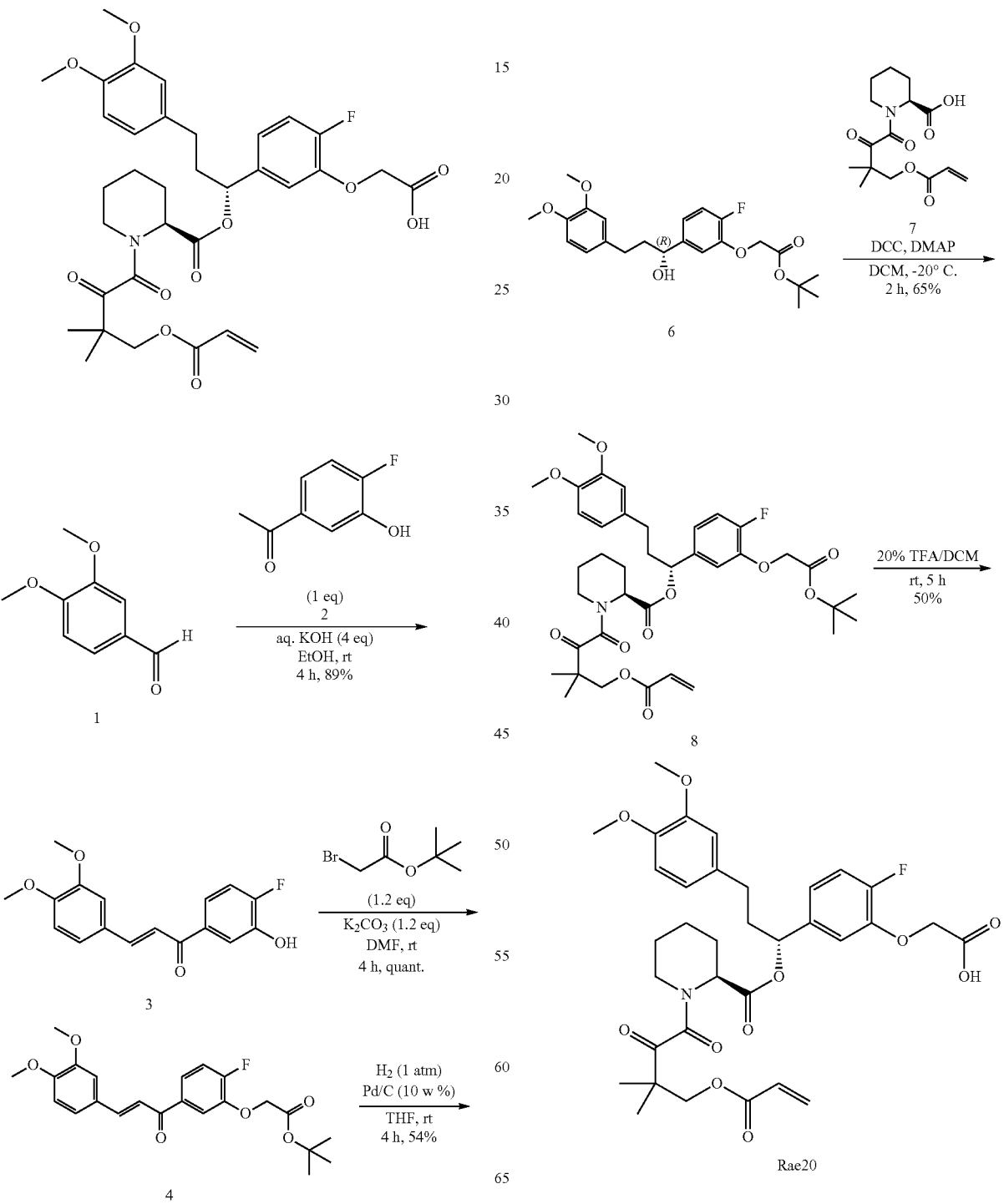

(E)-3-(3,4-dimethoxyphenyl)-1-(4-fluoro-3-hydroxyphenyl)prop-2-en-1-one (3). To the solution of 3,4-dimethoxybenzaldehyde 1 (6.391 g, 38.5 mmol) and 1-(4-fluoro-5-hydroxyphenyl)ethan-1-one 2 (5.39 g, 35 mmol) in EtOH (70 mL) was added a solution of 40% aqueous KOH (19.6 g, 140 mmol) at 0° C. The resulting solution was reacted at room temperature for 4 h. The yellow solid was filtrated to give compound 3 (9.368 g, 89%). [M+H]$^+$=303.2 tert-butyl (E)-2-(5-(3-(3,4-dimethoxyphenyl)acryloyl)-2-fluorophenoxy)acetate (4). A solution of 3 (9.368 g, 31 mmol) and K$_2$CO$_3$ (5.1 g, 37 mmol) in DMF (90 mL) was treated with tert-butyl bromoacetate (7.2 g, 37 mmol) and allowed to stir at room temperature for 4 h. After this time the reaction mixture was quenched by H$_2$O and extracted with EtOAc twice. The combined organic layers were concentrated in vacuo, which was used for the next step without purification (13 g, quant.). [M+Na]$^+$=438.9 tert-butyl 2-(5-(3-(3,4-dimethoxyphenyl)propanoyl)-2-fluorophenoxy)acetate (5). A solution of 4 (13 g, 31.2 mmol) and 10% Pd/C (1.3 g) in THF (200 mL) was hydrogenated with H$_2$ for 4 h at room temperature. The reaction mixture was then filtered and concentrated. The residue was purified by silica-gel flash column chromatography (AcOEt/PE 1:1) to give compound 5 as a colorless oil (7 g, 54%). [M+Na]$^+$=441.2 tert-butyl (R)-2-(5-(3-(3,4-dimethoxyphenyl)-1-hydroxypropyl)-2-fluorophenoxy)acetate (6). A solution of ketone 5 (7 g, 16.7 mmol) in dry THF (40 mL) at –20° C. was treated with a solution of (+)-DIPChloride (33.5 mmol) in heptane (1.7 M, 19.7 mL) at –20° C. The resulting mixture was reacted at –20° C. until complete conversion of 5, then quenched with 2,2'-(ethylenedioxy)diethylamine (4.89 mL) by forming an insoluble complex. After stirring at RT for another 30 min, the suspension was filtered through a pad of celite and concentrated. The crude compound was purified by silica-gel flash column chromatography (AcOEt/PE 1:5) to give compound 6 as a light yellow oil (4.9 g, 71%, ee 96% vs racemate). [M+Na]$^+$=443.3

(R)-1-(3-(2-(tert-butoxy)-2-oxoethoxy)-4-fluorophenyl)-3-(3,4-dimethoxyphenyl)propyl (S)-1-(4-(acryloyloxy)-3,3-dimethyl-2-oxobutanoyl)piperidine-2-carboxylate (8). A solution of 6 (1.8 g, 4.28 mmol) and 7 (2 g, 6.42 mmol) in CH$_2$Cl$_2$ (18 mL) was cooled to –20° C. before a solution of DCC (1.33 g, 6.42 mmol) in CH$_2$Cl$_2$ (5 mL) was added, followed by the addition of a solution of 4-(dimethylamino)pyridine (DMAP, 52 mg, 0.43 mmol) in CH$_2$Cl$_2$ (2 mL) under argon atmosphere. The resulting white suspension was allowed to stir at –20° C. for 2 h. The reaction mixture was then filtered, evaporated, and the crude compound was purified by silica-gel flash column chromatography (AcOEt/PE 1:1) to give compound 8 as a light yellow oil (2 g, 65%). [M+Na]$^+$=736.4

2-(5-((R)-1-(((S)-1-(4-(acryloyloxy)-3,3-dimethyl-2-oxobutanoyl)piperidine-2-carbonyl)oxy)-3-(3,4-dimethoxyphenyl)propyl)-2-fluorophenoxy)acetic acid (Rae20). A solution of 8 (1.8 g, 2.52 mmol) in CH$_2$Cl$_2$ (12 mL) was treated with a solution of 40% TFA in CH$_2$Cl$_2$ (12 mL) at 0° C. The mixture was allowed to react at room temperature until complete conversion. The reaction mixture was charged to silica-gel flash column directly (AcOEt/PE/AcOH 1:2:0.5%) to afford Rae20 (835 g, 50%) as a pale yellow solid.

FKBD Example 35

2-(3-((R)-1-(((S)-1-(4-(acryloyloxy)-3,3-dimethyl-2-oxobutanoyl)piperidine-2-carbonyl)oxy)-3-(3,4-dimethoxyphenyl)propyl)-2-fluorophenoxy)acetic acid (Rae21)

Scheme 38. Synthesis of Rae21 FKBD moiety.

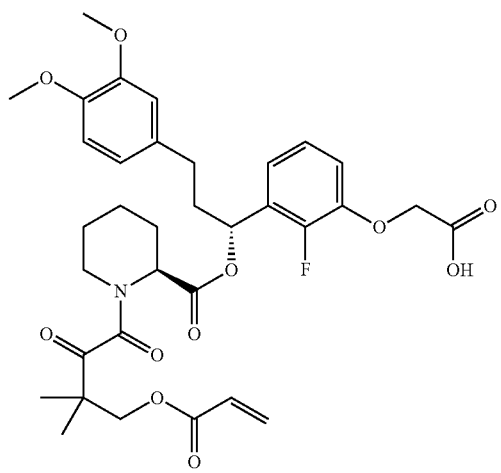

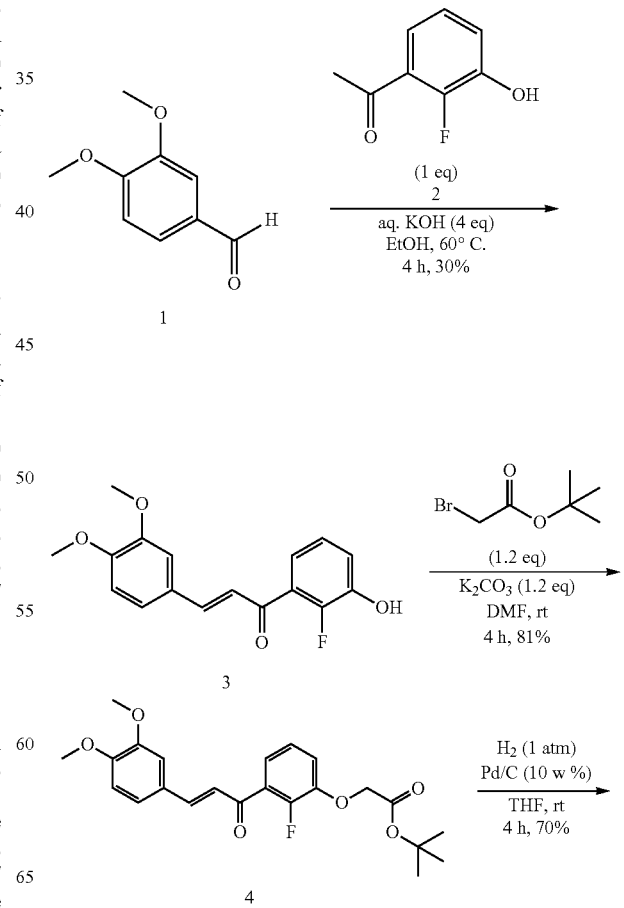

-continued

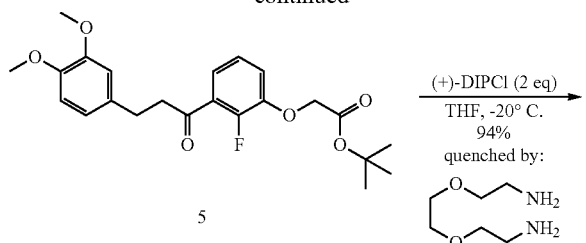

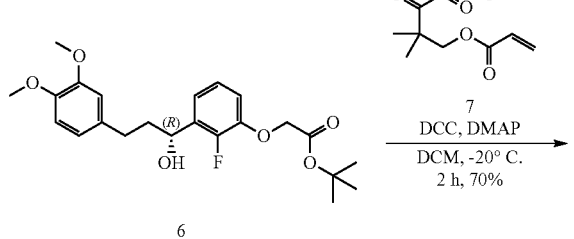

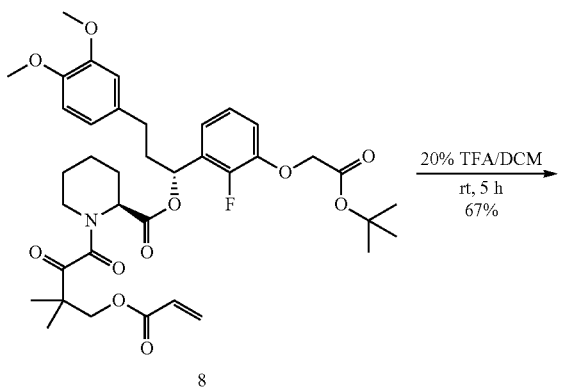

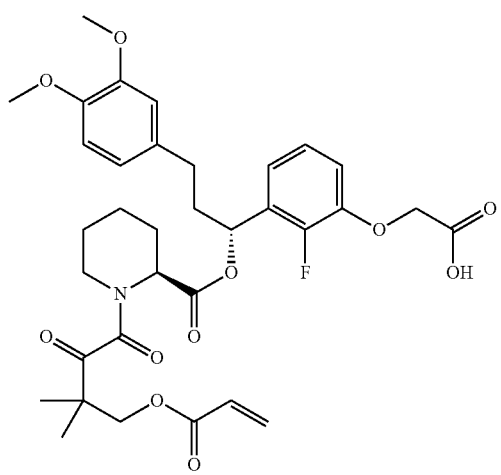

(E)-3-(3,4-dimethoxyphenyl)-1-(2-fluoro-3-hydroxyphenyl)prop-2-en-1-one (3). To the solution of 3,4-dimethoxybenzaldehyde 1 (9.7 g, 58.4 mmol) and 1-(2-fluoro-3-hydroxyphenyl)ethan-1-one 2 (5.39 g, 35 mmol) in EtOH (70 mL) was added a solution of 40% aqueous KOH (19.6 g, 140 mmol) at 0° C. The resulting solution was reacted at room temperature for 4 h. The yellow solid was filtrated to give compound 3 (3.5 g, 30%). $[M+H]^+=303.0$ tert-butyl (E)-2-(3-(3-(3,4-dimethoxyphenyl)acryloyl)-2-fluorophenoxy)acetate (4). A solution of 3 (3.5 g, 11.6 mmol) and $K_2CO_3$ (1.92 g, 13.9 mmol) in DMF (40 mL) was treated with tert-butyl bromoacetate (2.7 g, 13.9 mmol) and allowed to stir at room temperature for 4 h. After this time the reaction mixture was quenched by $H_2O$ and extracted with EtOAc twice. The combined organic layers were concentrated in vacuo, which was used for the next step without purification (3.9 g, 80%). $[M+H]^+=416.9$ tert-butyl 2-(3-(3-(3,4-dimethoxyphenyl)propanoyl)-2-fluorophenoxy)acetate (5). A solution of 4 (3.5 g, 8.4 mmol) and 10% Pd/C (350 mg) in THF (50 mL) was hydrogenated with $H_2$ for 4 h at room temperature. The reaction mixture was then filtered and concentrated. The residue was purified by silica-gel flash column chromatography (AcOEt/PE 1:1) to give compound 5 as a colorless oil (2.45 g, 70%). $[M+Na]^+=441.0$ tert-butyl (R)-2-(3-(3-(3,4-dimethoxyphenyl)-1-hydroxypropyl)-2-fluorophenoxy)acetate (6). A solution of ketone 5 (2.45 g, 5.85 mmol) in dry THF (30 mL) at −20° C. was treated with a solution of (+)-DIPChloride (17.6 mmol) in heptane (1.7 M, 10.3 mL) at −20° C. The resulting mixture was reacted at −20° C. until complete conversion of 5, then quenched with 2,2'-(ethylenedioxy)diethylamine (3 mL) by forming an insoluble complex. After stirring at RT for another 30 min, the suspension was filtered through a pad of celite and concentrated. The crude compound was purified by silica-gel flash column chromatography (AcOEt/PE 1:5) to give compound 6 as a light yellow oil (2.3 g, 94%, ee>99%). $[M+Na]^+=443.0$ (R)-1-(3-(2-(tert-butoxy)-2-oxoethoxy)-2-fluorophenyl)-3-(3,4-dimethoxyphenyl)propyl (S)-1-(4-(acryloyloxy)-3,3-dimethyl-2-oxobutanoyl)piperidine-2-carboxylate (8). A solution of 6 (1.728 g, 4.1 mmol) and 7 (1.919 g, 6.15 mmol) in $CH_2Cl_2$ (18 mL) was cooled to −20° C. before a solution of DCC (1.26 g, 6.15 mmol) in $CH_2Cl_2$ (5 mL) was added, followed by the addition of a solution of 4-(dimethylamino)pyridine (DMAP, 49 mg, 0.4 mmol) in $CH_2Cl_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:5) to give compound 8 as a light yellow oil (2 g, 70%). $[M+Na]^+=735.7$ 2-(3-((R)-1-(((S)-1-(4-(acryloyloxy)-3,3-dimethyl-2-oxobutanoyl)piperidine-2-carbonyl)oxy)-3-(3,4-dimethoxyphenyl)propyl)-2-fluorophenoxy)acetic acid (Rae21). A solution of 8 (2 g, 2.52 mmol) in $CH_2Cl_2$ (12 mL) was treated with a solution of 40% TFA in $CH_2Cl_2$ (12 mL) at 0° C. The mixture was allowed to react at room temperature until complete conversion. The reaction mixture was charged to silica-gel flash column directly (AcOEt/PE/AcOH 1:2:0.5%) to afford Rae21 (1.238 g, 67%) as a white solid.

FKBD Example 36
2-(5-((R)-1-(((S)-1-(4-(acryloyloxy)-3,3-dimethyl-2-oxobutanoyl)piperidine-2-carbonyl)oxy)-3-(3,4-dimethoxyphenyl)propyl)-2-hydroxyphenoxy)acetic acid (Rae24)
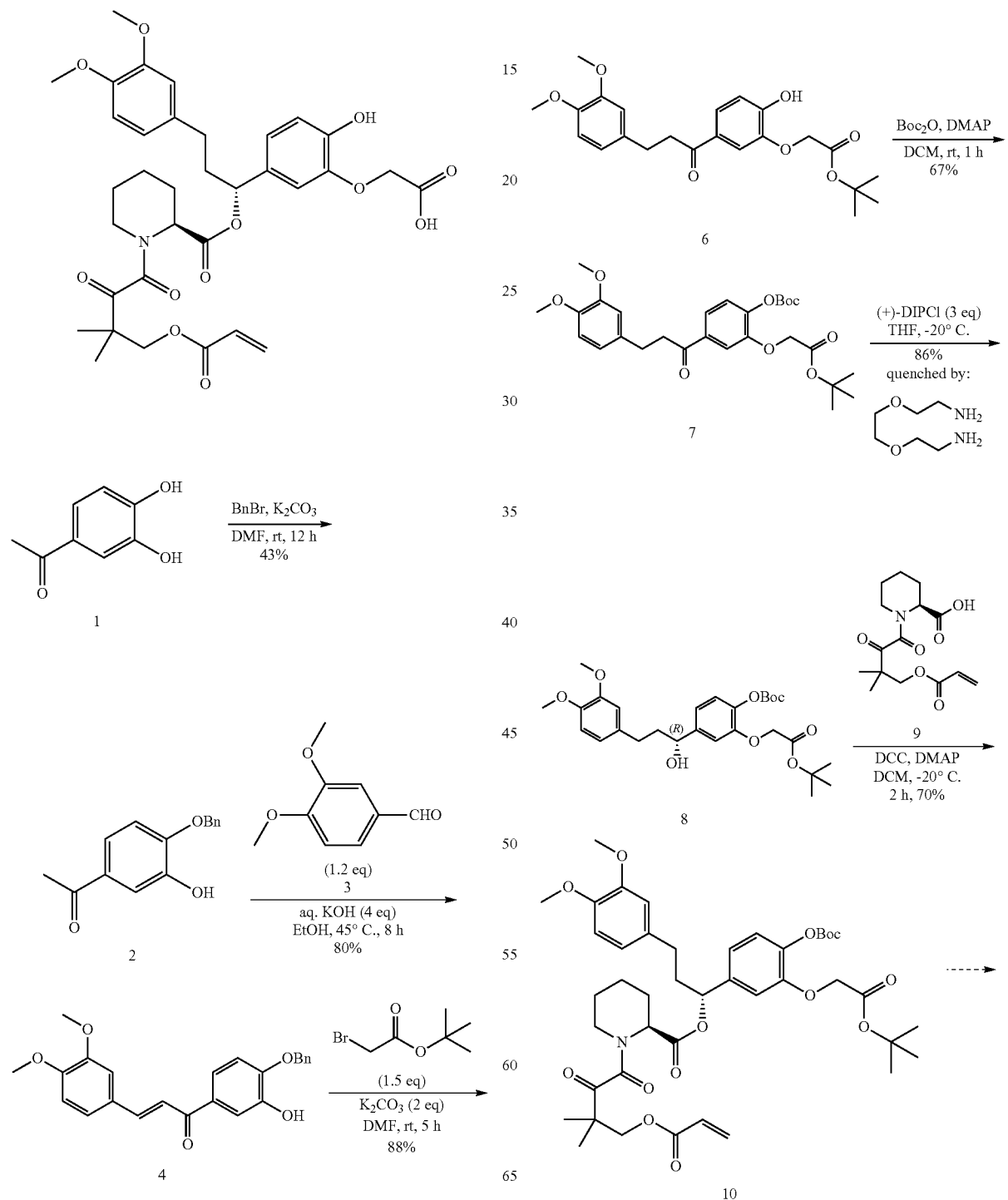

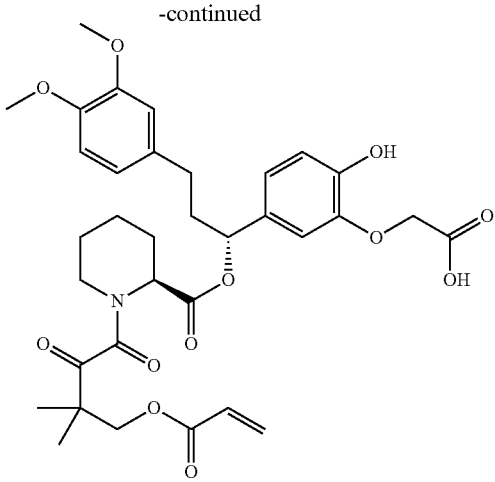

Rae24

1-(4-(benzyloxy)-3-hydroxyphenyl)ethan-1-one (2). A solution of 1(19 g, 125 mmol) and $K_2CO_3$ (17.2 g, 125 mmol) in DMF (250 mL) was treated with benzyl bromide (21.2 g, 125 mmol) and allowed to stir at room temperature for 12 h. After this time the reaction mixture was poured into ice, yellow solid was precipitated. The mixture was filtrated and the solid was washed with water (300 mL) to give 2 (13 g, 43%) as a white solid. $[M+H]^+=243.1$ (E)-1-(4-(benzyloxy)-3-hydroxyphenyl)-3-(3,4-dimethoxyphenyl)prop-2-en-1-one (4). To the solution of 2 (12.7 g, 52.47 mmol) and 3 (10.5 g, 62.97 mmol) in EtOH (60 mL) was added a solution of 40% aqueous KOH (8.4 g, 209.8 mmol) at 25° C. The resulting solution was heated to 45° C. for 8 h. The solution was adjusted to pH 4 by added 4M aqueous HCl dropwise at 0° C., generated a large of yellow solid. Then the mixture was filtered and the filter cake was washed with water (100 mL) to afford 4 (16.5 g, 80%) as a yellow solid. $[M+H]+=391.2$.

tert-butyl (E)-2-(2-(benzyloxy)-5-(3-(3,4-dimethoxyphenyl)acryloyl)phenoxy)acetate (5). A solution of 4 (16.4 g, 42 mmol) and $K_2CO_3$ (11.6 g, 84.1 mmol) in DMF (50 mL) was treated with tert-butyl bromoacetate (12.23 g, 63.07 mmol) and allowed to stir at room temperature for 12 h. After this time the reaction mixture was poured into ice, yellow solid was precipitated. The mixture was filtered and the solid was washed with water (100 mL). The crude product was washed by petroleum ether (100 mL) to give 5 (18.5 g, 88%) as a yellow solid. $[M+H]^+=504.9$.

tert-butyl 2-(5-(3-(3,4-dimethoxyphenyl)propanoyl)-2-hydroxyphenoxy)acetate (6). A solution of 5 (18.0 g, 35.7 mmol) and 10% Pd/C (2 g) in THF (400 mL) was hydrogenated with $H_2$ for 4 h at room temperature. The reaction mixture was then filtered and concentrated. The crude product 6 (16 g, 88%) was used to the next step directly. $[M+Na]^+=439.0$ tert-butyl 2-(2-((tert-butoxycarbonyl)oxy)-5-(3-(3,4-dimethoxyphenyl)propanoyl)phenoxy)acetate (7). A solution of 6 (3 g, 7.2 mmol) and $Boc_2O$ (2.35 g, 10.8 mmol) in dry DCM (60 mL) at 25° C. was treated with DMAP (0.87 g, 7.2 mmol) at 25° C. After stirring at room temperature for 1 h, the solution was concentrated in vacuum. The crude compound was purified by silica-gel flash column chromatography (AcOEt/PE 1:3) to give compound 7 (2.5 g, 67%) as a light yellow oil. $[M+Na]^+=538.9$.

tert-butyl (R)-2-(2-((tert-butoxycarbonyl)oxy)-5-(3-(3,4-dimethoxyphenyl)-1-hydroxypropyl)phenoxy)acetate (8). A solution of 7 (2.3 g, 4.45 mmol) in dry THF (20 mL) at −20° C. was treated with a solution of (+)-DIPChloride (13.3 mmol) in heptane (1.7 M, 8 mL) at −20° C. The resulting mixture was reacted at −20° C. until complete conversion of 7, then quenched with 2,2'-(ethylenedioxy)diethylamine (1.97 g) by forming an insoluble complex. After stirring at room temperature for another 30 min, the suspension was filtered through a pad of celite and concentrated. The crude compound was purified by silica-gel flash column chromatography (AcOEt/PE 1:4) to give compound 8 (2 g, 86%) as a light yellow oil. $[M+Na]^+=540.9$.

(R)-1-(3-(2-(tert-butoxy)-2-oxoethoxy)-4-((tert-butoxycarbonyl)oxy)phenyl)-3-(3,4-dimethoxyphenyl)propyl (S)-1-(4-(acryloyloxy)-3,3-dimethyl-2-oxobutanoyl)piperidine-2-carboxylate (10). A solution of 8 (2 g, 3.86 mmol) and 9 (1.8 g, 5.79 mmol) in $CH_2Cl_2$ (15 mL) was cooled to −20° C. before a solution of DCC (1.19 g, 5.79 mmol) in $CH_2Cl_2$ (5 mL) was added, followed by the addition of a solution of 4-(dimethylamino)pyridine (47 mg, 0.38 mmol) in $CH_2Cl_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:3) to give compound 10 (2.2 g, 70%) as a light yellow oil. $[M+Na]^+=833.8$.

2-(5-((R)-1-(((S)-1-(4-(acryloyloxy)-3,3-dimethyl-2-oxobutanoyl)piperidine-2-carbonyl)oxy)-3-(3,4-dimethoxyphenyl)propyl)-2-hydroxyphenoxy)acetic acid (Rae24). Condition 1: A solution of 10 (50 mg, 0.06 mmol) in $CH_2Cl_2$ (2 mL) was treated with a solution of 20% TFA in $CH_2Cl_2$ (1 mL) at 0° C. The mixture stirred at room temperature for 1 h. LCMS analysis showed no desired product and start material can be detected. Condition 2: A solution of 10 (50 mg, 0.06 mmol) in HCOOH (1 mL) was stirred at room temperature for 1 h. LCMS analysis showed no desired product and start material can be detected.

FKBD Example 37

2-((5-((R)-1-(((S)-1-(4-(acryloyloxy)-3,3-dimethyl-2-oxobutanoyl)piperidine-2-carbonyl)oxy)-3-(3,4-dimethoxyphenyl)propyl)pyridin-3-yl)oxy)acetic acid (Rae26)

Scheme 40. Synthesis of Rae26 FKBD moiety.

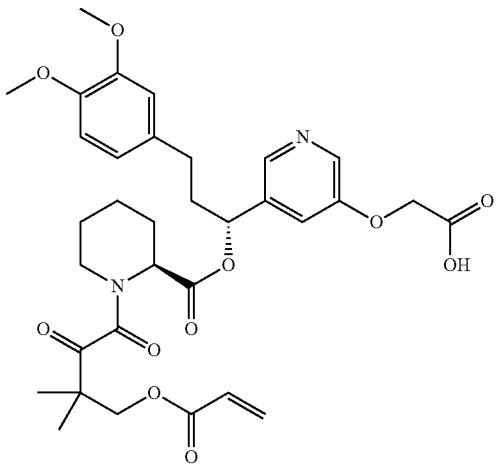

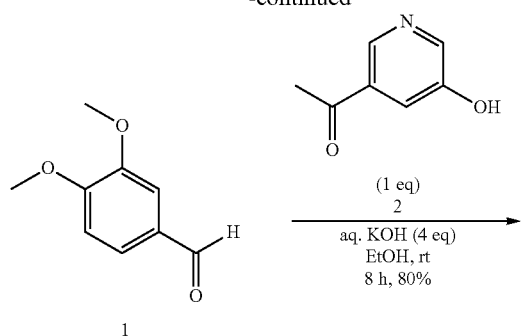

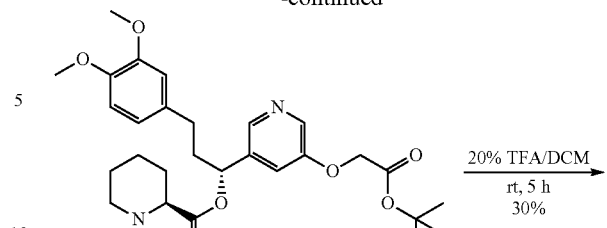

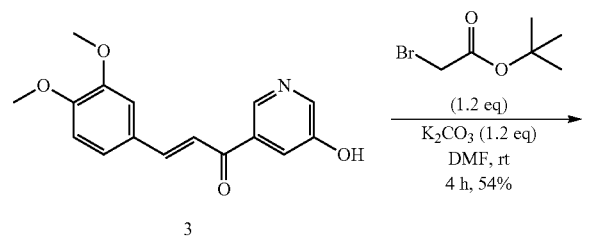

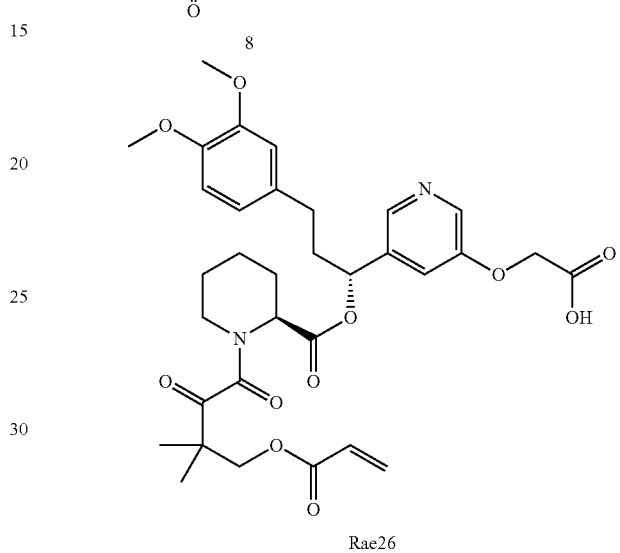

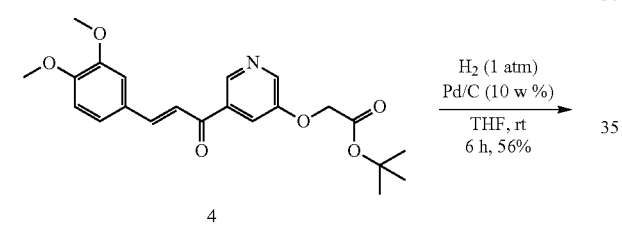

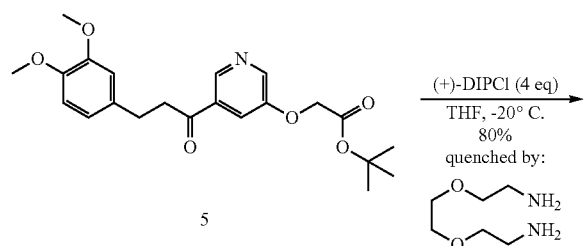

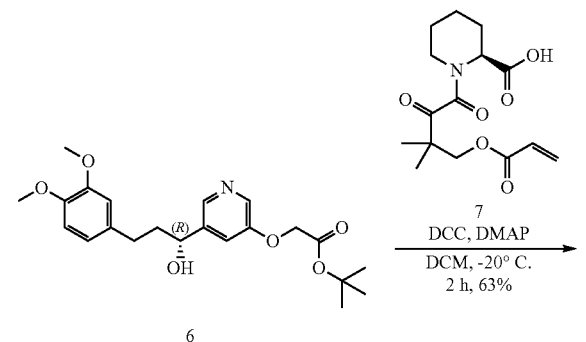

(E)-3-(3,4-dimethoxyphenyl)-1-(5-hydroxypyridin-3-yl)prop-2-en-1-one (3). To the solution of 3,4-dimethoxybenzaldehyde 1 (5.0 g, 30.1 mmol) and 1-(5-hydroxypyridin-3-yl)ethan-1-one 2 (4.95 g, 36.12 mmol) in EtOH (200 mL) was added a solution of 40% aqueous KOH (16.83 g, 120 mmol) at 0° C. The resulting solution was reacted at room temperature for 8 h, followed by dilution with EtOAc. The organic layer was washed by water, brine, dried over $Na_2SO_4$ and concentrated in vacuo. The residue was purified by silica-gel flash column chromatography (AcOEt/PE 1:3) to give compound 3 as a colorless oil (6.8 g, 80%). $[M+H]^+=$ 285.9 tert-butyl (E)-2-((5-(3-(3,4-dimethoxyphenyl)acryloyl)pyridin-3-yl)oxy)acetate (4). A solution of 3 (6 g, 21.03 mmol) and $K_2CO_3$ (3.5 g, 25.24 mmol) in DMF (150 mL) was treated with tert-butyl bromoacetate (4.93 g, 25.24 mmol) and allowed to stir at room temperature for 4 h. After this time the reaction mixture was quenched by $H_2O$ and extracted with EtOAc twice. The organic layers were dried over $Na_2SO_4$ and concentrated in vacuo. The residue was purified by silica-gel flash column chromatography (AcOEt/PE 1:5) to give compound 4 as a yellow oil (4.5 g, 54%). $[M+H]^+=399.9$ tert-butyl 2-((5-(3-(3,4-dimethoxyphenyl)propanoyl)pyridin-3-yl)oxy)acetate (5). A solution of 4 (4.5 g, 11.26 mmol) and 10% Pd/C (400 mg) in THF (100 mL) was hydrogenated with $H_2$ for 6 h at room temperature. The reaction mixture was then filtered and concentrated. The residue was purified by silica-gel flash column chromatography (AcOEt/PE 1:5) to give compound 5 as a yellow oil (2.5 g, 56%) $[M+H]^+=$ 402.2 tert-butyl (R)-2-((5-(3-(3,4-dimethoxyphenyl)-1-hydroxypropyl)pyridin-3-yl)oxy)acetate (6). A solution of ketone 5 (2.5 g, 6.23 mmol) in dry THF (40 mL) at −20° C. was treated with a solution of (+)-DIPChloride (24.9 mmol) in heptane (1.7 M, 14.7 mL) at −20° C. The resulting mixture was reacted at −20° C. until complete conversion of 5, then quenched with 2,2'-(ethylenedioxy)diethylamine (3.7 mL) by forming an insoluble complex. After stirring at RT for another 30 min, the suspension was filtered through a pad of celite and concentrated. The crude compound was purified by silica-gel flash column chromatography (AcOEt/PE 1:5) to give compound 6 as a colorless oil (2 g, 80%, ee>99%). [M+H]$^+$=404.0

(R)-1-(5-(2-(tert-butoxy)-2-oxoethoxy)pyridin-3-yl)-3-(3,4-dimethoxyphenyl)propyl (S)-1-(4-(acryloyloxy)-3,3-dimethyl-2-oxobutanoyl)piperidine-2-carboxylate (8). A solution of 6 (1.898 g, 4.7 mmol) and 7 (2.196 g, 7.1 mmol) in CH$_2$Cl$_2$ (18 mL) was cooled to −20° C. before a solution of DCC (1.46 g, 7.1 mmol) in CH$_2$Cl$_2$ (5 mL) was added, followed by the addition of a solution of 4-(dimethylamino)pyridine (DMAP, 61 mg, 0.5 mmol) in CH$_2$Cl$_2$ (2 mL) under argon atmosphere. The resulting white suspension was allowed to stir at −20° C. for 2 h. The reaction mixture was then filtered, evaporated, and the crude compound was purified by silica-gel flash column chromatography (AcOEt/PE 1:7) to give compound 8 as a light yellow oil (2.05 g, 63%). [M+H]$^+$=696.8

2-((5-((R)-1-(((S)-1-(4-(acryloyloxy)-3,3-dimethyl-2-oxobutanoyl)piperidine-2-carbonyl)oxy)-3-(3,4-dimethoxyphenyl)propyl)pyridin-3-yl)oxy)acetic acid (Rae26). A solution of 8 (2 g, 2.87 mmol) in CH$_2$Cl$_2$ (12 mL) was treated with a solution of 40% TFA in CH$_2$Cl$_2$ (12 mL) at 0° C. The mixture was allowed to react at room temperature until complete conversion. The reaction mixture was charged to silica-gel flash column directly (AcOEt/PE/AcOH 1:2:0.5%) to afford Rae26 (545.8 g, 30%) as a white solid.

Linker Example 1

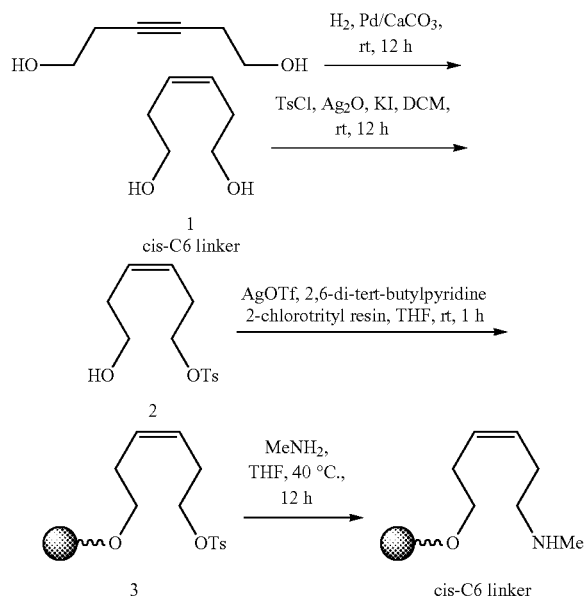

Scheme 41. Synthesis of cis-C6 linker.

(Z)-hex-3-ene-1,6-diol (1). Hex-3-yne-1,6-diol (2.0 g), quinoline (0.12 g) and Lindlar catalyst (0.30 g) were suspended in MeOH (15 mL). Hydrogen was filled in to the flask with a Schlenk line and a positive pressure was maintained with a balloon of hydrogen. The reaction was stirred at RT for 12 h before filtered and concentrated. The crude product (2.1 g) was co-evaporated with toluene (20 mL×2) to remove the residue of MeOH. The product 1 was used without further purification.

(Z)-6-hydroxyhex-3-en-1-yl 4-methylbenzenesulfonate (2). Monotosylation of diol was obtained by a reported Ag$_2$O-assisted method (10). The percentage yield of monotosylation is 90% for cis-C$_6$ linker on 2.0 g scale. $^1$H NMR (500 MHz, CDCl$_3$) δ 7.79 (d, J=8.3 Hz, 2H, aromatic), 7.35 (d, J=8.0 Hz, 2H, aromatic), 5.63-5.48 (m, 1H, =CH), 5.48-5.33 (m, 1H, =CH), 4.04 (t, J=6.7 Hz, 2H, OCH2), 3.64 (dd, J=12.3, 6.2 Hz, 2H, OCH2), 2.45 (s, 3H, CH3), 2.44 (q, J=6.5 Hz, 2H), 2.28 (q, J=6.5 Hz, 2H). $^{13}$C NMR (126 MHz, CDCl$_3$) δ 129.86 (aromatic), 129.51 (aromatic), 127.93 (=CH), 126.19 (=CH), 69.99 (OCH$_2$), 61.99 (OCH2), 30.89, 27.26, 21.69 (CH$_3$). HRMS for [M+H]$^+$ C13H18O4S, calculated: 271.1004, observed: 271.1004.

(3). To conjugate the Ts-protected alcohol on 2-chlorotrityl chloride solid support, briefly, the resin (9.6 mmol, 1.14 mmol/g), 2,6-di-tert-butylpyridine (10.5 mmol) and alcohol (5.9 mmol) was mixed in 100 mL CH$_2$Cl$_2$. AgOTf (10.0 mmol) was added in two aliquots over 15 min. The red color of the resin persisted and this indicates that the alcohol is depleted in the reaction mixture. MeOH (5 mL) was then added to quench the reaction and the color turned white or pale yellow over 5 min. The suspension was stirred at RT for another 1 h before it was filtered and the solid-support was transferred to a separatory funnel with CCl$_4$. After the mixture standing for 5 min to allow stratification, AgCl precipitation on the bottom was removed by draining the liquid to a level that most floating resin remained. The resin was then collected in a 250 mL solid-support reactor and washed with pyridine (50 mL×4) with extensive shaking.

(cis-C6 linker). The resin was then transferred into a 250 mL RB-flask with 100 mL THF. Methylamine (33% in MeOH) was added and stirred at 40° C. for 12 h. The resin was filtered and washed with THF (50 mL) for twice and CH$_2$Cl$_2$ (50 mL) for twice. For long time storage at −20° C., the resin was further washed with MeOH and air-dried for 20 min. The molarity of the NH group was determined by UV of the cleaved first coupled Fmoc group (0.40-0.45 mmol/g).

RAPAFUCIN EXAMPLES

General Automated Synthesis. Solid-phase peptide synthesis (SPPS) were applied with a split-pool strategy to assemble the tetrapeptide effector domains. The pre-assembled FKBD capped with a carboxylic acid at one end and an olefin at the other was subsequently coupled to the tetrapeptide that remained tethered on beads. To facilitate purification of the newly formed macrocycles, we adopted a coupled macrocyclization and cyclative release strategy whereby the macrocyclization is accompanied by the concurrent release of the macrocyclic products from the solid beads. After exploring different macrocyclization methods, ring-closing metathesis/cyclative release (RCM) can be used for efficient parallel synthesis of different Rapafucins. Both aFKBD and eFKBD possess high affinity for FKBP12, with $K_d$ values of 4 and 11 nM, respectively. Importantly, this enhanced affinity was largely retained on incorporation into macrocycles, with average $K_d$ values of 25 and 37 nM, respectively. Moreover, there was relatively low variation in binding affinity for FKBP12 among different macrocycles bearing aFKBD or eFKBD. These results suggested that both aFKBD and eFKBD are tolerant to different effector domain sequences, thus rendering them suitable FKBD building blocks for Rapafucin libraries.

Charged resin (4.800 g) was dissolved in DMF/DCM (1/4, v/v) and dispersed to each well of an Aapptec Vantage automated synthesizer (96 wells). Wells were drained and swelled with DMF for 20 mins before the solvent was drained and washed with 1× DMF. Fmoc-protected amino acid building blocks (3.0 eq., —0.3M in DMF), HATU (3.0 eq., ~0.1M in DMF), and DIEA (6 eq., ~0.3M in DMF) were added in order to each of the 96 wells. The resin and reagent mixture were mixed on the automated synthesizer for 2-3 hrs, then washed with DMF (5×) for 5 times. If coupling was difficult, the coupling reaction would be repeated. Resins were washed thoroughly with DMF (3×) for 3 times. Deprotection of the Fmoc group was achieved by shaking resins with 1 mL of piperidine/DMF (1/4, v/v) for 10 min and 1 mL piperidine/DMF (1/4, v/v) for 5 min. Resins were washed thoroughly with DMF 5 times. Coupling reaction was repeated 4 times to achieve the synthesis of tetrapeptide. Coupling reactions were repeated if Fmoc-valine or -isoleucine were to be coupled to N-methyl amino acids on resin or if Fmoc-proline was used. Then the deprotection of Fmoc group is performed. FKBD (3 eq., ~0.2 M in DMF), HATU (3 eq., ~0.1M in DMF), and DIEA (6 eq., ~0.3M in DMF) were added in order into the vessel of the prepared resin. The resin and reagent mixture were mixed on the automated synthesizer for 3 hrs, then washed with DMF (2×) for 2 times and DCM (2×) for 2 times. 1.25 mL of Ethyl Acetate and 0.25 mL of Hoveyda-Grubbs II (30 mol %) were added to each well. The reaction block was 80° C. for 5 hrs. Upon reaction completion, the resulting brown suspension was purified on 1 g solid phase extraction columns packed with 1 g silica gel. The columns were washed using dichloromethane and eluted with 10% methanol in dichloromethane. The eluate was concentrated under vacuum and weighted. The compounds were characterized using LC/MS analysis.

TABLE 9

Synthesis and characterization of compounds 1066, 1081, 1082, 1087, 1088, and 1522.

| Compound No. | Composition (FKBD/ monomer1/ monomer2/ monomer3/ monomer4) | Molecular weight | Retention time | Uptake, 293T | Molecular Structure |
|---|---|---|---|---|---|
| 1087 | aFKBD ra602 ra140 dp ml | 1289.54 | 3.92 | low | 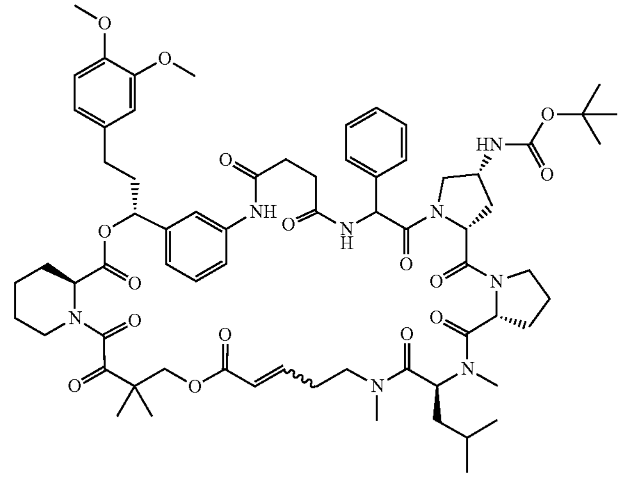 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H]3C[C@@H](NC(=O)OC(C)(C)C)CN3C(=O)C(c3ccccc3)NC(=O)CCC(=O)Nc3cccc2c3)cc1OC] |

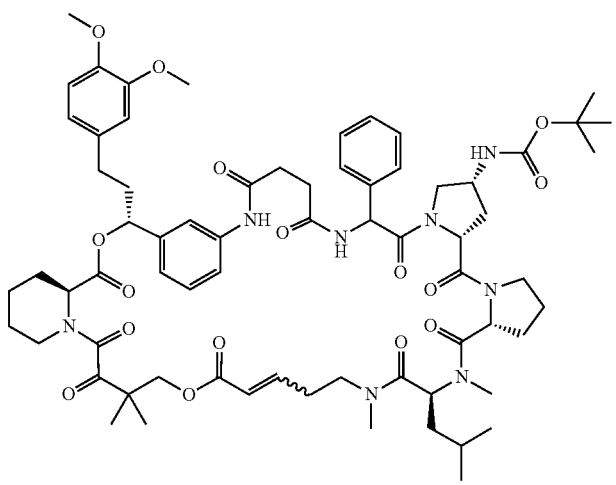

TABLE 9-continued

Synthesis and characterization of compounds 1066, 1081, 1082, 1087, 1088, and 1522.

| Compound No. | Composition (FKBD/ monomer1/ monomer2/ monomer3/ monomer4) | Molecular weight | Retention time | Uptake, 293T | Molecular Structure |
|---|---|---|---|---|---|
| 1088 | aFKBD ra348 mf dp ml | 1276.54 | 4.11 | low | 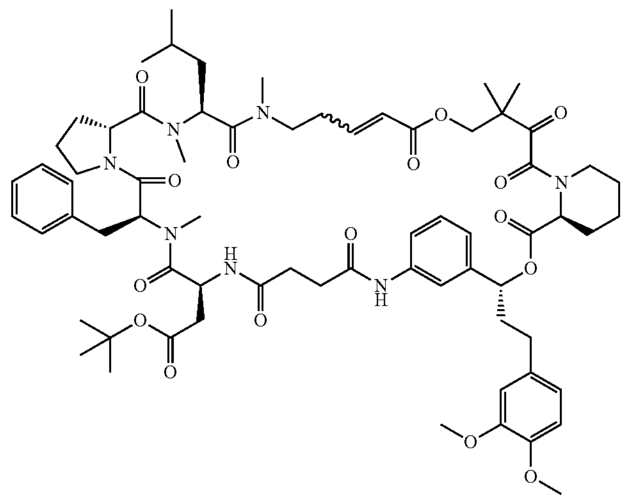 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccccc3)N(C)C(=O)[C@H](CC(=O)OC(C)(C)C)NC(=O)CCC(=O)Nc3cccc2c3)cc1OC] |
| 1081 | aFKBD ra602 ra553 dp ml | 1338.61 | 4.24 | medium | 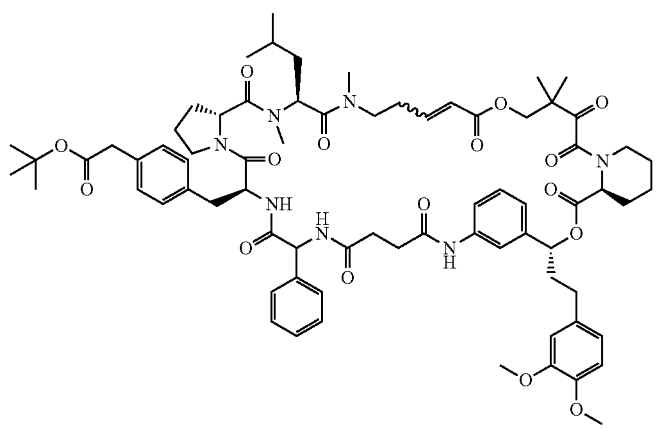 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(CC(=O)OC(C)(C)C)cc3)NC(=O)C(c3ccccc3)NC(=O)CCC(=O)Nc3cccc2c3)cc1OC] |
| 1082 | aFKBD ra602 ra73 dp ml | 1330.59 | 4.22 | low | 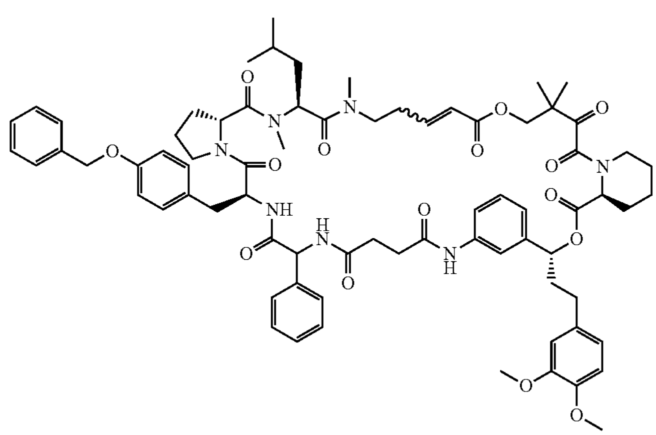 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(OCc4ccccc4)cc3)NC(=O)C(c3ccccc3)NC(=O)CCC(=O)Nc3cccc2c3)cc1OC] |

TABLE 9-continued
Synthesis and characterization of compounds 1066, 1081, 1082, 1087, 1088, and 1522.
| Compound No. | Composition (FKBD/ monomer1/ monomer2/ monomer3/ monomer4) | Molecular weight | Retention time | Uptake, 293T | Molecular Structure |
| --- | --- | --- | --- | --- | --- |
| 1522 | aFKBD ra602 y dp ml | 1240.46 | 3.65 | high | 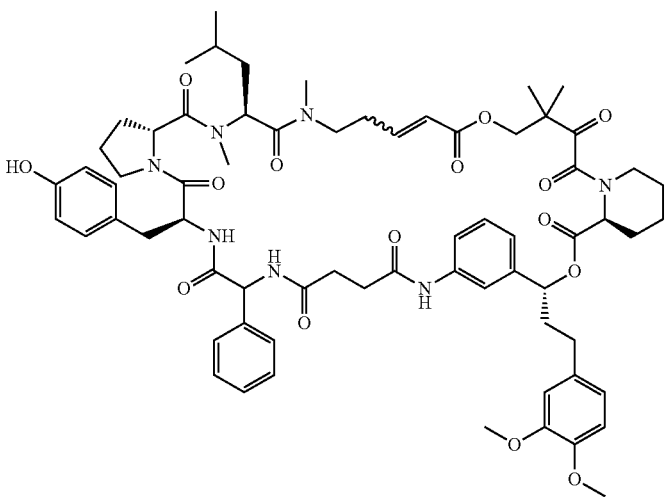 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(O)cc3)NC(=O)C(c3ccccc3)NC(=O)CCC(=O)Nc3cccc2c3)cc1OC] |
| 1066 | aFKBD ra602 ra559 dp ml | 1262.51 | 4.07 | high | 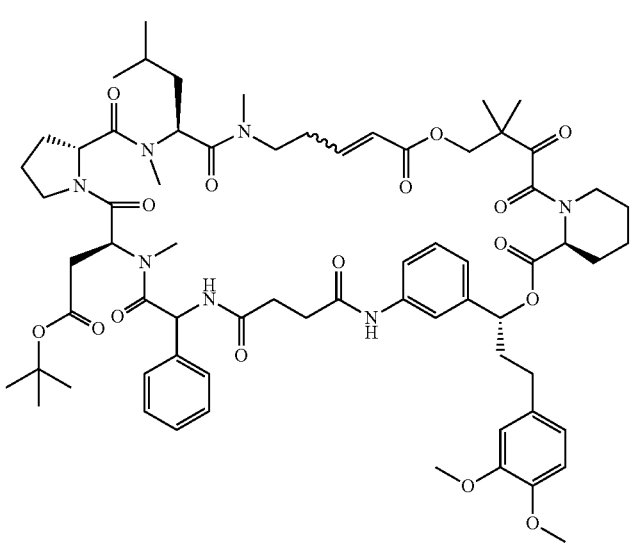 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](CC(=O)OC(C)(C)C)N(C)C(=O)C(c3ccccc3)NC(=O)CCC(=O)Nc3cccc2c3)cc1OC] |

General Manual Synthesis. Synthesized as previously described. (Guo et al. (2018) *Nat. Chem.* 11:254-63).

TABLE 10

Synthesis and characterization of compounds 560-574, 576, and 1563-65.

| Compound No. | Composition (FKBD/ monomer1/ monomer2/ monomer3/ monomer4) | Molecular weight | Retention time | Prolif, A549 | Chemical Structure |
|---|---|---|---|---|---|
| 560 | rae1 ra147 napA ra562 g | 1247.49 | 5.56 | medium | 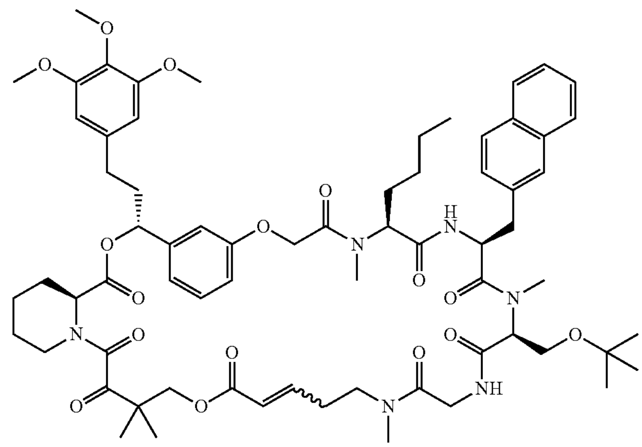 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2cc(OC)c(OC)c(OC)c2)c2cccc(c2)OCC(=O)N1C] |
| 561 | rae2 ra147 napA ra562 g | 1247.49 | 5.63 | medium | 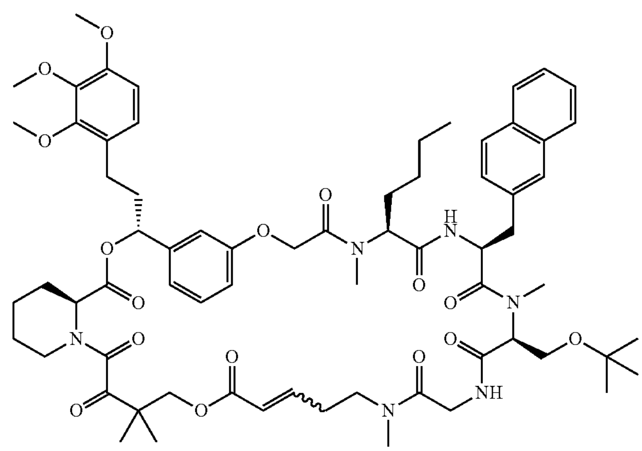 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2ccc(OC)c(OC)c2OC)c2cccc(c2)OCC(=O)N1C] |
| 562 | rae3 ra147 napA ra562 g | 1247.49 | 5.48 | medium | 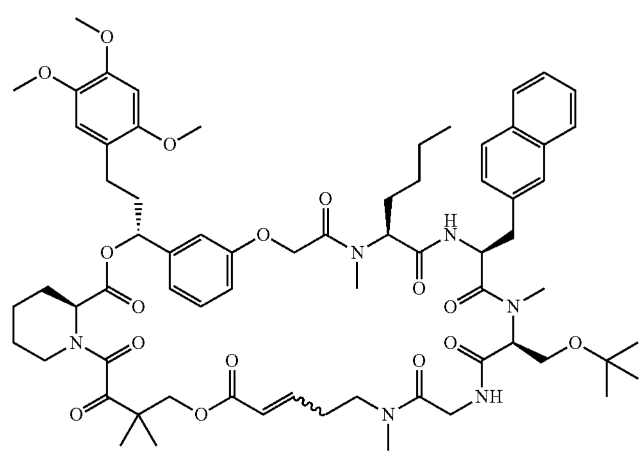 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2cc(OC)c(OC)cc2OC)c2cccc(c2)OCC(=O)N1C] |

TABLE 10-continued

Synthesis and characterization of compounds 560-574, 576, and 1563-65.

| Compound No. | Composition (FKBD/ monomer1/ monomer2/ monomer3/ monomer4) | Molecular weight | Retention time | Prolif, A549 | Chemical Structure |
|---|---|---|---|---|---|
| 563 | rae4 ra147 napA ra562 g | 1247.49 | 5.47 | low | 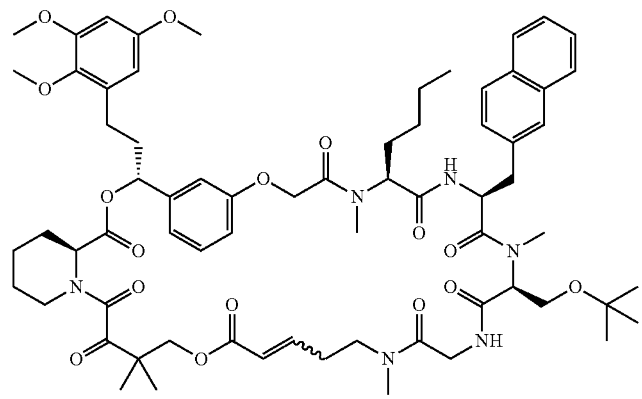 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2cc(OC)cc(OC)c2OC)c2cccc(c2)OCC(=O)N1C] |
| 564 | rae5 ra147 napA ra562 g | 1247.49 | 5.48 | low | 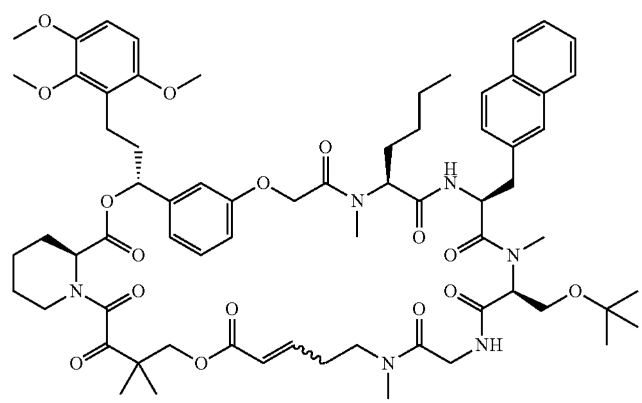 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2c(OC)ccc(OC)c2OC)c2cccc(c2)OCC(=O)N1C] |
| 565 | rae9 ra147 napA ra562 g | 1233.47 | 5.35 | medium | 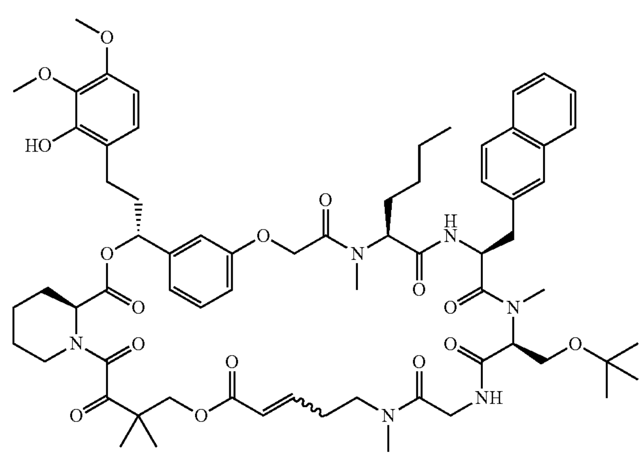 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2ccc(OC)c(OC)c2O)c2cccc(c2)OCC(=O)N1C] |

TABLE 10-continued

Synthesis and characterization of compounds 560-574, 576, and 1563-65.

| Compound No. | Composition (FKBD/ monomer1/ monomer2/ monomer3/ monomer4) | Molecular weight | Retention time | Prolif, A549 | Chemical Structure |
| --- | --- | --- | --- | --- | --- |
| 566 | rae10 ra147 napA ra562 g | 1233.47 | 5.10 | medium | 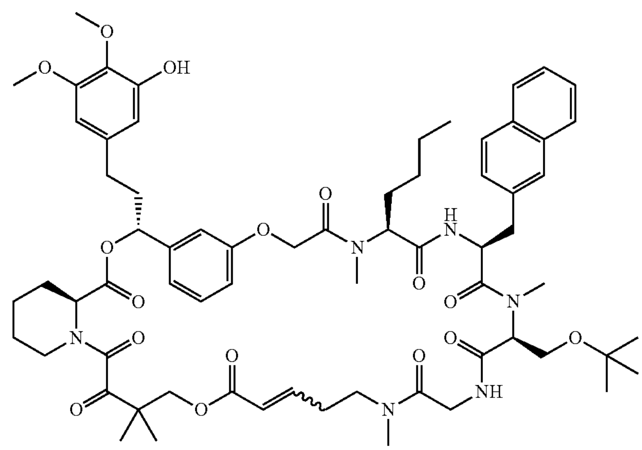 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2cc(O)c(OC)c(OC)c2)c2cccc(c2)OCC(=O)N1C] |
| 567 | rae11 ra147 napA ra562 g | 1233.47 | 5.11 | medium | 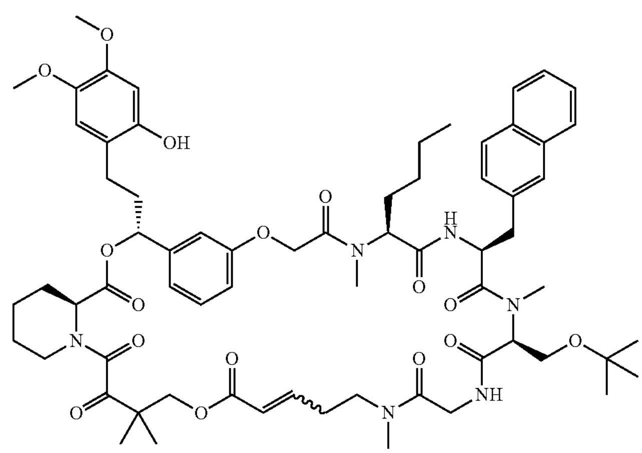 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2cc(OC)c(OC)cc2O)c2cccc(c2)OCC(=O)N1C] |
| 568 | rae12 ra147 napA ra562 g | 1235.46 | 5.74 | medium | 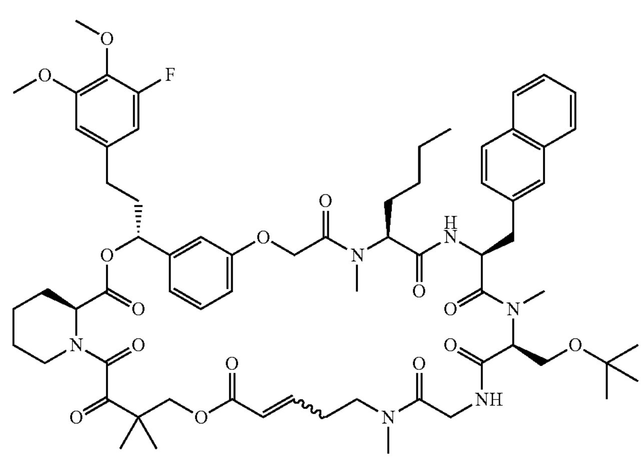 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2cc(F)c(OC)c(OC)c2)c2cccc(c2)OCC(=O)N1C] |

TABLE 10-continued
Synthesis and characterization of compounds 560-574, 576, and 1563-65.
| Compound No. | Composition (FKBD/ monomer1/ monomer2/ monomer3/ monomer4) | Molecular weight | Retention time | Prolif, A549 | Chemical Structure |
|---|---|---|---|---|---|
| 569 | rae13 ra147 napA ra562 g | 1235.46 | 5.27 | medium | 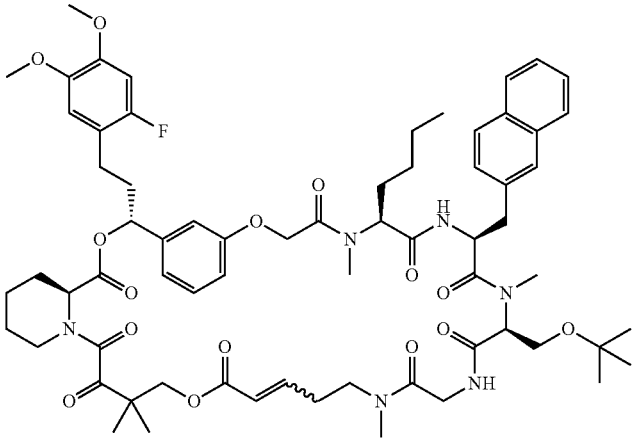 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2cc(OC)c(OC)cc2F)c2cccc(c2)OCC(=O)N1C] |
| 570 | rae14 ra147 napA ra562 g | 1235.46 | 5.72 | medium | 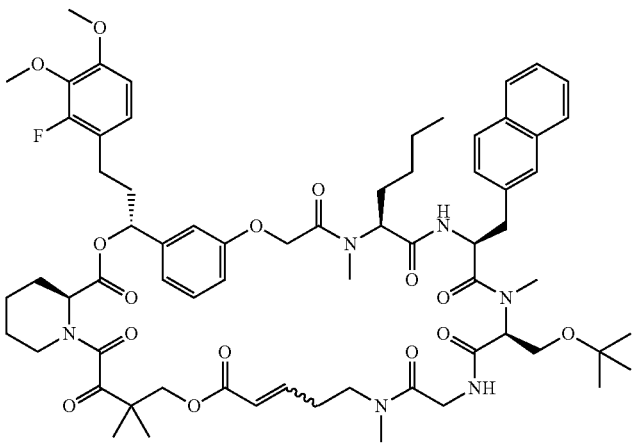 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2ccc(OC)c(OC)c2F)c2cccc(c2)OCC(=O)N1C] |
| 571 | rae16 ra147 napA ra562 g | 1440.70 | 5.93 | low | 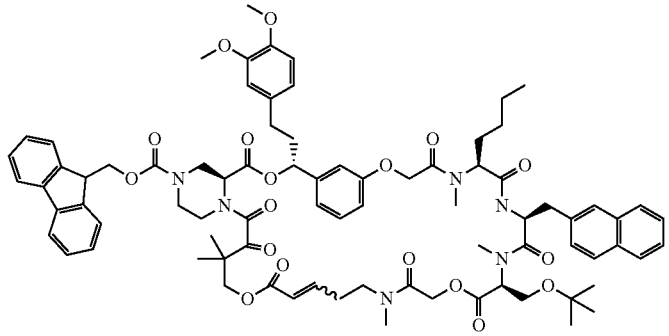 [SMILES: CCCC[C@H]1C(=O)N[C@@H](Cc2ccc3ccccc3c2)C(=O)N(C)[C@@H](COC(C)(C)C)C(=O)OCC(=O)N(C)CCC=CC(=O)OCC(C)(C)C(=O)C(=O)N2CCN(C(=O)OCC3c4ccccc4-c4ccccc43)C[C@H]2C(=O)O[C@H](CCc2ccc(OC)c(OC)c2)c2cccc(c2)OCC(=O)N1C] |

TABLE 10-continued
Synthesis and characterization of compounds 560-574, 576, and 1563-65.
| Compound No. | Composition (FKBD/ monomer1/ monomer2/ monomer3/ monomer4) | Molecular weight | Retention time | Prolif, A549 | Chemical Structure |
|---|---|---|---|---|---|
| 572 | rae17 ra147 napA ra562 g | 1232.48 | 4.41 | medium | 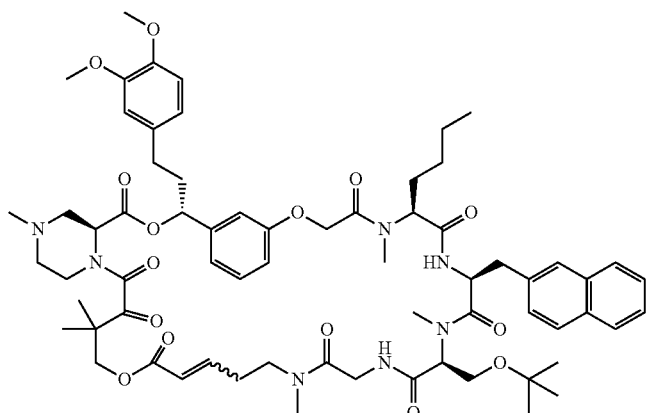 |
| 573 | rae18 ra147 napA ra562 g | 1235.46 | 5.49 | low | 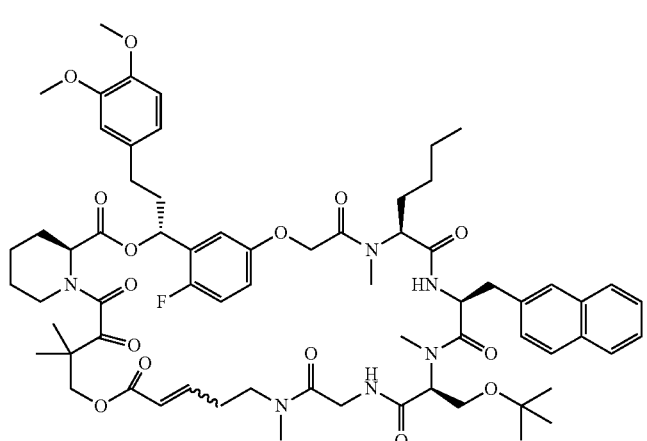 |
| 574 | rae19 ra147 napA ra562 g | 1235.46 | 5.60 | low | 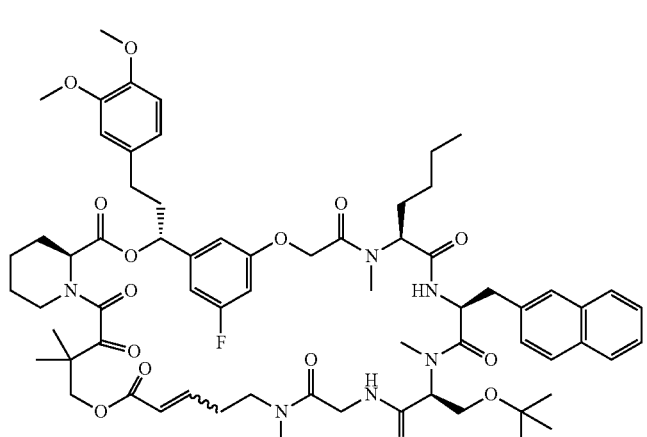 |

TABLE 10-continued
Synthesis and characterization of compounds 560-574, 576, and 1563-65.
| Compound No. | Composition (FKBD/ monomer1/ monomer2/ monomer3/ monomer4) | Molecular weight | Retention time | Prolif, A549 | Chemical Structure |
|---|---|---|---|---|---|
| 576 | rae20 ra147 napA ra562 g | 1235.46 | 5.56 | medium | 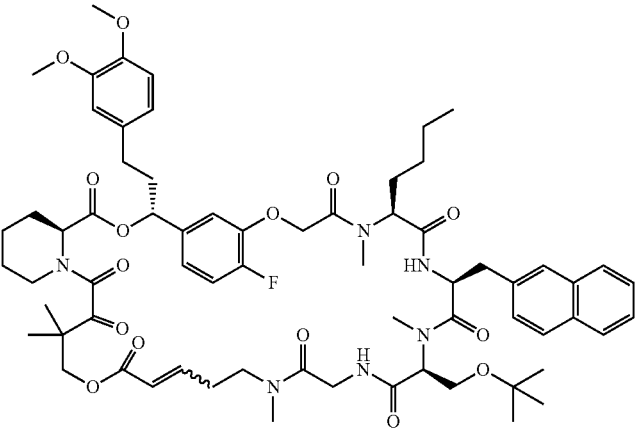 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2ccc(OC)c(OC)c2)c2ccc(F)c(c2)OCC(=O)N1C] |
| 1563 | rae21 ra147 napA ra562 g | 1235.46 | 6.94 | high | 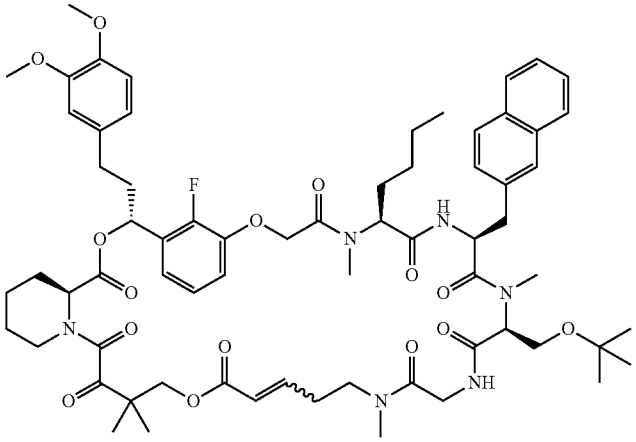 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2ccc(OC)c(OC)c2)c2cccc(c2F)OCC(=O)N1C] |
| 1564 | rae29 ra147 napA ra562 g | 1204.44 | 6.67 | high | 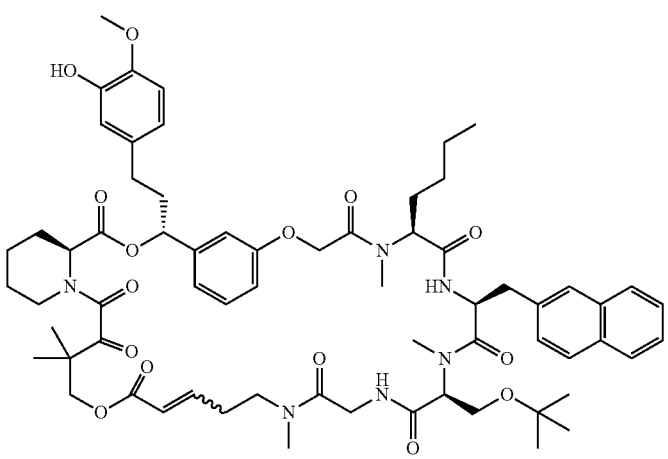 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2ccc(OC)c(O)c2)c2cccc(c2)OCC(=O)N1C] |

TABLE 10-continued

Synthesis and characterization of compounds 560-574, 576, and 1563-65.

| Compound No. | Composition (FKBD/ monomer1/ monomer2/ monomer3/ monomer4) | Molecular weight | Retention time | Prolif, A549 | Chemical Structure |
|---|---|---|---|---|---|
| 1565 | rae26 ra147 napA ra562 g | 1218.46 | | low | 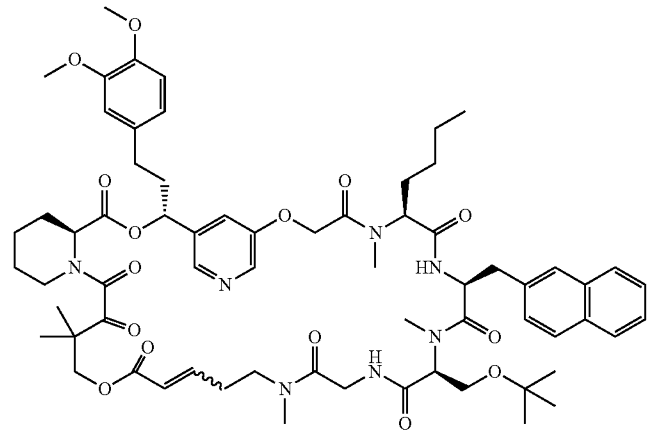 [SMILES: CCCC[C@H]1C(=O)N[C@@H](Cc2ccc3ccccc3c2)C(=O)N(C)[C@@H](COC(C)(C)C)C(=O)NCC(=O)N(C)CCC=CC(=O)OCC(C)(C)C(=O)C(=O)N2CCCC[C@H]2C(=O)O[C@H](CCc2ccc(OC)c(OC)c2)c2cncc(c2)OCC(=O)N1C] |

TABLE 11

Synthesis and characterization of compounds 1566-84.

| Compound No. | Composition (FKBD/ monomer1/ monomer2/ monomer3/ monomer4) | Molecular weight | Prolif, H929 | Chemical Structure |
|---|---|---|---|---|
| 1566 | rae1 my df sar df | 1251.44 | medium | 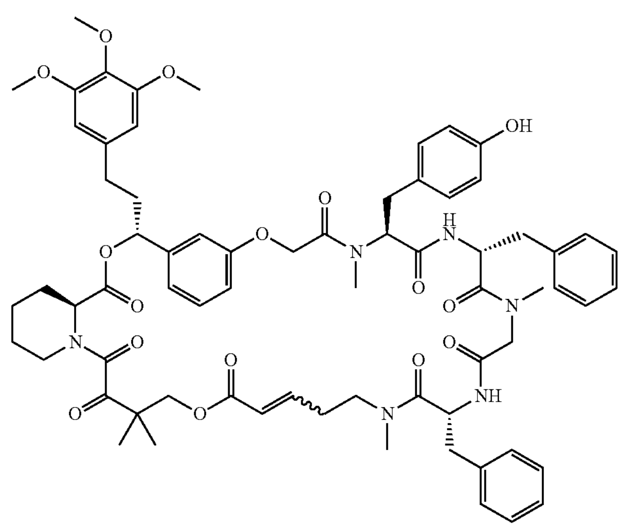 [SMILES: COc1cc(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cccc2c3)cc(OC)c1OC] |

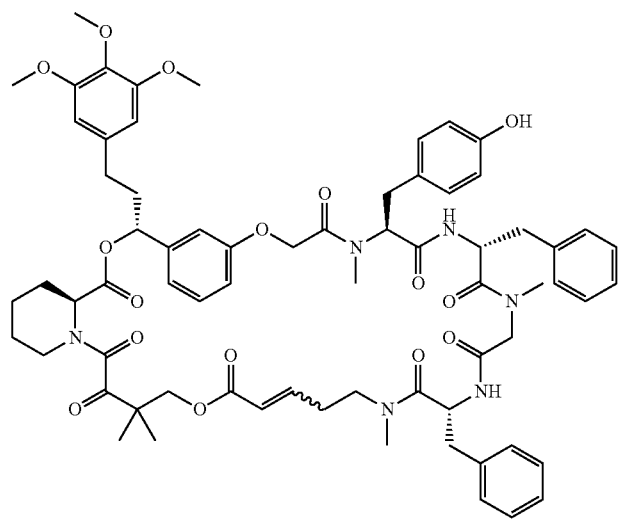

TABLE 11-continued
Synthesis and characterization of compounds 1566-84.
| Compound No. | Composition (FKBD/ monomer1/ monomer2/ monomer3/ monomer4) | Molecular weight | Prolif, H929 | Chemical Structure |
|---|---|---|---|---|
| 1567 | rae10 my df sar df | 1237.41 | medium | 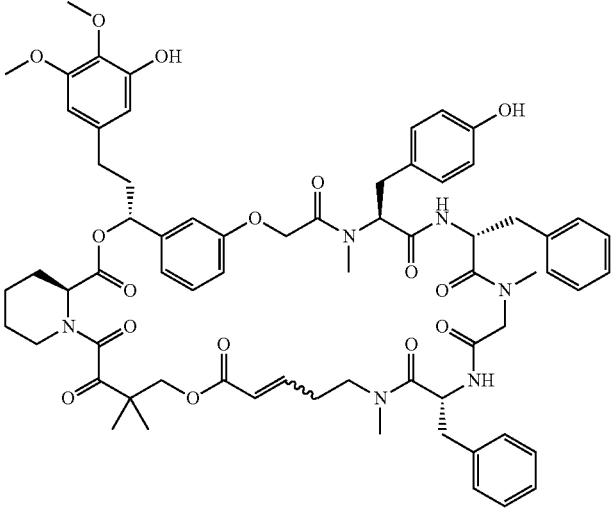 [SMILES: COc1cc(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cccc2c3)cc(O)c1OC] |
| 1568 | rae11 my df sar df | 1237.41 | low | 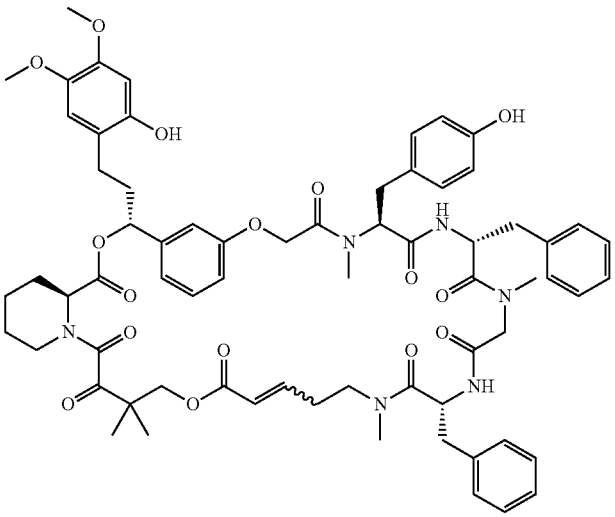 [SMILES: COc1cc(O)c(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cccc2c3)cc1OC] |

TABLE 11-continued
Synthesis and characterization of compounds 1566-84.
| Compound No. | Composition (FKBD/ monomer1/ monomer2/ monomer3/ monomer4) | Molecular weight | Prolif, H929 | Chemical Structure |
|---|---|---|---|---|
| 1569 | rae12 my df sar df | 1239.41 | low | 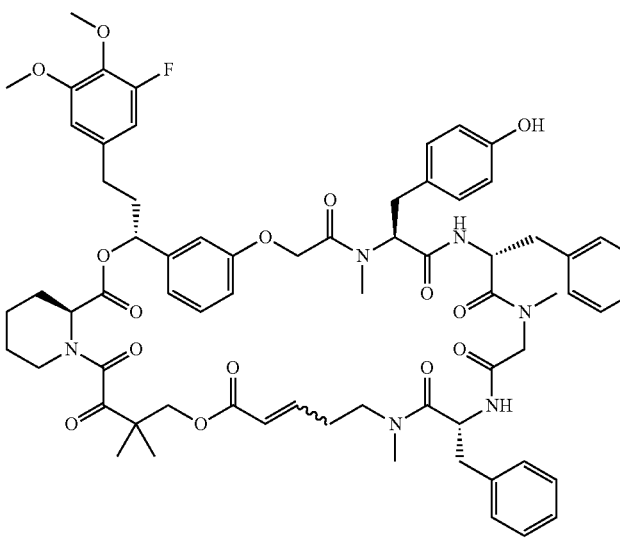 |
| 1570 | rae13 my df sar df | 1239.41 | medium | 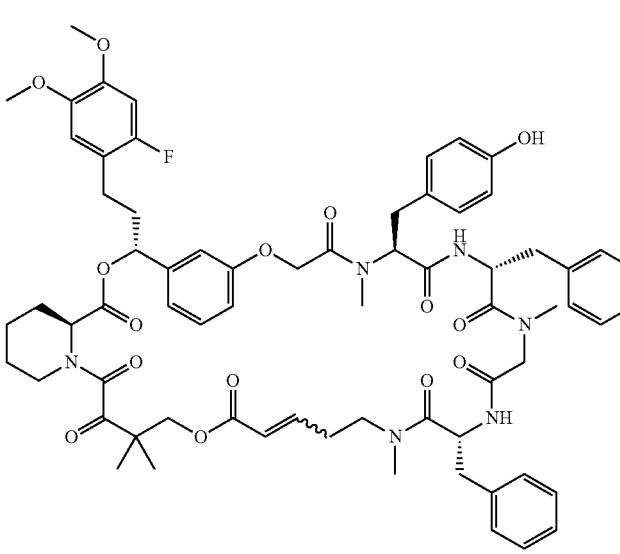 |

TABLE 11-continued
Synthesis and characterization of compounds 1566-84.
| Compound No. | Composition (FKBD/ monomer1/ monomer2/ monomer3/ monomer4) | Molecular weight | Prolif, H929 | Chemical Structure |
|---|---|---|---|---|
| 1571 | rae14 my df sar df | 1239.41 | low | 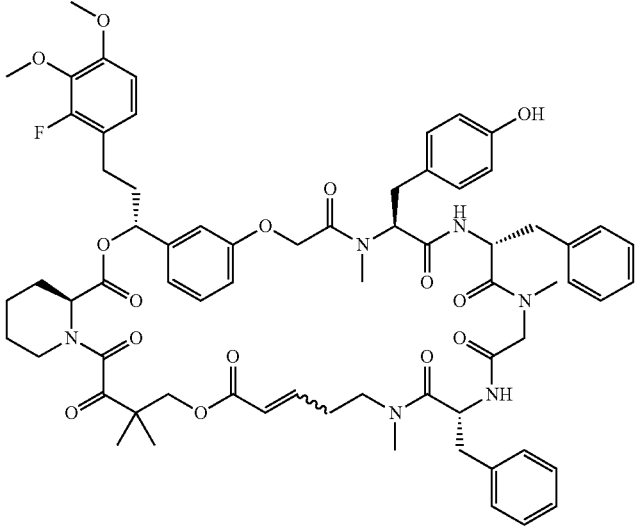 [SMILES: COc1ccc(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cccc2c3)c(F)c1OC] |
| 1572 | rae16 my df sar df | 1444.65 | low | 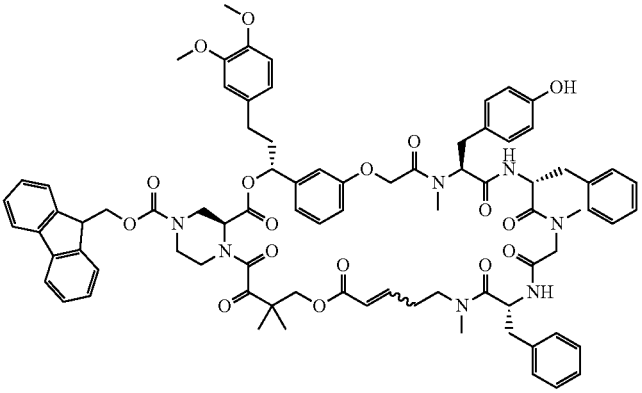 [SMILES: COc1ccc(CC[C@H]2OC(=O)[C@@H]3CN(C(=O)OCC4c5ccccc5-c5ccccc54)CCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cccc2c3)cc1OC] |
| 1573 | rae16a my df sar df | 1222.40 | low | 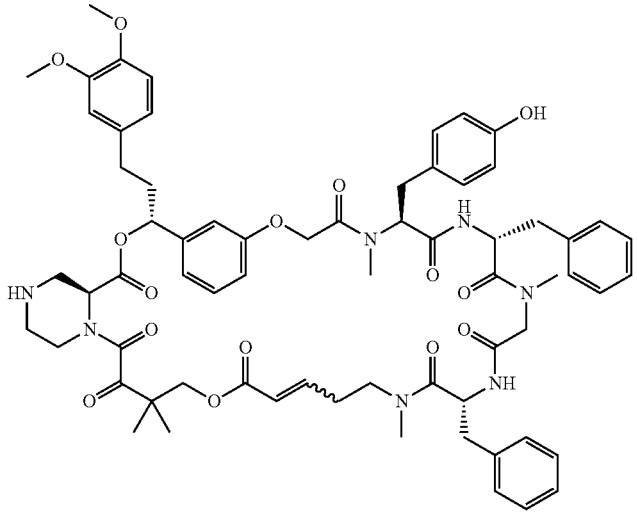 [SMILES: COc1ccc(CC[C@H]2OC(=O)[C@@H]3CNCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cccc2c3)cc1OC] |

TABLE 11-continued
Synthesis and characterization of compounds 1566-84.
| Compound No. | Composition (FKBD/ monomer1/ monomer2/ monomer3/ monomer4) | Molecular weight | Prolif, H929 | Chemical Structure |
|---|---|---|---|---|
| 1574 | rae17<br>my<br>df<br>sar<br>df | 1236.43 | low | 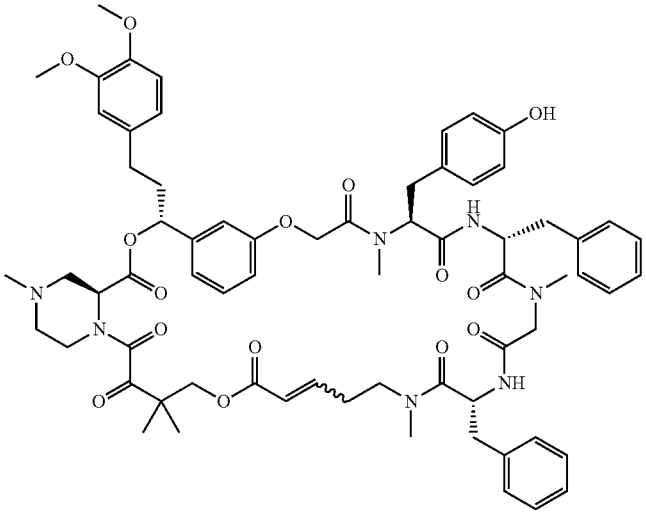 [SMILES: COc1ccc(CC[C@H]2OC(=O)[C@@H]3CN(C)CCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cccc2c3)cc1OC] |
| 1575 | rae18<br>my<br>df<br>sar<br>df | 1239.41 | low | 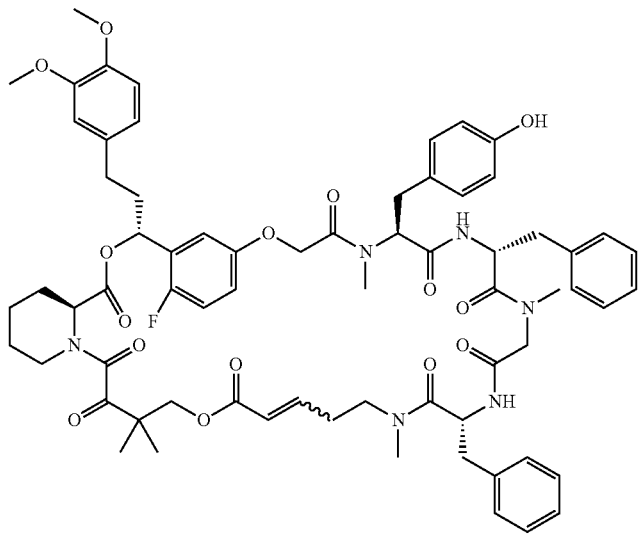 [SMILES: COc1ccc(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3ccc(F)c2c3)cc1OC] |

TABLE 11-continued
Synthesis and characterization of compounds 1566-84.
| Compound No. | Composition (FKBD/ monomer1/ monomer2/ monomer3/ monomer4) | Molecular weight | Prolif, H929 | Chemical Structure |
|---|---|---|---|---|
| 1576 | rae19 my df sar df | 1239.41 | medium | 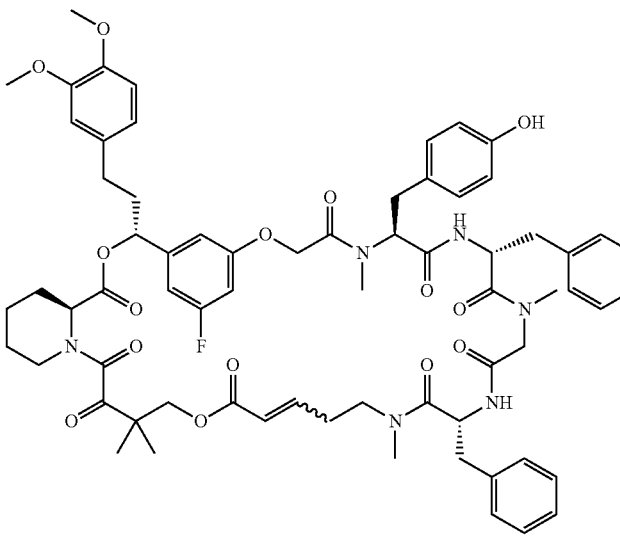 |
| 1577 | rae2 my df sar df | 1251.44 | medium | 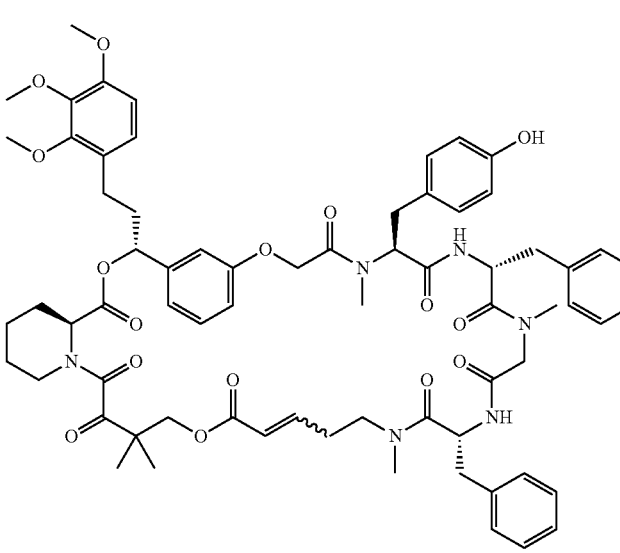 |

TABLE 11-continued

Synthesis and characterization of compounds 1566-84.

| Compound No. | Composition (FKBD/ monomer1/ monomer2/ monomer3/ monomer4) | Molecular weight | Prolif, H929 | Chemical Structure |
|---|---|---|---|---|
| 1578 | rae20 my df sar df | 1239.41 | low | 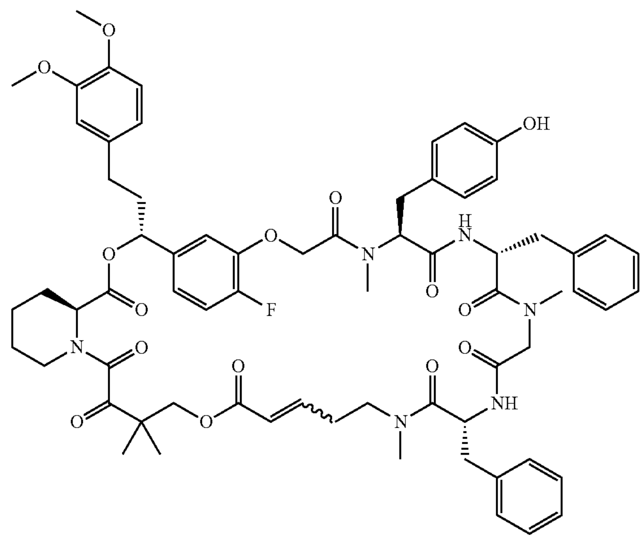 [SMILES: COc1ccc(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cc2ccc3F)cc1OC] |
| 1579 | rae21 my df sar df | 1239.41 | medium | 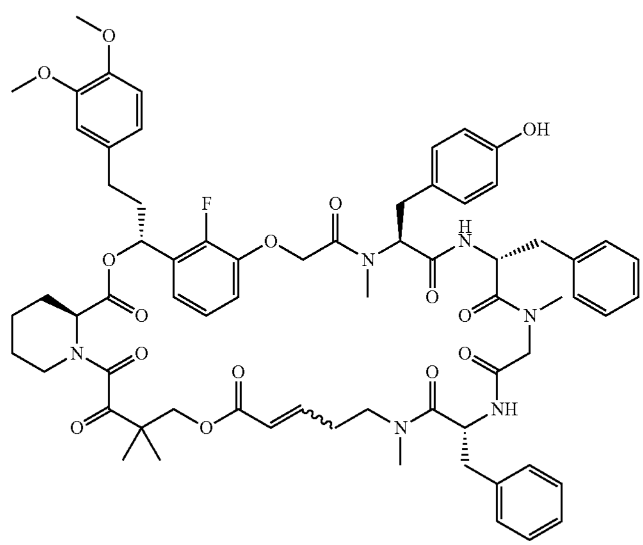 [SMILES: COc1ccc(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(O)cc3)N(C)C(=O)COc3cccc2c3F)cc1OC] |

TABLE 11-continued
Synthesis and characterization of compounds 1566-84.
| Compound No. | Composition (FKBD/ monomer1/ monomer2/ monomer3/ monomer4) | Molecular weight | Prolif, H929 | Chemical Structure |
| --- | --- | --- | --- | --- |
| 1580 | rae26 my df sar df | 1222.40 | low | 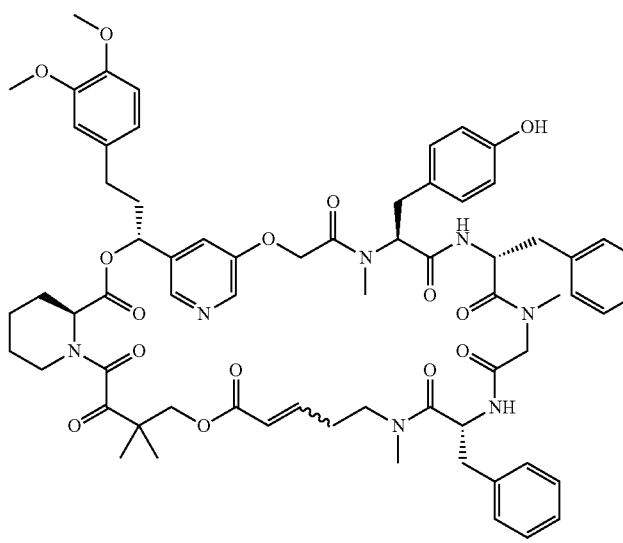 |
| 1581 | rae3 my df sar df | 1251.44 | medium | 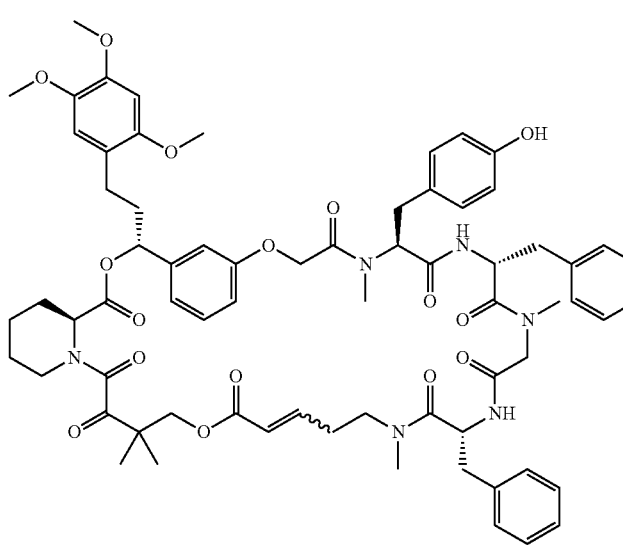 |

TABLE 11-continued
Synthesis and characterization of compounds 1566-84.
| Compound No. | Composition (FKBD/ monomer1/ monomer2/ monomer3/ monomer4) | Molecular weight | Prolif, H929 | Chemical Structure |
|---|---|---|---|---|
| 1582 | rae4 my df sar df | 1251.44 | low | 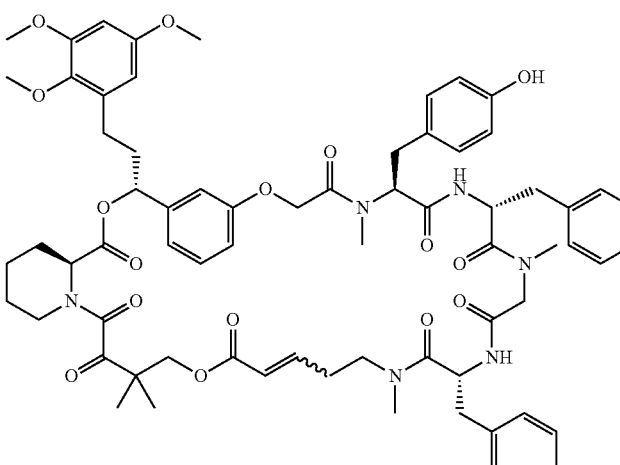 |
| 1583 | rae5 my df sar df | 1251.44 | low | 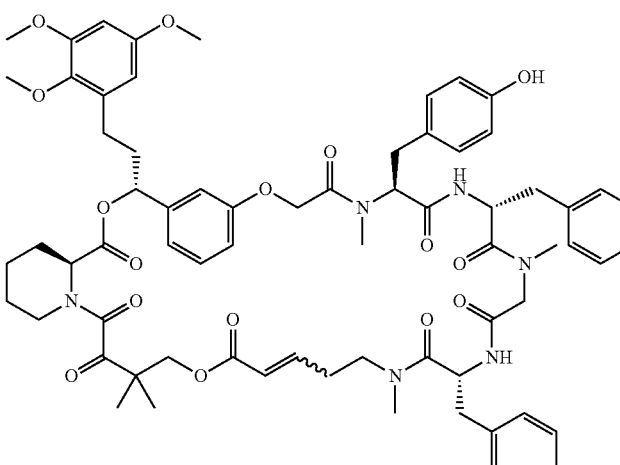 |

TABLE 11-continued

Synthesis and characterization of compounds 1566-84.

| Compound No. | Composition (FKBD/ monomer1/ monomer2/ monomer3/ monomer4) | Molecular weight | Prolif, H929 | Chemical Structure |
|---|---|---|---|---|
| 1584 | rae9 my df sar df | 1237.41 | low | 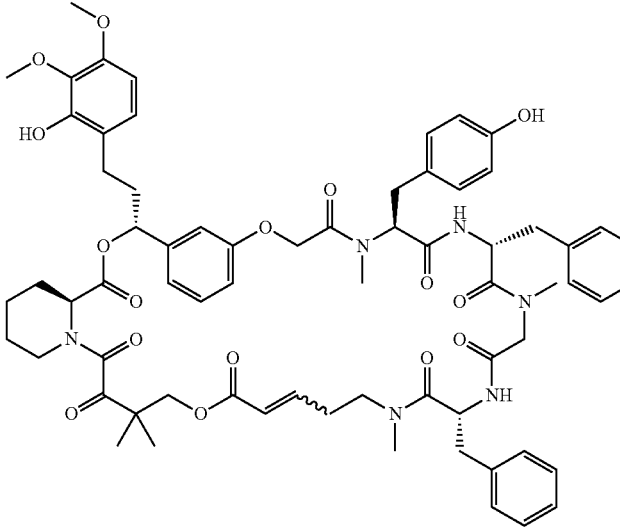 |

TABLE 12

Synthesis and characterization of compounds 1555-1557.

| Compound No. | Composition (FKBD/ monomer1/ monomer2/ monomer3/ monomer4) | Molecular weight | Retention time | Uptake, 293T | Chemical Structure |
|---|---|---|---|---|---|
| 1555 | raa18 ra602 mf dp ml | 1237.51 | 4.39 | high | 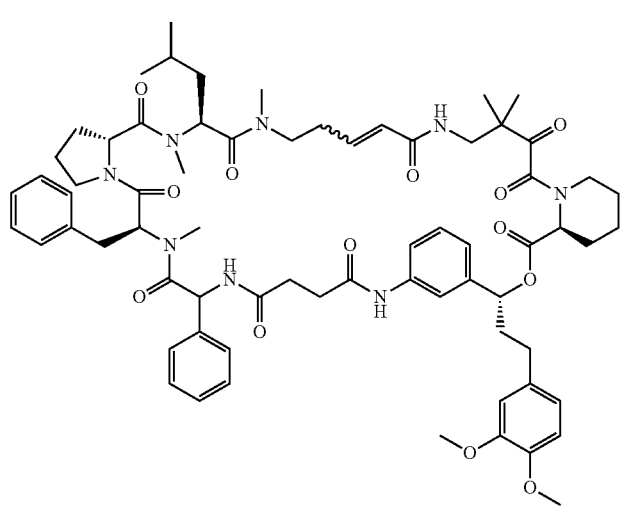 [SMILES: COc1ccc(CC[C@H]2OC(=O)[C@@H]3CCCCN3C(=O)C(=O)C(C)(C)CNC(=O)C=CCCN(C)C(=O)[C@H](CC(C)C)N(C)C(=O)[C@H]3CCCN3C(=O)[C@H](Cc3ccccc3)N(C)C(=O)C(c3ccccc3)NC(=O)CCC(=O)Nc3cccc2c3)cc1OC] |

TABLE 12-continued

Synthesis and characterization of compounds 1555-1557.

| Compound No. | Composition (FKBD/ monomer1/ monomer2/ monomer3/ monomer4) | Molecular weight | Retention time | Uptake, 293T | Chemical Structure |
|---|---|---|---|---|---|
| 1556 | rae27 ra602 mf dp ml | 1211.46 | 5.02 | low | 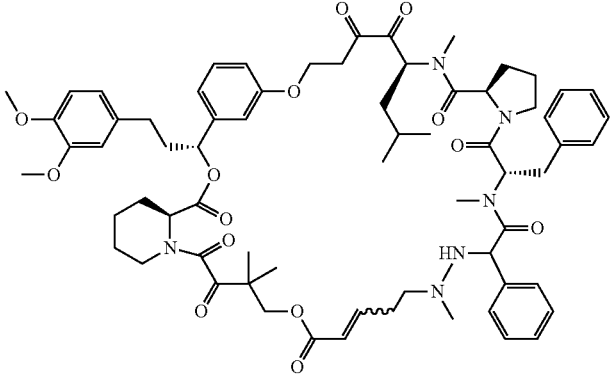 [SMILES: COc1ccc(CC[C@H]2OC(=O)[C@@H]3CCCCN3C(=O)C(=O)C(C)(C)COC(=O)C=CCCN(C)NC(c3ccccc3)C(=O)N(C)[C@@H](Cc3ccccc3)C(=O)N3CCC[C@@H]3C(=O)N(C)[C@@H](CC(C)C)C(=O)C(=O)CCOc3cccc2c3)cc1OC] |
| 1557 | raa17 ra602 mf dp ml | 1237.51 | 4.37 | high | 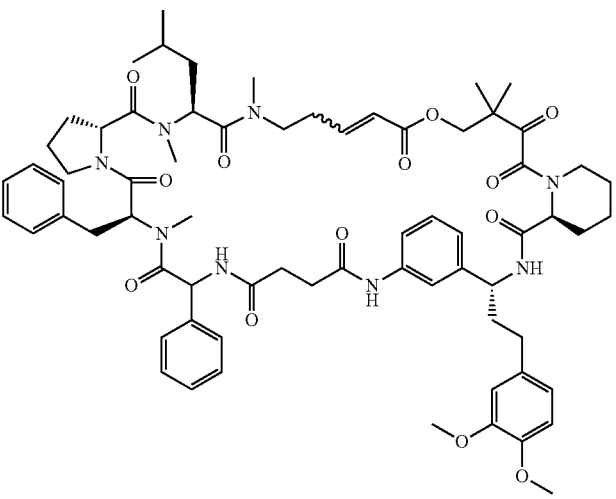 [SMILES: COc1ccc(CC[C@H]2NC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccccc3)N(C)C(=O)C(c3ccccc3)NC(=O)CCC(=O)Nc3cccc2c3)cc1OC] |

Post cyclization modification. Protecting groups may be removed before final purification. In some embodiments, a tert-butyl protecting group can be removed using TFA. A solution of protected Rapafucin is dissolved in DCM and triethylsilane (2 Eq) is added. TFA (20% final concentration) is added and stirred for 2 hours. The mixture is reduced under vacuum and purified via normal phase chromatography (1:9 MeOH/DCM) to give a yellow solid. The compound is further reunified using reverse phase chromatography (40→95% ACN/H$_2$O) to give a pale colored solid.

In some embodiments, a tert-butyloxycarbonyl protecting group may be removed using TFA. A solution of protected Rapafucin is dissolved in DCM and triethylsilane (2 Eq) is added. TFA (20% final concentration) is added and stirred for 2 hours. The mixture is reduced under vacuum and purified via normal phase chromatography (1:9 MeOH/DCM) to give a yellow solid. The compound is further reunified using reverse phase chromatography (40→95% ACN/H$_2$O) to give a pale colored solid.

Additional functional groups can be added to deprotected Rapafucins. In some embodiments, reactive functional groups can be deprotected to produce a chemical handle for additional modifications. These reactions include substitution, addition, and radical reactions.

In some embodiments, a carbamate group is appended to an alcohol containing rapafucin. Other functional groups would work as well. This is an example of attaching an electrophile to the exposed nucleophile, in this embodiment, a phenol group. A deprotected alcohol (or phenol) containing Rapafucin is dissolved in DCM, then pyridine (10 mol %) and DIEA (3 Eq) was added. A solution of carbonyl chloride (3 Eq) in DCM was added dropwise and stirred for 2 hours. The solution was washed with a saturated ammonium chloride solution (3×) and dried over Mg$_2$SO$_4$. The solution concentrated and purified via column chromatography (0→20% MeOH/EtOAc) to produce a white solid.

TABLE 13
Synthesis and characterization of compounds 867-869 and 877.
| Compound No. | Composition (FKBD/ monomer1/ monomer2/ monomer3/ monomer4) | Molecular weight | Retention time | Prolif. H929 | Chemical Structure |
| --- | --- | --- | --- | --- | --- |
| 877 | rae37 ra398 df sar df | 1319.52 | 4.181 | low | 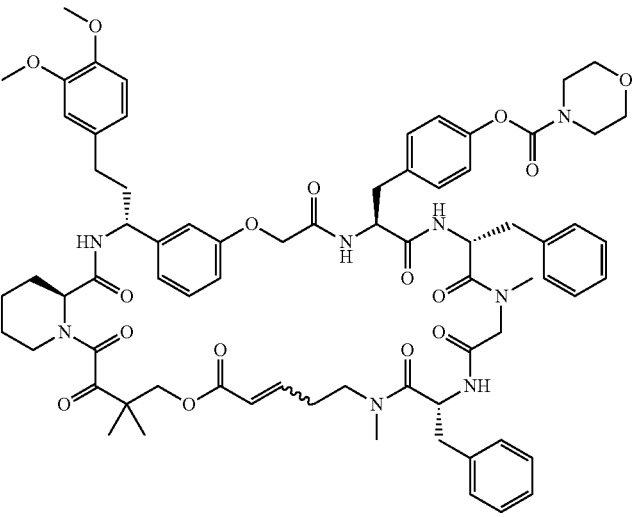 [SMILES: COc1ccc(CC[C@H]2NC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(OC(=O)N4CCOCC4)cc3)NC(=O)COc3cccc2c3)cc1OC] |
| 867 | rae21 ra492 df sar df | 1352.52 | 5.75 | low | 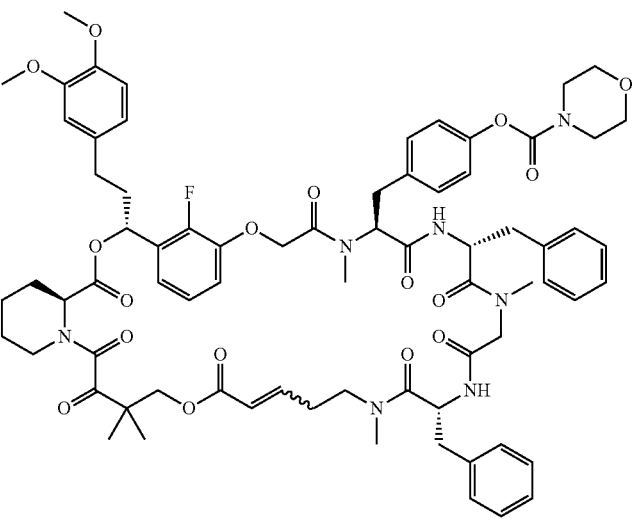 [SMILES: COc1ccc(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(OC(=O)N4CCOCC4)cc3)N(C)C(=O)COc3cccc2c3F)cc1OC] |

TABLE 13-continued
Synthesis and characterization of compounds 867-869 and 877.
| Compound No. | Composition (FKBD/ monomer1/ monomer2/ monomer3/ monomer4) | Molecular weight | Retention time | Prolif. H929 | Chemical Structure |
|---|---|---|---|---|---|
| 868 | rae19 ra492 df sar df | 1352.52 | 5.54 | low | 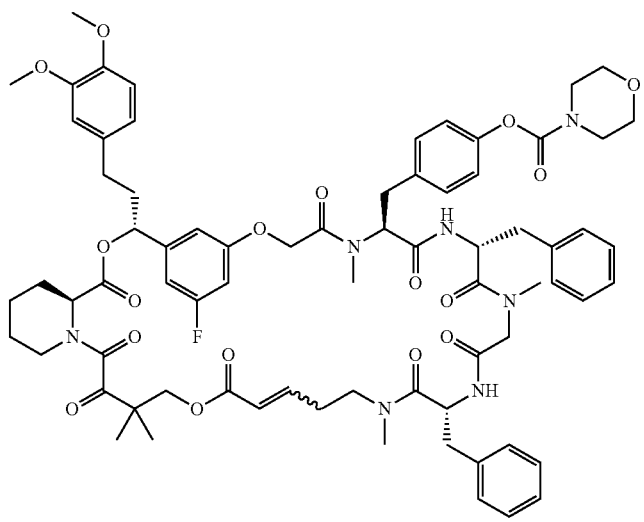 [SMILES: COc1ccc(CC[C@H]2OC(=O)[C@@H]3CCCCN3C(=O)C(=O)C(C)(C)COC(=O)C=CCCN(C)C(=O)[C@@H](Cc3ccccc3)NC(=O)CN(C)C(=O)[C@@H](Cc3ccccc3)NC(=O)[C@H](Cc3ccc(OC(=O)N4CCOCC4)cc3)N(C)C(=O)COc3cc(F)cc2c3)cc1OC] |
| 869 | aFKBD ra492 df sar df | 1375.58 | 5.403 | low | 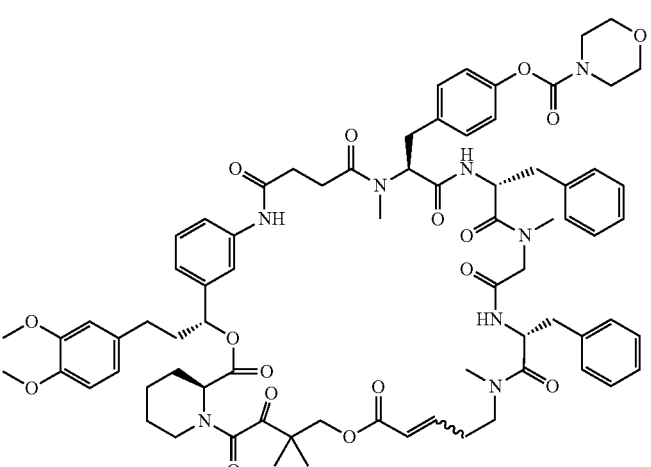 |

In some embodiments, an amide group is formed from an amine containing Rapafucin. A deprotected amine containing Rapafucin is dissolved in DCM, then acyl chloride (2 Eq) and DIEA (3 Eq) was added. The solution was washed with brine (3×) and dried over $Mg_2SO_4$. The solution concentrated and purified via column chromatography (0→20% MeOH/EtOAc) to produce a white solid.

TABLE 14

Synthesis and characterization of compounds 1585-1589.

| Compound No. | Composition (FKBD/ monomer1/ monomer2/ monomer3/ monomer4) | Molecular weight | Retention time | Uptake, 293T | Chemical Structure |
|---|---|---|---|---|---|
| 1585 | afkbd phg ra655 dp ml | 1357.60 | 3.72 | High | 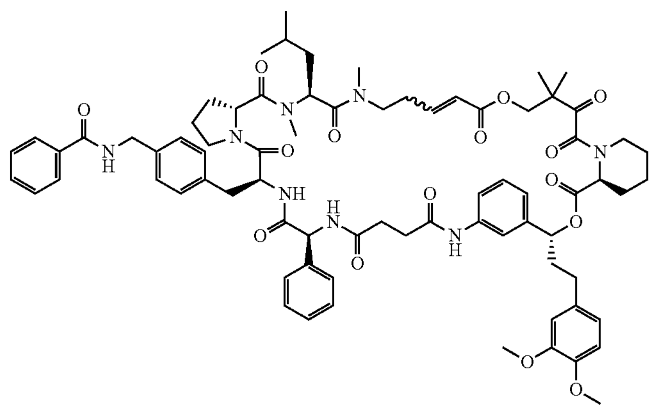 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(CNC(=O)c4ccccc4)cc3)NC(=O)[C@H](c3ccccc3)NC(=O)CCC(=O)Nc3cccc2c3)cc1OC] |
| 1586 | afkbd phg ra656 dp ml | 1370.70 | 3.74 | Med | 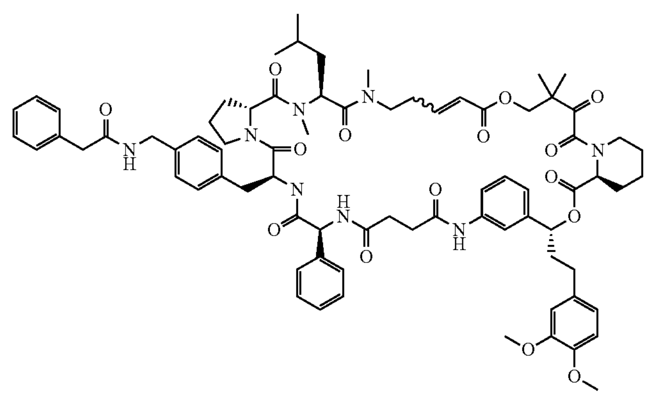 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(CNC(=O)Cc4ccccc4)cc3)NC(=O)[C@H](c3ccccc3)NC(=O)CCC(=O)Nc3cccc2c3)cc1OC] |
| 1587 | afkbd phg ra626 dp ml | 1338.60 | 3.15 | Low | 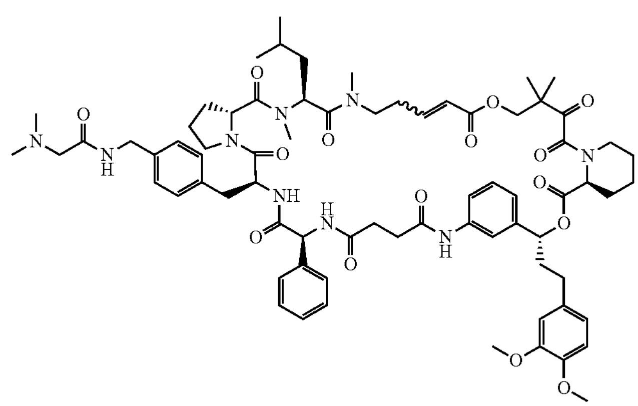 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(CNC(=O)CN(C)C)cc3)NC(=O)[C@H](c3ccccc3)NC(=O)CCC(=O)Nc3cccc2c3)cc1OC] |

TABLE 14-continued

Synthesis and characterization of compounds 1585-1589.

| Compound No. | Composition (FKBD/ monomer1/ monomer2/ monomer3/ monomer4) | Molecular weight | Retention time | Uptake, 293T | Chemical Structure |
|---|---|---|---|---|---|
| 1588 | afkbd phg ra592 dp ml | 1281.52 | 3.44 | High | 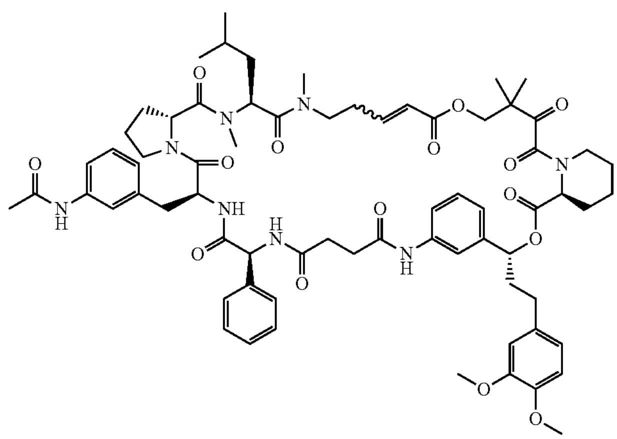 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3cccc(NC(C)=O)c3)NC(=O)[C@H](c3ccccc3)NC(=O)CCC(=O)Nc3cccc2c3)cc1OC] |
| 1589 | afkbd phg ra618 dp ml | 1358.60 | 3.10 | Low | 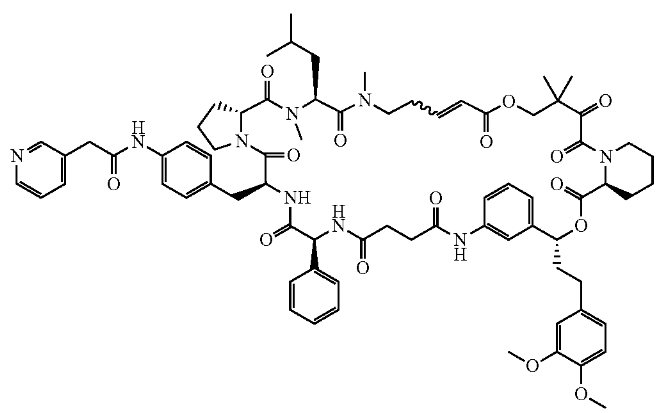 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(NC(=O)Cc4cccnc4)cc3)NC(=O)[C@H](c3ccccc3)NC(=O)CCC(=O)Nc3cccc2c3)cc1OC] |

In some embodiments, an amide group is formed from carboxylic acid containing rapafucin. A deprotected carboxylic acid containing Rapafucin is dissolved in ethyl acetate (5 mM), then an amine (2 Eq), DIEA (10 Eq), and T3P (2 Eq) was added. The reaction until the reaction was complete via LC/MS. The solution was washed with brine (3×) and the organic layer was dried over $Mg_2SO_4$. The solution concentrated and purified via column chromatography (0→20% MeOH/EtOAc) to produce a white solid.

TABLE 15

Synthesis and characterization of compounds 1558, 1559, 1562, 1590, and 1591.

| Compound No. | Composition (FKBD/ monomer1/ monomer2/ monomer3/ monomer4) | Molecular weight | Retention time | Uptake, 293T | Chemical structure |
|---|---|---|---|---|---|
| 1558 | afkbd phg ra500 dp ml | 1311.50 | 3.81 | high | 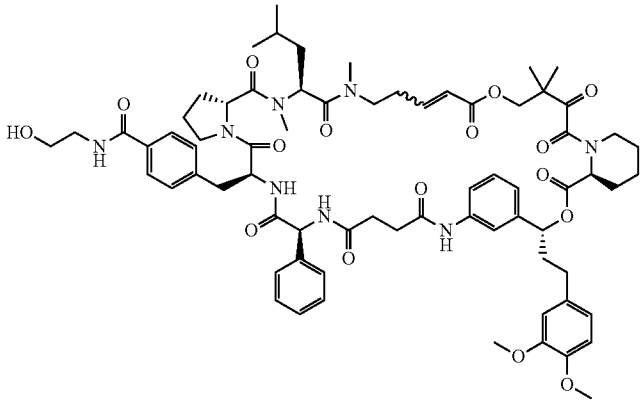 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(C(=O)NCCO)cc3)NC(=O)[C@H](c3ccccc3)NC(=O)CCC(=O)Nc3cccc2c3)cc1OC] |
| 1559 | afkbd phg ra501 dp ml | 1343.60 | 3.86 | medium | 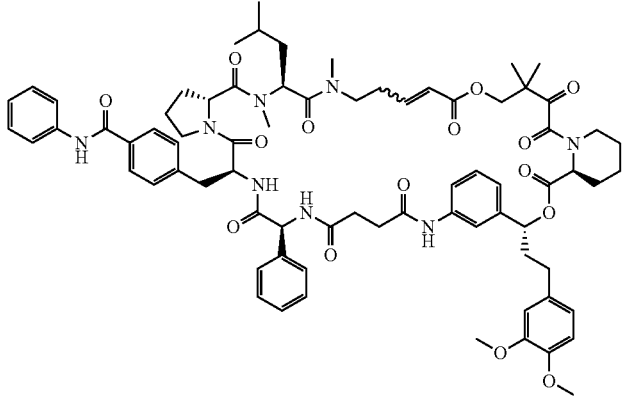 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(C(=O)Nc4ccccc4)cc3)NC(=O)[C@H](c3ccccc3)NC(=O)CCC(=O)Nc3cccc2c3)cc1OC] |
| 1562 | afkbd phg ra504 dp ml | 1344.60 | 3.22 | low | 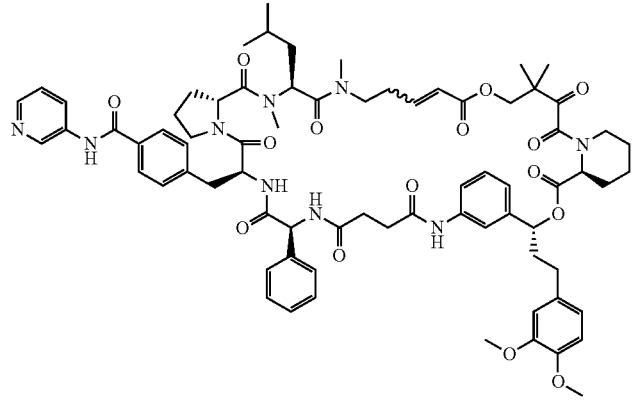 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(C(=O)Nc4cccnc4)cc3)NC(=O)[C@H](c3ccccc3)NC(=O)CCC(=O)Nc3cccc2c3)cc1OC] |

TABLE 15-continued
Synthesis and characterization of compounds 1558, 1559, 1562, 1590, and 1591.
| Compound No. | Composition (FKBD/ monomer1/ monomer2/ monomer3/ monomer4) | Molecular weight | Retention time | Uptake, 293T | Chemical structure |
|---|---|---|---|---|---|
| 1590 | afkbd phg ra620 dp ml | 1371.64 | 3.919 | Low | 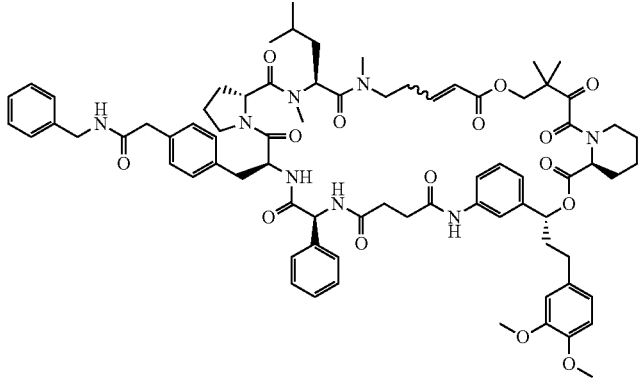 [SMILES: COc1ccc(CC[C@H]2OC(=O)[C@@H]3CCCCN3C(=O)C(=O)C(C)(C)COC(=O)C=CCCN(C)C(=O)[C@H](CC(C)C)N(C)C(=O)[C@H]3CCCN3C(=O)[C@H](Cc3ccc(CC(=O)NCc4ccccc4)cc3)NC(=O)[C@H](c3ccccc3)NC(=O)CCC(=O)Nc3cccc2c3)cc1OC] |
| 1591 | afkbd phg ra623 dp ml | 1365.68 | 3.956 | Low | 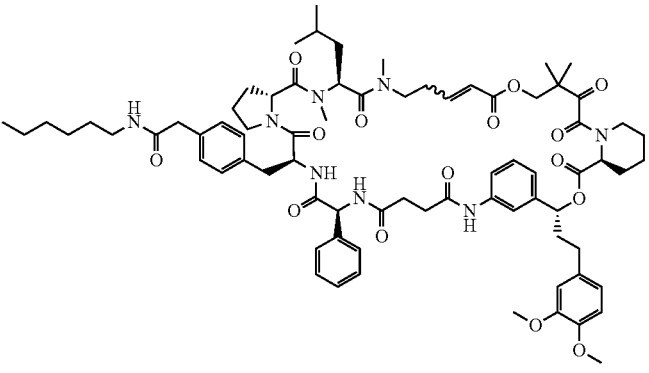 [SMILES: CCCCCCNC(=O)Cc1ccc(C[C@@H]2NC(=O)[C@H](c3ccccc3)NC(=O)CCC(=O)Nc3cccc(c3)[C@@H](CCc3ccc(OC)c(OC)c3)OC(=O)[C@@H]3CCCCN3C(=O)C(=O)C(C)(C)COC(=O)C=CCCN(C)C(=O)[C@H](CC(C)C)N(C)C(=O)[C@H]3CCCN3C2=O)cc1] |

In some embodiments, a phosphinate group may be added to a rapafucin. A deprotected alcohol (or phenol) containing Rapafucin is dissolved in DCM and pyridine (1:1 v/v) and dimethylphosphinic chloride (11 Eq) at room temperature and stirred for 16 hrs. The reaction mixture was diluted with DCM and washed with dilute HCl. The organic fraction was washed with water and dried over $Mg_2SO_4$. The solution concentrated and purified via column chromatography (0420% MeOH/EtOAc) to produce a white solid.

TABLE 16

Synthesis and characterization of compound 1520.

| Compound No. | Composition (FKBD/ monomer1/ monomer2/ monomer3/ monomer4) | Molecular weight | Retention time | Uptake, 293T | Chemical structure |
|---|---|---|---|---|---|
| 1520 | aFKBD ra602 ra515 dp ml | 1316.4 | 5.34 | low | 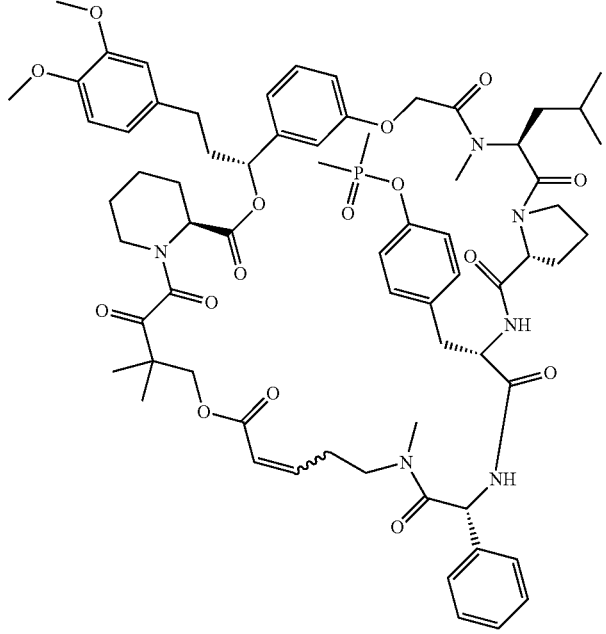 [SMILES: COc1ccc(CC[C@H]2OC(=O)[C@@H]3CCCCN3C(=O)C(=O)C(C)(C)COC(=O)C=CCCN(C)C(=O)[C@@H](c3ccccc3)NC(=O)[C@H](Cc3ccc(OP(C)(C)=O)cc3)NC(=O)[C@H]3CCCN3C(=O)[C@H](CC(C)C)N(C)C(=O)COc3cccc2c3)cc1OC] |

Manual Gram Scale Ring-Closing Metathesis. Charged Resin (Loading Capacity=0.2-0.3 mmol/g) is loaded in a 500 ml of SPPS vessel and swelled for 30 min with DCM (300 ml) on laboratory shaker (Kamush® LP360AMP, 360°, speed 6), then filtered and washed with DMF (200 ml×2) and dried under vacuum for 5 min.

A solution of Fmoc-AA (3 eq) and HATU (3 eq) in 150 ml of DMF was added to the resin. Then DIEA (6 eq) in 50 ml of DMF was added and shaken for 3 hrs. Solvent was filtered and washed with DMF (200 ml×5) and DCM (200 ml×5) and dried. 300 ml of 20% Piperidine in DMF was added and shaken for 20-30 min, filtered and again 300 ml of 20% Piperidine in DMF was added and shaken for 20-30 min. The solvent was filtered and washed carefully with DMF (200 ml×5), then immediately taken for next Fmoc-AA coupling.

After the peptidic portion is installed and deprotected, FKBD (2 eq) was also coupled similar manner was taken for next step (No de-protection of the FKBD necessary). LC-MS analysis was performed after every Fmoc-AA coupling.

Linear Rapafucin on resin and Hoveyda-Grubbs II (30 mol %) was taken in a 2 L round bottom flask with 8 cm long octagonal stir bar. Ethyl acetate (600 mL) was taken in 2 L conical flask and sparged with gentle stream of $N_2$ for ~10 min, then was added to the Resin/Catalyst mixture. A super air condenser was mounted and the flask was placed in oil bath and heated to 90° C. for 5 h (moderate reflux) under $N_2$ (Balloon). The solution was cooled to room temperature leaving a dark brown solution with suspended resin. The resin was checked using LC/MS and TLC for formation of desired product.

Resin was filtered off and the filtrate was evaporated in vacuo to generate a dark brown crude product which was dissolved in minimal DCM (60 mL) and subjected into normal phase column chromatography (0→10% MeOH/EtOAc). Fractions containing pure desired compound were pooled and concentrated in vacuo to yield a brownish powder. The product was then dissolved in a minimal amount of MeOH (20 mL) and subjected into reverse phase column chromatography (10 to 95% ACN/$H_2O$). Fractions containing pure desired compound were pooled and concentrated in vacuo to get off-white solid, which was dissolved in 20-25 ml of 2-MeTHF and dripped into the 250 ml of Heptane in a 1 L flask with gentle stirring. Formed white precipitate was filtered and dried to get pale grayish white powder.

TABLE 17

Synthesis and characterization of compound 1592.

| Compound No. | Composition (FKBD/ monomer1/ monomer2/ monomer3/ monomer4) | Molecular weight | Retention time | A549 Prolif | Molecular Structure |
|---|---|---|---|---|---|
| 1592 | aFKBD ml df mi g | 1178.44 | 6.48 | High | 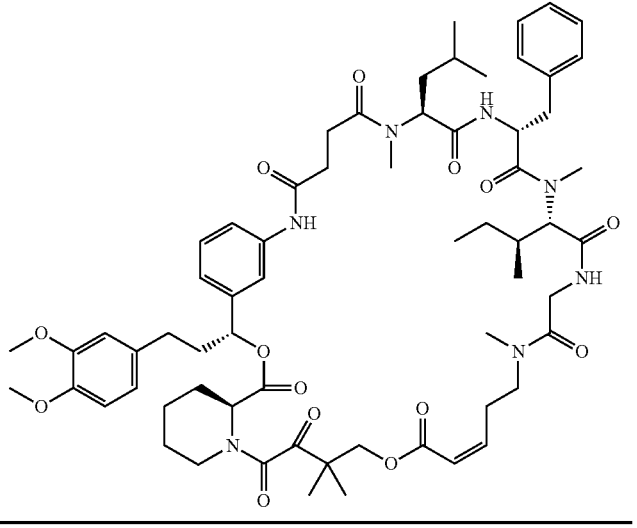 |

Ring Closing via Macrolactamization. Unmodified 2-chloro-chlorotrityl resin (Loading Capacity=1.5 mmol/g) is loaded into a solid phase reaction vessel (60 mL) and peptidic portion is synthesized under normal solid phase synthesis conditions. (see above section).

For peptide residues that need alternative coupling conditions for racemization, the resin may be treated to the following conditions: Deprotected resin is cooled to 0° C. Resin was treated with a cold (0° C.) pre-mixed (5 minutes) solution of FMOC-Amino Acid (3 Eq) in DMF, Oxyma (3 Eq) in DMF and DIEA (3 Eq); shaken for 3 hours. The resultant resin was filtered and washed with DMF (5×3 ml), DCM (5×3 ml) and dried.

After deprotection of the peptidic portion on resin, a FKBD containing a protected amine functionality can be installed using normal synthetic procedures. The resultant fragment can be deprotected and released from the resin.

The FKBD containing linear rapafucin can be further cyclized to produce the cyclic Rapafucin. Acyclic Rapafucin is taken up in DMF and treated with COMU-PF6 (3 Eq) and DIEA (3 Eq), let stir for 1 hour. The reaction is monitored by LC/MS. Upon completion, the mixture is diluted with water and extracted with EtOAc (3×). Combined extracts were washed with brine, dried over $MgSO_4$ and reduced under vacuum. The crude product is purified via column chromatography (1:9 MeOH/EtOAc) to give an orange solid and repurified via reverse phase chromatography (40→95% ACN/$H_2O$) to give a tan solid.

If required protecting groups may be removed before final purification. In some embodiments, a tert-butyl protecting group can be removed using TFA. A solution of protected Rapafucin is dissolved in DCM and triethylsilane (2 Eq) is added. TFA (20% final concentration) is added and stirred for 2 hours. The mixture is reduced under vacuum and purified via normal phase chromatography (1:9 MeOH/DCM) to give a yellow solid. The compound is further reunified using reverse phase chromatography (40→95% ACN/$H_2O$) to give a pale colored solid.

PROPHETIC EXAMPLES—DNA-ENCODED LIBRARY

Prophetic Example 1—Preparation of a Rapafucin DNA-Encoding Library Via Split-and-Pool Cycles A rapafucin DNA-encoding library is synthesized by a sequence of split-and-pool cycles wherein the oligonucleotide is attached to the FKBD. First, an initial oligonucleotide of Formula (XIII) is synthesized and HPLC purified. A first building block comprising an FKBD building block is then covalently bound to the oligonucleotide of Formula (XIII) via click chemistry. Subsequently, a second oligonucleotide, encoding the first building block, is appended to the oligonucleotide of Formula (XIII). The resulting product is pooled and split into a second set of separate reaction vessels and a second building block comprising an effector domain building block is coupled to the first building block using a ring-closing reaction. The reaction is then encoded by the attachment of a unique oligonucleotide sequence to the unique oligonucleotide attached to the first building block. The encoded two-building-block molecules yields the final library.

Prophetic Example 2—Preparation of a Rapafucin DNA-Encoding Library Via Split-and-Pool Cycles A rapafucin DNA-encoding library is synthesized by a sequence of split-and-pool cycles wherein the oligonucleotide is attached to a linking region. First, an initial oligonucleotide of Formula (XIII) is synthesized and HPLC purified. Then, the oligonucleotide of Formula (XIII) is covalently bound to a first linking region via click chemistry.

A first building block comprising an FKBD building block is encoded by a second oligonucleotide which is appended to the initial oligonucleotide of Formula (XIII). The resulting product is pooled and split into a second set of separate reaction vessels and a second building block comprising an effector domain building block is coupled to the first building block using a ring-closing reaction. The reaction is then encoded by the attachment of a unique oligonucleotide sequence to the unique oligonucleotide attached to the first building block. The encoded two-building-block molecules yields the final library.

Prophetic Example 3—Preparation of a Rapafucin DNA-Encoding Library Via DNA-Recorded Synthesis and Ligation A rapafucin DNA-encoding library is synthesized by DNA-recorded synthesis wherein the oligonucleotide is attached to the FKBD. First, an initial oligonucleotide of Formula (XIII) is synthesized and HPLC purified. A first building block comprising an FKBD building block is then covalently bound to the oligonucleotide of Formula (XIII) via click chemistry. Then, a second building block comprising an effector domain building block is coupled to the first building block via the first and second linking region through a ring-closing reaction. The reaction is encoded by DNA-recorded synthesis by ligation of a unique oligonucleotide to the initial oligonucleotide of formula (XIII).

Prophetic Example 4—Preparation of a Rapafucin DNA-Encoding Library Via DNA-Recorded Synthesis and Enzymatic Reactions A rapafucin DNA-encoding library is synthesized by DNA-recorded synthesis wherein the oligonucleotide is attached to the FKBD. First, an initial oligonucleotide of Formula (XIII) is synthesized and HPLC purified. A first building block comprising an FKBD building block is then covalently bound to the oligonucleotide of Formula (XIII) via click chemistry. Then, a second building block comprising an effector domain building block is coupled to the first building block via the first and second linking region through a ring-closing reaction. The reaction is then encoded by DNA-recorded synthesis by polymerase-catalyzed fill-in reactions.

Prophetic Example 5—Preparation of a Rapafucin DNA-Encoding Library Via DNA-Templated Synthesis A rapafucin DNA-encoding library is synthesized by DNA-temaplted synthesis. First, a second building block comprising an effector domain building block is coupled to the first building block comprising the FKBD via the first and second linking regions. Then, the reaction is encoded by DNA-templated synthesis, wherein a plurality of conjugate molecules of oligonucleotide-tagged building blocks are prepared and the spatial proximity of the two distinct oligonucleotides of Formula (XIII) facilitates the bimolecular chemical reactions between the two building blocks.

EXAMPLES—BIOLOGICAL ASSAYS

Nucleoside Uptake Assay (uptake). Nuceloside uptake assays were performed with using 3H-Thymidine as described in Guo et al. (2018) Nat. Chem. 11:254-63. Specific cell lines are indicated in each assay and cultured in complete growth media. Activity is scored according to the $IC_{50}$ values relative to DMSO control. "Low" indicates an $IC_{50}$ greater than 600 nM, "Medium" indicates an $IC_{50}$ between 300 nM and 600 nM "High" indicates an $IC_{50}$ less than 300 nM. "Rel.Uptake" refers to uptake activity characterization relative to a single concentration assay. "Low" indicates a response greater than 0.6 times the activity relative to DMSO, "Medium" indicates a response between 0.6 and 0.3 times the activity relative to DMSO, "High" indicates a response less than 0.3 times the activity relative to DMSO.

Cell Proliferation Assay (Prolif) Guo et al. (2018) Nat. Chem. 11:254-63. Specific cell lines are indicated in each assay and cultured in complete growth media. Activity is scored according to the $IC_{50}$ values relative to DMSO control. "Low" indicates an $IC_{50}$ greater than 600 nM, "Medium" indicates an $IC_{50}$ between 300 nM and 600 nM "High" indicates an $IC_{50}$ less than 300 nM. "Rel.Uptake" refers to uptake activity characterization relative to a single concentration assay. "Low" indicates a response greater than 0.6 times the activity relative to DMSO, "Medium" indicates a response between 0.6 and 0.3 times the activity relative to DMSO, "High" indicates a response less than 0.3 times the activity relative to DMSO.

Those skilled in the art will recognize, or be able to ascertain, using no more than routine experimentation, numerous equivalents to the specific composition and procedures described herein. Such equivalents are considered to be within the scope of this disclosure, and are covered by the following claims.

What is claimed is:
1. A compound of Formula (V)

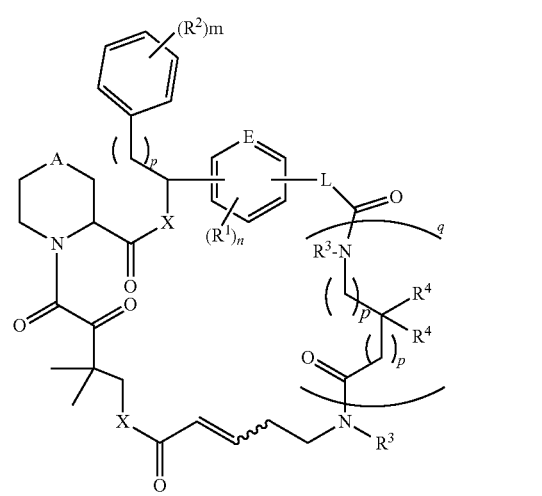

Formula (V)

or an optically pure stereoisomer or pharmaceutically acceptable salt thereof,
wherein L is optionally substituted $(CH_2)_n NR_{20} C_{1-6}$ alkylene;
A is NH, NMe, O, $S(O)_2$ or S;
each X is O;
E is CH or N;
$R^1$ is H;
$R^2$ is $C_{1-20}$alkoxy;
$R^3$ is $C_{1-20}$alkyl;

$R^4$ is independently selected from the group consisting of H;
or $R^4$ forms a cyclic structure formed with $R^3$, the cyclic structure is $C_{2-10}$ heterocyclyl $R^{20}$ is H;
n is 0;
m is an integer selected from 2;
p is 2; and
q is 4.

2. The compound of claim 1, wherein $R^2$ is methoxy.

3. The compound of claim 1, wherein E is CH.

4. A pharmaceutical composition comprising the compound of claim 1 or an optically pure stereoisomer or pharmaceutically acceptable salt and a pharmaceutically acceptable carrier.

\* \* \* \* \*